US012031122B2

(12) United States Patent
Westbrook

(10) Patent No.: US 12,031,122 B2
(45) **Date of Patent: *Jul. 9, 2024**

(54) RECOMBINANT BACTERIAL CELLS AND METHODS FOR PRODUCING POLY(3-HYDROXYBUTYRATE-CO-3-HYDROXYVALERATE)

(71) Applicant: GENECIS BIOINDUSTRIES INC., Scarborough (CA)

(72) Inventor: Adam William Westbrook, Milton (CA)

(73) Assignee: Genecis Bioindustries Inc., Scarborough (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,442

(22) Filed: May 17, 2023

(65) Prior Publication Data

US 2023/0374445 A1 Nov. 23, 2023

Related U.S. Application Data

(60) Provisional application No. 63/426,558, filed on Nov. 18, 2022, provisional application No. 63/342,707, filed on May 17, 2022.

(51) Int. Cl.

| | |
|---|---|
| ***C12N 1/20*** | (2006.01) |
| ***C07K 14/21*** | (2006.01) |
| ***C12N 1/21*** | (2006.01) |
| ***C12N 9/04*** | (2006.01) |
| ***C12N 9/10*** | (2006.01) |
| ***C12N 9/90*** | (2006.01) |
| ***C12N 15/52*** | (2006.01) |
| ***C12P 7/52*** | (2006.01) |
| ***C12P 7/625*** | (2022.01) |
| ***C12R 1/19*** | (2006.01) |

(52) U.S. Cl.

CPC ................ *C12N 1/20* (2013.01); *C07K 14/21* (2013.01); *C12N 1/205* (2021.05); *C12N 9/0006* (2013.01); *C12N 9/1029* (2013.01); *C12N 9/13* (2013.01); *C12N 9/90* (2013.01); *C12N 15/52* (2013.01); *C12P 7/52* (2013.01); *C12P 7/625* (2013.01); *C12Y 101/01036* (2013.01); *C12Y 203/01009* (2013.01); *C12Y 203/01016* (2013.01); *C12Y 208/03001* (2013.01); *C12Y 504/99002* (2013.01); *C12R 2001/19* (2021.05)

(58) Field of Classification Search

None

See application file for complete search history.

(56) References Cited

U.S. PATENT DOCUMENTS

| | | | |
|---|---|---|---|
| 2014/0073022 A1 | 3/2014 | Pfleger et al. | |
| 2023/0374557 A1 | 11/2023 | Westbrook | |

FOREIGN PATENT DOCUMENTS

| | | | | |
|---|---|---|---|---|
| CN | 105063790 A | | 11/2015 | |
| CN | 107022556 A | * | 8/2017 | .............. A62D 3/02 |
| WO | WO-9000067 A1 | | 1/1990 | |
| WO | WO-2022103799 A1 | | 5/2022 | |

OTHER PUBLICATIONS

Uniprot, Accession No. A0A6N1BR68, 2020, www.uniprot.org. (Year: 2020).*

Kweon et al., Isolation of a novel species in the genus *Cupriavidus*, PLoS One 15, 2020, e0232850. (Year: 2020).*

Genbank, Accession No. WP_174781755.1, May 2021, www.ncbi.nlm.nih.gov. (Year: 2021).*

Genbank, Accession No. HE610111, 2012, ncbi.nlm.nih.gov. (Year: 2012).*

Genbank, Accession No. CP054626.1, 2020, www.ncbi.nlm.nih.gov. (Year: 2020).*

International Search Report and Written Opinion for International Application No. PCT/US2023/067152, mailed Nov. 14, 2023, 13 pages.

Agus et al., "Molecular weight characterization of poly[(R)-3-hydroxybutyrate] synthesized by genetically engineered strains of *Escherichia coli*", Polymer degradation and stability 2006, 91: 1138-1146.

Amann et al., "Tightly regulated tac promoter vectors useful for the expression of unfused and fused proteins in *Escherichia coli*. Gene", Sep. 30, 1988; 69(2): 301-15.

Arab, et al., "A Toolkit for Effective and Successive Genome Engineering of *Escherichia coli*", Fermentation. 2023; 9(1): 14, 17 pages.

Chen et al., "PHBV microspheres as neural tissue engineering scaffold support neuronal cell growth and axon-dendrite polarization", Acta Biomater. Feb. 2012; 8(2): 540-8. Epub Sep. 28, 2011.

Gupta et al., "Dynamic regulation of metabolic flux in engineered bacteria using a pathway-independent quorum-sensing circuit", Nat Biotechnol. Mar. 2017; 35(3):273-279. Epub Feb. 13, 2017.

Herring et al., "Comparative genome sequencing of *Escherichia coli* allows observation of bacterial evolution on a laboratory timescale", Nat Genet. Dec. 2006; 38(12): 1406-12 Epub Nov. 5, 2006.

Ho et al., "Expanding the active pH range of *Escherichia coli* glutamate decarboxylase by breaking the cooperativeness", J Biosci Bioeng. Feb. 2013; 115(2): 154-8. Epub Sep. 29, 2012.

Hwang et al., "Engineering and application of synthetic nar promoter for fine-tuning the expression of metabolic pathway genes in *Escherichia coli*", Biotechnol Biofuels. Apr. 7, 2018; 11: 103, 13 pages.

Jechlinger et al., "Modulation of gene expression by promoter mutants of the lambdacl857/pRM/pR system", J Biotechnol. Mar. 2, 2005; 116(1): 11-20. Epub Nov. 18, 2004.

(Continued)

*Primary Examiner* — Todd M Epstein

(74) *Attorney, Agent, or Firm* — COOLEY LLP

(57) ABSTRACT

The disclosure provides recombinant bacterial host cells that metabolize and convert glycerol or volatile fatty acids (VFAs) to poly(3-hydroxybutyrate-co-3-hydroxyvalerate) or PHBV. The disclosure further provides methods of producing PHBV using the recombinant bacteria disclosed herein.

29 Claims, 7 Drawing Sheets

Specification includes a Sequence Listing.

(56) References Cited

OTHER PUBLICATIONS

Jenkins et al., "Genetic and molecular characterization of the genes involved in short-chain fatty acid degradation in *Escherichia coli*: the ato system",. J Bacteriol. Jan. 1987; 169(1): 42-52.
Jobling et al., "Construction of vectors with the p15a replicon, kanamycin resistance, inducible lacZ alpha and pUC18 or pUC19 multiple cloning sites" Nucleic Acids Res. Sep. 11, 1990; 18(17): 5315-6.
Kang et al., "Inactivation of a Mismatch-Repair System Diversifies Genotypic Landscape of *Escherichia coli* During Adaptive Laboratory Evolution", Front Microbiol. Aug. 16, 2019; 10: 1845, 13 pages.
Kim et al., "Adaptive laboratory evolution of *Escherichia coli* W enhances gamma-aminobutyric acid production using glycerol as the carbon source", Metab Eng. Jan. 2022; 69: 59-72.
Masood et al., "Encapsulation of Ellipticine in poly-(3-hydroxybutyrate-co-3-hydroxyvalerate) based nanoparticles and its in vitro application", Mater Sci Eng C Mater Biol Appl. Apr. 1, 2013; 33(3): 1054-60. Epub Nov. 28, 2012.
Miscevic et al., "Bio-based production of poly(3-hydroxybutyrate-co-3-hydroxyvalerate) with modulated monomeric fraction in *Escherichia coli*", Appl Microbiol Biotechnol. Feb. 2021; 105(4): 1435-1446. Epub Jan. 23, 2021.
Miscevic et al., "Heterologous production of 3-hydroxyvalerate in engineered *Escherichia coli*", Metab Eng. Sep. 2020; 61: 141-151. Epub Nov. 12, 2019.
Miscevic et al., "High-level heterologous production of propionate in engineered *Escherichia coli*", Biotechnol Bioeng. May 2020; 117(5): 1304-1315. Epub Feb. 3, 2020.
Miscevic et al., "Production of cellulosic butyrate and 3-hydroxybutyrate in engineered *Escherichia coli*", Appl Microbiol Biotechnol. Jul. 2019; 103(13): 5215-5230. Epub May 2, 2019.
Nakamura et al., "Codon usage tabulated from international DNA sequence databases: status for the year 200", Nucleic Acids Res. Jan. 1, 2000; 28(1): 292.
Normi et al., "Characterization and properties of G4X mutants of Ralstonia eutropha PHA synthase for poly(3-hydroxybutyrate) biosynthesis in *Escherichia coli*", Macromol Biosci. Mar. 15, 2005; 5(3): 197-206.
Olins et al., "A novel sequence element derived from bacteriophage T7 mRNA acts as an enhancer of translation of the lacZ gene in *Escherichia coli*", J Biol Chem. Oct. 15, 1989; 264(29): 16973-6.
Pauli et al., "ato Operon: a highly inducible system for acetoacetate and butyrate degradation in *Escherichia coli*", Eur J Biochem. Sep. 25, 1972; 29(3): 553-62.
Phan et al., "Development of a strong intracellular expression system for Bacillus subtilis by optimizing promoter elements", J Biotechnol. Jan. 2012; 157(1): 167-72. Epub Nov. 10, 2011.
Pramual et al., "Development and characterization of bio-derived polyhydroxyalkanoate nanoparticles as a delivery system for hydrophobic photodynamic therapy agents", J Mater Sci Mater Med. Feb. 2016; 27(2): 40. Epub Dec. 28, 2015, 11 pages.
Puigbo et al., "HEG-DB: a database of predicted highly expressed genes in prokaryotic complete genomes under translational selection", Nucleic Acids Res. Jan. 2008; 36(Database issue): D524-7. Epub Oct. 11, 2007.
Puigbo et al., "Optimizer: a web server for optimizing the codon usage of DNA sequences. Nucleic Acids Res. Jul. 2007; 35(Web Server issue): W126-31", Epub Apr. 16, 2007.
Rand et al., "A metabolic pathway for catabolizing levulinic acid in bacteria", Nat Microbiol. Dec. 2017; 2(12): 1624-1634. Epub Sep. 25, 2017.
Rathbone et al., "Biocompatibility of polyhydroxyalkanoate as a potential material for ligament and tendon scaffold material", J Biomed Mater Res A. Jun. 15, 2010; 93(4): 1391-403.
Sheu et al., "Mutations derived from the thermophilic polyhydroxyalkanoate synthase PhaC enhance the thermostability and activity of PhaC from Cupriavidus necator H16", J Bacteriol. May 2012; 194(10): 2620-9. Epub Mar. 9, 2012.
Shi et al., "Directed evolution and mutagenesis of glutamate decarboxylase from Lactobacillus brevis Lb85 to broaden the range of its activity toward a near-neutral pH", Enzyme Microb Technol. Jul.-Aug. 2014; 61-62: 35-43. Epub May 1, 2014.
Shong et al., "Directed evolution of the quorum-sensing regulator EsaR for increased signal sensitivity", ACS Chem Biol. Apr. 19, 2013; 8(4): 789-95. Epub Feb. 6, 2013.
Sievers et al., "Fast, scalable generation of high-quality protein multiple sequence alignments using Clustal Omega", Mol Syst Biol. Oct. 11, 2011; 7:539, 6 pages.
Soma et al., "Reconstruction of a metabolic regulatory network in *Escherichia coli* for purposeful switching from cell growth mode to production mode in direct GABA fermentation from glucose", Metab Eng. Sep. 2017; 43(Pt A): 54-63.
Srirangan et al., "Biochemical, genetic, and metabolic engineering strategies to enhance coproduction of 1-propanol and ethanol in engineered *Escherichia coli*", Appl Microbiol Biotechnol. Nov. 2014; 98(22): 9499-515. Epub Oct. 10, 2014.
Srirangan et al., "Engineering of Escherichia coli for direct and modulated biosynthesis of poly(3-hydroxybutyrate-co-3-hydroxyvalerate) copolymer using unrelated carbon sources", Sci Rep. Nov. 7, 2016; 6: 36470, 11 pages.
Tang et al., "Efficient expression of novel glutamate decarboxylases and high level production of γ-aminobutyric acid catalyzed by engineered *Escherichia coli*", Int J Biol Macromol. Oct. 1, 2020; 160: 372-379.
Turesin et al., "Biodegradable polyhydroxyalkanoate implants for osteomyelitis therapy: in vitro antibiotic release", J Biomater Sci Polym Ed. 2001; 12(2): 195-207.
Wang et al., "Metabolic modeling of the substrate competition among multiple VFAs for PHA production by mixed microbial cultures", J Biotechnol. Aug. 20, 2018; 280: 62-69. Epub Jun. 19, 2018.
Xue et al., "Anti-infective biomaterials with surface-decorated tachyplesin I", Biomaterials. Sep. 2018; 178:351-362. Epub May 9, 2018.
Yin et al., "Effects of chromosomal gene copy number and locations on polyhydroxyalkanoate synthesis by *Escherichia coli* and *Halomonas* sp", Appl Microbiol Biotechnol. Jul. 2015; 99(13): 5523-34. Epub Mar. 12, 2015.
Zhang et al., "Engineering cell wall synthesis mechanism for enhanced PHB accumulation in *E. coli*", Metab Eng. Jan. 2018; 45: 32-42. Epub Nov. 24, 2017.
Zhuang et al., "Engineering the pathway in *Escherichia coli* for the synthesis of medium-chain-length polyhydroxyalkanoates consisting of both even- and odd-chain monomers" Microb Cell Fact. Aug. 13, 2019; 18(1): 135, 13 pages.
Bhatia et al., "Poly(3-hydroxybutyrate-co-3-hydroxyhexanoate) production from engineered Ralstonia eutropha using synthetic and anaerobically digested food waste derived volatile fatty acids", Int. J. Biol. Macromol. 133, 2019, 1-10 (Year: 2019).
Chen et al., "Manipulation of pathway regulation in Streptomyces globisporus for overproduction of the enediyne antitumor antibiotic C-1027", J Antibiot (Tokyo). Aug. 2010; 63(8): 482-5.
Jeon et al., "Biosynthesis of poly(3-hydroxybutyrate-co-3-hydroxyhexanoate) (P(HB-co-HHx)) from butyrate using engineered Ralstonia eutropha", Appl. Microb. Biotechnol. 98, 2014, 5461-69. (Year: 2014).
Miscevic et al., "Integrated strain engineering and bioprocessing strategies for high-level bio-based production of 3-hydroxyvalerate in *Escherichia coli*", Applied Microbiol. Biotechnol. 104, 2020, 5259-72. (Year: 2020).
Park et al., "Enrichment of specific monomer in medium-chain-length poly(3-hydroxyalkanoates) by amplification of fadD and fadE genes in recombinant *Escherichia coli*", Enz. Microb. Technol. 33, 2003, 62-70. (Year: 2003).
Sjoberg et al., "Characterization of volatile fatty-acid utilization in *Escherichia coli* aiming for robust valorisation of food residues", AMB Expr. 10, 2020, 184, 1-9 (Year: 2020).

* cited by examiner

RECOMBINANT BACTERIAL CELLS AND METHODS FOR PRODUCING POLY(3-HYDROXYBUTYRATE-CO-3-HYDROXYVALERATE)

CROSS REFERENCE TO RELATED APPLICATIONS

The present application claims the benefit of priority to U.S. Provisional Application No. 63/342,707, filed on May 17, 2022, and U.S. Provisional Application No. 63/426,558, filed on Nov. 18, 2022, the contents of each of which are hereby incorporated by reference in their entireties.

REFERENCE TO AN ELECTRONIC SEQUENCE LISTING

The contents of the electronic sequence listing (GNBI_001_02WO_SeqList_ST26.xml; Size: 467,880 bytes; and Date of Creation: May 17, 2023) are herein incorporated by reference in its entirety.

FIELD

The disclosure relates to recombinant bacteria and methods for producing poly(3-hydroxybutyrate-co-3-hydroxyvalerate).

BACKGROUND

Poly(3-hydroxybutyrate-co-3-hydroxyvalerate) (PHBV) is a polyhydroxyalkanoate-type microbial biopolymer that is biocompatible and biodegradable and could serve as a viable alternative for many petroleum-derived polymers. The many useful features of PHBV, for example, absorption capacity, low cytotoxicity, piezoelectricity, and thermoplasticity, render it a very promising material with broad applications in a wide range of applications, in particular biomaterial applications. Amongst the different biomaterial applications, PHBV may be suited for absorbable surgical sutures, drug release and delivery systems, medical packaging, and tissue engineering such as biodegradable medical implants, biosensors, porous scaffolds, and tissue patches.

The vast array of potential applications of PHBV may be achieved by varying properties such as composition, molecular weight (MW) and crystallinity, which affect the mechanical and thermal characteristics of the biopolymer. These properties are influenced by, for example, the species or strains of microbes, carbon source, and growth parameters. There are inherent difficulties in maintaining consistent polymer properties (i.e. Mw and composition) and in achieving a specific composition (i.e. tailoring 3-hydroxyvalerate (HV) content) when the microbial culture is highly heterogeneous. A recombinant approach that generates specific strains that modulates the expression level or activity of specific enzymes, including heterologous enzymes, involved in metabolic pathways may provide an avenue for controlling production of PHBV with consistent polymer properties (such as, a desired Mw) and specific compositions.

SUMMARY

The disclosure provides recombinantly-modified bacterial host cells that exhibit improved production of poly(3-hydroxybutyrate-co-3-hydroxyvalerate) or PHBV from substrates, such as, volatile fatty acids (VFAs) and glycerol. The disclosed recombinant bacterial host cells have been engineered to express catalytic proteins that enhance flux through metabolic pathways, thereby promoting uptake of the substrates and their conversion to PHBV. Notably, the disclosed recombinantly-modified bacterial host cells may be used for the small-scale and large-scale production of PHBV per the methods disclosed herein.

The disclosure provides bacterial host cells, comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway.

In embodiments, the bacterial host cells comprise: a first operon comprising: (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, (c) a nucleic acid molecule encoding a PhaB protein, wherein the PhaB protein is a *Cupriavidus* sp. S-6 PhaB protein; a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein; and a sleeping beauty mutase (Sbm) operon comprising a promoter, wherein each of the first and the second operons comprises a promoter comprising the nucleic acid sequence of SEQ ID NO: 233 (Pgracmax2). In embodiments, the bacterial host cells are capable of converting glycerol to poly(3-hydroxybutyrate-co-3-hydroxyvalerate) or PHBV.

The disclosure further provides bacterial host cells comprising: comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, (e) a nucleic acid molecule encoding a LvaE protein, (f) a nucleic acid molecule encoding a propionate-CoA transferase, (g) a nucleic acid molecule encoding a FadE protein, (h) a nucleic acid molecule encoding a FadB protein, and (i) a nucleic acid molecule encoding a AtoB protein, wherein the bacterial host cell comprises an activated sleeping beauty mutase (Sbm) pathway. In embodiments, the bacterial host cells are capable of converting one or more volatile fatty acids (VFAs) to poly(3-hydroxybutyrate-co-3-hydroxyvalerate) or PHBV.

The disclosure also provides methods of producing poly(3-hydroxybutyrate-co-3-hydroxyvalerate) (PHBV) using the bacterial host cells disclosed herein, as well as methods of metabolizing glycerol or VFAs using the bacterial host cells disclosed herein.

DETAILED DESCRIPTION

Definitions

Figure 1:
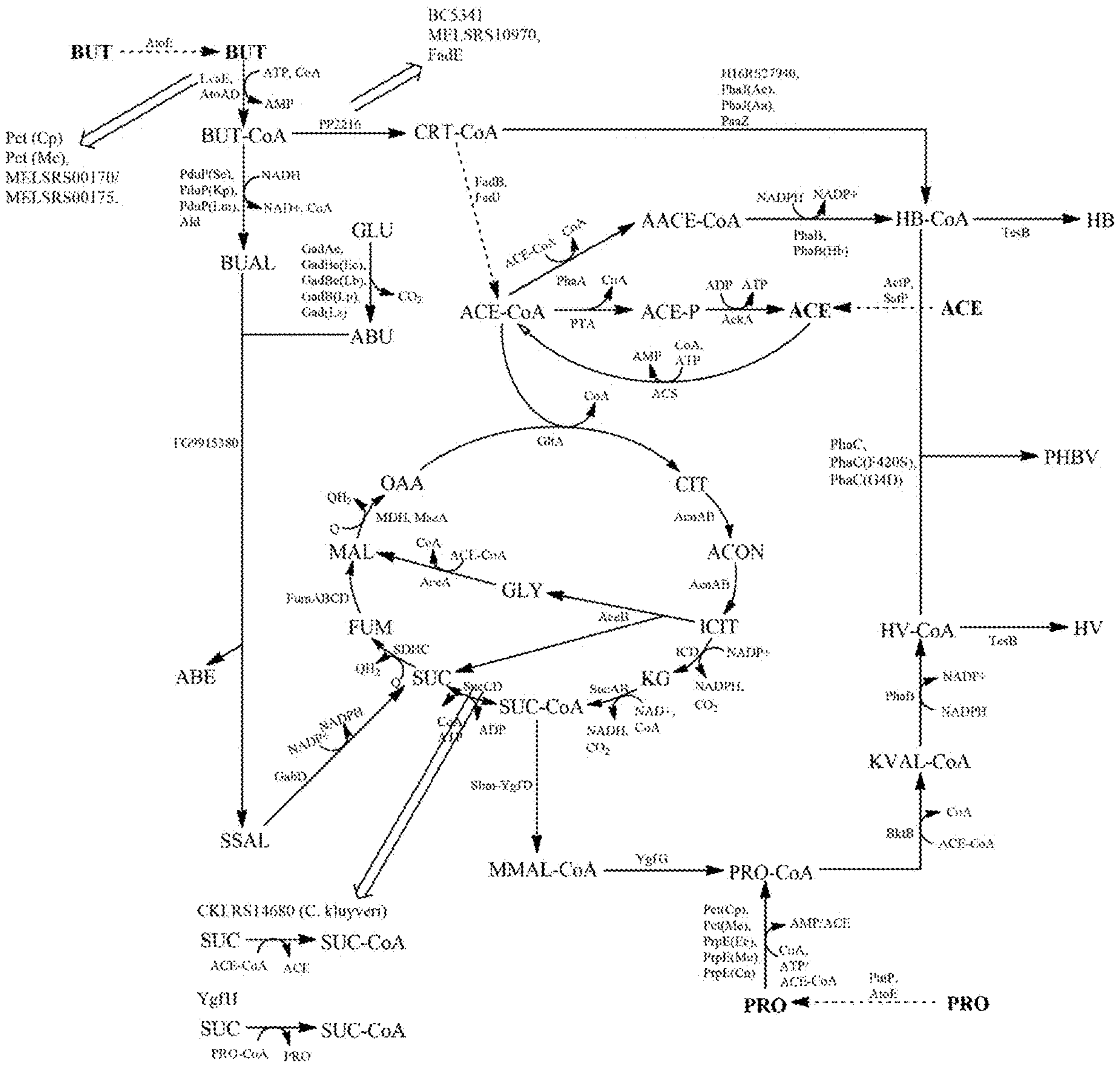
FIG. 1 shows metabolic pathways for the conversion of acetate, propionate, and butyrate to PHBV. ABU, 4-aminobutyrate; AACE-CoA, acetoacetyl-CoA; ACE, acetate; ACE-CoA, acetyl-CoA; ACE-P, acetylphosphate; ACON, aconitate; BUAL, butyraldehyde; BUT, butyrate; BUT-CoA, butyryl-CoA; CIT, citrate; CRT-CoA, crotonyl-CoA; FUM, fumarate; GLU, glutamate; GLY, glyoxylate; HB, 3-hydroxybutyrate; HB-CoA, (R)-3-hydroxybutyryl-CoA; HV, (R)-3-hydroxyvalerate; HV-CoA, (R)-3-hydroxyvaleryl-CoA; ICIT, isocitrate; KG, ketoglutarate; KVAL-CoA, ketovaleryl-CoA; MAL, malate; MMAL-CoA, L-methylmalonyl-CoA; OAA, oxaloacetate; PHBV, poly(3-hydroxybutyrate-co-3-hydroxyvalerate); PRO, propionate; PRO-CoA, propionyl-CoA; SSAL, succinate semialdehyde; SUC, succinate; SUC-CoA, succinyl-CoA.

Throughout the disclosure, a reference may be made using an abbreviation of a gene name or a polypeptide name, and it is understood that such an abbreviated gene or polypeptide name represents the genus of genes or polypeptides, respectively. Such gene names include all genes encoding the same polypeptide and homologous polypeptides having the same physiological function. Polypeptide names include all polypeptides that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A.

EC numbers are established by the Nomenclature Committee of the International Union of Biochemistry and Molecular Biology (NC-IUBMB). The EC numbers referenced herein are derived from the KEGG Ligand database, maintained by the Kyoto Encyclopedia of Genes and Genomics, sponsored in part by the University of Tokyo.

The term "recombinant", or a derivative thereof as used herein refers to a cell or a polynucleotide molecule that has been modified by the introduction of a heterologous polynucleotide sequence, or that the cell is derived from a cell so modified. For example, recombinant cells express genes that are not found in identical form within the native (non-recombinant) form of the cells, or the recombinant cells express, as a result of deliberate human intervention, native genes that are otherwise abnormally expressed, underexpressed or not expressed at all. The terms "recombination," "recombining," and generating a "recombined" polynucleotide molecule refer generally to the assembly of two or more polynucleotide fragments wherein the assembly gives rise to a chimeric polynucleotide made from the assembled parts.

The term "poly(3-hydroxybutyrate-co-3-hydroxyvalerate)", "PHBV", or "PHBV polymer", or a derivative thereof as used herein refers to a polyhydroxyalkanoate-type polymer that can be produced by bacteria through fermentation of a carbon source, for example, sugar, lipids, polyol, or fatty acids. PHBV is a copolymer of 3-hydroxybutyric acid (HB) and 3-hydroxyvaleric acid (HV; also known as 3-hydroxypentanoic acid). PHBV can have varying HB and HV content. PHBV is biocompatible, biodegradable, and non-toxic, and is useful in the production of bioplastics. The many useful features of PHBV include absorption capacity, low cytotoxicity, piezoelectricity, and thermoplasticity. PHBV has a broad range of applications, including biomaterial applications such as production of absorbable surgical sutures, drug release and delivery systems, medical packaging, and tissue engineering, e.g. biodegradable medical implants, biosensors, porous scaffolds, and tissue patches.

The term "acyl-CoA synthetase" as used herein refers to an enzyme which can catalyze the esterification, in some cases concomitant with transport, of fatty acids into metabolically active CoA thioesters for subsequent degradation or incorporation into phospholipids. Acyl-CoA synthetase enzymes can be categorized based on their specificity to short, medium, or long chain fatty acids. For example, short chain acyl-CoA synthetase catalyzes chemical reactions with fatty acid with fewer than 6 carbons. Medium chain acyl-CoA synthetase catalyzes chemical reactions with fatty acids with 6 to 12 carbons. Acyl-CoA synthetase includes, but is not limited to, fatty acid-CoA ligase. In embodiments, an acyl-CoA synthetase comprises an enzyme under the enzyme classification numbers EC 6.2.1.1, EC 6.2.1.2, EC 6.2.1.3, EC 6.2.1.17, or EC 6.2.1.40. Additionally, one of ordinary skill in the art will appreciate that some enzymes classified under a different enzyme class can have acyl-CoA synthetase activity as well. Such non-specific "acyl-CoA synthetase" are, therefore, also included in this definition. Nucleic acid sequences encoding acyl-CoA synthetase are known in the art, and such acyl-CoA synthetase are publicly available.

The term "acetate-CoA transferase" as used herein refers to an enzyme that can act upon a fatty acid substrate and an acetyl-CoA substrate to catalyze a reversible chemical reaction to produce acetate and a corresponding acyl-CoA. The enzyme can also act upon a VFA substrate and an acetyl-CoA substrate to produce a corresponding acyl-CoA and acetate. A person of ordinary skill in the art would readily understand that the enzyme is capable of catalyzing the reversible reaction in both forward and reverse directions. In embodiments, an acetate CoA transferase has broad substrate specificity for short-chain acyl-CoA thioesters with the activity decreasing when the length of the carboxylic acid chain exceeds four carbons. The enzyme includes, but is not limited to, short-chain acyl-CoA:acetate-CoA transferase. In embodiments, an acetate-CoA transferase is an enzyme under the enzyme classification number EC 2.8.3.8. The terms "acetate" and "acetic acid" are used interchangeably herein. Similarly, the use of any term which describes an organic acid likewise includes, and is used interchangeably with, the corresponding salt form of the organic acid. In embodiments, the acetate-CoA transferase comprises a first subunit, optionally a MELS_RS00170 polypeptide or an AtoA polypeptide, and a second subunit, optionally a MELS_RS00175 polypeptide or AtoD polypeptide. In embodiments, the acetate-CoA transferase comprises a MELS_RS00170 polypeptide and a MELS_RS00175 polypeptide. In embodiments, the acetate-CoA transferase comprises an AtoD polypeptide and an AtoA polypeptide.

The term "propionate-CoA transferase" as used herein refers to an enzyme that acts upon substrates acetyl-CoA and propionate. Propionate-CoA transferase catalyzes a chemical reaction with its substrates to produce acetate and propionyl-CoA. The enzyme can also include, but is not limited to, acetyl-CoA:propionate-CoA transferase, propionate-coenzyme A transferase, propionate-CoA:lactoyl-CoA transferase, propionyl-CoA:acetate-CoA transferase, or propionyl-CoA transferase. In embodiments, a propionate-CoA transferase comprises an enzyme under the enzyme classification number EC 2.8.3.1.

The term "β-ketothiolase" as used herein refers to an enzyme that acts upon substrates acetyl-CoA and acyl-CoA. β-ketothiolase catalyzes a chemical reaction to produce 3-oxoacyl-CoA and CoA. The enzyme can also include, but is not limited to, acetyl-CoA synthetase, acetyl-CoA acyltransferase, acyl-CoA ligase, 3-ketoacyl-CoA thiolase, or fatty acid oxidation complex subunit beta. In embodiments, a β-ketothiolase comprises an enzyme under the enzyme classification number EC 2.3.1.16.

The term "polyhydroxyalkanoate synthase" as used herein refers to an enzyme that acts upon substrates hydroxybutyryl-CoA and poly(hydroxybutyrate)$_n$. Polyhydroxyalkanoate synthase catalyzes a chemical reaction to produce poly(hydroxylalkanoate)$_{n+1}$ and CoA. The chemical reaction can yield hydroxylalkanoate polymers. The enzyme can also include, but is not limited to, poly(3-hydroxyalkanoate) polymerase, poly(3-hydroxybutyrate) polymerase, or polyhydroxyalkanoic acid synthase. In embodiments, a polyhydroxyalkanoate synthase comprises an enzyme under the enzyme classification number EC 2.3.1. In embodiments, a polyhydroxyalkanoate synthase comprises short-chain polyhydroxyalkanoate synthase. In embodiments, a polyhydroxyalkanoate synthase polymerizes (R)-HB-CoA and (R)-HV-CoA to produce PHBV.

The term "methylmalonyl-CoA mutase" as used herein refers to an enzyme that catalyzes interconversion of succinyl-CoA and methylmalonyl-CoA. In embodiments, methylmalonyl-CoA mutase comprises an enzyme under the enzyme classification number EC 5.4.99.2.

The term "methylmalonyl-CoA mutase interacting protein", or a derivative thereof as used herein refers to a protein that interacts with methylmalonyl-CoA mutase and is a member of the G3E family of P-loop GTPases. In embodiments, a methylmalonyl-CoA mutase interacting protein comprises methylmalonyl-CoA mutase-interacting GTPase. The enzyme can also include, but is not limited to, GTPase ArgK, G-protein chaperone, or YgfD protein. In embodiments, a methylmalonyl-CoA mutase interacting protein comprises an enzyme under the enzyme classification number EC 3.6.5.

The term "methylmalonyl-CoA decarboxylase" as used herein refers to an enzyme that acts upon substrate methylmalonyl-CoA and catalyzes decarboxylation of methylmalonyl-CoA into propionyl-CoA. The enzyme can also include, but is not limited to, transcarboxylase. In embodiments, a methylmalonyl-CoA decarboxylase comprises an enzyme under the enzyme classification number EC 4.1.1.

The term "propionyl-CoA:succinate CoA transferase" as used herein refers to an enzyme that acts upon substrates propionyl-CoA and succinate. The enzyme catalyzes the transfer of CoA from propionyl-CoA to succinate. The enzyme produces the products propionate and succinyl-CoA. In embodiments, a propionyl-CoA:succinate CoA transferase comprises an enzyme under the enzyme classification number EC 2.8.3. In embodiments, the bacterial host cell shows reduced or eliminated expression and/or activity, of propionyl-CoA:succinate CoA transferase.

The expression "at least one recombinant nucleic acid molecule encoding a polypeptide that catalyzes the conversion of butyryl-CoA to succinate", or a derivative thereof as used herein refers to an enzymatic pathway that starts with butyryl-CoA as a substrate and through at least one enzyme produces the product succinate. This pathway may involve the production of intermediates such as butyraldehyde and succinate semialdehyde. In embodiments, the pathway for conversion of butyrl-CoA to succinate comprises enzymes CoA-dependent propanal dehydrogenase, optionally PduP, β-alanine transaminase, optionally KES23458, and NADP+-dependent succinate semialdehyde dehydrogenase, optionally GabD.

The term "CoA-dependent propanal dehydrogenase" or "CoA-dependent propionaldehyde dehydrogenase" as used herein refers to an enzyme that reversibly converts 1-propanal (propionaldehyde) to propionyl-CoA (propionyl-CoA). In some instances, CoA-dependent propanal dehydrogenase enzymes, for example PduP, may have preferences for substrates with 2-4 or 2-6 carbons, and are able to reversibly convert butyryl-CoA to butyraldehyde. In some instances, CoA-dependent propanal dehydrogenase enzymes may have specificity for aldehydes containing 4 carbons. In embodiments, a CoA-dependent propanal dehydrogenase comprises an enzyme under the enzyme classification number EC 1.2.1.10.

The term "CoA-acylating aldehyde dehydrogenase" as used herein refers to an enzyme that can convert acetyl-CoA and butyryl-CoA to the corresponding aldehydes. In some instances, CoA-acylating aldehyde dehydrogenase enzymes may have preferences for substrates with 2-4 or 2-6 carbons, and are able to convert butyryl-CoA to butyraldehyde. In embodiments, a CoA-acylating aldehyde dehydrogenase comprises an enzyme under the enzyme classification number EC 1.2.1.27.

The term "β-alanine transaminase" as used herein refers to an enzyme that acts upon substrates β-alanine and pyruvate. β-alanine transaminase catalyzes a chemical reaction to produce 3-oxopropionate and L-alanine. The enzyme can also include, but is not limited to, β-alanine:pyruvate aminotransferase, β-alanine:pyruvate transaminase, Ω-amino acid aminotransferase, or Ω-amino acid:pyruvate aminotransferase. In embodiments, a β-alanine transaminase comprises an enzyme under the enzyme classification number EC 2.6.1.18.

The term "NADP+-dependent succinate semialdehyde dehydrogenase", or a derivative thereof as used herein refers to an enzyme that acts upon substrates $NADP^+$, $H_2O$, and succinate semialdehyde. NADP+-dependent succinate semialdehyde dehydrogenase catalyzes a chemical reaction to produce succinate, NADPH and two $H^+$ ions. The enzyme can include, but is not limited to, succinic semialdehyde dehydrogenase (NADP+), succinyl semialdehyde dehydrogenase (NADP+), succinate semialdehyde:NADP+ oxidoreductase, or NADP-dependent succinate-semialdehyde dehydrogenase. In embodiments, a NADP+-dependent succinate semialdehyde dehydrogenase is an enzyme under the enzyme classification number EC 1.2.1.79.

The expression "at least one recombinant nucleic acid molecule encoding a polypeptide that catalyzes the conversion of butyryl-CoA to 3-hydroxybutyryl-CoA", or a derivative thereof as used herein refers to an enzymatic pathway that starts with butyryl-CoA as a substrate and through at least one enzyme produces the product 3-hydroxybutyryl-CoA. This pathway may involve the production of intermediates such as, for example, crotonyl-CoA. In embodiments, the pathway for conversion of butyryl-CoA to 3-hydroxybutyryl-CoA comprises enzymes acyl-CoA dehydrogenase, optionally a short-chain acyl-CoA dehydrogenase, optionally at least one of PP_2216, BC_5341, MELS_RS10970, and FadE, and an enoyl-CoA hydratase/isomerase, optionally at least one of H16_RS27940, PhaJ, and PaaZ.

The term "acyl-CoA dehydrogenase", or a derivative thereof as used herein refers to an enzyme that catalyzes the dehydrogenation of acyl-coenzymes A (acyl-CoAs) to 2-enoyl-CoAs. Acyl-CoA dehydrogenase enzymes can be categorized based on their specificity to short, medium, or long chain fatty acids. For example, short-chain acyl-CoA dehydrogenase catalyzes fatty acid oxidation of acyl-CoAs with 4-6 carbons. In embodiments, an acyl-CoA dehydrogenase comprises an enzyme under the enzyme classification number EC 1.3.8.7 or EC 1.3.8.8. Additionally, one of ordinary skill in the art will appreciate that some enzymes classified under a different enzyme class can have acyl-CoA dehydrogenase activity as well. Such non-specific "acyl-CoA dehydrogenase" are, therefore, also included in this definition. Nucleic acid sequences encoding acyl-CoA dehydrogenase are known in the art, and such acyl-CoA dehydrogenase are publicly available.

The term "enoyl-CoA hydratase/isomerase", or a derivative thereof as used herein refers to an enzyme that acts upon substrates hydroxyacyl-CoA and $NAD^+$. The enzyme catalyzes a chemical reaction to produce 3-oxoacyl-CoA, NADH, and a $H^+$ ion. The enzyme can also include, but is not limited to, fatty acid oxidation complex subunit-α, enoyl-CoA hydratase, delta-(2)-trans-enoyl-CoA isomerase, 2-hydroxybutyryl-CoA epimerase, or 3-hydroxyacyl-CoA dehydrogenase. In embodiments, an enoyl-CoA hydratase/isomerase is an enzyme under the enzyme classification number EC 4.2.1.17, EC 5.1.2.3, EC 5.3.3.8, EC 1.1.1.35, EC 3.3.2.12 or EC 1.12.1.91.

The term "propionyl-CoA synthetase" as used herein refers to an enzyme that catalyzes the synthesis of propionyl-CoA from propionate and CoA, using ATP. Propionyl-CoA synthetase can also include, but is not limited to, propionate-CoA ligase. In embodiments, a propionyl-CoA synthetase is an enzyme under the enzyme classification number EC 6.2.1.17.

The term "glutamate decarboxylase" as used herein refers to an enzyme that catalyzes a chemical reaction to convert L-glutamate into gamma-aminobutyrate (GABA). The chemical reaction consumes an $H^+$ ion and produces $CO_2$. Glutamate decarboxylase can also include, but is not limited to, glutamate decarboxylase-α or glutamate decarboxylase-β. In embodiments, a glutamate decarboxylase comprises an enzyme under the enzyme classification number EC 4.1.1.15.

The term "succinyl-CoA transferase" as used herein refers to an enzyme that acts upon substrates succinate and 3-oxoacyl-CoA. The enzyme catalyzes a chemical reaction to produce succinyl-CoA and 3-oxo acid. Succinyl-CoA transferase can include, but is not limited to, 3-oxoacid coenzyme A-transferase, 3-ketoacid CoA-transferase, 3-ketoacid coenzyme A transferase, 3-oxo-CoA transferase, 3-oxoacid CoA dehydrogenase, acetoacetate succinyl-CoA transferase, acetoacetyl coenzyme A-succinic thiophorase, succinyl coenzyme A-acetoacetyl coenzyme A-transferase, or succinyl-CoA transferase. In embodiments, a succinyl-CoA transferase comprises an enzyme under the enzyme classification number EC 2.8.3.5.

The term "succinyl-CoA synthetase" as used herein refers to an enzyme that acts upon substrates succinate and CoA. The enzyme catalyzes a chemical reaction which consumes ATP to produce succinyl-CoA and ADP. The enzyme can also include, but is not limited to, a succinate-CoA ligase. In embodiments, succinyl-CoA synthetase comprises an enzyme under the enzyme classification number EC 6.2.1.5. In embodiments, the succinyl-CoA synthetase comprises a first subunit, optionally a SucC polypeptide, and a second subunit optionally a SucD polypeptide. In embodiments, the succinyl-CoA synthetase comprises a SucC polypeptide and a SucD polypeptide.

The term "glutamate dehydrogenase" as used herein refers to an enzyme that catalyzes the reversible conversion of ketoglutarate to glutamate, such as L-glutamate. In embodiments, the glutamate dehydrogenase comprises an enzyme under the enzyme classification number EC 1.4.1.4. In embodiments, the glutamate dehydrogenase is GdhA.

The term "attenuate", or a derivative thereof as used here means to weaken, reduce or diminish. In one example, the sensitivity of a particular enzyme to feedback inhibition or inhibition caused by a composition that is not a product or a reactant (non-pathway specific feedback) is reduced such that the enzyme activity is not impacted by the presence of a compound. In a particular example, an enzyme that has been modified to be less active can be referred to as attenuated. A functional modification of the sequence encoding an enzyme can be used to attenuate expression of an enzyme. Sequence modifications may include, for example, a mutation, deletion, or insertion of one or more nucleotides in a gene sequence or a sequence controlling the transcription or translation of a gene sequence, which modification results in a reduction or inhibition of production of the gene product, or renders the gene product non-functional. In some examples, a functional deletion is described as a knock-out mutation. Other methods are available for attenuating expression of an enzyme. For example, attenuation can be accomplished by modifying the sequence encoding any gene described herein, e.g. by mutation, placing the gene under the control of a less active promoter, expressing interfering RNAs, ribozymes, clustered regularly interspaced short palindromic repeats (CRISPR)-mediated transcriptional interference, or antisense sequences that target the gene of interest, and/or by changing the physical or chemical environment, such as temperature, pH, or solute concentration, such that the optimal activity of the gene or gene product is not realized. The skill person will appreciate that such attenuation effects can be achieved through any other techniques known in the art.

The term "homologous genes", or a derivative thereof as used herein refers to a pair of genes from different but related species, which correspond to each other and which are identical or similar to each other. The term encompasses genes that are separated by the speciation process during the development of new species (e.g., orthologous genes), as well as genes that have been separated by genetic duplication (e.g., paralogous genes). Homologous polypeptides are polypeptides that are encoded by these homologous genes, and/or polypeptides having the same physiological function. The term "homolog", or a derivative thereof as used herein refers to a homologous protein and to the gene encoding it.

The term "operably linked", or a derivative thereof as used herein in the context of a polynucleotide sequence, refers to an arrangement of two or more components, wherein the components so described are in a relationship permitting them to function in a coordinated manner, for instance, the placement of one polynucleotide sequence into a functional relationship with another polynucleotide sequence. For example, a transcriptional regulatory sequence or a promoter is operably linked to a coding sequence if the transcriptional regulatory sequence or promoter facilitates aspects of the transcription of the coding sequence. A ribosome binding site is operably linked to a coding sequence if it is positioned so as to facilitate translation. Aspects of the transcription process include, but not limited to, initiation, elongation, attenuation and termination. In general, an operably linked transcriptional regulatory sequence joined in cis with the coding sequence, but it is not necessarily directly adjacent to it, and the polynucleotide sequences being linked are contiguous and in the same reading frame.

The term "operon region" as used herein refers to a group of contiguous genes that are transcribed as a single transcription unit from a common promoter, and are thereby subject to co-regulation. In other words, an operon comprises a common promoter is operably linked to the group of contiguous genes in the operon. In embodiments, the operon comprises a regulator segment.

The term "orthologs" or "orthologous genes", or a derivative thereof as used herein refers to genes in different species that have evolved from a common ancestral gene by speciation. Typically, orthologs retain the same function during the course of evolution. Identification of orthologs finds use in the reliable prediction of gene function in genomes of different species.

A "promoter" as used herein refers to a polynucleotide sequence that functions to direct transcription of a downstream gene. In embodiments, the promoter is appropriate to a host cell, such as a bacterial cell, in which the target gene is being expressed. The promoter, together with other transcriptional and translational regulatory polynucleotide sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The term "regulatory segment", "regulatory sequence", or "expression control sequence", or a derivative thereof as used herein refers to a polynucleotide sequence that is operatively linked with another polynucleotide sequence that encodes the amino acid sequence of a polypeptide chain to effect the expression of that encoded amino acid sequence. The regulatory sequence can inhibit, repress, promote, or drive the expression of the operably linked polynucleotide sequence encoding the amino acid sequence.

The terms "proportional yield" and "percentage yield" are used interchangeably herein referring to the amount of a desired product in relation to other products that are within the same mixture produced by a recombinant bacterial cell of the present disclosure. For example, the proportional yield of a desired product can be improved such that it is more predominant over the other components in the product mixture to reduce the burden of purification. In another example, the proportional yield of an undesired product (i.e. a component that will need to be removed from the desired product) can be reduced such that it is less predominant over the desired component in the product mixture to achieve the same end.

The term "substitution", or a derivative thereof as used herein means replacing an amino acid in the sequence of a precursor polypeptide with another amino acid at a particular position, resulting in a mutant of the precursor polypeptide. The amino acid used as a substitute can be a naturally-occurring amino acid, or can be a synthetic or non naturally-occurring amino acid.

The term "surfactants" as used herein refers to substances that are capable of reducing the surface tension of a liquid in which they are dissolved. Surfactants are typically composed of a water-soluble head and a hydrocarbon chain or tail. The water-soluble head is hydrophilic and can be either ionic or nonionic, whereas the hydrocarbon chain is hydrophobic. Surfactants are used in a variety of products, including detergents and cleaners, and in chemical processes. Surfactants can be used to aid in the extraction and isolation of biopolymers such as those described herein. There are four types of surfactants: anionic surfactants, cationic surfactants, amphoteric surfactants, and non-ionic surfactants, any of which may be used for extraction and isolation of biopolymers, and/or treatment of biopolymers.

The term "wild-type" as used herein means, in the context of gene or protein, a polynucleotide or protein sequence that occurs in nature. In embodiments, the wild-type sequence refers to a sequence of interest that is a starting point for recombinant protein engineering.

The term "volatile fatty acid" or "VFA", or a derivative thereof as used herein refers to fatty acids with less than six carbon atoms. For example, VFA includes, but not limited to formic acid, acetic acid, propionic acid, butyric acid, isobutyric acid, valeric acid, and isovaleric acid. The VFA and salt thereof described herein are useful energy and carbon source, and as source materials to be converted to PHBV by bacteria. In embodiments, the carbon or energy source comprises at least one VFA. In embodiments, the at least one VFA comprises at least one of acetic acid, propionic acid, and butyric acid.

The term "biomass" refers to an organic or biological material that can be converted into an energy source. One exemplary source of biomass is plant matter. For example, corn, sugar cane, and switchgrass can be used as biomass. Another non-limiting example of biomass is animal matter, for example cow manure. Biomass also includes waste products from industry, agriculture, forestry, food, perennial grasses, and households. Examples of such waste products which can be used as biomass are fermentation waste, straw, lumber, sewage, garbage and food leftovers. Biomass also includes sources of carbon, such as carbohydrates (e.g., sugars). In embodiments, the biomass comprises pretreated biomass. Biomass may be pretreated by methods including, but not limited to, mechanical chipping, shredding, grinding. Methods of pretreating biomass can also include methods of biological degradation of lignin, hemicellulose, and polyphenols via fungi or chemical treatments with acids, alkali, organic solvents, and ionic liquids to increase internal surface area, and decrease degree of polymerization and crystallinity. In embodiments, physiochemical methods such as steam and other forms of heat can also be used to pretreat biomass. Methods of pretreating biomass produces pretreated biomass.

The term "carbon source" refers to a nutrient (such as sugar) that provides carbon needed for cellular respiration, cellular combustion, and/or synthesis of new organic molecules. A volatile fatty acid is useful as a carbon source for a recombinant bacterial cell described herein. In embodiments, at least one carbon source comprises at least one volatile fatty acid.

The term "granule", or a derivative thereof as used herein relating to PHBV refers to the form of PHBV accumulated inside bacteria. PHBV is stored inside bacteria as discrete water-insoluble intracellular granules. PHBV granules can be extracted from bacteria by the methods described herein.

The term "mmol/L", or a derivative thereof as used herein refers to a measure of the concentration of a solute in a solution in the unit of mmol of the solute per litre solution.

The term "Cmmol/L", or a derivative thereof as used herein refers to a measure of the concentration of a solute in a solution in the unit of mmol of carbon per litre solution.

The term "VFA mmol/L", or a derivative thereof as used herein refers to a measure of the concentration of total VFA in a solution in the unit of mmol of VFA per litre solution.

The term "mol %", or a derivative thereof as used herein when relating to HV content in PHBV refers to a measure of molar percentage of HV in PHBV. For example, PHBV can have a HV content of 0-5 mol %, 5-10 mol %, 10-20 mol %, 20-50 mol %, 1-20 mol %, 1-30 mol %, 1-40 mol %, or 1-50 mol %, 1-60 mol %, 1-70 mol %, or 1-80 mol %.

The phrase "substantially free", or a derivative thereof as used herein is used to refer to the complete or near complete lack of an action, characteristic, property, state, structure, item, or result. For example, a medium or a composition that is "substantially free of" glycerol would either completely lack glycerol, or so nearly completely lack glycerol that the effect would be the same as if it completely lacked glycerol. In other words, a composition that is "substantially free of" an element may still actually contain such item as long as there is no measurable effect thereof. For example, a medium or a composition that is substantially free of an ingredient or element comprises less than about 1% by wt or less than about 1% vol/vol of the ingredient or element in the composition.

The term (w/v), or a derivative thereof as used herein refers to a measure of the concentration of a solution or mixture obtained by dividing the mass or weight of the solute by the volume of the solution or mixture.

The term (w/w), or a derivative thereof as used herein refers to a measure of the concentration of a solution or mixture obtained by dividing the mass or weight of the solute by the weight of the solution or mixture.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", or a derivative thereof as used herein, is intended to specify the presence of the stated features, elements, components, groups, integers, and/or steps as well as those that do not materially affect the basic and novel characteristic(s) of features, elements, components, groups, integers, and/or steps. Finally, terms of degree such as "substantially", "about" and "approximately", or a derivative thereof as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. It should also be noted that the term "or" is generally employed in its sense including "and/or" unless the content clearly dictates otherwise.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

As used herein, the term "polypeptide" as used herein encompasses both peptides and proteins, unless indicated otherwise. The 3-letter code as well as the 1-letter code for amino acid residues as defined in conformity with the IUPAC-IUB Joint Commission on Biochemical Nomenclature (JCBN) is used throughout this disclosure. It is also understood that a polypeptide may be coded for by more than one polynucleotide sequence due to the degeneracy of the genetic code. An enzyme is a protein that is also a biocatalyst, which accelerate chemical reactions. It is understood that the enzymes described herein, unless otherwise stated, have substrate specificities and enzymatic activity (e.g. catalytic rate) with respect to their substrates. For example, an acyl-CoA synthetase polypeptide has acyl-CoA synthetase activity.

The term "nucleic acid molecule" or its derivatives thereof as used herein, is intended to include unmodified DNA or RNA or modified DNA or RNA. For example, the nucleic acid molecules of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

As used herein "sequence identity" refers to the extent to which two optimally aligned polynucleotides or polypeptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. The extent of identity (homology) between two sequences can be ascertained using a computer program and mathematical algorithm. Percentage identity can be calculated using the alignment program Clustal Omega, available at www.ebi.ac.uk/Tools/msa/clustalo using default parameters. See, Sievers et al., "Fast, scalable generation of high-quality protein multiple sequence alignments using Clustal Omega." (2011 Oct. 11) Molecular systems biology 7:539. For the purposes of calculating identity to a sequence, extensions such as tags are not included.

The term "plasmid", "vector", or "construct" as used herein refers to a circular double-stranded (ds) DNA construct used as a cloning vector, and which forms an extra-chromosomal self-replicating genetic element in some microorganism such as bacteria, or integrates into the host chromosome. The plasmid can be part of an expression system. The plasmid is useful for creating a recombinant bacterial cell, for example, that produces polypeptides which catalyze the synthesis of a biopolymer, including PHBV described herein.

The terms "expression" or "express" refers to the production of mRNA from the polynucleotide sequence of a gene or portion of a gene. The production of any polypeptide which is encoded by the mRNA, gene, or portion of the gene is also included within the scope of the terms.

The term "encoding" refers to the property of polynucleotide sequences to behave as templates for the production of other macromolecules such as mRNA, polypeptides, and cDNA.

The term "host strain" or "host cell" refers to a suitable host for an expression vector or genomically-integrated expression cassette comprising polynucleotide of the present disclosure.

A "segment" of a nucleotide sequence is a sequence of contiguous nucleotides. A segment can be at least about 5, 10, 15, 20, 25, 30, 35, 40, 45, 50, 60, 75, 85, 100, 110, 120, 130, 145, 150, 160, 175, 200, 250, 300, 350, 400, 450, 500 or more contiguous nucleotides.

The definitions and embodiments described in particular sections are intended to be applicable to other embodiments herein described for which they are suitable as would be understood by a person skilled in the art.

Recombinant Bacterial Host Cells

The disclosure provides bacterial host cells, comprising one or more of the following nucleic acid molecules: (a) a nucleic acid molecule encoding a PhaC protein, (b) a nucleic acid molecule encoding a PhaB protein, (c) a nucleic acid molecule encoding a PhaA protein, and (d) a nucleic acid molecule encoding a BktB protein. In embodiments, the bacterial host cells disclosed herein comprise more than one copy (for example, two copies, three copies, 4 hours copies, or 5 or more copies) of the nucleic acid molecule encoding a PhaC protein.

In embodiments, the bacterial host cell comprises an activated sleeping beauty mutase (Sbm) pathway. Further details are provided in Miscevic D et al., *Applied Microbiology and Biotechnology* 2021, 105:1435-1446, and Srirangan K et al., *Scientific Reports* 2016, 6:36470, the contents of each of which are incorporated herein by reference in their entireties for all purposes. In embodiments, the bacterial host cell comprises a sleeping beauty mutase (Sbm) operon comprising a promoter. In embodiments, the bacterial host cell comprises a sleeping beauty mutase (Sbm) operon comprising a $P_{trc}$ promoter. In embodiments, the $P_{trc}$ promoter comprises a nucleic acid sequence having at least 95% (for example, about 96%, about 97%, about 98%, about 99% or about 100%) identity to SEQ ID NO: 254. In embodiments, the $P_{trc}$ promoter comprises the nucleic acid sequence of SEQ ID NO: 254. In embodiments, the $P_{trc}$ promoter consists of the nucleic acid sequence of SEQ ID NO: 254.

In embodiments, one or more of the PhaA protein, the PhaB protein, the PhaC protein and the BktB protein are catalytically active at a temperature in the range of about 30° C. to about 50° C. In embodiments, each of the PhaA protein, the PhaB protein, the PhaC protein and the BktB protein are catalytically active at a temperature in the range of about 30° C. to about 50° C. In embodiments, each of the PhaA protein, the PhaB protein, the PhaC protein and the BktB protein are catalytically active at a temperature in the range of about 37° C. to about 50° C.

In embodiments, the PhaA protein is a *Cupriavidus* sp. S-6 PhaA protein, a *Cupriavidus gilardii* QJ1 PhaA protein, or a *Cupriavidus necator* PhaA protein. In embodiments, the PhaA protein comprises an amino acid sequence having at least 80% (for example, about 85%, about 90%, about 95%, about 96%, about 97%, about 98%, about 99%, or 100%) identity to SEQ ID NO: 241. In embodiments, the PhaA protein comprises an amino acid sequence having at least 90% identity to SEQ ID NO: 241. In embodiments, the PhaA protein comprises or consists of the amino acid sequence of SEQ ID NO: 241. Further details are provided in Sheu D-S et al., *Journal of bacteriology* 2012, 194:2620-2629, the contents of which are incorporated herein by reference in its entirety for all purposes.

In embodiments, the nucleic acid molecule encoding a PhaA protein comprises a nucleic acid sequence having at least 80% (for example, about 85%, about 90%, about 95%, about 96%, about 97%, about 98%, about 99%, or 100%) identity to SEQ ID NO: 248. In embodiments, the nucleic acid molecule encoding a PhaA protein comprises a nucleic acid sequence having at least 80% identity to SEQ ID NO: 248. In embodiments, the nucleic acid molecule encoding a PhaA protein comprises or consists of the nucleic acid sequence of SEQ ID NO: 248.

In embodiments, the PhaB protein is a *Cupriavidus* sp. S-6 PhaB protein, a *Cupriavidus gilardii* QJ1 PhaB protein, or a *Cupriavidus necator* PhaB protein. In embodiments, the PhaB protein comprises an amino acid sequence having at least 80% (for example, about 85%, about 90%, about 95%, about 96%, about 97%, about 98%, about 99%, or 100%) identity to SEQ ID NO: 242. In embodiments, the PhaB protein comprises an amino acid sequence having at least 90% identity to SEQ ID NO: 242. In embodiments, the PhaB protein comprises or consists of the amino acid sequence of SEQ ID NO: 242.

In embodiments, the nucleic acid molecule encoding a PhaB protein comprises a nucleic acid sequence having at least 80% (for example, about 85%, about 90%, about 95%, about 96%, about 97%, about 98%, about 99%, or 100%) identity to SEQ ID NO: 249. In embodiments, the nucleic acid molecule encoding a PhaB protein comprises a nucleic acid sequence having at least 80% identity to SEQ ID NO: 249. In embodiments, the nucleic acid molecule encoding a PhaB protein comprises or consists of the nucleic acid sequence of SEQ ID NO: 249.

In embodiments, the PhaC protein is a *Cupriavidus* sp. S-6 PhaC protein, a *Cupriavidus gilardii* QJ1 PhaC protein, or a *Cupriavidus necator* PhaC protein. In embodiments, the PhaC protein comprises an amino acid sequence having at least 80% (for example, about 85%, about 90%, about 95%, about 96%, about 97%, about 98%, about 99%, or 100%) identity to SEQ ID NO: 243. In embodiments, the PhaC protein comprises an amino acid sequence having at least 90% identity to SEQ ID NO: 243. In embodiments, the PhaC protein comprises or consists of the amino acid sequence of SEQ ID NO: 243.

In embodiments, the nucleic acid molecule encoding a PhaC protein comprises a nucleic acid sequence having at least 80% (for example, about 85%, about 90%, about 95%, about 96%, about 97%, about 98%, about 99%, or 100%) identity to SEQ ID NO: 250. In embodiments, the nucleic acid molecule encoding a PhaC protein comprises a nucleic acid sequence having at least 80% identity to SEQ ID NO: 250. In embodiments, the nucleic acid molecule encoding a PhaC protein comprises or consists of the nucleic acid sequence of SEQ ID NO: 250.

In embodiments, the BtkB protein is a *Cupriavidus* sp. S-6 BtkB protein, a *Cupriavidus gilardii* QJ1 BtkB protein, or a *Cupriavidus necator* BtkB protein. In embodiments, the BtkB protein comprises an amino acid sequence having at least 80% (for example, about 85%, about 90%, about 95%, about 96%, about 97%, about 98%, about 99%, or 100%) identity to SEQ ID NO: 245. In embodiments, the BtkB protein comprises an amino acid sequence having at least 90% identity to SEQ ID NO: 245. In embodiments, the BtkB protein comprises or consists of the amino acid sequence of SEQ ID NO: 245.

In embodiments, the nucleic acid molecule encoding a BtkB protein comprises a nucleic acid sequence having at least 80% (for example, about 85%, about 90%, about 95%, about 96%, about 97%, about 98%, about 99%, or 100%) identity to SEQ ID NO: 251. In embodiments, the nucleic acid molecule encoding a BtkB protein comprises a nucleic acid sequence having at least 80% identity to SEQ ID NO: 251. In embodiments, the nucleic acid molecule encoding a BtkB protein comprises or consists of the nucleic acid sequence of SEQ ID NO: 251.

In embodiments, the bacterial host cell comprises: a first operon, comprising: (a) a nucleic acid molecule encoding a PhaC protein, (b) a nucleic acid molecule encoding a PhaB protein, and (c) a nucleic acid molecule encoding a PhaA protein. In embodiments, the bacterial host cell comprises: a second operon comprising: (i) a nucleic acid molecule encoding a BktB protein and (ii) a nucleic acid molecule encoding a PhaB protein. In embodiments, the bacterial host cell comprises: a first operon, comprising: (a) a nucleic acid molecule encoding a PhaC protein, (b) a nucleic acid molecule encoding a PhaB protein, (c) a nucleic acid molecule encoding a PhaA protein; and a second operon comprising: (i) a nucleic acid molecule encoding a BktB protein and (ii) a nucleic acid molecule encoding a PhaB protein.

In embodiments, the first and/or second operons comprise a promoter operably linked to the genes in the first and/or the second operons. In embodiments, the promoter comprises the nucleic acid sequence of SEQ ID NO: 233 ($P_{gracmax2}$) or the nucleic acid sequence of SEQ ID NO: 254 ($P_{trc}$). In embodiments of the first operon, the nucleic acid molecule encoding the PhaC protein is operably linked to a promoter. In embodiments, the first operon comprises the following nucleic acid molecules in the order (i) through (iii): (i) a nucleic acid molecule encoding a PhaC protein, (ii) a nucleic acid molecule encoding a PhaA protein, and (iii) a nucleic acid molecule encoding a PhaB protein.

The disclosure further provides bacterial host cells, comprising: a first operon comprising: (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, and (c) a nucleic acid molecule encoding a PhaB protein, wherein the PhaB protein is a *Cupriavidus* sp. S-6 PhaB protein; a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein; and a sleeping beauty mutase (Sbm) operon comprising a promoter. In embodiments, each of the first and the second operons comprises the promoter comprising the nucleic acid sequence of SEQ ID NO: 233 ($P_{gracmax2}$).

The disclosure further provides bacterial host cells, comprising: a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, (c) a nucleic acid molecule encoding a PhaB protein, wherein the nucleic acid molecule comprises a sequence having at least 90% identity to SEQ ID NO: 249, and; a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249; and a sleeping beauty mutase (Sbm) operon comprises a promoter that is operably linked to the genes in the Sbm operon. In embodiments, each of the first and the second operons comprises a promoter comprising the nucleic acid sequence of SEQ ID NO: 233 ($P_{gracmax2}$).

In embodiments, the bacterial host cells disclosed herein are capable of converting glycerol to poly(3-hydroxybutyrate-co-3-hydroxyvalerate) or PHBV. In embodiments, the bacterial host cell is capable of converting glycerol into poly(3-hydroxybutyrate-co-3-hydroxyvalerate) or PHBV at a temperature in the range of about 30° C. to about 50° C. In embodiments, the bacterial host cells disclosed herein are capable of converting glycerol to poly(3-hydroxybutyrate-co-3-hydroxyvalerate) or PHBV with a weight average molecular weight (Mw) of about 0.5 MDa to about 2.0 MDa, for example, about 0.6 MDa, about 0.7 MDa, about 0.8 MDa, about 0.9 MDa, about 1 MDa, about 1.1 MDa, about 1.2 MDa, about 1.3 MDa, about 1.4 MDa, about 1.5 MDa, about 1.6 MDa, about 1.7 MDa, about 1.8 MDa, about 1.9 MDa or about 2 MDa, including all subranges and values that lie therebetween. In embodiments, the bacterial host cells disclosed herein are capable of converting glycerol to poly(3-hydroxybutyrate-co-3-hydroxyvalerate) or PHBV with a weight average molecular weight (Mw) of about 1 MDa to about 1.5 MDa.

In embodiments, the bacterial host cell exhibits reduced or eliminated succinate dehydrogenase (sdhA) function. In embodiments, the bacterial host cell comprises a nucleic acid molecule encoding a fusion protein, comprising sdhA and a protease degradation tag, wherein the expression of the fusion protein is regulated by a EsaR quorum sensing system. Further details are provided in Gupta A et al., *Nature biotechnology* 2017, 35:273-279 and Shong J et al., *ACS chemical biology* 2013, 8:789-795, the contents of each of which are incorporated herein by reference in their entireties for all purposes.

In embodiments, the bacterial host cell comprises a nucleic acid molecule encoding sulA, wherein the nucleic acid molecule is operably linked to an inducible promoter. In embodiments, the inducible promoter is a temperature-inducible promoter. Further details are provided in Zhang X-C et al., *Metabolic Engineering* 2018, 45:32-42, and Jechlinger W, et al., *Journal of biotechnology* 2005, 116:11-20, the contents of each of which are incorporated herein by reference in its entirety for all purposes.

In embodiments, the bacterial host cell comprises one or more of the following: (a) a nucleic acid molecule encoding a LvaE protein, (b) a nucleic acid molecule encoding a propionate-CoA transferase, (c) a nucleic acid molecule encoding a FadE protein, (d) a nucleic acid molecule encoding a FadB protein, and (e) a nucleic acid molecule encoding a AtoB protein. In embodiments, the bacterial host cell comprises: a third operon, comprising: (a) a nucleic acid molecule encoding a FadE protein, and (b) a nucleic acid molecule encoding a FadB protein.

In embodiments, the bacterial host cell comprises: a third operon, comprising: (a) a nucleic acid molecule encoding a FadE protein, (b) a nucleic acid molecule encoding a FadB protein, and (c) a nucleic acid molecule encoding a AtoB protein. In embodiments, the bacterial host cell comprises: a fourth operon, comprising: (a) a nucleic acid molecule encoding a LvaE protein, and (b) a nucleic acid molecule encoding a propionate-CoA transferase. In embodiments, the FadE protein, the FadB protein and/or the AtoB protein are expressed in *Escherichia coli* str. K-12 substr. MG1655.

In some embodiments, the bacterial host cell has reduced or eliminated activity of the AtoB protein. In some embodiments, the heterologous and/or the endogenous nucleic acid sequences that encode the AtoB protein in the bacterial host cell are inactivated and/or deleted.

In embodiments, the bacterial host cell comprises: a third operon, comprising: (a) a nucleic acid molecule encoding a FadE protein, and (b) a nucleic acid molecule encoding a FadB protein; and a fourth operon, comprising: (a) a nucleic acid molecule encoding a LvaE protein, and (b) a nucleic acid molecule encoding a propionate-CoA transferase. In embodiments, the bacterial host cell comprises: a third operon, comprising: (a) a nucleic acid molecule encoding a FadE protein, (b) a nucleic acid molecule encoding a FadB protein, and (c) a nucleic acid molecule encoding a AtoB protein; and a fourth operon, comprising: (a) a nucleic acid molecule encoding a LvaE protein, and (b) a nucleic acid molecule encoding a propionate-CoA transferase.

In embodiments, the propionate CoA-transferase is a *Clostridium propionicum* propionate CoA-transferase (Pct (Cp)) or a *Megasphaera elsdenii* propionate CoA-transferase (Pct(Me)). In embodiments, the propionate CoA-transferase is a *Clostridium propionicum* (Pct(Cp)). Further details are provided in Zhuang Q et al. *Microb Cell Fact* 18, 135 (2019), the contents of which are incorporated herein by reference in its entirety for all purposes. In embodiments, the Pct(Cp) protein comprises an amino acid sequence having at least 80% (for example, about 85%, about 90%, about 95%, about 96%, about 97%, about 98%, about 99%, or 100%) identity to SEQ ID NO: 30. In embodiments, the Pct(Cp) protein comprises an amino acid sequence having at least 90% identity to SEQ ID NO: 30. In embodiments, the Pct(Cp) protein comprises or consists of the amino acid sequence of SEQ ID NO: 30.

In embodiments, the nucleic acid molecule encoding a Pct(Cp) protein comprises a nucleic acid sequence having at least 80% (for example, about 85%, about 90%, about 95%, about 96%, about 97%, about 98%, about 99%, or 100%) identity to SEQ ID NO: 89. In embodiments, the nucleic acid molecule encoding a Pct(Cp) protein comprises a nucleic acid sequence having at least 80% identity to SEQ ID NO: 89. In embodiments, the nucleic acid molecule encoding a Pct(Cp) protein comprises or consists of the nucleic acid sequence of SEQ ID NO: 89.

In embodiments, the LvaE protein is a *Pseudomonas putida* LvaE protein. Further details are provided in Rand J M et al., *Nature microbiology* 2017, 2:1624-1634, the contents of which are incorporated herein by reference in its entirety for all purposes. In embodiments, the LvaE protein comprises an amino acid sequence having at least 80% (for example, about 85%, about 90%, about 95%, about 96%, about 97%, about 98%, about 99%, or 100%) identity to SEQ ID NO: 247. In embodiments, the LvaE protein comprises an amino acid sequence having at least 90% identity to SEQ ID NO: 247. In embodiments, the LvaE protein comprises or consists of the amino acid sequence of SEQ ID NO: 247.

In embodiments, the nucleic acid molecule encoding a LvaE protein comprises a nucleic acid sequence having at least 80% (for example, about 85%, about 90%, about 95%, about 96%, about 97%, about 98%, about 99%, or 100%) identity to SEQ ID NO: 253. In embodiments, the nucleic acid molecule encoding a LvaE protein comprises a nucleic acid sequence having at least 80% identity to SEQ ID NO: 253. In embodiments, the nucleic acid molecule encoding a LvaE protein comprises or consists of the nucleic acid sequence of SEQ ID NO: 253.

In embodiments, the FadE protein comprises an amino acid sequence having at least 80% (for example, about 85%, about 90%, about 95%, about 96%, about 97%, about 98%, about 99%, or 100%) identity to SEQ ID NO: 13. In embodiments, the FadE protein comprises an amino acid sequence having at least 90% identity to SEQ ID NO: 13. In embodiments, the FadE protein comprises or consists of the amino acid sequence of SEQ ID NO: 13. In embodiments, the nucleic acid molecule encoding a FadE protein comprises a nucleic acid sequence having at least 80% (for example, about 85%, about 90%, about 95%, about 96%, about 97%, about 98%, about 99%, or 100%) identity to SEQ ID NO: 72. In embodiments, the nucleic acid molecule encoding a FadE protein comprises a nucleic acid sequence having at least 80% identity to SEQ ID NO: 72. In embodiments, the nucleic acid molecule encoding a FadE protein comprises or consists of the nucleic acid sequence of SEQ ID NO: 72.

In embodiments, the FadB protein comprises an amino acid sequence having at least 80% (for example, about 85%, about 90%, about 95%, about 96%, about 97%, about 98%, about 99%, or 100%) identity to SEQ ID NO: 12. In embodiments, the FadB protein comprises an amino acid sequence having at least 90% identity to SEQ ID NO: 12. In embodiments, the FadB protein comprises or consists of the amino acid sequence of SEQ ID NO: 12. In embodiments, the nucleic acid molecule encoding a FadB protein comprises a nucleic acid sequence having at least 80% (for example, about 85%, about 90%, about 95%, about 96%, about 97%, about 98%, about 99%, or 100%) identity to SEQ ID NO: 71. In embodiments, the nucleic acid molecule encoding a FadB protein comprises a nucleic acid sequence having at least 80% identity to SEQ ID NO: 71. In embodiments, the nucleic acid molecule encoding a FadB protein comprises or consists of the the nucleic acid sequence of SEQ ID NO: 71.

In embodiments, the AtoB protein comprises an amino acid sequence having at least 80% (for example, about 85%, about 90%, about 95%, about 96%, about 97%, about 98%, about 99%, or 100%) identity to SEQ ID NO: 182. In embodiments, the AtoB protein comprises an amino acid sequence having at least 90% identity to SEQ ID NO: 182. In embodiments, the AtoB protein comprises or consists of the amino acid sequence of SEQ ID NO: 182. In embodiments, the nucleic acid molecule encoding a AtoB protein comprises a nucleic acid sequence having at least 80% (for example, about 85%, about 90%, about 95%, about 96%, about 97%, about 98%, about 99%, or 100%) identity to SEQ ID NO: 191. In embodiments, the nucleic acid molecule encoding a AtoB protein comprises a nucleic acid sequence having at least 80% identity to SEQ ID NO: 191. In embodiments, the nucleic acid molecule encoding a AtoB protein comprises or consists of the nucleic acid sequence of SEQ ID NO: 191.

In embodiments, each of the first, second, third and fourth operons comprises a promoter operably linked to the genes in the first, second, third and fourth operons. In embodiments, the promoter comprises the nucleic acid sequence of SEQ ID NO: 233 ($P_{gracmax2}$) or the nucleic acid sequence of SEQ ID NO: 254 ($P_{trc}$). In embodiments, each of the first, second, third and fourth operons comprises an inducible or a constitutive promoter. In embodiments, each of the first, second and fourth operons comprises a promoter comprising the nucleic acid sequence of SEQ ID NO: 233 ($P_{gracmax2}$), and the third operon comprises a promoter comprising the nucleic acid sequence of SEQ ID NO: 254 ($P_{trc}$).

In embodiments, the promoter comprising a $P_{trc}$ promoter. In embodiments, the promoter comprises a $P_{gracmax2}$ promoter. In embodiments, the $P_{gracmax2}$ promoter comprises a nucleic acid sequence having at least 95% (for example, about 96%, about 97%, about 98%, about 99% or about 100%) identity to SEQ ID NO: 233. In embodiments, the $P_{gracmax2}$ promoter comprises the nucleic acid sequence of SEQ ID NO: 233. In embodiments, the $P_{gracmax2}$ promoter consists of the nucleic acid sequence of SEQ ID NO: 233.

The disclosure provides bacterial host cells, comprising: a first operon comprising (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, (c) a nucleic acid molecule encoding a PhaB protein, wherein the PhaB protein is a *Cupriavidus* sp. S-6 PhaB protein; a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein; a third operon, comprising: (a) a nucleic acid molecule encoding a FadE protein, (b) a nucleic acid molecule encoding a FadB protein, and (c) a nucleic acid molecule encoding a AtoB protein; a fourth operon, comprising: (a) a nucleic acid molecule encoding a LvaE protein, wherein the LvaE protein is a *Pseudomonas putida* LvaE protein, and (b) a nucleic acid molecule encoding a propionate-CoA transferase, wherein the propionate CoA-transferase is a *Clostridium propionicum* propionate CoA-transferase (Pct(Cp)), and a sleeping beauty mutase (Sbm) operon comprises an inducible promoter, The disclosure further provides bacterial host cells, comprising:

- a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, and (c) a nucleic acid molecule encoding a PhaB protein, wherein the nucleic acid molecule comprises a sequence having at least 90% identity to SEQ ID NO: 249;
- a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249;
- a third operon, comprising: (a) a nucleic acid molecule encoding a FadE protein, wherein the nucleic acid molecule comprises a sequence having at least 80% identity to SEQ ID NO: 72, (b) a nucleic acid molecule encoding a FadB protein, wherein the nucleic acid molecule comprises a sequence having at least 80% identity to SEQ ID NO: 71, and (c) a nucleic acid molecule encoding a AtoB protein, and wherein the nucleic acid molecule comprises a sequence having at least 80% identity to SEQ ID NO: 191;
- a fourth operon, comprising: (a) a nucleic acid molecule encoding a LvaE protein, wherein the nucleic acid molecule comprises a sequence having at least 80% identity to SEQ ID NO: 253 and (b) a nucleic acid molecule encoding a propionate CoA-transferase, wherein the nucleic acid molecule comprises a sequence having at least 80% identity to SEQ ID NO: 89, and a sleeping beauty mutase (Sbm) operon comprising a promoter.

In embodiments, the bacterial host cell exhibits reduced or eliminated function of an endogenous lacI repressor. In embodiments, the bacterial host cell comprises a deletion of the nucleic acid sequence encoding an endogenous lacI repressor. In embodiments, the bacterial host cell comprises a nucleic acid molecule encoding an enoyl-CoA hydratase/isomerase PhaJ. In embodiments, the nucleic acid molecule encoding an enoyl-CoA hydratase/isomerase PhaJ is derived from *Aeromonas caviae*, or a homolog thereof.

In embodiments, the bacterial host cell comprises one or more of the following nucleic acid molecules: (a) a nucleic acid molecule encoding an CoA-acylating aldehyde dehydrogenase (Ald); (b) a nucleic acid molecule encoding an glutamate decarboxylase GadB; and (c) β-alanine transaminase KES23458. In embodiments, the CoA-acylating aldehyde dehydrogenase (Ald) is derived from *Clostridium beijerinckii*, or a homolog thereof. In embodiments, the nucleic acid molecule encoding an glutamate decarboxylase GadB is derived from *E. coli* or *Lactobacillus senmaizukei*. In embodiments, the nucleic acid molecule encoding the β-alanine transaminase KES23458 is derived from *Pseudomonas* sp. strain AAC.

In embodiments, the bacterial host cell is capable of converting one or more volatile fatty acids (VFAs) to poly(3-hydroxybutyrate-co-3-hydroxyvalerate) or PHBV. In embodiments, the bacterial host cell is capable of growing in a medium containing more than 100 mM VFAs. In embodiments, the bacterial host cell has a doubling time of at least about 0.1 $hour^{-1}$ (1/hour) in a medium containing more than 100 mM VFAs, for example, about 0.1 $hour^{-1}$ (1/hour), 0.2 $hour^{-1}$, 0.3 $hour^{-1}$, 0.4 $hour^{-1}$, 0.5 $hour^{-1}$, 0.6 $hour^{-1}$, 0.7 $hour^{-1}$, 0.8 $hour^{-1}$, 0.9 $hour^{-1}$, 1 $hour^{-1}$, 2 $hour^{-1}$, 3 $hour^{-1}$, 4 $hour^{-1}$, 5 $hour^{-1}$, or about 6 $hour^{-1}$ in a medium containing more than 100 mM VFAs. In embodiments, the bacterial host cell is capable of growing in a medium containing more than 225 mM VFAs. In embodiments, the bacterial host cell has a doubling time of at least about 0.1 $hour^{-1}$ (1/hour) in a medium containing more than 225 mM VFAs. In embodiments, the bacterial host cell has a doubling time of at least about 0.1 $hour^{-1}$ (1/hour) in a medium containing more than 225 mM VFAs, for example, about 0.1 $hour^{-1}$ (1/hour), 0.2 $hour^{-1}$, 0.3 $hour^{-1}$, 0.4 $hour^{-1}$, 0.5 $hour^{-1}$, 0.6 $hour^{-1}$, 0.7 $hour^{-1}$, 0.8 $hour^{-1}$, 0.9 $hour^{-1}$, 1 $hour^{-1}$, 2 $hour^{-1}$, 3 $hour^{-1}$, 4 $hour^{-1}$, 5 $hour^{-1}$, or about 6 $hour^{-1}$ in a medium containing more than 225 mM VFAs.

In embodiments, the bacterial host cell is capable of growing in a medium containing a concentration of VFAs in the range of about 100 mM to about 1000 mM. In embodiments, the bacterial host cell has a doubling time of at least about 0.1 $hour^{-1}$ (1/hour) in a medium containing a concentration of VFAs in the range of about 100 mM to about 1000 mM, for example, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1000 mM, including all values and subranges that lie therebetween.

In embodiments, the one or more volatile fatty acids comprises a mixture of acetate, propionate, and butyrate. In embodiments, the mixture of acetate, propionate, and butyrate comprises 50 mol % acetate, 20 mol % propionate, and 30 mol % butyrate. In embodiments, the bacterial host cell is *Escherichia coli*. In embodiments, at least one of the one or more nucleic acid molecules is integrated into the bacterial host cell genome. In embodiments, all of the one or more nucleic acid molecules are integrated into the bacterial host cell genome. In embodiments, the bacterial host cell comprises at least one plasmid, wherein the at least one plasmid comprises at least one of the one or more nucleic acid molecules.

In embodiments, the bacterial host cells disclosed herein may be engineered to improve glycerol uptake. For instance, In embodiments, the bacterial host cells disclosed herein may express a mutant glycerol kinase GlpK that is not inhibited by fructose bisphosphate. The mutant glycerol kinase GlpK may be expressed from constitutive or inducible promoters. Further details are provided in Kim K et al., *Metabolic Engineering* 2022, 69:59-72, Herring C D et al., *Nature genetics* 2006, 38:1406-1412, and Kang M, et al., *Frontiers in microbiology* 2019, 10:1845, the contents of which are incorporated herein by reference in its entirety for all purposes.

In embodiments, the bacterial host cells disclosed herein are engineered to express one or more copies of a polyhydroxyalkanoate (PHA) depolymerase.

Exemplary recombinant bacteria host cells disclosed herein are listed below in Table 10:

TABLE 10

| Strain name | Strain Genotype |
|---|---|
| MES1 | CPC-Sbm(endA::λ-Red, ghrB::($P_{trc}$::pct(Cp)), gadC::($P_{gracmax2}$::lvaE)) |
| MES2 | CPC-Sbm(endA::λ-Red, ghrB::($P_{trc}$::pct(Cp)), gadC::($P_{gracmax}$)::lvaE), ΔfadR, tesB::(atoS:atoC(I129S))) |
| MES3 | CPC-Sbm(intF::(PtetA::spc.P279T-cas9), yjcS::(Pgracmax2::IvaE:pct(Cp)), bcsA::(Ptrc::fadE:fadB:atoB)) |
| MES3-PHBV | CPC-Sbm(intF::(PtetA::spc.P279T-cas9), yjcS::(Pgracmax2::IvaE:pct(Cp)), bcsA::(Ptrc::fadE:fadB:atoB), ghrB::(Pgracmax2::phaCAB(S-6))) |
| MES4 | CPC-Sbm(intF::(Pgracmax2::lvaE:pct(Cp)), bcsA::(Ptrc::fadE:fadB:atoB), ΔlacI) |
| MES4-PHBV | CPC-Sbm(intF::(Pgracmax2::lvaE:pct(Cp)), bcsA::(Ptrc::fadE:fadB:atoB), ΔlacI, endA::(Pgracmax2::(RBS-T7)phaCAB(S-6)), yjcS::(Pgracmax2::(RBS-T7)bktB(QJ1):phaB(S-6))) |
| MES4-PHBV2 | CPC-Sbm(intFF::(Pgracmax2::lvaE:pct(Cp)), bcsA::(Ptrc::fadE:fadB:ΔatoB), ΔlacI, endA::(Pgracmax2::(RBS-T7)phaCAB(S-6)), yjcS::(Pgracmax2::(RBS-T7)bktB(QJ1):phaB(S-6)), ΔatoB) |
| CPC-Sbm-BP1 | CPC-Sbm(endA::λ-Red, ghrB::(Ptrc::pct(Cp)), ΔpaaZ, ΔfadE, ΔgabT, ΔyqhD) |
| CPC-Sbm-BP1-GadBe(Ec) | CPC-Sbm(endA::λ-Red, ghrB::(Ptrc::pct(Cp)), ΔpaaZ, ΔfadE, ΔgabT, ΔyqhD, pK-Ptrc::gadBe1-Pgracmax2::lvaE, Ptrc-FG99RS13575:ald:gabD) |
| CPC-Sbm-BP1-Gad(Ls)) | CPC-Sbm(endA::λ-Red, ghrB::(Ptrc::pct(Cp)), ΔpaaZ, ΔfadE, ΔgabT, ΔyqhD, pK-Plac::gad(Ls)-Pgracmax2::lvaE, Ptrc-FG99RS13575:ald:gabD) |
| GEN-EC-GLY-01 | CPC-Sbm(endA::λ-Red, yjcS::(PtetA::spc.P279T-cas9), bcsA::(Pgracmax2::(RBS-T7)bktB(Cn):phaB(Cn)), intF::(Pgracmax2::(RBS-T7)phaC(Cn):phaA(Cn))) |
| GEN-EC-GLY-17 | CPC-Sbm(yjcS::(Pgracmax2::phaCAB(S-6))), bcsA::(Pgracmax2::(RBS-T7)bktB(QJ1):phaB(S-6))) |

Methods of Metabolizing Glycerol Using Recombinant Bacterial Host Cells

The disclosure provides methods of metabolizing glycerol using a bacterial host cell, the method comprising: growing bacterial host cells, comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway in a medium containing glycerol, wherein the method results in the conversion of glycerol to one or more metabolic products by the bacterial host cell. In embodiments, the medium is a liquid medium.

The disclosure provides methods of producing poly(3-hydroxybutyrate-co-3-hydroxyvalerate) (PHBV), the method comprising: growing bacterial host cells, comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway in a medium containing glycerol, wherein the method results in the conversion of glycerol to PHBV by the bacterial host cell.

The disclosure provides methods of producing poly(3-hydroxybutyrate-co-3-hydroxyvalerate) (PHBV), the method comprising: (a) growing bacterial host cells, comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway in a medium containing glycerol at a first temperature for a first period to form a bacterial culture, and (b) incubating the bacterial culture at a second temperature for a second period. In embodiments, the method results in the conversion of glycerol to PHBV by the bacterial host cell.

In embodiments, the first temperature is in a range of about 30° C. to about 37° C., for example, about 30° C., about 31° C., about 32° C., about 33° C., about 34° C., about 35° C., about 36° C., or about 37° C., including all values and subranges that lie therebetween. In embodiments, the first temperature is about 37° C. In embodiments, the second temperature is in a range of about 37° C. to about 50° C., for example, about 38° C., about 39° C., about 40° C., about 41° C., about 42° C., about 43° C., about 44° C., about 45° C., about 46° C., about 47° C., about 48° C., about 49° C., or about 50° C., including all values and subranges that lie therebetween. In embodiments, the second temperature is in a range of about 37° C. to about 45° C.

In embodiments, the first period is in the range of about 1 hour to about 24 hours. In embodiments, the first period is in the range of about 1 hour to about 16 hours. In embodiments, the first period lasts for about 16 hours to about 36 hours—for example, about 16 hours, about 17 hours, about 18 hours, about 19 hours, about 20 hours, about 21 hours, about 22 hours, about 23 hours, about 24 hours, about 25 hours, about 26 hours about 27 hours, about 28 hours, about 29 hours, about 30 hours, about 31 hours, about 32 hours, about 33 hours, about 34 hours, about 35 hours, or about 36 hours. In embodiments, the first period lasts for about 16 hours to about 24 hours. In embodiments, optical density, dissolved oxygen, or base consumption are used as metrics for determining when the growth phase is complete. Maximum optical density during growth phase may depend on a number of factors, such as, for example, inoculation density, fermentation conditions, type of spectrophotometer used for measurements, and media composition.

In embodiments, the second period is in the range of about 24 hours to about 44 hours. In embodiments, the second period is in the range of about 12 hours to about 60 hours, for example, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, about 50 hours, about 52 hours, about 54 hours, about 56 hours, about 58 hours, or about 69 hours, including all values and subranges that lie therebetween.

In embodiments of the methods disclosed herein, the bacterial host cells are grown at a first temperature in a range of about 30° C. to about 37° C. until about the 16 hour-timepoint to about the 24 hour-timepoint to form a bacterial culture, and thereafter, incubating the bacterial culture at a second temperature until about the 48 hour-timepoint to about the 60 hour-timepoint.

In embodiments, the methods disclosed herein comprise producing PHBV from glycerol with a weight average molecular weight (Mw) of about 0.5 MDa to about 2.0 MDa, for example, about 0.6 MDa, about 0.7 MDa, about 0.8 MDa, about 0.9 MDa, about 1 MDa, about 1.1 MDa, about 1.2 MDa, about 1.3 MDa, about 1.4 MDa, about 1.5 MDa, about 1.6 MDa, about 1.7 MDa, about 1.8 MDa, about 1.9 MDa or about 2 MDa, including all subranges and values that lie therebetween. In embodiments, the methods disclosed herein comprise producing PHBV from glycerol with a weight average molecular weight (Mw) of about 1 MDa to about 1.5 MDa. In embodiments, the weight average molecular weight (Mw) is determined using gel permeation chromatography. In specific embodiments, the Mw is determined using conventional gel permeation chromatography with a single refractive index detector, against a polystyrene standard for Mw calibration. In embodiments, the medium contains more than about 0.7 g/g glycerol.

Methods of Metabolizing Volatile Fatty Acids (VFAs) Using Recombinant Bacterial Host Cells The disclosure provides methods of metabolizing volatile fatty acids (VFAs) in a bacterial medium, the method comprising: growing bacterial host cells comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, (e) a nucleic acid molecule encoding a LvaE protein, (f) a nucleic acid molecule encoding a propionate-CoA transferase, (g) a nucleic acid molecule encoding a FadE protein, (h) a nucleic acid molecule encoding a FadB protein, and (i) a nucleic acid molecule encoding a AtoB protein in a medium containing one or more volatile fatty acids (VFAs). In embodiments, the methods disclosed herein result in the conversion of VFAs to one or more metabolic products by the bacterial host cell.

The disclosure provides methods of producing poly(3-hydroxybutyrate-co-3-hydroxyvalerate) (PHBV), the method comprising: growing bacterial host cells comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, (e) a nucleic acid molecule encoding a LvaE protein, (f) a nucleic acid molecule encoding a propionate-CoA transferase, (g) a nucleic acid molecule encoding a FadE protein, (h) a nucleic acid molecule encoding a FadB protein, and (i) a nucleic acid molecule encoding a AtoB protein, wherein the bacterial host cell comprises an activated sleeping beauty mutase (Sbm) pathway in a medium containing one or more volatile fatty acids (VFAs). In embodiments, the methods disclosed herein result in the conversion of VFAs to PHBV by the bacterial host cell. In embodiments, the methods disclosed herein comprise producing PHBV from VFAs with a weight average molecular weight (Mw) of about 3 MDa.

Metabolic Pathways for the Conversion of VFAs to PHBV

*E. coli* has a natural capacity to dissimilate acetate as sole carbon source, and acetate can be converted to (R)-HB-CoA. The pathway to dissimilate acetate can be manipulated, without wishing to be bound by theory, and begins with the conversion of acetate to acetyl-CoA via an acetate kinase polypeptide and a phosphate acetyltransferase AckA-Pta polypeptide (encoded by ackA-pta), an acetyl-CoA synthetase Acs or AcsA polypeptide (encoded by acs and acsA from *Bacillus subtilis*, respectively), and/or a propionyl-CoA synthetase PrpE polypeptide (encoded by prpE and can be derived from *Salmonella enterica, Cupriavidus necator*, or *E. coli*) followed by the fusion of two acetyl-CoA moieties to yield acetoacetyl-CoA via a β-ketothiolase BktB polypeptide or PhaA polypeptide (encoded by bktB and phaA, respectively, from *C. necator*). Acetoacetyl-CoA is then reduced to (R)-HB-CoA by a NADPH-dependent acetoacetyl-CoA reductase PhaB polypeptide (encoded by phaB from *C. necator*) or by a NADH-dependent acetoacetyl-CoA reductase PhaB(Hb) polypeptide (encoded by phaB(Hb) from *Halomonas bluephagenesis* TD01). Alternatively, acetate can be converted to succinate via the glyoxylate shunt, and succinate can be converted to succinyl-CoA by blocking its conversion to fumarate by knocking out or down sdhA (encoding succinate:quinone oxidoreductase, FAD binding protein SdhA).

This disclosure provides conversion of succinate to succinyl-CoA by expression of a succinyl-CoA transferase CKL_RS14680 polypeptide (encoded by CKL_RS14680 from *Clostridium kluyveri*), succinyl-CoA synthetase polypeptides (encoded by sucC and sucD), or a propionyl-CoA transferase YgfH polypeptide (encoded by ygfH). Without wishing to be bound by theory, the Sbm pathway is a dormant pathway in *E. coli* for the production of various chemicals derived from propionyl-CoA (including PHBV) using glycerol as carbon source. This disclosure also provides coupling of the Sbm pathway with pathways for VFA dissimilation to provide control over HV content, i.e. by diverting succinate produced from acetate and butyrate toward (R)-HV-CoA production. In this pathway, succinyl-CoA is converted to L-methylmalonyl-CoA by a methylmalonyl-CoA mutase Sbm polypeptide (encoded by sbm), which is subsequently converted to propionyl-CoA via a methylmalonyl-CoA decarboxylase YgfG polypeptide (encoded by ygfG). Propionyl-CoA is fused with acetyl-CoA via a PhaA polypeptide or a BktB polypeptide to yield 3-ketovaleryl-CoA, which is subsequently converted to (R)-HV-CoA via a PhaB polypeptide or a PhaB(Hb) polypeptide. On the other hand, propionate is converted directly to propionyl-CoA by a PrpE polypeptide or a propionate-CoA transferase Pct polypeptide (derived from *Clostridium propionicum* or *Megasphaera elsdenii*, i.e. Pct(Cp) or Pct (Me)), following propionate uptake into the cell by passive diffusion, or via a proline:Na+ symporter PutP polypeptide or a short-chain fatty acid transporter AtoE polypeptide (encoded by putP and atoE, respectively).

This disclosure provides conversion of butyrate to HB-CoA or succinate through distinct engineered pathways. Without wishing to be bound by theory, the first pathway may exist in natural PHA producers and begins with the uptake of butyrate into the cell by passive diffusion or a short-chain fatty acid transporter AtoE polypeptide (encoded by atoE), followed by conversion of butyrate to butyryl-CoA via a short/medium chain acyl-CoA synthetase LvaE polypeptide (encoded by lvaE from *Pseudomonas putida*), propionate-CoA transferase Pct polypeptide, or an acetate CoA-transferase AtoD polypeptide and an AtoA polypeptide or an acetate CoA-transferase MELS_RS00170 polypeptide and a MELS_RS00175 polypeptide (encoded by atoD and atoA, and MELS_RS00170 and MELS_RS00175 from *M. elsdenii*, respectively).

Butyryl-CoA is then converted to crotonyl-CoA via a short-chain acyl-CoA dehydrogenase PP_2216 polypeptide, a BC_5341 polypeptide, a MELS_RS10970 polypeptide, or a FadE polypeptide (encoded by PP_2216 from *P. putida*, BC_5341 from *Bacillus cereus*, MELS_RS10970 from *M. elsdenii*, and fadE, respectively), which is subsequently converted to (R)-HB-CoA via an enoyl-CoA hydratase/isomerase H16_RS27940 polypeptide, an enoyl-CoA hydratase/isomerase PhaJ polypeptide, or bifunctional protein PaaZ polypeptide (encoded by H16_RS27940 from *C. necator*, phaJ from *Aeromonas caviae* (Ac) or *Aromatoleum aromaticum* (Aa), and paaZ, respectively). Further details are provided in Wang X et al., *Journal of biotechnology* 2018, 280:62-69, the contents of which are incorporated herein by reference in its entirety for all purposes.

The bifunctional protein PaaZ polypeptide has enoyl-CoA hydratase activity that converts crotonyl-CoA to (R)-HB-CoA. Crotonyl-CoA can also be sequentially converted to (S)-HB-CoA and acetoacetyl-CoA by native multifunctional enoyl-CoA hydratase/3-hydroxyacyl-CoA epimerase/Δ3-cis-Δ2-trans-enoyl-CoA isomerase/L-3-hydroxyacyl-CoA dehydrogenase polypeptides FadB and FadJ. This disclosure provides conversion of butyrate to succinate which occurs through a synthetic pathway in which butyrate is converted to butyryl-CoA, which is then converted to butyraldehyde via a CoA-dependent propanal dehydrogenase PduP polypeptide (encoded by pduP from *S. enterica, Klebsiella pneumoniae*, or *Listeria monocytogenes*) or a CoA-acylating aldehyde dehydrogenase Ald polypeptide (encoded by ald from *Clostridium beijerinckii*). In parallel, without wishing to be bound by theory, L-glutamate is converted to 4-aminobutyrate by an engineered glutamate decarboxylase GadAe polypeptide, an engineered glutamate decarboxylase GadBe(Ec) polypeptide (with the same modifications as GadAe), an engineered glutamate decarboxylase GadBe(Lb) polypeptide with amino acid substitutions K17I, D294G, E312S, and Q346H (further details provided in Shi et al., *Enzyme and Microbial Technology* 2014, 61:35-43, the contents of which are incorporated herein by reference in its entirety for all purposes), a glutamate decarboxylase GadB (Lp) polypeptide, a glutamate decarboxylase Gad(Ls) polypeptide, or a glutamate decarboxylase Gad polypeptide (encoded by gadAe, gadBe(Ec), gadBe(Lb) from *Lactobacillus brevis*, gadB(Lp) from *Lactobacillus plantarum*, gad (Ls) from *Lactobacillus senmaizukei*, and gad from *Arabidopsis thaliana*, respectively). L-glutamate production can be enhanced by expressing a glutamate dehydrogenase GdhA polypeptide (encoded by gdhA), that converts keto-glutarate to L-glutamate, for increased 4-aminobutyrate production (further details are provided in Soma Y et al., *Metabolic Engineering* 2017, 43:54-63, the contents of which are incorporated herein by reference in its entirety for all purposes). This disclosure provides conversion of butyraldehyde and 4-aminobutyrate to succinate semialdehyde via a β-alanine transaminase KES23458 polypeptide (encoded by FG99_15380 from *Pseudomonas* sp. strain AAC). Succinate semialdehyde is oxidized to succinate by a NADP+-dependent succinate semialdehyde dehydrogenase GabD polypeptide (encoded by gabD). (R)-HB-CoA and (R)-HV-CoA are polymerized by a short-chain polyhydroxyalkanoate synthase PhaC polypeptide (encoded by phaC from *C. necator*) to yield PHBV. PhaC mutants are also useful for polymerizing (R)-HB-CoA and (R)-HV-CoA. For example, PhaC(F420S) (SEQ ID NO: 226) can dimerize at a faster rate relative to wild-type PhaC [25], and the PhaC (G4D) mutation (SEQ ID NO: 230) increases soluble expression relative to wild-type PhaC [26]. These are beneficial attributes for increasing PHBV biosynthesis and molecular weight.

Further details are provided in Tang C-D, et al., International Journal of Biological Macromolecules 2020, 160:372-379; and Ho NAT, et al., Journal of Bioscience and Bioengineering 2013, 115:154-158, Yin J, et al., Applied microbiology and biotechnology 2015, 99:5523-5534, Phan T T P, et al., Journal of biotechnology 2012, 157:167-172, Olins P O, et al., Journal of Biological Chemistry 1989, 264:16973-16976, Arab B, et al., Fermentation 2023, 9:14, Puigbo P et al., Nucleic acids research 2007, 36:D524-D527, Agus J, et al., Polymer degradation and stability 2006, 91:1138-1146; Normi Y M, et al., Macromolecular bioscience 2005, 5:197-206, Chinese Patent Application CN105063790A, International Patent Application WO1990000067A1, the contents of each which are incorporated herein by reference in its entirety for all purposes.

In embodiments, the Pct polypeptide comprises a Pct(Cp) polypeptide or a Pct(Me) polypeptide. In embodiments, the PduP polypeptide comprises a PduP(Kp) polypeptide or a PduP(Se) polypeptide. In embodiments, the recombinant bacterial cell further comprises a proline:Na+ symporter, optionally a PutP polypeptide, or a short-chain fatty acid transporter, optionally an AtoE polypeptide.

In embodiments, the recombinant bacterial cell comprises at least one recombinant nucleic acid molecule encoding a polypeptide that catalyzes the conversion of butyrate to butyryl-CoA. In embodiments, the recombinant bacterial cell comprises at least one recombinant nucleic acid molecule encoding a polypeptide that catalyzes the conversion of butyryl-CoA to butyraldehyde. In embodiments, the recombinant bacterial cell comprises at least one recombinant nucleic acid molecule encoding a polypeptide that catalyzes the conversion of butyraldehyde and optionally 4-aminobutyrate to succinate semialdehyde. In embodiments, the recombinant bacterial cell comprises at least one recombinant nucleic acid molecule encoding a polypeptide that catalyzes the conversion of succinate semialdehyde to succinate. In embodiments, the recombinant bacterial cell comprises at least one recombinant nucleic acid molecule encoding a polypeptide that catalyzes the conversion of L-glutamate to 4-aminobutyrate. In embodiments, the recombinant bacterial cell comprises at least one recombinant nucleic acid molecule encoding a polypeptide that catalyzes the conversion of butyryl-CoA to crotonyl-CoA. In embodiments, the recombinant bacterial cell comprises at least one recombinant nucleic acid molecule encoding a polypeptide that catalyzes the conversion of crotonyl-CoA to 3-hydroxybutyryl-CoA. In embodiments, the recombinant bacterial cell comprises at least one recombinant nucleic acid molecule encoding a polypeptide that catalyzes the conversion of succinate to succinyl-CoA.

In embodiments, the recombinant bacterial cell comprises at least one recombinant nucleic acid molecule encoding at least one, at least two, at least three, at least four, or at least five of a polypeptide that catalyzes the conversion of butyrate to butyryl-CoA, a polypeptide that catalyzes the conversion of butyryl-CoA to butyraldehyde, a polypeptide that catalyzes the conversion of butyraldehyde and 4-aminobutyrate to succinate semialdehyde, a polypeptide that catalyzes the conversion of succinate semialdehyde to succinate, and a polypeptide that catalyzes the conversion of L-glutamate to 4-aminobutyrate.

In embodiments, the recombinant bacterial cell comprises at least one recombinant nucleic acid molecule encoding at least one, at least two, or at least three of a polypeptide that catalyzes the conversion of butyrate to butyryl-CoA, a polypeptide that catalyzes the conversion of butryryl-CoA to crotonyl-CoA, and a polypeptide that catalyzes the conversion of crotonyl-CoA to 3-hydroxybutyryl-CoA.

In a specific embodiment, the recombinant bacterial cell for producing PHBV comprises:

i) an acyl-CoA synthetase, optionally a short chain acyl-CoA synthetase polypeptide, optionally a LvaE polypeptide, acetate-CoA transferase polypeptides, optionally a MELS_RS00170 polypeptide and a MELS_RS00175 polypeptide or an AtoD polypeptide and an AtoA polypeptide, or a propionate-CoA transferase polypeptide, optionally a Pct polypeptide;

ii) a NADPH-dependent acetoacetyl-CoA reductase polypeptide, optionally a PhaB polypeptide, or a NADH-dependent acetoacetyl-CoA reductase polypeptide, optionally a PhaB(Hb) polypeptide; and a first β-ketothiolase polypeptide, optionally a BktB polypeptide;

iii) a short-chain polyhydroxyalkanoate synthase polypeptide, optionally a PhaC polypeptide, or an engineered short-chain polyhydroxyalkanoate synthase polypeptide, optionally a PhaC(F420S) polypeptide or a PhaC(G4D) polypeptide;

iv) a methylmalonyl-CoA mutase polypeptide, optionally a Sbm polypeptide, a methylmalonyl-CoA mutase interacting protein polypeptide, optionally a methylmalonyl-CoA mutase-interacting GTPase polypeptide, optionally a YgfD polypeptide, a methylmalonyl-CoA decarboxylase polypeptide, optionally a YgfG polypeptide, and optionally a propionyl-CoA:succinate CoA transferase polypeptide, optionally a YgfH polypeptide; and v) at least one of at least one recombinant nucleic acid molecule encoding a polypeptide that catalyzes a conversion of butyryl-CoA to succinate and at least one recombinant nucleic acid molecule encoding a polypeptide that catalyzes a conversion of butyryl-CoA to 3-hydroxybutyryl-CoA, wherein the at least one recombinant nucleic acid molecule encoding a polypeptide that catalyzes the conversion of butyryl-CoA to succinate comprises a CoA-dependent propanal dehydrogenase polypeptide, optionally a PduP polypeptide, or a CoA-acylating aldehyde dehydrogenase polypeptide, optionally an Ald polypeptide, a β-alanine transaminase polypeptide, optionally a KES23458 polypeptide, and a NADP+-dependent succinate semialdehyde dehydrogenase polypeptide, optionally a GabD polypeptide, and wherein the at least one recombinant nucleic acid molecule encoding a polypeptide that catalyzes the conversion of butyryl-CoA to 3-hydroxybutyryl-CoA comprises an acyl-CoA dehydrogenase polypeptide, optionally a short-chain acyl-CoA dehydrogenase polypeptide, optionally at least one of a PP_2216 polypeptide, a BC_5341 polypeptide, a MELS_RS10970 polypeptide, and a FadE polypeptide, an enoyl-CoA hydratase/isomerase polypeptide, optionally at least one of a H16_RS27940 polypeptide and a PhaJ polypeptide, and a PaaZ polypeptide; and vi) optionally a propionyl-CoA synthetase polypeptide, optionally a PrpE polypeptide, wherein the enzymes in i) and v) are encoded by at least one recombinant nucleic acid molecule in the bacterial cell.

In embodiments, the recombinant bacterial cell further comprises a glutamate decarboxylase polypeptide, optionally a GadAe polypeptide, a GadBe(Ec) polypeptide, a GadBe(Lb) polypeptide, a GadB(Lp) polypeptide, a Gad (Ls) polypeptide, or a Gad polypeptide. In embodiments, the recombinant bacterial cell further comprises a second β-ketothiolase polypeptide, optionally a PhaA polypeptide. In embodiments, the recombinant bacterial cell further comprises a succinyl-CoA transferase polypeptide, optionally a CKL_RS14680 polypeptide, or succinyl-CoA synthetase polypeptides, optionally a SucC polypeptide and a SucD polypeptide.

In embodiments, the recombinant bacterial cell comprises a Pct(Cp) polypeptide, an LvaE polypeptide, a PhaJ(Ac) polypeptide, a FadE polypeptide, a GadAe polypeptide, a FG99_15380 polypeptide, a PduP(Se) polypeptide, a GabD polypeptide, a CKL_RS14680 polypeptide, and an AtoC (Con) polypeptide comprising a serine at the position corresponding to position 129 of SEQ ID NO: 203. In some embodiment, the recombinant bacterial cell further comprises a PhaC polypeptide, a PhaB polypeptide, a BktB polypeptide, and a PhaA polypeptide.

In embodiments, the nucleic acid molecule described herein is optionally a heterologous nucleic acid molecule having a nucleic acid sequence encoding a recombinant polypeptide described herein. In embodiments, the recombinant bacterial cell comprises stably incorporated into the genome a heterologous nucleic acid molecule having a nucleic acid sequence encoding a recombinant polypeptide described herein.

The bacterial strain described herein can include heterologous nucleic acid that contains transcriptional and translational regulatory elements. For example, transcriptional regulatory elements can include promoter such as $P_{gracmax2}$ and transcriptional terminator, and translational regulatory elements can include ribosomal binding site (RBS) such as RBS from gene 10 of Phage T7 (T7.RBS) that can significantly enhance translation efficiency relative to the consensus RBS of *E. coli*. Translation efficiency may also be enhanced by combining other RBSs, e.g. the consensus Gram-positive RBS (i.e. AAGGAGG), with a nine bp sequence derived from T7.RBS (i.e. TTAACTTTA) to facilitate base-pairing with the 16S rRNA of *E. coli* (e.g. RBS1). In embodiments, the recombinant bacterial cell comprises a nucleic acid molecule having promoter $P_{gracmax2}$. In embodiments, the recombinant bacterial cell comprises a nucleic acid molecule having translational regulatory element T7.RBS. In embodiments, the recombinant bacterial cell comprises a nucleic acid molecule having promoter $P_{gracmax2}$ and at least one translational regulatory element. In embodiments, the at least one translational regulatory element is T7.RBS, Gram-positive RBS, or RBS1. In embodiments, the at least one translational regulatory element is combined T7.RBS and Gram-positive RBS. In embodiments, the at least one translational regulatory element is combined T7.RBS and Gram-positive RBS, and RBS1. In embodiments, the recombinant bacterial cell comprises a nucleic acid molecule having the sequence of SEQ ID NO: 232. In embodiments, the recombinant bacterial cell comprises a nucleic acid molecule having the sequence of SEQ ID NO: 233. In embodiments, the recombinant bacterial cell comprises a nucleic acid molecule having the sequence of SEQ ID NO: 234. In embodiments, the recombinant bacterial cell comprises a nucleic acid molecule having the sequence of SEQ ID NO: 235. In embodiments, the recombinant bacterial cell comprises a nucleic acid molecule having the sequence of SEQ ID NO: 236. In embodiments, the recombinant bacterial cell comprises a nucleic acid molecule having the sequence of SEQ ID NO: 233, 234, and 236. In embodiments, the recombinant bacterial cell comprises a nucleic acid molecule having the sequence of SEQ ID NO: 232 and 236. In embodiments, the recombinant bacterial cell comprises a nucleic acid molecule having the sequence of SEQ ID NO: 237. In embodiments, the recombinant bacterial cell comprises a nucleic acid molecule having the sequence of SEQ ID NOs: 233, 234, 236, and 237. In embodiments, the recombinant bacterial cell comprises a nucleic acid molecule having the sequence of SEQ ID NOs: 232, 236, and 237. In embodiments, the recombinant bacterial cell comprises a nucleic acid molecule having a transcriptional terminator. In embodiments, the recombinant bacterial cell comprises a nucleic acid molecule having the sequence of SEQ ID NO: 238. In embodiments, the recombinant bacterial cell comprises a nucleic acid molecule having $P_{gracmax2}$, combined T7.RBS and Gram-positive RBS, RBS1, and transcriptional terminator. In embodiments, the recombinant bacterial cell comprises a nucleic acid molecule having the sequence of SEQ ID NOs: 233, 234, 236, and 238. In embodiments, the recombinant bacterial cell comprises a nucleic acid molecule having the sequence of SEQ ID NOs: 232, 236, and 238. In embodiments, the recombinant bacterial cell comprises a nucleic acid molecule having the sequence of SEQ ID NO: 239. In embodiments, the recombinant bacterial cell comprises a nucleic acid molecule having the sequence of SEQ ID NO: 240. In embodiments, the recombinant bacterial cell comprises a nucleic acid molecule having the sequence of SEQ ID NOs: 239 and 240. In embodiments, the nucleic acid molecule having the sequence of SEQ ID NO: 239 is integrated into a nonessential gene locus. In embodiments, the nucleic acid molecule having the sequence of SEQ ID NO: 239 is integrated into the bcsA locus. In embodiments, the nucleic acid molecule having the sequence of SEQ ID NO: 240 is integrated into a nonessential gene locus. In embodiments, the nucleic acid molecule having the sequence of SEQ ID NO: 240 is integrated into the intF locus. In embodiments, the nucleic acid molecule is integrated into one or more loci of bacterial strain CPC-Sbm. In embodiments, the nucleic acid molecule is integrated into one or more loci of K-12 derived bacterial strain. In embodiments, the nucleic acid molecule having the sequence of SEQ ID NO: 239 is integrated into the bcsA locus of strain CPC-Sbm and the nucleic acid molecule having the sequence of SEQ ID NO: 240 is integrated into the intF locus of strain CPC-Sbm. In embodiments, the nucleic acid molecule having the sequence of SEQ ID NO: 236 is integrated into the bcsA locus of K-12 derived strain and the nucleic acid molecule having the sequence of SEQ ID NO: 240 is integrated into the intF locus of K-12 derived strain. In embodiments, the nucleic acid molecule comprises $P_{gracmax2}$::(T7.RBS)bktB:(RBS1)phaB.

In embodiments, the nucleic acid molecule comprises $P_{gracmax2}$::(T7.RBS)phaC:(RBS1)phaA. In embodiments, the nucleic acid molecule comprises $P_{gracmax2}$::(T7.RBS) bktB:(RBS1)phaB) and ($P_{gracmax2}$::(T7.RBS)phaC:(RBS1) phaA. In embodiments, the recombinant bacterial strain is CPC-Sbm(bcsA::($P_{gracmax2}$::(T7.RBS)bktB:(RBS1)phaB), intF::($P_{gracmax2}$::(T7.RBS)phaC:(RBS1)phaA).

The expression of recombinant polypeptide in a particular bacteria species can be improved by codon optimization. In some examples described herein, codon optimization was completed by first optimizing a gene sequence for expression in *E. coli* K12 using the Codon Optimization Tool provided by Integrated DNA Technologies (USA), followed by further optimization of the optimized sequence via the OPTIMIZER web server using the "guided random" method that is based on a Monte Carlo algorithm (further details are provided in Puigbo P et al., *Nucleic acids research* 2007, 36:D524-D527, and Puigbo P et al., *Nucleic acids research* 2007, 35:W126-W131, the contents of which are incorporated herein by reference in its entirety for all purposes). Finally, manual adjustments were made to the sequence resulting from the second optimization procedure using the codon frequency table for *E. coli* K12 from the Codon Usage Database (as provided at Nakamura Y, et al., *Nucleic acids research* 2000, 28:292-292) as a reference and the manual optimization option found in the Codon Optimization Tool provided by Integrated DNA Technologies. In embodiments, the heterologous nucleic acid molecule has an optimized nucleic acid sequence for encoding a recombinant polypeptide described herein for expression in a bacterial cell described herein.

Amino acid sequences described herein are set out in Table 1.

TABLE 1

Amino Acid Sequences

| SEQ ID NO | Amino Acid Sequence |
|---|---|
| SEQ ID NO: 1 amino acid sequence of ackA with the accession # NP_416799 | MSSKLVLVLNCGSSSLKFAIIDAVNGEEYLSGLAECFHLPEARIKWKMDGNKQEAALGAGAAHSEALNFIVNTILAQKPELS<br>AQLTAIGHRIVHGGEKYTSSVVIDESVIQGIKDAASFAPLHNPAHLIGIEEALKSFPQLKDKNVAVFDTAFHQTMPEESYLYAL<br>PYNLYKEHGIRRYGAHGTSHFYVTQEAAKMLNKPVEELNIITCHLGNGGSVSAIRNGKCVDTSMGLTPLEGLVMGTRSGDI<br>DPAIIFHLHDTLGMSVDAINKLLTKESGLLGLTEVTSDCRYVEDNYATKEDAKRAMDVYCHRLAKYIGAYTALMDGRLDA<br>VVFTGGIGENAAMVRELSLGKLGVLGFEVDHERNLAARFGKSGFINKEGTRPAVVIPTNEELVIAQDASRLTA |
| SEQ ID NO: 2 amino acid sequence of acs with the accession # NP_418493 | MSQIHKHTIPANIADRCLINPQQYEAMYQQSINVPDTFWGEQGKILDWIKPYQKVKNTSFAPGNVSIKWYEDGTLNLAANCL<br>DRHLQENGDRTAIIWEGDDASQSKHISYKELHRDVCRFANTLLELGIKKGDVVAIYMPMVPEAAVAMLACARIGAVHSVIF<br>GGFSPEAVAGRIIDSNSRLVITSDEGVRAGRSIPLKKNVDDALKNPNVTSVEHVVVLKRTGGKIDWQEGRDLWWHDLVEQA<br>SDQHQAEEMNAEDPLFILYTSGSTGKPKGVLHTTGGLYVYAALTFKYVFDYHPGDIYWCTADVGWVTGHSYLLYGPLACG<br>ATTLMFEGVPNWPTPARMAQVVDKHQVNILYTAPTAIRALMAEGDKAIEGTDRSSLRILGSVGEPINPEAWEWYWKKIGNE<br>KCPVVDTWWQTETGGFMITPLPGATELKAGSATRPFFGVQPALVDNEGNPLEGATEGSLVITDSWPGQARTLFGDHERFEQ<br>TYFSTFKNMYFSGDGARRDEDGYYWITGRVDDVLNVSGHRLGTAEIESALVAHPKIAEAAVVGIPHNIKGQAIYAYVTLNH<br>GEEPSPELYAEVRNWVRKEIGPLATPDVLHWTDSLPKTRSGKIMRRILRKIAAGDTSNLGDTSTLADPGVVEKLLEEKQAIA<br>MPS |
| SEQ ID NO: 3 amino acid sequence of acsA with the accession # NP_390846 | MNLKALPAIEGDHNLKNYEETYRHFDWAEAEKHFSWHETGKLNAAYEAIDRHAESFRKNKVALYYKDAKRDEKYTFKEM<br>KEESNRAGNVLRRYGNVEKGDRVFIFMPRSPELYFIMLGAIKIGAIAGPLFEAFMEGAVKDRLENSEAKVVVTTPELLERIPV<br>DKLPHLQHVFVVGGEAESGTNIINYDEAAKQESTRLDIEWMDKKDGFLLHYTSGSTGTPKGVLHVHEAMIQQYQTGKWVL<br>DLKEEDIYWCTADPGWVTGTVYGIFAPWLNGATNVIVGGRFSPESWYGTIEQLGVNVWYSAPTAFRMLMGAGDEMAAKY<br>DLTSLRHVLSVGEPLNPEVIRWGHKVFNKRIHDTWWMTETGSQLICNYPCMDIKPGSMGKPIPGVEAAIVDNQGNELPPYR<br>MGNLAIKKGWPSMMHTIWNNPEKYESYFMPGGWYVSGDSAYMDEEGYFWFQGRVDDVIMTSGERVGPFEVESKLVEHPA<br>IAEAGVIGKPDPVRGEIIKAFIALREGFEPSDKLKEEIRLFVKQGLAAHAAPREIEFKDKLPKTRSGKIMRRVLKAWELNLPAG<br>DLSTMED |
| SEQ ID NO: 4 amino acid sequence of AtoA with the accession # NP_416726 | MDAKQRIARRVAQELRDGDIVNLGIGLPTMVANYLPEGIHITLQSENGFLGLGPVTTAHPDLVNAGGQPCGVLPGAAMFDS<br>AMSFALIRGGHIDACVLGGLQVDEEANLANWVVPGKMVPGMGGAMDLVTGSRKVIIAMEHCAKDGSAKILRRCTMPLTA<br>QHAVHMLVTELAVFRFIDGKMWLTEIADGCDLATVRAKTEARFEVAADLNTQRGDL |
| SEQ ID NO: 5 amino acid sequence of AtoD with the accession # NP_416725 | MKTKLMTLQDATGFFRDGMTIMVGGFMGIGTPSRLVEALLESGVRDLTLIANDTAFVDTGIGPLIVNGRVRKVIASHIGTNPE<br>TGRRMISGEMDVVLVPQGTLIEQIRCGGAGLGGFLTPTGVGTVVEEGKQTLTLDGKTWLLERPLRADLALIRAHRCDTLGNL<br>TYQLSARNFNPLIALAADITLVEPDELVETGELQPDHIVTPGAVIDHIIVSQESK |
| SEQ ID NO: 6 amino acid sequence of AtoE with the accession # NP_416727 | MIGRISRFMTRFVSRWLPDPLIFAMLLTLLTFVIALWLTPQTPISMVKMWGDGFWNLLAFGMQMALIIVTGHALASSAPVKS<br>LLRTAASAAKTPVQGVMLVTFFGSVACVINWGFGLVVGAMFAREVARRVPGSDYPLLIACAYIGFLTWGGGFSGSMPLLAA<br>TPGNPVEHIAGLIPVGDTLFSGFNIFITVALIVVMPFITRMMMPKPSDVVSIDPKLLMEEADFQKQLPKDAPPSERLEESRILTL<br>IIGALGIAYLAMYFSEHGFNITINTVNLMFMIAGLLLHKTPMAYMRAISAAARSTAGILVQFPFYAGIQLMMEHSGLGGLITEF<br>FINVANKDTFPVMTFFSSALINFAVPSGGGHWVIQGPFVIPAAQALGADLGKSVMAIAYGEQWMNMAQPFWALPALAIAGL<br>GVRDIMGYCITALLFSGVIFVIGLTLF |
| SEQ ID NO: 7 amino acid sequence of BC_5341 with the accession # NP_835003 | MHFKLSEEHEMIRKMVRDFAKNEVAPTAAERDEEERFDRELFDQMAELGLTGIPWPEEYGGIGSDYLAYVIAIEELSRVCAS<br>TGVTLSAHTSLAGWPIFKFGTEEQKQKFLRPMAEGKKIGAYGLTEPGSGSDAGGMKTIAKRDGDHYILNGSKIFITNGGIADI<br>YVVFALTDPESKQRGTSAFIVESDTPGFSVGKKESKLGIRSSPTTEIMFEDCRIPVENLLGEEGQGFKVAMQTLDGGRNGIAA<br>QAVGIAQGALDASVEYARERHQFGKPIAAQQGIGFKLADMATDVEAARLLTYQAAWLESEGLPYGKESAMSKVFAGDTA<br>MRVTTEAVQVFGGYGYTKDYPVERYMRDAKITQIYEGTQEIQRLVISRMLTK |
| SEQ ID NO: 8 amino acid sequence of BktB with the accession # WP_011615089 | MTREVVVVSGVRTAIGTFGGSLKDVAPAELGALVVREALARAQVSGDDVGHVVFGNVIQTEPRDMYLGRVAAVNGGVTIN<br>APALTVNRLCGSGLQAIVSAAQTILLGDTDVAIGGGAESMSRAPYLAPAARWGARMGDAGLVDMMLGALHDPFHRIHMG<br>VTAENVAKEYDISRAQQDEAALESHRRASAAIKAGYFKDQIVPVVSKGRKGDVTFDTDEHVRHDATIDDMTKLRPVFVKEN<br>GTVTAGNASGLNDAAAAVVMMERAEAERRGLKPLARLVSYGHAGVDPKAMGIGPVPATKIALERAGLQVSDLDVIEANEA<br>FAAQACAVTKALGLDPAKVNPNGSGISLGHPIGATGALITVKALHELNRVQGRYALVTMCIGGGQGIAAIFERI |
| SEQ ID NO: 9 amino acid sequence of cadA with the accession # NP_418555 | MNVIAILNHMGVYFKEEPIRELHRALERLNFQIVYPNDRDDLLKLIENNARLCGVIFDWDKYNLELCEEISKMNENLPLYAFA<br>NTYSTLDVSLNDLRLQISFFEYALGAAEDIANKIKQTTDEYINTILPPLTKALFKYVREGKYTFCTPGHMGGTAFQKSPVGSLF<br>YDFFGPNTMKSDISISVSELGSLLDHSGPHKEAEQYIARVFNADRSYMVTNGTSTANKIVGMYSAPAGSTILIDRNCHKSLTH<br>LMMMSDVTPIYFRPTRNAYGILGGIPQSEFQHATIAKRVKETPNATWPVHAVITNSTYDGLLYNTDFIKKTLDVKSIHFDSAW<br>VPYTNFSPIYEGKCGMSGGRVEGKVIYETQSTHKLLAAFSQASMIHVKGDVNEETFNEAYMMHTTTSPHYGIVASTETAAA<br>MMKGNAGKRLINGSIERAIKFRKEIKRLRTESDGWFFDVWQPDHIDTTECWPLRSDSTWHGFKNIDNEHMYLDPIKVTLLTP<br>GMEKDGTMSDFGIPASIVAKYLDEHGIVVEKTGPYNLLFLFSIGIDKTKALSLLRALTDFKRAFDLNLRVKNMLPSLYREDPE<br>FYENMRIQELAQNIHKLIVHHNLPDLMYRAFEVLPTMVMTPYAAFQKELHGMTEEVYLDEMVGRINANMILPYPPGVPLV<br>MPGEMITEESRPVLEFLQMLCEIGAHYPGFETDIHGAYRQADGRYTVKVLKEESKK |
| SEQ ID NO: 10 amino acid sequence of CKL_RS14680 with the | MSKGIKNSQLKKKNVKASNVAEKIEEKVEKTDKVVEKAAEVTEKRIRNLKLQEKVVTADVAADMIENGMIVAISGFTPSGY<br>PKEVPKALTKKVNALEEEFKVTLYTGSSTGADIDGEWAKAGIIERRIPYQTNSDMRKKINDGSIKYADMHLSHMAQYINYSV<br>IPKVDIAIIEAVAITEEGDIIPSTGIGNTATFVENADKVIVEINEAQPLELEGMADIYTLKNPPRREPIPIVNAGNRIGTTYVTCG<br>SEKICAIVMTNTQDKTRPLTEVSPVSQAISDNLIGFLNKEVEEGKLPKNLLPIQSGVGSVANAVLAGLCESNFKNLSCYTEVIQD<br>SMLKLIKCGKADVVSGTSISPSPEMLPEFIKDINFFREKIVLRPQEISNNPEIARRIGVISINTALEVDIYGNVNSTHVMGSKMM |

TABLE 1-continued

| Amino Acid Sequences | |
|---|---|
| SEQ ID NO | Amino Acid Sequence |
| accession # WP_012103359 | NGIGGSGDFARNAYLTIFTTESIAKKGDISSIVPMVSHVDHTEHDVMVIVTEQGVADLRGLSPREKAVAIIENCVHPDYKDML<br>MEYFEEACKSSGGNTPHNLEKALSWHTKFIKTGSMK |
| SEQ ID NO: 11 amino acid sequence of endA with the accession # NP_417420 | MYRYLSIAAVVLSAAFSGPALAEGINSFSQAKAAAVKVHADAPGTFYCGCKINWQGKKGVVDLQSCGYQVRKNENRASRV<br>EWEHVVPAWQFGHQRQCWQDGGRKNCAKDPVYRKMESDMHNLQPSVGEVNGDRGNFMYSQWNGGEGQYGQCAMKV<br>DFKEKAAEPPARARGAIARTYFYMRDQYNLTLSRQQTQLFNAWNKMYPVTDWECERDERIAKVQGNHNPYVQRACQARK<br>S |
| SEQ ID NO: 12 amino acid sequence of fadB with the accession # NP_418288 | MLYKGDTLYLDWLEDGIAELVFDAPGSVNKLDTATVASLGEAIGVLEQQSDLKGLLLRSNKAAFIVGADITEFLSLFLVPEE<br>QLSQWLHFANSVFNRLEDLPVPTIAAVNGYALGGGCECVLATDYRLATPDLRIGLPETKLGIMPGFGGSVRMPRMLGADSA<br>LEIIAAGKDVGADQALKIGLVDGVVKAEKLVEGAKAVLRQAINGDLDWKAKRQPKLEPLKLSKIEATMSFTIAKGMVAQTA<br>GKHYPAPITAVKTIEAAARFGREEALNLENKSFVPLAHTNEARALVGIFLNDQYVKGKAKKLTKDVETPKQAAVLGAGIMG<br>GGIAYQSAWKGVPVVMKDINDKSLTLGMTEAAKLLNKQLERGKIDGLKLAGVISTIHPTLDYAGFDRVDIVVEAVVENPKV<br>KKAVLAETEQKVRQDTVLASNTSTIPISELANALERPENFCGMHFFNPVHRMPLVEIIRGEKSSDETIAKVVAWASKMGKTPI<br>VVNDCPGFFVNRVLFPYFAGFSQLLRDGADFRKIDKVMEKQFGWPMGPAYLLDVVGIDTAHHAQAVMAAGFPQRMQKDY<br>RDAIDALFDANRFGQKNGLGFWRYKEDSKGKPKKEEDAAVEDLLAEVSQPKRDFSEEEIIARMMIPMVNEVVRCLEEGIIAT<br>PAEADMALVYGLGFPPFHGGAFRWLDTLGSAKYLDMAQQYQHLGPLYEVPEGLRNKARHNEPYYPPVEPARPVGDLKTA |
| SEQ ID NO: 13 amino acid sequence of fadE with the accession # NP_414756 | MMILSILATVVLLGALFYHRVSLFISSLILLAWTAALGVAGLWSAWVLVPLAIILVPFNFAPMRKSMISAPVFRGFRKVMPPM<br>SRTEKEAIDAGTTWWEGDLFQGKPDWKKLHNYPQPRLTAEEQAFLDGPVEEACRMANDFQITHELADLPPELWAYLKEHR<br>FFAMIIKKEYGGLEFSAYAQSRVLQKLSGVSGILAITVGVPNSLGPGELLQHYGTDEQKDHYLPRLARGQEIPCFALTSPEAGS<br>DAGAIPDTGIVCMGEWQGQQVLGMRLTWNKRYITLAPIATVLGLAFKLSDPEKLLGGAEDLGITCALIPTTTPGVEIGRRHFP<br>LNVPFQNGPTRGKDVFVPIDYIIGGPKMAGQGWRMLVECLSVGRGITLPSNSTGGVKSVALATGAYAHIRRQFKISIGKMEGI<br>EEPLARIAGNAYVMDAAASLITYGIMLGEKPAVLSAIVKYHCTHRGQQSIIDAMDITGGKGIMLGQSNFLARAYQGAPIAITV<br>EGANILTRSMMIFGQGAIRCHPYVLEEMEAAKNNDVNAFDKLLFKHIGHVGSNKVRSFWLGLTRGLTSSTPTGDATKRYYQ<br>HLNRLSANLALLSDVSMAVLGGSLKRRERISARLGDILSQLYLASAVLKRYDDEGRNEADLPLVHWGVQDALYQAEQAMD<br>DLLQNFPNRVVAGLLNVVIFPTGRHYLAPSDKLDHKVAKILQVPNATRSRIGRGQYLTPSEHNPVGLLEEALVDVIAADPIHQ<br>RICKELGKNLPFTRLDELAHNALVKGLIDKDEAAILVKAEESRLRSINVDDFDPEELATKPVKLPEKVRKVEAA |
| SEQ ID NO: 14 amino acid sequence of fadJ with the accession # NP_416843 | MEMTSAFTLNVRLDNIAVITIDVPGEKMNTLKAEFASQVRAIIKQLRENKELRGVVFVSAKPDNFIAGADINMIGNCKTAQE<br>AEALARQGQQLMAEIHALPIQVIAAIHGACLGGGLELALACHGRVCTDDPKTVLGLPEVQLGLLPGSGGTQRLPRLIGVSTA<br>LEMILTGKQLRAKQALKLGLVDDVVPHSILLEAAVELAKKERPSSRPLPVRERILAGPLGRALLFKMVGKKTEHKTQGNYPA<br>TERILEVVETGLAQGTSSGYDAEARAFGELAMTPQSQALRSIFFASTDVKKDPGSDAPPAPLNSVGILGGGLMGGGIAYVTA<br>CKAGIPVRIKDINPQGINHALKYSWDQLEGKVRRRHLKASERDKQLALISGTTDYRGFAHRDLIIEAVFENLELKQQMVAEV<br>EQNCAAHTIFASNTSSLPIGDIAAHATRPEQVIGLHFFSPVEKMPLVEIIPHAGTSAQTIATTVKLAKKQGKTPIVVRDKAGFY<br>VNRILAPYINEAIRMLTQGERVEHIDAALVKFGFPVGPIQLLDEVGIDTGTKIIPVLEAAYGERFSAPANVVSSILNDDRKGRK<br>NGRGFYLYGQKGRKSKKQVDPAIYPLIGTQGQGRISAPQVAERCVMLMLNEAVRCVDEQVIRSVRDGDIGAVFGIGFPPFLG<br>GPFRYIDSLGAGEVVAIMQRLATQYGSRFTPCERLVEMGARGESFWKTTATDLQ |
| SEQ ID NO: 15 amino acid sequence of FG99_15380 with the accession # KES23458 | MNQQVNVAPSAAADLNLKAHWMPFSANRNFHKDPRIIVAAEGSWLVDDKGRRIYDSLSGLWTCGAGHSRKEIADAVAKQI<br>GTLDYSPGFQYGHPLSFQLAEKIAQMTPGTLDHVFFTGSGSECADTSIKMARAYWRIKGQAQKTKLIGRARGYHGVNVAGT<br>SLGGIGGNRKMFGPLMDVDHLPHTLQPGMAFTKGAAETGGVELANELLKLIELHDASNIAAVIVEPMSGSAGVIVPPKGYLQ<br>RLREICDANDILLIFDEVITAFGRMGKATGAEYFGVTPDIMNVAKQVTNGAVPMGAVIASSEIYDTFMNQNLPEYAVEFGHG<br>YTYSAHPVACAAGIAALDLLQKENLIQQSAELAPHFEKALHGLKGTKNVIDIRNCGLAGAIQIAARDGDAIVRPFEASMKLW<br>KEGFYVRFGGDTLQFGPTFNAKPEDLDRLFDAVGEALNGVA |
| SEQ ID NO: 16 amino acid sequence of FG99_15380 optimized for *E.coli* with the accession # KES23458 | MNQQVNVAPSAAADLNLKAHWMPFSANRNFHKDPRIIVAAEGSWLVDDKGRRIYDSLSGLWTCGAGHSRKEIADAVAKQI<br>GTLDYSPGFQYGHPLSFQLAEKIAQMTPGTLDHVFFTGSGSECADTSIKMARAYWRIKGQAQKTKLIGRARGYHGVNVAGT<br>SLGGIGGNRKMFGPLMDVDHLPHTLQPGMAFTKGAAETGGVELANELLKLIELHDASNIAAVIVEPMSGSAGVIVPPKGYLQ<br>RLREICDANDILLIFDEVITAFGRMGKATGAEYFGVTPDIMNVAKQVTNGAVPMGAVIASSEIYDTFMNQNLPEYAVEFGHG<br>YTYSAHPVACAAGIAALDLLQKENLIQQSAELAPHFEKALHGLKGTKNVIDIRNCGLAGAIQIAARDGDAIVRPFEASMKLW<br>KEGFYVRFGGDTLQFGPTFNAKPEDLDRLFDAVGEALNGVA |
| SEQ ID NO: 17 amino acid sequence of GabD with the accession # NP_417147 | MKLNDSNLFRQQALINGEWLDANNGEAIDVTNPANGDKLGSVPKMGADETRAAIDAANRALPAWRALTAKERATILRNW<br>FNLMMEHQDDLARLMTLEQGKPLAEAKGEISYAASFIEWFAEEGKRIYGDTIPGHQADKRLIVIKQPIGVTAAITPWNFPAA<br>MITRKAGPALAAGCTMVLKPASQTPFSALALAELAIRAGVPAGVFNVVTGSAGAVGNELTSNPLVRKLSFTGSTEIGRQLME<br>QCAKDIKKVSLELGGNAPFIVFDDADLDKAVEGALASKFRNAGQTCVCANRLYVQDGVYDRFAEKLQQAVSKLHIGDGLD<br>NGVTIGPLIDEKAVAKVEEHIADALEKGARVVCGGKAHERGGNFFQPTILVDVPANAKVSKEETFGPLAPLFRFKDEADVIA<br>QANDTEFGLAAYFYARDLSRVFRVGEALEYGIVGINTGIISNEVAPFGGIKASGLGREGSKYGIEDYLEIKYMCIGL |
| SEQ ID NO: 18 amino acid sequence of gabT with the accession # NP_417148 | MNSNKELMQRRSQAIPRGVGQIHPIFADRAENCRVWDVEGREYLDFAGGIAVLNTGHLHPKVVAAVEAQLKKLSHTCFQV<br>LAYEPYLELCEIMNQKVPGDFAKKTLLVTTGSEAVENAVKIARAATKRSGTIAFSGAYHGRTHYTLALTGKVNPYSAGMGL<br>MPGHVYRALYPCPLHGISEDDAIASIHRIFKNDAAPEDIAAIVIEPVQGEGGFYASSPAFMQRLRALCDEHGIMLIADEVQSGA<br>GRTGTLFAMEQMGVAPDLTTFAKSIAGGFPLAGVTGRAEVMDAVAPGGLGGTYAGNPIACVAALEVLKVFEQENLLQKAN<br>DLGQKLKDGLLAIAEKHPEIGDVRGLGAMIAIELFEDGDHNKPDAKLTAEIVARARDKGLILLSCGPYYNVLRILVPLTIEDA<br>QIRQGLEIISQCFDEAKQ |
| SEQ ID NO: 19 amino acid sequence of Gad with accession # | MVLSHAVSESDVSVHSTFASRYVRTSLPRFKMPENSIPKEAAYQIINDELMLDGNPRLNLASFVTTWMEPECDKLIMSSINKN<br>YVDMDEYPVTTELQNRCVNMIAHLFNAPLEEAETAVGVGTVGSSEAIMLAGLAFKRKWQNKRKAEGKPVDKPNIVTGANV<br>QVCWEKFARYFEVELKEVKLSEGYYVMDPQQAVDMVDENTICVADILGSTLNGEFEDVKLLNDLLVEKNKETGWDTPIHV<br>DAASGGFIAPFLYPELEWDFRLPLVKSINVSGHKYGLVYAGIGWVIWRNKEDLPEELIFHINYLGADQPTFTLNFSKGSSQVIA |

TABLE 1-continued

| Amino Acid Sequences | |
|---|---|
| SEQ ID NO | Amino Acid Sequence |
| U10034 | QYYQLIRLGHEGYRNVMENCRENMIVLREGLEKTERFNIVSKDEGVPLVAFSLKDSSCHTEFEISDMLRRYGWIVPAYTMPP NAQHITVLRVVIREDFSRTLAERLVIDIEKVMRELDELPSRVIHKISLGQEKSESNSDNLMVTVKKSDIDKQRDIITGWKKFVA DRKKTSGIC |
| SEQ ID NO: 20 amino acid sequence of GadAe | MDQKLLTDFRSELLDSRFGAKAISTIAESKRFPLHEMRDDVAFQIINDELYLDGNARQNLATFCQTWDDENVHKLMDLSINK NWIDKEQYPQSAAIDLRCVNMVADLWHAPAPKNGQAVGTNTIGSSEACMLGGMAMKWRWRKRMEAAGKPTDKPNLVC GPVQICWHKFARYWDVELREIPMRPGQLFMDPKRMIEACDENTIGVVPTFGVTYTGNYEFPQPLHDALDKFQADTGIDIDM HIDAASGGFLAPFVAPDIVWDFRLPRVKSISASGHKFGLAPLGCGWVIWRDEEALPQELVFNVDYLGGQIGTFAINFSRPAGQ VIAQYYEFLRLGREGYTKVQNASYQVAAYLADEIAKLGPYEFICTGRPDEGIPAVCFKLKDGEDPGYTLYDLSERLRLRGWQ VPAFTLGGEATDIVVMRIMCRRGFEMDFAELLLEDYKASLKYLSDH |
| SEQ ID NO: 21 amino acid sequence of ghrB with the accession # NP_418009 | MKPSVILYKALPDDLLQRLQEHFTVHQVANLSPQTVEQNAAIFAEAEGLLGSNENVNAALLEKMPKLRATSTISVGYDNFD VDALTARKILLMHTPTVLTETVADTLMALVLSTARRVVEVAERVKAGEWTASIGPDWYGTDVHHKTLGIVGMGRIGMALA QRAHFGFNMPILYNARRHHKEAEERFNARYCDLDTLLQESDFVCLILPLTDETHHLFGAEQFAKMKSSAIFINAGRGPVVDE NALIAALQKGEIHAAGLDVFEQEPLSVDSPLLSMANVVAVPHIGSATHETRYGMAACAVDNLIDALQGKVEKNCVNPHVA D |
| SEQ ID NO: 22 amino acid sequence of H16_RS27940 with the accession # WP_011617503 | MYAAKDITVEERAGGALWITIDRAQKHNALARHVLAGLAQVVSAAAAQPGVRCIVLTGAGQRFFAAGGDLVELSGVRDRE ATLAMSEQARGALDAVRDCPLPVLAYLNGDAIGGGAELALACDMRLQSASARIGFIQARLAITSAWGGGPDLCRIVGAARA MRMMSRCELVDAQQALQWGLADAVVTDGPAGKDIHAFLQPLLGCAPQVLRGIKAQTAASRRGESHDAARTIEQQQLLHT WLHADHWNAAEGILSRRAQ |
| SEQ ID NO: 23 amino acid sequence of Hbd with the accession # NP_349314 | MKKVCVIGAGTMGSGIAQAFAAKGFEVVLRDIKDEFVDRGLDFINKNLSKLVKKGKIEEATKVEILTRISGTVDLNMAADCD LVIEAAVERMDIKKQIFADLDNICKPETILASNTSSLSITEVASATKRPDKVIGMHFFNPAPVMKLVEVIRGIATSQETFDAVKE TSIAIGKDPVEVAEAPGFVVNRILIPMINEAVGILAEGIASVEDIDKAMKLGANHPMGPLELGDFIGLDICLAIMDVLYSETGD SKYRPHTLLKKYVRAGWLGRKSGKGFYDYSK |
| SEQ ID NO: 24 amino acid sequence of iclR with the accession # NP_418442 | MVAPIPAKRGRKPAVATAPATGQVQSLTRGLKLLEWIAESNGSVALTELAQQAGLPNSTTHRLLTTMQQQGFVRQVGELGH WAIGAHAFMVGSSFLQSRNLLAIVHPILRNLMEESGETVNMAVLDQSDHEAIIIDQVQCTHLMRMSAPIGGKLPMHASGAG KAFLAQLSEEQVTKLLHRKGLHAYTHATLVSPVHLKEDLAQTRKRGYSFDDEEHALGLRCLAACIFDEHREPFAAISISGPIS RITDDRVTEFGAMVIKAAKEVTLAYGGMR |
| SEQ ID NO: 25 amino acid sequence of lacI with the accession # NP_414879 | MKPVTLYDVAEYAGVSYQTVSRVVNQASHVSAKTREKVEAAMAELNYIPNRVAQQLAGKQSLLIGVATSSLALHAPSQIV AAIKSRADQLGASVVVSMVERSGVEACKAAVHNLLAQRVSGLIINYPLDDQDAIAVEAACTNVPALFLDVSDQTPINSIIFSH EDGTRLGVEHLVALGHQQIALLAGPLSSVSARLRLAGWHKYLTRNQIQPIAEREGDWSAMSGFQQTMQMLNEGIVPTAML VANDQMALGAMRAITESGLRVGADISVVGYDDTEDSSCYIPPLTTIKQDFRLLGQTSVDRLLQLSQGQAVKGNQLLPVSLVK RKTTLAPNTQTASPRALADSLMQLARQVSRLESGQ |
| SEQ ID NO: 26 amino acid sequence of LvaE with the accession # NP_744939 | MMVPTLEHELAPNEANHVPLSPLSFLKRAAQVYPQRDAVIYGARRYSYRQLHERSRALASALERVGVQPGERVAILAPNIPE MLEAHYGVPGAGAVLVCINIRLEGRSIAFILRHCAAKVLICDREFGAVANQALAMLDAPPLLVGIDDDQAERADLAHDLDY EAFLAQGDPARPLSAPQNEWQSIAINYTSGTTGDPKGVVLHHRGAYLNACAGALIFQLGPRSVYLWTLPMFHCNGWSHTW AVTLSGGTHVCLRKVQPDAINAAIAEHAVTHLSAAPVVMSMLIHAEHASAPPVPVSVITGGAAPPSAVIAAMEARGFNITHA YGMTESYGPSTLCLWQPGVDELPLEARAQFMSRQGVAHPLLEEATVLDTDTGRPVPADGLTLGELVVRGNTVMKGYLHNP EATRAALANGWLHTGDLAVLHLDGYVEIKDRAKDIIISGGENISSLEIEEVLYQHPEVVEAAVVARPDSRWGETPHAFVTLR ADALASGDDLVRWCRERLAHFKAPRHVSLVDLPKTATGKIQKFVLREWARQQEAQIADAEH |
| SEQ ID NO: 28 amino acid sequence of MELS_RS10970 with the accession # WP_014017064 | MDFNLTDIQQDFLKLAHDFGEKKLAPTVTERDHKGIYDKELIDELLSLGITGAYFEEKYGGSGDDGGDVLSYILAVEELAKY DAGVAITLSATVSLCANPIWQFGTEAQKEKFLVPLVEGTKLGAFGLTEPNAGTDASGQQTIATKNDDGTYTLNGSKIFITNGG AADIYIVFAMTDKSKGNHGITAFILEDGTPGFTYGKKEDKMGIHTSQTMELVFQDVKVPAENMLGEEGKGFKIAMMTLDGG RIGVAAQALGIAEAALADAVEYSKQRVQFGKPLCKFQSISFKLADMKMQIEAARNLVYKAACKKQEGKPFTVDAAIAKRV ASDVAMRVTTEAVQIFGGYGYSEEYPVARHMRDAKITQIYEGTNEVQLMVTGGALLR |
| SEQ ID NO: 29 amino acid sequence of PaaZ with the accession # NP_415905 | MQQLASFLSGTWQSGRGRSRLIHHAISGEALWEVTSEGLDMAAARQFAIEKGAPALRAMTFIERAAMLKAVAKHLLSEKER FYALSAQTGATRADSWVDIEGGIGTLFTYASLGSRELPDDTLWPEDELIPLSKEGGFAARHLLTSKSGVAVHINAFNFPCWG MLEKLAPTWLGGMPAIIKPATATAQLTQAMVKSIVDSGLVPEGAISLICGSAGDLLDHLDSQDVVTFTGSAATGQMLRVQP NIVAKSIPFTMEADSLNCCVLGEDVTPDQPEFALFIREVVREMTTKAGQKCTAIRRIIVPQALVNAVSDALVARLQKVVVGDP AQEGVKMGALVNAEQRADVQEKVNILLAAGCEIRLGGQADLSAAGAFFPPTLLYCPQPDETPAVHATEAFGPVATLMPAQ NQRHALQLACAGGGSLAGTLVTADPQIARQFIADAARTHGRIQILNEESAKESTGHGSPLPQLVHGGPGRAGGGEELGGLRA VKHYMQRTAVQGSPTMLAAISKQWVRGAKVEEDRIHPFRKYFEELQPGDSLLTPRRTMTEADIVNFACLSGDHFYAHMDKI AAAESIFGERVVHGYFVLSAAAGLFVDAGVGPVIANYGLESLRFIEPVKPGDTIQVRLTCKRKTLKKQRSAEEKPTGVVEWA VEVFNQHQTPVALYSILTLVARQHGDFVD |
| SEQ ID NO: 30 amino acid sequence of | MRKVPIITADEAAKLIKDGDTVTTSGFVGNAIPEALDRAVEKRFLETGEPKNITYVYCGSQGNRDGRGAEHFAHEGLLKRYI AGHWATVPALGKMAMENKMEAYNVSQGALCHLFRDIASHKPGVFTKVGIGTFIDPRNGGGKVNDITKEDIVELVEIKGQEY LFYPAFPIHVALIRGTYADESGNITFEKEVAPLEGTSVCQAVKNSGGIVVVQVERVVKAGTLDPRHVKVPGIYVDYVVVADP |

TABLE 1-continued

| Amino Acid Sequences | |
|---|---|
| SEQ ID NO | Amino Acid Sequence |
| Pct(Cp) with the accession # WP_066048121 | EDHQQSLDCEYDPALSGEHRRPEVVGEPLPLSAKKVIGRRGAIELEKDVAVNLGVGAPEYVASVADEEGIVDFMTLTAESGA IGGVPAGGVRFGASYNADALIDQGYQFDYYDGGGLDLCYLGLAECDEKGNINVSRFGPRIAGCGGFINITQNTPKVFFCGTF TAGGLKVKIEDGKVIIVQEGKQKKFLKAVEQITFNGDVALANKQQVTYITERCVFLLKEDGLHLSEIAPGIDLQTQILDVMDF APIIDRDANGQIKLMDAALFAEGLMGLKEMKS |
| SEQ ID NO: 31 amino acid sequence of Pct(Me) with the accession # WP_014015705 | MRKVEIITAEQAAQLVKDNDTITSIGFVSSAHPEALTKALEKRFLDTNTPQNLTYIYAGSQGKRDGRAAEHLAHTGLLKRAII GHWQTVPAIGKLAVENKIEAYNFSQGTLVHWFRALAGHKLGVFTDIGLETFLDPRQLGGKLNDVTKEDLVKLIEVDGHEQL FYPTFPVNVAFLRGTYADESGNITMDEEIGPFESTSVAQAVHNCGGKVVVQVKDVVAHGSLDPRMVKIPGIYVDYVVVAAP EDHQQTYDCEYDPSLSGEHRAPEGATDAALPMSAKKIIGRRGALELTENAVVNLGVGAPEYVASVAGEEGIADTITLTVEGG AIGGVPQGGARFGSSRNADAIIDHTYQFDFYDGGGLDIAYLGLAQCDGSGNINVSKFGTNVAGCGGFPNISQQTPNVYFCGT FTAGGLKIAVEDGKVKILQEGKAKKFIKAVDQITFNGSYAARNGKHVLYITERCVFELTKEGLKLIEVAPGIDIEKDILAHMD FKPIIDNPKLMDARLFQDGPMGLKK |
| SEQ ID NO: 32 amino acid sequence of PduP(Kp) with the accession # AEW62977 | MNTAELETLIRTILSEKLAPTPPAPQQEQGIFCDVGSAIDAAHQAFLRYQQCPLKTRSAIISALRETLAPELATLAEESATETGM GNKEDKYLKNKAALENTPGIEDLTTSALTGDGGMVLFEYSPFGVIGAVAPSTNPTETIINNSISMLAAGNSVYFSPHPGAKKV SLKLIARIEEIAYRCSGIRNLVVTVAEPTFEATQQMMSHPLIAVLAITGGPGIVAMGMKSGKKVIGAGAGNPPCIVDETADLV KAAEDIISGAAFDYNLPCIAEKSLIVVASVADRLIQQMQDFDALLLSRQEADTLRTVCLPDGAANKKLVGKSPAALLAAAGL AVPPRPPRLLIAEVEANDPWVTCEQLMPVLPIVRVADFDSALALALRVEEGLHHTAIMHSQNVSRLNLAARTLQTSIFVKNG PSYAGIGVGGEGFTTFTIATPTGEGTTSARTFARLRRCVLTNGFSIR |
| SEQ ID NO: 33 amino acid sequence of PduP(Se) with the accession # NP_460996 | MNTSELETLIRTILSEQLTTPAQTPVQPQGKGIFQSVSEAIDAAHQAFLRYQQCPLKTRSAIISAMRQELTPLLAPLAEESANET GMGNKEDKFLKNKAALDNTPGVEDLTTTALTGDGGMVLFEYSPFGVIGSVAPSTNPTETIINNSISMLAAGNSIYFSPHPGAK KVSLKLISLIEEIAFRCCGIRNLVVTVAEPTFEATQQMMAHPRIAVLAITGGPGIVAMGMKSGKKVIGAGAGNPPCIVDETAD LVKAAEDIINGASFDYNLPCIAEKSLIVVESVAERLVQQMQTFGALLLSPADTDKLRAVCLPEGQANKKLVGKSPSAMLEAA GIAVPAKAPRLLIALVNADDPWVTSEQLMPMLPVVKVSDFDSALALALKVEEGLHHTAIMHSQNVSRLNLAARTLQTSIFV KNGPSYAGIGVGGEGFTTFTIATPTGEGTTSARTFARSRRCVLTNGFSIR |
| SEQ ID NO: 34 amino acid sequence of PhaA with the accession # WP_010810132 | MTDVVIVSAARTAVGKFGGSLAKIPAPELGAVVIKAALERAGVKPEQVSEVIMGQVLTAGSGQNPARQAAIKAGLPAMVPA MTINKVCGSGLKAVMLAANAIMAGDAEIVVAGGQENMSAAPHVLPGSRDGFRMGDAKLVDTMIVDGLWDVYNQYHMGI TAENVAKEYGITREAQDEFAVGSQNKAEAAQKAGKFDEEIVPVLIPQRKGDPVAFKTDEFVRQGATLDSMSGLKPAFDKAG TVTAANASGLNDGAAAVVVMSAAKAKELGLTPLATIKSYANAGVDPKVMGMGPVPASKRALSRAEWTPQDLDLMEINEA FAAQALAVHQQMGWDTSKVNVNGGAIAIGHPIGASGCRILVTLLHEMKRRDAKKGLASLCIGGGMGVALAVERK |
| SEQ ID NO: 35 amino acid sequence of PhaB with the accession # WP_010810131 | MTQRIAYVTGGMGGIGTAICQRLAKDGFRVVAGCGPNSPRREKWLEQQKALGFDFIASEGNVADWDSTKTAFDKVKSEVG EVDVLINNAGITRDVVFRKMTRADWDAVIDTNLTSLFNVTKQVIDGMADRGWGRIVNISSVNGQKGQFGQTNYSTAKAGL HGFTMALAQEVATKGVTVNTVSPGYIATDMVKAIRQDVLDKIVATIPVKRLGLPEEIASICAWLSSEESGFSTGADFSLNGGL HMG |
| SEQ ID NO: 36 amino acid sequence of PhaC with the accession # WP_011615085 | MATGKGAAASTQEGKSQPFKVTPGPFDPATWLEWSRQWQGTEGNGHAAASGIPGLDALAGVKIAPAQLGDIQQRYMKDFS ALWQAMAEGKAEATGPLHDRRFAGDAWRTNLPYRFAAAFYLLNARALTELADAVEADAKTRQRIRFAISQWVDAMSPAN FLATNPEAQRLLIESGGESLRAGVRNMMEDLTRGKISQTDESAFEVGRNVAVTEGAVVFENEYFQLLQYKPLTDKVHARPL LMVPPCINKYYILDLQPESSLVRHVVEQGHTVFLVSWRNPDASMAGSTWDDYIEHAAIRAIEVARDISGQDKINVLGFCVGG TIVSTALAVLAARGEHPAASVTLLTTLLDFADTGILDVFVDEGHVQLREATLGGGAGAPCALLRGLELANTFSFLRPNDLVW NYVVDNYLKGNTPVPFDLLFWNGDATNLPGPWYCWYLRHTYLQNELKVPGKLTVCGVPVDLASIDVPTYIYGSREDHIVP WTAAYASTALLANKLRFVLGASGHIAGVINPPAKNKRSHWTNDALPESPQQWLAGAIEHHGSWWPDWTAWLAGQAGAK RAAPANYGNARYRAIEPAPGRYVKAKA |
| SEQ ID NO: 37 amino acid sequence of PhaJ with the accession # WP_042016563 | MSTQTLAVGQKARLTKRFGPAEVAAFAGLSEDFNPLHLDPDFAATTVFERPIVHGMLLASLFSGLLGQQLPGKGSIYLGQSL GFKLPVFVGDEVTAEVEVIALRSDKPIATLATRIFTQGGALAVTGEAVVKLP |
| SEQ ID NO: 38 amino acid sequence of PP_2216 with the accession # NP_744365 | MLVNDEQQQIADAVRAFAQERLKPFAEQWDKDHRFPKEAIDEMAELGLFGMLVPEQWGGSDTGYVAYAMALEEIAAGDG ACSTIMSVHNSVGCVPILRFGNEQQKEQFLTPLATGAMLGAFALTEPQAGSDASSLKTRARLEGDHYVLNGSKQFITSGQNA GVVIVFAVTDPEAGKRGISAFIVPTDSPGYQVARVEDKLGQHASDTCQIVFDNVQVPVANRLGAEGEGYKIALANLEGGRIG IASQAVGMARAAFEVARDYANERQSFGKPLIEHQAVAFRLADMATKISVARQMVLHAAALRDAGRPALVEASMAKLFASE MAEKVCSDALQTLGGYGYLSDFPLERIYRDVRVCQIYEGTSDIQRMVIARNL |
| SEQ ID NO: 40 amino acid sequence of PrpB with the accession # NP_414865 | MSLHSPGKAFRAALTKENPLQIVGTINANHALLAQRAGYQAIYLSGGGVAAGSLGLPDLGISTLDDVLTDIRRITDVCSLPLL VDADIGFGSSAFNVARTVKSMIKAGAAGLHIEDQVGAKRCGHRPNKAIVSKEEMVDRIRAAVDAKTDPDFVIMARTDALAV EGLDAAIERAQAYVEAGAEMLFPEAITELAMYRQFADAVQVPILANITEFGATPLFTTDELRSAHVAMALYPLSAFRAMNRA AEHVYNVLRQEGTQKSVIDTMQTRNELYESINYYQYEEKLDNLFARSQVK |
| SEQ ID NO: 41 amino acid sequence of | MSDTTILQNSTHVIKPKKSVALSGVPAGNTALCTVGKSGNDLHYRGYDILDLAKHCEFEEVAHLLIHGKLPTRDELAAYKTK LKALRGLPANVRTVLEALPAASHPMDVMRTGVSALGCTLPEKEGHTVSGARDIADKLLASLSSILLYWYHYSHNGERIQPET DDDSIGGHFLHLLHGEKPSQSWEKAMHISLVLYAEHEFNASTFTSRVIAGTGSDMYSAIIGAIGALRGPKHGGANEVSLEIQQ |

TABLE 1-continued

| Amino Acid Sequences | |
|---|---|
| SEQ ID NO | Amino Acid Sequence |
| PrpC with the accession # NP_414867 | RYETPDEAEADIRKRVENKEVVIGFGHPVYTIADPRHQVIKRVAKQLSQEGGSLKMYNIADRLETVMWESKKMFPNLDWFS AVSYNMMGVPTEMFTPLFVIARVTGWAAHIIEQRQDNKIIRPSANYVGPEDRPFVALDKRQ |
| SEQ ID NO: 42 amino acid sequence of PrpD with the accession # NP_414868 | MSAQINNIRPEFDREIVDIVDYVMNYEISSKVAYDTAHYCLLDTLGCGLEALEYPACKKLLGPIVPGTVVPNGVRVPGTQFQL DPVQAAFNIGAMIRWLDFNDTWLAAEWGHPSDNLGGILATADWLSRNAVASGKAPLTMKQVLTAMIKAHEIQGCIALENS FNRVGLDHVLLVKVASTAVVAEMLGLTREEILNAVSLAWVDGQSLRTYRHAPNTGTRKSWAAGDATSRAVRLALMAKTG EMGYPSALTAPVWGFYDVSFKGESFRFQRPYGSYVMENVLFKISFPAEFHSQTAVEAAMTLYEQMQAAGKTAADIEKVTIR THEACIRIIDKKGPLNNPADRDHCIQYMVAIPLLFGRLTAADYEDNVAQDKRIDALREKINCFEDPAFTADYHDPEKRAIANA ITLEFTDGTRFEEVVVEYPIGHARRRQDGIPKLVDKFKINLARQFPTRQQQRILEVSLDRARLEQMPVNEYLDLYVI |
| SEQ ID NO: 43 amino acid sequence of PrpE(Cn) with the accession # WP_081225789 | MTADAEETDMTASHAVHARSLADPEGFWAEQAARIDWETPFGQVLDNSRAPFTRWFVGGRTNLCHNAVDRHLAARASQP ALHWVSTETDQARTFTYAELHDEVSRMAAILQGLDVQKGDRVLIYMPMIPEAAFAMLACARIGAIHSVVFGGFASVSLAAR IEDARPRVVVSADAGSRAGKVVPYKPLLDEAIRLSSHQPGKVLLVDRQLAQMPRTEGRDEDYAAWRERVAGVQVPCVWLE SSEPSYVLYTSGTTGKPKGVQRDTGGYAVALATSMEYIFCGKPGDTMFTASDIGWVVGHSYIVYGPLLAGMATLMYEGTPI RPDGGILWRLVEQYKVNLMFSAPTAIRVLKKQDPAWLTRYDLSSLRLLFLAGEPLDEPTARWIQDGLGKPVVDNYWQTESG WPILAIQRGIEALPPKLGSPGVPAYGYDLKIVDENTGAECPPGQKGVVAIDGPLPPGCMSTVWGDDDRFVRTYWQAVPNRL CYSTFDWGVRDADGYVFILGRTDDVINVAGHRLGTREIEESLSSNAAVAEVAVVGVQDALKGQVAMAFCIARDPARTATA EARLALEGELMKTVEQQLGAVARPARVFFVNALPKTRSGKLLRRAMQAVAEGRDPGDLTTIEDPGALEQLQAALKG |
| SEQ ID NO: 44 amino acid sequence of PrpE(Ec) with the accession # NP_414869 | MSFSEFYQRSINEPEQFWAEQARRIDWQTPFTQTLDHSNPPFARWFCEGRTNLCHNAIDRWLEKQPEALALIAVSSETEEERT FTFRQLHDEVNAVASMLRSLGVQRGDRVLVYMPMIAEAHITLLACARIGAIHSVVFGGFASHSVAARIDDAKPVLIVSADAG ARGGKIIPYKKLLDDAISQAQHQPRHVLLVDRGLAKMARVSGRDVDFASLRHQHIGARVPVAWLESNETSCILYTSGTTGKP KGVQRDVGGYAVALATSMDTIFGGKAGSVFFCASDIGWVVGHSYIVYAPLLAGMATIVYEGLPTWPDCGVWWTIVEKYQ VSRMFSAPTAIRVLKKFPTAEIRKHDLSSLEVLYLAGEPLDEPTASWVSNTLDVPVIDNYWQTESGWPIMAIARGLDDRPTRL GSPGVPMYGYNVQLLNEVTGEPCGVNEKGMLVVEGPLPPGCIQTIWGDDGRFVKTYWSLFSRPVYATFDWGIRDADGYHFI LGRTDDVINVAGHRLGTREIEESISSHPGVAEVAVVGVKDALKGQVAVAFVIPKESDSLEDRDVAHSQEKAIMALVDSQIGN FGRPAHVWFVSQLPKTRSGKMLRRTIQAICEGRDPGDLTTIDDPASLDQIRQAMEE |
| SEQ ID NO: 45 amino acid sequence of PrpE(Se) with the accession # NP_459366 | MSFSEFYQRSINEPEAFWAEQARRIDWRQPFTQTLDHSRPPFARWFCGGTTNLCHNAVDRWRDKQPEALALIAVSSETDEER TFTFSQLHDEVNIVAAMLLSLGVQRGDRVLVYMPMIAEAQITLLACARIGAIHSVVFGGFASHSVAARIDDARPALIVSADA GARGGKILPYKKLLDDAIAQAQHQPKHVLLVDRGLAKMAWVDGRDLDFATLRQQHLGASVPVAWLESNETSCILYTSGTT GKPKGVQRDVGGYAVALATSMDTIFGGKAGGVFFCASDIGWVVGHSYIVYAPLLAGMATIVYEGLPTYPDCGVWWKIVEK YQVNRMFSAPTAIRVLKKFPTAQIRNHDLSSLEALYLAGEPLDEPTASWVTETLGVPVIDNYWQTESGWPIMALARALDDRP SRLGSPGVPMYGYNVQLLNEVTGEPCGINEKGMLVIEGPLPPGCIQTIWGDDARFVKTYWSLFNRQVYATFDWGIRDAEGY YFILGRTDDVINIAGHRLGTREIEESISSYPNVAEVAVVGIKDALKGQVAVAFVIPKQSDTLADREAARDEENAIMALVDNQI GHFGRPAHVWFVSQLPKTRSGKMLRRTIQAICEGRDPGDLTTIDDPASLQQIRQAIEE |
| SEQ ID NO: 46 amino acid sequence of Pta with the accession # NP_416800 | MSRIIMLIPTGTSVGLTSVSLGVIRAMERKGVRLSVFKPIAQPRTGGDAPDQTTTIVRANSSTTTAAEPLKMSYVEGLLSSNQK DVLMEEIVANYHANTKDAEVVLVEGLVPTRKHQFAQSLNYEIAKTLNAEIVFVMSQGTDTPEQLKERIELTRNSFGGAKNT NITGVIVNKLNAPVDEQGRTRPDLSEIFDDSSKAKVNNVDPAKLQESSPLPVLGAVPWSFDLIATRAIDMARHLNATIINEGDI NTRRVKSVTFCARSIPHMLEHFRAGSLLVTSADRPDVLVAACLAAMNGVEIGALLLTGGYEMDARISKLCERAFATGLPVF MVNTNTWQTSLSLQSFNLEVPVDDHERIEKVQEYVANYINADWIESLTATSERSRRLSPPAFRYQLTELARKAGKRIVLPEG DEPRTVKAAAICAERGIATCVLLGNPAEINRVAASQGVELGAGIEIVDPEVVRESYVGRLVELRKNKGMTETVAREQLEDNV VLGTLMLEQDEVDGLVSGAVHTTANTIRPPLQLIKTAPGSSLVSSVFFMLLPEQVYVYGDCAINPDPTAEQLAEIAIQSADSA AAFGIEPRVAMLSYSTGTSGAGSDVEKVREATRLAQEKRPDLMIDGPLQYDAAVMADVAKSKAPNSPVAGRATVFIFPDLN TGNTTYKAVQRSADLISIGPMLQGMRKPVNDLSRGALVDDIVYTIALTAIQSAQQQ |
| SEQ ID NO: 47 amino acid sequence of PuuE with the accession # NP_415818 | MSNNEFHQRRLSATPRGVGVMCNFFAQSAENATLKDVEGNEYIDFAAGIAVLNTGHRHPDLVAAVEQQLQQFTHTAYQIVP YESYVTLAEKINALAPVSGQAKTAFFTTGAEAVENAVKIARAHTGRPGVIAFSGGFHGRTYMTMALTGKVAPYKIGFGPFPG SVYHVPYPSDLHGISTQDSLDAIERLFKSDIEAKQVAAIIFEPVQGEGGFNVAPKELVAAIRRLCDEHGIVMIADEVQSGFART GKLFAMDHYADKPDLMTMAKSLAGGMPLSGVVGNANIMDAPAPGGLGGTYAGNPLAVAAAHAVLNIIDKESLCERANQL GQRLKNTLIDAKESVPAIAAVRGLGSMIAVEFNDPQTGEPSAAIAQKIQQRALAQGLLLLTCGAYGNVIRFLYPLTIPDAQFD AAMKILQDALSD |
| SEQ ID NO: 48 amino acid sequence of Sbm with the accession # NP_417392 | MSNVQEWQQLANKELSRREKTVDSLVHQTAEGIAIKPLYTEADLDNLEVTGTLPGLPPYVRGPRATMYTAQPWTIRQYAGF STAKESNAFYRRNLAAGQKGLSVAFDLATHRGYDSDNPRVAGDVGKAGVAIDTVEDMKVLFDQIPLDKMSVSMTMNGAV LPVLAFYIVAAEEQGVTPDKLTGTIQNDILKEYLCRNTYTYPPKPSMRIIADIIAWCSGNMPRFNTISISGYHMGEAGANCVQQ VAFTLADGIEYIKAAISAGLKIDDFAPRLSFFFGIGMDLFMNVAMLRAARYLWSEAVSGFGAQDPKSLALRTHCQTSGWSLT EQDPYNNVIRTTIEALAATLGGTQSLHTNAFDEALGLPTDFSARIARNTQIIIQEESELCRTVDPLAGSYYIESLTDQIVKQARA IIQQIDEAGGMAKAIEAGLPKRMIEEASAREQSLIDQGKRVIVGVNKYKLDHEDETDVLEIDNVMVRNEQIASLERIRATRDD AAVTAALNALTHAAQHNENLLAAAVNAARVRATLGEISDALEVAFDRYLVPSQCVTGVIAQSYHQSEKSASEFDAIVAQTE QFLADNGRRPRILIAKMGQDGHDRGAKVIASAYSDLGFDVDLSPMFSTPEEIARLAVENDVHVVGASSLAAGHKTLIPELVE ALKKWGREDICVVAGGVIPPQDYAFLQERGVAAIYGPGTPMLDSVRDVLNLISQHHD |
| SEQ ID NO: 49 amino acid sequence of SdhA with the accession # NP_415251 | MKLPVREFDAVVIGAGGAGMRAALQISQSGQTCALLSKVFPTRSHTVSAQGGITVALGNTHEDNWEWHMYDTVKGSDYIG DQDAIEYMCKTGPEAILELEHMGLPFSRLDDGRIYQRPFGGQSKNFGGEQAARTAAAADRTGHALLHTLYQQNLKNHTTIFS EWYALDLVKNQDGAVVGCTALCIETGEVVYFKARATVLATGGAGRIYQSTTNAHINTGDGVGMAIRAGVPVQDMEMWQF HPTGIAGAGVLVTEGCRGEGGYLLNKHGERFMERYAPNAKDLAGRDVVARSIMIEIREGRGCDGPWGPHAKLKLDHLGKE VLESRLPGILELSRTFAHVDPVKEPIPVIPTCHYMMGGIPTKVTGQALTVNEKGEDVVVPGLFAVGEIACVSVHGANRLGGNS LLDLVVFGRAAGLHLQESIAEQGALRDASESDVEASLDRLNRWNNNRNGEDPVAIRKALQECMQHNFSVFREGDAMAKGL EQLKVIRERLKNARLDDTSSEFNTQRVECLELDNLMETAYATAVSANFRTESRGAHSRFDFPDRDDENWLCHSLYLPESESM TRRSVNMEPKLRPAFPPKIRTY |
| SEQ ID NO: 50 amino acid | MNLHEYQAKQLFARYGLPAPVGYACTTPREAEEAASKIGAGPWVVKCQVHAGGRGKAGGVKVVNSKEDIRAFAENWLGK RLVTYQTDANGQPVNQILVEAATDIAKELYLGAVVDRSSRRVVFMASTEGGVEIEKVAEETPHLIHKVALDPLTGPMPYQG |

TABLE 1-continued

| Amino Acid Sequences | |
|---|---|
| SEQ ID NO | Amino Acid Sequence |
| sequence of SucC with the accession # NP_415256 | RELAFKLGLEGKLVQQFTKIFMGLATIFLERDLALIEINPLVITKQGDLICLDGKLGADGNALFRQPDLREMRDQSQEDPREA QAAQWELNYVALDGNIGCMVNGAGLAMGTMDIVKLHGGEPANFLDVGGGATKERVTEAFKIILSDDKVKAVLVNIFGGIV RCDLIADGIIGAVAEVGVNVPVVVRLEGNNAELGAKKLADSGLNIIAAKGLTDAAQQVVAAVEGK |
| SEQ ID NO: 51 amino acid sequence of SucD with the accession # NP_415257 | MSILIDKNTKVICQGFTGSQGTFHSEQAIAYGTKMVGGVTPGKGGTTHLGLPVFNTVREAVAATGATASVIYVPAPFCKDSIL EAIDAGIKLIITITEGIPTLDMLTVKVKLDEAGVRMIGPNCPGVITPGECKIGIQPGHIHKPGKVGIVSRSGTLTYEAVKQTTDY GFGQSTCVGIGGDPIPGSNFIDILEMFEKDPQTEAIVMIGEIGGSAEEEAAAYIKEHVTKPVVGYIAGVTAPKGKRMGHAGAII AGGKGTADEKFAALEAAGVKTVRSLADIGEALKTVLK |
| SEQ ID NO: 52 amino acid sequence of TesB with the accession # NP_414986 | MSQALKNLLTLLNLEKIEEGLFRGQSEDLGLRQVFGGQVVGQALYAAKETVPEERLVHSFHSYFLRPGDSKKPIIYDVETLR DGNSFSARRVAAIQNGKPIFYMTASFQAPEAGFEHQKTMPSAPAPDGLPSETQIAQSLAHLLPPVLKDKFICDRPLEVRPVEF HNPLKGHVAEPHRQVWIRANGSVPDDLRVHQYLLGYASDLNFLPVALQPHGIGFLEPGIQIATIDHSMWFHRPFNLNEWLLY SVESTSASSARGFVRGEFYTQDGVLVASTVQEGVMRNHN |
| SEQ ID NO: 53 amino acid sequence of YbgC with the accession # NP_415264 | MNTTLFRWPVRVYYEDTDAGGVVYHASYVAFYERARTEMLRHHHFSQQALMAERVAFVVRKMTVEYYAPARLDDMLEI QTEITSMRGTSLVFTQRIVNAENTLLNEAEVLVVCVDPLKMKPRALPKSIVAEFKQ |
| SEQ ID NO: 54 amino acid sequence of YciA with the accession # NP_415769 | MSTTHNVPQGDLVLRTLAMPADTNANGDIFGGWLMSQMDIGGAILAKEIAHGRVVTVRVEGMTFLRPVAVGDVVCCYAR CVQKGTTSVSINIEVWVKKVASEPIGQRYKATEALFKYVAVDPEGKPRALPVE |
| SEQ ID NO: 55 amino acid sequence of YgfD with the accession # NP_417393 | MINEATLAESIRRLRQGERATLAQAMTLVESRHPRHQALSTQLLDAIMPYCGNTLRLGVTGTPGAGKSTFLEAFGMLLIREG LKVAVIAVDPSSPVTGGSILGDKTRMNDLARAEAAFIRPVPSSGHLGGASQRARELMLLCEAAGYDVVIVETVGVGQSETEV ARMVDCFISLQIAGGGDDLQGIKKGLMEVADLIVINKDDGDNHTNVAIARHMYESALHILRRKYDEWQPRVLTCSALEKRG IDEIWHAIIDFKTALTASGRLQQVRQQQSVEWLRKQTEEEVLNHLFANEDFDRYYRQTLLAVKNNTLSPRTGLRQLSEFIQTQ YFD |
| SEQ ID NO: 56 amino acid sequence of YgfG with the accession # NP_417394 | MSYQYVNVVTINKVAVIEFNYGRKLNALSKVFIDDLMQALSDLNRPEIRCIILRAPSGSKVFSAGHDIHELPSGGRDPLSYDD PLRQITRMIQKFPKPIISMVEGSVWGGAFEMIMSSDLIIAASTSTFSMTPVNLGVPYNLVGIHNLTRDAGFHIVKELIFTASPITA QRALAVGILNHVVEVEELEDFTLQMAHHISEKAPLAIAVIKEELRVLGEAHTMNSDEFERIQGMRRAVYDSEDYQEGMNAF LEKRKPNFVGH |
| SEQ ID NO: 57 amino acid sequence of YgfH with the accession # NP_417395 | METQWTRMTANEAAEIIQHNDMVAFSGFTPAGSPKALPTAIARRANEQHEAKKPYQIRLLTGASISAAADDVLSDADAVSW RAPYQTSSGLRKKINQGAVSFVDLHLSEVAQMVNYGFFGDIDVAVIEASALAPDGRVWLTSGIGNAPTWLLRAKKVIIELNH YHDPRVAELADIVIPGAPPRRNSVSIFHAMDRVGTRYVQIDPKKIVAVVETNLPDAGNMLDKQNPMCQQIADNVVTFLLQE MAHGRIPPEFLPLQSGVGNINNAVMARLGENPVIPPFMMYSEVLQESVVHLLETGKISGASASSLTISADSLRKIYDNMDYFA SRIVLRPQEISNNPEIIRRLGVIALNVGLEFDIYGHANSTHVAGVDLMNGIGGSGDFERNAYLSIFMAPSIAKEGKISTVVPMCS HVDHSEHSVKVIITEQGIADLRGLSPLQRARTIIDNCAHPMYRDYLHRYLENAPGGHIHHDLSHVFDLHRNLIATGSMLG |
| SEQ ID NO: 58 amino acid sequence of YigI with the accession # NP_418264 | MSAVLTAEQALKLVGEMFVYHMPFNRALGMELERYEKEFAQLAFKNQPMMVGNWAQSILHGGVIASALDVAAGLVCVGS TLTRHETISEDELRQRLSRMGTIDLRVDYLRPGRGERFTATSSLLRAGNKVAVARVELHNEEQLYIASATATYMVG |
| SEQ ID NO: 59 amino acid sequence of YjcS with the accession # NP_418507 | MNNSRLFRLSRIVIALTAASGMMVNTANAKEEAKAATQYTQQVNQNYAKSLPFSDRQDFDDAQRGFIAPLLDEGILRDANG KVYYYRADDYKFDINAAAPETVNPSLWRQSQINGISGLFKVTDKMYQVRGQDISNITFVEGEKGIIVIDPLVTPPAAKAALDLY FQHRPQKPIVAVIYTHSHTDHYGGVKGIISEADVKSGKVQVIAPAGFMDEAISENVLAGNIMSRRALYSYGLLLPHNAQGNV GNGLGVTLATGDPSIIAPTKTIVRTGEKMIIDGLEFDFLMTPGSEAPAEMHFYIPALKALCTAENATHTLHNFYTLRGAKTRD TSKWTEYLNETLDMWGNDAEVLFMPHTWPVWGNKHINDYIGKYRDTIKYIHDQTLHLANQGYTMNEIGDMIKLPPALAN NWASRGYYGSVSHNARAVYNFYLGYYDGNPANLHPYGQVEMGKRYVQALGGSARVINLAQEANKQGDYRWSAELLKQ VIAANPGDQVAKNLQANNFEQLGYQAESATWRGFYLTGAKELREGVHKFSHGTTGSPDTIRGMSVEMLFDFMAVRLDSAK AAGKNISLNFNMSNGDNLNLTLNDSVLNYRKTLQPQADASFYISREDLHAVLTGQAKMADLVKAKKAKIIGNGAKLEEIIA CLDNFDLWVNIVTPN |

TABLE 1-continued

| Amino Acid Sequences | |
|---|---|
| SEQ ID NO | Amino Acid Sequence |
| SEQ ID NO: 172 amino acid sequence of MELS_RS00170 with the accession number WP_041647040 | MVERKGRALIAWRCAQFFKNGDFVNLGIGLPLMCVNYLPEGVSLWLEAEIGTVGSGPSPDWNHVDIDVIDAGGQPASVITG GSVYDHETSFAFIRGGHIDATVLGTLQVDQEGNIANWTIPGKFVPGMGGAMDLCAGVKKIIVATDHCEKSGHSKILKKCTLP LTGARCVTDIVTERCYFEVTPQGLVLRELAPGYTVEDIRACTEADFIVPETIAVMGE |
| SEQ ID NO: 173 amino acid sequence of MELS_RS00175 with the accession number WP_014015004 | MLSKVFSLQDILEHIHDGQTIMFGDWHGQFAADEIIDGMLEKGVKDIKAIAVSAGYPGQGVGKLIVAHRVSSIVTTHIGLNPE ALKQMLAGELAVEFVPQGTWAERVRCGGAGLGGVLTPTGVGTSVEEGKQKLVIDGKEYLLELPLHADVALVKATKADTA GNLYFRMNSRATNSTIAYAADFVAAEVEEIVPVGQLLPEEIAIPAPVVDMVYERQGEKRFICPMWKKARARAEAKARERQE RG |
| SEQ ID NO: 176 amino acid sequence of ArcA with the accession number NP_418818 | MQTPHILIVEDELVTRNTLKSIFEAEGYDVFEATDGAEMHQILSEYDINLVIMDINLPGKNGLLLARELREQANVALMFLTGR DNEVDKILGLEIGADDYITKPFNPRELTIRARNLLSRTMNLGTVSEERRSVESYKFNGWELDINSRSLIGPDGEQYKLPRSEFR AMLHFCENPGKIQSRAELLKKMTGRELKPHDRTVDVTIRRIRKHFESTPDTPEIIATIHGEGYRFCGDLED |
| SEQ ID NO: 177 amino acid sequence of Fnr with the accession number NP_415850 | MIPEKRIIRRIQSGGCAIHCQDCSISQLCIPFTLNEHELDQLDNIIERKKPIQKGQTLFKAGDELKSLYAIRSGTIKSYTITEQG DEQITGFHLAGDLVGFDAIGSGHHPSFAQALETSMVCEIPFETLDDLSGKMPNLRQQMMRLMSGEIKGDQDMILLLSKKNAEER LAAFIYNLSRRFAQRGFSPREFRLTMTRGDIGNYLGLTVETISRLLGRFQKSGMLAVKGKYITIENNDALAQLAGHTRNVA |
| SEQ ID NO: 178 amino acid sequence of Sad with the accession number NP_416042 | MTITPATHAISINPATGEQLSVLPWAGADDIENALQLAAAGFRDWRETNIDYRAEKLRDIGKALRARSEEMAQMITREMGKP INQARAEVAKSANLCDWYAEHGPAMLKAEPTLVENQQAVIEYRPLGTILAIMPWNFPLWQVMRGAVPIILAGNGYLLKHAP NVMGCAQLIAQVFKDAGIPQGVYGWLNADNDGVSQMIKDSRIAAVTVTGSVRAGAAIGAQAGAALKKCVLELGGSDPFIV LNDADLELAVKAAVAGRYQNTGQVCAAAKRFIIEEGIASAFTERFVAAAAALKMGDPRDEENALGPMARFDLRDELHHQV EKTLAQGARLLLGGEKMAGAGNYYPPTVLANVTPEMTAFREEMFGPVAAITIAKDAEHALELANDSEFGLSATIFTTDETQA RQMAARLECGGVFINGYCASDARVAFGGVKKSGFGRELSHFGLHEFCNIQTVWKDRI |
| SEQ ID NO: 179 amino acid sequence of VqeF with the accession number NP_417321 | MKDVVIVGALRTPIGCFRGALAGHSAVELGSLVVKALIERTGVPAYAVDEVILGQVLTAGAGQNPARQSAIKGGLPNSVSAI TINDVCGSGLKALHLATQAIQCGEADIVIAGGQENMSRAPHVLTDSRTGAQLGNSQLVDSLVHDGLWDAFNDYHIGVTAEN LAREYGISRQLQDAYALSSQQKARAAIDAGRFKDEIVPVMTQSNGQTLVVDTDEQPRTDASAEGLARLNPSFDSLGSVTAG NASSINDGAAAVMMMSEAKARALNLPVLARIRAFASVGVDPALMGIAPVYATRRCLERVGWQLAEVDLIEANEAFAAQAL SVGKMLEWDERRVNVNGGAIALGHPIGASGCRILVSLVHEMVKRNARKGLATLCIGGGQGVALTIERDE |
| SEQ ID NO: 180 amino acid sequence of FadA with the accession number YP_026272 | MEQVVIVDAIRTPMGRSKGGAFRNVRAEDLSAHLMRSLLARNPALEAAALDDIYWGCVQQTLEQGFNIARNAALLAEVPH SVPAVTVNRLCGSSMQALHDAARMIMTGDAQACLVGGVEHMGHVPMSHGVDFHPGLSRNVAKAAGMMGLTAEMLARM HGISREMQDAFAARSHARAWAATQSAAFKNEIIPTGGHDADGVLKQFNYDEVIRPETTVEALATLRPAFDPVNGMVTAGTS SALSDGAAAMLVMSESRAHELGLKPRARVRSMAVVGCDPSIMGYGPVPASKLALKKAGLSASDIGVFEMNEAFAAQILPCI KDLGLIEQIDEKINLNGGAIALGHPLGCSGARISTTLLNLMERKDVQFGLATMCIGLGQGIATVFERV |
| SEQ ID NO: 181 amino acid sequence of Gcl with the accession number NP_415040 | MAKMRAVDAAMYVLEKEGITTAFGVPGAAINPFYSAMRKHGGIRHILARHVEGASHMAEGYTRATAGNIGVCLGTSGPAG TDMITALYSASADSIPILCITGQAPRARLHKEDFQAVDIEAIAKPVSKMAVTVREAALVPRVLQQAFHLMRSGRPGPVLVDLP FDVQVAEIEFDPDMYEPLPVYKPAASRMQIEKAVEMLIQAERPVIVAGGGVINADAAALLQQFAELTSVPVIPTLMGWGCIP DDHELMAGMVGLQTAHRYGNATLLASDMVFGIGNRFANRHTGSVEKYTEGRKIVHIDIEPTQIGRVLCPDLGIVSDAKAAL TLLVEVAQEMQKAGRLPCRKEWVADCQQRKRTLLRKTHFDNVPVKPQRVYEEMNKAFGRDVCYVTTIGLSQIAAAQMLH VFKDRHWINCGQAGPLGWTIPAALGVCAADPKRNVVAISGDFDFQFLIEELAVGAQFNIPYIHVLVNNAYLGLIRQSQRAFD MDYCVQLAFENINSSEVNGYGVDHVKVAEGLGCKAIRVFKPEDIAPAFEQAKALMAQYRVPVVVEVILERVTNISMGSELD NVMEFEDIADNAADAPTETCFMHYE |
| SEQ ID NO: 182 amino acid sequence of AtoB with the accession number NP_416728 | MKNCVIVSAVRTAIGSFNGSLASTSAIDLGATVIKAAIERAKIDSQHVDEVIMGNVLQAGLGQNPARQALLKSGLAETVCGF TVNKVCGSGLKSVALAAQAIQAGQAQSIVAGGMENMSLAPYLLDAKARSGYRLGDGQVYDVILRDGLMCATHGYHMGIT AENVAKEYGITREMQDELALHSQRKAAAAIESGAFTAEIVPVNVVTRKKTFVFSQDEFPKANSTAEALGALRPAFDKAGTVT AGNASGINDGAAALVIMEESAALAAGLTPLARIKSYASGGVPPALMGMGPVPATQKALQLAGLQLADIDLIEANEAFAAQF LAVGKNLGFDSEKVNVNGGAIALGHPIGASGARILVTLLHAMQARDKTLGLATLCIGGGQGIAMVIERLN |

TABLE 1-continued

| Amino Acid Sequences | |
|---|---|
| SEQ ID NO | Amino Acid Sequence |
| SEQ ID NO: 183 amino acid sequence of TesA with the accession number NP_415027 | MMNFNNVFRWHLPFLFLVLLTFRAAAADTLLILGDSLSAGYRMSASAAWPALLNDKWQSKTSVVNASISGDTSQQGLARL PALLKQHQPRWVLVELGGNDGLRGFQPQQTEQTLRQILQDVKAANAEPLLMQIRLPANYGRRYNEAFSAIYPKLAKEFDVP LLPFFMEEVYLKPQWMQDDGIHPNRDAQPFIADWMAKQLQPLVNHDS |
| SEQ ID NO: 184 amino acid sequence of Ald with the accession number WP_012059995.1 | MNKDTLIPTTKDLKVKTNGENINLKNYKDNSSCFGVFENVENAISSAVHAQKILSLHYTKEQREKIITEIRKAALQNKEVLAT MILEETHMGRYEDKILKHELVAKYTPGTEDLTTTAWSGDNGLTVVEMSPYGVIGAITPSTNPTETVICNSIGMIAAGNAVVF NGHPCAKKCVAFAVEMINKAIISCGGPENLVTTIKNPTMESLDAIIKHPSIKLLCGTGGPGMVKTLLNSGKKAIGAGAGNPPVI VDDTADIEKAGRSIIEGCSFDNNLPCIAEKEVFVFENVADDLISNMLKNNAVIINEDQVSKLIDLVLQKNNETQEYFINKKWV GKDAKLFLDEIDVESPSNVKCIICEVNANHPFVMTELMMPILPIVRVKDIDEAIKYAKIAEQNRKHSAYIYSKNIDNLNRFEREI DTTIFVKNAKSFAGVGYEAEGFTTFTIAGSTGEGITSARNFTRQRRCVLAG |
| SEQ ID NO: 194 amino acid sequence of GadBe(Ec) | MDKKQVTDLRSELLDSRFGAKSISTIAESKRFPLHEMRDDVAFQIINDELYLDGNARQNLATFCQTWDDENVHKLMDLSINK NWIDKEEQYPQSAAIDLRCVNMVADLWHAPAPKNGQAVGTNTIGSSEACMLGGMAMKWRWRKRMEAAGKPTDKPNLVC GPVQICWHKFARYWDVELREIPMRPGQLFMDPKRMIEACDENTIGVVPTFGVTYTGNYEFPQPLHDALDKFQADTGIDIDM HIDAASGGFLAPFVAPDIVWDFRLPRVKSISASGHKFGLAPLGCGWVIWRDEEALPQELVFNVDYLGGQIGTFAINFSRPAGQ VIAQYYEFLRLGREGYTKVQNASYQVAAYLADEIAKLGPYEFICTGRPDEGIPAVCFKLKDGEDPGYTLYDLSERLRLRGWQ VPAFTLGGEATDIVVMRIMCRRGFEMDFAELLLEDYKASLKYLSDH |
| SEQ ID NO: 195 amino acid sequence of PutP with the accession number NP_415535.1 | MAISTPMLVTFCVYIFGMILIGFIAWRSTKNFDDYILGGRSLGPFVTALSAGASDMSGWLLMGLPGAVFLSGISESWIAIGLTL GAWINWKLVAGRLRVHTEYNNNALTLPDYFTGRFEDKSRILRIISALVILLFFTIYCASGIVAGARLFESTFGMSYETALWAG AAATILYTFIGGFLAVSWTDTVQASLMIFALILTPVIVIISVGGFGDSLEVIKQKSIENVDMLKGLNFVAIISLMGWGLGYFGQP HILARFMAADSHHSIVHARRISMTWMILCLAGAVAVGFFGIAYFNDHPALAGAVNQNAERVFIELAQILFNPWIAGILLSAIL AAVMSTLSCQLLVCSSAITEDLYKAFLRKHASQKELVWVGRVMVLVVALVAIALAANPENRVLGLVSYAWAGFGAAFGPV VLFSVMWSRMTRNGALAGMIIGALTVIVWKQFGWLGLYEIIPGFIFGSIGIVVFSLLGKAPSAAMQKRFAEADAHYHSAPPSR LQES |
| SEQ ID NO: 196 amino acid sequence of PhaJ(Aa) with the accession number CAI08632.1 | MSEAVRDFSQCYGHDFEDLKVGMSAAIGRTVTEADIAIFAGISGDTNPVHLDAEFAASTMFGERIAHGMLSASFISAVFGTKL PGPGCIYLGQSLNFKASVKVGETVVARVTVRELVAHKRRAFFDTVCTVAGKVVLEGHAEIYLPARQ |
| SEQ ID NO: 197 amino acid sequence of IntF with the accession number NP_414815.1 | MFIPSIYLHQQLHYCKTAILNWSRKMALSRQKFTFERLRRFTLPEGKKQTFLWDADVTTLACRATSGAKAFVFQSVYAGKT LRMTIGNINDWKIDDARAEARRLQTLIDTGIDPRIAKAVKIAEAESLQAESRKTKVTFSVAWEDYLQELRTGISAKTKRPYST RYIADHINLSSRGGESKKRGQGPTSAGPLASLLNLPLSELTPDYIAAWLSTERQNRPTVTAHAYRLLRAFIKWSNYQKKYQGI IPGDLAQDYNVRKMVPVSASKADDCLQKEQLKSWFSAVRSLNNPIASAYLQVLLLTGARREEIASLRWSDVDFKWSSMRIK DKIEGERIIPLTPYVSELLNVLAQSPNSDVNKEGWVFRSNSKSGKIIEPRSAHNRALVLAELPHISLHGLRRSFGTLAEWVEVP TGIVAQIMGHKPSALAEKHYRRRPLDLLRKWHEKIETWILNEAGITIKNNVDMR |
| SEQ ID NO: 198 amino acid sequence of BcsA with the accession number NP_417990.4 | MSILTRWLLIPPVNARLIGRYRDYRRHGASAFSATLGCFWMILAWIFIPLEHPRWQRIRAEHKNLYPHINASRPRPLDPVRYLI QTCWLLIGASRKETPKPRRRAFSGLQNIRGRYHQWMNELPERVSHKTQHLDEKKELGHLSAGARRLILGIIVTFSLILALICVT QPFNPLAQFIFLMLLWGVALIVRRMPGRFSALMLIVLSLTVSCRYIWWRYTSTLNWDDPVSLVCGLILLFAETYAWIVLVLG YFQVVWPLNRQPVPLPKDMSLWPSVDIFVPTYNEDLNVVKNTIYASLGIDWPKDKLNIWILDDGGREEFRQFAQNVGVKYI ARTTHEHAKAGNINNALKYAKGEFVSIFDCDHVPTRSFLQMTMGWFLKEKQLAMMQTPHHFFSPDPFERNLGRFRKTPNEG TLFYGLVQDGNDMWDATFFCGSCAVIRRKPLDEIGGIAVETVTEDAHTSLRLHRRGYTSAYMRIPQAAGLATESLSAHIGQR IRWARGMVQIFRLDNPLTGKGLKFAQRLCYVNAMFHFLSGIPRLIFLTAPLAFLLLHAYIIYAPALMIALFVLPHMIHASLTNS KIQGKYRHSFWSEIYETVLAWYIAPPTLVALINPHKGKFNVTAKGGLVEEEYVDWVISRPYIFLVLLNLVGVAVGIWRYFYG PPTEMLTVVVSMVWVFYNLIVLGGAVAVSVESKQVRRSHRVEMTMPAAIAREDGHLFSCTVQDFSDGGLGIKINGQAQILE GQKVNLLLKRGQQEYVFPTQVARVMGNEVGLKLMPLTTQQHIDFVQCTFARADTWALWQDSYPEDKPLESLLDILKLGFR GYRHLAEFAPSSVKGIFRVLTSLVSWVVSFIPRRPERSETAQPSDQALAQQ |
| SEQ ID NO: 199 amino acid sequence of BcsC with the accession number YP_026226.4 | MRKFTLNIFTLSLGLAVMPMVEAAPTAQQQLLEQVRLGEATHREDLVQQSLYRLELIDPNNPDVVAARFRSLLRQGDIDGA QKQLDRLSQLAPSSNAYKSSRTTMLLSTPDGRQALQQARLQATTGHAEEAVASYNKLFNGAPPEGDIAVEYWSTVAKIPAR RGEAINQLKRINADAPGNTGLQNNLALLLFSSDRRDEGFAVLEQMAKSNAGREGASKIWYGQIKDMPVSDASVSALKKYLS IFSDGDSVAAAQSQLAEQQKQLADPAFRARAQGLAAVDSGMAGKAIPELQQAVRANPKDSEALGALGQAYSQKGDRANA VANLEKALALDPHSSNNDKWNSLLKVNRYWLAIQQGDAALKANNPDRAERLFQQARNVDNTDSYAVLGLGDVAMARKD YPAAERYYQQTLRMDSGNTNAVRGLANIYRQQSPEKAEAFIASLSASQRRSIDDIERSLQNDRLAQQAEALENQGKWAQAA ALQRQRLALDPGSVWITYRLSQDLWQAGQRSQADTLMRNLAQQKSNDPEQVYAYGLYLSGHDQDRAALAHINSLPRAQW NSNIQELVNRLQSDQVLETANRLRESGKEAEAEAMLRQQPPSTRIDLTLADWAQQRRDYTAARAAYQNVLTREPANADAIL GLTEVDIAAGDKAAARSQLAKLPATDNASLNTQRRVALAQAQLGDTAAAQRTFNKLIPQAKSQPPSMESAMVLRDGAKFE ALQRQRLALDPGSVWITYRLSQDLWQAGQRSQADTLMRNLAQQKSNPEQVYAYGLYLSGHDQDRAALAHINSLPRAQW GYSDLKAHTTMLQVDAPYSDGRMFFRSDFVNMNVGSFSTNADGKWDDNWGTCTLQDCSGNRSQSDSGASVAVGWRNDV WSWDIGTTPMGFNVVDVVGGISYSDDIGPLGYTVNAHRRPISSSLLAFGGQKDSPSNTGKKWGGVRADGVGLSLSYDKGEA NGVWASLSGDQLTGKNVEDNWVRVRWMTGYYYKVINQNNRRVTIGLNNMIWHYDKDLSGYSLGQGGYYSPQEYLSFAIPV MWRERTENWSWELGASGSWSHSRTKTMPRYPLMNLIPTDWQEEAARQSNDGGSSQGFGYTARALLERRVTSNWFVGTAI DIQQAKDYAPSHFLLYVRYSAAGWQGDMDLPPQPLIPYADW |

TABLE 1-continued

Amino Acid Sequences

| SEQ ID NO | Amino Acid Sequence |
|---|---|
| SEQ ID NO: 200 amino acid sequence of GadC with the accession number NP_416009.1 | MATSVQTGKAKQLTLLGFFAITASMVMAVYEYPTFATSGFSLVFFLLLGGILWFIPVGLCAAEMATVDGWEEGGVFAWVSN<br>TLGPRWGFAAISFGYLQIAIGFIPMLYFVLGALSYILKWPALNEDPITKTIAALIILWALALTQFGGTKYTARIAKVGFFAGILL<br>PAFILIALAAIYLHSGAPVAIEMDSKTFFPDFSKVGTLVVFVAFILSYMGVEASATHVNEMSNPGRDYPLAMLLLMVAAICLS<br>SVGGLSIAMVIPGNEINLSAGVMQTFTVLMSHVAPEIEWTVRVISALLLLGVLAEIASWIVGPSRGMYVTAQKNLLPAAFAK<br>MNKNGVPVTLVISQLVITSIALIILTNTGGGNNMSFLIALALTVVIYLCAYFMLFIGYIVLVLKHPDLKRTFNIPGGKGVKLVV<br>AIVGLLTSIMAFIVSFLPPDNIQGDSTDMYVELLVVSFLVVLALPFILYAVHDRKGKANTGVTLEPINSQNAPKGHFFLHPRAR<br>SPHYIVMNDKKH |
| SEQ ID NO: 201 amino acid sequence of FadR with the accession number NP_415705.1 | MVIKAQSPAGFAEEYIIESIWNNRFPPGTILPAERELSELIGVTRTTLREVLQRLARDGWLTIQHGKPTKVNNFWETSGLNILET<br>LARLDHESVPQLIDNLLSVRTNISTIFIRTAFRQHPDKAQEVLATANEVADHADAFAELDYNIFRGLAFASGNPIYGLILNGMK<br>GLYTRIGRHYFANPEARSLALGFYHKLSALCSEGAHDQVYETVRRYGHESGEIWHRMQKNLPGDLAIQGR |
| SEQ ID NO: 202 amino acid sequence of YqhD with the accession number NP_417484.1 | MNNFNLHTPTRILFGKGAIAGLREQIPHDARVLITYGGGSVKKTGVLDQVLDALKGMDVLEFGGIEPNPAYETLMNAVKLV<br>REQKVTFLLAVGGGSVLDGTKFIAAAANYPENIDPWHILQTGGKEIKSAIPMGCVLTLPATGSESNAGAVISRKTTGDKQAF<br>HSAHVQPVFAVLDPVYTYTLPPRQVANGVVDAFVHTVEQYVTKPVDAKIQDRFAEGILLTLIEDGPKALKEPENYDVRANV<br>MWAATQALNGLIGAGVPQDWATHMLGHELTAMHGLDHAQTLAIVLPALWNEKRDTKRAKLLQYAERVWNITEGSDDERI<br>DAAIAATRNFFEQLGVPTHLSDYGLDGSSIPALLKKLEEHGMTQLGENHDITLDVSRRIYEAAR |
| SEQ ID NO: 203 amino acid sequence of AtoC(Con) with the accession number WP_077989191.1 | MTAINRILIVDDEDNVRRMLSTAFALQGFETHCANNGRTALHLFADIHPDVVLMDIRMPEMDGIKALKEMRSHETRTPVILM<br>TAYAEVETAVEALRCGAFDYVIKPFDLDELNLIVQRALQLQSMKKESRHLHQALSTSWQWGHILTNSPAMMDICKDTAKIA<br>LSQASVLISGESGTGKELIARAIHYNSRRAKGPFIKVNCAALPESLLESELFGHEKGAFTGAQTLRQGLFERANEGTLLLDEIG<br>EMPLVLQAKLLRILQEREFERIGGHQTIKVDIRIIAATNRDLQAMVKEGTFREDLFYRLNVIHLILPPLRDRREDISLLANHFLQ<br>KFSSENQRDIIDIDPMAMSLLTAWSWPGNIRELSNVIERAVVMNSGPIIFSEDLPPQIRQPVCNAGEVKTAPVGERNLKEEIKR<br>VEKRIIMEVLEQQEGNRTRTALMLGISRRALMYKLQEYGIDPADV |
| SEQ ID NO: 215 amino acid sequence of GdhA with the accession number NP_416275.1 | MDQTYSLESFLNHVQKRDPNQTEFAQAVREVMTTLWPFLEQNPKYRQMSLLERLVEPERVIQFRVVWVDDRNQIQVNRAW<br>RVQFSSAIGPYKGGMRFHPSVNLSILKFLGFEQTFKNALTTLPMGGGKGGSDFDPKGKSEGEVMRFCQALMTELYRHLGAD<br>TDVPAGDIGVGGREVGFMAGMMKKLSNNTACVFTGKGLSFGGSLIRPEATGYGLVYFTEAMLKRHGMGFEGMRVSVSGS<br>GNVAQYAIEKAMEFGARVITASDSSGTVVDESGFTKEKLARLIEIKASRDGRVADYAKEFGLVYLEGQQPWSLPVDIALPCA<br>TQNELDVDAAHQLIANGVKAVAEGANMPTTIEATELFQQAGVLFAPGKAANAGGVATSGLEMAQNAARLGWKAEKVDA<br>RLHHIMLDIHHACVEHGGEGEQTNYVQGANIAGFVKVADAMLAQGVI |
| SEQ ID NO: 216 amino acid sequence of GadBe(Lb) | MAMLYGKHTHETDETLIPIFGASAERHDLPKYKLAKHALEPREADRLVRDQLLDEGNSRLNLATFCQTYMEPEAVELMKDT<br>LEKNAIDKSEYPRTAEIENRCVNIIANLWHAPEAESFTGTSTIGSSEACMLAGLAMKFAWRKRAKANGLDLTAHQPNIVISAG<br>YQVCWEKFCVYWDIDMHVVPMDDDHMSLNVDHVLDYVDDYTIGIVGIMGITYTGQYDDLARLDAVVERYNRTTKFPVYI<br>HVDAASGGFYTPFIEPELKWDFRLNNVISINASGHKYGLVYPGVGWVIWRGQQYLPKELVFKVSYLGGSLPTMAINFSHSAS<br>QLIGQYYNFIRFGFDGYREIHEKTHDVARYLAKSLTKLGGFSLINDGHELPLICYELTADSDREWTLYDLSDRLLMKGWQVP<br>TYPLPKNMTDRVIQRIVVRADFGMSMAHDFIDDLTQAIHDLDQAHIVFHSDPQPKKYGFTH |
| SEQ ID NO: 217 amino acid sequence of GadB(Lp) with the accession number EFK28268.1 | MAMLYGKHNHEAEEYLEPVFGAPSEQHDLPKYRLPKHSLSPREADRLVRDELLDEGNSRLNLATFCQTYMEPEAVELMKD<br>TLAKNAIDKSEYPRTAEIENRCVNIIANLWHAPDDEHFTGTSTIGSSEACMLGGLAMKFAWRKRAQAAGLDLNAHRPNLVIS<br>AGYQVCWEKFCVYWDVDMHVVPMDEQHMALDVNHVLDYVDEYTIGIVGIMGITYTGQYDDLAALDKVVTHYNHQHPK<br>LPVYIHVDAASGGFYTPFIEPQLIWDFRLANVVSINASGHKYGLVYPGVGWVVWRDRQFLPPELVFKVSYLGGELPTMAINF<br>SHSAAQLIGQYYNFIRFGMDGYREIQTKTHDVARYLAAALDKVGEFKMINNGHQLPLICYQLAPREDREWTLYDLSDRLLM<br>NGWQVPTYPLPANLEQQVIQRIVVRADFGMNMAHDFMDDLTKAVHDLNHAHIVYHHDAAPKKYGFTH |
| SEQ ID NO: 224 amino acid sequence of Gad(Ls) with the accession number WP_082622401.1 | MSKNDQETQQMLDAAQLEKTFLGSTAAGESLPKNTMPAGPMAPDVAVEMVDHFRLNEAKANQNLATFCTTEMEPQADQL<br>MMRTLNTNAIDKSEYPKTSAMENYCVSMIAHLWGIPDEEKFGDDFIGTSTVGSSEGCMLGGLALLHTWKHRAKAAGLDID<br>DLHAHKPNLVIMSGNQVVWEKFCTYWNVDFRQVPINGDQVSLDLDHVMDYVDENTIGIIGIEGITYTGSVDDIQGLDKLVT<br>EYNKTAALPVRIHVDAAFGGLFAPFVDGFKPWDFRLDNVVSINVSGHKYGMVYPGLGWIVWRKNSYDILPKEMRFSVPYL<br>GSSVDSIAINFSHSGAHINAQYYNFLRFGLAGYKAIMNNVRKVSLKLTDELRKFGIFDILVDGKELPINCWKLSDNANVSWSL<br>YDMEDALAKYGWQVPAYPLPKNREETITSRIVVRPGMTMAIADDFIDDLKLAIADLNHSFGDVKDVNDKNKTTVR |
| SEQ ID NO: 225 amino acid sequence of PhaB(Hb) with the accession number WP_009724067.1 | MANQAPVAWVTGGTGGIGTSICHSLADAGYLVVAGYHNPEKAKTWLETQQAAGYDNIALSGVDLSDHNACLEGAREIQEK<br>YGPVSVLVNCAGITRDGTMKKMSYEQWHQVIDTNLNSVFNTCRSVIEMMLEQGYGRIINISSINGRKGQFGQVNYAAAKAG<br>MHGLTMSLAQETATKGITVNTVSPGYIATDMIMKIPEQVREAIRETIPVKRYGTPEEIGRLVTFLADKESGFITGANIDINGGQ<br>FMG |
| SEQ ID NO: 226 amino acid sequence of PhaC(F420S) | MATGKGAAASTQEGKSQPFKVTPGPFDPATWLEWSRQWQGTEGNGHAAASGIPGLDALAGVKIAPAQLGDIQQRYMKDFS<br>ALWQAMAEGKAEATGPLHDRRFAGDAWRTNLPYRFAAAFYLLNARALTELADAVEADAKTRQRIRFAISQWVDAMSPAN<br>FLATNPEAQRLLIESGGESLRAGVRNMMEDLTRGKISQTDESAFEVGRNVAVTEGAVVFENEYFQLLQYKPLTDKVHARPL<br>LMVPPCINKYYILDLQPESSLVRHVVEQGHTVFLVSWRNPDASMAGSTWDDYIEHAAIRAIEVARDISGQDKINVLGFCVGG |

TABLE 1-continued

| Amino Acid Sequences | |
|---|---|
| SEQ ID NO | Amino Acid Sequence |
| | TIVSTALAVLAARGEHPAASVTLLTTLLDFADTGILDVFVDEGHVQLREATLGGGAGAPCALLRGLELANTFSFLRPNDLVW NYVVDNYLKGNTPVPSDLLFWNGDATNLPGPWYCWYLRHTYLQNELKVPGKLTVCGVPVDLASIDVPTYIYGSREDHIVP WTAAYASTALLANKLRFVLGASGHIAGVINPPAKNKRSHWTNDALPESPQQWLAGAIEHHGSWWPDWTAWLAGQAGAK RAAPANYGNARYRAIEPAPGRYVKAKA |
| SEQ ID NO: 230 amino acid sequence of PhaC(G4D) | MATDKGAAASTQEGKSQPFKVTPGPFDPATWLEWSRQWQGTEGNGHAAASGIPGLDALAGVKIAPAQLGDIQQRYMKDFS ALWQAMAEGKAEATGPLHDRRFAGDAWRTNLPYRFAAAFYLLNARALTELADAVEADAKTRQRIRFAISQWVDAMSPAN FLATNPEAQRLLIESGGESLRAGVRNMMEDLTRGKISQTDESAFEVGRNVAVTEGAVVFENEYFQLLQYKPLTDKVHARPL LMVPPCINKYYILDLQPESSLVRHVVEQGHTVFLVSWRNPDASMAGSTWDDYIEHAAIRAIEVARDISGQDKINVLGFCVGG TIVSTALAVLAARGEHPAASVTLLTTLLDFADTGILDVFVDEGHVQLREATLGGGAGAPCALLRGLELANTFSFLRPNDLVW NYVVDNYLKGNTPVPFDLLFWNGDATNLPGPWYCWYLRHTYLQNELKVPGKLTVCGVPVDLASIDVPTYIYGSREDHIVP WTAAYASTALLANKLRFVLGASGHIAGVINPPAKNKRSHWTNDALPESPQQWLAGAIEHHGSWWPDWTAWLAGQAGAK RAAPANYGNARYRAIEPAPGRYVKAKA |

In embodiments, the recombinant bacterial cell for producing PHBV comprises at least one polypeptide having an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to any one of SEQ ID NO: 1-26, 28-38, 40-59, 172-173, 176-184, 194-203, 215-217, 224-226, and 230, or a polypeptide having an accession no. shown in Table 6. In embodiments, the polypeptide is a recombinant polypeptide. In embodiments, the acyl-CoA synthetase has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 26, the acetate CoA-transferase polypeptides having an amino acid sequence having at least 75% sequence identity to SEQ ID NO: 4 and 5 or 172 and 173, or a polypeptide having an accession no. WP_053001645.1, QGU62017.1, WP_155555734.1, WP_038355059.1, MLY49728.1, WP_105269001.1, WP_105284960.1, WP_149476985.1, WP_108188772.1, WP_000850520.1, WP_138957179.1, WP_123267594.1, WP_114680602.1, WP_047500919.1, or WP_004184954.1, and the propionate-CoA transferase polypeptide has an amino acid sequence having at least 75% sequence identity to SEQ ID NO: 30 or 31 or a polypeptide having an accession no. WP_066087637.1, NCC15629.1, WP_054329786.1, WP_072853413.1, CDC28613.1, WP_016408311.1, WP_088107724.1, WP_160302233.1, WP_004038625.1, WP_054336166.1, WP_036203125.1, WP_044502862.1, WP_065360594.1, KXA66894.1, WP_095629974.1, WP_087478516.1, WP_107195767.1, WP_048515067.1, WP_101912966.1, WP_156208970.1, KXB92430.1, WP_023053187.1, WP_039891686.1, or KXB92214.1. In embodiments, the PutP polypeptide has an amino acid sequence having at least 75% sequence identity to SEQ ID NO: 195. In embodiments, the AtoE polypeptide has an amino acid sequence having at least 75% sequence identity to SEQ ID NO: 6. In embodiments, the first β-ketothiolase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 8, or a polypeptide having an accession no. WP_013956457.1, WP_035820088.1, WP_092317205.1, WP_115013782.1, WP_116382528.1, WP_018311404.1, WP_063238655.1, WP_116321050.1, AGW89814.1, WP_062798985.1, WP_133094381.1, AGW95651.1, WP_140952189.1, WP_144195740.1, or WP_011516125.1. In embodiments, the NADPH-dependent acetoacetyl-CoA reductase polypeptide has an amino acid sequence having at least 75%, 80%, 85%, 90%, 91%, 92%, 93%, 94%, 95%, 96%, 97%, 98%, 99%, 99.1%, 99.2%, 99.3% 99.4% 99.5% 99.6%, 99.7%, 99.8%, 99.9%, or 100% sequence identity to SEQ ID NO: 35, or a polypeptide having an accession no. RWA53825.1, WP_042885115.1, WP_039016191.1, WP_116336746.1, WP_112777371.1, WP_006577377.1, WP_135705030.1, WP_133096842.1, WP_124684436.1, WP_116321053.1, WP_006155939.1, WP_045241722.1, WP_011297519.1, WP_144195744.1, or ODV43053.1. In embodiments, the NADH-dependent acetoacetyl-CoA reductase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 225, or a polypeptide having an accession no. WP_162219671.1, WP_126946472.1, WP_120385833.1, WP_030074446.1, WP_188637499.1, WP_058579713.1, WP_083023226.1, WP_039183428.1, WP_159340906.1, or WP_096653461.1. In embodiments, the short-chain polyhydroxyalkanoate synthase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 36, 226, or 230, or a polypeptide having an accession no. ACZ57807.1, WP_010810133.1, WP_013956451.1, AAW65074.1, WP_018311399.1, AGW89808.1, WP_115678329.1, WP_062798976.1, WP_115013788.1, or WP_115680054.1, WP_112777370.1. In embodiments, the CoA-dependent propanal dehydrogenase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 32 or 33, or a polypeptide having an accession no. WP_109231734.1, WP_109848747.1, WP_136028274.1, WP_100680758.1, WP_100631313.1, WP_049157539.1, WP_029884370.1, MXH33721.1, WP_144232363.1, WP_153679752.1, WP_148849915.1, EBS2830838.1, WP_112213940.1, WP_064370270.1, WP_001097684.1, WP_001528442.1, WP_080203692.1, WP_108450871.1, WP_009652778.1, WP_142983670.1, WP_105274032.1, WP_070556870.1, WP_142502560.1, WP_012131760.1, WP_012906342.1, WP_006683971.1, WP_103775053.1, WP_060570657.1, or WP_135321437.1, the β-alanine transaminase polypeptide has an amino acid sequence having at least 75% sequence identity to SEQ ID NO: 15 or 16, or a polypeptide having an accession no.

WP_116425784.1, WP_069862932.1, WP_043315988.1, WP_009614288.1, WP_089392503.1, WP_109934365.1, WP_090268322.1, WP_138519936.1, WP_138213347.1, WP_015474919.1, WP_043256620.1, WP_084311461.1, WP_053816481.1, WP_070656248.1, or WP_077524299.1, or the NADP+-dependent succinate semialdehyde dehydrogenase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 17 or a polypeptide having an accession no. WP_105285925.1, WP_135494970.1, WP_094315749.1, WP_161983589.1, WP_000772895.1, WP_078167276.1, WP_016249103.1, WP_105267583.1, WP_149461599.1, WP_128880059.1, WP_149461599.1, WP_060773285.1, WP_153257801.1, or WP_108418849.1, WP_045446520.1. In embodiments, the short-chain acyl-CoA dehydrogenase polypeptide has an amino acid sequence having at least 75% sequence identity to SEQ ID NO: 38, 7, 28, or 13, or a polypeptide having accession no. WP_003250094.1, WP_104887321.1, WP_039614175.1, WP_023662689.1, WP_085706434.1, WP_070087269.1, WP_060512757.1, WP_144171976.1, WP_054884005.1, WP_051100719.1, WP_099814118.1, WP_125859423.1, WP_125464833.1, WP_090345830.1, WP_110994568.1, WP_088022147.1, WP_098448816.1, WP_149216716.1, WP_101167410.1, WP_143881711.1, WP_085450733.1, WP_144504985.1, BCA34359.1, WP_098299175.1, WP_071710801.1, CKE48212.1, WP_163095898.1, WP_071725959.1, WP_136445333.1, WP_128975345.1, WP_020723925.1, WP_048514244.1, WP_074501184.1, KXB91325.1, WP_154877386.1, WP_107195291.1, WP_087477538.1, WP_095630133.1, WP_091647756.1, WP_023053225.1, WP_101912630.1, WP_075572446.1, WP_006790232.1, WP_006942404.1, WP_094316844.1, WP_130224094.1, WP_135404353.1, WP_046076114.1, WP_011069257.1, WP_135489829.1, WP_085448671.1, WP_124782953.1, WP_153879457.1, EDR1571704.1, WP_103776898.1, WP_008783785.1, WP_087053141.1, WP_079225425.1, or WP_137366593.1, WP_000973041.1, and the enoyl-CoA hydratase/isomerase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 22, 37, or 196, or a polypeptide having accession no. WP_051591491.1, WP_114130480.1, WP_078200706.1, EON20731.1, PKO64515.1, WP_092007571.1, WP_162566377.1, WP_137921632.1, WP_162591754.1, WP_103260220.1, WP_104454254.1, OJW67134.1, WP_041998622.1, WP_043760202.1, WP_043129860.1, WP_042076944.1, WP_100860962.1, WP_163157368.1, WP_042638062.1, WP_106886672.1, WP_033131291.1, WP_025327110.1, WP_040094291.1, WP_139745378.1, WP_169200570.1, WP_053422493.1, WP_169118971.1, WP_169202263.1, AUL99438.1, WP_136349851.1, WP_136385326.1, WP_187719679.1, or WP_107493682.1, WP_169262136.1. In embodiments, the propionyl-CoA synthetase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 43, 44, or 45, or a polypeptide having an accession no. WP_081623799.1, WP_115213214.1, WP_082818978.1, WP_116324638.1, WP_092309442.1, AMR79067.1, WP_151072146.1, WP_029046365.1, AGW91162.1, WP_116321975.1, WP_039006728.1, WP_092134378.1, WP_109580644.1, WP_035882297.1, WP_149135646.1, WP_024249411.1, WP_130258507.1, WP_000010307.1, WP_138159881.1, WP_105281240.1, WP_000010239.1, WP_000010244.1, WP_160524152.1, WP_105270931.1, WP_160530253.1, WP_016235155.1, WP_061090735.1, WP_103014998.1, WP_094761423.1, ATX90159.1, WP_127836169.1, WP_103776706.1, WP_044259075.1, WP_012904755.1, WP_043015332.1, WP_008783866.1, WP_153690685.1, WP_058587683.1, WP_101700584.1, WP_042324663.1, WP_123268908.1, WP_137351112.1, WP_048219548.1, or WP_160955604.1, WP_012133646.1. In embodiments, the glutamate decarboxylase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 19, 20, 194, 216, 217, or 224, or a polypeptide having an accession no. XP_002871761.1, KFK41557.1, VVB14898.1, RID41892.1, XP_013661825.1, VDC86651.1, XP_006400267.1, XP_010420446.1, XP_010453919.1, CAA7061503.1, XP_006400266.1, ESQ41721.1, XP_013627326.1, XP_031273023.1, WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, EAB0955940.1, WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, EAB0955940.1, WP_125641322.1, WP_226457942.1, BAN05709.1, MBL3537851.1, WP_039105805.1, WP_052957185.1, KIR08754.1, WP_125574762.1, WP_063488771.1, or WP_017262688.1. In embodiments, the glutamate dehydrogenase polypeptide has an amino acid sequence having at least 75%, 80%, 85%, 90%, 91%, 92%, 93%, 94%, 95%, 96%, 97%, 98%, 99%, 99.1%, 99.2%, 99.3% 99.4% 99.5% 99.6%, 99.7%, 99.8%, 99.9%, or 100% sequence identity to SEQ ID NO: 215. In embodiments, the second β-ketothiolase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 34, or a polypeptide having an accession no. WP_013956452.1, SCU96900.1, WP_035820078.1, 4O9C_A, WP_116382525.1, WP_092317196.1, WP_062798979.1, WP_116321054.1, AGW89809.1, WP_039016192.1, WP_063238652.1, WP_029049660.1, WP_011297518.1, WP_124684437.1, or WP_109580845.1. In embodiments, the succinyl-CoA transferase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 10 or a polypeptide having an accession no. WP_073539834.1, or WP_010236491.1, or the succinyl-CoA synthetase polypeptides having an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 50 and 51 or a polypeptide having an accession no. WP_111780024.1, WP_105268114.1, WP_149508492.1, EBH0782533.1, WP_079789068.1, EAA0703253.1, WP_001048612.1, WP_103776364.1, HAC6539881.1, WP_139538723.1, WP_040076526.1, WP_152308781.1, WP_061708388.1, WP_159152251.1, WP_159754306.1, WP_148048643.1, WP_161983406.1, WP_128882005.1, SEK68167.1, WP_064567804.1, WP_090133347.1, EDS6037479.1, WP_015965312.1, WP_154777294.1, WP_108473875.1, WP_162082208.1, or WP_154158334.1. In embodiments, the CoA-acylating aldehyde dehydrogenase polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 184 or a polypeptide having an accession no. WP_077830381.1, WP_065419149.1, WP_017211959.1, WP_077844109.1, AAD31841.1, WP_087702529.1, WP_077868466.1, WP_077366605.1, WP_026888070.1, WP_077860531.1, WP_022747467.1, WP_077863550.1, WP_009171375.1, WP_128214949.1, WP_160679606.1, WP_012059995.1, WP_041898834.1, or WP_015395720.1. In embodiments, the bifunctional protein polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 29 or a polypeptide having an accession no. WP_160599600.1, WP_152066042.1, WP_094316530.1, WP_032252644.1, WP_001186464.1, WP_125401136.1, WP_001186494.1, WP_119163289.1, WP_095281943.1, WP_045888522.1, WP_058840681.1, WP_095440732.1, WP_162382197.1, WP_059385322.1, or WP_045286529.1.

In embodiments, the recombinant bacterial cell for producing PHBV comprises a recombinant nucleic acid molecule having at least 75% sequence identity to at least one, two, three, four, five, six, seven, eight, or nine of SEQ ID NO: 89, 85, 97, 96, 79, 93, 94, 95, 67, 228, 229, and 231, optionally wherein the recombinant bacterial cell comprises inactivation of iclR, optionally inactivation of SdhA, optionally wherein the recombinant bacterial cell comprises inactivation of at least one nonessential gene.

In embodiments, the recombinant bacterial cell for producing PHBV comprises a recombinant nucleic acid molecule having at least 75% sequence identity to at least one, two, three, four, five, six, seven, eight, nine, ten, eleven, or twelve of SEQ ID NO: 89, 85, 97, 96, 79, 74, 92, 76, 93, 94, 95, 67, 228, 229, and 231, optionally wherein the recombinant bacterial cell comprises inactivation of iclR, optionally inactivation of SdhA, optionally wherein the recombinant bacterial cell comprises inactivation of at least one nonessential gene. In embodiments, the at least one nonessential gene is a nucleic acid molecule encoding a polypeptide having an amino acid sequence selected from the group consisting of SEQ ID NO: 49, 21, 18, 47, 12, 14, 13, 53, 58, 52, 54, 176, 177, 178, 179, 180, 181, 182, 183, 40, 41, 42, 197, 198, 199, 200, 201, and 202.

For example, fadR is a nonessential gene that can be inactivated without significantly affecting cell viability, said inactivation of fadR would derepress expression of fadE, and the derepression of fadE facilitates the conversion of butyryl-CoA to crotonyl-CoA. Further details are provided in Jenkins L S et al., *Journal of Bacteriology* 1987, 169:42-52, the contents of which are incorporated herein by reference in its entirety for all purposes. Cell viability can be measured, for example, by BacTiter-Glo™, LIVE/DEAD™ BacLight™ Bacterial Viability assay, or LIVE BacLight™ Bacterial Gram Stain, where cells with inactivated genes having +/−25% viability on a quantifiable index as compared to parental and/or wildtype are considered to be not significantly affected. In embodiments, the recombinant bacterial cell comprises inactivation of FadR. In embodiments, the FadR comprises a nucleic acid molecule encoding a polypeptide having an amino acid sequence of SEQ ID NO: 201. In embodiments, the FadR comprises a nucleic acid molecule having a nucleic acid sequence of SEQ ID NO: 211.

In embodiments, the recombinant bacterial cell for producing PHBV comprises a recombinant nucleic acid molecule having at least 75% sequence identity to at least one, two, three, four, five, six, seven, eight, nine, ten, eleven, twelve, or thirteen of SEQ ID NO: 89, 85, 97, 96, 79, 74, 92, 76, 69, 93, 94, 95, 67, 228, 229, and 231, optionally wherein the recombinant bacterial cell comprises inactivation of iclR.

In addition, AtoC(Con) which is a DNA-binding transcriptional activator/ornithine decarboxylase inhibitor that activates transcription of the atoDAEB operon for enhanced VFA uptake and conversion to acyl-CoAs, can be mutated at position 129 from isoleucine to serine to confer constitutive expression of the atoDAEB operon. Accordingly, In embodiments, the recombinant bacterial cell for producing PHBV comprises a DNA-binding transcriptional activator/ornithine decarboxylase inhibitor, optionally an AtoC polypeptide. Further details are provided in Pauli G et al. *European Journal of Biochemistry* 1972, 29:553-562, the contents of which are incorporated herein by reference in its entirety for all purposes. In embodiments, the AtoC polypeptide has an amino acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 203, wherein the AtoC(Con) polypeptide comprises a serine at the position corresponding to position 129 of SEQ ID NO: 203.

The presence of acetate or butyrate can affect bacterial cell viability. Expression of small noncoding RNAs, such as DsrA, RprA and ArcZ, can increase the tolerance of bacterial cells to the presence of acetate and/or butyrate. In embodiments, the recombinant bacterial cell for producing PHBV comprises noncoding RNAs, optionally DsrA, RprA, or ArcZ. In embodiments, the recombinant bacterial cell for producing PHBV comprises noncoding RNA DsrA, noncoding RNA RprA, and noncoding RNA ArcZ. In embodiments, the recombinant bacterial cell for producing PHBV comprises a DNA nucleic acid molecule having nucleic acid sequence encoding for noncoding RNA DsrA, RprA, or ArcZ. In embodiments, the recombinant bacterial cell for producing PHBV comprises a DNA nucleic acid molecule having nucleic acid sequence encoding for noncoding RNA DsrA, RprA, and ArcZ. In embodiments, the recombinant bacterial cell for producing PHBV comprises a nucleic acid molecule having nucleic acid sequence of SEQ ID NO: 27, 39, or 214. In embodiments, the recombinant bacterial cell for producing PHBV comprises a nucleic acid molecule having nucleic acid sequence of SEQ ID NO: 27, 39, and 214. In embodiments, the recombinant bacterial cell for producing PHBV comprises a nucleic acid molecule having nucleic acid sequence of SEQ ID NO: 221, a nucleic acid molecule having nucleic acid sequence of SEQ ID NO: 222, and a nucleic acid molecule having nucleic acid sequence of SEQ ID NO: 223.

Exemplary nucleic acid sequences described herein are set out in Table 2, Table 3A, Table 3B, Table 3C, Table 3D, and Table 4.

TABLE 2

| Nucleic Acid Sequences: Genes | |
|---|---|
| SEQ ID NO | Nucleic Acid Sequence |
| SEQ ID NO: 60<br>nucleic acid<br>coding sequence<br>of the gene ackA<br>at locus b2296 | ATGTCGAGTAAGTTAGTACTGGTTCTGAACTGCGGTAGTTCTTCACTGAAATTTGCCATCATCGATGCAGTAAATGGT<br>GAAGAGTACCTTTCTGGTTTAGCCGAATGTTTCCACCTGCCCGAAGCACGTATCAAATGGAAAATGGACGGCAATAA<br>ACAGGAAGCGGCTTTAGGTGCAGGCGCCGCTCACAGCGAAGCGCTCAACTTTATCGTTAATACTATTCTGGCACAAAA<br>ACCAGAACTGTCTGCGCAGCTGACTGCTATCGGTCACCGTATCGTACACGGCGGCGAAAAGTATACCAGCTCCGTAGT<br>GATCGATGAGTCTGTTATTCAGGGTATCAAAGATGCAGCTTCTTTTGCACCGCTGCACAACCCGGCTCACCTGATCGG<br>TATCGAAGAAGCTCTGAAATCTTTCCCACAGCTGAAAGACAAAAACGTTGCTGTATTTGACACCGCGTTCCACCAGAC<br>TATGCCGGAAGAGTCTTACCTCTACGCCCTGCCTTACAACCTGTACAAAGAGCACGGCATCCGTCGTTACGGCGCGCA<br>CGGCACCAGCCACTTCTATGTAACCCAGGAAGCGGCAAAAATGCTGAACAAACCGGTAGAAGAACTGAACATCATCA<br>CCTGCCACCTGGGCAACGGTGGTTCCGTTTCTGCTATCCGCAACGGTAAATGCGTTGACACCTCTATGGGCCTGACCC<br>CGCTGGAAGGTCTGGTCATGGGTACCCGTTCTGGTGATATCGATCCGGCGATCATCTTCCACCTGCACGACACCCTGG<br>GCATGAGCGTTGACGCAATCAACAAACTGCTGACCAAAGAGTCTGGCCTGCTGGGTCTGACCGAAGTGACCAGCGAC<br>TGCCGCTATGTTGAAGACAACTACGCGACGAAAGAAGACGCGAAGCGCGCAATGGACGTTTACTGCCACCGCCTGGC<br>GAAATACATCGGTGCCTACACTGCGCTGATGGATGGTCGTCTGGACGCTGTTGTATTCACTGGTGGTATCGGTGAAAA<br>TGCCGCAATGGTTCGTGAACTGTCTCTGGGCAAACTGGGCGTGCTGGGCTTTGAAGTTGATCATGAACGCAACCTGGC<br>TGCACGTTTCGGCAAATCTGGTTTCATCAACAAAGAAGGTACCCGTCCTGCGGTGGTTATCCCAACCAACGAAGAACT<br>GGTTATCGCGCAAGACGCGAGCCGCCTGACTGCCTGA |
| SEQ ID NO: 61<br>nucleic acid<br>coding sequence<br>of the gene acs at<br>locus b4069 | ATGAGCCAAATTCACAAACACACCATTCCTGCCAACATCGCAGACCGTTGCCTGATAAACCCTCAGCAGTACGAGGC<br>GATGTATCAACAATCTATTAACGTACCTGATACCTTCTGGGGCGAACAGGGAAAAATTCTTGACTGGATCAAACCTTA<br>CCAGAAGGTGAAAAACACCTCCTTTGCCCCCGGTAATGTGTCCATTAAATGGTACGAGGACGGCACGCTGAATCTGG<br>CGGCAAACTGCCTTGACCGCCATCTGCAAGAAAACGGCGATCGTACCGCCATCATCTGGGAAGGCGACGACGCCAGC<br>CAGAGCAAACATATCAGCTATAAAGAGCTGCACCGCGACGTCTGCCGCTTCGCCAATACCCTGCTCGAGCTGGGCATT<br>AAAAAAGGTGATGTGGTGGCGATTTATATGCCGATGGTGCCGGAAGCCGCGGTTGCGATGCTGGCCTGCGCCCGCAT<br>TGGCGCGGTGCATTCGGTGATTTTCGGCGGCTTCTCGCCGGAAGCCGTTGCCGGGCGCATTATTGATTCCAACTCACG<br>ACTGGTGATCACTTCCGACGAAGGTGTGCGTGCCGGGCGCAGTATTCCGCTGAAGAAAAACGTTGATGACGCGCTGA<br>AAAACCCGAACGTCACCAGCGTAGAGCATGTGGTGGTACTGAAGCGTACTGGCGGGAAAATTGACTGGCAGGAAGG<br>GCGCGACCTGTGGTGGCACGACCTGGTTGAGCAAGCGAGCGATCAGCACCAGGCGGAAGAGATGAACGCCGAAGAT<br>CCGCTGTTTATTCTCTACACCTCCGGTTCTACCGGTAAGCCAAAAGGTGTGCTGCATACTACCGGCGGTTATCTGGTGT<br>ACGCGGCGCTGACCTTTAAATATGTCTTTGATTATCATCCGGGTGATATCTACTGGTGCACCGCCGATGTGGGCTGGG<br>TGACCGGACACAGTTACTTGCTGTACGGCCCGCTGGCCTGCGGTGCGACCACGCTGATGTTTGAAGGCGTACCCAACT<br>GGCCGACGCCTGCCCGTATGGCGCAGGTGGTGGACAAGCATCAGGTCAATATTCTCTATACCGCACCCACGGCGATCC<br>GCGCGCTGATGGCGGAAGGCGATAAAGCGATCGAAGGCACCGACCGTTCGTCGCTGCGCATTCTCGGTTCCGTGGGC<br>GAGCCAATTAACCCGGAAGCGTGGGAGTGGTACTGGAAAAAAATCGGCAACGAGAAATGTCCGGTGGTCGATACCTG<br>GTGGCAGACCGAAACCGGCGGTTTCATGATCACCCCGCTGCCTGGCGCTACCGAGCTGAAAGCCGGTTCGGCAACAC<br>GTCCGTTCTTCGGCGTGCAACCGGCGCTGGTCGATAACGAAGGTAACCCGCTGGAGGGGGCCACCGAAGGTAGCCTG<br>GTAATCACCGACTCCTGGCCGGGTCAGGCGCGTACGCTGTTTGGCGATCACGAACGTTTTGAACAGACCTACTTCTCC<br>ACCTTCAAAAATATGTATTTCAGCGGCGACGGCGCGCGTCGCGATGAAGATGGCTATTACTGGATAACCGGGCGTGT<br>GGACGACGTGCTGAACGTCTCCGGTCACCGTCTGGGGACGGCAGAGATTGAGTCGGCGCTGGTGGCGCATCCGAAGA<br>TTGCCGAAGCCGCCGTAGTAGGTATTCCGCACAATATTAAAGGTCAGGCGATCTACGCCTACGTCACGCTTAATCACG<br>GGGAGGAACCGTCACCAGAACTGTACGCAGAAGTCCGCAACTGGGTGCGTAAAGAGATTGGCCCGCTGGCGACGCCA<br>GACGTGCTGCACTGGACCGACTCCCTGCCTAAAACCCGCTCCGGCAAAATTATGCGCCGTATTCTGCGCAAAATTGCG<br>GCGGGCGATACCAGCAACCTGGGCGATACCTCGACGCTTGCCGATCCTGGCGTAGTCGAGAAGCTGCTTGAAGAGAA<br>GCAGGCTATCGCGATGCCATCGTAA |
| SEQ ID NO: 62<br>nucleic acid<br>coding sequence<br>of the gene acsA<br>at locus<br>BSU_29680 | ATGAACTTGAAAGCGTTACCAGCAATAGAGGGGGATCATAACTTAAAAAACTATGAAGAAACGTACCGGCATTTTGA<br>TTGGGCCGAGGCAGAGAAACATTTCTCTTGGCATGAGACAGGGAAACTGAATGCGGCGTATGAAGCGATTGACCGCC<br>ATGCCGAATCGTTTCGAAAAAACAAAGTAGCGCTTTATTATAAAGACGCAAAAAGGGATGAAAAATACACATTTAAA<br>GAAATGAAGGAAGAATCAAACAGAGCCGGGAATGTGCTGAGACGGTATGGAAATGTGGAAAAAGGGGACCGCGTTT<br>TTATTTTTATGCCGAGATCACCCGAGCTTTATTTTATTATGCTTGGCGCAATCAAAATTGGCGCCATCGCCGGGCCGCT<br>GTTCGAAGCATTTATGGAGGGAGCGGTGAAAGACCGGCTTGAAAACAGTGAGGCAAAGGTTGTTGTCACAACGCCTG<br>AGCTGCTGGAGAGAATACCGGTAGACAAACTGCCTCACTTGCAGCATGTCTTCGTAGTCGGGGGAGAGGCTGAGAGC<br>GGCACGAATATCATCAATTATGATGAAGCAGCGAAACAGGAAAGCACAAGATTGGATATCGAATGGATGGATAAAA<br>AAGACGGCTTTCTGCTTCACTATACATCAGGTTCCACTGGTACGCCAAAGGGCGTGTTGCATGTCCATGAAGCGATGA<br>TTCAGCAATATCAAACAGGAAAGTGGGTCCTTGATTTAAAGGAAGAAGACATTTATTGGTGCACGGCTGATCCAGGC<br>TGGGTGACAGGTACGGTATACGGCATTTTTGCACCGTGGCTGAACGGAGCGACAAATGTCATCGTCGGCGGACGTTTC<br>AGCCCGGAAAGCTGGTATGGAACGATTGAACAGCTTGGCGTCAATGTCTGGTACAGCGCGCCGACAGCTTTTCGGAT<br>GCTGATGGGAGCGGGAGATGAAATGGCTGCGAAATATGATCTAACTTCACTCCGGCATGTGCTCAGTGTCGGTGAGC<br>CGCTAAATCCGGAAGTCATCAGATGGGGACATAAAGTTTTTAACAAACGAATCCATGATACCTGGTGGATGACCGAA<br>ACGGGCAGTCAGCTCATCTGCAACTATCCTTGCATGGATATTAAACCGGGTTCAATGGGTAAGCCGATTCCAGGAGTG<br>GAGGCAGCGATCGTTGACAATCAAGGCAACGAGCTACCGCCGTACCGAATGGGCAATCTCGCCATCAAAAAGGGCTG<br>GCCTTCCATGATGCATACCATTTGGAATAACCCTGAAAAGTATGAATCGTATTTCATGCCGGGCGGCTGGTATGTGTC<br>TGGGGATTCTGCTTACATGGATGAAGAGGGATACTTTTGGTTCCAAGGCAGAGTTGATGACGTCATCATGACCTCCGG<br>TGAGCGCGTCGGCCCATTTGAAGTGGAAAGCAAGCTTGTCGAACATCCGGCTATTGCAGAAGCAGGCGTTATCGGAA<br>AGCCTGACCCGGTGCGTGGAGAAATCATTAAAGCCTTTATTGCACTCAGGGAAGGATTTGAGCCGTCTGATAAACTGA<br>AAGAAGAGATCCGCCTATTTGTAAAGCAGGGTCTTGCAGCCCATGCGGCTCCGCGTGAGATCGAATTTAAAGATAAG<br>CTTCCGAAAACCAGAAGCGGAAAGATCATGAGGCGCGTGCTGAAGGCATGGGAGCTTAATCTGCCGGCTGGAGATCT<br>GTCAACAATGGAGGATTAA |
| SEQ ID NO: 63<br>nucleic acid<br>coding sequence<br>of the gene atoA<br>at locus b2222 | ATGGATGCGAAACAACGTATTGCGCGCCGTGTGGCGCAAGAGCTTCGTGATGGTGACATCGTTAACTTAGGGATCGG<br>TTTACCCACAATGGTCGCCAATTATTTACCGGAGGGTATTCATATCACTCTGCAATCGGAAAACGGCTTCCTCGGTTTA<br>GGCCCGGTCACGACAGCGCATCCAGATCTGGTGAACGCTGGCGGGCAACCGTGCGGTGTTTTACCCGGTGCAGCCAT<br>GTTTGATAGCGCCATGTCATTTGCGCTAATCCGTGGCGGTCATATTGATGCCTGCGTGCTCGGCGGTTTGCAAGTAGA<br>CGAAGAAGCAAACCTCGCGAACTGGGTAGTGCCTGGGAAAATGGTGCCCGGTATGGGTGGCGCGATGGATCTGGTGA<br>CCGGGTCGCGCAAAGTGATCATCGCCATGGAACATTGCGCCAAAGATGGTTCAGCAAAAATTTTGCGCCGCTGCACC |

TABLE 2-continued

Nucleic Acid Sequences: Genes

| SEQ ID NO | Nucleic Acid Sequence |
|---|---|
| | ATGCCACTCACTGCGCAACATGCGGTGCATATGCTGGTTACTGAACTGGCTGTCTTTCGTTTTATTGACGGCAAAATGT<br>GGCTCACCGAAATTGCCGACGGGTGTGATTTAGCCACCGTGCGTGCCAAAACAGAAGCTCGGTTTGAAGTCGCCGCC<br>GATCTGAATACGCAACGGGGTGATTTATGA |
| SEQ ID NO: 64<br>nucleic acid<br>coding sequence<br>of the gene atoD<br>at locus b2221 | ATGAAAACAAAATTGATGACATTACAAGACGCCACCGGCTTCTTTCGTGACGGCATGACCATCATGGTGGGCGGATTT<br>ATGGGGATTGGCACTCCATCCCGCCTGGTTGAAGCATTACTGGAATCTGGTGTTCGCGACCTGACATTGATAGCCAAT<br>GATACCGCGTTTGTTGATACCGGCATCGGTCCGCTCATCGTCAATGGTCGAGTCCGCAAAGTGATTGCTTCACATATC<br>GGCACCAACCCGGAAACAGGTCGGCGCATGATATCTGGTGAGATGGACGTCGTTCTGGTGCCGCAAGGTACGCTAAT<br>CGAGCAAATTCGCTGTGGTGGAGCTGGACTTGGTGGTTTTCTCACCCCAACGGGTGTCGGCACCGTCGTAGAGGAAGG<br>CAAACAGACACTGACACTCGACGGTAAAACCTGGCTGCTCGAACGCCCACTGCGCGCCGACCTGGCGCTAATTCGCG<br>CTCATCGTTGCGACACACTTGGCAACCTGACCTATCAACTTAGCGCCCGCAACTTTAACCCCCTGATAGCCCTTGCGG<br>CTGATATCACGCTGGTAGAGCCAGATGAACTGGTCGAAACCGGCGAGCTGCAACCTGACCATATTGTCACCCCTGGTG<br>CCGTTATCGACCACATCATCGTTTCACAGGAGAGCAAATAA |
| SEQ ID NO: 65<br>nucleic acid<br>coding sequence<br>of the gene atoE<br>at locus b2223 | ATGATTGGTCGCATATCGCGTTTTATGACGCGTTTTGTCAGCCGGTGGCTTCCCGATCCACTGATCTTTGCCATGTTGC<br>TGACATTGCTAACATTCGTGATCGCGCTTTGGTTAACACCACAAACGCCGATCAGCATGGTGAAAATGTGGGGTGACG<br>GTTTCTGGAACTTGCTGGCGTTTGGTATGCAGATGGCGCTTATCATCGTTACCGGTCATGCCCTTGCCAGCTCTGCTCC<br>GGTGAAAAGTTTGCTGCGTACTGCCGCCTCCGCCGCAAAGACGCCCGTACAGGGCGTCATGCTGGTCACTTTCTTCGG<br>TTCAGTCGCTTGTGTCATCAACTGGGGATTTGGTTTGGTTGTCGGCGCAATGTTTGCCCGTGAAGTCGCCCGGCGAGTC<br>CCCGGTTCTGATTATCCGTTGCTCATTGCCTGCGCCTACATTGGTTTTCTCACCTGGGGTGGCGGCTTCTCTGGATCAA<br>TGCCTCTGTTGGCTGCAACACCGGGCAACCCGGTTGAGCATATCGCCGGGCTGATCCCGGTGGGCGATACTCTGTTCA<br>GTGGTTTTAACATTTTCATCACTGTGGCGTTGATTGTGGTGATGCCATTTATCACCCGCATGATGATGCCAAAACCGTC<br>TGACGTGGTGAGTATCGATCCAAAACTACTCATGGAAGAGGCTGATTTTCAAAAGCAGCTACCGAAAGATGCCCCAC<br>CATCCGAGCGACTGGAAGAAAGCCGCATTCTGACGTTGATCATCGGCGCACTCGGTATCGCTTACCTTGCGATGTACT<br>TCAGCGAACATGGCTTCAACATCACCATCAATACCGTCAACCTGATGTTTATGATTGCGGGTCTGCTGCTACATAAAA<br>CGCCAATGGCTTATATGCGTGCTATCAGCGCGGCAGCACGCAGTACTGCCGGTATTCTGGTGCAATTCCCCTTCTACG<br>CTGGGATCCAACTGATGATGGAGCATTCCGGTCTGGGCGGACTCATTACCGAATTCTTCATCAATGTTGCGAACAAAG<br>ACACCTTCCCGGTAATGACCTTTTTAGTTCTGCACTGATTAACTTCGCCGTTCCGTCTGGCGGCGGTCACTGGGTTAT<br>TCAGGGACCTTTCGTGATACCCGCAGCCCAGGCGCTGGGCGCTGATCTCGGTAAATCGGTAATGGCGATCGCCTACGG<br>CGAGCAATGGATGAACATGGCACAACCATTCTGGGCGCTGCCAGCACTGGCAATCGCCGGACTCGGTGTCCGCGACA<br>TCATGGGCTACTGCATCACTGCCCTGCTCTTCTCCGGTGTCATTTTCGTCATTGGTTTAACGCTGTTCTGA |
| SEQ ID NO: 66<br>nucleic acid<br>coding sequence<br>of the gene<br>BC_5341 | ATGCATTTTAAACTATCAGAAGAACATGAAATGATAAGAAAAATGGTTCGAGATTTTGCTAAAAATGAAGTGGCACC<br>AACAGCAGCTGAGCGTGATGAGGAAGAGCGATTTGATCGAGAATTATTTGATCAAATGGCAGAGCTTGGTTTAACCG<br>GTATTCCGTGGCCTGAAGAGTACGGTGGAATTGGAAGCGATTACTTAGCGTACGTAATCGCTATTGAAGAATTATCCC<br>GCGTTTGTGCTTCAACAGGCGTAACACTGTCCGCGCATACTTCACTTGCAGGATGGCCAATTTTTAAATTTGGGACGG<br>AAGAGCAAAAGCAAAAGTTTTTACGACCGATGGCTGAAGGAAAGAAAATTGGTGCATACGGCTTAACGGAGCCAGG<br>ATCTGGATCGGATGCTGGTGGAATGAAGACAATCGCAAAGAGAGATGGAGACCATTATATTTTAAATGGATCAAAAA<br>TTTTCATTACAAATGGCGGTATTGCTGATATTTACGTTGTTTTTGCGCTAACTGATCCTGAATCAAAGCAGCGCGGTAC<br>GAGTGCATTTATTGTAGAAAGTGATACACCGGGATTTTCAGTTGGGAAGAAGGAGAGCAAGCTAGGGATTCGCTCTT<br>CACCAACGACTGAAATTATGTTTGAAGATTGCCGTATTCCTGTAGAGAATCTACTTGGAGAAGAGGGGCAAGGGTTTA<br>AAGTTGCGATGCAAACATTAGATGGAGGTCGTAACGGTATTGCGGCGCAAGCTGTTGGTATTGCACAAGGGGCTTTA<br>GATGCTTCTGTAGAATATGCAAGGGAGCGCCATCAATTTGGAAAACCAATTGCGGCGCAGCAAGGGATTGGCTTTAA<br>ACTTGCGGATATGGCAACAGATGTAGAAGCGGCACGCCTTTTAACATATCAAGCGGCTTGGCTTGAATCAGAAGGGC<br>TTCCGTATGGAAAAGAGTCAGCGATGTCAAAAGTATTTGCAGGAGATACAGCGATGAGGGTGACGACTGAAGCGGTG<br>CAAGTATTTGGTGGTTACGGTTATACGAAAGATTATCCAGTAGAGCGTTATATGCGAGATGCAAAAATTACACAAATA<br>TATGAAGGAACACAAGAGATTCAGAGGCTTGTAATTTCTCGTATGTTAACGAAGTAG |
| SEQ ID NO: 67<br>nucleic acid<br>coding sequence<br>of the gene bktB<br>at locus<br>H16_RS07175 | ATGACGCGTGAAGTGGTAGTGGTAAGCGGTGTCCGTACCGCGATCGGGACCTTTGGCGGCAGCCTGAAGGATGTGGC<br>ACCGGCGGAGCTGGGCGCACTGGTGGTGCGCGAGGCGCTGGCGCGCGCGCAGGTGTCGGGCGACGATGTCGGCCACG<br>TGGTATTCGGCAACGTGATCCAGACCGAGCCGCGCGACATGTATCTGGGCCGCGTCGCGGCCGTCAACGGCGGGGTG<br>ACGATCAACGCCCCCGCGCTGACCGTGAACCGCCTGTGCGGCTCGGGCCTGCAGGCCATTGTCAGCGCCGCGCAGAC<br>CATCCTGCTGGGCGATACCGACGTCGCCATCGGCGGCGGCGCGGAAAGCATGAGCCGCGCACCGTACCTGGCGCCGG<br>CAGCGCGCTGGGGCGCACGCATGGGCGACGCCGGCCTGGTCGACATGATGCTGGGTGCGCTGCACGATCCCTTCCAT<br>CGCATCCACATGGGCGTGACCGCCGAGAATGTCGCCAAGGAATACGACATCTCGCGCGCGCAGCAGGACGAGGCCGC<br>GCTGGAATCGCACCGCCGCGCTTCGGCAGCGATCAAGGCCGGCTACTTCAAGGACCAGATCGTCCCGGTGGTGAGCA<br>AGGGCCGCAAGGGCGACGTGACCTTCGACACCGACGAGCACGTGCGCCATGACGCCACCATCGACGACATGACCAAG<br>CTCAGGCCGGTCTTCGTCAAGGAAAACGGCACGGTCACGGCCGGCAATGCCTCGGGCCTGAACGACGCCGCCGCCGC<br>GGTGGTGATGATGGAGCGCGCCGAAGCCGAGCGCCGCGGCCTGAAGCCGCTGGCCCGCCTGGTGTCGTACGGCCATG<br>CCGGCGTGGACCCGAAGGCCATGGGCATCGGCCCGGTGCCGGCGACGAAGATCGCGCTGGAGCGCGCCGGCCTGCAG<br>GTGTCGGACCTGGACGTGATCGAAGCCAACGAAGCCTTTGCCGCACAGGCGTGCGCCGTGACCAAGGCGCTCGGTCT<br>GGACCCGGCCAAGGTTAACCCGAACGGCTCGGGCATCTCGCTGGGCCACCCGATCGGCGCCACCGGTGCCCTGATCA<br>CGGTGAAGGCGCTGCATGAGCTGAACCGCGTGCAGGGCCGCTACGCGCTGGTGACGATGTGCATCGGCGGCGGGCAG<br>GGCATTGCCGCCATCTTCGAGCGTATCTGA |
| SEQ ID NO: 68<br>nucleic acid<br>coding sequence<br>of the gene cadA<br>at locus b4131 | ATGAACGTTATTGCAATATTGAATCACATGGGGGTTTATTTTAAAGAAGAACCCATCCGTGAACTTCATCGCGCGCTT<br>GAACGTCTGAACTTCCAGATTGTTTACCCGAACGACCGTGACGACTTATTAAAACTGATCGAAAACAATGCGCGTCTG<br>TGCGGCGTTATTTTTGACTGGGATAAATATAATCTCGAGCTGTGCGAAGAAATTAGCAAAATGAACGAGAACCTGCC<br>GTTGTACGCGTTCGCTAATACGTATTCCACTCTCGATGTAAGCCTGAATGACCTGCGTTTACAGATTAGCTTCTTTGAA<br>TATGCGCTGGGTGCTGCTGAAGATATTGCTAATAAGATCAAGCAGACCACTGACGAATATATCAACACTATTCTGCCT<br>CCGCTGACTAAAGCACTGTTTAAATATGTTCGTGAAGGTAAATATACTTTCTGTACTCCTGGTCACATGGGCGGTACT<br>GCATTCCAGAAAAGCCCGGTAGGTAGCCTGTTCTATGATTTCTTTGGTCCGAATACCATGAAATCTGATATTTCCATTT<br>CAGTATCTGAACTGGGTTCTCTGCTGGATCACAGTGGTCCACACAAAGAAGCAGAACAGTATATCGCTCGCGTCTTTA<br>ACGCAGACCGCAGCTACATGGTGACCAACGGTACTTCCACTGCGAACAAAATTGTTGGTATGTACTCTGCTCCAGCAG<br>GCAGCACCATTCTGATTGACCGTAACTGCCACAAATCGCTGACCCACCTGATGATGATGAGCGATGTTACGCCAATCT<br>ATTTCCGCCCGACCCGTAACGCTTACGGTATTCTTGGTGGTATCCCACAGAGTGAATTCCAGCACGCTACCATTGCTA |

TABLE 2-continued

| Nucleic Acid Sequences: Genes | |
|---|---|
| SEQ ID NO | Nucleic Acid Sequence |
| | AGCGCGTGAAAGAAACACCAAACGCAACCTGGCCGGTACATGCTGTAATTACCAACTCTACCTATGATGGTCTGCTGT<br>ACAACACCGACTTCATCAAGAAAACACTGGATGTGAAATCCATCCACTTTGACTCCGCGTGGGTGCCTTACACCAACT<br>TCTCACCGATTTACGAAGGTAAATGCGGTATGAGCGGTGGCCGTGTAGAAGGGAAAGTGATTTACGAAACCCAGTCC<br>ACTCACAAACTGCTGGCGGCGTTCTCTCAGGCTTCCATGATCCACGTTAAAGGTGACGTAAACGAAGAAACCTTTAAC<br>GAAGCCTACATGATGCACACCACCACTTCTCCGCACTACGGTATCGTGGCGTCCACTGAAACCGCTGCGGCGATGATG<br>AAAGGCAATGCAGGTAAGCGTCTGATCAACGGTTCTATTGAACGTGCGATCAAATTCCGTAAAGAGATCAAACGTCT<br>GAGAACGGAATCTGATGGCTGGTTCTTTGATGTATGGCAGCCGGATCATATCGATACGACTGAATGCTGGCCGCTGCG<br>TTCTGACAGCACCTGGCACGGCTTCAAAAACATCGATAACGAGCACATGTATCTTGACCCGATCAAAGTCACCCTGCT<br>GACTCCGGGGATGGAAAAAGACGGCACCATGAGCGACTTTGGTATTCCGGCCAGCATCGTGGCGAAATACCTCGACG<br>AACATGGCATCGTTGTTGAGAAAACCGGTCCGTATAACCTGCTGTTCCTGTTCAGCATCGGTATCGATAAGACCAAAG<br>CACTGAGCCTGCTGCGTGCTCTGACTGACTTTAAACGTGCGTTCGACCTGAACCTGCGTGTGAAAAACATGCTGCCGT<br>CTCTGTATCGTGAAGATCCTGAATTCTATGAAAACATGCGTATTCAGGAACTGGCTCAGAATATCCACAAACTGATTG<br>TTCACCACAATCTGCCGGATCTGATGTATCGCGCATTTGAAGTGCTGCCGACGATGGTAATGACTCCGTATGCTGCAT<br>TCCAGAAAGAGCTGCACGGTATGACCGAAGAAGTTTACCTCGACGAAATGGTAGGTCGTATTAACGCCAATATGATC<br>CTTCCGTACCCGCCGGGAGTTCCTCTGGTAATGCCGGGTGAAATGATCACCGAAGAAAGCCGTCCGGTTCTGGAGTTC<br>CTGCAGATGCTGTGTGAAATCGGCGCTCACTATCCGGGCTTTGAAACCGATATTCACGGTGCATACCGTCAGGCTGAT<br>GGCCGCTATACCGTTAAGGTATTGAAAGAAGAAAGCAAAAAATAA |
| SEQ ID NO: 69<br>nucleic acid<br>coding sequence<br>of the gene<br>CKL_RS14680 | ATGAGTAAAGGGATAAAGAATTCACAATTGAAAAAAAAGAATGTAAAGGCTAGTAATGTGGCAGAAAAGATTGAAG<br>AGAAAGTTGAAAAAACAGATAAGGTTGTTGAAAAGGCAGCTGAGGTTACAGAAAAACGAATTAGAAACTTGAAGCT<br>TCAGGAAAAAGTTGTAACAGCAGATGTGGCAGCTGATATGATAGAAAACGGTATGATTGTTGCAATTAGCGGATTTA<br>CTCCTTCCGGGTATCCTAAAGAAGTACCTAAAGCATTGACTAAAAAAGTTAATGCCTTAGAGGAAGAATTCAAGGTA<br>ACACTTTATACAGGTTCATCTACAGGAGCCGATATAGACGGAGAATGGGCAAAAGCAGGAATAATAGAAAGAAGAA<br>TTCCATATCAGACAAATTCTGATATGAGGAAAAAAATAAATGATGGTTCTATTAAGTATGCTGATATGCATTTAAGCC<br>ATATGGCTCAATATATTAATTATTCTGTAATTCCTAAAGTAGATATAGCTATAATAGAGGCAGTAGCTATTACAGAAG<br>AAGGGGATATTATTCCTTCAACAGGAATTGGAAATACAGCTACTTTTGTGGAAAATGCAGATAAGGTAATAGTGGAA<br>ATTAATGAGGCTCAACCGCTTGAATTGGAAGGTATGGCAGATATATATACATTAAAAAACCCTCCAAGAAGAGAGCC<br>CATACCTATAGTTAATGCAGGCAATAGGATAGGGACCACATATGTGACCTGTGGTTCTGAAAAAATATGCGCTATAGT<br>GATGACAAATACCCAGGATAAAACAAGACCTCTTACAGAAGTGTCTCCTGTATCTCAGGCTATATCCGATAATCTTAT<br>AGGATTTTTAAATAAAGAGGTTGAAGAGGGAAAATTACCTAAGAACCTGCTTCCTATACAGTCAGGAGTTGGAAGTG<br>TAGCAAATGCAGTTTTGGCCGGACTTTGTGAATCAAATTTTAAAAATTTGAGTTGTTATACAGAAGTTATACAGGATT<br>CTATGCTGAAGCTTATAAAATGTGGTAAAGCAGATGTGGTGTCAGGCACTTCCATAAGTCCTTCACCGGAGATGTTGC<br>CTGAGTTCATAAAGGACATAAATTTCTTTAGAGAAAAGATAGTATTAAGACCACAGGAAATAAGTAATAATCCAGAG<br>ATAGCAAGAAGAATAGGAGTTATATCCATAAACACTGCTTTGGAAGTAGATATATATGGTAATGTAAACTCCACTCAT<br>GTTATGGGAAGCAAAATGATGAATGGTATAGGCGGTTCTGGAGACTTTGCCAGAAATGCATATTTGACTATATTCACT<br>ACAGAGTCTATCGCCAAAAAAGGAGATATATCATCTATAGTTCCTATGGTATCCCATGTGGATCATACAGAACATGAT<br>GTAATGGTAATTGTTACAGAACAGGGAGTAGCAGATTTAAGAGGTCTTTCTCCTAGGGAAAAGGCCGTGGCTATAAT<br>AGAAAATTGTGTTCATCCTGATTACAAGGATATGCTTATGGAATATTTTGAAGAGGCTTGTAAGTCATCAGGTGGAAA<br>TACACCACATAATCTTGAAAAAGCTCTTTCCTGGCATACAAAATTTATAAAAACTGGTAGTATGAAATAA |
| SEQ ID NO: 70<br>nucleic acid<br>coding sequence<br>of the gene endA<br>at locus b2945 | ATGTACCGTTATTTGTCTATTGCTGCGGTGGTACTGAGCGCAGCATTTTCCGGCCCGGCGTTGGCCGAAGGTATCAAT<br>AGTTTTTCTCAGGCGAAAGCCGCGGCGGTAAAAGTCCACGCTGACGCGCCCGGTACGTTTTATTGCGGATGTAAAATT<br>AACTGGCAGGGCAAAAAAGGCGTTGTTGATCTGCAATCGTGCGGCTATCAGGTGCGCAAAAATGAAAACCGCGCCAG<br>CCGCGTAGAGTGGGAACATGTCGTTCCCGCCTGGCAGTTCGGTCACCAGCGCCAGTGCTGGCAGGACGGTGGACGTA<br>AAAACTGCGCTAAAGATCCGGTCTATCGCAAGATGGAAAGCGATATGCATAACCTGCAGCCGTCAGTCGGTGAGGTG<br>AATGGCGATCGCGGCAACTTTATGTACAGCCAGTGGAATGGCGGTGAAGGCCAGTACGGTCAATGCGCCATGAAGGT<br>CGATTTCAAAGAAAAAGCTGCCGAACCACCAGCGCGTGCACGCGGTGCCATTGCGCGCACCTACTTCTATATGCGCG<br>ACCAATACAACCTGACACTCTCTCGCCAGCAAACGCAGCTGTTCAACGCATGGAACAAGATGTATCCGGTTACCGACT<br>GGGAGTGCGAGCGCGATGAACGCATCGCGAAGGTGCAGGGCAATCATAACCCGTATGTGCAACGCGCTTGCCAGGCG<br>CGAAAGAGCTAA |
| SEQ ID NO: 71<br>nucleic acid<br>coding sequence<br>of the gene fadB<br>at locus b3846 | ATGCTTTACAAAGGCGACACCCTGTACCTTGACTGGCTGGAAGATGGCATTGCCGAACTGGTATTTGATGCCCCAGGT<br>TCAGTTAATAAACTCGACACTGCGACCGTCGCCAGCCTCGGCGAGGCCATCGGCGTGCTGGAACAGCAATCAGATCT<br>AAAAGGGCTGCTGCTGCGTTCGAACAAAGCAGCCTTTATCGTCGGTGCTGATATCACCGAATTTTTGTCCCTGTTCCTC<br>GTTCCTGAAGAACAGTTAAGTCAGTGGCTGCACTTTGCCAATAGCGTGTTTAATCGCCTGGAAGATCTGCCGGTGCCG<br>ACCATTGCTGCCGTCAATGGCTATGCGCTGGGCGGTGGCTGCGAATGCGTGCTGGCGACCGATTATCGTCTGGCGACG<br>CCGGATCTGCGCATCGGTCTGCCGGAAACCAAACTGGGCATCATGCCTGGCTTTGGCGGTTCTGTACGTATGCCACGT<br>ATGCTGGGCGCTGACAGTGCGCTGGAAATCATTGCCGCCGGTAAAGATGTCGGCGCGGATCAGGCGCTGAAAATCGG<br>TCTGGTGGATGGCGTAGTCAAAGCAGAAAAACTGGTTGAAGGCGCAAAGGCGGTTTTACGCCAGGCCATTAACGGCG<br>ACCTCGACTGGAAAGCAAAACGTCAGCCGAAGCTGGAACCACTAAAACTGAGCAAGATTGAAGCCACCATGAGCTTC<br>ACCATCGCTAAAGGGATGGTCGCACAAACAGCGGGGAAACATTATCCGGCCCCCATCACCGCAGTAAAAACCATTGA<br>AGCTGCGGCCCGTTTTGGTCGTGAAGAAGCCTTAAACCTGGAAAACAAAAGTTTTGTCCCGCTGGCGCATACCAACGA<br>AGCCCGCGCACTGGTCGGCATTTTCCTTAACGATCAATATGTAAAAGGCAAAGCGAAGAAACTCACCAAAGACGTTG<br>AAACCCCGAAACAGGCCGCGGTGCTGGGTGCAGGCATTATGGGCGGCGGCATCGCTTACCAGTCTGCGTGGAAAGGC<br>GTGCCGGTTGTCATGAAAGATATCAACGACAAGTCGTTAACCCTCGGCATGACCGAAGCCGCGAAACTGCTGAACAA<br>GCAGCTTGAGCGCGGCAAGATCGATGGTCTGAAACTGGCTGGCGTGATCTCCACAATCCACCCAACGCTCGACTACG<br>CCGGATTTGACCGCGTGGATATTGTGGTAGAAGCGGTTGTTGAAAACCCGAAAGTGAAAAAAGCCGTACTGGCAGAA<br>ACCGAACAAAAAGTACGCCAGGATACCGTGCTGGCGTCTAACACTTCAACCATTCCTATCAGCGAACTGGCCAACGC<br>GCTGGAACGCCCGGAAAACTTCTGCGGGATGCACTTCTTTAACCCGGTCCACCGAATGCCGTTGGTAGAAATTATTCG<br>CGGCGAGAAAAGCTCCGACGAAACCATCGCGAAAGTTGTCGCCTGGGCGAGCAAGATGGGCAAGACGCCGATTGTG<br>GTTAACGACTGCCCCGGCTTCTTTGTTAACCGCGTGCTGTTCCCGTATTTCGCCGGTTTCAGCCAGCTGCTGCGCGACG<br>GCGCGGATTTCCGCAAGATCGACAAAGTGATGGAAAAACAGTTTGGCTGGCCGATGGGCCCGGCATATCTGCTGGAC<br>GTTGTGGGCATTGATACCGCGCATCACGCTCAGGCTGTCATGGCAGCAGGCTTCCCGCAGCGGATGCAGAAAGATTA<br>CCGCGATGCCATCGACGCGCTGTTTGATGCCAACCGCTTTGGTCAGAAGAACGGCCTCGGTTTCTGGCGTTATAAAGA<br>AGACAGCAAAGGTAAGCCGAAGAAAGAAGAAGACGCCGCCGTTGAAGACCTGCTGGCAGAAGTGAGCCAGCCGAAG<br>CGCGATTTCAGCGAAGAAGAGATTATCGCCCGCATGATGATCCCGATGGTCAACGAAGTGGTGCGCTGTCTGGAGGA |

TABLE 2-continued

| Nucleic Acid Sequences: Genes | |
|---|---|
| SEQ ID NO | Nucleic Acid Sequence |
| | AGGCATTATCGCCACTCCGGCGGAAGCGGATATGGCGCTGGTCTACGGCCTGGGCTTCCCTCCGTTCCACGGCGGCGC GTTCCGCTGGCTGGACACCCTCGGTAGCGCAAAATACCTCGATATGGCACAGCAATATCAGCACCTCGGCCCGCTGTA TGAAGTGCCGGAAGGTCTGCGTAATAAAGCGCGTCATAACGAACCGTACTATCCTCCGGTTGAGCCAGCCCGTCCGGT TGGCGACCTGAAAACGGCTTAA |
| SEQ ID NO: 72 nucleic acid coding sequence of the gene fadE at locus b0221 | ATGATGATTTTGAGTATTCTCGCTACGGTTGTCCTGCTCGGCGCGTTGTTCTATCACCGCGTGAGCTTATTTATCAGCA GTCTGATTTTGCTCGCCTGGACAGCCGCCCTCGGCGTTGCTGGTCTGTGGTCGGCGTGGGTACTGGTGCCTCTGGCCAT TATCCTCGTGCCATTTAACTTTGCGCCTATGCGTAAGTCGATGATTTCCGCGCCGGTATTTCGCGGTTTCCGTAAGGTG ATGCCGCCGATGTCGCGCACTGAGAAAGAAGCGATTGATGCGGGCACCACCTGGTGGGAGGGCGACTTGTTCCAGGG CAAGCCGGACTGGAAAAAGCTGCATAACTATCCGCAGCCGCGCCTGACCGCCGAAGAGCAAGCGTTTCTCGACGGCC CGGTAGAAGAAGCCTGCCGGATGGCGAATGATTTCCAGATCACCCATGAGCTGGCGGATCTGCCGCCGGAGTTGTGG GCGTACCTTAAAGAGCATCGTTTCTTCGCGATGATCATCAAAAAAGAGTACGGCGGGCTGGAGTTCTCGGCTTATGCC CAGTCTCGCGTGCTGCAAAAACTCTCCGGCGTGAGCGGGATCCTGGCGATTACCGTCGGCGTGCCAAACTCATTAGGC CCGGGCGAACTGTTGCAACATTACGGCACTGACGAGCAGAAAGATCACTATCTGCCGCGTCTGGCGCGTGGTCAGGA GATCCCCTGCTTTGCACTGACCAGCCCGGAAGCGGGTTCCGATGCGGGCGCGATTCCGGACACCGGGATTGTCTGCAT GGGCGAATGGCAGGGCCAGCAGGTGCTGGGGATGCGTCTGACCTGGAACAAACGCTACATTACGCTGGCACCGATTG CGACCGTGCTTGGGCTGGCGTTTAAACTCTCCGACCCGGAAAAATTACTCGGCGGTGCAGAAGATTTAGGCATTACCT GTGCGCTGATCCCAACCACCACGCCGGGCGTGGAAATTGGTCGTCGCCACTTCCCGCTGAACGTACCGTTCCAGAACG GACCGACGCGCGGTAAAGATGTCTTCGTGCCGATCGATTACATCATCGGCGGGCCGAAAATGGCCGGGCAAGGCTGG CGGATGCTGGTGGAGTGCCTCTCGGTAGGCCGCGGCATCACCCTGCCTTCCAACTCAACCGGCGGCGTGAAATCGGTA GCGCTGGCAACCGGCGCGTATGCTCACATTCGCCGTCAGTTCAAAATCTCTATTGGTAAGATGGAAGGGATTGAAGA GCCGCTGGCGCGTATTGCCGGTAATGCCTACGTGATGGATGCTGCGGCATCGCTGATTACCTACGGCATTATGCTCGG CGAAAAACCTGCCGTGCTGTCGGCTATCGTTAAGTATCACTGTACCCACCGCGGGCAGCAGTCGATTATTGATGCGAT GGATATTACCGGCGGTAAAGGCATTATGCTCGGGCAAAGCAACTTCCTGGCGCGTGCTTACCAGGGCGCACCGATTG CCATCACCGTTGAAGGGGCTAACATTCTGACCCGCAGCATGATGATCTTCGGACAAGGAGCGATTCGTTGCCATCCGT ACGTGCTGGAAGAGATGGAAGCGGCGAAGAACAATGACGTCAACGCGTTCGATAAACTGTTGTTCAAACATATCGGT CACGTCGGTAGCAACAAAGTTCGCAGCTTCTGGCTGGGCCTGACGCGCGGTTTAACCAGCAGCACGCCAACCGGCGA TGCCACTAAACGCTACTATCAGCACCTGAACCGCCTGAGCGCCAACCTCGCCCTGCTTTCTGATGTCTCGATGGCAGT GCTGGGCGGCAGCCTGAAACGTCGCGAGCGCATCTCGGCCCGTCTGGGGGATATTTTAAGCCAGCTCTACCTCGCCTC TGCCGTGCTGAAGCGTTATGACGACGAAGGCCGTAATGAAGCCGACCTGCCGCTGGTGCACTGGGGCGTACAAGATG CGCTGTATCAGGCTGAACAGGCGATGGATGATTTACTGCAAAACTTCCCGAACCGCGTGGTTGCCGGGCTGCTGAATG TGGTGATCTTCCCGACCGGACGTCATTATCTGGCACCTTCTGACAAGCTGGATCATAAAGTGGCGAAGATTTTACAAG TGCCGAACGCCACCCGTTCCCGCATTGGTCGCGGTCAGTACCTGACGCCGAGCGAGCATAATCCGGTTGGCTTGCTGG AAGAGGCGCTGGTGGATGTGATTGCCGCCGACCCAATTCATCAGCGGATCTGTAAAGAGCTGGGTAAAAACCTGCCG TTTACCCGTCTGGATGAACTGGCGCACAACGCGCTGGTGAAGGGGCTGATTGATAAAGATGAAGCCGCTATTCTGGTG AAAGCTGAAGAAAGCCGTCTGCGCAGTATTAACGTTGATGACTTTGATCCGGAAGAGCTGGCGACGAAGCCGGTAAA GTTGCCGGAGAAAGTGCGGAAAGTTGAAGCCGCGTAA |
| SEQ ID NO: 73 nucleic acid coding sequence of the gene fadJ at locus b2341 | ATGGAAATGACATCAGCGTTTACCCTTAATGTTCGTCTGGACAACATTGCCGTTATCACCATCGACGTACCGGGTGAG AAAATGAATACCCTGAAGGCGGAGTTTGCCTCGCAGGTGCGCGCCATTATTAAGCAACTCCGTGAAAACAAAGAGTT GCGAGGCGTGGTGTTTGTCTCCGCTAAACCGGACAACTTCATTGCTGGCGCAGACATCAACATGATCGGCAACTGCAA AACGGCGCAAGAAGCGGAAGCTCTGGCGCGGCAGGGCCAACAGTTGATGGCGGAGATTCATGCTTTGCCCATTCAGG TTATCGCGGCTATTCATGGCGCTTGCCTGGGTGGTGGGCTGGAGTTGGCGCTGGCGTGCCACGGTCGCGTTTGTACTG ACGATCCTAAAACGGTGCTCGGTTTGCCTGAAGTACAACTTGGATTGTTACCCGGTTCAGGCGGCACCCAGCGTTTAC CGCGTCTGATAGGCGTCAGCACAGCATTAGAGATGATCCTCACCGGAAAACAACTTCGGGCGAAACAGGCATTAAAG CTGGGGCTGGTGGATGACGTTGTTCCGCACTCCATTCTGCTGGAAGCCGCTGTTGAGCTGGCAAAGAAGGAGCGCCCA TCTTCCCGCCCTCTACCTGTACGCGAGCGTATTCTGGCGGGGCCGTTAGGTCGTGCGCTGCTGTTCAAAATGGTCGGC AAGAAAACAGAACACAAAACTCAAGGCAATTATCCGGCGACAGAACGCATCCTGGAGGTTGTTGAAACGGGATTAG CGCAGGGCACCAGCAGCGGTTATGACGCCGAAGCTCGGGCGTTTGGCGAACTGGCGATGACGCCACAATCGCAGGCG CTGCGTAGTATCTTTTTTGCCAGTACGGACGTGAAGAAAGATCCCGGCAGTGATGCGCCGCCTGCGCCATTAAACAGC GTGGGGATTTTAGGTGGTGGCTTGATGGGCGGCGGTATTGCTTATGTCACTGCTTGTAAAGCGGGGATTCCGGTCAGA ATTAAAGATATCAACCCGCAGGGCATAAATCATGCGCTGAAGTACAGTTGGGATCAGCTGGAGGGCAAAGTTCGCCG TCGTCATCTCAAAGCCAGCGAACGTGACAAACAGCTGGCATTAATCTCCGGAACGACGGACTATCGCGGCTTTGCCCA TCGCGATCTGATTATTGAAGCGGTGTTTGAAAATCTCGAATTGAAACAACAGATGGTGGCGGAAGTTGAGCAAAATT GCGCCGCTCATACCATCTTTGCTTCGAATACGTCATCTTTACCGATTGGTGATATCGCCGCTCACGCCACGCGACCTGA GCAAGTTATCGGCCTGCATTTCTTCAGTCCGGTGGAAAAAATGCCGCTGGTGGAGATTATTCCTCATGCGGGGACATC GGCGCAAACCATCGCTACCACAGTAAAACTGGCGAAAAAACAGGGTAAAACGCCAATTGTCGTGCGTGACAAAGCC GGTTTTTACGTCAATCGCATCTTAGCGCCTTACATTAATGAAGCTATCCGCATGTTGACCCAAGGTGAACGGGTAGAG CACATTGATGCCGCGCTAGTGAAATTTGGTTTTCCGGTAGGCCCAATCCAACTTTTGGATGAGGTAGGAATCGACACC GGGACTAAAATTATTCCTGTACTGGAAGCCGCTTATGGAGAACGTTTTAGCGCGCCTGCAAATGTTGTTTCTTCAATTT TGAACGACGATCGCAAAGGCAGAAAAAATGGCCGGGGTTTCTATCTTTATGGTCAGAAAGGGCGTAAAAGCAAAAA ACAGGTCGATCCCGCCATTTACCCGCTGATTGGCACACAAGGGCAGGGGCGAATCTCCGCACCGCAGGTTGCTGAAC GGTGTGTGATGTTGATGCTGAATGAAGCAGTACGTTGTGTTGATGAGCAGGTTATCCGTAGCGTGCGTGACGGGGATA TTGGCGCGGTATTTGGCATTGGTTTTCCGCCATTTCTCGGTGGACCGTTCCGCTATATCGATTCTCTCGGCGCGGGCGA AGTGGTTGCAATAATGCAACGACTTGCCACGCAGTATGGTTCCCGTTTTACCCCTTGCGAGCGTTTGGTCGAGATGGG CGCGCGTGGGGAAAGTTTTTGGAAAACAACTGCAACTGACCTGCAATAA |
| SEQ ID NO: 74 nucleic acid coding sequence of the gene FG99_15380 | ATGAACCAGCAAGTGAACGTAGCGCCGTCGGCCGCCGCCGACCTGAACCTGAAGGCCCACTGGATGCCCTTCAGCGC CAACCGCAACTTCCACAAGGACCCGCGCATCATCGTGGCCGCCGAGGGCAGCTGGCTGGTGGACGACAAGGGCCGGC GCATCTACGACAGCCTGTCCGGCCTGTGGACCTGCGGCGCCGGTCACTCGCGCAAGGAAATCGCCGACGCGGTGGCC AAGCAGATTGGCACCCTCGACTACTCCCCGGGCTTCCAGTACGGCCACCCGCTGTCCTTCCAGCTGGCCGAGAAGATC GCCCAGATGACCCCCGGCACCCTCGACCACGTGTTCTTCACCGGCTCCGGTTCCGAGTGCGCCGACACCTCGATCAAG ATGGCCCGCGCCTACTGGCGCATCAAAGGCCAGGCGCAGAAGACCAAGCTGATCGGCCGCGCCCGTGGCTACCACGG CGTGAACGTCGCCGGCACCTCCCTGGGCGGCATCGGCGGCAACCGCAAGATGTTCGGCCCGCTGATGGACGTCGACC ACCTGCCGCACACCCTGCAGCCGGGCATGGCCTTTACCAAGGGTGCGGCCGAGACCGGCGGCGTCGAGCTGGCCAAC GAACTGCTGAAGCTGATCGAGCTGCACGACGCCTCCAACATCGCCGCGGTGATCGTCGAGCCGATGTCCGGCTCCGCC |

TABLE 2-continued

Nucleic Acid Sequences: Genes

| SEQ ID NO | Nucleic Acid Sequence |
|---|---|
| | GGCGTGATCGTGCCGCCGAAGGGCTACCTGCAGCGCCTGCGGGAAATCTGCGACGCCAACGACATCCTGCTGATCTTC<br>GACGAAGTCATCACCGCCTTCGGCCGCATGGGCAAGGCCACCGGCGCCGAATACTTCGGCGTGACCCCGGACATCAT<br>GAACGTCGCCAAGCAGGTCACCAACGGCGCCGTGCCCATGGGCGCGGTGATCGCCAGCAGCGAAATCTACGACACCT<br>TCATGAACCAGAACCTGCCGGAATACGCGGTGGAGTTCGGCCATGGCTACACCTACTCCGCGCACCCGGTCGCCTGCG<br>CCGCCGGCATCGCCGCGCTGGACCTGCTGCAGAAGGAAAACCTGATCCAGCAGTCCGCCGAACTGGCGCCGCACTTC<br>GAGAAGGCCCTGCACGGCCTCAAGGGCACGAAGAACGTCATCGACATCCGCAACTGCGGCCTGGCCGGCGCCATCCA<br>GATCGCCGCCCGCGACGGCGACGCCATCGTCCGCCCGTTCGAAGCCAGCATGAAGCTGTGGAAGGAAGGCTTCTACG<br>TGCGCTTCGGCGGCGACACCCTGCAGTTCGGGCCGACCTTCAACGCCAAGCCCGAAGACCTCGACCGCCTGTTCGACG<br>CGGTCGGCGAAGCCCTCAACGGGGTGGCGTAA |
| SEQ ID NO: 75<br>nucleic acid<br>coding sequence<br>of the gene<br>FG99_15380<br>optimized for<br>*E.coli* | ATGAATCAACAGGTAAATGTGGCCCCCAGCGCGGCAGCAGACTTAAATCTGAAAGCGCATTGGATGCCTTTTAGCGC<br>CAACCGCAACTTCCACAAGGACCCCCGCATCATCGTAGCTGCCGAAGGATCGTGGCTGGTAGACGATAAGGGACGCC<br>GTATCTACGACTCATTGAGTGGCTTGTGGACCTGCGGCGCGGGTCACTCTCGTAAGGAAATTGCCGACGCAGTGGCGA<br>AACAGATTGGGACCCTGGACTACTCGCCAGGGTTTCAATATGGCCACCCTCTGTCGTTTCAGCTTGCAGAGAAGATTG<br>CGCAAATGACGCCTGGCACGCTGGATCATGTCTTCTTTACAGGAAGTGGGAGTGAATGCGCGGACACATCTATCAAA<br>ATGGCTCGCGCCTACTGGCGCATCAAGGGCCAAGCGCAGAAGACCAAGTTGATCGGCCGTGCTCGCGGATATCACGG<br>CGTCAACGTGGCCGGAACATCGCTTGGAGGTATTGGGGGAAACCGTAAAATGTTCGGACCCCTGATGGATGTCGATC<br>ATTTGCCTCACACATTACAACCTGGAATGGCATTCACTAAGGGCGCAGCAGAAACAGGTGGGGTGGAGCTTGCCAAT<br>GAATTGCTGAAGTTAATTGAGTTACATGATGCTTCGAATATCGCCGCAGTGATTGTGGAGCCTATGTCTGGCAGTGCC<br>GGTGTGATTGTGCCACCAAAAGGTTATCTTCAGCGTTTACGTGAGATTTGCGACGCTAACGATATCCTGTTAATCTTCG<br>ACGAGGTGATTACAGCTTTTGGCCGTATGGGCAAAGCAACGGGTGCCGAGTATTTTGGAGTAACTCCCGATATCATGA<br>ACGTGGCTAAGCAAGTAACCAACGGGGCCGTTCCGATGGGAGCCGTTATCGCCTCCTCTGAAATTTATGACACCTTCA<br>TGAACCAAAACTTGCCCGAATACGCCGTGGAATTTGGACATGGTTATACTTACAGCGCTCATCCAGTGGCATGTGCCG<br>CCGGCATCGCGGCGCTGGATCTGCTTCAAAAAGAGAATTTAATCCAGCAGTCGGCCGAGCTTGCACCTCACTTCGAAA<br>AGGCCTTACATGGCTTAAAGGGCACTAAAAACGTTATCGATATCCGCAACTGTGGCCTTGCTGGAGCGATTCAAATCG<br>CGGCGCGCGACGGAGACGCGATCGTGCGCCCCTTTGAGGCGAGCATGAAGTTGTGGAAGGAAGGCTTCTACGTGCGT<br>TTCGGCGGTGATACCCTGCAATTTGGCCCTACTTTCAACGCCAAACCGGAAGACTTAGATCGCCTTTTCGATGCAGTT<br>GGAGAGGCACTGAACGGGGTCGCTTAA |
| SEQ ID NO: 76<br>nucleic acid<br>coding sequence<br>of the gene gabD<br>at locus b2661 | ATGAAACTTAACGACAGTAACTTATTCCGCCAGCAGGCGTTGATTAACGGGGAATGGCTGGACGCCAACAATGGTGA<br>AGCCATCGACGTCACCAATCCGGCGAACGGCGACAAGCTGGGTAGCGTGCCGAAAATGGGCGCGGATGAAACCCGC<br>GCCGCTATCGACGCCGCCAACCGCGCCCTGCCCGCCTGGCGCGCGCTCACCGCCAAAGAACGCGCCACCATTCTGCGC<br>AACTGGTTCAATTTGATGATGGAGCATCAGGACGATTTAGCGCGCCTGATGACCCTCGAACAGGGTAAACCACTGGC<br>CGAAGCGAAAGGCGAAATCAGCTACGCCGCCTCCTTTATTGAGTGGTTTGCCGAAGAAGGCAAACGCATTTATGGCG<br>ACACCATTCCTGGTCATCAGGCCGATAAACGCCTGATTGTTATCAAGCAGCCGATTGGCGTCACCGCGGCTATCACGC<br>CGTGGAACTTCCCGGCGGCGATGATTACCCGCAAAGCCGGTCCGGCGCTGGCAGCAGGCTGCACCATGGTGCTGAAG<br>CCCGCCAGTCAGACGCCGTTCTCTGCGCTGGCGCTGGCGGAGCTGGCGATCCGCGCGGGCGTTCCGGCTGGGGTATTT<br>AACGTGGTCACCGGTTCGGCGGGCGCGGTCGGTAACGAACTGACCAGTAACCCGCTGGTGCGCAAACTGTCGTTTAC<br>CGGTTCGACCGAAATTGGCCGCCAGTTAATGGAACAGTGCGCGAAAGACATCAAGAAAGTGTCGCTGGAGCTGGGCG<br>GTAACGCGCCGTTTATCGTCTTTGACGATGCCGACCTCGACAAAGCCGTGGAAGGCGCGCTGGCCTCGAAATTCCGCA<br>ACGCCGGGCAAACCTGCGTCTGCGCCAACCGCCTGTATGTGCAGGACGGCGTGTATGACCGTTTTGCCGAAAAATTGC<br>AGCAGGCAGTGAGCAAACTGCACATCGGCGACGGGCTGGATAACGGCGTCACCATCGGGCCGCTGATCGATGAAAA<br>AGCGGTAGCAAAAGTGGAAGAGCATATTGCCGATGCGCTGGAGAAAGGCGCGCGCGTGGTTTGCGGCGGTAAAGCG<br>CACGAACGCGGCGGCAACTTCTTCCAGCCGACCATTCTGGTGGACGTTCCGGCCAACGCCAAAGTGTCGAAAGAAGA<br>GACGTTCGGCCCCCTCGCCCCGCTGTTCCGCTTTAAAGATGAAGCTGATGTGATTGCGCAAGCCAATGACACCGAGTT<br>TGGCCTTGCCGCCTATTTCTACGCCCGTGATTTAAGCCGCGTCTTCCGCGTGGGCGAAGCGCTGGAGTACGGCATCGT<br>CGGCATCAATACCGGCATTATTTCCAATGAAGTGGCCCCGTTCGGCGGCATCAAAGCCTCGGGTCTGGGTCGTGAAGG<br>TTCGAAGTATGGCATCGAAGATTACTTAGAAATCAAATATATGTGCATCGGTCTTTAA |
| SEQ ID NO: 77<br>nucleic acid<br>coding sequence<br>of the gene gabT<br>at locus b2662 | ATGAACAGCAATAAAGAGTTAATGCAGCGCCGCAGTCAGGCGATTCCCCGTGGCGTTGGGCAAATTCACCCGATTTTC<br>GCTGACCGCGCGGAAAACTGCCGGGTGTGGGACGTTGAAGGCCGTGAGTATCTTGATTTCGCGGGCGGGATTGCGGT<br>GCTCAATACCGGGCACCTGCATCCGAAGGTGGTGGCCGCGGTGGAAGCGCAGTTGAAAAAACTGTCGCACACCTGCT<br>TCCAGGTGCTGGCTTACGAGCCGTATCTGGAGCTGTGCGAGATTATGAATCAGAAGGTGCCGGGCGATTTCGCCAAG<br>AAAACGCTGCTGGTTACGACCGGTTCCGAAGCGGTGGAAAACGCGGTAAAAATCGCCCGCGCCGCCACCAAACGTAG<br>CGGCACCATCGCTTTTAGCGGCGCGTATCACGGGCGCACGCATTACACGCTGGCGCTGACCGGCAAGGTGAATCCGT<br>ACTCTGCGGGCATGGGGCTGATGCCGGGTCATGTTTATCGCGCGCTTTATCCTTGCCCGCTGCACGGCATAAGCGAGG<br>ATGACGCTATCGCCAGCATCCACCGGATCTTCAAAAATGATGCCGCGCCGGAAGATATCGCCGCCATCGTGATTGAGC<br>CGGTTCAGGGCGAAGGCGGTTTCTACGCCTCGTCGCCAGCCTTTATGCAGCGTTTACGCGCTCTGTGTGACGAGCACG<br>GGATCATGCTGATTGCCGATGAAGTGCAGAGCGGCGCGGGGCGTACCGGCACGCTGTTTGCGATGGAGCAGATGGGC<br>GTTGCGCCGGATCTTACCACCTTTGCGAAATCGATCGCGGGCGGCTTCCCGCTGGCGGGCGTCACCGGGCGCGCGGAA<br>GTAATGGATGCCGTCGCTCCAGGCGGTCTGGGCGGCACCTATGCGGGTAACCCGATTGCCTGCGTGGCTGCGCTGGAA<br>GTGTTGAAGGTGTTTGAGCAGGAAAATCTGCTGCAAAAAGCCAACGATCTGGGGCAGAAGTTGAAAGACGGATTGCT<br>GGCGATAGCCGAAAAACACCCGGAGATCGGCGACGTACGCGGGCTGGGGGCGATGATCGCCATTGAGCTGTTTGAAG<br>ACGGCGATCACAACAAGCCGGACGCCAAACTCACCGCCGAGATCGTGGCTCGCGCCCGCGATAAAGGCCTGATTCTT<br>CTCTCCTGCGGCCCGTATTACAACGTGCTGCGCATCCTTGTACCGCTCACCATTGAAGACGCTCAGATCCGTCAGGGT<br>CTGGAGATCATCAGCCAGTGTTTTGATGAGGCGAAGCAGTAG |
| SEQ ID NO: 78<br>nucleic acid<br>coding sequence<br>of the gene gad at<br>locus U10034 | ATGGTGCTCTCCCACGCCGTATCGGAGTCGGACGTCTCCGTCCACTCCACATTCGCATCACGTTACGTCCGTACTTCAC<br>TTCCTAGGTTCAAGATGCCGGAAAACTCGATTCCTAAGGAAGCGGCGTATCAGATCATCAACGACGAGCTGATGCTTG<br>ACGGGAATCCACGGTTGAACTTAGCCTCCTTTGTGACGACATGGATGGAGCCTGAGTGTGATAAACTCATCATGTCCT<br>CCATCAACAAGAACTATGTTGACATGGACGAGTACCCCGTCACCACCGAACTTCAGAACCGATGTGTGAACATGATT<br>GCACATCTATTCAATGCACCGTTAGAAGAGGCGGAGACCGCCGTCGGAGTAGGAACCGTTGGATCATCGGAGGCCAT<br>AATGTTGGCCGGTTTGGCCTTCAAGCGTAAATGGCAGAACAAGCGCAAAGCTGAAGGCAAACCCGTCGATAAACCCA<br>ACATTGTCACCGGAGCCAATGTTCAAGTGTGTTGGGAGAAATTCGCTAGGTACTTTGAGGTTGAACTTAAGGAAGTGA<br>AATTGAGTGAAGGATACTATGTGATGGACCCTCAACAAGCTGTTGATATGGTTGATGAGAACACCATTTGTGTTGCGG<br>ACATTCTTGGTTCCACTCTTAATGGAGAATTCGAAGATGTTAAACTCTTGAACGATCTCTTGGTCGAAAAGAACAAAG |

TABLE 2-continued

Nucleic Acid Sequences: Genes

| SEQ ID NO | Nucleic Acid Sequence |
|---|---|
| | AAACCGGATGGGATACACCAATCCACGTGGATGCGGCAAGTGGAGGATTCATTGCACCGTTTTTGTATCCGGAATTGG<br>AATGGGACTTTAGACTTCCCTTGGTGAAGAGTATCAATGTGAGTGGTCACAAGTATGGACTTGTGTACGCAGGGATTG<br>GTTGGGTGATCTGGAGAAACAAAGAGGATTTGCCTGAGGAACTCATCTTCCATATCAATTATCTTGGTGCTGACCAAC<br>CCACCTTTACTCTCAATTTCTCCAAAGGTTCAAGTCAAGTCATTGCTCAATACTACCAACTTATCCGATTGGGCCACGA<br>GGGTTACAGAAATGTGATGGAGAATTGCAGAGAGAATATGATCGTCCTAAGGGAAGGACTTGAGAAGACAGAAAGG<br>TTCAACATCGTCTCAAAGGACGAGGGAGTGCCACTTGTCGCTTTCTCCTTGAAAGATAGCAGCTGTCACACTGAGTTC<br>GAAATCTCCGACATGCTTCGCAGGTATGGATGGATAGTGCCGGCCTACACAATGCCTCCAAATGCACAACACATCACT<br>GTTCTTCGTGTGGTTATCAGAGAAGATTTCTCGAGAACACTCGCTGAGAGACTTGTGATCGATATAGAGAAAGTGATG<br>CGTGAGCTCGATGAGCTTCCTTCGAGAGTGATTCACAAAATATCACTTGGACAAGAGAAGAGTGAATCTAACAGCGA<br>TAACTTGATGGTCACGGTGAAGAAGAGCGATATCGACAAGCAGAGAGATATCATCACTGGCTGGAAGAAGTTTGTCG<br>CCGACAGGAAGAAGACGAGTGGTATCTGCTAA |
| SEQ ID NO: 79<br>nucleic acid<br>coding sequence<br>of the gene gadAe | ATGGACCAGAAGCTGTTAACGGATTTCCGCTCAGAACTACTCGATTCACGTTTTGGCGCAAAGGCCATTTCTACTATC<br>GCGGAGTCAAAACGATTTCCGCTGCACGAAATGCGCGATGATGTCGCATTTCAGATTATCAATGATGAATTATATCTT<br>GATGGCAACGCTCGTCAGAACCTGGCCACTTTCTGCCAGACCTGGGACGACGAAAACGTCCATAAATTGATGGATTTG<br>TCGATCAATAAAAACTGGATCGACAAAGAACAGTATCCGCAATCCGCAGCCATCGACCTGCGTTGCGTAAATATGGT<br>TGCCGATCTGTGGCATGCGCCTGCGCCGAAAAATGGTCAGGCCGTTGGCACCAACACCATTGGTTCTTCCGAGGCCTG<br>TATGCTCGGCGGGATGGCGATGAAATGGCGTTGGCGCAAGCGTATGGAAGCTGCAGGCAAACCAACGGATAAACCA<br>AACCTGGTGTGCGGTCCGGTACAAATCTGCTGGCATAAATTCGCCCGCTACTGGGATGTGGAGCTGCGTGAGATCCCT<br>ATGCGCCCCGGTCAGTTGTTTATGGACCCGAAACGCATGATTGAAGCCTGTGACGAAAACACCATCGGCGTGGTGCC<br>GACTTTCGGCGTGACCTACACCGGTAACTATGAGTTCCCACAACCGCTGCACGATGCGCTGGATAAATTCCAGGCCGA<br>CACCGGTATCGACATCGACATGCACATCGACGCTGCCAGCGGTGGCTTCCTGGCACCGTTCGTCGCCCCGGATATCGT<br>CTGGGACTTCCGCCTGCCGCGTGTGAAATCGATCAGTGCTTCAGGCCATAAATTCGGTCTGGCTCCGCTGGGCTGCGG<br>CTGGGTTATCTGGCGTGACGAAGAAGCGCTGCCGCAGGAACTGGTGTTCAACGTTGACTACCTGGGTGGTCAAATTGG<br>TACTTTTGCCATCAACTTCTCCCGCCCGGCGGGTCAGGTAATTGCACAGTACTATGAATTCCTGCGCCTCGGTCGTGAA<br>GGCTATACCAAAGTACAGAACGCCTCTTACCAGGTTGCCGCTTATCTGGCGGATGAAATCGCCAAACTGGGGCCGTAT<br>GAGTTCATCTGTACGGGTCGCCCGGACGAAGGCATCCCGGCGGTTTGCTTCAAACTGAAAGATGGTGAAGATCCGGG<br>ATACACCCTGTACGACCTCTCTGAACGTCTGCGTCTGCGCGGCTGGCAGGTTCCGGCCTTCACTCTCGGCGGTGAAGC<br>CACCGACATCGTGGTGATGCGCATTATGTGTCGTCGCGGCTTCGAAATGGACTTTGCTGAACTGTTGCTGGAAGACTA<br>CAAAGCCTCCCTGAAATATCTCAGCGATCACTAA |
| SEQ ID NO: 80<br>nucleic acid<br>coding sequence<br>of the gene ghrB<br>at locus b3553 | ATGAAGCCGTCCGTTATCCTCTACAAAGCCTTACCTGATGATTTACTGCAACGCCTGCAAGAGCATTTCACCGTTCACC<br>AGGTGGCAAACCTCAGCCCACAAACCGTCGAACAAAATGCAGCAATTTTTGCCGAAGCTGAAGGTTTACTGGGTTCA<br>AACGAGAATGTAAATGCCGCATTGCTGGAAAAAATGCCGAAACTGCGTGCCACATCAACGATCTCCGTCGGCTATGA<br>CAATTTTGATGTCGATGCGCTTACCGCCCGAAAAATTCTGCTGATGCACACGCCAACCGTATTAACAGAAACCGTCGC<br>CGATACGCTGATGGCGCTGGTGTTGTCTACCGCTCGTCGGGTTGTGGAGGTAGCAGAACGGGTAAAAGCAGGCGAAT<br>GGACCGCGAGCATAGGCCCGGACTGGTACGGCACTGACGTTCACCATAAAACACTGGGCATTGTCGGGATGGGACGG<br>ATCGGCATGGCGCTGGCACAACGTGCGCACTTTGGCTTCAACATGCCCATCCTCTATAACGCGCGCCGCCACCATAAA<br>GAAGCAGAAGAACGCTTCAACGCCCGCTACTGCGATTTGGATACTCTGTTACAAGAGTCAGATTTCGTTTGCCTGATC<br>CTGCCGTTAACTGATGAGACGCATCATCTGTTTGGCGCAGAACAATTCGCCAAAATGAAATCCTCCGCCATTTTCATT<br>AATGCCGGACGTGGCCCGGTGGTTGACGAAAATGCACTGATCGCAGCATTGCAGAAAGGCGAAATTCACGCTGCCGG<br>GCTGGATGTCTTCGAACAAGAGCCACTGTCCGTAGATTCGCCGTTGCTCTCAATGGCCAACGTCGTCGCAGTACCGCA<br>TATTGGATCTGCCACCCATGAGACGCGTTATGGCATGGCCGCCTGTGCCGTGGATAATTTGATTGATGCGTTACAAGG<br>AAAGGTTGAGAAGAACTGTGTGAATCCGCACGTCGCGGACTAA |
| SEQ ID NO: 81<br>nucleic acid<br>coding sequence<br>of the gene<br>H16_RS27940 | GTGTACGCAGCTAAGGACATCACCGTGGAGGAGCGCGCCGGCGGCGCGCTATGGATCACGATCGACCGGGCGCAGA<br>AACACAATGCGCTGGCCCGCCACGTGCTGGCGGGATTGGCGCAGGTGGTGAGCGCCGCGGCGGCGCAGCCCGGGGTG<br>CGCTGCATCGTGCTGACCGGCGCCGGCCAGCGCTTCTTTGCGGCAGGCGGCGATCTGGTCGAGCTGTCCGGCGTGCGC<br>GACCGGGAGGCTACGCTGGCCATGAGCGAGCAGGCGCGCGGTGCCCTGGATGCGGTGCGCGACTGCCCGCTGCCGGT<br>GCTGGCCTACCTGAACGGCGATGCCATCGGCGGCGGCGCCGAGCTGGCATTGGCCTGCGACATGCGGCTGCAGTCGG<br>CGAGCGCGCGCATCGGCTTTATCCAGGCGCGGCTGGCCATCACCTCGGCCTGGGGCGGCGGCCCCGACCTGTGCCGG<br>ATCGTCGGCGCGGCGCGGGCCATGCGCATGATGAGCCGTTGCGAGCTTGTCGATGCGCAGCAGGCGCTGCAGTGGGG<br>CTTGGCCGATGCGGTGGTCACGGACGGACCCGCCGGCAAGGACATCCACGCCTTCCTGCAACCGCTGCTGGGCTGCG<br>CCCCGCAGGTGCTGCGCGGCATCAAGGCGCAGACCGCGGCCAGCCGGCGCGGCGAGTCGCATGACGCTGCCCGCACC<br>ATCGAGCAGCAGCAACTGTTGCATACCTGGCTCCATGCGGACCATTGGAACGCTGCCGAGGGCATCCTCTCCAGGAG<br>GGCCCAATGA |
| SEQ ID NO: 82<br>nucleic acid<br>coding sequence<br>of the gene hbd at<br>locus CA_C2708 | ATGAAAAAGGTATGTGTTATAGGTGCAGGTACTATGGGTTCAGGAATTGCTCAGGCATTTGCAGCTAAAGGATTTGAA<br>GTAGTATTAAGAGATATTAAAGATGAATTTGTTGATAGAGGATTAGATTTTATCAATAAAAATCTTTCTAAATTAGTT<br>AAAAAAGGAAAGATAGAAGAAGCTACTAAAGTTGAAATCTTAACTAGAATTTCCGGAACAGTTGACCTTAATATGGC<br>AGCTGATTGCGATTTAGTTATAGAAGCAGCTGTTGAAAGAATGGATATTAAAAAGCAGATTTTTGCTGACTTAGACAA<br>TATATGCAAGCCAGAAACAATTCTTGCATCAAATACATCATCACTTTCAATAACAGAAGTGGCATCAGCAACTAAAAC<br>TAATGATAAGGTTATAGGTATGCATTTCTTTAATCCAGCTCCTGTTATGAAGCTTGTAGAGGTAATAAGAGGAATAGC<br>TACATCACAAGAAACTTTTGATGCAGTTAAAGAGACATCTATAGCAATAGGAAAAGATCCTGTAGAAGTAGCAGAAG<br>CACCAGGATTTGTTGTAAATAGAATATTAATACCAATGATTAATGAAGCAGTTGGTATATTAGCAGAAGGAATAGCTT<br>CAGTAGAAGACATAGATAAAGCTATGAAACTTGGAGCTAATCACCCAATGGGACCATTAGAATTAGGTGATTTTATA<br>GGTCTTGATATATGTCTTGCTATAATGGATGTTTTATACTCAGAAACTGGAGATTCTAAGTATAGACCACATACATTAC<br>TTAAGAAGTATGTAAGAGCAGGATGGCTTGGAAGAAAATCAGGAAAAGGTTTCTACGATTATTCAAAATAA |
| SEQ ID NO: 83<br>nucleic acid<br>coding sequence<br>of the gene iclR at<br>locus b4018 | ATGGTCGCACCCATTCCCGCGAAACGCGGCAGAAAACCCGCCGTTGCCACCGCACCAGCGACTGGACAGGTTCAGTC<br>TTTAACGCGTGGCCTGAAATTACTGGAGTGGATTGCCGAATCCAATGGCAGTGTGGCACTCACGGAACTGGCGCAAC<br>AAGCCGGGTTACCCAATTCCACGACCCACCGCCTGCTAACCACGATGCAACAGCAGGGTTTCGTGCGTCAGGTTGGCG<br>AACTGGGACATTGGGCAATCGGCGCACATGCCTTTATGGTCGGCAGCAGCTTTCTCCAGAGCCGTAATTTGTTAGCGA<br>TTGTTCACCCTATCCTGCGCAATCTAATGGAAGAGTCTGGCGAAACGGTCAATATGGCGGTGCTTGATCAAAGCGATC<br>ACGAAGCGATTATTATCGACCAGGTACAGTGTACGCATCTGATGCGAATGTCCGCGCCTATCGGCGGTAAATTGCCGA<br>TGCACGCTTCCGGTGCGGGTAAAGCCTTTTTAGCCCAACTGAGCGAAGAACAGGTGACGAAGCTGCTGCACCGCAAA |

TABLE 2-continued

| SEQ ID NO | Nucleic Acid Sequence |
|---|---|
| Nucleic Acid Sequences: Genes | |
| | GGGTTACATGCCTATACCCACGCAACGCTGGTGTCTCCTGTGCATTTAAAAGAAGATCTCGCCCAAACGCGCAAACGG<br>GGTTATTCATTTGACGATGAGGAACATGCACTGGGGCTACGTTGCCTTGCAGCGTGTATTTTCGATGAGCACCGTGAA<br>CCGTTTGCCGCAATTTCTATTTCCGGACCGATTTCACGTATTACCGATGACCGCGTGACCGAGTTTGGCGCGATGGTGA<br>TTAAAGCGGCGAAGGAAGTGACGCTGGCGTACGGTGGAATGCGCTGA |
| SEQ ID NO: 84<br>nucleic acid<br>coding sequence<br>of the gene lacI at<br>locus b0345 | GTGAAACCAGTAACGTTATACGATGTCGCAGAGTATGCCGGTGTCTCTTATCAGACCGTTTCCCGCGTGGTGAACCAG<br>GCCAGCCACGTTTCTGCGAAAACGCGGGAAAAAGTGGAAGCGGCGATGGCGGAGCTGAATTACATTCCCAACCGCGT<br>GGCACAACAACTGGCGGGCAAACAGTCGTTGCTGATTGGCGTTGCCACCTCCAGTCTGGCCCTGCACGCGCCGTCGCA<br>AATTGTCGCGGCGATTAAATCTCGCGCCGATCAACTGGGTGCCAGCGTGGTGGTGTCGATGGTAGAACGAAGCGGCG<br>TCGAAGCCTGTAAAGCGGCGGTGCACAATCTTCTCGCGCAACGCGTCAGTGGGCTGATCATTAACTATCCGCTGGATG<br>ACCAGGATGCCATTGCTGTGGAAGCTGCCTGCACTAATGTTCCGGCGTTATTTCTTGATGTCTCTGACCAGACACCCAT<br>CAACAGTATTATTTTCTCCCATGAAGACGGTACGCGACTGGGCGTGGAGCATCTGGTCGCATTGGGTCACCAGCAAAT<br>CGCGCTGTTAGCGGGCCCATTAAGTTCTGTCTCGGCGCGTCTGCGTCTGGCTGGCTGGCATAAATATCTCACTCGCAAT<br>CAAATTCAGCCGATAGCGGAACGGGAAGGCGACTGGAGTGCCATGTCCGGTTTTCAACAAACCATGCAAATGCTGAA<br>TGAGGGCATCGTTCCCACTGCGATGCTGGTTGCCAACGATCAGATGGCGCTGGGCGCAATGCGCGCCATTACCGAGTC<br>CGGGCTGCGCGTTGGTGCGGATATCTCGGTAGTGGGATACGACGATACCGAAGACAGCTCATGTTATATCCCGCCGTT<br>AACCACCATCAAACAGGATTTTCGCCTGCTGGGGCAAACCAGCGTGGACCGCTTGCTGCAACTCTCTCAGGGCCAGGC<br>GGTGAAGGGCAATCAGCTGTTGCCCGTCTCACTGGTGAAAAGAAAAACCACCCTGGCGCCCAATACGCAAACCGCCT<br>CTCCCCGCGCGTTGGCCGATTCATTAATGCAGCTGGCACGACAGGTTTCCCGACTGGAAAGCGGGCAGTGA |
| SEQ ID NO: 85<br>nucleic acid<br>coding sequence<br>of the gene lvaE<br>at locus PP_2795 | ATGATGGTTCCAACCCTCGAACACGAGCTTGCTCCCAACGAAGCCAACCATGTCCCGCTGTCGCCGCTGTCGTTCCTC<br>AAGCGTGCCGCGCAGGTGTACCCGCAGCGCGATGCGGTGATCTATGGCGCAAGGCGCTACAGCTACCGTCAGTTGCA<br>CGAGCGCAGCCGCGCCCTGGCCAGTGCCTTGGAGCGGGTCGGTGTTCAGCCGGGCGAGCGGGTGGCGATATTGGCGC<br>CGAACATCCCGGAAATGCTCGAGGCCCACTATGGCGTGCCCGGTGCCGGGGCGGTGCTGGTGTGCATCAACATCCGC<br>CTGGAGGGGCGCAGCATTGCCTTCATCCTGCGTCACTGCGCGGCCAAGGTATTGATCTGCGATCGTGAGTTCGGTGCC<br>GTGGCCAATCAGGCGCTGGCCATGCTCGATGCGCCGCCCTTGCTGGTGGGCATCGACGATGATCAGGCCGAGCGCGC<br>CGATTTGGCCCACGACCTGGACTACGAAGCGTTCTTGGCCCAGGGCGACCCCGCGCGGCCGTTGAGTGCGCCACAGA<br>ACGAATGGCAGTCGATCGCCATCAACTACACCTCCGGCACCACGGGGGACCCCAAGGGCGTGGTGCTGCATCACCGC<br>GGCGCCTACCTCAACGCCTGCGCCGGGGCGCTGATCTTCCAGTTGGGGCCGCGCAGCGTCTACTTGTGGACCTTGCCG<br>ATGTTCCACTGCAACGGCTGGAGCCATACCTGGGCGGTGACGTTGTCCGGTGGCACCCACGTGTGTCTGCGCAAGGTC<br>CAGCCTGATGCGATCAACGCCGCCATCGCCGAGCATGCCGTGACTCACCTGAGCGCCGCCCCAGTGGTGATGTCGATG<br>CTGATCCACGCCGAGCATGCCAGCGCCCCTCCGGTGCCGGTTTCGGTGATCACTGGCGGTGCCGCCCCGCCCAGTGCG<br>GTCATCGCGGCGATGGAGGCGCGTGGCTTCAACATCACCCATGCCTATGGCATGACCGAAAGCTACGGTCCCAGCAC<br>ATTGTGCCTGTGGCAGCCGGGTGTCGACGAGTTGCCGCTGGAGGCCCGGGCCCAGTTCATGAGCCGCCAGGGCGTCG<br>CCCACCCGCTGCTCGAGGAGGCCACGGTGCTGGATACCGACACCGGCCGCCCGGTCCCGGCCGACGGCCTTACCCTC<br>GGCGAGCTGGTGGTGCGGGGCAACACTGTGATGAAAGGCTACCTGCACAACCCAGAGGCTACCCGTGCCGCGTTGGC<br>CAACGGCTGGCTGCACACGGGCGACCTGGCCGTGCTGCACCTGGACGGCTATGTGGAAATCAAGGACCGAGCCAAGG<br>ACATCATCATTTCTGGCGGCGAGAACATCAGTTCGCTGGAGATAGAAGAAGTGCTCTACCAGCACCCCGAGGTGGTC<br>GAGGCTGCGGTGGTGGCGCGTCCGGATTCGCGCTGGGGCGAGACACCTCACGCTTTCGTCACGCTGCGCGCTGATGCA<br>CTGGCCAGCGGGGACGACCTGGTCCGCTGGTGCCGTGAGCGTCTGGCGCACTTCAAGGCGCCGCGCCATGTGTCGCTC<br>GTGGACCTGCCCAAGACCGCCACTGGAAAAATACAGAAGTTCGTCCTGCGTGAGTGGGCCCGGCAACAGGAGGCGCA<br>GATCGCCGACGCCGAGCATTGA |
| SEQ ID NO: 86<br>nucleic acid<br>coding sequence<br>of the gene lvaE<br>optimized for<br>*E.coli* | ATGATGGTTCCGACCCTGGAGCATGAACTGGCGCCGAATGAAGCGAACCATGTGCCGTTAAGCCCGCTGAGCTTTCTG<br>AAACGTGCCGCCCAGGTCTATCCTCAGCGTGATGCCGTGATTTACGGCGCCCGTCGTTATAGCTATCGTCAGCTGCAC<br>GAACGCAGCCGCGCCCTGGCTTCCGCCTTAGAGCGTGTGGGTGTGCAGCCTGGTGAGCGCGTTGCAATTCTTGCCCCG<br>AACATTCCGGAAATGCTGGAGGCGCACTACGGCGTGCCTGGCGCCGGTGCGGTGCTGGTTTGCATTAACATCCGCCTG<br>GAGGGCCGCAGCATTGCCTTCATTTTACGCCATTGTGCGGCGAAGGTGCTGATTTGTGATCGTGAATTCGGTGCCGTT<br>GCTAATCAAGCGCTGGCGATGCTGGATGCGCCGCCGCTGCTGGTGGGTATCGATGATGACCAGGCGGAGCGCGCGGA<br>TCTGGCACATGATCTGGACTATGAGGCCTTTTTAGCGCAGGGCGATCCGGCCCGTCCGTTGTCAGCGCCGCAGAATGA<br>ATGGCAGAGCATTGCGATTAACTATACCTCGGGCACCACCGGTGATCCAAAAGGTGTAGTGCTGCATCACCGTGGTGC<br>GTATCTGAATGCATGCGCAGGCGCCTTAATCTTTCAGTTAGGCCCTCGCTCGGTCTATCTTTGGACGCTGCCGATGTTT<br>CACTGTAACGGTTGGAGCCACACGTGGGCGGTTACCCTGTCAGGTGGTACGCACGTTTGCTTACGCAAAGTTCAGCCG<br>GACGCGATTAACGCAGCAATCGCCGAGCATGCCGTGACTCATCTGTCTGCAGCCCCGGTGGTGATGTCTATGCTGATT<br>CACGCCGAGCATGCTAGCGCGCCGCCGGTGCCTGTGTCTGTGATCACCGGCGGTGCAGCCCCGCCTAGCGCCGTGATT<br>GCGGCAATGGAAGCTCGTGGCTTCAATATCACGCACGCGTATGGTATGACCGAATCCTACGGTCCAAGCACCCTGTGC<br>CTGTGGCAACCAGGTGTGGATGAACTGCCGTTAGAAGCACGTGCGCAGTTTATGAGCCGTCAGGGTGTCGCGCATCC<br>GTTACTGGAAGAAGCGACCGTTTTAGATACCGATACTGGCCGTCCGGTACCGGCGGACGGTCTGACCCTGGGCGAAC<br>TGGTTGTGCGTGGTAATACCGTTATGAAAGGGTACTTACACAATCCGGAAGCGACGCGCGCAGCACTGGCGAACGGT<br>TGGTTACATACCGGCGATCTGGCCGTATTGCATCTGGATGGCTACGTTGAAATTAAAGATCGTGCAAAAGATATTATC<br>ATTTCGGGCGGCGAAAACATTTCTAGCCTGGAAATCGAAGAAGTCCTGTATCAGCACCCGGAGGTTGTGGAGGCAGC<br>CGTCGTGGCACGCCCGGACAGCCGTTGGGGCGAGACCCCGCACGCCTTTGTTACTCTGCGTGCCGACGCCCTTGCGTC<br>TGGTGACGATCTGGTGCGTTGGTGCCGTGAGCGTCTTGCCCACTTCAAAGCGCCGCGCCATGTTAGCCTTGTGGATCT<br>GCCGAAAACCGCCACGGGCAAAATTCAGAAATTTGTATTACGTGAATGGGCACGCCAGCAGGAGGCCCAGATTGCCG<br>ACGCAGAACACTAA |
| SEQ ID NO: 87<br>nucleic acid<br>coding sequence<br>of the gene<br>MELS_RS10970 | ATGGATTTTAACTTAACAGATATTCAACAGGACTTCTTAAAACTCGCTCATGATTTCGGCGAAAAGAAATTAGCACCG<br>ACCGTTACGGAACGCGACCACAAAGGTATTTATGACAAAGAACTCATCGACGAATTGCTCAGCCTCGGTATTACCGG<br>CGCTTACTTCGAAGAAAAATACGGCGGTTCCGGCGATGACGGCGGCGACGTTTTGAGCTACATCCTCGCTGTTGAAGA<br>ATTGGCTAAATACGACGCTGGTGTTGCTATCACCTTGTCGGCAACGGTTTCCCTTTGCGCTAACCCGATTTGGCAGTTC<br>GGTACAGAAGCTCAGAAAGAAAAATTCCTCGTTCCTTTGGTTGAAGGCACTAAACTCGGCGCTTTCGGCTTGACCGAA<br>CCGAACGCAGGTACTGATGCTTCCGGCCAGCAGACCATTGCTACGAAGAACGATGACGGCACTTACACGTTGAACGG<br>CTCCAAGATCTTCATCACCAACGGCGGCGCTGCTGACATCTACATTGTCTTCGCTATGACCGATAAGAGCAAAGGCAA<br>CCACGGCATTACAGCCTTCATCCTCGAAGACGGTACTCCGGGCTTTACTTACGGCAAGAAAGAAGACAAGATGGGCA<br>TCCATACTTCGCAGACCATGGAACTCGTATTCCAGGACGTCAAAGTTCCGGCTGAAAACATGCTCGGCGAAGAAGGC<br>AAAGGCTTCAAGATTGCTATGATGACCTTGGACGGCGGCCGTATCGGCGTTGCTGCTCAGGCTCTCGGCATTGCAGAA |

TABLE 2-continued

| Nucleic Acid Sequences: Genes | |
|---|---|
| SEQ ID NO | Nucleic Acid Sequence |
| | GCTGCTTTGGCAGATGCTGTTGAATACTCCAAACAGCGTGTACAGTTCGGCAAACCGCTCTGCAAATTCCAGTCCATT<br>TCCTTCAAACTGGCTGACATGAAGATGCAGATCGAAGCTGCTCGTAACCTCGTTTACAAAGCTGCTTGCAAGAAACAG<br>GAAGGCAAACCCTTCACCGTTGACGCTGCTATCGCAAAACGCGTTGCTTCCGACGTCGCTATGCGCGTAACGACCGAA<br>GCTGTCCAGATCTTCGGCGGCTATGGCTACAGCGAAGAATATCCGGTTGCTCGTCACATGCGCGATGCTAAGATTACT<br>CAGATCTACGAAGGCACGAACGAAGTTCAGCTCATGGTTACAGGCGGTGCTCTGTTAAGATAA |
| SEQ ID NO: 88<br>nucleic acid<br>coding sequence<br>of the gene paaZ<br>at locus B1387 | ATGCAGCAGTTAGCCAGTTTCTTATCCGGTACCTGGCAGTCTGGCCGGGGCCGTAGCCGTTTGATTCACCACGCTATT<br>AGCGGCGAGGCGTTATGGGAAGTGACCAGTGAAGGTCTTGATATGGCGGCTGCCCGCCAGTTTGCCATTGAAAAAGG<br>TGCCCCCGCCCTTCGCGCTATGACCTTTATCGAACGTGCGGCGATGCTTAAAGCGGTCGCTAAACATCTGCTGAGTGA<br>AAAAGAGCGTTTCTATGCTCTTTCTGCGCAAACAGGCGCAACGCGGGCAGACAGTTGGGTTGATATTGAAGGTGGCA<br>TTGGGACGTTATTTACTTACGCCAGCCTCGGTAGCCGGGAGCTGCCTGACGATACGCTGTGGCCGGAAGATGAATTGA<br>TCCCCTTATCGAAAGAAGGTGGATTTGCCGCGCGCCATTTACTGACCTCAAAGTCAGGCGTGGCAGTGCATATTAACG<br>CCTTTAACTTCCCCTGCTGGGGAATGCTGGAAAAGCTGGCACCAACGTGGCTGGGCGGAATGCCAGCCATCATCAAA<br>CCAGCTACCGCGACGGCCCAACTGACTCAGGCGATGGTGAAATCAATTGTCGATAGTGGTCTTGTTCCCGAAGGCGCA<br>ATTAGTCTGATCTGCGGTAGTGCTGGCGACTTGTTGGATCATCTGGACAGCCAGGATGTGGTGACTTTCACGGGGTCA<br>GCGGCGACCGGACAGATGCTGCGAGTTCAGCCAAATATCGTCGCCAAATCTATCCCCTTCACTATGGAAGCTGATTCC<br>CTGAACTGCTGCGTACTGGGCGAAGATGTCACCCCGGATCAACCGGAGTTTGCGCTGTTTATTCGTGAAGTTGTGCGT<br>GAGATGACCACAAAAGCCGGGCAAAAATGTACGGCAATCCGGCGGATTATTGTGCCGCAGGCATTGGTTAATGCTGT<br>CAGTGATGCTCTGGTTGCGCGATTACAGAAAGTCGTGGTCGGTGATCCTGCTCAGGAAGGCGTGAAAATGGGCGCAC<br>TGGTAAATGCTGAGCAGCGTGCCGATGTGCAGGAAAAAGTGAACATATTGCTGGCTGCAGGATGCGAGATTCGCCTC<br>GGTGGTCAGGCGGATTTATCTGCTGCGGGTGCCTTCTTCCCGCCAACCTTATTGTACTGTCCGCAGCCGGATGAAACA<br>CCGGCGGTACATGCAACAGAAGCCTTTGGCCCTGTCGCAACGCTGATGCCAGCACAAAACCAGCGACATGCTCTGCA<br>ACTGGCTTGTGCAGGCGGCGGTAGCCTTGCGGGAACGCTGGTGACGGCTGATCCGCAAATTGCGCGTCAGTTTATTGC<br>CGACGCGGCACGTACGCATGGGCGAATTCAGATCCTCAATGAAGAGTCGGCAAAAGAATCCACCGGGCATGGCTCCC<br>CACTGCCACAACTGGTACATGGTGGGCCTGGTCGCGCAGGAGGCGGTGAAGAATTAGGCGGTTTACGAGCGGTGAAA<br>CATTACATGCAGCGAACCGCTGTTCAGGGTAGTCCGACGATGCTTGCCGCTATCAGTAAACAGTGGGTGCGCGGTGCG<br>AAAGTCGAAGAAGATCGTATTCATCCGTTCCGCAAATATTTTGAGGAGCTACAACCAGGCGACAGCCTGTTGACTCCC<br>CGCCGCACAATGACAGAGGCCGATATTGTTAACTTTGCTTGCCTCAGCGGCGATCATTTCTATGCACATATGGATAAG<br>ATTGCTGCTGCCGAATCTATTTTCGGTGAGCGGGTGGTGCATGGGTATTTTGTGCTTTCTGCGGCTGCGGGTCTGTTTG<br>TCGATGCCGGTGTCGGTCCGGTCATTGCTAACTACGGGCTGGAAAGCTTGCGTTTTATCGAACCCGTAAAGCCAGGCG<br>ATACCATCCAGGTGCGTCTCACCTGTAAGCGCAAGACGCTGAAAAAACAGCGTAGCGCAGAAGAAAAACCAACAGG<br>TGTGGTGGAATGGGCTGTAGAGGTATTCAATCAGCATCAAACCCCGGTGGCGCTGTATTCAATTCTGACGCTGGTGGC<br>CAGGCAGCACGGTGATTTTGTCGATTAA |
| SEQ ID NO: 89<br>nucleic acid<br>coding sequence<br>of the gene<br>pct(Cp) at locus<br>CPRO_RS04110 | ATGAGAAAGGTTCCCATTATTACCGCAGATGAGGCTGCAAAGCTTATTAAAGACGGTGATACAGTTACAACAAGTGG<br>TTTCGTTGGAAATGCAATCCCTGAGGCTCTTGATAGAGCTGTAGAAAAAAGATTCTTAGAAACAGGCGAACCCAAAA<br>ACATTACATATGTTTATTGTGGTTCTCAAGGTAACAGAGACGGAAGAGGTGCTGAGCACTTTGCTCATGAAGGCCTTT<br>TAAAACGTTACATCGCTGGTCACTGGGCTACAGTTCCTGCTTTGGGTAAAATGGCTATGGAAAATAAAATGGAAGCAT<br>ATAATGTATCTCAGGGTGCATTGTGTCATTTGTTCCGTGATATAGCTTCTCATAAGCCAGGCGTATTTACAAAGGTAGG<br>TATCGGTACTTTCATTGACCCCAGAAATGGCGGCGGTAAAGTAAATGATATTACCAAAGAAGATATTGTTGAATTGGT<br>AGAGATTAAGGGTCAGGAATATTTATTCTACCCTGCTTTTCCTATTCATGTAGCTCTTATTCGTGGTACTTACGCTGAT<br>GAAAGCGGAAATATCACATTTGAGAAAGAAGTTGCTCCTCTGGAAGGAACTTCAGTATGCCAGGCTGTTAAAAACAG<br>TGGCGGTATCGTTGTAGTTCAGGTTGAAAGAGTAGTAAAAGCTGGTACTCTTGACCCTCGTCATGTAAAAGTTCCAGG<br>AATTTATGTTGACTATGTTGTTGTTGCTGACCCAGAAGATCATCAGCAATCTTTAGATTGTGAATATGATCCTGCATTA<br>TCAGGCGAGCATAGAAGACCTGAAGTTGTTGGAGAACCACTTCCTTTGAGTGCAAAGAAAGTTATTGGTCGTCGTGGT<br>GCCATTGAATTAGAAAAAGATGTTGCTGTAAATTTAGGTGTTGGTGCGCCTGAATATGTAGCAAGTGTTGCTGATGAA<br>GAAGGTATCGTTGATTTTATGACTTTAACTGCTGAAAGTGGTGCTATTGGTGGTGTTCCTGCTGGTGGCGTTCGCTTTG<br>GTGCTTCTTATAATGCGGATGCATTGATCGATCAAGGTTATCAATTCGATTACTATGATGGCGGCGGCTTAGACCTTTG<br>CTATTTAGGCTTAGCTGAATGCGATGAAAAAGGCAATATCAACGTTTCAAGATTTGGCCCTCGTATCGCTGGTTGTGG<br>TGGTTTCATCAACATTACACAGAATACACCTAAGGTATTCTTCTGTGGTACTTTCACAGCAGGTGGCTTAAAGGTTAA<br>AATTGAAGATGGCAAGGTTATTATTGTTCAAGAAGGCAAGCAGAAAAAATTCTTGAAAGCTGTTGAGCAGATTACAT<br>TCAATGGTGACGTTGCACTTGCTAATAAGCAACAAGTAACTTATATTACAGAAAGATGCGTATTCCTTTTGAAGGAAG<br>ATGGTTTGCACTTATCTGAAATTGCACCTGGTATTGATTTGCAGACACAGATTCTTGACGTTATGGATTTTGCACCTAT<br>TATTGACAGAGATGCAAACGGCCAAATCAAATTGATGGACGCTGCTTTGTTTGCAGAAGGCTTAATGGGTCTGAAGG<br>AAATGAAGTCCTGA |
| SEQ ID NO: 90<br>nucleic acid<br>coding sequence<br>of the gene<br>pct(Me) at locus<br>MELS_RS03915 | ATGAGAAAAGTAGAAATCATTACAGCTGAACAAGCAGCTCAGCTCGTAAAAGACAACGACACGATTACGTCTATCGG<br>CTTTGTCAGCAGCGCCCATCCGGAAGCACTGACCAAAGCTTTGGAAAAACGGTTCCTGGACACGAACACCCCGCAGA<br>ACTTGACCTACATCTATGCAGGCTCTCAGGGCAAACGCGATGGCCGTGCCGCTGAACATCTGGCACACACAGGCCTTT<br>TGAAACGCGCCATCATCGGTCACTGGCAGACTGTACCGGCTATCGGTAAACTGGCTGTCGAAAACAAGATTGAAGCT<br>TACAACTTCTCGCAGGGCACGTTGGTCCACTGGTTCCGCGCCTTGGCAGGTCATAAGCTCGGCGTCTTCACCGACATC<br>GGTCTGGAAACTTTCCTCGATCCCCGTCAGCTCGGCGGCAAGCTCAATGACGTAACCAAAGAAGACCTCGTCAAACTG<br>ATCGAAGTCGATGGTCATGAACAGCTTTTCTACCCGACCTTCCCGGTCAACGTAGCTTTCCTCCGCGGTACGTATGCTG<br>ATGAATCCGGCAATATCACCATGGACGAAGAAATCGGGCCTTTCGAAAGCACTTCCGTAGCCCAGGCCGTTCACAAC<br>TGTGGCGGTAAAGTCGTCGTCCAGGTCAAAGACGTCGTCGCTCACGGCAGCCTCGACCCGCGCATGGTCAAGATCCCT<br>GGCATCTATGTCGACTACGTCGTCGTAGCAGCTCCGGAAGACCATCAGCAGACGTATGACTGCGAATACGATCCGTCC<br>CTCAGCGGTGAACATCGTGCTCCTGAAGGCGCTACCGATGCAGCTCTCCCCATGAGCGCTAAGAAAATCATCGGCCGC<br>CGCGGCGCTTTGGAATTGACTGAAAACGCTGTCGTCAACCTCGGCGTCGGTGCTCCGGAATACGTTGCTTCTGTTGCC<br>GGTGAAGAAGGTATCGCCGATACCATTACCCTGACCGTCGAAGGTGGCGCCATCGGTGGCGTACCGCAGGGCGGTGC<br>CCGCTTCGGTTCGTCCCGCAATGCCGATGCCATCATCGACCACACCTATCAGTTCGACTTCTACGATGGCGGCGGTCT<br>GGACATCGCTTACCTCGGCCTGGCCCAGTGCGATGGCTCGGGCAACATCAACGTCAGCAAGTTCGGTACTAACGTTGC<br>CGGCTGCGGCGGTTTCCCCAACATTTCCCAGCAGACACCGAATGTTTACTTCTGCGGCACCTTCACGGCTGGCGGCTT<br>GAAAATCGCTGTCGAAGACGGCAAAGTCAAGATCCTCCAGGAAGGCAAAGCCAAGAAGTTCATCAAAGCTGTCGACC<br>AGATCACTTTCAACGGTTCCTATGCAGCCCGCAACGGCAAACACGTTCTCTACATCACAGAACGCTGCGTATTTGAAC<br>TGACCAAAGAAGGCTTGAAACTCATCGAAGTCGCACCGGGCATCGATATTGAAAAAGATATCCTCGCTCACATGGAC<br>TTCAAGCCGATCATTGATAATCCGAAACTCATGGATGCCCGCCTCTTCCAGGACGGTCCCATGGGACTGAAAAAATAA |

TABLE 2-continued

| Nucleic Acid Sequences: Genes | |
|---|---|
| SEQ ID NO | Nucleic Acid Sequence |
| SEQ ID NO: 91 nucleic acid coding sequence of the gene pduP(Kp) at locus KPHS_42790 | ATGAATACAGCAGAACTGGAAACCCTTATCCGCACCATCCTCAGTGAAAAGCTCGCGCCGACGCCCCCTGCCCCTCAG CAAGAGCAGGGCATTTTCTGCGATGTCGGCAGCGCCATCGACGCCGCTCATCAGGCTTTTCTCCGCTATCAGCAGTGT CCGCTAAAAACCCGCAGCGCCATTATCAGCGCCCTGCGGGAGACGCTGGCCCCCGAGCTGGCGACGCTGGCGGAAGA GAGCGCCACGGAAACCGGCATGGGCAACAAAGAAGATAAATATCTGAAAAATAAAGCCGCTCTTGAAAACACGCCG GGCATAGAGGATCTCACTACCAGCGCCCTCACCGGCGATGGCGGGATGGTGCTGTTTGAGTACTCGCCGTTCGGGGTT ATTGGCGCCGTGGCGCCCAGCACCAACCCAACGGAAACCATTATCAACAACAGTATCAGCATGCTGGCGGCGGGTAA CAGCGTCTATTTCAGCCCCCATCCCGGCGCGAAAAAGGTCTCGTTGAAGCTTATCGCCAGGATCGAAGAGATCGCCTA CCGCTGCAGCGGGATCCGTAACCTGGTGGTGACCGTTGCCGAGCCGACCTTTGAAGCCACCCAGCAAATGATGTCCCA CCCGCTGATTGCCGTTCTGGCTATCACCGGCGGCCCTGGCATTGTGGCGATGGGCATGAAAAGCGGTAAAAAAGTGA TCGGCGCTGGCGCCGGCAATCCGCCGTGCATCGTTGATGAAACCGCCGATCTCGTCAAAGCCGCCGAAGATATTATCA GCGGCGCCGCCTTCGATTACAACCTGCCCTGTATCGCCGAAAAAAGCCTGATCGTCGTCGCCTCCGTCGCTGACCGCC TGATCCAGCAGATGCAGGATTTTGACGCGCTGCTGTTGAGCCGACAGGAGGCCGATACCCTGCGTACCGTCTGCCTGC CCGACGGCGCGGCGAATAAAAAACTGGTCGGTAAAAGCCCGGCTGCGCTGCTGGCGGCGGCGGGTCTCGCCGTTCCG CCTCGCCCCCCTCGCCTGCTGATAGCCGAGGTGGAGGCGAACGACCCCTGGGTGACCTGCGAGCAGCTGATGCCGGT GCTGCCGATCGTCAGGGTCGCCGACTTTGACAGCGCCCTGGCGCTGGCCCTGCGCGTAGAGGAGGGTCTGCACCACA CCGCCATTATGCACTCGCAGAATGTCTCGCGGCTCAATCTGGCGGCACGCACCCTGCAGACCTCCATTTTTGTCAAAA ATGGCCCGTCTTACGCGGGAATCGGCGTCGGCGGCGAAGGGTTTACCACCTTCACCATCGCCACGCCAACCGGAGAA GGCACCACCTCCGCGCGGACGTTCGCCCGCCTGCGGCGCTGCGTGTTGACCAACGGTTTTTCCATTCGCTAA |
| SEQ ID NO: 92 nucleic acid coding sequence of the gene pduP(Se) at locus STM2051 | ATGAATACTTCTGAACTCGAAACCCTGATTCGCACCATTCTTAGCGAGCAATTAACCACGCCGGCGCAAACGCCGGTC CAGCCTCAGGGCAAAGGGATTTTCCAGTCCGTGAGCGAGGCCATCGACGCCGCGCACCAGGCGTTCTTACGTTATCAG CAGTGCCCGCTAAAAACCCGCAGCGCCATTATCAGCGCGATGCGTCAGGAGCTGACGCCGCTGCTGGCGCCCCTGGC GGAAGAGAGCGCCAATGAAACGGGGATGGGCAACAAAGAAGATAAATTTCTCAAAAACAAGGCTGCGCTGGACAAC ACGCCGGGCGTAGAAGATCTCACCACCACCGCGCTGACCGGCGACGGCGGCATGGTGCTGTTTGAATACTCACCGTTT GGCGTTATCGGTTCGGTCGCCCCAAGCACCAACCCGACGGAAACCATCATCAACAACAGTATCAGCATGCTGGCGGC GGGCAACAGTATCTACTTTAGCCCGCATCCGGGAGCGAAAAAGGTCTCTCTGAAGCTGATTAGCCTGATTGAAGAGA TTGCCTTCCGCTGCTGCGGCATCCGCAATCTGGTGGTGACCGTGGCGGAACCCACCTTCGAAGCGACCCAGCAGATGA TGGCCCACCCGCGAATCGCAGTACTGGCCATTACCGGCGGCCCGGGCATTGTGGCAATGGGCATGAAGAGCGGTAAG AAGGTGATTGGCGCTGGCGCGGGTAACCCGCCCTGCATCGTTGATGAAACGGCGGACCTGGTGAAAGCGGCGGAAGA TATCATCAACGGCGCGTCATTCGATTACAACCTGCCCTGCATTGCCGAGAAGAGCCTGATCGTAGTGGAGAGTGTCGC CGAACGTCTGGTGCAGCAAATGCAAACCTTCGGCGCGCTGCTGTTAAGCCCTGCCGATACCGACAAACTCCGCGCCGT CTGCCTGCCTGAAGGCCAGGCGAATAAAAAACTGGTCGGCAAGAGCCCATCGGCCATGCTGGAAGCCGCCGGGATCG CTGTCCCTGCAAAAGCGCCGCGTCTGCTGATTGCGCTGGTTAACGCTGACGATCCGTGGGTCACCAGCGAACAGTTGA TGCCGATGCTGCCAGTGGTAAAAGTCAGCGATTTCGATAGCGCGCTGGCGCTGGCCCTGAAGGTTGAAGAGGGGCTG CATCATACCGCCATTATGCACTCGCAGAACGTGTCACGCCTGAACCTCGCGGCCCGCACGCTGCAAACCTCGATATTC GTCAAAAACGGCCCCTCTTATGCCGGGATCGGCGTCGGCGGCGAAGGCTTTACCACCTTCACTATCGCCACACCAACC GGTGAAGGGACCACGTCAGCGCGTACTTTTGCCCGTTCCCGGCGCTGCGTACTGACCAACGGCTTTTCTATTCGCTAA |
| SEQ ID NO: 93 nucleic acid coding sequence of the gene phaA at locus H16_RS07140 | ATGACTGACGTTGTCATCGTATCCGCCGCCCGCACCGCGGTCGGCAAGTTTGGCGGCTCGCTGGCCAAGATCCCGGCA CCGGAACTGGGTGCCGTGGTCATCAAGGCCGCGCTGGAGCGCGCCGGCGTCAAGCCGGAGCAGGTGAGCGAAGTCAT CATGGGCCAGGTGCTGACCGCCGGTTCGGGCCAGAACCCCGCACGCCAGGCCGCGATCAAGGCCGGCCTGCCGGCGA TGGTGCCGGCCATGACCATCAACAAGGTGTGCGGCTCGGGCCTGAAGGCCGTGATGCTGGCCGCCAACGCGATCATG GCGGGCGACGCCGAGATCGTGGTGGCCGGCGGCCAGGAAAACATGAGCGCCGCCCCGCACGTGCTGCCGGGCTCGCG CGATGGTTTCCGCATGGGCGATGCCAAGCTGGTCGACACCATGATCGTCGACGGCCTGTGGGACGTGTACAACCAGT ACCACATGGGCATCACCGCCGAGAACGTGGCCAAGGAATACGGCATCACACGCGAGGCGCAGGATGAGTTCGCCGTC GGCTCGCAGAACAAGGCCGAAGCCGCGCAGAAGGCCGGCAAGTTTGACGAAGAGATCGTCCCGGTGCTGATCCCGCA GCGCAAGGGCGACCCGGTGGCCTTCAAGACCGACGAGTTCGTGCGCCAGGGCGCCACGCTGGACAGCATGTCCGGCC TCAAGCCCGCCTTCGACAAGGCCGGCACGGTGACCGCGGCCAACGCCTCGGGCCTGAACGACGGCGCCGCCGCGGTG GTGGTGATGTCGGCGGCCAAGGCCAAGGAACTGGGCCTGACCCCGCTGGCCACGATCAAGAGCTATGCCAACGCCGG TGTCGATCCCAAGGTGATGGGCATGGGCCCGGTGCCGGCCTCCAAGCGCGCCCTGTCGCGCGCCGAGTGGACCCCGC AAGACCTGGACCTGATGGAGATCAACGAGGCCTTTGCCGCGCAGGCGCTGGCGGTGCACCAGCAGATGGGCTGGGAC ACCTCCAAGGTCAATGTGAACGGCGGCGCCATCGCCATCGGCCACCCGATCGGCGCGTCGGGCTGCCGTATCCTGGTG ACGCTGCTGCACGAGATGAAGCGCCGTGACGCGAAGAAGGGCCTGGCCTCGCTGTGCATCGGCGGCGGCATGGGCGT GGCGCTGGCAGTCGAGCGCAAATAA |
| SEQ ID NO: 94 nucleic acid coding sequence of the gene phaB at locus H16_RS07145 | ATGACTCAGCGCATTGCGTATGTGACCGGCGGCATGGGTGGTATCGGAACCGCCATTTGCCAGCGGCTGGCCAAGGA TGGCTTTCGTGTGGTGGCCGGTTGCGGCCCCAACTCGCCGCGCCGCGAAAAGTGGCTGGAGCAGCAGAAGGCCCTGG GCTTCGATTTCATTGCCTCGGAAGGCAATGTGGCTGACTGGGACTCGACCAAGACCGCATTCGACAAGGTCAAGTCCG AGGTCGGCGAGGTTGATGTGCTGATCAACAACGCCGGTATCACCCGCGACGTGGTGTTCCGCAAGATGACCCGCGCC GACTGGGATGCGGTGATCGACACCAACCTGACCTCGCTGTTCAACGTCACCAAGCAGGTGATCGACGGCATGGCCGA CCGTGGCTGGGGCCGCATCGTCAACATCTCGTCGGTGAACGGGCAGAAGGGCCAGTTCGGCCAGACCAACTACTCCA CCGCCAAGGCCGGCCTGCATGGCTTCACCATGGCACTGGCGCAGGAAGTGGCGACCAAGGGCGTGACCGTCAACACG GTCTCTCCGGGCTATATCGCCACCGACATGGTCAAGGCGATCCGCCAGGACGTGCTCGACAAGATCGTCGCGACGATC CCGGTCAAGCGCCTGGGCCTGCCGGAAGAGATCGCCTCGATCTGCGCCTGGTTGTCGTCGGAGGAGTCCGGTTTCTCG ACCGGCGCCGACTTCTCGCTCAACGGCGGCCTGCATATGGGCTGA |
| SEQ ID NO: 95 nucleic acid coding sequence of the gene phaC at locus H16_RS07135 | ATGGCGACCGGCAAAGGCGCGGCAGCTTCCACGCAGGAAGGCAAGTCCCAACCATTCAAGGTCACGCCGGGGCCATT CGATCCAGCCACATGGCTGGAATGGTCCCGCCAGTGGCAGGGCACTGAAGGCAACGGCCACGCGGCCGCGTCCGGCA TTCCGGGCCTGGATGCGCTGGCAGGCGTCAAGATCGCGCCGGCGCAGCTGGGTGATATCCAGCAGCGCTACATGAAG GACTTCTCAGCGCTGTGGCAGGCCATGGCCGAGGGCAAGGCCGAGGCCACCGGTCCGCTGCACGACCGGCGCTTCGC CGGCGACGCATGGCGCACCAACCTCCCATATCGCTTCGCTGCCGCGTTCTACCTGCTCAATGCGCGCGCCTTGACCGA GCTGGCCGATGCCGTCGAGGCCGATGCCAAGACCCGCCAGCGCATCCGCTTCGCGATCTCGCAATGGGTCGATGCGA TGTCGCCCGCCAACTTCCTTGCCACCAATCCCGAGGCGCAGCGCCTGCTGATCGAGTCGGGCGGCGAATCGCTGCGTG CCGGCGTGCGCAACATGATGGAAGACCTGACACGCGGCAAGATCTCGCAGACCGACGAGAGCGCGTTTGAGGTCGGC CGCAATGTCGCGGTGACCGAAGGCGCCGTGGTCTTCGAGAACGAGTACTTCCAGCTGTTGCAGTACAAGCCGCTGAC |

TABLE 2-continued

Nucleic Acid Sequences: Genes

| SEQ ID NO | Nucleic Acid Sequence |
| --- | --- |
| | CGACAAGGTGCACGCGCGCCCGCTGCTGATGGTGCCGCCGTGCATCAACAAGTACTACATCCTGGACCTGCAGCCGG<br>AGAGCTCGCTGGTGCGCCATGTGGTGGAGCAGGGACATACGGTGTTTCTGGTGTCGTGGCGCAATCCGGACGCCAGC<br>ATGGCCGGCAGCACCTGGGACGACTACATCGAGCACGCGGCCATCCGCGCCATCGAAGTCGCGCGCGACATCAGCGG<br>CCAGGACAAGATCAACGTGCTCGGCTTCTGCGTGGGCGGCACCATTGTCTCGACCGCGCTGGCGGTGCTGGCCGCGCG<br>CGGCGAGCACCCGGCCGCCAGCGTCACGCTGCTGACCACGCTGCTGGACTTTGCCGACACGGGCATCCTCGACGTCTT<br>TGTCGACGAGGGCCATGTGCAGTTGCGCGAGGCCACGCTGGGCGGCGGCGCCGGCGCGCCGTGCGCGCTGCTGCGCG<br>GCCTTGAGCTGGCCAATACCTTCTCGTTCTTGCGCCCGAACGACCTGGTGTGGAACTACGTGGTCGACAACTACCTGA<br>AGGGCAACACGCCGGTGCCGTTCGACCTGCTGTTCTGGAACGGCGACGCCACCAACCTGCCGGGGCCGTGGTACTGC<br>TGGTACCTGCGCCACACCTACCTGCAGAACGAGCTCAAGGTACCGGGCAAGCTGACCGTGTGCGGCGTGCCGGTGGA<br>CCTGGCCAGCATCGACGTGCCGACCTATATCTACGGCTCGCGCGAAGACCATATCGTGCCGTGGACCGCGGCCTATGC<br>CTCGACCGCGCTGCTGGCGAACAAGCTGCGCTTCGTGCTGGGTGCGTCGGGCCATATCGCCGGTGTGATCAACCCGCC<br>GGCCAAGAACAAGCGCAGCCACTGGACTAACGATGCGCTGCCGGAGTCGCCGCAGCAATGGCTGGCCGGCGCCATCG<br>AGCATCACGGCAGCTGGTGGCCGGACTGGACCGCATGGCTGGCCGGGCAGGCCGGCGCGAAACGCGCCGCGCCCGCC<br>AACTATGGCAATGCGCGCTATCGCGCAATCGAACCCGCGCCTGGGCGATACGTCAAAGCCAAGGCATGA |
| SEQ ID NO: 96<br>nucleic acid<br>coding sequence<br>of the gene<br>phaJ(Ac) at locus<br>DQN91_RS09635 | ATGAGTACACAAACCCTTGCCGTGGGCCAGAAGGCTCGCCTGACCAAGCGCTTCGGCCCGGCCGAGGTGGCGGCCTT<br>CGCCGGCCTCTCGGAGGATTTCAATCCCCTGCACCTGGACCCGGACTTCGCCGCCACGACGGTGTTCGAGCGCCCCAT<br>CGTCCACGGCATGCTGCTGGCGAGCCTCTTCTCCGGGCTCCTCGGGCAGCAACTGCCCGGGAAAGGGAGCATCTATCT<br>GGGCCAGAGCCTCGGCTTCAAACTGCCGGTGTTCGTGGGGGACGAGGTGACGGCGGAGGTGGAGGTGATTGCCCTTC<br>GAAGCGACAAGCCCATCGCCACCCTGGCCACCCGCATCTTCACCCAGGGCGGCGCCCTCGCCGTGACGGGGGAAGCG<br>GTGGTAAAACTCCCTTGA |
| SEQ ID NO: 97<br>nucleic acid<br>coding sequence<br>of the gene<br>PP_2216 | ATGCTGGTAAATGACGAGCAACAACAGATCGCCGACGCGGTACGTGCGTTCGCCCAGGAACGCCTGAAGCCGTTTGC<br>CGAGCAATGGGACAAGGACCATCGCTTCCCGAAAGAGGCCATCGACGAGATGGCCGAACTGGGCCTGTTCGGCATGC<br>TGGTGCCGGAGCAGTGGGGCGGTAGCGACACCGGTTATGTGGCCTATGCCATGGCCTTGGAGGAAATCGCTGCGGGC<br>GATGGCGCCTGCTCGACCATCATGAGCGTGCACAACTCGGTGGGTTGCGTGCCGATCCTGCGCTTCGGCAACGAGCAG<br>CAGAAAGAGCAGTTCCTCACCCCGCTGGCGACAGGTGCGATGCTCGGTGCTTTCGCCCTGACCGAGCCGCAGGCTGG<br>CTCCGATGCCAGCAGCCTGAAGACCCGCGCACGCCTGGAAGGCGACCATTACGTGCTCAATGGCAGCAAGCAGTTCA<br>TTACCTCGGGGCAGAACGCCGGCGTAGTGATCGTGTTTGCGGTCACCGACCCGGAGGCCGGCAAGCGTGGCATCAGC<br>GCCTTCATCGTGCCGACCGATTCGCCGGGCTACCAGGTAGCGCGGGTGGAGGACAAACTCGGCCAGCACGCCTCCGA<br>CACCTGCCAGATCGTTTTCGACAATGTGCAAGTGCCAGTGGCCAACCGGCTGGGGGCGGAGGGTGAAGGCTACAAGA<br>TCGCCCTGGCCAACCTTGAAGGCGGCCGTATCGGCATCGCCTCGCAAGCGGTGGGTATGGCCCGCGCGGCGTTCGAA<br>GTGGCGCGGGACTATGCCAACGAGCGCCAGAGCTTTGGCAAACCGCTGATCGAGCACCAGGCCGTGGCGTTTCGCCT<br>GGCCGACATGGCAACGAAAATTTCCGTTGCCCGGCAGATGGTATTGCACGCCGCTGCCCTTCGTGATGCGGGGCGCCC<br>GGCGCTGGTGGAAGCGTCGATGGCCAAGCTGTTCGCCTCGGAAATGGCCGAAAAGGTCTGTTCGGACGCCTTGCAGA<br>CCCTGGGCGGTTATGGCTATCTGAGTGACTTCCCGCTGGAGCGGATCTACCGCGACGTTCGGGTTTGCCAGATCTACG<br>AAGGCACCAGCGACATTCAGCGCATGGTCATTGCGCGCAATCTTTGA |
| SEQ ID NO: 98<br>nucleic acid<br>coding sequence<br>of the gene<br>PP_2216<br>optimized for<br>*E.coli* | ATGCTGGTGAACGACGAACAGCAGCAAATTGCCGATGCTGTGCGCGCCTTTGCTCAAGAGCGTTTAAAACCGTTCGCG<br>GAGCAGTGGGACAAAGACCACCGTTTCCCGAAAGAAGCGATTGATGAGATGGCAGAACTGGGCCTGTTTGGCATGTT<br>AGTCCCGGAGCAATGGGGCGGCTCGGACACCGGTTATGTGGCATATGCGATGGCGCTGGAAGAGATTGCGGCCGGTG<br>ATGGCGCTTGTAGCACCATTATGAGCGTCCACAATTCGGTGGGTTGCGTGCCGATTCTGCGCTTTGGTAACGAACAGC<br>AGAAAGAACAGTTCCTGACCCCTTTAGCAACGGGTGCGATGCTGGGCGCGTTTGCCTTAACCGAACCTCAGGCGGGCT<br>CGGACGCAAGCTCGTTGAAAACCCGTGCGCGCCTGGAAGGTGATCACTACGTGTTGAATGGCAGTAAGCAATTCATT<br>ACCAGCGGCCAAAATGCCGGTGTGGTGATCGTGTTTGCGGTGACTGACCCGGAAGCGGGCAAACGCGGCATTAGTGC<br>GTTCATCGTGCCGACCGATAGCCCGGGCTATCAGGTCGCCCGTGTTGAAGATAAGCTTGGTCAGCATGCGAGCGATAC<br>CTGTCAAATCGTGTTTGACAACGTACAAGTTCCGGTAGCCAATCGCCTGGGTGCTGAAGGTGAAGGTTATAAAATCGC<br>ACTGGCAAACCTTGAAGGTGGCCGCATTGGCATCGCGAGTCAGGCCGTTGGCATGGCACGCGCCGCGTTTGAAGTTG<br>CGCGCGATTACGCAAACGAACGTCAGAGCTTCGGCAAACCGCTCATTGAACATCAGGCGGTTGCCTTTCGTCTGGCCG<br>ATATGGCCACGAAAATCAGCGTGGCGCGCCAGATGGTTCTGCATGCGGCTGCCCTGCGTGATGCGGGCCGTCCGGCG<br>CTGGTTGAAGCATCAATGGCGAAGCTGTTCGCCTCAGAAATGGCTGAAAAAGTCTGCTCAGATGCGCTGCAGACGCT<br>GGGCGGTTACGGTTACCTGAGCGATTTTCCACTGGAACGTATTTATCGTGATGTTCGCGTATGCCAGATCTATGAGGG<br>TACTAGCGACATTCAGCGCATGGTAATCGCCCGTAACCTGTAA |
| SEQ ID NO: 99<br>nucleic acid<br>coding sequence<br>of the gene prpB<br>at locus b0331 | ATGTCTCTACACTCTCCAGGTAAAGCGTTTCGCGCTGCACTGACTAAAGAAAATCCATTGCAGATTGTTGGCACCATC<br>AACGCTAATCATGCGCTGTTGGCGCAGCGTGCCGGATATCAGGCAATTTATCTTTCTGGCGGTGGCGTGGCGGCAGGT<br>TCGCTGGGGCTGCCCGATCTCGGTATTTCTACCCTTGATGATGTGCTGACCGACATTCGCCGTATCACCGACGTTTGTT<br>CGCTGCCGCTGCTGGTGGATGCGGATATCGGTTTTGGTTCTTCGGCCTTTAACGTGGCGCGCACCGTGAAATCGATGA<br>TTAAAGCCGGTGCGGCAGGATTGCATATTGAAGATCAGGTTGGTGCGAAACGCTGCGGTCATCGTCCGAATAAAGCG<br>ATCGTCTCGAAAGAAGAGATGGTGGATCGGATCCGCGCGGCGGTGGATGCGAAAACCGATCCTGATTTTGTGATCAT<br>GGCGCGCACCGATGCTCTGGCGGTAGAGGGGCTGGATGCGGCGATCGAGCGTGCGCAGGCCTATGTTGAAGCGGGTG<br>CCGAGATGTTGTTCCCGGAGGCGATTACCGAACTCGCCATGTACCGCCAGTTTGCCGATGCGGTGCAGGTGCCGATCC<br>TCGCCAACATCACCGAATTTGGTGCCACGCCGCTGTTTACCACCGACGAATTACGCAGCGCCCATGTCGCAATGGCGC<br>TGTACCCACTTTCAGCGTTCCGCGCCATGAACCGCGCCGCTGAACATGTCTACAACGTCCTGCGCCAGGAAGGCACGC<br>AGAAAAGCGTCATCGACACCATGCAGACCCGCAACGAGCTGTACGAAAGCATCAACTACTACCAGTACGAAGAGAA<br>GCTCGACAACCTGTTTGCCCGTAGCCAGGTGAAATAA |
| SEQ ID NO: 100<br>nucleic acid<br>coding sequence<br>of the gene prpC<br>at locus b0333 | ATGAGCGACACAACGATCCTGCAAAACAGTACCCATGTCATTAAACCGAAAAAATCTGTGGCACTTTCTGGCGTTCCG<br>GCGGGCAATACGGCGCTCTGCACCGTGGGTAAAAGTGGCAATGACCTGCATTACCGCGGCTACGATATTCTTGATCTG<br>GCGAAACATTGCGAATTTGAAGAAGTGGCGCATCTGCTGATCCACGGCAAACTGCCGACCCGTGACGAACTCGCCGC<br>TTACAAAACGAAACTGAAAGCCCTGCGCGGTTTACCGGCTAACGTGCGTACCGTGCTGGAAGCCTTACCGGCGGCGT<br>CGCACCCGATGGATGTTATGCGCACCGGTGTTTCCGCGCTCGGCTGCACGCTGCCAGAAAAAGAGGGGCATACCGTCT<br>CTGGCGCGCGGGATATTGCCGACAAACTGCTGGCGTCGCTTAGCTCGATTCTCCTTTATTGGTATCACTACAGCCACA<br>ACGGCGAACGCATCCAACCGGAAACCGATGACGACTCCATCGGCGGTCACTTCCTGCATCTGCTGCACGGCGAAAAG<br>CCATCGCAAAGCTGGGAAAAGGCGATGCATATCTCGCTGGTGCTGTACGCCGAACACGAGTTTAACGCCTCCACCTTT<br>ACCAGTCGGGTGATTGCGGGCACCGGCTCTGATATGTATTCCGCGATTATTGGCGCGATTGGCGCACTGCGCGGGCCA |

TABLE 2-continued

Nucleic Acid Sequences: Genes

| SEQ ID NO | Nucleic Acid Sequence |
|---|---|
| | AAACACGGCGGGGCGAATGAAGTGTCGCTGGAGATCCAGCAACGCTACGAAACGCCGGACGAAGCCGAAGCAGATA<br>TCCGCAAGCGCGTGGAAAACAAAGAAGTGGTCATTGGTTTTGGTCATCCGGTTTACACCATCGCTGACCCGCGCCACC<br>AGGTGATTAAACGTGTGGCGAAGCAGCTCTCGCAGGAAGGCGGCTCGCTGAAGATGTACAACATCGCCGATCGCCTG<br>GAAACGGTGATGTGGGAGAGCAAAAAGATGTTCCCCAATCTCGACTGGTTCTCTGCTGTTTCCTACAACATGATGGGC<br>GTTCCCACCGAGATGTTCACACCACTGTTTGTTATCGCCCGCGTCACCGGCTGGGCGGCGCACATTATCGAACAACGT<br>CAGGACAACAAAATTATCCGTCCTTCCGCCAATTATGTTGGACCGGAAGACCGCCCGTTTGTCGCGCTGGATAAGCGC<br>CAGTAA |
| SEQ ID NO: 101 nucleic acid coding sequence of the gene prpD at locus b0334 | ATGTCAGCTCAAATCAACAACATCCGCCCGGAATTTGATCGTGAAATCGTTGATATCGTCGATTACGTCATGAACTAC<br>GAAATCAGCTCTAAAGTGGCCTACGACACCGCACATTACTGCCTGCTCGACACGCTCGGCTGCGGTCTGGAAGCTCTC<br>GAATACCCGGCCTGTAAAAAACTGCTGGGGCCAATTGTTCCCGGCACCGTCGTACCCAACGGCGTGCGCGTCCCCGG<br>AACTCAGTTCCAGCTCGACCCCGTCCAGGCGGCATTTAACATCGGCGCGATGATCCGCTGGCTCGATTTCAACGATAC<br>CTGGCTGGCGGCGGAGTGGGGCCATCCTTCCGACAACCTCGGCGGCATTCTGGCAACGGCGGACTGGCTTTCGCGCA<br>ACGCGGTCGCCAGCGGCAAAGCGCCGTTGACCATGAAACAGGTGCTGACCGCAATGATCAAAGCCCATGAAATTCAG<br>GGCTGCATCGCGCTGGAAAACTCCTTTAACCGCGTCGGCCTCGACCACGTTCTGTTAGTGAAAGTGGCTTCCACCGCC<br>GTGGTCGCCGAAATGCTCGGCCTGACCCGCGAGGAAATTCTCAACGCCGTTTCGCTGGCGTGGGTGGACGGTCAGTCG<br>CTGCGCACCTATCGCCATGCGCCGAACACCGGCACGCGTAAATCCTGGGCGGCGGGCGATGCCACTTCCCGCGCGGT<br>ACGTCTGGCACTGATGGCGAAAACGGGCGAAATGGGTTACCCGTCAGCCCTGACTGCGCCGGTGTGGGGCTTCTACG<br>ACGTCTCCTTTAAAGGTGAATCGTTCCGCTTCCAGCGCCCGTACGGTTCCTACGTTATGGAAAATGTGCTGTTCAAAAT<br>CTCCTTCCCGGCGGAGTTCCACTCCCAGACGGCAGTTGAAGCAGCGATGACGCTCTATGAACAGATGCAGGCAGCAG<br>GCAAAACGGCGGCGGATATCGAAAAAGTGACCATTCGCACCCACGAAGCCTGTATTCGCATCATCGACAAAAAAGGG<br>CCGCTCAATAACCCGGCAGACCGCGATCACTGCATTCAGTACATGGTGGCGATCCCGCTGCTATTCGGGCGCTTAACG<br>GCGGCAGATTACGAGGACAACGTTGCGCAAGATAAACGCATTGACGCCCTGCGCGAGAAGATCAATTGCTTTGAAGA<br>TCCGGCATTTACCGCTGACTACCACGACCCGGAAAAACGCGCCATCGCCAATGCCATTACCCTTGAGTTCACCGACGG<br>CACACGATTTGAAGAAGTGGTGGTGGAGTACCCCATTGGTCATGCTCGCCGCCGTCAGGATGGTATTCCGAAACTGGT<br>CGATAAATTCAAAATCAATCTCGCGCGCCAGTTCCCGACTCGCCAACAGCAGCGCATTCTGGAGGTTTCTCTCGACAG<br>AGCTCGCCTGGAACAGATGCCGGTCAATGAGTATCTCGACCTGTACGTCATTTAA |
| SEQ ID NO: 102 nucleic acid coding sequence of the gene prpE(Cn) at locus H16_RS12300 | ATGACCGCAGACGCGGAGGAGACAGACATGACGGCAAGCCATGCCGTGCATGCCCGTTCGCTGGCCGACCCCGAGGG<br>GTTCTGGGCCGAACAGGCGGCGCGCATCGACTGGGAAACCCCGTTCGGCCAGGTGCTCGACAACAGCCGCGCGCCCT<br>TTACGCGCTGGTTCGTCGGCGGGCGCACCAACCTGTGCCACAACGCGGTCGACCGCCACCTGGCGGCCCGCGCCAGC<br>CAGCCGGCGCTGCACTGGGTCTCGACCGAGACCGACCAGGCCCGCACCTTTACCTACGCCGAGCTGCACGACGAAGT<br>CAGCCGCATGGCCGCGATCCTGCAGGGCCTGGACGTGCAGAAGGGCGACCGCGTGCTGATCTACATGCCGATGATCC<br>CGGAAGCCGCCTTTGCCATGCTGGCCTGCGCGCGCATCGGCGCGATCCATTCGGTGGTGTTCGGCGGCTTTGCCTCGG<br>TCAGCCTGGCCGCGCGCATCGAGGATGCCCGGCCGCGCGTGGTGGTCAGCGCCGACGCCGGCTCGCGTGCCGGCAAG<br>GTGGTGCCCTACAAGCCGCTGCTGGACGAGGCCATCCGGCTCTCGTCGCACCAGCCCGGGAAGGTGCTGCTGGTGGA<br>CCGGCAACTGGCGCAAATGCCCCGTACCGAGGGCCGCGATGAGGACTACGCCGCCTGGCGCGAACGCGTGGCCGGCG<br>TGCAGGTGCCGTGCGTGTGGCTGGAATCGAGCGAGCCGTCGTACGTGCTATACACCTCCGGCACCACCGGCAAGCCC<br>AAGGGCGTGCAGCGCGATACCGGCGGCTACGCGGTGGCGCTGGCCACCTCGATGGAATACATCTTCTGCGGCAAGCC<br>CGGCGACACCATGTTCACCGCGTCGGACATCGGCTGGGTGGTGGGGCACAGCTATATCGTCTACGGCCCGCTGCTGGC<br>CGGCATGGCCACGCTGATGTATGAAGGCACGCCGATCCGCCCCGACGGTGGCATCCTGTGGCGGCTGGTGGAGCAAT<br>ACAAGGTCAACCTGATGTTCAGCGCGCCGACCGCGATCCGCGTGCTGAAGAAGCAGGACCCGGCCTGGCTGACCCGC<br>TACGACCTGTCCAGCCTGCGCCTGCTGTTCCTGGCCGGCGAGCCGCTGGACGAGCCCACCGCGCGCTGGATCCAGGAC<br>GGCCTGGGCAAGCCCGTGGTCGACAACTACTGGCAGACCGAATCCGGCTGGCCGATCCTCGCGATCCAGCGCGGCAT<br>CGAGGCGCTGCCGCCCAAGCTGGGCTCGCCCGGCGTGCCCGCCTACGGCTATGACCTGAAGATCGTCGACGAGAACA<br>CCGGCGCTGAATGCCCGCCGGGGCAGAAGGGTGTGGTCGCCATCGACGGCCCGCTGCCGCCGGGATGCATGAGCACG<br>GTCTGGGGCGACGACGACCGCTTCGTGCGCACCTACTGGCAGGCGGTGCCGAACCGGCTGTGCTATTCGACCTTCGAC<br>TGGGGCGTGCGCGACGCCGACGGCTATGTTTTTATCCTGGGCCGCACCGACGACGTGATCAACGTTGCCGGCCACCGG<br>CTGGGCACCCGCGAGATCGAGGAAAGCCTGTCGTCCAACGCTGCCGTGGCCGAGGTGGCGGTGGTGGGCGTGCAGGA<br>CGCGCTCAAGGGGCAGGTGGCGATGGCCTTCTGCATCGCCCGCGATCCGGCGCGCACGGCCACGGCCGAAGCGCGGC<br>TGGCATTGGAGGGCGAGTTGATGAAGACGGTGGAGCAGCAACTGGGTGCCGTGGCGCGGCCGGCGCGCGTATTCTTT<br>GTCAATGCACTGCCCAAGACCCGCTCCGGCAAGTTGCTGCGGCGCGCCATGCAGGCGGTGGCCGAAGGGCGCGATCC<br>GGGCGACCTGACCACGATCGAGGACCCGGGTGCGCTGGAACAGTTGCAGGCAGCGCTGAAAGGCTAG |
| SEQ ID NO: 103 nucleic acid coding sequence of the gene prpE(Ec) at locus b0335 | ATGTCTTTTAGCGAATTTTATCAGCGTTCGATTAACGAACCGGAGCAGTTCTGGGCCGAGCAGGCCCGGCGTATTGAC<br>TGGCAGACGCCCTTTACGCAAACGCTCGATCACAGCAATCCGCCGTTTGCCCGTTGGTTTTGTGAAGGCCGAACCAAC<br>TTGTGCCACAACGCCATCGACCGCTGGCTGGAGAAACAGCCAGAGGCGCTGGCGCTGATTGCCGTCTCTTCGGAAAC<br>AGAAGAAGAGCGCACCTTTACCTTTCGTCAGCTGCATGACGAAGTGAACGCGGTGGCCTCAATGTTGCGTTCATTGGG<br>TGTGCAGCGCGGCGATCGGGTGCTGGTGTATATGCCGATGATTGCCGAAGCGCATATTACTCTGCTGGCCTGCGCGCG<br>CATTGGCGCTATTCACTCGGTGGTGTTTGGTGGATTTGCCTCGCACAGCGTGGCGGCGCGAATTGATGACGCTAAACC<br>GGTGCTGATTGTCTCGGCTGATGCCGGAGCGCGCGGTGGCAAAATCATTCCCTATAAAAAATTGCTCGACGATGCGAT<br>AAGTCAGGCGCAGCACCAGCCACGCCATGTTTTGCTGGTGGATCGCGGGCTGGCGAAAATGGCGCGCGTCAGCGGGC<br>GGGATGTCGATTTCGCGTCGTTGCGCCATCAACACATCGGCGCGCGGGTACCGGTGGCGTGGCTGGAATCCAACGAA<br>ACCTCCTGCATTCTCTACACTTCCGGCACGACCGGCAAACCTAAAGGCGTGCAGCGTGACGTCGGCGGATATGCGGTG<br>GCGCTGGCGACCTCGATGGACACCATTTTTGGCGGCAAAGCGGGCAGCGTGTTCTTTTGCGCATCGGATATCGGCTGG<br>GTGGTGGGGCATTCGTATATCGTTTACGCGCCGCTGCTGGCGGGGATGGCGACTATCGTTTACGAAGGATTGCCGACC<br>TGGCCGGACTGCGGCGTGTGGTGGACAATCGTCGAGAAATATCAGGTTAGCCGGATGTTCTCAGCGCCGACCGCCATT<br>CGCGTGCTGAAAAAATTCCCTACCGCTGAAATTCGCAAACACGATCTCTCGTCGCTGGAAGTGCTCTATCTGGCTGGA<br>GAACCGCTGGACGAGCCGACCGCCAGTTGGGTGAGCAATACGCTGGATGTGCCGGTCATCGACAACTACTGGCAGAC<br>CGAATCCGGCTGGCCGATTATGGCGATTGCTCGCGGTCTGGACGACAGGCCGACGCGTCTGGGAAGCCCCGGTGTGC<br>CGATGTATGGCTATAACGTGCAGTTGCTTAATGAAGTCACCGGCGAACCGTGTGGCGTCAACGAGAAAGGGATGCTG<br>GTGGTGGAAGGGCCGCTGCCGCCGGGGTGTATTCAGACCATCTGGGGCGACGACGGCCGCTTTGTGAAGACTTACTG<br>GTCGCTGTTTTCCCGCCCGGTGTACGCCACCTTTGACTGGGGCATCCGTGACGCTGACGGTTATCACTTTATTCTCGGG<br>CGCACTGACGATGTAATTAACGTTGCCGGGCATCGGCTGGGGACGCGCGAGATTGAAGAGAGTATCTCCAGCCATCC<br>GGGCGTTGCCGAAGTGGCGGTGGTTGGGGTGAAAGATGCGCTGAAAGGGCAGGTGGCGGTGGCGTTTGTCATTCCGA<br>AAGAGAGCGACAGTCTGGAAGATCGTGATGTGGCGCACTCGCAAGAGAAGGCGATTATGGCGCTGGTGGACAGCCA |

TABLE 2-continued

Nucleic Acid Sequences: Genes

| SEQ ID NO | Nucleic Acid Sequence |
|---|---|
| | GATTGGCAACTTTGGCCGCCCGGCGCACGTCTGGTTTGTCTCGCAATTGCCAAAAACGCGATCCGGAAAAATGCTGCG<br>CCGCACGATCCAGGCGATTTGCGAAGGACGCGATCCTGGAGATCTGACGACCATTGATGATCCTGCGTCGTTGGATCA<br>GATCCGCCAGGCGATGGAAGAGTAG |
| SEQ ID NO: 104 nucleic acid coding sequence of the gene prpE(Se) at locus STM0371 | ATGTCTTTTAGCGAATTTTATCAGCGTTCCATTAACGAACCGGAGGCGTTCTGGGCCGAGCAGGCCCGGCGTATCGAC<br>TGGCGACAGCCGTTTACGCAGACGCTGGATCATAGCCGTCCACCGTTTGCCCGCTGGTTTTGCGGCGGCACCACTAAC<br>TTATGTCATAACGCCGTCGACCGCTGGCGGGATAAACAGCCGGAGGCGCTGGCGCTGATTGCCGTCTCATCAGAGAC<br>CGATGAAGAGCGCACATTTACCTTCAGCCAGTTGCATGATGAAGTCAACATTGTGGCCGCCATGTTGCTGTCGCTGGG<br>CGTGCAGCGTGGCGATCGCGTATTGGTCTATATGCCGATGATTGCCGAAGCGCAGATAACCCTGCTGGCCTGCGCGCG<br>CATTGGCGCGATCCATTCGGTGGTCTTTGGCGGTTTTGCCTCGCACAGCGTGGCGGCGCGCATTGACGATGCCAGACC<br>GGCGCTGATTGTGTCGGCGGATGCCGGAGCGCGGGGCGGTAAAATCCTGCCGTATAAAAAGCTGCTCGATGACGCTA<br>TTGCGCAGGCGCAGCATCAGCCGAAACACGTTCTGCTGGTGGACAGAGGGCTGGCGAAAATGGCATGGGTGGATGGG<br>CGCGATCTGGATTTTGCCACGTTGCGCCAGCAGCATCTCGGCGCGAGCGTGCCGGTGGCGTGGCTGGAATCCAACGA<br>AACCTCGTGCATTCTTTACACCTCCGGCACTACCGGCAAACCGAAAGGCGTCCAGCGCGACGTCGGCGGTTATGCGGT<br>GGCGCTGGCAACCTCGATGGACACCATTTTTGGCGGCAAGGCGGGCGGCGTATTCTTTTGCGCATCGGATATCGGCTG<br>GGTCGTCGGCCACTCCTATATCGTTTACGCGCCGTTGCTGGCAGGCATGGCGACTATTGTTTACGAAGGACTGCCGAC<br>GTACCCGGACTGCGGGGTCTGGTGGAAAATTGTCGAGAAATACCAGGTTAACCGGATGTTTTCCGCCCCGACCGCGAT<br>TCGCGTGCTGAAAAAATTCCCGACGGCGCAAATCCGCAATCACGATCTCTCCTCGCTGGAGGCGCTTTATCTGGCCGG<br>TGAGCCGCTGGACGAGCCGACGGCCAGTTGGGTAACGGAGACGCTGGGCGTACCGGTCATCGACAATTATTGGCAGA<br>CGGAGTCCGGCTGGCCGATCATGGCGCTGGCCCGCGCGCTGGACGACAGGCCGTCGCGTCTGGGAAGTCCCGGCGTG<br>CCGATGTACGGTTATAACGTCCAGCTACTCAATGAAGTCACCGGCGAACCTTGCGGCATAAATGAAAAGGGGATGCT<br>GGTGATCGAAGGGCCGCTGCCGCCGGGCTGTATTCAGACTATTTGGGGCGACGATGCGCGTTTTGTGAAGACTTACTG<br>GTCGCTGTTTAACCGTCAGGTTTATGCCACTTTCGACTGGGGAATCCGCGACGCCGAGGGGTATTACTTTATTCTGGGC<br>CGTACCGATGATGTGATTAATATTGCGGGTCATCGGCTGGGGACGCGAGAAATAGAAGAAAGTATCTCCAGCTACCC<br>GAACGTAGCGGAAGTGGCGGTAGTGGGGATAAAAGACGCTCTGAAAGGGCAGGTAGCGGTGGCGTTTGTCATTCCGA<br>AGCAGAGCGATACGCTGGCGGATCGCGAGGCGGCGCGCGACGAGGAAAACGCGATTATGGCGCTGGTGGACAACCA<br>GATCGGTCACTTTGGTCGTCCGGCGCATGTCTGGTTTGTTTCGCAGCTCCCCAAAACGCGTTCCGGAAAGATGCTTCGC<br>CGCACGATCCAGGCGATCTGCGAAGGCCGCGATCCGGGCGATCTGACAACCATTGACGATCCCGCGTCGTTGCAGCA<br>AATTCGCCAGGCGATCGAAGAATAG |
| SEQ ID NO: 105 nucleic acid coding sequence of the gene pta at locus b2297 | GTGTCCCGTATTATTATGCTGATCCCTACCGGAACCAGCGTCGGTCTGACCAGCGTCAGCCTTGGCGTGATCCGTGCA<br>ATGGAACGCAAAGGCGTTCGTCTGAGCGTTTTCAAACCTATCGCTCAGCCGCGTACCGGTGGCGATGCGCCCGATCAG<br>ACTACGACTATCGTGCGTGCGAACTCTTCCACCACGACGGCCGCTGAACCGCTGAAAATGAGCTACGTTGAAGGTCTG<br>CTTTCCAGCAATCAGAAAGATGTGCTGATGGAAGAGATCGTCGCAAACTACCACGCTAACACCAAAGACGCTGAAGT<br>CGTTCTGGTTGAAGGTCTGGTCCCGACACGTAAGCACCAGTTTGCCCAGTCTCTGAACTACGAAATCGCTAAAACGCT<br>GAATGCGGAAATCGTCTTCGTTATGTCTCAGGGCACTGACACCCCGGAACAGCTGAAAGAGCGTATCGAACTGACCC<br>GCAACAGCTTCGGCGGTGCCAAAAACACCAACATCACCGGCGTTATCGTTAACAAACTGAACGCACCGGTTGATGAA<br>CAGGGTCGTACTCGCCCGGATCTGTCCGAGATTTTCGACGACTCTTCCAAAGCTAAAGTAAACAATGTTGATCCGGCG<br>AAGCTGCAAGAATCCAGCCCGCTGCCGGTTCTCGGCGCTGTGCCGTGGAGCTTTGACCTGATCGCGACTCGTGCGATC<br>GATATGGCTCGCCACCTGAATGCGACCATCATCAACGAAGGCGACATCAATACTCGCCGCGTTAAATCCGTCACTTTC<br>TGCGCACGCAGCATTCCGCACATGCTGGAGCACTTCCGTGCCGGTTCTCTGCTGGTGACTTCCGCAGACCGTCCTGAC<br>GTGCTGGTGGCCGCTTGCCTGGCAGCCATGAACGGCGTAGAAATCGGTGCCCTGCTGCTGACTGGCGGTTACGAAATG<br>GACGCGCGCATTTCTAAACTGTGCGAACGTGCTTTCGCTACCGGCCTGCCGGTATTTATGGTGAACACCAACACCTGG<br>CAGACCTCTCTGAGCCTGCAGAGCTTCAACCTGGAAGTTCCGGTTGACGATCACGAACGTATCGAGAAAGTTCAGGA<br>ATACGTTGCTAACTACATCAACGCTGACTGGATCGAATCTCTGACTGCCACTTCTGAGCGCAGCCGTCGTCTGTCTCCG<br>CCTGCGTTCCGTTATCAGCTGACTGAACTTGCGCGCAAAGCGGGCAAACGTATCGTACTGCCGGAAGGTGACGAACC<br>GCGTACCGTTAAAGCAGCCGCTATCTGTGCTGAACGTGGTATCGCAACTTGCGTACTGCTGGGTAATCCGGCAGAGAT<br>CAACCGTGTTGCAGCGTCTCAGGGTGTAGAACTGGGTGCAGGGATTGAAATCGTTGATCCAGAAGTGGTTCGCGAAA<br>GCTATGTTGGTCGTCTGGTCGAACTGCGTAAGAACAAAGGCATGACCGAAACCGTTGCCCGCGAACAGCTGGAAGAC<br>AACGTGGTGCTCGGTACGCTGATGCTGGAACAGGATGAAGTTGATGGTCTGGTTTCCGGTGCTGTTCACACTACCGCA<br>AACACCATCCGTCCGCCGCTGCAGCTGATCAAAACTGCACCGGGCAGCTCCCTGGTATCTTCCGTGTTCTTCATGCTGC<br>TGCCGGAACAGGTTTACGTTTACGGTGACTGTGCGATCAACCCGGATCCGACCGCTGAACAGCTGGCAGAAATCGCG<br>ATTCAGTCCGCTGATTCCGCTGCGGCCTTCGGTATCGAACCGCGCGTTGCTATGCTCTCCTACTCCACCGGTACTTCTG<br>GTGCAGGTAGCGACGTAGAAAAAGTTCGCGAAGCAACTCGTCTGGCGCAGGAAAAACGTCCTGACCTGATGATCGAC<br>GGTCCGCTGCAGTACGACGCTGCGGTAATGGCTGACGTTGCGAAATCCAAAGCGCCGAACTCTCCGGTTGCAGGTCG<br>CGCTACCGTGTTCATCTTCCCGGATCTGAACACCGGTAACACCACCTACAAAGCGGTACAGCGTTCTGCCGACCTGAT<br>CTCCATCGGGCCGATGCTGCAGGGTATGCGCAAGCCGGTTAACGACCTGTCCCGTGGCGCACTGGTTGACGATATCGT<br>CTACACCATCGCGCTGACTGCGATTCAGTCTGCACAGCAGCAGTAA |
| SEQ ID NO: 106 nucleic acid coding sequence of the gene puuE at locus b1302 | ATGAGCAACAATGAATTCCATCAGCGTCGTCTTTCTGCCACTCCGCGCGGGGTTGGCGTGATGTGTAACTTCTTCGCCC<br>AGTCGGCTGAAAACGCCACGCTGAAGGATGTTGAGGGCAACGAGTACATCGATTTCGCCGCAGGCATTGCGGTGCTG<br>AATACCGGACATCGCCACCCTGATCTGGTCGCGGCGGTGGAGCAGCAACTGCAACAGTTTACCCACACCGCGTATCA<br>GATTGTGCCGTATGAAAGCTACGTCACCCTGGCGGAGAAAATCAACGCCCTTGCCCCGGTGAGCGGGCAGGCCAAAA<br>CCGCGTTCTTCACCACCGGTGCGGAAGCGGTGGAAAACGCGGTGAAAATTGCTCGCGCCCATACCGGACGCCCTGGC<br>GTGATTGCGTTTAGCGGCGGCTTTCACGGTCGTACGTATATGACCATGGCGCTGACCGGAAAAGTTGCGCCGTACAAA<br>ATCGGCTTCGGCCCGTTCCCTGGTTCGGTGTATCACGTACCTTATCCGTCAGATTTACACGGCATTTCAACACAGGACT<br>CCCTCGACGCCATCGAACGCTTGTTTAAATCAGACATCGAAGCGAAGCAGGTGGCGGCGATTATTTTCGAACCGGTGC<br>AGGGCGAGGGCGGTTTCAACGTTGCGCCAAAAGAGCTGGTTGCCGCTATTCGCCGCCTGTGCGACGAGCACGGTATT<br>GTGATGATTGCTGATGAAGTGCAAAGCGGCTTTGCGCGTACCGGTAAGCTGTTTGCCATGGATCATTACGCCGATAAG<br>CCGGATTTAATGACGATGGCGAAAAGCCTCGCGGGCGGGATGCCGCTTTCGGGCGTGGTCGGTAACGCGAATATTAT<br>GGACGCACCCGCGCCGGGCGGGCTTGGCGGCACCTACGCCGGTAACCCGCTGGCGGTGGCTGCCGCGCACGCGGTGC<br>TCAACATTATCGACAAAGAATCACTCTGCGAACGCGCGAATCAACTGGGCCAGCGTCTCAAAAACACGTTGATTGAT<br>GCCAAAGAAAGCGTTCCGGCCATTGCTGCGGTACGCGGCCTGGGGTCGATGATTGCGGTAGAGTTTAACGATCCGCA<br>AACGGGCGAGCCGTCAGCGGCGATTGCACAGAAAATCCAGCAACGCGCGCTGGCGCAGGGGCTGCTCCTGCTGACCT<br>GTGGCGCATACGGCAACGTGATTCGCTTCCTGTATCCGCTGACCATCCCGGATGCGCAATTCGATGCGGCAATGAAAA<br>TTTTGCAGGATGCGCTGAGCGATTAA |

TABLE 2-continued

| Nucleic Acid Sequences: Genes | |
|---|---|
| SEQ ID NO | Nucleic Acid Sequence |
| SEQ ID NO: 107<br>nucleic acid<br>coding sequence<br>of the gene sbm at<br>locus b2917 | ATGTCTAACGTGCAGGAGTGGCAACAGCTTGCCAACAAGGAATTGAGCCGTCGGGAGAAAACTGTCGACTCGCTGGT<br>TCATCAAACCGCGGAAGGGATCGCCATCAAGCCGCTGTATACCGAAGCCGATCTCGATAATCTGGAGGTGACAGGTA<br>CCCTTCCTGGTTTGCCGCCCTACGTTCGTGGCCCGCGTGCCACTATGTATACCGCCCAACCGTGGACCATCCGTCAGTA<br>TGCTGGTTTTTCAACAGCAAAAGAGTCCAACGCTTTTTATCGCCGTAACCTGGCCGCCGGGCAAAAAGGTCTTTCCGT<br>TGCGTTTGACCTTGCCACCCACCGTGGCTACGACTCCGATAACCCGCGCGTGGCGGGCGACGTCGGCAAAGCGGGCG<br>TCGCTATCGACACCGTGGAAGATATGAAAGTCCTGTTCGACCAGATCCCGCTGGATAAAATGTCGGTTTCGATGACCA<br>TGAATGGCGCAGTGCTACCAGTACTGGCGTTTTATATCGTCGCCGCAGAAGAGCAAGGTGTTACACCTGATAAACTGA<br>CCGGCACCATTCAAAACGATATTCTCAAAGAGTACCTCTGCCGCAACACCTATATTTACCCACCAAAACCGTCAATGC<br>GCATTATCGCCGACATCATCGCCTGGTGTTCCGGCAACATGCCGCGATTTAATACCATCAGTATCAGCGGTTACCACA<br>TGGGTGAAGCGGGTGCCAACTGCGTGCAGCAGGTAGCATTTACGCTCGCTGATGGGATTGAGTACATCAAAGCAGCA<br>ATCTCTGCCGGACTGAAAATTGATGACTTCGCTCCTCGCCTGTCGTTCTTCTTCGGCATCGGCATGGATCTGTTTATGA<br>ACGTCGCCATGTTGCGTGCGGCACGTTATTTATGGAGCGAAGCGGTCAGTGGATTTGGCGCACAGGACCCGAAATCA<br>CTGGCGCTGCGTACCCACTGCCAGACCTCAGGCTGGAGCCTGACTGAACAGGATCCGTATAACAACGTTATCCGCACC<br>ACCATTGAAGCGCTGGCTGCGACGCTGGGCGGTACTCAGTCACTGCATACCAACGCCTTTGACGAAGCGCTTGGTTTG<br>CCTACCGATTTCTCAGCACGCATTGCCCGCAACACCCAGATCATCATCCAGGAAGAATCAGAACTCTGCCGCACCGTC<br>GATCCACTGGCCGGATCCTATTACATTGAGTCGCTGACCGATCAAATCGTCAAACAAGCCAGAGCTATTATCCAACAG<br>ATCGACGAAGCCGGTGGCATGGCGAAAGCGATCGAAGCAGGTCTGCCAAAACGAATGATCGAAGAGGCCTCAGCGC<br>GCGAACAGTCGCTGATCGACCAGGGCAAGCGTGTCATCGTTGGTGTCAACAAGTACAAACTGGATCACGAAGACGAA<br>ACCGATGTACTTGAGATCGACAACGTGATGGTGCGTAACGAGCAAATTGCTTCGCTGGAACGCATTCGCGCCACCCGT<br>GATGATGCCGCCGTAACCGCCGCGTTGAACGCCCTGACTCACGCCGCACAGCATAACGAAAACCTGCTGGCTGCCGC<br>TGTTAATGCCGCTCGCGTTCGCGCCACCCTGGGTGAAATTTCCGATGCGCTGGAAGTCGCTTTCGACCGTTATCTGGTG<br>CCAAGCCAGTGTGTTACCGGCGTGATTGCGCAAAGCTATCATCAGTCTGAGAAATCGGCCTCCGAGTTCGATGCCATT<br>GTTGCGCAAACGGAGCAGTTCCTTGCCGACAATGGTCGTCGCCCGCGCATTCTGATCGCTAAGATGGGCCAGGATGG<br>ACACGATCGCGGCGCGAAAGTGATCGCCAGCGCCTATTCCGATCTCGGTTTCGACGTAGATTTAAGCCCGATGTTCTC<br>TACACCTGAAGAGATCGCCCGCCTGGCCGTAGAAAACGACGTTCACGTAGTGGGCGCATCCTCACTGGCTGCCGGTC<br>ATAAAACGCTGATCCCGGAACTGGTCGAAGCGCTGAAAAAATGGGGACGCGAAGATATCTGCGTGGTCGCGGGTGGC<br>GTCATTCCGCCGCAGGATTACGCCTTCCTGCAAGAGCGCGGCGTGGCGGCGATTTATGGTCCAGGTACACCTATGCTC<br>GACAGTGTGCGCGACGTACTGAATCTGATAAGCCAGCATCATGATTAA |
| SEQ ID NO: 108<br>nucleic acid<br>coding sequence<br>of the gene sdhA<br>at locus b0723 | ATGAAATTGCCAGTCAGAGAATTTGATGCAGTTGTGATTGGTGCCGGTGGCGCAGGTATGCGCGCGGCGCTGCAAATT<br>TCCCAGAGCGGCCAGACCTGTGCGCTGCTCTCTAAAGTCTTCCCGACCCGTTCCCATACCGTTTCTGCGCAAGGCGGC<br>ATTACCGTTGCGCTGGGTAATACCCATGAAGATAACTGGGAATGGCATATGTACGACACCGTGAAAGGGTCGGACTA<br>TATCGGTGACCAGGACGCGATTGAATATATGTGTAAAACCGGGCCGGAAGCGATTCTGGAACTCGAACACATGGGCC<br>TGCCGTTCTCGCGTCTCGATGATGGTCGTATCTATCAACGTCCGTTTGGCGGTCAGTCGAAAAACTTCGGCGGCGAGC<br>AGGCGGCACGCACTGCGGCAGCAGCTGACCGTACCGGTCACGCACTGTTGCACACGCTTTATCAGCAGAACCTGAAA<br>AACCACACCACCATTTTCTCCGAGTGGTATGCGCTGGATCTGGTGAAAAACCAGGATGGCGCGGTGGTGGGTTGTACC<br>GCACTGTGCATCGAAACCGGTGAAGTGGTTTATTTCAAAGCCCGCGCTACCGTGCTGGCGACTGGCGGAGCAGGGCG<br>TATTTATCAGTCCACCACCAACGCCCACATTAACACCGGCGACGGTGTCGGCATGGCTATCCGTGCCGGCGTACCGGT<br>GCAGGATATGGAAATGTGGCAGTTCCACCCGACCGGCATTGCCGGTGCGGGCGTACTGGTCACCGAAGGTTGCCGTG<br>GTGAAGGCGGTTATCTGCTGAACAAACATGGCGAACGTTTTATGGAGCGTTATGCGCCGAACGCCAAAGACCTGGCG<br>GGCCGTGACGTGGTTGCGCGTTCCATCATGATCGAAATCCGTGAAGGTCGCGGCTGTGATGGTCCGTGGGGGCCACAC<br>GCGAAACTGAAACTCGATCACCTGGGTAAAGAAGTTCTCGAATCCCGTCTGCCGGGTATCCTGGAGCTTTCCCGTACC<br>TTCGCTCACGTCGATCCGGTGAAAGAGCCGATTCCGGTTATCCCAACCTGTCACTACATGATGGGCGGTATTCCGACC<br>AAAGTTACCGGTCAGGCACTGACTGTGAATGAGAAAGGCGAAGATGTGGTTGTTCCGGGACTGTTTGCCGTTGGTGA<br>AATCGCTTGTGTATCGGTACACGGCGCTAACCGTCTGGGCGGCAACTCGCTGCTGGACCTGGTGGTCTTTGGTCGCGC<br>GGCAGGTCTGCATCTGCAAGAGTCTATCGCCGAGCAGGGCGCACTGCGCGATGCCAGCGAGTCTGATGTTGAAGCGT<br>CTCTGGATCGCCTGAACCGCTGGAACAATAATCGTAACGGTGAAGATCCGGTGGCGATCCGTAAAGCGCTGCAAGAA<br>TGTATGCAGCATAACTTCTCGGTCTTCCGTGAAGGTGATGCGATGGCGAAAGGGCTTGAGCAGTTGAAAGTGATCCGC<br>GAGCGTCTGAAAAATGCCCGTCTGGATGACACTTCCAGCGAGTTCAACACCCAGCGCGTTGAGTGCCTGGAACTGGA<br>TAACCTGATGGAAACGGCGTATGCAACGGCTGTTTCTGCCAACTTCCGTACCGAAAGCCGTGGCGCGCATAGCCGCTT<br>CGACTTCCCGGATCGTGATGATGAAAACTGGCTGTGCCACTCCCTGTATCTGCCAGAGTCGGAATCCATGACGCGCCG<br>AAGCGTCAACATGGAACCGAAACTGCGCCCGGCATTCCCGCCGAAGATTCGTACTTACTAA |
| SEQ ID NO: 109<br>nucleic acid<br>coding sequence<br>of the gene sucC<br>at locus b0728 | ATGAACTTACATGAATATCAGGCAAAACAACTTTTTGCCCGCTATGGCTTACCAGCACCGGTGGGTTATGCCTGTACT<br>ACTCCGCGCGAAGCAGAAGAAGCCGCTTCAAAAATCGGTGCCGGTCCGTGGGTAGTGAAATGTCAGGTTCACGCTGG<br>TGGCCGCGGTAAAGCGGGCGGTGTGAAAGTTGTAAACAGCAAAGAAGACATCCGTGCTTTTGCAGAAAACTGGCTGG<br>GCAAGCGTCTGGTAACGTATCAAACAGATGCCAATGGCCAACCGGTTAACCAGATTCTGGTTGAAGCAGCGACCGAT<br>ATCGCTAAAGAGCTGTATCTCGGTGCCGTTGTTGACCGTAGTTCCCGTCGTGTGGTCTTTATGGCCTCCACCGAAGGCG<br>GCGTGGAAATCGAAAAAGTGGCGGAAGAAACTCCGCACCTGATCCATAAAGTTGCGCTTGATCCGCTGACTGGCCCG<br>ATGCCGTATCAGGGACGCGAGCTGGCGTTCAAACTGGGTCTGGAAGGTAAACTGGTTCAGCAGTTCACCAAAATCTTC<br>ATGGGCCTGGCGACCATTTTCCTGGAGCGCGACCTGGCGTTGATCGAAATCAACCCGCTGGTCATCACCAAACAGGGC<br>GATCTGATTTGCCTCGACGGCAAACTGGGCGCTGACGGCAACGCACTGTTCCGCCAGCCTGATCTGCGCGAAATGCGT<br>GACCAGTCGCAGGAAGATCCGCGTGAAGCACAGGCTGCACAGTGGGAACTGAACTACGTTGCGCTGGACGGTAACAT<br>CGGTTGTATGGTTAACGGCGCAGGTCTGGCGATGGGTACGATGGACATCGTTAAACTGCACGGCGGCGAACCGGCTA<br>ACTTCCTTGACGTTGGCGGCGGCGCAACCAAAGAACGTGTAACCGAAGCGTTCAAAATCATCCTCTCTGACGACAAA<br>GTGAAAGCCGTTCTGGTTAACATCTTCGGCGGTATCGTTCGTTGCGACCTGATCGCTGACGGTATCATCGGCGCGGTA<br>GCAGAAGTGGGTGTTAACGTACCGGTCGTGGTACGTCTGGAAGGTAACAACGCCGAACTCGGCGCGAAGAAACTGGC<br>TGACAGCGGCCTGAATATTATTGCAGCAAAAGGTCTGACGGATGCAGCTCAGCAGGTTGTTGCCGCAGTGGAGGGGA<br>AATAA |
| SEQ ID NO: 110<br>nucleic acid<br>coding sequence<br>of the gene sucD<br>at locus b0729 | ATGTCCATTTTAATCGATAAAAACACCAAGGTTATCTGCCAGGGCTTTACCGGTAGCCAGGGGACTTTCCACTCAGAA<br>CAGGCCATTGCATACGGCACTAAAATGGTTGGCGGCGTAACCCCAGGTAAAGGCGGCACCACCCACCTCGGCCTGCC<br>GGTGTTCAACACCGTGCGTGAAGCCGTTGCTGCCACTGGCGCTACCGCTTCTGTTATCTACGTACCAGCACCGTTCTGC<br>AAAGACTCCATTCTGGAAGCCATCGACGCAGGCATCAAACTGATTATCACCATCACTGAAGGCATCCCGACGCTGGA<br>TATGCTGACCGTGAAAGTGAAGCTGGATGAAGCAGGCGTTCGTATGATCGGCCCGAACTGCCCAGGCGTTATCACTCC |

TABLE 2-continued

| Nucleic Acid Sequences: Genes | |
|---|---|
| SEQ ID NO | Nucleic Acid Sequence |
| | GGGTGAATGCAAAATCGGTATCCAGCCTGGTCACATTCACAAACCGGGTAAAGTGGGTATCGTTTCCCGTTCCGGTAC ACTGACCTATGAAGCGGTTAAACAGACCACGGATTACGGTTTCGGTCAGTCGACCTGTGTCGGTATCGGCGGTGACCC GATCCCGGGCTCTAACTTTATCGACATTCTCGAAATGTTCGAAAAAGATCCGCAGACCGAAGCGATCGTGATGATCGG TGAGATCGGCGGTAGCGCTGAAGAAGCAGCTGCGTACATCAAAGAGCACGTTACCAAGCCAGTTGTGGGTTACA TCGCTGGTGTGACTGCGCCGAAAGGCAAACGTATGGGCCACGCGGGTGCCATCATTGCCGGTGGGAAAGGGACTGCG GATGAGAAATTCGCTGCTCTGGAAGCCGCAGGCGTGAAAACCGTTCGCAGCCTGGCGGATATCGGTGAAGCACTGAA AACTGTTCTGAAATAA |
| SEQ ID NO: 111 nucleic acid coding sequence of the gene tesB at locus b0452 | ATGAGTCAGGCGCTAAAAAATTTACTGACATTGTTAAATCTGGAAAAAATTGAGGAAGGACTCTTTCGCGGCCAGAG TGAAGATTTAGGTTTACGCCAGGTGTTTGGCGGCCAGGTCGTGGGTCAGGCCTTGTATGCTGCAAAAGAGACCGTCCC TGAAGAGCGGCTGGTACATTCGTTTCACAGCTACTTTCTTCGCCCTGGCGATAGTAAGAAGCCGATTATTTATGATGTC GAAACGCTGCGTGACGGTAACAGCTTCAGCGCCCGCCGGGTTGCTGCTATTCAAAACGGCAAACCGATTTTTTATATG ACTGCCTCTTTCCAGGCACCAGAAGCGGGTTTCGAACATCAAAAAACAATGCCGTCCGCGCCAGCGCCTGATGGCCTC CCTTCGGAAACGCAAATCGCCCAATCGCTGGCGCACCTGCTGCCGCCAGTGCTGAAAGATAAATTCATCTGCGATCGT CCGCTGGAAGTCCGTCCGGTGGAGTTTCATAACCCACTGAAAGGTCACGTCGCAGAACCACATCGTCAGGTGTGGATC CGCGCAAATGGTAGCGTGCCGGATGACCTGCGCGTTCATCAGTATCTGCTCGGTTACGCTTCTGATCTTAACTTCCTGC CGGTAGCTCTACAGCCGCACGGCATCGGTTTTCTCGAACCGGGGATTCAGATTGCCACCATTGACCATTCCATGTGGT TCCATCGCCCGTTTAATTTGAATGAATGGCTGCTGTATAGCGTGGAGAGCACCTCGGCGTCCAGCGCACGTGGCTTTG TGCGCGGTGAGTTTTATACCCAAGACGGCGTACTGGTTGCCTCGACCGTTCAGGAAGGGGTGATGCGTAATCACAATT AA |
| SEQ ID NO: 112 nucleic acid coding sequence of the gene ybgC at locus b0736 | GTGAATACAACGCTGTTTCGATGGCCGGTTCGCGTCTACTATGAAGATACCGATGCCGGTGGTGTGGTGTACCACGCC AGTTACGTCGCTTTTTATGAAAGAGCACGCACAGAGATGCTGCGTCATCATCACTTCAGTCAGCAGGCGCTGATGGCT GAACGCGTTGCCTTTGTGGTACGTAAAATGACGGTGGAATATTACGCACCTGCGCGGCTCGACGATATGCTCGAAATA CAGACTGAAATAACATCAATGCGTGGCACCTCTTTGGTTTTCACGCAACGTATTGTCAACGCCGAGAATACTTTGCTG AATGAAGCAGAGGTTCTGGTTGTTTGCGTTGACCCACTCAAAATGAAGCCTCGTGCGCTTCCCAAGTCTATTGTCGCG GAGTTTAAGCAGTGA |
| SEQ ID NO: 113 nucleic acid coding sequence of the gene yciA at locus b1253 | ATGTCTACAACACATAACGTCCCTCAGGGCGATCTTGTTTTACGTACTTTAGCCATGCCCGCCGATACCAATGCCAAT GGTGACATCTTTGGTGGTTGGTTAATGTCACAAATGGATATTGGCGGCGCTATTCTGGCAAAAGAAATTGCCCACGGT CGCGTAGTGACTGTGCGGGTTGAAGGAATGACTTTCTTACGGCCGGTTGCGGTCGGCGATGTGGTGTGCTGCTATGCA CGCTGTGTCCAGAAAGGGACGACATCGGTCAGCATTAATATTGAAGTGTGGGTGAAAAAAGTAGCGTCTGAACCAAT TGGGCAACGCTATAAAGCGACAGAAGCATTATTTAAGTATGTCGCGGTTGATCCTGAAGGAAAACCTCGCGCCTTACC TGTTGAGTAA |
| SEQ ID NO: 114 nucleic acid coding sequence of the gene ygfD at locus b2918 | ATGATTAATGAAGCCACGCTGGCAGAAAGTATTCGCCGCTTACGTCAGGGTGAGCGTGCCACACTCGCCCAGGCCAT GACGCTGGTGGAAAGCCGTCACCCGCGTCATCAGGCACTAAGTACGCAGCTGCTTGATGCCATTATGCCGTACTGCGG TAACACCCTGCGACTGGGCGTTACCGGCACCCCCGGCGCGGGGAAAAGTACCTTTCTTGAGGCCTTTGGCATGTTGTT GATTCGAGAGGGATTAAAGGTCGCGGTTATTGCGGTCGATCCCAGCAGCCCGGTCACTGGCGGTAGCATTCTCGGGG ATAAAACCCGCATGAATGACCTGGCGCGTGCCGAAGCGGCGTTTATTCGCCCGGTACCATCCTCCGGTCATCTGGGCG GTGCCAGTCAGCGAGCGCGGGAATTAATGCTGTTATGCGAAGCAGCGGGTTATGACGTAGTGATTGTCGAAACGGTT GGCGTCGGGCAGTCGGAAACAGAAGTCGCCCGCATGGTGGACTGTTTTATCTCGTTGCAAATTGCCGGTGGCGGCGAT GATCTGCAGGGCATTAAAAAAGGGCTGATGGAAGTGGCTGATCTGATCGTTATCAACAAAGACGATGGCGATAACCA TACCAATGTCGCCATTGCCCGGCATATGTACGAGAGTGCCCTGCATATTCTGCGACGTAAATACGACGAATGGCAGCC ACGGGTTCTGACTTGTAGCGCACTGGAAAAACGTGGAATCGATGAGATCTGGCACGCCATCATCGACTTCAAAACCG CGCTAACTGCCAGTGGTCGTTTACAACAAGTGCGGCAACAACAATCGGTGGAATGGCTGCGTAAGCAGACCGAAGAA GAAGTACTGAATCACCTGTTCGCGAATGAAGATTTCGATCGCTATTACCGCCAGACGCTTTTAGCGGTCAAAAACAAT ACGCTCTCACCGCGCACCGGCCTGCGGCAGCTCAGTGAATTTATCCAGACGCAATATTTTGATTAA |
| SEQ ID NO: 115 nucleic acid coding sequence of the gene ygfG at locus b2919 | ATGTCTTATCAGTATGTTAACGTTGTCACTATCAACAAAGTGGCGGTCATTGAGTTTAACTATGGCCGAAAACTTAAT GCCTTAAGTAAAGTCTTTATTGATGATCTTATGCAGGCGTTAAGCGATCTCAACCGGCCGGAAATTCGCTGTATCATTT TGCGCGCACCGAGTGGATCCAAAGTCTTCTCCGCAGGTCACGATATTCACGAACTGCCGTCTGGCGGTCGCGATCCGC TCTCCTATGATGATCCATTGCGTCAAATCACCCGCATGATCCAAAAATTCCCGAAACCGATCATTTCGATGGTGGAAG GTAGTGTTTGGGGTGGCGCATTTGAAATGATCATGAGTTCCGATCTGATCATCGCCGCCAGTACCTCAACCTTCTCAAT GACGCCTGTAAACCTCGGCGTCCCGTATAACCTGGTCGGCATTCACAACCTGACCCGCGACGCGGGCTTCCACATTGT CAAAGAGCTGATTTTTACCGCTTCGCCAATCACCGCCCAGCGCGCGCTGGCTGTCGGCATCCTCAACCATGTTGTGGA AGTGGAAGAACTGGAAGATTTCACCTTACAAATGGCGCACCACATCTCTGAGAAAGCGCCGTTAGCCATTGCCGTTAT CAAAGAAGAGCTGCGTGTACTGGGCGAAGCACACACCATGAACTCCGATGAATTTGAACGTATTCAGGGGATGCGCC GCGCGGTGTATGACAGCGAAGATTACCAGGAAGGGATGAACGCTTTCCTCGAAAAACGTAAACCTAATTTCGTTGGT CATTAA |
| SEQ ID NO: 116 nucleic acid coding sequence of the gene ygfH at locus b2920 | ATGGAAACTCAGTGGACAAGGATGACCGCCAATGAAGCGGCAGAAATTATCCAGCATAACGACATGGTGGCATTTAG CGGCTTTACCCCGGCGGGTTCGCCGAAAGCCCTACCCACCGCGATTGCCCGCAGAGCTAACGAACAGCATGAGGCCA AAAAGCCGTATCAAATTCGCCTTCTGACGGGTGCGTCAATCAGCGCCGCCGCTGACGATGTACTTTCTGACGCCGATG CTGTTTCCTGGCGTGCGCCATATCAAACATCGTCCGGTTTACGTAAAAAGATCAATCAGGGCGCGGTGAGTTTCGTTG ACCTGCATTTGAGCGAAGTGGCGCAAATGGTCAATTACGGTTTCTTCGGCGACATTGATGTTGCCGTCATTGAAGCAT CGGCACTGGCACCGGATGGTCGAGTCTGGTTAACCAGCGGGATCGGTAATGCGCCGACCTGGCTGCTGCGGGCGAAG AAAGTGATCATTGAACTCAATCACTATCACGATCCGCGCGTTGCAGAACTGGCGGATATTGTGATTCCTGGCGCGCCA CCGCGGCGCAATAGCGTGTCGATCTTCCATGCAATGGATCGCGTCGGTACCCGCTATGTGCAAATCGATCCGAAAAAG ATTGTCGCCGTCGTGGAAACCAACTTGCCCGACGCCGGTAATATGCTGGATAAGCAAAATCCCATGTGCCAGCAGATT GCCGATAACGTGGTCACGTTCTTATTGCAGGAAATGGCGCATGGGCGTATTCCGCCGGAATTTCTGCCGCTGCAAAGT GGCGTGGGCAATATCAATAATGCGGTAATGGCGCGTCTGGGGGAAAACCCGGTAATTCCTCCGTTTATGATGTATTCG GAAGTGCTACAGGAATCGGTGGTGCATTTACTGGAAACCGGCAAAATCAGCGGGGCCAGCGCCTCCAGCCTGACAAT CTCGGCCGATTCCCTGCGCAAGATTTACGACAATATGGATTACTTTGCCAGCCGCATTGTGTTGCGTCCGCAGGAGAT TTCCAATAACCCGGAAATCATCCGTCGTCTGGGCGTCATCGCTCTGAACGTCGGCCTGGAGTTTGATATTTACGGGCA TGCCAACTCAACACACGTAGCCGGGGTCGATCTGATGAACGGCATCGGCGGCAGCGGTGATTTTGAACGCAACGCGT |

TABLE 2-continued

| Nucleic Acid Sequences: Genes | |
|---|---|
| SEQ ID NO | Nucleic Acid Sequence |
| | ATCTGTCGATCTTTATGGCCCCGTCGATTGCTAAAGAAGGCAAGATCTCAACCGTCGTGCCAATGTGCAGCCATGTTG<br>ATCACAGCGAACACAGCGTCAAAGTGATCATCACCGAACAAGGGATCGCCGATCTGCGCGGTCTTTCCCCGCTTCAAC<br>GCGCCCGCACTATCATTGATAATTGTGCACATCCTATGTATCGGGATTATCTGCATCGCTATCTGGAAAATGCGCCTG<br>GCGGACATATTCACCACGATCTTAGCCACGTCTTCGACTTACACCGTAATTTAATTGCAACCGGCTCGATGCTGGGTT<br>AA |
| SEQ ID NO: 117<br>nucleic acid<br>coding sequence<br>of the gene yigI at<br>locus b3820 | ATGTCTGCCGTACTGACCGCTGAACAAGCCCTGAAATTAGTGGGTGAGATGTTTGTTTATCACATGCCATTTAACCGC<br>GCATTGGGGATGGAACTGGAGCGTTACGAAAAAGAGTTCGCACAGCTGGCCTTTAAAAATCAGCCAATGATGGTGGG<br>CAACTGGGCGCAAAGCATTTTGCACGGCGGGGTCATTGCGTCGGCGCTGGATGTCGCCGCCGGTCTGGTGTGCGTGGG<br>AAGTACCTTAACCCGCCACGAAACCATCAGTGAAGATGAACTACGCCAGCGGCTATCGCGGATGGGGACCATTGATC<br>TTCGCGTTGATTATCTGCGCCCAGGCAGGGGCGAGCGTTTTACTGCTACTAGTAGCCTGTTGCGTGCAGGCAATAAAG<br>TCGCCGTCGCCCGCGTTGAATTACACAATGAAGAACAGCTTTATATTGCCAGTGCCACCGCCACCTATATGGTAGGTT<br>GA |
| SEQ ID NO: 118<br>nucleic acid<br>coding sequence<br>of the gene yjcS at<br>locus b4083 | ATGAATAACTCTCGGTTATTCCGTTTGAGCAGGATTGTTATTGCGTTAACTGCCGCCAGCGGCATGATGGTAAATACC<br>GCTAACGCGAAAGAGGAAGCGAAAGCCGCCACTCAATATACCCAACAGGTTAATCAGAATTACGCCAAATCATTACC<br>GTTTAGCGATCGTCAGGATTTTGACGATGCCCAGCGTGGATTTATCGCCCCGCTGCTGGATGAAGGTATTCTGCGTGA<br>TGCGAACGGTAAAGTTTACTACCGCGCGGACGATTACAAATTTGATATTAATGCCGCAGCGCCGGAAACCGTAAACC<br>CCAGCCTGTGGCGTCAGTCGCAAATCAACGGTATTTCTGGCCTGTTCAAAGTCACCGATAAAATGTATCAGGTGCGCG<br>GCCAGGATATCTCTAACATTACGTTCGTTGAGGGCGAGAAAGGCATTATTGTTATCGACCCGCTGGTGACGCCGCCTG<br>CCGCAAAAGCCGCACTTGACCTTTACTTCCAGCATCGTCCGCAAAAACCGATTGTTGCCGTTATCTACACTCACAGCC<br>ACACCGACCACTATGGTGGCGTGAAAGGCATTATCTCTGAAGCCGATGTTAAATCCGGCAAAGTTCAGGTGATTGCCC<br>CTGCAGGCTTTATGGACGAAGCCATCAGCGAAAACGTGCTGGCGGGTAACATCATGAGCCGCCGTGCGCTCTACTCTT<br>ACGGTCTGTTACTGCCGCACAACGCGCAAGGCAATGTGGGTAATGGCCTTGGCGTGACGCTGGCAACGGGCGACCCG<br>AGCATTATTGCACCGACGAAAACTATCGTCAGAACTGGCGAGAAGATGATTATCGACGGCCTGGAGTTTGACTTCCTG<br>ATGACCCCAGGTAGCGAAGCGCCAGCCGAAATGCACTTCTATATTCCGGCCCTGAAAGCCCTGTGTACCGCCGAGAA<br>CGCCACGCATACCCTGCACAACTTCTACACTCTGCGCGGCGCGAAAACCCGCGACACCAGCAAGTGGACCGAGTATC<br>TGAACGAAACGCTGGATATGTGGGGTAACGACGCGGAAGTGCTGTTTATGCCGCACACCTGGCCGGTCTGGGGCAAT<br>AAGCATATCAATGATTATATTGGTAAATACCGCGATACCATCAAGTACATTCACGACCAGACCCTGCACCTGGCGAAC<br>CAGGGCTACACCATGAATGAAATCGGCGACATGATTAAGCTGCCGCCTGCACTTGCCAATAACTGGGCCAGCCGCGG<br>CTATTACGGTTCTGTCAGCCACAACGCCCGCGCGGTGTATAACTTCTATCTTGGCTATTACGACGGTAACCCGGCTAA<br>CCTGCATCCGTATGGTCAGGTGGAGATGGGTAAACGTTACGTGCAGGCGCTGGGCGGTTCTGCCCGTGTCATCAACCT<br>GGCGCAAGAAGCGAACAAGCAAGGTGATTACCGCTGGTCGGCAGAACTGCTGAAACAGGTGATTGCCGCCAACCCG<br>GGTGACCAGGTCGCGAAGAATCTGCAAGCGAATAACTTTGAACAGCTGGGCTATCAGGCCGAGTCCGCCACATGGCG<br>CGGTTTCTACCTGACCGGCGCGAAAGAGCTGCGCGAAGGGGTGCATAAGTTCAGCCACGGCACCACCGGTTCCCCGG<br>ACACCATTCGCGGGATGTCGGTCGAAATGCTGTTCGACTTTATGGCCGTTCGCCTCGATAGCGCGAAAGCTGCGGGTA<br>AAAATATCAGCCTGAACTTCAATATGAGCAACGGCGATAACCTCAACCTGACGCTGAACGATAGCGTGCTTAACTAC<br>CGGAAAACGCTGCAACCGCAAGCCGACGCCTCTTTCTACATCAGCCGTGAAGATCTGCACGCCGTGCTGACCGGACA<br>AGCCAAAATGGCGGATCTGGTAAAAGCGAAGAAAGCCAAAATTATTGGCAATGGCGCGAAACTGGAAGAAATTATC<br>GCCTGTCTGGATAATTTCGATTTGTGGGTGAATATCGTAACCCCAAATTAA |
| SEQ ID NO: 174<br>nucleic acid<br>coding sequence<br>of the gene<br>MELS_RS00170 | ATGGTTGAACGGAAAGGAAGAGCTTTGATTGCCTGGCGTTGTGCCCAATTCTTCAAAAATGGGGACTTCGTCAACTTA<br>GGGATCGGCCTGCCCCTGATGTGCGTCAACTATCTGCCCGAAGGCGTATCCCTCTGGCTGGAAGCTGAAATCGGCACC<br>GTTGGCAGCGGCCCGTCGCCGGACTGGAATCATGTCGATATCGACGTCATCGATGCTGGCGGCCAGCCGGCTTCGGTC<br>ATTACCGGCGGCAGTGTCTACGACCACGAAACGTCCTTCGCTTTCATCCGCGGTGGCCATATTGACGCGACTGTCTTG<br>GGGACGCTGCAAGTCGACCAGGAAGGGAATATCGCCAACTGGACCATCCCCGGGAAATTCGTGCCCGGTATGGGCGG<br>GGCCATGGACCTCTGTGCCGGTGTCAAGAAGATCATCGTCGCCACGGACCATTGCGAAAAGAGCGGCCATTCCAAGA<br>TACTGAAGAAATGCACGCTGCCCCTGACGGGAGCCCGTTGCGTGACCGACATCGTAACCGAACGCTGCTACTTTGAA<br>GTCACGCCGCAAGGCCTGGTCCTGCGGGAACTGGCCCCGGGCTATACCGTAGAAGATATCCGGGCCTGCACCGAAGC<br>GGACTTCATCGTCCCCGAAACCATCGCCGTCATGGGCGAGTGA |
| SEQ ID NO: 175<br>nucleic acid<br>coding sequence<br>of the gene<br>MELS_RS00175 | GTGTTATCGAAGGTATTTTCTCTCCAAGATATCCTGGAGCATATCCATGACGGACAGACCATCATGTTCGGTGACTGG<br>CATGGCCAATTCGCGGCTGATGAAATCATCGACGGCATGCTGGAAAAAGGCGTCAAGGATATCAAAGCCATCGCCGT<br>ATCGGCCGGCTATCCCGGCCAGGGCGTAGGCAAGCTGATCGTGGCTCATCGCGTGTCGTCCATCGTTACGACGCATAT<br>CGGCCTCAATCCGGAAGCGCTGAAACAGATGCTGGCCGGTGAACTGGCCGTCGAATTCGTCCCCCAGGGGACCTGGG<br>CCGAACGCGTGCGCTGCGGCGGTGCCGGCCTGGGCGGCGTCCTGACGCCGACCGGTGTCGGTACGAGTGTCGAAGAA<br>GGGAAACAGAAGCTGGTCATCGATGGGAAGGAATATCTCCTGGAATTACCGCTCCATGCCGACGTAGCCCTGGTCAA<br>GGCGACCAAAGCCGATACGGCAGGGAACCTCTATTTCCGCATGAATTCGCGGGCGACGAACAGTACCATCGCTTATG<br>CGGCTGATTTCGTCGCCGCCGAAGTCGAAGAAATCGTCCCCGTCGGCCAGCTCTTGCCGGAAGAAATCGCCATCCCGG<br>CTCCTGTCGTCGACATGGTCTATGAACGGCAGGGCGAAAAACGGTTTATCTGCCCGATGTGGAAAAAGGCCAGGGCC<br>CGTGCCGAAGCCAAGGCGCGGGAACGGCAGGAAAGGGGATGA |
| SEQ ID NO: 185<br>nucleic acid<br>coding sequence<br>of the gene arcA<br>at locus b4401 | ATGCAGACCCCGCACATTCTTATCGTTGAAGACGAGTTGGTAACACGCAACACGTTGAAAAGTATTTTCGAAGCGGA<br>AGGCTATGATGTTTTCGAAGCGACAGATGGCGCGGAAATGCATCAGATCCTCTCTGAATATGACATCAACCTGGTGAT<br>CATGGATATCAATCTGCCGGGTAAGAACGGTCTTCTGTTAGCGCGTGAACTGCGCGAGCAGGCGAATGTTGCGTTGAT<br>GTTCCTGACTGGCCGTGACAACGAAGTCGATAAAATTCTCGGCCTCGAAATCGGTGCAGATGACTACATCACCAAACC<br>GTTCAACCCGCGTGAACTGACGATTCGTGCACGCAACCTACTGTCCCGTACCATGAATCTGGGTACTGTCAGCGAAGA<br>ACGTCGTAGCGTTGAAAGCTACAAGTTCAATGGTTGGGAACTGGACATCAACAGCCGTTCGTTGATCGGCCCTGATGG<br>CGAGCAGTACAAGCTGCCGCGCAGCGAGTTCCGCGCCATGCTTCACTTCTGTGAAAACCCAGGCAAAATTCAGTCCCG<br>TGCTGAACTGCTGAAGAAAATGACCGGCCGTGAGCTGAAACCGCACGACCGTACTGTAGACGTGACGATCCGCCGTA<br>TTCGTAAACATTTCGAATCTACGCCGGATACGCCGGAAATCATCGCCACCATTCACGGTGAAGGTTATCGCTTCTGCG<br>GTGATCTGGAAGATTAA |
| SEQ ID NO: 186<br>nucleic acid<br>coding sequence | ATGATCCCGGAAAAGCGAATTATACGGCGCATTCAGTCTGGCGGTTGTGCTATCCATTGCCAGGATTGCAGCATCAGC<br>CAGCTTTGCATCCCGTTCACACTCAACGAACATGAGCTTGATCAGCTTGATAATATCATTGAGCGGAAGAAGCCTATT<br>CAGAAAGGCCAGACGCTGTTTAAGGCTGGTGATGAACTTAAATCGCTTTATGCCATCCGCTCCGGTACGATTAAAAGT |

TABLE 2-continued

Nucleic Acid Sequences: Genes

| SEQ ID NO | Nucleic Acid Sequence |
| --- | --- |
| of the gene fnr at locus b1334 | TATACCATCACTGAGCAAGGCGACGAGCAAATCACTGGTTTCCATTTAGCAGGCGACCTGGTGGGATTTGACGCCATC<br>GGCAGCGGCCATCACCCGAGCTTCGCGCAGGCGCTGGAAACCTCGATGGTATGTGAAATCCCGTTCGAAACGCTGGA<br>CGATTTGTCCGGTAAAATGCCGAATCTGCGTCAGCAGATGATGCGTCTGATGAGCGGTGAAATCAAAGGCGATCAGG<br>ACATGATCCTGCTGTTGTCGAAGAAAAATGCCGAGGAACGTCTGGCTGCATTCATCTACAACCTGTCCCGTCGTTTTG<br>CCCAACGCGGCTTCTCCCCTCGTGAATTCCGCCTGACGATGACTCGTGGCGATATCGGTAACTATCTGGGCCTGACGG<br>TAGAAACCATCAGCCGTCTGCTGGGTCGCTTCCAGAAAAGCGGCATGCTGGCAGTCAAAGGTAAATACATCACCATC<br>GAAAATAACGATGCGCTGGCCCAGCTTGCTGGTCATACGCGTAACGTTGCCTGA |
| SEQ ID NO: 187 nucleic acid coding sequence of the gene sad at locus b1525 | ATGACCATTACTCCGGCAACTCATGCAATTTCGATAAATCCTGCCACGGGTGAACAACTTTCTGTGCTGCCGTGGGCT<br>GGCGCTGACGATATCGAAAACGCACTTCAGCTGGCGGCAGCAGGCTTTCGCGACTGGCGCGAGACAAATATAGATTA<br>TCGTGCTGAAAAACTGCGTGATATCGGTAAGGCTCTGCGCGCTCGTAGCGAAGAAATGGCGCAAATGATCACCCGCG<br>AAATGGGCAAACCAATCAACCAGGCGCGCGCTGAAGTGGCGAAATCGGCGAATTTGTGTGACTGGTATGCAGAACAT<br>GGTCCGGCAATGCTGAAGGCGGAACCTACGCTGGTGGAAAATCAGCAGGCGGTTATTGAGTATCGACCGTTGGGGAC<br>GATTCTGGCGATTATGCCGTGGAATTTTCCGTTATGGCAGGTGATGCGTGGCGCTGTTCCCATCATTCTTGCAGGTAAC<br>GGCTACTTACTTAAACATGCGCCGAATGTGATGGGCTGTGCACAGCTCATTGCCCAGGTGTTTAAAGATGCGGGTATC<br>CCACAAGGCGTATATGGCTGGCTGAATGCCGACAACGACGGTGTCAGTCAGATGATTAAAGACTCGCGCATTGCTGC<br>TGTCACGGTGACCGGAAGTGTTCGTGCGGGAGCGGCTATTGGCGCACAGGCTGGAGCGGCACTGAAAAAATGCGTAC<br>TGGAACTGGGCGGTTCGGATCCGTTTATTGTGCTTAACGATGCCGATCTGGAACTGGCGGTGAAAGCGGCGGTAGCCG<br>GACGTTATCAGAATACCGGACAGGTATGTGCAGCGGCAAAACGCTTTATTATCGAAGAGGGAATTGCTTCGGCATTTA<br>CCGAACGTTTTGTGGCAGCTGCGGCAGCCTTGAAAATGGGCGATCCCCGTGACGAAGAGAACGCTCTCGGACCAATG<br>GCTCGTTTTGATTTACGTGATGAGCTGCATCATCAGGTGGAGAAAACCCTGGCGCAGGGTGCGCGTTTGTTACTGGGC<br>GGGGAAAAGATGGCTGGGGCAGGTAACTACTATCCGCCAACGGTTCTGGCGAATGTTACCCCAGAAATGACCGCGTT<br>TCGGGAAGAAATGTTTGGCCCCGTTGCGGCAATCACCATTGCGAAAGATGCAGAACATGCACTGGAACTGGCTAATG<br>ATAGTGAGTTCGGCCTTTCAGCGACCATTTTTACCACTGACGAAACACAGGCCAGACAGATGGCGGCACGTCTGGAAT<br>GCGGTGGGGTGTTTATCAATGGTTATTGTGCCAGCGACGCGCGAGTGGCCTTTGGTGGCGTGAAAAAGAGTGGCTTTG<br>GTCGTGAGCTTTCCCATTTCGGCTTACACGAATTCTGTAATATCCAGACGGTGTGGAAAGACCGGATCTGA |
| SEQ ID NO: 188 nucleic acid coding sequence of the gene yqeF at locus b2844 | ATGAAAGACGTTGTGATTGTCGGGGCGTTACGGACACCTATCGGCTGCTTTCGTGGTGCGTTAGCGGGTCATTCCGCC<br>GTGGAACTTGGTAGTCTGGTCGTGAAAGCGTTAATAGAACGTACCGGCGTTCCTGCATATGCGGTGGATGAAGTAATT<br>CTTGGTCAGGTGTTGACTGCAGGGGCAGGGCAGAATCCGGCAAGGCAATCGGCTATTAAAGGTGGTCTGCCTAATAG<br>CGTTTCTGCAATCACTATTAATGACGTTTGCGGTTCCGGGCTTAAAGCACTGCATCTGGCTACTCAGGCGATACAGTGT<br>GGCGAGGCTGATATTGTCATCGCCGGTGGCCAGGAAAACATGAGCCGCGCACCACATGTTCTGACTGATAGCCGCAC<br>CGGTGCACAGCTTGGCAATAGCCAGTTGGTTGACAGTCTTGTGCATGATGGGTTGTGGGATGCCTTCAATGATTATCA<br>TATTGGTGTCACCGCCGAAAATCTGGCTCGCGAATATGGCATCAGCCGTCAGTTGCAGGATGCTTACGCACTTAGCTC<br>GCAACAAAAAGCGCGAGCGGCGATTGACGCCGGACGATTTAAAGATGAGATCGTCCCGGTAATGACCCAAAGTAAC<br>GGGCAGACGTTGGTTGTTGATACCGATGAACAGCCACGCACTGACGCCAGCGCAGAAGGCTTAGCCCGTTTAAATCC<br>TTCATTTGATAGTCTCGGTTCTGTGACAGCGGGTAATGCATCATCCATAAACGATGGCGCAGCTGCGGTAATGATGAT<br>GAGCGAAGCCAAAGCACGAGCGTTGAATTTACCCGTGCTGGCCCGCATTCGCGCATTTGCCAGCGTTGGTGTAGATCC<br>GGCATTGATGGGAATTGCGCCGGTGTATGCGACCCGCCGTTGCCTGGAGCGTGTAGGCTGGCAGTTGGCTGAAGTCG<br>ATCTTATCGAGGCTAATGAAGCGTTTGCTGCACAGGCGCTTTCGGTTGGCAAGATGCTTGAGTGGGATGAGCGTCGGG<br>TCAATGTCAATGGTGGCGCGATCGCACTCGGTCACCCGATAGGCGCTTCCGGTTGCCGAATCCTGGTTTCTCTGGTTCA<br>TGAAATGGTGAAACGTAATGCCCGCAAAGGACTGGCAACGCTTTGTATCGGCGGGGGCCAGGGTGTGGCATTGACCA<br>TTGAACGTGACGAATAG |
| SEQ ID NO: 189 nucleic acid coding sequence of the gene fadA at locus b3845 | ATGGAACAGGTTGTCATTGTCGATGCAATTCGCACCCCGATGGGCCGTTCGAAGGGCGGTGCTTTTCGTAACGTGCGT<br>GCAGAAGATCTCTCCGCTCATTTAATGCGTAGCCTGCTGGCGCGTAACCCGGCGCTGGAAGCGGCGGCCCTCGACGAT<br>ATTTACTGGGGTTGTGTGCAGCAGACGCTGGAGCAGGGTTTTAATATCGCCCGTAACGCGGCGCTGCTGGCAGAAGTA<br>CCACACTCTGTCCCGGCGGTTACCGTTAATCGCTTGTGTGGTTCATCCATGCAGGCACTGCATGACGCAGCACGAATG<br>ATCATGACTGGCGATGCGCAGGCATGTCTGGTTGGCGGCGTGGAGCATATGGGCCATGTGCCGATGAGTCACGGCGT<br>CGATTTTCACCCCGGCCTGAGCCGCAATGTCGCCAAAGCGGCGGGCATGATGGGCTTAACGGCAGAAATGCTGGCGC<br>GTATGCACGGTATCAGCCGTGAAATGCAGGATGCCTTTGCCGCGCGGTCACACGCCCGCGCCTGGGCCGCCACGCAG<br>TCGGCCGCATTTAAAAATGAAATCATCCCGACCGGTGGTCACGATGCCGACGGCGTCCTGAAGCAGTTTAATTACGAC<br>GAAGTGATTCGCCCGGAAACCACCGTGGAAGCCCTCGCCACGCTGCGTCCGGCGTTTGATCCAGTAAACGGTATGGT<br>AACGGCGGGCACATCTTCTGCACTTTCCGATGGCGCAGCTGCCATGCTGGTGATGAGTGAAAGCCGCGCCCATGAATT<br>AGGTCTTAAGCCGCGCGCTCGTGTGCGTTCGATGGCGGTCGTTGGTTGTGACCCATCGATTATGGGTTACGGCCCGGT<br>TCCGGCCTCGAAACTGGCGCTGAAAAAAGCGGGGCTTTCTGCCAGCGATATCGGCGTGTTTGAAATGAACGAAGCCT<br>TTGCCGCGCAGATCCTGCCATGTATTAAAGATCTGGGACTAATTGAGCAGATTGACGAGAAGATCAACCTCAACGGT<br>GGCGCGATCGCGCTGGGTCATCCGCTGGGTTGTTCCGGTGCGCGTATCAGCACCACGCTGCTGAATCTGATGGAACGC<br>AAAGACGTTCAGTTTGGTCTGGCGACGATGTGTATCGGTCTGGGTCAGGGTATTGCGACGGTGTTTGAGCGGGTTTAA |
| SEQ ID NO: 190 nucleic acid coding sequence of the gene gcl at locus b0507 | ATGGCAAAAATGAGAGCCGTTGACGCGGCAATGTATGTGCTGGAGAAAGAAGGTATCACTACCGCCTTCGGTGTTCC<br>GGGAGCTGCAATCAATCCGTTCTACTCAGCGATGCGTAAGCACGGCGGTATTCGTCACATTCTGGCGCGTCATGTGGA<br>AGGTGCTTCGCACATGGCGGAAGGTTATACCCGCGCAACGGCAGGGAATATCGGCGTATGTCTGGGGACTTCCGGTC<br>CTGCGGGCACGGACATGATCACCGCGCTCTATTCCGCTTCTGCTGATTCCATTCCTATTCTGTGCATTACCGGCCAGGC<br>ACCGCGCGCCCGTCTGCATAAAGAAGATTTTCAGGCCGTAGATATTGAAGCAATTGCTAAACCGGTCAGCAAAATGG<br>CGGTTACAGTTCGTGAAGCGGCGCTGGTGCCTCGCGTGCTGCAACAGGCATTTCACCTGATGCGTTCTGGTCGTCCGG<br>GTCCGGTACTGGTGGATTTACCGTTCGACGTTCAGGTTGCGGAAATCGAGTTTGATCCTGACATGTACGAACCGCTGC<br>CGGTCTACAAACCTGCTGCCAGCCGTATGCAGATCGAAAAAGCTGTAGAAATGTTAATCCAGGCCGAACGTCCGGTG<br>ATTGTTGCCGGGGGCGGGGTAATTAATGCTGACGCAGCTGCACTGTTACAACAGTTTGCTGAACTGACCAGCGTTCCG<br>GTGATCCCAACGCTAATGGGCTGGGGCTGTATCCCGGACGATCATGAACTGATGGCCGGGATGGTGGGTCTGCAAAC<br>CGCGCATCGTTACGGTAACGCAACGCTGCTGGCGTCTGACATGGTGTTTGGTATCGGTAACCGTTTTGCTAACCGTCA<br>TACCGGCTCGGTAGAGAAATACACCGAAGGGCGCAAAATCGTTCATATTGATATTGAGCCGACGCAAATTGGTCGCG<br>TGCTGTGTCCGGATCTCGGTATTGTCTCTGATGCTAAAGCGGCGCTGACACTGCTGGTTGAAGTGGCGCAGGAGATGC<br>AAAAAGCGGGTCGTCTGCCGTGTCGTAAAGAATGGGTCGCCGACTGCCAGCAGCGTAAACGCACTTTGCTGCGCAAA<br>ACCCACTTCGACAACGTGCCGGTGAAACCGCAGCGCGTGTATGAAGAGATGAACAAAGCCTTTGGTCGCGATGTTTG<br>TTATGTCACCACCATTGGTCTGTCACAAATCGCTGCGGCACAAATGCTGCATGTCTTTAAAGACCGCCACTGGATCAA |

TABLE 2-continued

Nucleic Acid Sequences: Genes

| SEQ ID NO | Nucleic Acid Sequence |
|---|---|
| | CTGTGGTCAGGCTGGTCCGTTAGGCTGGACGATTCCGGCTGCGCTAGGGGTTTGTGCCGCTGATCCGAAACGCAATGT<br>GGTGGCGATTTCTGGCGACTTTGACTTCCAGTTCCTGATTGAAGAGTTAGCTGTTGGCGCGCAGTTCAACATTCCGTAC<br>ATCCATGTGCTGGTCAACAACGCTTATCTGGGGCTGATTCGTCAGTCACAACGCGCTTTTGACATGGACTACTGCGTG<br>CAACTCGCTTTCGAGAATATCAACTCCAGTGAAGTGAATGGCTACGGTGTTGACCACGTAAAAGTAGCGGAAGGTTT<br>AGGTTGTAAAGCTATTCGGGTCTTCAAACCGGAAGATATTGCGCCAGCCTTTGAACAGGCGAAAGCCTTAATGGCGC<br>AATATCGGGTACCGGTAGTCGTGGAAGTTATTCTCGAGCGTGTGACCAATATTTCGATGGGCAGCGAACTGGATAACG<br>TCATGGAATTTGAAGATATCGCCGATAACGCAGCGGACGCACCGACTGAAACCTGCTTCATGCACTATGAATAA |
| SEQ ID NO: 191<br>nucleic acid<br>coding sequence<br>of the gene atoB<br>at locus b2224 | ATGAAAAATTGTGTCATCGTCAGTGCGGTACGTACTGCTATCGGTAGTTTTAACGGTTCACTCGCTTCCACCAGCGCC<br>ATCGACCTGGGGGCGACAGTAATTAAAGCCGCCATTGAACGTGCAAAAATCGATTCACAACACGTTGATGAAGTGAT<br>TATGGGTAACGTGTTACAAGCCGGGCTGGGGCAAAATCCGGCGCGTCAGGCACTGTTAAAAAGCGGGCTGGCAGAAA<br>CGGTGTGCGGATTCACGGTCAATAAAGTATGTGGTTCGGGTCTTAAAAGTGTGGCGCTTGCCGCCCAGGCCATTCAGG<br>CAGGTCAGGCGCAGAGCATTGTGGCGGGGGGTATGGAAAATATGAGTTTAGCCCCCTACTTACTCGATGCAAAAGCA<br>CGCTCTGGTTATCGTCTTGGAGACGGACAGGTTTATGACGTAATCCTGCGCGATGGCCTGATGTGCGCCACCCATGGT<br>TATCATATGGGGATTACCGCCGAAAACGTGGCTAAAGAGTACGGAATTACCCGTGAAATGCAGGATGAACTGGCGCT<br>ACATTCACAGCGTAAAGCGGCAGCCGCAATTGAGTCCGGTGCTTTTACAGCCGAAATCGTCCCGGTAAATGTTGTCAC<br>TCGAAAGAAAACCTTCGTCTTCAGTCAAGACGAATTCCCGAAAGCGAATTCAACGGCTGAAGCGTTAGGTGCATTGC<br>GCCCGGCCTTCGATAAAGCAGGAACAGTCACCGCTGGGAACGCGTCTGGTATTAACGACGGTGCTGCCGCTCTGGTG<br>ATTATGGAAGAATCTGCGGCGCTGGCAGCAGGCCTTACCCCCCTGGCTCGCATTAAAAGTTATGCCAGCGGTGGCGTG<br>CCCCCCGCATTGATGGGTATGGGGCCAGTACCTGCCACGCAAAAAGCGTTACAACTGGCGGGGCTGCAACTGGCGGA<br>TATTGATCTCATTGAGGCTAATGAAGCATTTGCTGCACAGTTCCTTGCCGTTGGGAAAAACCTGGGCTTTGATTCTGAG<br>AAAGTGAATGTCAACGGCGGGGCCATCGCGCTCGGGCATCCTATCGGTGCCAGTGGTGCTCGTATTCTGGTCACACTA<br>TTACATGCCATGCAGGCACGCGATAAAACGCTGGGGCTGGCAACACTGTGCATTGGCGGCGGTCAGGGAATTGCGAT<br>GGTGATTGAACGGTTGAATTAA |
| SEQ ID NO: 192<br>nucleic acid<br>coding sequence<br>of the gene tesA<br>at locus b0494 | ATGATGAACTTCAACAATGTTTTCCGCTGGCATTTGCCCTTCCTGTTCCTGGTCCTGTTAACCTTCCGTGCCGCCGCAG<br>CGGACACGTTATTGATTCTGGGTGATAGCCTGAGCGCCGGGTATCGAATGTCTGCCAGCGCGGCCTGGCCTGCCTTGT<br>TGAATGATAAGTGGCAGAGTAAAACGTCGGTAGTTAATGCCAGCATCAGCGGCGACACCTCGCAACAAGGACTGGCG<br>CGCCTTCCGGCTCTGCTGAAACAGCATCAGCCGCGTTGGGTGCTGGTTGAACTGGGCGGCAATGACGGTTTGCGTGGT<br>TTTCAGCCACAGCAAACCGAGCAAACGCTGCGCCAGATTTTGCAGGATGTCAAAGCCGCCAACGCTGAACCATTGTT<br>AATGCAAATACGTCTGCCTGCAAACTATGGTCGCCGTTATAATGAAGCCTTTAGCGCCATTTACCCCAAACTCGCCAA<br>AGAGTTTGATGTTCCGCTGCTGCCCTTTTTTATGGAAGAGGTCTACCTCAAGCCACAATGGATGCAGGATGACGGTAT<br>TCATCCCAACCGCGACGCCCAGCCGTTTATTGCCGACTGGATGGCGAAGCAGTTGCAGCCTTTAGTAAATCATGACTC<br>ATAA |
| SEQ ID NO: 193<br>nucleic acid<br>coding sequence<br>of the gene ald at<br>locus AAT48939 | ATGAATAAAGACACACTAATACCTACAACTAAAGATTTAAAAGTAAAAACAAATGGTGAAAACATTAATTTAAAGAA<br>CTACAAGGATAATTCTTCATGTTTCGGAGTATTCGAAAATGTTGAAAATGCTATAAGCAGCGCTGTACACGCACAAAA<br>GATATTATCCCTTCATTATACAAAAGAGCAAAGAGAAAAAATCATAACTGAGATAAGAAAGGCCGCATTACAAAATA<br>AAGAGGTCTTGGCTACAATGATTCTAGAAGAAACACATATGGGAAGATATGAGGATAAAATATTAAAACATGAATTG<br>GTAGCTAAATATACTCCTGGTACAGAAGATTTAACTACTACTGCTTGGTCAGGTGATAATGGTCTTACAGTTGTAGAA<br>ATGTCTCCATATGGTGTTATAGGTGCAATAACTCCTTCTACGAATCCAACTGAAACTGTAATATGTAATAGCATAGGC<br>ATGATAGCTGCTGGAAATGCTGTAGTATTTAACGGACACCCATGCGCTAAAAAATGTGTTGCCTTTGCTGTTGAAATG<br>ATAAATAAGGCAATTATTTCATGTGGCGGTCCTGAAAATCTAGTAACAACTATAAAAAATCCAACTATGGAGTCTCTA<br>GATGCAATTATTAAGCATCCTTCAATAAAACTTCTTTGCGGAACTGGGGGTCCAGGAATGGTAAAAACCCTCTTAAAT<br>TCTGGTAAGAAAGCTATAGGTGCTGGTGCTGGAAATCCACCAGTTATTGTAGATGATACTGCTGATATAGAAAAGGCT<br>GGTAGGAGCATCATTGAAGGCTGTTCTTTTGATAATAATTTACCTTGTATTGCAGAAAAAGAAGTATTTGTTTTTGAGA<br>ATGTTGCAGATGATTTAATATCTAACATGCTAAAAAATAATGCTGTAATTATAAATGAAGATCAAGTATCAAAATTAA<br>TAGATTTAGTATTACAAAAAAATAATGAAACTCAAGAATACTTTATAAACAAAAAATGGGTAGGAAAAGATGCAAAA<br>TTATTCTTAGATGAAATAGATGTTGAGTCTCCTTCAAATGTTAAATGCATAATCTGCGAAGTAAATGCAAATCATCCA<br>TTTGTTATGACAGAACTCATGATGCCAATATTGCCAATTGTAAGAGTTAAAGATATAGATGAAGCTATTAAATATGCA<br>AAGATAGCAGAACAAAATAGAAAACATAGTGCCTATATTTATTCTAAAAATATAGACAACCTAAATAGATTTGAAAG<br>AGAAATAGATACTACTATTTTTGTAAAGAATGCTAAATCTTTTGCTGGTGTTGGTTATGAAGCAGAAGGATTTACAAC<br>TTTCACTATTGCTGGATCTACTGGTGAGGGAATAACCTCTGCAAGGAATTTTACAAGACAAAGAAGATGTGTACTTGC<br>CGGCTAA |
| SEQ ID NO: 204<br>nucleic acid<br>coding sequence<br>of the gene<br>gadBe(Ec) | ATGGATAAGAAGCAAGTAACGGATTTAAGGTCGGAACTACTCGATTCACGTTTTGGTGCGAAGTCTATTTCCACTATC<br>GCAGAATCAAAACGTTTTCCGCTGCACGAAATGCGCGACGATGTCGCATTCCAGATTATCAATGACGAATTATATCTT<br>GATGGCAACGCTCGTCAGAACCTGGCCACTTTCTGCCAGACCTGGGACGACGAAAATGTCCACAAATTGATGGATTTA<br>TCCATTAACAAAAACTGGATCGACAAAGAACAGTATCCGCAATCCGCAGCCATCGACCTGCGTTGCGTAAATATGGTT<br>GCCGATCTGTGGCATGCGCCTGCGCCGAAAAATGGTCAGGCCGTTGGCACCAACACCATTGGTTCTTCCGAGGCCTGT<br>ATGCTCGGCGGGATGGCGATGAAATGGCGTTGGCGCAAGCGTATGGAAGCTGCAGGCAAACCAACGGATAAACCAA<br>ACCTGGTGTGCGGTCCGGTACAAATCTGCTGGCATAAATTCGCCCGCTACTGGGATGTGGAGCTGCGTGAGATCCCTA<br>TGCGCCCCGGTCAGTTGTTTATGGACCCGAAACGCATGATTGAAGCCTGTGACGAAAACACCATCGGCGTGGTGCCG<br>ACTTTCGGCGTGACCTACACTGGTAACTATGAGTTCCCACAACCGCTGCACGATGCGCTGGATAAATTCCAGGCCGAT<br>ACCGGTATCGACATCGACATGCACATCGACGCTGCCAGCGGTGGCTTCCTGGCACCGTTCGTCGCCCCGGATATCGTC<br>TGGGACTTCCGCCTGCCGCGTGTGAAATCGATCAGTGCTTCAGGCCATAAATTCGGTCTGGCTCCGCTGGGCTGCGGC<br>TGGGTTATCTGGCGTGACGAAGAAGCGCTGCCGCAGGAACTGGTGTTCAACGTTGACTACCTGGGTGGTCAAATTGGT<br>ACTTTTGCCATCAACTTCTCCCGCCCGGCGGGTCAGGTAATTGCACAGTACTATGAATTCCTGCGCCTCGGTCGTGAA<br>GGCTATACCAAAGTACAGAACGCCTCTTACCAGGTTGCCGCTTATCTGGCGGATGAAATCGCCAAACTGGGGCCGTAT<br>GAGTTCATCTGTACGGGTCGCCCGGACGAAGGCATCCCGGCGGTTTGCTTCAAACTGAAAGATGGTGAAGATCCGGG<br>ATACACCCTGTATGACCTCTCTGAACGTCTGCGTCTGCGCGGCTGGCAGGTTCCGGCCTTCACTCTCGGCGGTGAAGC<br>CACCGACATCGTGGTGATGCGCATTATGTGTCGTCGCGGCTTCGAAATGGACTTTGCTGAACTGTTGCTGGAAGACTA<br>CAAAGCCTCCCTGAAATATCTCAGCGATCACTAA |
| SEQ ID NO: 205<br>nucleic acid | ATGGCTATTAGCACACCGATGTTGGTGACATTTTGTGTCTATATCTTTGGCATGATATTGATTGGGTTTATCGCCTGGC<br>GATCAACGAAAAACTTTGACGACTATATTCTGGGCGGTCGTAGTCTTGGGCCATTCGTGACGGCATTATCGGCGGGTG |

TABLE 2-continued

| Nucleic Acid Sequences: Genes | |
|---|---|
| SEQ ID NO | Nucleic Acid Sequence |
| coding sequence<br>of the gene putP<br>at locus b1015 | CGTCGGATATGAGCGGCTGGCTGTTAATGGGGTTGCCGGGCGCTGTTTTTCTTTCCGGGATTTCCGAAAGCTGGATCG<br>CCATTGGCCTGACATTAGGCGCGTGGATTAACTGGAAGCTGGTGGCCGGGCGGTTGCGTGTGCATACCGAATACAAC<br>AATAACGCCTTAACACTGCCGGATTATTTCACCGGGCGCTTTGAAGATAAAAGCCGCATTTTGCGCATTATCTCTGCG<br>CTGGTTATTTTGCTGTTCTTCACCATTTATTGCGCTTCGGGCATTGTGGCAGGCGCGCGTCTGTTTGAAAGTACCTTTG<br>GCATGAGCTACGAAACGGCTCTGTGGGCGGGCGCTGCGGCGACGATCCTTTACACCTTTATTGGCGGTTTCCTCGCGG<br>TGAGCTGGACTGACACTGTACAGGCCAGCCTGATGATTTTTGCCCTGATCCTGACGCCGGTTATCGTCATTATCAGTGT<br>CGGTGGCTTTGGTGACTCGCTGGAAGTGATCAAACAAAAGAGCATCGAAAACGTTGATATGCTCAAAGGTCTGAACT<br>TTGTTGCCATTATCTCACTGATGGGTTGGGGGCTGGGTTACTTCGGGCAGCCGCACATTCTGGCGCGTTTTATGGCGGC<br>GGATTCTCACCACAGCATTGTCCATGCGCGTCGTATTAGTATGACCTGGATGATCCTCTGCCTGGCAGGGGCGGTGGC<br>TGTCGGCTTCTTTGGGATTGCTTACTTTAACGATCATCCGGCGTTGGCTGGTGCGGTAAATCAGAACGCCGAGCGTGT<br>GTTTATCGAACTGGCGCAAATTCTGTTTAACCCGTGGATTGCCGGGATTCTGCTGTCGGCAATTCTGGCGGCGGTAAT<br>GTCAACCTTAAGTTGCCAGCTGCTGGTGTGCTCCAGTGCGATTACCGAAGATTTGTACAAAGCGTTTCTGCGTAAACA<br>TGCCAGCCAGAAAGAGCTGGTGTGGGTAGGGCGTGTGATGGTGCTGGTGGTGGCGCTGGTGGCGATTGCGCTGGCGG<br>CAAACCCGGAAAACCGCGTGCTGGGCTTAGTGAGCTACGCGTGGGCAGGCTTTGGCGCGGCGTTTGGTCCAGTGGTG<br>CTGTTCTCGGTGATGTGGTCACGCATGACGCGTAACGGTGCGCTGGCGGGGATGATCATCGGTGCGCTGACGGTTATC<br>GTCTGGAAACAGTTCGGCTGGCTGGGACTGTACGAAATTATTCCGGGCTTTATCTTCGGCAGTATTGGGATTGTAGTG<br>TTTAGTTTGCTGGGTAAAGCGCCGTCAGCGGCGATGCAAAAACGCTTTGCCGAGGCCGATGCGCACTATCATTCGGCT<br>CCGCCGTCACGGTTGCAGGAAAGCTAA |
| SEQ ID NO: 206<br>nucleic acid<br>coding sequence<br>of the gene<br>phaJ(Aa) at locus<br>ebA4434 | ATGAGTGAAGCGGTCCGCGACTTTTCGCAGTGCTACGGTCACGATTTCGAGGACCTGAAAGTTGGTATGTCAGCGGCC<br>ATCGGGCGCACCGTGACGGAGGCGGATATCGCTATTTTCGCTGGCATTTCGGGTGATACGAATCCCGTTCACCTCGAT<br>GCCGAATTTGCGGCGTCGACGATGTTTGGCGAACGAATCGCTCATGGGATGCTGTCGGCGAGCTTCATTTCTGCAGTG<br>TTCGGTACGAAGCTGCCAGGACCGGGATGCATCTATCTCGGGCAGTCGCTGAACTTCAAGGCCTCAGTGAAAGTCGG<br>CGAAACGGTCGTCGCCCGTGTGACAGTACGCGAGCTCGTGGCTCACAAGCGCCGGGCGTTCTTTGATACTGTCTGTAC<br>GGTGGCCGGAAAAGTGGTACTCGAAGGCCATGCGGAGATCTACCTTCCCGCCAGGCAATAA |
| SEQ ID NO: 207<br>nucleic acid<br>coding sequence<br>of the gene intF at<br>locus b0281 | ATGTTTATTCCCTCCATTTACTTACACCAGCAGTTACATTATTGTAAGACAGCAATTCTCAACTGGAGCCGAAAAATG<br>GCGCTTTCAAGACAAAAATTTACCTTCGAAAGACTTCGCAGATTCACCTTACCGGAAGGGAAAAAACAAACTTTTCTT<br>TGGGATGCAGATGTAACAACCCTGGCATGCCGAGCAACTAGCGGAGCAAAAGCCTTTGTATTCCAAAGCGTATATGC<br>GGGGAAAACCCTTCGCATGACTATTGGCAACATTAACGACTGGAAGATTGATGATGCGAGAGCCGAGGCAAGACGGT<br>TACAAACATTGATCGATACAGGGATAGATCCACGAATTGCTAAGGCTGTAAAAATCGCAGAAGCAGAATCCCTGCAG<br>GCAGAATCACGTAAAACAAAAGTGACTTTCTCCGTCGCCTGGGAAGACTATCTTCAAGAATTGAGAACCGGTATCAG<br>TGCAAAAACTAAACGCCCATATTCTACTCGATACATTGCCGATCACATTAACTTGTCCAGTCGTGGAGGCGAAAGTAA<br>AAAAAGAGGCCAAGGCCCGACTTCGGCTGGACCATTGGCTAGTTTGCTCAACCTGCCGTTATCGGAGCTAACCCCAG<br>ATTACATAGCAGCGTGGCTGAGTACAGAAAGGCAAAATAGACCTACCGTCACTGCTCACGCTTATCGCCTACTACGTG<br>CTTTCATCAAATGGAGTAATTATCAGAAAAAATATCAAGGGATCATTCCTGGCGATCTGGCACAAGATTACAACGTAA<br>GAAAAATGGTTCCCGTGTCAGCGAGTAAAGCTGATGATTGCCTGCAAAAGGAACAACTAAAAAGCTGGTTTAGTGCC<br>GTGCGTAGCCTCAATAATCCTATTGCATCGGCCTATCTCCAAGTACTTTTGCTCACTGGTGCTCGGCGTGAAGAAATTG<br>CGTCGCTTCGCTGGTCAGACGTAGATTTCAAATGGTCAAGCATGCGAATTAAAGACAAGATCGAAGGTGAACGTATC<br>ATCCCTCTCACTCCTTATGTTTCTGAATTGTTAAATGTACTAGCGCAATCCCCAAATTCTGACGTAAATAAGGAGGGTT<br>GGGTTTTCAGAAGTAACAGTAAAAGTGGCAAAATTATTGAGCCGCGTTCAGCGCACAACAGAGCATTAGTGCTGGCT<br>GAGTTACCACATATCAGCCTTCACGGTTTACGTCGTAGTTTTGGTACTTTGGCCGAGTGGGTTGAAGTTCCCACTGGTA<br>TTGTTGCTCAAATTATGGGACACAAACCCAGCGCTCTTGCCGAAAAACACTATCGCCGTCGTCCGTTAGATCTGTTAC<br>GAAAATGGCACGAGAAAATTGAGACATGGATCTTAAATGAAGCAGGTATTACCATAAAAAACAACGTTGATATGCGT<br>TGA |
| SEQ ID NO: 208<br>nucleic acid<br>coding sequence<br>of the gene bcsA<br>at locus b3533 | ATGAGTATCCTGACCCGGTGGTTGCTTATCCCGCCGGTCAACGCGCGGCTTATCGGGCGTTATCGCGATTATCGTCGTC<br>ACGGTGCGTCGGCTTTCAGCGCGACGCTCGGCTGTTTCTGGATGATCCTGGCCTGGATTTTTATTCCGCTGGAGCACCC<br>GCGCTGGCAGCGTATTCGCGCAGAACATAAAAACCTGTATCCGCATATCAACGCCTCGCGTCCGCGTCCGCTGGACCC<br>GGTCCGTTATCTCATTCAAACATGCTGGTTATTGATCGGTGCATCGCGCAAAGAAACGCCGAAACCGCGCAGGCGGG<br>CATTTTCAGGTCTGCAAAATATTCGTGGACGTTACCATCAATGGATGAACGAGCTGCCTGAGCGCGTTAGCCATAAAA<br>CACAGCATCTGGATGAGAAAAAAGAGCTCGGTCATTTGAGTGCCGGGGCGCGGCGGTTGATCCTCGGTATCATCGTC<br>ACCTTCTCGCTGATTCTGGCGTTAATCTGCGTTACTCAGCCGTTTAACCCGCTGGCGCAGTTTATCTTCCTGATGCTGCT<br>GTGGGGGGTAGCGCTGATCGTACGGCGGATGCCGGGGCGCTTCTCGGCGCTAATGTTGATTGTGCTGTCGCTGACCGT<br>TTCTTGCCGTTATATCTGGTGGCGTTACACCTCTACGCTGAACTGGGACGATCCGGTCAGCCTGGTGTGCGGGCTTATT<br>CTGCTCTTCGCTGAAACGTACGCGTGGATTGTGCTGGTGCTCGGCTACTTCCAGGTAGTATGGCCGCTGAATCGTCAG<br>CCGGTGCCATTGCCGAAAGATATGTCGCTGTGGCCGTCGGTGGATATCTTTGTCCCGACTTACAACGAAGATCTCAAC<br>GTGGTGAAAAATACCATTTACGCCTCGCTGGGTATCGACTGGCCGAAAGATAAGCTGAATATCTGGATCCTTGATGAC<br>GGCGGCAGGGAAGAGTTTCGCCAGTTTGCGCAAAACGTGGGGGTGAAATATATCGCCCGCACCACTCATGAACATGC<br>GAAAGCAGGCAACATCAACAATGCGCTGAAATATGCCAAAGGCGAGTTCGTGTCGATTTTCGACTGCGACCACGTAC<br>CAACGCGATCGTTCTTGCAAATGACCATGGGCTGGTTCCTGAAAGAAAAACAGCTGGCGATGATGCAGACGCCGCAC<br>CACTTCTTCTCACCGGACCCGTTTGAACGCAACCTGGGGCGTTTCCGTAAAACGCCGAACGAAGGCACGCTGTTCTAT<br>GGTCTGGTGCAGGATGGCAACGATATGTGGGACGCCACTTTCTTCTGCGGTTCCTGTGCGGTGATTCGTCGTAAGCCG<br>CTGGATGAAATTGGCGGCATTGCTGTCGAAACCGTGACTGAAGATGCGCATACTTCTCTGCGGTTGCACCGTCGTGGC<br>TATACCTCCGCGTATATGCGTATTCCGCAGGCGGCGGGGCTGGCGACCGAAAGTCTGTCGGCGCATATCGGTCAGCGT<br>ATTCGCTGGGCGCGCGGGATGGTACAAATCTTCCGTCTCGATAACCCGCTCACCGGTAAAGGGCTGAAGTTTGCTCAG<br>CGGCTATGTTACGTCAACGCCATGTTCCACTTCTTGTCGGGCATTCCACGGCTGATCTTCCTGACTGCGCCGCTGGCGT<br>TCCTGCTGCTTCATGCCTACATCATCTATGCGCCAGCGTTGATGATCGCCCTATTCGTGCTGCCGCATATGATCCATGC<br>CAGCCTGACCAACTCCAAGATCCAGGGCAAATATCGCCACTCTTTCTGGAGTGAAATCTACGAAACGGTGCTGGCGTG<br>GTATATCGCACCACCGACGCTGGTGGCGCTGATTAACCCGCACAAAGGCAAATTTAACGTCACCGCCAAAGGTGGAC<br>TGGTGGAAGAAGAGTACGTCGACTGGGTGATCTCGCGGCCCTACATCTTCCTTGTCCTGCTCAACCTGGTGGGCGTTG<br>CGGTAGGCATCTGGCGCTACTTCTATGGCCCGCCAACCGAGATGCTCACCGTGGTCGTCAGTATGGTGTGGGTGTTCT<br>ACAACCTGATTGTTCTTGGCGGCGCAGTTGCGGTATCGGTAGAAAGCAAACAGGTACGCCGATCGCACCGCGTGGAG<br>ATGACGATGCCCGCGGCAATTGCCCGCGAAGATGGTCACCTCTTCTCGTGTACCGTTCAGGATTTCTCCGACGGTGGT<br>TTGGGGATCAAGATCAACGGTCAGGCGCAGATTCTGGAAGGGCAGAAAGTGAATCTGTTGCTTAAACGCGGTCAGCA<br>GGAATACGTCTTCCCGACCCAGGTGGCGCGCGTGATGGGTAATGAAGTTGGGCTGAAATTAATGCCGCTCACCACCC |

TABLE 2-continued

| Nucleic Acid Sequences: Genes | |
|---|---|
| SEQ ID NO | Nucleic Acid Sequence |
| | AGCAACATATCGATTTTGTGCAGTGTACGTTTGCCCGTGCGGATACATGGGCGCTCTGGCAGGACAGCTACCCGGAAG<br>ATAAGCCGCTGGAAAGTCTGCTGGATATTCTGAAGCTCGGCTTCCGTGGCTACCGCCATCTGGCGGAGTTTGCGCCTT<br>CTTCGGTGAAGGGCATATTCCGTGTGCTGACTTCTCTGGTTTCCTGGGTTGTATCGTTTATTCCGCGCCGCCCGGAGCG<br>GAGCGAAACGGCACAACCATCGGATCAGGCTTTGGCTCAACAATGA |
| SEQ ID NO: 209<br>nucleic acid<br>coding sequence<br>of the gene bcsC<br>at locus b3530 | ATGCGCAAATTCACACTAAACATATTCACGCTTTCCCTCGGTCTGGCCGTCATGCCGATGGTCGAGGCAGCACCAACC<br>GCTCAGCAACAGTTGCTGGAGCAAGTTCGGTTAGGCGAAGCGACCCATCGTGAAGATCTGGTGCAACAGTCGTTATA<br>TCGGCTGGAACTTATTGATCCGAATAACCCGGACGTCGTTGCCGCCCGTTTCCGTTCTTTGTTACGTCAGGGCGATATT<br>GATGGCGCGCAAAAACAGCTCGATCGGCTGTCGCAGTTAGCGCCGAGTTCAAATGCGTATAAATCGTCGCGGACTAC<br>GATGCTACTTTCCACGCCGGATGGTCGTCAGGCACTGCAACAGGCACGATTGCAGGCGACGACCGGTCATGCAGAAG<br>AAGCTGTGGCGAGTTACAACAAACTGTTCAACGGTGCGCCGCCGGAAGGTGACATTGCTGTCGAGTACTGGAGTACG<br>GTGGCGAAAATTCCGGCTCGCCGTGGCGAAGCGATTAATCAGTTAAAACGCATCAATGCGGATGCACCGGGCAATAC<br>GGGCCTGCAAAACAATCTGGCGCTATTGCTGTTTAGTAGCGATCGCCGTGACGAAGGTTTTGCCGTCCTGGAACAGAT<br>GGCAAAATCGAACGCCGGGCGCGAAGGGGCCTCTAAAATCTGGTACGGGCAGATTAAAGACATGCCCGTCAGTGATG<br>CCAGTGTGTCGGCGCTGAAAAAATATCTCTCGATCTTTAGTGATGGCGATAGCGTGGCGGCTGCGCAATCGCAACTGG<br>CAGAACAGCAAAAACAGCTGGCCGATCCTGCTTTCCGCGCTCGTGCGCAAGGTTTAGCGGCGGTGGACTCTGGTATG<br>GCGGGTAAAGCCATTCCCGAACTACAACAGGCGGTGCGGGCGAACCCGAAAGACAGTGAAGCTCTGGGGGCGCTGG<br>GCCAGGCGTATTCTCAGAAAGGCGATCGCGCCAATGCAGTGGCGAATCTGGAAAAAGCCCTCGCACTGGACCCGCAC<br>AGCAGCAACAACGACAAATGGAACAGTCTGCTGAAAGTAAACCGCTACTGGCTGGCGATCCAGCAGGGCGATGCTGC<br>GCTGAAAGCCAATAATCCTGACCGGGCAGAACGCCTGTTCCAGCAGGCGCGTAATGTCGATAACACCGACAGTTATG<br>CAGTGCTGGGGCTGGGCGATGTGGCGATGGCGCGAAAAGATTATCCCGCCGCCGAACGTTATTATCAGCAGACCTTG<br>CGTATGGACAGCGGCAACACTAACGCCGTGCGCGGGCTGGCAAATATTTACCGCCAGCAATCGCCAGAAAAAGCTGA<br>AGCGTTTATCGCCTCGCTCTCTGCCAGTCAGCGGCGTAGCATTGATGATATCGAACGCAGCCTGCAAAACGACCGTCT<br>GGCACAGCAGGCAGAGGCACTGGAAAACCAGGGCAAATGGGCGCAGGCGGCAGCACTTCAGCGGCAACGACTGGCG<br>CTGGACCCCGGCAGCGTATGGATTACTTACCGACTTTCGCAGGATCTCTGGCAGGCCGGACAACGCAGCCAGGCCGA<br>TACGTTAATGCGCAATCTGGCGCAGCAGAAGTCGAACGACCCGGAGCAGGTTTACGCTTACGGGCTGTACCTCTCTGG<br>TCATGACCAGGACAGAGCGGCGCTGGCGCATATCAATAGCCTGCCGCGTGCGCAGTGGAACAGCAATATTCAGGAGC<br>TGGTTAATCGACTGCAAAGCGATCAGGTGCTGGAAACCGCTAACCGCCTGCGAGAAAGCGGCAAAGAGGCAGAAGC<br>GGAAGCGATGCTGCGCCAGCAACCACCTTCCACGCGTATTGACCTCACGCTGGCTGACTGGGCGCAACAACGACGTG<br>ATTACACCGCCGCCCGCGCTGCATATCAGAATGTCCTGACGCGGGAGCCAGCTAACGCCGACGCCATTCTTGGTCTGA<br>CGGAAGTGGATATTGCTGCCGGTGACAAAGCGGCGGCACGTAGCCAGCTGGCGAAACTGCCCGCTACCGATAACGCC<br>TCGCTGAACACACAGCGGCGCGTGGCGCTGGCACAGGCGCAGCTTGGCGATACCGCAGCAGCGCAGCGGACGTTTAA<br>TAAGTTGATCCCGCAGGCAAAATCTCAGCCACCGTCGATGGAAAGCGCGATGGTGCTGCGTGATGGTGCGAAGTTTG<br>AAGCGCAGGCGGGCGATCCAACGCAGGCGCTGGAAACCTACAAAGACGCCATGGTCGCATCCGGTGTGACTACGACG<br>CGTCCGCAGGATAACGACACCTTTACCCGACTGACCCGTAACGACGAGAAAGATGACTGGCTGAAACGTGGCGTGCG<br>CAGCGATGCGGCGGACCTCTATCGCCAGCAGGATCTTAACGTCACCCTTGAGCACGATTACTGGGGTTCGAGCGGCAC<br>CGGTGGTTACTCCGATCTGAAAGCGCACACTACCATGTTGCAGGTGGATGCGCCGTATTCTGACGGGCGGATGTTCTT<br>TCGCAGTGATTTCGTCAATATGAACGTCGGCAGTTTCTCCACTAATGCCGATGGCAAATGGGATGACAACTGGGGCAC<br>CTGTACATTACAGGACTGTAGCGGCAACCGCAGCCAGTCGGATTCCGGTGCCAGCGTGGCGGTCGGCTGGCGAAATG<br>ACGTCTGGAGCTGGGATATCGGTACCACGCCGATGGGCTTCAACGTGGTGGATGTGGTCGGCGGCATCAGTTACAGC<br>GATGATATCGGGCCGCTGGGTTACACCGTTAACGCCCACCGTCGGCCCATCTCCAGTTCTTTGCTGGCCTTTGGTGGGC<br>AAAAAGACTCCCCGAGCAATACCGGGAAAAAATGGGGTGGCGTACGTGCCGACGGTGTGGGGCTAAGTCTGAGCTAC<br>GATAAAGGTGAAGCAAACGGCGTCTGGGCATCGCTTAGTGGCGACCAGTTAACCGGTAAAAATGTCGAAGATAACTG<br>GCGCGTGCGCTGGATGACGGGCTATTACTATAAGGTCATTAACCAGAACAATCGCCGCGTCACAATCGGCCTGAACA<br>ACATGATCTGGCATTACGACAAAGATCTGAGTGGCTACTCACTCGGTCAGGGCGGTTACTACAGTCCGCAGGAATACC<br>TGTCGTTTGCCATACCGGTGATGTGGCGGGAGCGCACGGAAAACTGGTCGTGGGAGCTGGGTGCGTCTGGCTCGTGGT<br>CGCATTCACGCACCAAAACCATGCCGCGTTATCCGCTGATGAATCTGATCCCGACCGACTGGCAGGAAGAAGCTGCG<br>CGGCAATCCAACGATGGCGGCAGCAGTCAGGGCTTCGGCTACACGGCGCGGGCATTACTTGAACGACGTGTTACTTC<br>CAACTGGTTTGTTGGCACGGCAATTGATATCCAGCAGGCGAAAGATTACGCACCCAGCCATTTCCTGCTCTACGTACG<br>TTATTCCGCCGCCGGATGGCAGGGTGACATGGATTTACCGCCGCAGCCGCTGATACCTTACGCCGACTGGTAA |
| SEQ ID NO: 210<br>nucleic acid<br>coding sequence<br>of the gene gadC<br>at locus b1492 | ATGGCTACATCAGTACAGACAGGTAAAGCTAAGCAGCTCACATTACTTGGATTCTTTGCCATAACGGCATCGATGGTA<br>ATGGCTGTTTATGAATACCCTACCTTCGCAACATCGGGCTTTTCATTAGTCTTCTTCCTGCTATTAGGCGGGATTTTATG<br>GTTTATTCCCGTGGGACTTTGTGCTGCGGAAATGGCCACCGTCGACGGCTGGGAAGAAGGTGGTGTCTTCGCCTGGGT<br>ATCAAATACTCTGGGGCCGAGATGGGGATTTGCAGCGATCTCATTTGGCTATCTGCAAATCGCCATTGGTTTTATTCCG<br>ATGCTCTATTTCGTGTTAGGGGCACTCTCCTACATCCTGAAATGGCCAGCGCTGAATGAAGACCCCATTACCAAAACT<br>ATTGCAGCACTCATCATTCTTTGGGCGCTGGCATTAACGCAGTTTGGTGGCACGAAATACACGGCGCGAATTGCTAAA<br>GTTGGCTTCTTCGCCGGTATCCTGTTACCTGCATTTATTTTGATCGCATTAGCGGCTATTTATCTGCACTCCGGTGCCCC<br>CGTTGCTATCGAAATGGATTCGAAGACCTTCTTCCCTGACTTCTCTAAAGTGGGCACCCTGGTAGTATTTGTTGCCTTC<br>ATTTTGAGTTATATGGGCGTAGAAGCATCCGCAACCCACGTCAATGAAATGAGCAACCCAGGGCGCGACTATCCGTT<br>GGCTATGTTACTGCTGATGGTGGCGGCAATCTGCTTAAGCTCTGTTGGTGGTTTGTCTATTGCGATGGTCATTCCGGGT<br>AATGAAATCAACCTCTCCGCAGGGGTAATGCAAACCTTTACCGTTCTGATGTCCCATGTGGCACCAGAAATTGAGTGG<br>ACGGTTCGCGTGATCTCCGCACTGCTGTTGCTGGGTGTTCTGGCGGAAATCGCCTCCTGGATTGTTGGTCCTTCTCGCG<br>GGATGTATGTAACAGCGCAGAAAAACCTGCTGCCAGCGGCATTCGCTAAAATGAACAAAAATGGCGTACCGGTAACG<br>CTGGTCATTTCGCAGCTGGTGATTACGTCTATCGCGTTGATCATCCTCACCAATACCGGTGGCGGTAACAACATGTCCT<br>TCCTGATCGCACTGGCGCTGACGGTGGTGATTTATCTGTGTGCTTATTTCATGCTGTTTATTGGCTACATTGTGTTGGTT<br>CTTAAACATCCTGACTTAAAACGCACATTTAATATCCCTGGTGGTAAAGGGGTGAAACTGGTCGTGGCAATTGTCGGT<br>CTGCTGACTTCAATTATGGCGTTTATTGTTTCCTTCCTGCCGCCGGATAACATCCAGGGTGATTCTACCGATATGTATG<br>TTGAATTACTGGTTGTTAGTTTCCTGGTGGTACTTGCCCTGCCCTTTATTCTCTATGCTGTTCATGATCGTAAAGGCAAA<br>GCAAATACCGGCGTCACTCTGGAGCCAATCAACAGTCAGAACGCACCAAAAGGTCACTTCTTCCTGCACCCGCGTGC<br>ACGTTCACCACACTATATTGTGATGAATGACAAGAAACACTAA |
| SEQ ID NO: 211<br>nucleic acid<br>coding sequence<br>of the gene fadR | ATGGTCATTAAGGCGCAAAGCCCGGCGGGTTTCGCGGAAGAGTACATTATTGAAAGTATCTGGAATAACCGCTTCCCT<br>CCCGGGACTATTTTGCCCGCAGAACGTGAACTTTCAGAATTAATTGGCGTAACGCGTACTACGTTACGTGAAGTGTTA<br>CAGCGTCTGGCACGAGATGGCTGGTTGACCATTCAACATGGCAAGCCGACGAAGGTGAATAATTTCTGGGAAACTTC<br>CGGTTTAAATATCCTTGAAACACTGGCGCGACTGGATCACGAAAGTGTGCCGCAGCTTATTGATAATTTGCTGTCGGT |

TABLE 2-continued

| Nucleic Acid Sequences: Genes | |
|---|---|
| SEQ ID NO | Nucleic Acid Sequence |
| at locus b1187 | GCGTACCAATATTTCCACTATTTTTATTCGCACCGCGTTTCGTCAGCATCCCGATAAAGCGCAGGAAGTGCTGGCTACC<br>GCTAATGAAGTGGCCGATCACGCCGATGCCTTTGCCGAGCTGGATTACAACATATTCCGCGGCCTGGCGTTTGCTTCC<br>GGCAACCCGATTTACGGTCTGATTCTTAACGGGATGAAAGGGCTGTATACGCGTATTGGTCGTCACTATTTCGCCAAT<br>CCGGAAGCGCGCAGTCTGGCGCTGGGCTTCTACCACAAACTGTCGGCGTTGTGCAGTGAAGGCGCGCACGATCAGGT<br>GTACGAAACAGTGCGTCGCTATGGGCATGAGAGTGGCGAGATTTGGCACCGGATGCAGAAAAATCTGCCGGGTGATT<br>TAGCCATTCAGGGGCGATAA |
| SEQ ID NO: 212 nucleic acid coding sequence of the gene yqhD at locus b3011 | ATGAACAACTTTAATCTGCACACCCCAACCCGCATTCTGTTTGGTAAAGGCGCAATCGCTGGTTTACGCGAACAAATT<br>CCTCACGATGCTCGCGTATTGATTACCTACGGCGGCGGCAGCGTGAAAAAAACCGGCGTTCTCGATCAAGTTCTGGAT<br>GCCCTGAAAGGCATGGACGTGCTGGAATTTGGCGGTATTGAGCCAAACCCGGCTTATGAAACGCTGATGAACGCCGT<br>GAAACTGGTTCGCGAACAGAAAGTGACTTTCCTGCTGGCGGTTGGCGGCGGTTCTGTACTGGACGGCACCAAATTTAT<br>CGCCGCAGCGGCTAACTATCCGGAAAATATCGATCCGTGGCACATTCTGCAAACGGGCGGTAAAGAGATTAAAAGCG<br>CCATCCCGATGGGCTGTGTGCTGACGCTGCCAGCAACCGGTTCAGAATCCAACGCAGGCGCGGTGATCTCCCGTAAA<br>ACCACAGGCGACAAGCAGGCGTTCCATTCTGCCCATGTTCAGCCGGTATTTGCCGTGCTCGATCCGGTTTATACCTAC<br>ACCCTGCCGCCGCGTCAGGTGGCTAACGGCGTAGTGGACGCCTTTGTACACACCGTGGAACAGTATGTTACCAAACCG<br>GTTGATGCCAAAATTCAGGACCGTTTCGCAGAAGGCATTTTGCTGACGCTAATCGAAGATGGTCCGAAAGCCCTGAA<br>AGAGCCAGAAAACTACGATGTGCGCGCCAACGTCATGTGGGCGGCGACTCAGGCGCTGAACGGTTTGATTGGCGCTG<br>GCGTACCGCAGGACTGGGCAACGCATATGCTGGGCCACGAACTGACTGCGATGCACGGTCTGGATCACGCGCAAACA<br>CTGGCTATCGTCCTGCCTGCACTGTGGAATGAAAAACGCGATACCAAGCGCGCTAAGCTGCTGCAATATGCTGAACGC<br>GTCTGGAACATCACTGAAGGTTCCGATGATGAGCGTATTGACGCCGCGATTGCCGCAACCCGCAATTTCTTTGAGCAA<br>TTAGGCGTGCCGACCCACCTCTCCGACTACGGTCTGGACGGCAGCTCCATCCCGGCTTTGCTGAAAAAACTGGAAGAG<br>CACGGCATGACCCAACTGGGCGAAAATCATGACATTACGTTGGATGTCAGCCGCCGTATATACGAAGCCGCCCGCTA<br>A |
| SEQ ID NO: 213 nucleic acid coding sequence of the gene atoC(Con) at locus b2220 | ATGACTGCTATTAATCGCATCCTTATTGTGGATGATGAAGATAATGTTCGCCGTATGCTGAGCACCGCTTTTGCACTAC<br>AAGGATTCGAAACACATTGTGCGAACAACGGACGCACAGCATTACACCTGTTTGCCGATATTCACCCTGATGTGGTGT<br>TGATGGATATCCGCATGCCAGAGATGGACGGCATCAAGGCACTAAAGGAGATGCGCAGCCATGAGACCCGGACACCC<br>GTTATTCTGATGACGGCCTATGCGGAAGTGGAAACCGCCGTCGAAGCGCTACGCTGCGGAGCCTTCGACTATGTTATT<br>AAACCGTTTGATCTCGATGAGTTGAATTTAATCGTTCAGCGCGCTTTACAACTCCAGTCAATGAAAAAAGAatcgCGTCA<br>TCTGCACCAGGCACTGAGCACCAGCTGGCAATGGGGGCACATTCTCACCAACAGCCCGGCGATGATGGACATCTGCA<br>AAGACACCGCCAAAATTGCCCTTTCTCAGGCCAGCGTCTTGATTAGCGGTGAAAGCGGCACCGGGAAAGAGTTGATT<br>GCCAGAGCGATTCACTACAATTCGCGGCGGGCAAAGGGGCCGTTCATTAAAGTCAACTGCGCGGCGCTGCCGGAATC<br>GTTGCTCGAAAGTGAACTGTTTGGTCATGAAAAAGGTGCATTTACTGGTGCACAAACCTTGCGTCAGGGATTATTTGA<br>ACGAGCCAACGAAGGTACTCTGCTCCTCGACGAAATTGGCGAAATGCCGCTGGTACTACAAGCCAAATTACTACGCA<br>TTCTACAGGAACGGGAATTTGAACGGATTGGCGGCCATCAGACCATAAAAGTTGATATCCGCATCATTGCTGCCACCA<br>ACCGCGACTTGCAGGCAATGGTAAAAGAAGGCACCTTCCGTGAAGATCTCTTTTATCGCCTTAACGTTATTCATTTAA<br>TACTGCCGCCTCTGCGCGATCGCCGGGAAGATATTTCCCTGTTAGCTAATCACTTTTTGCAAAAATTCAGTAGTGAGA<br>ATCAGCGCGATATTATCGACATCGATCCGATGGCAATGTCACTGCTTACCGCCTGGTCATGGCCGGGAAATATTCGAG<br>AGCTTTCCAACGTTATTGAACGCGCCGTCGTGATGAATTCAGGCCCGATCATTTTTTCTGAGGATCTTCCGCCACAGAT<br>TCGTCAGCCAGTCTGTAATGCTGGCGAGGTAAAAACAGCCCCTGTCGGTGAGCGTAATTTAAAAGAGGAAATTAAAC<br>GCGTCGAAAAACGCATCATTATGGAAGTGCTGGAACAACAAGAAGGAAACCGAACCCGCACTGCTTTAATGCTGGGC<br>ATCAGTCGCCGTGCATTGATGTATAAACTCCAGGAATACGGTATCGATCCGGCGGATGTATAA |
| SEQ ID NO: 218 nucleic acid coding sequence of the gene gdhA at locus b1761 | ATGGATCAGACATATTCTCTGGAGTCATTCCTCAACCATGTCCAAAAGCGCGACCCGAATCAAACCGAGTTCGCGCAA<br>GCCGTTCGTGAAGTAATGACCACACTCTGGCCTTTTCTTGAACAAAATCCAAAATATCGCCAGATGTCATTACTGGAG<br>CGTCTGGTTGAACCGGAGCGCGTGATCCAGTTTCGCGTGGTATGGGTTGATGATCGCAACCAGATACAGGTCAACCGT<br>GCATGGCGTGTGCAGTTCAGCTCTGCCATCGGCCCGTACAAAGGCGGTATGCGCTTCCATCCGTCAGTTAACCTTTCC<br>ATTCTCAAATTCCTCGGCTTTGAACAAACCTTCAAAAATGCCCTGACTACTCTGCCGATGGGCGGTGGTAAAGGCGGC<br>AGCGATTTCGATCCGAAAGGAAAAAGCGAAGGTGAAGTGATGCGTTTTTGCCAGGCGCTGATGACTGAACTGTATCG<br>CCACCTGGGCGCGGATACCGACGTTCCGGCAGGTGATATCGGGGTTGGTGGTCGTGAAGTCGGCTTTATGGCGGGGA<br>TGATGAAAAAGCTCTCCAACAATACCGCCTGCGTCTTCACCGGTAAGGGCCTTTCATTTGGCGGCAGTCTTATTCGCC<br>CGGAAGCTACCGGCTACGGTCTGGTTTATTTCACAGAAGCAATGCTAAAACGCCACGGTATGGGTTTTGAAGGGATGC<br>GCGTTTCCGTTTCTGGCTCCGGCAACGTCGCCCAGTACGCTATCGAAAAAGCGATGGAATTTGGTGCTCGTGTGATCA<br>CTGCGTCAGACTCCAGCGGCACTGTAGTTGATGAAAGCGGATTCACGAAAGAGAAACTGGCACGTCTTATCGAAATC<br>AAAGCCAGCCGCGATGGTCGAGTGGCAGATTACGCCAAAGAATTTGGTCTGGTCTATCTCGAAGGCCAACAGCCGTG<br>GTCTCTACCGGTTGATATCGCCCTGCCTTGCGCCACCCAGAATGAACTGGATGTTGACGCCGCGCATCAGCTTATCGC<br>TAATGGCGTTAAAGCCGTCGCCGAAGGGGCAAATATGCCGACCACCATCGAAGCGACTGAACTGTTCCAGCAGGCAG<br>GCGTACTATTTGCACCGGGTAAAGCGGCTAATGCTGGTGGCGTCGCTACATCGGGCCTGGAAATGGCACAAAACGCT<br>GCGCGCCTGGGCTGGAAAGCCGAGAAAGTTGACGCACGTTTGCATCACATCATGCTGGATATCCACCATGCCTGTGTT<br>GAGCATGGTGGTGAAGGTGAGCAAACCAACTACGTGCAGGGCGCGAACATTGCCGGTTTTGTGAAGGTTGCCGATGC<br>GATGCTGGCGCAGGGTGTGATTTAA |
| SEQ ID NO: 219 nucleic acid coding sequence of the gene gadBe(Lb) | ATGGCTATGTTGTATGGAAAACACACGCATGAAACAGATGAGACGCTCAttCCAATCTTCGGGGCCAGCGCTGAACGC<br>CACGACCTCCCCAAATATAAATTGGCAAAGCACGCGCTCGAGCCCCGTGAAGCCGATCGATTGGTTCGCGATCAACT<br>ATTGGATGAAGGAAACTCGCGGCTGAATCTCGCCACGTTCTGTCAGACTTACATGGAACCGGAAGCGGTTGAACTCAT<br>GAAAGATACACTGGAGAAAAACGCCATCGATAAATCCGAGTATCCTCGGACCGCTGAAATTGAAAATCGTTGCGTTA<br>ATATCATTGCCAACCTCTGGCATGCTCCAGAAGCTGAGTCGTTCACTGGCACCTCGACGATTGGTTCCTCCGAGGCCT<br>GCATGCTGGCCGGTTTGGCGATGAAGTTTGCTTGGCGTAAGCGCGCCAAAGCGAACGGTCTTGACTTAACTGCCCATC<br>AACCTAATATTGTCATCTCAGCCGGTTATCAAGTTTGTTGGGAAAAATTCTGTGTCTATTGGGACATCGACATGCATGT<br>CGTTCCCATGGACGATGACCACATGTCCTTGAATGTCGATCACGTGTTAGATTACGTGGATGACTACACCATTGGTAT<br>CGTTGGCATTATGGGCATCACTTATACTGGACAATACGACGATTTAGCCCGATTAGATGCCGTTGTAGAGCGGTACAA<br>TCGGACGACTAAGTTCCCGGTATATATCCATGTCGATGCCGCTTCCGGCGGATTTTACACGCCGTTTATTGAACCCGA<br>GCTCAAGTGGGACTTCCGTTTAAACAACGTGATTTCCATCAATGCCTCCGGCCACAAATATGGCTTGGTTTATCCCGG<br>AGTCGGCTGGGTAATCTGGCGTGgCCAACAGTATCTACCAAAAGAGCTGGTCTTTAAGGTCAGCTACTTGGGTGGTagc<br>CTACCTACGATGGCCATCAACTTCTCCCACAGTGCCTCCCAATTAATCGGTCAGTATTACAACTTTATTCGCTTTGGTT<br>TTGATGGCTATCGTGAAATTCAtGAAAAAACTCACGACGTTGCCCGCTATCTCGCGAAATCGCTCACTAAATTAGGGG |

TABLE 2-continued

| Nucleic Acid Sequences: Genes | |
|---|---|
| SEQ ID NO | Nucleic Acid Sequence |
| | GCTTTTCCCTCATTAATGACGGCCACGAGTTACCGCTGATCTGTTATGAACTCACTGCCGATTCTGATCGCGAATGGAC<br>CCTCTACGATTTATCCGATCGGTTATTAATGAAGGGCTGGCAGGTTCCCACCTATCCCTTACCAAAAAACATGACGGA<br>CCGCGTTATTCAACGGATCGTGGTTCGGGCTGACTTTGGTATGAGTATGGCCCACGACTTTATTGATGATCTAACCCA<br>AGCCATTCACGATCTCGACCAAGCACACATCGTTTTCCATAGTGATCCGCAACCTAAAAAATACGGGTTCACGCACTA<br>A |
| SEQ ID NO: 220<br>nucleic acid<br>coding sequence<br>of the gene<br>gadB(Lp) at locus<br>HMPREF0531_12685 | ATGGCAATGTTATACGGTAAACACAATCATGAAGCTGAAGAATACTTGGAACCAGTCTTTGGTGCGCCTTCTGAACAA<br>CATGATCTTCCTAAGTATCGGTTACCAAAGCATTCATTATCCCCTCGAGAAGCCGATCGCTTAGTTCGTGATGAATTAT<br>TAGATGAAGGCAATTCACGACTGAACCTGGCAACTTTTTGTCAGACCTATATGGAACCCGAAGCCGTTGAATTGATGA<br>AGGATACGCTGGCTAAGAATGCCATCGACAAATCTGAGTACCCCCGCACGGCCGAGATTGAAAATCGGTGTGTGAAC<br>ATTATTGCCAATCTGTGGCACGCACCTGATGACGAACACTTTACGGGTACCTCTACGATTGGCTCCTCTGAAGCTTGTA<br>TGTTAGGCGGTTTAGCAATGAAATTCGCCTGGCGTAAACGCGCTCAAGCGGCAGGTTTAGATCTGAATGCCCATCGAC<br>CTAACCTCGTTATTTCGGCTGGCTATCAAGTTTGCTGGGAAAAGTTTTGTGTCTACTGGGACGTTGACATGCACGTGGT<br>CCCAATGGATGAGCAACACATGGCCCTTGACGTTAACCACGTCTTAGACTACGTGGACGAATACACAATTGGTATCGT<br>CGGTATCATGGGCATCACTTATACCGGTCAATATGACGACCTAGCCGCACTCGATAAGGTCGTTACTCACTACAATCA<br>TCAGCATCCCAAATTACCAGTCTACATTCACGTTGACGCAGCGTCAGGTGGCTTCTATACCCCATTTATTGAGCCGCA<br>ACTCATCTGGGACTTCCGGTTGGCTAACGTCGTTTCGATCAACGCCTCCGGGCACAAGTACGGTTTAGTTTATCCCGG<br>GGTCGGCTGGGTCGTTTGGCGTGATCGTCAGTTTTTACCGCCAGAATTAGTCTTCAAAGTTAGTTATTTAGGTGGGGA<br>GTTGCCGACAATGGCGATCAACTTCTCACATAGTGCAGCCCAGCTCATTGGACAATACTATAATTTCATTCGCTTTGGT<br>ATGGACGGTTACCGCGAGATTCAAACAAAGACTCACGATGTTGCCCGCTACCTGGCAGCCGCTCTGGATAAAGTTGGT<br>GAGTTTAAGATGATCAATAACGGACACCAACTCCCCCTGATTTGTTACCAACTAGCCCCGCGCGAAGATCGTGAATGG<br>ACCCTTTATGATTTATCGGATCGCCTATTAATGAACGGTTGGCAAGTACCAACGTATCCTTTACCTGCTAATCTGGAAC<br>AACAAGTCATCCAACGAATCGTCGTTCGGGCTGACTTTGGCATGAATATGGCCCACGATTTCATGGATGACCTGACCA<br>AGGCTGTCCATGACTTAAACCACGCCCACATTGTCTATCATCATGACGCGGCACCTAAGAAATACGGATTCACACACT<br>GA |
| SEQ ID NO: 227<br>nucleic acid<br>coding sequence<br>of the gene<br>gad(Ls) (codon-<br>optimized) | ATGAGCAAAAACGATCAGGAGACGCAGCAGATGCTGGATGCAGCACAGCTGGAAAAAACGTTTCTGGGAAGCACCG<br>CAGCCGGGGAATCGCTTCCCAAAAATACAATGCCGGCAGGCCCAATGGCCCCAGATGTAGCCGTAGAAATGGTGGAC<br>CACTTTCGCCTGAACGAGGCAAAAGCGAATCAGAATCTGGCGACCTTTTGTACCACTGAGATGGAACCGCAAGCGGA<br>TCAACTGATGATGCGTACCCTGAACACCAACGCCATTGATAAGTCCGAATACCCCAAAACGTCCGCAATGGAAAATT<br>ATTGTGTGAGTATGATTGCGCATCTGTGGGGCATTCCGGACGAAGAGAAGTTCGGCGATGATTTCATTGGGACCTCAA<br>CCGTTGGGTCTTCTGAAGGATGCATGTTAGGAGGACTTGCATTGCTGCATACCTGGAAACATCGCGCGAAAGCGGCG<br>GGCCTTGATATCGATGATCTGCACGCGCACAAACCCAATTTAGTGATTATGAGCGGCAATCAGGTGGTGTGGGAAAA<br>GTTCTGCACGTACTGGAACGTCGATTTTCGCCAAGTCCCGATTAATGGCGATCAGGTGTCGCTGGACCTCGACCATGT<br>GATGGACTACGTCGATGAGAACACCATTGGCATCATTGGCATTGAAGGGATTACCTATACTGGTTCCGTCGATGATAT<br>CCAGGGCCTGGATAAACTGGTGACCGAGTACAATAAGACTGCTGCTTTGCCGGTCCGCATTCATGTGGATGCTGCCTT<br>TGGTGGTTTGTTTGCCCCGTTTGTTGACGGCTTCAAACCGTGGGATTTCCGCCTCGATAACGTGGTTAGCATTAATGTT<br>TCGGGCCACAAATATGGCATGGTGTATCCGGGTTTAGGCTGGATTGTATGGCGTAAAAACAGCTACGACATCCTCCCG<br>AAGGAAATGCGTTTCAGCGTTCCTTATCTTGGTTCAAGTGTCGATTCAATCGCCATCAATTTCTCGCATTCTGGTGCGC<br>ACATTAACGCCCAGTACTACAACTTCCTGCGCTTTGGTTTAGCAGGCTATAAAGCGATCATGAACAATGTACGCAAAG<br>TGTCACTGAAACTGACAGACGAATTACGTAAGTTTGGCATCTTTGACATCCTCGTGGATGGTAAAGAATTACCGATCA<br>ACTGCTGGAAACTGAGCGACAATGCCAATGTAAGTTGGAGTCTGTACGACATGGAAGATGCTCTGGCGAAATATGGC<br>TGGCAAGTACCTGCGTATCCACTTCCGAAAAACCGTGAAGAGACTATTACCAGCCGCATTGTTGTTCGTCCTGGTATG<br>ACAATGGCCATTGCCGATGACTTCATCGATGACTTGAAGCTGGCGATTGCGGATTTGAATCATAGCTTTGGTGATGTT<br>AAAGATGTTAACGACAAGAACAAAACGACGGTGCGTTAA |
| SEQ ID NO: 228<br>nucleic acid<br>coding sequence<br>of the gene<br>phab(Hb)<br>(codon-<br>optimized) | ATGGCGAATCAGGCTCCGGTCGCTTGGGTTACCGGAGGTACGGGCGGAATTGGCACGTCGATCTGCCACTCACTGGCC<br>GATGCCGGTTATCTTGTGGTAGCGGGTTATCATAACCCTGAAAAAGCAAAGACTTGGTTAGAAACGCAGCAGGCCGC<br>CGGTTACGATAACATTGCGCTGTCCGGTGTGGACTTAAGCGACCACAACGCCTGTTTGGAAGGAGCGCGTGAGATCC<br>AGGAAAAATACGGACCGGTTAGCGTGCTGGTGAACTGTGCGGGTATCACCCGTGATGGCACCATGAAAAAGATGTCC<br>TACGAACAATGGCATCAAGTTATTGACACCAACTTGAACTCGGTGTTTAATACCTGCCGTAGTGTAATTGAAATGATG<br>CTGGAACAAGGCTATGGCCGTATCATTAATATTAGCTCAATTAACGGCCGCAAAGGCCAGTTTGGGCAGGTCAATTAT<br>GCGGCAGCCAAAGCAGGCATGCATGGCCTGACCATGAGTCTTGCGCAAGAAACGGCGACCAAGGGCATTACAGTTAA<br>TACCGTGTCTCCGGGCTATATTGCAACGGATATGATTATGAAAATTCCCGAACAGGTCCGCGAGGCCATCCGCGAAAC<br>TATCCCAGTGAAACGCTACGGCACCCCGGAAGAGATTGGTCGCCTGGTAACTTTTCTCGCGGATAAAGAGAGCGGGT<br>TCATTACAGGCGCAAATATCGATATCAATGGTGGCCAGTTCATGGGGTAA |
| SEQ ID NO: 229<br>nucleic acid<br>coding sequence<br>of the gene<br>phaC(F420S) | ATGGCGACCGGCAAAGGCGCGGCAGCTTCCACGCAGGAAGGCAAGTCCCAACCATTCAAGGTCACGCCGGGGCCATT<br>CGATCCAGCCACATGGCTGGAATGGTCCCGCCAGTGGCAGGGCACTGAAGGCAACGGCCACGCGGCCGCGTCCGGCA<br>TTCCGGGCCTGGATGCGCTGGCAGGCGTCAAGATCGCGCCGGCGCAGCTGGGTGATATCCAGCAGCGCTACATGAAG<br>GACTTCTCAGCGCTGTGGCAGGCCATGGCCGAGGGCAAGGCCGAGGCCACCGGTCCGCTGCACGACCGGCGCTTCGC<br>CGGCGACGCATGGCGCACCAACCTCCCATATCGCTTCGCTGCCGCGTTCTACCTGCTCAATGCGCGCGCCTTGACCGA<br>GCTGGCCGATGCCGTCGAGGCCGATGCCAAGACCCGCCAGCGCATCCGCTTCGCGATCTCGCAATGGGTCGATGCGA<br>TGTCGCCCGCCAACTTCCTTGCCACCAATCCCGAGGCGCAGCGCCTGCTGATCGAGTCGGGCGGCGAATCGCTGCGTG<br>CCGGCGTGCGCAACATGATGGAAGACCTGACACGCGGCAAGATCTCGCAGACCGACGAGAGCGCGTTTGAGGTCGGC<br>CGCAATGTCGCGGTGACCGAAGGCGCCGTGGTCTTCGAGAACGAGTACTTCCAGCTGTTGCAGTACAAGCCGCTGAC<br>CGACAAGGTGCACGCGCGCCCGCTGCTGATGGTGCCGCCGTGCATCAACAAGTACTACATCCTGGACCTGCAGCCGG<br>AGAGCTCGCTGGTGCGCCATGTGGTGGAGCAGGGACATACGGTGTTTCTGGTGTCGTGGCGCAATCCGGACGCCAGC<br>ATGGCCGGCAGCACCTGGGACGACTACATCGAGCACGCGGCCATCCGCGCCATCGAAGTCGCGCGCGACATCAGCGG<br>CCAGGACAAGATCAACGTGCTCGGCTTCTGCGTGGGCGGCACCATTGTCTCGACCGCGCTGGCGGTGCTGGCCGCGCG<br>CGGCGAGCACCCGGCCGCCAGCGTCACGCTGCTGACCACGCTGCTGGACTTTGCCGACACGGGCATCCTCGACGTCTT<br>TGTCGACGAGGGCCATGTGCAGTTGCGCGAGGCCACGCTGGGCGGCGGCGCCGGCGCGCCGTGCGCGCTGCTGCGCG<br>GCCTTGAGCTGGCCAATACCTTCTCGTTCTTGCGCCCGAACGACCTGGTGTGGAACTACGTGGTCGACAACTACCTGA<br>AGGGCAACACGCCGGTGCCGAGCGACCTGCTGTTCTGGAACGGCGACGCCACCAACCTGCCGGGGCCGTGGTACTGC<br>TGGTACCTGCGCCACACCTACCTGCAGAACGAGCTCAAGGTACCGGGCAAGCTGACCGTGTGCGGCGTGCCGGTGGA<br>CCTGGCCAGCATCGACGTGCCGACCTATATCTACGGCTCGCGCGAAGACCATATCGTGCCGTGGACCGCGGCCTATGC |

TABLE 2-continued

| Nucleic Acid Sequences: Genes | |
|---|---|
| SEQ ID NO | Nucleic Acid Sequence |
| | CTCGACCGCGCTGCTGGCGAACAAGCTGCGCTTCGTGCTGGGTGCGTCGGGCCATATCGCCGGTGTGATCAACCCGCC<br>GGCCAAGAACAAGCGCAGCCACTGGACTAACGATGCGCTGCCGGAGTCGCCGCAGCAATGGCTGGCCGGCGCCATCG<br>AGCATCACGGCAGCTGGTGGCCGGACTGGACCGCATGGCTGGCCGGGCAGGCCGGCGCGAAACGCGCCGCGCCCGCC<br>AACTATGGCAATGCGCGCTATCGCGCAATCGAACCCGCGCCTGGGCGATACGTCAAAGCCAAGGCATGA |
| SEQ ID NO: 231<br>nucleic acid<br>coding sequence<br>of the gene<br>phaC(G4D) | ATGGCGACCGATAAAGGCGCGGCAGCTTCCACGCAGGAAGGCAAGTCCCAACCATTCAAGGTCACGCCGGGGCCATT<br>CGATCCAGCCACATGGCTGGAATGGTCCCGCCAGTGGCAGGGCACTGAAGGCAACGGCCACGCGGCCGCGTCCGGCA<br>TTCCGGGCCTGGATGCGCTGGCAGGCGTCAAGATCGCGCCGGCGCAGCTGGGTGATATCCAGCAGCGCTACATGAAG<br>GACTTCTCAGCGCTGTGGCAGGCCATGGCCGAGGGCAAGGCCGAGGCCACCGGTCCGCTGCACGACCGGCGCTTCGC<br>CGGCGACGCATGGCGCACCAACCTCCCATATCGCTTCGCTGCCGCGTTCTACCTGCTCAATGCGCGCGCCTTGACCGA<br>GCTGGCCGATGCCGTCGAGGCCGATGCCAAGACCCGCCAGCGCATCCGCTTCGCGATCTCGCAATGGGTCGATGCGA<br>TGTCGCCCGCCAACTTCCTTGCCACCAATCCCGAGGCGCAGCGCCTGCTGATCGAGTCGGGCGGCGAATCGCTGCGTG<br>CCGGCGTGCGCAACATGATGGAAGACCTGACACGCGGCAAGATCTCGCAGACCGACGAGAGCGCGTTTGAGGTCGGC<br>CGCAATGTCGCGGTGACCGAAGGCGCCGTGGTCTTCGAGAACGAGTACTTCCAGCTGTTGCAGTACAAGCCGCTGAC<br>CGACAAGGTGCACGCGCGCCCGCTGCTGATGGTGCCGCCGTGCATCAACAAGTACTACATCCTGGACCTGCAGCCGG<br>AGAGCTCGCTGGTGCGCCATGTGGTGGAGCAGGGACATACGGTGTTTCTGGTGTCGTGGCGCAATCCGGACGCCAGC<br>ATGGCCGGCAGCACCTGGGACGACTACATCGAGCACGCGGCCATCCGCGCCATCGAAGTCGCGCGCGACATCAGCGG<br>CCAGGACAAGATCAACGTGCTCGGCTTCTGCGTGGGCGGCACCATTGTCTCGACCGCGCTGGCGGTGCTGGCCGCGCG<br>CGGCGAGCACCCGGCCGCCAGCGTCACGCTGCTGACCACGCTGCTGGACTTTGCCGACACGGGCATCCTCGACGTCTT<br>TGTCGACGAGGGCCATGTGCAGTTGCGCGAGGCCACGCTGGGCGGCGGCGCCGGCGCGCCGTGCGCGCTGCTGCGCG<br>GCCTTGAGCTGGCCAATACCTTCTCGTTCTTGCGCCCGAACGACCTGGTGTGGAACTACGTGGTCGACAACTACCTGA<br>AGGGCAACACGCCGGTGCCGTTCGACCTGCTGTTCTGGAACGGCGACGCCACCAACCTGCCGGGGCCGTGGTACTGC<br>TGGTACCTGCGCCACACCTACCTGCAGAACGAGCTCAAGGTACCGGGCAAGCTGACCGTGTGCGGCGTGCCGGTGGA<br>CCTGGCCAGCATCGACGTGCCGACCTATATCTACGGCTCGCGCGAAGACCATATCGTGCCGTGGACCGCGGCCTATGC<br>CTCGACCGCGCTGCTGGCGAACAAGCTGCGCTTCGTGCTGGGTGCGTCGGGCCATATCGCCGGTGTGATCAACCCGCC<br>GGCCAAGAACAAGCGCAGCCACTGGACTAACGATGCGCTGCCGGAGTCGCCGCAGCAATGGCTGGCCGGCGCCATCG<br>AGCATCACGGCAGCTGGTGGCCGGACTGGACCGCATGGCTGGCCGGGCAGGCCGGCGCGAAACGCGCCGCGCCCGCC<br>AACTATGGCAATGCGCGCTATCGCGCAATCGAACCCGCGCCTGGGCGATACGTCAAAGCCAAGGCATGA |

TABLE 3A

| Nucleic Acid Sequences: Primers | |
|---|---|
| SEQ ID NO | Nucleotide Sequence |
| SEQ ID NO: 119 nucleic acid sequence the primer P01 | TGAAGGAAATGAAGTCCTGAGCGAGAGTAGGGAACTGCC |
| SEQ ID NO: 120 nucleic acid sequence the primer P02 | TATCTTTACCTCCTTTGCTAGCTCAGCCCATATGCAGGCCG |
| SEQ ID NO: 121 nucleic acid sequence the primer P03 | GCTAGCAAAGGAGGTAAAGATAATGAGAAAGGTTCCCATTATTACC |
| SEQ ID NO: 122 nucleic acid sequence the primer P04 | TCAGGACTTCATTTCCTTCAGAC |
| SEQ ID NO: 123 nucleic acid sequence the primer P05 | CCATGGGACTGAAAAAAATAAGCGAGAGTAGGGAACTGCC |
| SEQ ID NO: 124 nucleic acid sequence the primer P06 | GCTAGCAAAGGAGGTAAAGATAATGAGAAAAGTAGAAATCATTACAGC |
| SEQ ID NO: 125 nucleic acid sequence the primer P07 | TTATTTTTTCAGTCCCATGGGAC |
| SEQ ID NO: 126 nucleic acid sequence the primer P08 | CAATTTCACACAGGAGGAATCAAAAATGATGGTTCCAACCCTCGAACAC |
| SEQ ID NO: 127 nucleic acid sequence the primer P09 | CATTATCTTATCCTCCTTTCTCGAGTCAATGCTCGGCGTCGGCGATC |
| SEQ ID NO: 128 nucleic acid sequence the primer P10 | TGACTCGAGAAAGGAGGATAAGATAATGAGTCAGGCGCTAAAAAATTTACTGAC |
| SEQ ID NO: 129 nucleic acid sequence the primer P11 | GGTTGGAACCATCATTTTTGATTCCTCCTGTGTGAAATTGTTATCCGCTCACAATTC<br>C |
| SEQ ID NO: 130 nucleic acid sequence the primer P12 | CAATTTCACACAGGAGGAATCAAAAATGCTGGTAAATGACGAGCAAC |
| SEQ ID NO: 131 nucleic acid sequence the primer P13 | CATTATCTTTACCTCCTTTGCTAGCTCAAAGATTGCGCGCAATGACC |

TABLE 3A-continued

| Nucleic Acid Sequences: Primers | |
|---|---|
| SEQ ID NO | Nucleotide Sequence |
| SEQ ID NO: 132 nucleic acid sequence the primer P14 | TGAGCTAGCAAAGGAGGTAAAGATAATGTACGCAGCTAAGGACATCACC |
| SEQ ID NO: 133 nucleic acid sequence the primer P15 | TCTCTCATCCGCCAAAACAGCCTCATTGGGCCCTCCTGGAGAG |
| SEQ ID NO: 134 nucleic acid sequence the primer P16 | TCTCCAGGAGGGCCCAATGAGGCTGTTTTGGCGGATGAGAG |
| SEQ ID NO: 135 nucleic acid sequence the primer P17 | GTCATTTACCAGCATTTTTGATTCCTCCTGTGTGAAATTGTTATCCGCTC |
| SEQ ID NO: 136 nucleic acid sequence the primer P18 | TTCACACAGGAGGAATCAAAAATGCATTTTAAACTATCAGAAGAAC |
| SEQ ID NO: 137 nucleic acid sequence the primer P19 | TATCTTTACCTCCTTTGCTAGCCTACTTCGTTAACATACGAGAAATTAC |
| SEQ ID NO: 138 nucleic acid sequence the primer P20 | CTCGTATGTTAACGAAGTAGGCTAGCAAAGGAGGTAAAGATAATG |
| SEQ ID NO: 139 nucleic acid sequence the primer P21 | TTCTGATAGTTTAAAATGCATTTTTGATTCCTCCTGTGTGAAATTG |
| SEQ ID NO: 140 nucleic acid sequence the primer P22 | TTGTGAGCGGATAACAATTTCGGTGTATGCAAGAGGGATAAAAAATG |
| SEQ ID NO: 141 nucleic acid sequence the primer P23 | TCTTATCCTCCTTTCTCGAGTCAGAACAGCGTTAAACCAATGAC |
| SEQ ID NO: 142 nucleic acid sequence the primer P24 | TATCCCTCTTGCATACACCGAAATTGTTATCCGCTCACAATTCCAC |
| SEQ ID NO: 143 nucleic acid sequence the primer P25 | CGGTGGTAAAACTCCCTTGAGGCTGTTTTGGCGGATGAG |
| SEQ ID NO: 144 nucleic acid sequence the primer P26 | GCAAGGGTTTGTGTACTCATTATCTTTACCTCCTTTGCTAGC |
| SEQ ID NO: 145 nucleic acid sequence the primer P27 | TAGCAAAGGAGGTAAAGATAATGAGTACACAAACCCTTGCC |
| SEQ ID NO: 146 nucleic acid sequence the primer P28 | TCTCATCCGCCAAAACAGCCTCAAGGGAGTTTTACCACCGC |
| SEQ ID NO: 147 nucleic acid sequence the primer P29 | TGACTCGAGAAAGGAGGATAAGATAATGGACCAGAAGCTGTTAACGG |
| SEQ ID NO: 148 nucleic acid sequence the primer P30 | CTTTCTACGTGTTCCGCTTCCTTTAGTGATCGCTGAGATATTTCAGG |
| SEQ ID NO: 149 nucleic acid sequence the primer P31 | AATATCTCAGCGATCACTAAAGGAAGCGGAACACGTAGAAAGC |
| SEQ ID NO: 150 nucleic acid sequence the primer P32 | CAATTTCACACAGGAGGAATCAAAAATGAATCAACAGGTAAATGTGGCC |
| SEQ ID NO: 151 nucleic acid sequence the primer P33 | CATTATCTTTACCTCCTTTGCTAGCTTAAGCGACCCCGTTCAGTGC |
| SEQ ID NO: 152 nucleic acid sequence the primer P34 | TAAGCTAGCAAAGGAGGTAAAGATAATGAATACTTCTGAACTCGAAACCC |
| SEQ ID NO: 153 nucleic acid sequence the primer P35 | CATTTAGTTATCCTCCTTTCTCGAGTTAGCGAATAGAAAAGCCGTTGG |
| SEQ ID NO: 154 nucleic acid sequence the primer P36 | TAACTCGAGAAAGGAGGATAACTAAATGAAACTTAACGACAGTAACTTATTCC |
| SEQ ID NO: 155 nucleic acid sequence the primer P37 | TCTCTCATCCGCCAAAACAGCCTTAAAGACCGATGCACATATATTTGATTTCTAAG |
| SEQ ID NO: 156 nucleic acid sequence the primer P38 | ATATGTGCATCGGTCTTTAAGGCTGTTTTGGCGGATGAGAG |

TABLE 3A-continued

Nucleic Acid Sequences: Primers

| SEQ ID NO | Nucleotide Sequence |
| --- | --- |
| SEQ ID NO: 157 nucleic acid sequence the primer P39 | TACCTGTTGATTCATTTTTGATTCCTCCTGTGTGAAATTGTTATCCGCTC |
| SEQ ID NO: 158 nucleic acid sequence the primer P40 | CTCGAGAAAGGAGGATAACTAAATG |
| SEQ ID NO: 159 nucleic acid sequence the primer P41 | CATTATCTTTACCTCCTTTGCTAGC |
| SEQ ID NO: 160 nucleic acid sequence the primer P42 | TAGCAAAGGAGGTAAAGATAATGAATACAGCAGAACTGGAAACC |
| SEQ ID NO: 161 nucleic acid sequence the primer P43 | AGTTATCCTCCTTTCTCGAGTTAGCGAATGGAAAAACCGTTGGT |

TABLE 3B

Nucleic Acid Sequences: DNA encoding Small Noncoding RNA

| SEQ ID NO | Nucleotide Sequence |
| --- | --- |
| SEQ ID NO: 27 nucleic acid sequence dsrA encoding for small noncoding RNA DsrA at locus b1954 | AACACATCAGATTTCCTGGTGTAACGAATTTTTTAAGTGCTTCTTGCTTAAGCAAGTTTCATCC CGACCCCCTCAGGGTCGGGATTT |
| SEQ ID NO: 39 nucleic acid sequence rprA encoding for small noncoding RNA RprA at locus b4431 | ACGGTTATAAATCAACATATTGATTTATAAGCATGGAAATCCCCTGAGTGAAACAACGAATTG CTGTGTGTAGTCTTTGCCCATCTCCCACGATGGGCTTTTTTT |
| SEQ ID NO: 214 nucleic acid sequence arcZ encoding for small noncoding RNA ArcZ at locus b4450 | GTGCGGCCTGAAAAACAGTGCTGTGCCCTTGTAACTCATCATAATAATTTACGGCGCAGCCAA GATTTCCCTGGTGTTGGCGCAGTATTCGCGCACCCCGGTCTAGCCGGGGTCATTTTTT |

TABLE 3C

Nucleic Acid Sequences: Small Noncoding RNA

| SEQ ID NO | Nucleotide Sequence |
| --- | --- |
| SEQ ID NO: 221 nucleic acid sequence for small noncoding RNA DsrA | AACACAUCAGAUUUCCUGGUGUAACGAAUUUUUUAAGUGCUUCUUGCUUAAGCAAGUUUCAU CCCGACCCCCUCAGGGUCGGGAUUU |
| SEQ ID NO: 222 nucleic acid sequence for small noncoding RNA RprA | ACGGUUAUAAAUCAACAUAUUGAUUUAUAAGCAUGGAAAUCCCCUGAGUGAAACAACGAAUU GCUGUGUGUAGUCUUUGCCCAUCUCCCACGAUGGGCUUUUUUU |
| SEQ ID NO: 223 nucleic acid sequence for small noncoding RNA ArcZ | GUGCGGCCUGAAAAACAGUGCUGUGCCCUUGUAACUCAUCAUAAUAAUUUACGGCGCAGCCA AGAUUUCCCUGGUGUUGGCGCAGUAUUCGCGCACCCCGGUCUAGCCGGGGUCAUUUUUU |

TABLE 3D

Nucleic Acid Sequences: Regulatory Elements and Cassettes

| SEQ ID NO | Nucleotide Sequence |
| --- | --- |
| SEQ ID NO: 232; $P_{gracmax2}$::(T7.RBS) | TGCCTGAACGAGAAGCTATCACCGCCCAGCCTAAACGGATATCATCATCGCTCATCCGAAAAGAATG ATGGATCACTAGAAAATTTTTTAAAAAATCTCTTGACATTGGAAGGGAGATATGTTATAATAAGAATT GCGGAATTGTGAGCGGATAACAATTTCTAGAAATAATTTTGTTTAACTTTAAGAAGGAGATATACAT |

TABLE 3D-continued

| Nucleic Acid Sequences: Regulatory Elements and Cassettes | |
|---|---|
| SEQ ID NO | Nucleotide Sequence |
| SEQ ID NO: 233; Pgracmax2 | GAAAAGAATGATGGATCACTAGAAAATTTTTTAAAAAATCTCTTGACATTGGAAGGGAGATATGTTAT<br>AATAAGAATTGCGGAATTGTGAGCGGATAACAATT |
| SEQ ID NO: 234; T7.RBS with 9 bp TTAACTTTA sequence for 16S rRNA | TTAACTTTAAGAAGGAG |
| SEQ ID NO: 235; Gram-positive RBS | AAGGAGG |
| SEQ ID NO: 236; RBSI with 9 bp TTAACTTTA sequence for 16S rRNA | TTAACTTTAAAAAGGAGG |
| SEQ ID NO: 237; 16S rRNA base-pair facilitator from RBS1 and T7.RBS | TTAACTTTA |
| SEQ ID NO: 238; transcriptional terminator | GCAGCCCGCCTAATGAGCGGGCTTTTTT |
| SEQ ID NO: 239; nucleic acid sequence of $P_{gracmax2}$::(T7.RBS)bktB:(RBS1)phaB | TGCCTGAACGAGAAGCTATCACCGCCCAGCCTAAACGGATATCATCATCGCTCATCCGAAAAGAATG<br>ATGGATCACTAGAAAATTTTTTAAAAAATCTCTTGACATTGGAAGGGAGATATGTTATAATAAGAATT<br>GCGGAATTGTGAGCGGATAACAATTTCTAGAAATAATTTTGTTTAACTTTAAGAAGGAGATATACATA<br>TGACGCGTGAAGTGGTAGTGGTAAGCGGTGTCCGTACCGCGATCGGGACCTTTGGCGGCAGCCTGAA<br>GGATGTGGCACCGGCGGAGCTGGGCGCACTGGTGGTGCGCGAGGCGCTGGCGCGCGCGCAGGTGTCG<br>GGCGACGATGTCGGCCACGTGGTATTCGGCAACGTGATCCAGACCGAGCCGCGCGACATGTATCTGG<br>GCCGCGTCGCGGCCGTCAACGGCGGGGTGACGATCAACGCCCCCGCGCTGACCGTGAACCGCCTGTG<br>CGGCTCGGGCCTGCAGGCCATTGTCAGCGCCGCGCAGACCATCCTGCTGGGCGATACCGACGTCGCCA<br>TCGGCGGCGGCGCGGAAAGCATGAGCCGCGCACCGTACCTGGCGCCGGCAGCGCGCTGGGGCGCACG<br>CATGGGCGACGCCGGCCTGGTCGACATGATGCTGGGTGCGCTGCACGATCCCTTCCATCGCATCCACA<br>TGGGCGTGACCGCCGAGAATGTCGCCAAGGAATACGACATCTCGCGCGCGCAGCAGGACGAGGCCGC<br>GCTGGAATCGCACCGCCGCGCTTCGGCAGCGATCAAGGCCGGCTACTTCAAGGACCAGATCGTCCCG<br>GTGGTGAGCAAGGGCCGCAAGGGCGACGTGACCTTCGACACCGACGAGCACGTGCGCCATGACGCCA<br>CCATCGACGACATGACCAAGCTCAGGCCGGTCTTCGTCAAGGAAAACGGCACGGTCACGGCCGGCAA<br>TGCCTCGGGCCTGAACGACGCCGCCGCCGCGGTGGTGATGATGGAGCGCGCCGAAGCCGAGCGCCGC<br>GGCCTGAAGCCGCTGGCCCGCCTGGTGTCGTACGGCCATGCCGGCGTGGACCCGAAGGCCATGGGCA<br>TCGGCCCGGTGCCGGCGACGAAGATCGCGCTGGAGCGCGCCGGCCTGCAGGTGTCGGACCTGGACGT<br>GATCGAAGCCAACGAAGCCTTTGCCGCACAGGCGTGCGCCGTGACCAAGGCGCTCGGTCTGGACCCG<br>GCCAAGGTTAACCCGAACGGCTCGGGCATCTCGCTGGGCCACCCGATCGGCGCCACCGGTGCCCTGAT<br>CACGGTGAAGGCGCTGCATGAGCTGAACCGCGTGCAGGGCCGCTACGCGCTGGTGACGATGTGCATC<br>GGCGGCGGGCAGGGCATTGCCGCCATCTTCGAGCGTATCTGAGCTAGCATTAACTTTAAAAAGGAGG<br>AAGAATTCATGACTCAGCGCATTGCGTATGTGACCGGCGGCATGGGTGGTATCGGAACCGCCATTTGC<br>CAGCGGCTGGCCAAGGATGGCTTTCGTGTGGTGGCCGGTTGCGGCCCCAACTCGCCGCGCCGCGAAA<br>AGTGGCTGGAGCAGCAGAAGGCCCTGGGCTTCGATTTCATTGCCTCGGAAGGCAATGTGGCTGACTGG<br>GACTCGACCAAGACCGCATTCGACAAGGTCAAGTCCGAGGTCGGCGAGGTTGATGTGCTGATCAACA<br>ACGCCGGTATCACCCGCGACGTGGTGTTCCGCAAGATGACCCGCGCCGACTGGGATGCGGTGATCGA<br>CACCAACCTGACCTCGCTGTTCAACGTCACCAAGCAGGTGATCGACGGCATGGCCGACCGTGGCTGGG<br>GCCGCATCGTCAACATCTCGTCGGTGAACGGGCAGAAGGGCCAGTTCGGCCAGACCAACTACTCCAC<br>CGCCAAGGCCGGCCTGCATGGCTTCACCATGGCACTGGCGCAGGAAGTGGCGACCAAGGGCGTGACC<br>GTCAACACGGTCTCTCCGGGCTATATCGCCACCGACATGGTCAAGGCGATCCGCCAGGACGTGCTCGA<br>CAAGATCGTCGCGACGATCCCGGTCAAGCGCCTGGGCCTGCCGGAAGAGATCGCCTCGATCTGCGCCT<br>GGTTGTCGTCGGAGGAGTCCGGTTTCTCGACCGGCGCCGACTTCTCGCTCAACGGCGGCCTGCATATG<br>GGCTGAACCGGTGCAGCCCGCCTAATGAGCGGGCTTTTTT |
| SEQ ID NO: 240; nucleic acid sequence of $P_{gracmax2}$::(T7.RBS)phaC:(RBS1)phaA | TGCCTGAACGAGAAGCTATCACCGCCCAGCCTAAACGGATATCATCATCGCTCATCCGAAAAGAATG<br>ATGGATCACTAGAAAATTTTTTAAAAAATCTCTTGACATTGGAAGGGAGATATGTTATAATAAGAATT<br>GCGGAATTGTGAGCGGATAACAATTTCTAGAAATAATTTTGTTTAACTTTAAGAAGGAGATATACATA<br>TGGCGACCGGCAAAGGCGCGGCAGCTTCCACGCAGGAAGGCAAGTCCCAACCATTCAAGGTCACGCC<br>GGGGCCATTCGATCCAGCCACATGGCTGGAATGGTCCCGCCAGTGGCAGGGCACTGAAGGCAACGGC<br>CACGCGGCCGCGTCCGGCATTCCGGGCCTGGATGCGCTGGCAGGCGTCAAGATCGCGCCGGCGCAGC<br>TGGGTGATATCCAGCAGCGCTACATGAAGGACTTCTCAGCGCTGTGGCAGGCCATGGCCGAGGGCAA<br>GGCCGAGGCCACCGGTCCGCTGCACGACCGGCGCTTCGCCGGCGACGCATGGCGCACCAACCTCCCA<br>TATCGCTTCGCTGCCGCGTTCTACCTGCTCAATGCGCGCGCCTTGACCGAGCTGGCCGATGCCGTCGA<br>GGCCGATGCCAAGACCCGCCAGCGCATCCGCTTCGCGATCTCGCAATGGGTCGATGCGATGTCGCCCG<br>CCAACTTCCTTGCCACCAATCCCGAGGCGCAGCGCCTGCTGATCGAGTCGGGCGGCGAATCGCTGCGT<br>GCCGGCGTGCGCAACATGATGGAAGACCTGACACGCGGCAAGATCTCGCAGACCGACGAGAGCGCGT<br>TTGAGGTCGGCCGCAATGTCGCGGTGACCGAAGGCGCCGTGGTCTTCGAGAACGAGTACTTCCAGCTG<br>TTGCAGTACAAGCCGCTGACCGACAAGGTGCACGCGCGCCCGCTGCTGATGGTGCCGCCGTGCATCAA<br>CAAGTACTACATCCTGGACCTGCAGCCGGAGAGCTCGCTGGTGCGCCATGTGGTGGAGCAGGGACAT<br>ACGGTGTTTCTGGTGTCGTGGCGCAATCCGGACGCCAGCATGGCCGGCAGCACCTGGGACGACTACAT<br>CGAGCACGCGGCCATCCGCGCCATCGAAGTCGCGCGCGACATCAGCGGCCAGGACAAGATCAACGTG<br>CTCGGCTTCTGCGTGGGCGGCACCATTGTCTCGACCGCGCTGGCGGTGCTGGCCGCGCGCGGCGAGCA<br>CCCGGCCGCCAGCGTCACGCTGCTGACCACGCTGCTGGACTTTGCCGACACGGGCATCCTCGACGTCT<br>TTGTCGACGAGGGCCATGTGCAGTTGCGCGAGGCCACGCTGGGCGGCGGCGCCGGCGCGCCGTGCGC |

TABLE 3D-continued

Nucleic Acid Sequences: Regulatory Elements and Cassettes

| SEQ ID NO | Nucleotide Sequence |
|---|---|
| | GCTGCTGCGCGGCCTTGAGCTGGCCAATACCTTCTCGTTCTTGCGCCCGAACGACCTGGTGTGGAACT<br>ACGTGGTCGACAACTACCTGAAGGGCAACACGCCGGTGCCGTTCGACCTGCTGTTCTGGAACGGCGAC<br>GCCACCAACCTGCCGGGGCCGTGGTACTGCTGGTACCTGCGCCACACCTACCTGCAGAACGAGCTCAA<br>GGTACCGGGCAAGCTGACCGTGTGCGGCGTGCCGGTGGACCTGGCCAGCATCGACGTGCCGACCTAT<br>ATCTACGGCTCGCGCGAAGACCATATCGTGCCGTGGACCGCGGCCTATGCCTCGACCGCGCTGCTGGC<br>GAACAAGCTGCGCTTCGTGCTGGGTGCGTCGGGCCATATCGCCGGTGTGATCAACCCGCCGGCCAAGA<br>ACAAGCGCAGCCACTGGACTAACGATGCGCTGCCGGAGTCGCCGCAGCAATGGCTGGCCGGCGCCAT<br>CGAGCATCACGGCAGCTGGTGGCCGGACTGGACCGCATGGCTGGCCGGGCAGGCCGGCGCGAAACGC<br>GCCGCGCCCGCCAACTATGGCAATGCGCGCTATCGCGCAATCGAACCCGCGCCTGGGCGATACGTCA<br>AAGCCAAGGCATGAGCTAGCATTAACTTTAAAAAGGAGGATAAGATAATGACTGACGTTGTCATCGT<br>ATCCGCCGCCCGCACCGCGGTCGGCAAGTTTGGCGGCTCGCTGGCCAAGATCCCGGCACCGGAACTG<br>GGTGCCGTGGTCATCAAGGCCGCGCTGGAGCGCGCCGGCGTCAAGCCGGAGCAGGTGAGCGAAGTCA<br>TCATGGGCCAGGTGCTGACCGCCGGTTCGGGCCAGAACCCCGCACGCCAGGCCGCGATCAAGGCCGG<br>CCTGCCGGCGATGGTGCCGGCCATGACCATCAACAAGGTGTGCGGCTCGGGCCTGAAGGCCGTGATG<br>CTGGCCGCCAACGCGATCATGGCGGGCGACGCCGAGATCGTGGTGGCCGGCGGCCAGGAAAACATGA<br>GCGCCGCCCCGCACGTGCTGCCGGGCTCGCGCGATGGTTTCCGCATGGGCGATGCCAAGCTGGTCGAC<br>ACCATGATCGTCGACGGCCTGTGGGACGTGTACAACCAGTACCACATGGGCATCACCGCCGAGAACG<br>TGGCCAAGGAATACGGCATCACACGCGAGGCGCAGGATGAGTTCGCCGTCGGCTCGCAGAACAAGGC<br>CGAAGCCGCGCAGAAGGCCGGCAAGTTTGACGAAGAGATCGTCCCGGTGCTGATCCCGCAGCGCAAG<br>GGCGACCCGGTGGCCTTCAAGACCGACGAGTTCGTGCGCCAGGGCGCCACGCTGGACAGCATGTCCG<br>GCCTCAAGCCCGCCTTCGACAAGGCCGGCACGGTGACCGCGGCCAACGCCTCGGGCCTGAACGACGG<br>CGCCGCCGCGGTGGTGGTGATGTCGGCGGCCAAGGCCAAGGAACTGGGCCTGACCCCGCTGGCCACG<br>ATCAAGAGCTATGCCAACGCCGGTGTCGATCCCAAGGTGATGGGCATGGGCCCGGTGCCGGCCTCCA<br>AGCGCGCCCTGTCGCGCGCCGAGTGGACCCCGCAAGACCTGGACCTGATGGAGATCAACGAGGCCTT<br>TGCCGCGCAGGCGCTGGCGGTGCACCAGCAGATGGGCTGGGACACCTCCAAGGTCAATGTGAACGGC<br>GGCGCCATCGCCATCGGCCACCCGATCGGCGCGTCGGGCTGCCGTATCCTGGTGACGCTGCTGCACGA<br>GATGAAGCGCCGTGACGCGAAGAAGGGCCTGGCCTCGCTGTGCATCGGCGGCGGCATGGGCGTGGCG<br>CTGGCAGTCGAGCGCAAATAAACCGGTGCAGCCCGCCTAATGAGCGGGCTTTTT |

TABLE 4

Nucleic Acid Sequences: Plasmids

| SEQ ID NO | Nucleotide Sequence |
|---|---|
| SEQ ID NO: 162 nucleic acid sequence for the plasmid pTrc-phaAB:pct(Cp) | GTTTGACAGCTTATCATCGACTGCACGGTGCACCAATGCTTCTGGCGTCAGGCAGCCATCGGAAGCTGTGGTATGGCTGTG<br>CAGGTCGTAAATCACTGCATAATTCGTGTCGCTCAAGGCGCACTCCCGTTCTGGATAATGTTTTTTGCGCCGACATCATAA<br>CGGTTCTGGCAAATATTCTGAAATGAGCTGTTGACAATTAATCATCCGGCTCGTATAATGTGTGGAATTGTGAGCGGATAA<br>CAATTTCACACAGGAAACAGACTGACTGACGTTGTCATCGTATCCGCCGCCCGCACCGCGGTCGGCAAGTTTGGCGGCTC<br>GCTGGCCAAGATCCCGGCACCGGAACTGGGTGCCGTGGTCATCAAGGCCGCGCTGGAGCGCGCCGGCGTCAAGCCGGAG<br>CAGGTGAGCGAAGTCATCATGGGCCAGGTGCTGACCGCCGGTTCGGGCCAGAACCCCGCACGCCAGGCCGCGATCAAGG<br>CCGGCCTGCCGGCGATGGTGCCGGCCATGACCATCAACAAGGTGTGCGGCTCGGGCCTGAAGGCCGTGATGCTGGCCGCC<br>AACGCGATCATGGCGGGCGACGCCGAGATCGTGGTGGCCGGCGGCCAGGAAAACATGAGCGCCGCCCCGCACGTGCTGC<br>CGGGCTCGCGCGATGGTTTCCGCATGGGCGATGCCAAGCTGGTCGACACCATGATCGTCGACGGCCTGTGGGACGTGTAC<br>AACCAGTACCACATGGGCATCACCGCCGAGAACGTGGCCAAGGAATACGGCATCACACGCGAGGCGCAGGATGAGTTCG<br>CCGTCGGCTCGCAGAACAAGGCCGAAGCCGCGCAGAAGGCCGGCAAGTTTGACGAAGAGATCGTCCCGGTGCTGATCCC<br>GCAGCGCAAGGGCGACCCGGTGGCCTTCAAGACCGACGAGTTCGTGCGCCAGGGCGCCACGCTGGACAGCATGTCCGGCC<br>TCAAGCCCGCCTTCGACAAGGCCGGCACGGTGACCGCGGCCAACGCCTCGGGCCTGAACGACGGCGCCGCCGCGGTGGTG<br>GTGATGTCGGCGGCCAAGGCCAAGGAACTGGGCCTGACCCCGCTGGCCACGATCAAGAGCTATGCCAACGCCGGTGTCGA<br>TCCCAAGGTGATGGGCATGGGCCCGGTGCCGGCCTCCAAGCGCGCCCTGTCGCGCGCCGAGTGGACCCCGCAAGACCTGG<br>ACCTGATGGAGATCAACGAGGCCTTTGCCGCGCAGGCGCTGGCGGTGCACCAGCAGATGGGCTGGGACACCTCCAAGGTC<br>AATGTGAACGGCGGCGCCATCGCCATCGGCCACCCGATCGGCGCGTCGGGCTGCCGTATCCTGGTGACGCTGCTGCACGA<br>GATGAAGCGCCGTGACGCGAAGAAGGGCCTGGCCTCGCTGTGCATCGGCGGCGGCATGGGCGTGGCGCTGGCAGTCGAG<br>CGCAAATAAGGAAGGGGTTTTCCGGGGCCGCGCGCGGTTGGCGCGGACCCGGCGACGATAACGAAGCCAATCAAGGAGT<br>GGACATGACTCAGCGCATTGCGTATGTGACCGGCGGCATGGGTGGTATCGGAACCGCCATTTGCCAGCGGCTGGCCAAGG<br>ATGGCTTTCGTGTGGTGGCCGGTTGCGGCCCCAACTCGCCGCGCCGCGAAAAGTGGCTGGAGCAGCAGAAGGCCCTGGGC<br>TTCGATTTCATTGCCTCGGAAGGCAATGTGGCTGACTGGGACTCGACCAAGACCGCATTCGACAAGGTCAAGTCCGAGGT<br>CGGCGAGGTTGATGTGCTGATCAACAACGCCGGTATCACCCGCGACGTGGTGTTCCGCAAGATGACCCGCGCCGACTGGG<br>ATGCGGTGATCGACACCAACCTGACCTCGCTGTTCAACGTCACCAAGCAGGTGATCGACGGCATGGCCGACCGTGGCTGG<br>GGCCGCATCGTCAACATCTCGTCGGTGAACGGGCAGAAGGGCCAGTTCGGCCAGACCAACTACTCCACCGCCAAGGCCGG<br>CCTGCATGGCTTCACCATGGCACTGGCGCAGGAAGTGGCGACCAAGGGCGTGACCGTCAACACGGTCTCTCCGGGCTATA<br>TCGCCACCGACATGGTCAAGGCGATCCGCCAGGACGTGCTCGACAAGATCGTCGCGACGATCCCGGTCAAGCGCCTGGGC<br>CTGCCGGAAGAGATCGCCTCGATCTGCGCCTGGTTGTCGTCGGAGGAGTCCGGTTTCTCGACCGGCGCCGACTTCTCGCTC<br>AACGGCGGCCTGCATATGGGCTGAGCTAGCAAAGGAGGTAAAGATAATGAGAAAGGTTCCCATTATTACCGCAGATGAG<br>GCTGCAAAGCTTATTAAAGACGGTGATACAGTTACAACAAGTGGTTTCGTTGGAAATGCAATCCCTGAGGCTCTTGATAG<br>AGCTGTAGAAAAAAGATTCTTAGAAACAGGCGAACCCAAAAACATTACATATGTTTATTGTGGTTCTCAAGGTAACAGAG<br>ACGGAAGAGGTGCTGAGCACTTTGCTCATGAAGGCCTTTTAAAACGTTACATCGCTGGTCACTGGGCTACAGTTCCTGCTT<br>TGGGTAAAATGGCTATGGAAAATAAAATGGAAGCATATAATGTATCTCAGGGTGCATTGTGTCATTTGTTCCGTGATATAG<br>CTTCTCATAAGCCAGGCGTATTTACAAAGGTAGGTATCGGTACTTTCATTGACCCCAGAAATGGCGGCGGTAAAGTAAAT<br>GATATTACCAAAGAAGATATTGTTGAATTGGTAGAGATTAAGGGTCAGGAATATTTATTCTACCCTGCTTTTCCTATTCAT<br>GTAGCTCTTATTCGTGGTACTTACGCTGATGAAAGCGGAAATATCACATTTGAGAAAGAAGTTGCTCCTCTGGAAGGAACT<br>TCAGTATGCCAGGCTGTTAAAAACAGTGGCGGTATCGTTGTAGTTCAGGTTGAAAGAGTAGTAAAAGCTGGTACTCTTGA |

TABLE 4-continued

| Nucleic Acid Sequences: Plasmids | |
|---|---|
| SEQ ID NO | Nucleotide Sequence |
| | CCCTCGTCATGTAAAAGTTCCAGGAATTTATGTTGACTATGTTGTTGTTGCTGACCCAGAAGATCATCAGCAATCTTTAGAT<br>TGTGAATATGATCCTGCATTATCAGGCGAGCATAGAAGACCTGAAGTTGTTGGAGAACCACTTCCTTTGAGTGCAAAGAA<br>AGTTATTGGTCGTCGTGGTGCCATTGAATTAGAAAAAGATGTTGCTGTAAATTTAGGTGTTGGTGCGCCTGAATATGTAGC<br>AAGTGTTGCTGATGAAGAAGGTATCGTTGATTTTATGACTTTAACTGCTGAAAGTGGTGCTATTGGTGGTGTTCCTGCTGG<br>TGGCGTTCGCTTTGGTGCTTCTTATAATGCGGATGCATTGATCGATCAAGGTTATCAATTCGATTACTATGATGGCGGCGG<br>CTTAGACCTTTGCTATTTAGGCTTAGCTGAATGCGATGAAAAAGGCAATATCAACGTTTCAAGATTTGGCCCTCGTATCGC<br>TGGTTGTGGTGGTTTCATCAACATTACACAGAATACACCTAAGGTATTCTTCTGTGGTACTTTCACAGCAGGTGGCTTAAA<br>GGTTAAAATTGAAGATGGCAAGGTTATTATTGTTCAAGAAGGCAAGCAGAAAAAATTCTTGAAAGCTGTTGAGCAGATTA<br>CATTCAATGGTGACGTTGCACTTGCTAATAAGCAACAAGTAACTTATATTACAGAAAGATGCGTATTCCTTTTGAAGGAAG<br>ATGGTTTGCACTTATCTGAAATTGCACCTGGTATTGATTTGCAGACACAGATTCTTGACGTTATGGATTTTGCACCTATTAT<br>TGACAGAGATGCAAACGGCCAAATCAAATTGATGGACGCTGCTTTGTTTGCAGAAGGCTTAATGGGTCTGAAGGAAATGA<br>AGTCCTGAGCGAGAGTAGGGAACTGCCAGGCATCAAATAAAACGAAAGGCTCAGTCGAAAGACTGGGCCTTTCGTTTTAT<br>CTGTTGTTTGTCGGTGAACGCTCTCCTGAGTAGGACAAATCCGCCGGGAGCGGATTTGAACGTTGCGAAGCAACGGCCCG<br>GAGGGTGGCGGGCAGGACGCCCGCCATAAACTGCCAGGCATCAAATTAAGCAGAAGGCCATCCTGACGGATGGCCTTTTT<br>GCGTTTCTACAAACTCTTTTTGTTTATTTTTCTAAATACATTCAAATATGTATCCGCTCATGAGACAATAACCCTGATAAAT<br>GCTTCAATAATATTGAAAAAGGAAGAGTATGAGTATTCAACATTTCCGTGTCGCCCTTATTCCCTTTTTTGCGGCATTTTGC<br>CTTCCTGTTTTTGCTCACCCAGAAACGCTGGTGAAAGTAAAAGATGCTGAAGATCAGTTGGGTGCACGAGTGGGTTACATC<br>GAACTGGATCTCAACAGCGGTAAGATCCTTGAGAGTTTTCGCCCCGAAGAACGTTTTCCAATGATGAGCACTTTTAAAGTT<br>CTGCTATGTGGCGCGGTATTATCCCGTGTTGACGCCGGGCAAGAGCAACTCGGTCGCCGCATACACTATTCTCAGAATGAC<br>TTGGTTGAGTACTCACCAGTCACAGAAAAGCATCTTACGGATGGCATGACAGTAAGAGAATTATGCAGTGCTGCCATAAC<br>CATGAGTGATAACACTGCGGCCAACTTACTTCTGACAACGATCGGAGGACCGAAGGAGCTAACCGCTTTTTTGCACAACA<br>TGGGGGATCATGTAACTCGCCTTGATCGTTGGGAACCGGAGCTGAATGAAGCCATACCAAACGACGAGCGTGACACCACG<br>ATGCCTACAGCAATGGCAACAACGTTGCGCAAACTATTAACTGGCGAACTACTTACTCTAGCTTCCCGGCAACAATTAATA<br>GACTGGATGGAGGCGGATAAAGTTGCAGGACCACTTCTGCGCTCGGCCCTTCCGGCTGGCTGGTTTATTGCTGATAAATCT<br>GGAGCCGGTGAGCGTGGGTCTCGCGGTATCATTGCAGCACTGGGGCCAGATGGTAAGCCCTCCCGTATCGTAGTTATCTAC<br>ACGACGGGGAGTCAGGCAACTATGGATGAACGAAATAGACAGATCGCTGAGATAGGTGCCTCACTGATTAAGCATTGGTA<br>ACTGTCAGACCAAGTTTACTCATATATACTTTAGATTGATTTAAAACTTCATTTTTAATTTAAAAGGATCTAGGTGAAGATC<br>CTTTTTGATAATCTCATGACCAAAATCCCTTAACGTGAGTTTTCGTTCCACTGAGCGTCAGACCCCGTAGAAAAGATCAAA<br>GGATCTTCTTGAGATCCTTTTTTTCTGCGCGTAATCTGCTGCTTGCAAACAAAAAAACCACCGCTACCAGCGGTGGTTTGTT<br>TGCCGGATCAAGAGCTACCAACTCTTTTTCCGAAGGTAACTGGCTTCAGCAGAGCGCAGATACCAAATACTGTCCTTCTAG<br>TGTAGCCGTAGTTAGGCCACCACTTCAAGAACTCTGTAGCACCGCCTACATACCTCGCTCTGCTAATCCTGTTACCAGTGG<br>CTGCTGCCAGTGGCGATAAGTCGTGTCTTACCGGGTTGGACTCAAGACGATAGTTACCGGATAAGGCGCAGCGGTCGGGC<br>TGAACGGGGGGTTCGTGCACACAGCCCAGCTTGGAGCGAACGACCTACACCGAACTGAGATACCTACAGCGTGAGCTATG<br>AGAAAGCGCCACGCTTCCCGAAGGGAGAAAGGCGGACAGGTATCCGGTAAGCGGCAGGGTCGGAACAGGAGAGCGCAC<br>GAGGGAGCTTCCAGGGGGAAACGCCTGGTATCTTTATAGTCCTGTCGGGTTTCGCCACCTCTGACTTGAGCGTCGATTTTT<br>GTGATGCTCGTCAGGGGGGCGGAGCCTATGGAAAAACGCCAGCAACGCGGCCTTTTTACGGTTCCTGGCCTTTTGCTGGCC<br>TTTTGCTCACATGTTCTTTCCTGCGTTATCCCCTGATTCTGTGGATAACCGTATTACCGCCTTTGAGTGAGCTGATACCGCTC<br>GCCGCAGCCGAACGACCGAGCGCAGCGAGTCAGTGAGCGAGGAAGCGGAAGAGCGCCTGATGCGGTATTTTCTCCTTACG<br>CATCTGTGCGGTATTTCACACCGCATATGGTGCACTCTCAGTACAATCTGCTCTGATGCCGCATAGTTAAGCCAGTATACA<br>CTCCGCTATCGCTACGTGACTGGGTCATGGCTGCGCCCCGACACCCGCCAACACCCGCTGACGCGCCCTGACGGGCTTGTC<br>TGCTCCCGGCATCCGCTTACAGACAAGCTGTGACCGTCTCCGGGAGCTGCATGTGTCAGAGGTTTTCACCGTCATCACCGA<br>AACGCGCGAGGCAGCAGATCAATTCGCGCGCGAAGGCGAAGCGGCATGCATTTACGTTGACACCATCGAATGGTGCAAA<br>ACCTTTCGCGGTATGGCATGATAGCGCCCGGAAGAGAGTCAATTCAGGGTGGTGAATGTGAAACCAGTAACGTTATACGA<br>TGTCGCAGAGTATGCCGGTGTCTCTTATCAGACCGTTTCCCGCGTGGTGAACCAGGCCAGCCACGTTTCTGCGAAAACGCG<br>GGAAAAAGTGGAAGCGGCGATGGCGGAGCTGAATTACATTCCCAACCGCGTGGCACAACAACTGGCGGGCAAACAGTCG<br>TTGCTGATTGGCGTTGCCACCTCCAGTCTGGCCCTGCACGCGCCGTCGCAAATTGTCGCGGCGATTAAATCTCGCGCCGAT<br>CAACTGGGTGCCAGCGTGGTGGTGTCGATGGTAGAACGAAGCGGCGTCGAAGCCTGTAAAGCGGCGGTGCACAATCTTCT<br>CGCGCAACGCGTCAGTGGGCTGATCATTAACTATCCGCTGGATGACCAGGATGCCATTGCTGTGGAAGCTGCCTGCACTA<br>ATGTTCCGGCGTTATTTCTTGATGTCTCTGACCAGACACCCATCAACAGTATTATTTTCTCCCATGAAGACGGTACGCGACT<br>GGGCGTGGAGCATCTGGTCGCATTGGGTCACCAGCAAATCGCGCTGTTAGCGGGCCCATTAAGTTCTGTCTCGGCGCGTCT<br>GCGTCTGGCTGGCTGGCATAAATATCTCACTCGCAATCAAATTCAGCCGATAGCGGAACGGGAAGGCGACTGGAGTGCCA<br>TGTCCGGTTTTCAACAAACCATGCAAATGCTGAATGAGGGCATCGTTCCCACTGCGATGCTGGTTGCCAACGATCAGATGG<br>CGCTGGGCGCAATGCGCGCCATTACCGAGTCCGGGCTGCGCGTTGGTGCGGATATCTCGGTAGTGGGATACGACGATACC<br>GAAGACAGCTCATGTTATATCCCGCCGTTAACCACCATCAAACAGGATTTTCGCCTGCTGGGGCAAACCAGCGTGGACCG<br>CTTGCTGCAACTCTCTCAGGGCCAGGCGGTGAAGGGCAATCAGCTGTTGCCCGTCTCACTGGTGAAAAGAAAAACCACCC<br>TGGCGCCCAATACGCAAACCGCCTCTCCCCGCGCGTTGGCCGATTCATTAATGCAGCTGGCACGACAGGTTTCCCGACTGG<br>AAAGCGGGCAGTGAGCGCAACGCAATTAATGTGAGTTAGCGCGAATTGATCTG |
| SEQ ID NO: 163 nucleic acid sequence for the plasmid pTrc-phaAB:pct(Me) | GTTTGACAGCTTATCATCGACTGCACGGTGCACCAATGCTTCTGGCGTCAGGCAGCCATCGGAAGCTGTGGTATGGCTGTG<br>CAGGTCGTAAATCACTGCATAATTCGTGTCGCTCAAGGCGCACTCCCGTTCTGGATAATGTTTTTTGCGCCGACATCATAA<br>CGGTTCTGGCAAATATTCTGAAATGAGCTGTTGACAATTAATCATCCGGCTCGTATAATGTGTGGAATTGTGAGCGGATAA<br>CAATTTCACACAGGAAACAGACTGACTGACGTTGTCATCGTATCCGCCGCCCGCACCGCGGTCGGCAAGTTTGGCGGCTC<br>GCTGGCCAAGATCCCGGCACCGGAACTGGGTGCCGTGGTCATCAAGGCCGCGCTGGAGCGCGCCGGCGTCAAGCCGGAG<br>CAGGTGAGCGAAGTCATCATGGGCCAGGTGCTGACCGCCGGTTCGGGCCAGAACCCCGCACGCCAGGCCGCGATCAAGG<br>CCGGCCTGCCGGCGATGGTGCCGGCCATGACCATCAACAAGGTGTGCGGCTCGGGCCTGAAGGCCGTGATGCTGGCCGCC<br>AACGCGATCATGGCGGGCGACGCCGAGATCGTGGTGGCCGGCGGCCAGGAAAACATGAGCGCCGCCCCGCACGTGCTGC<br>CGGGCTCGCGCGATGGTTTCCGCATGGGCGATGCCAAGCTGGTCGACACCATGATCGTCGACGGCCTGTGGGACGTGTAC<br>AACCAGTACCACATGGGCATCACCGCCGAGAACGTGGCCAAGGAATACGGCATCACACGCGAGGCGCAGGATGAGTTCG<br>CCGTCGGCTCGCAGAACAAGGCCGAAGCCGCGCAGAAGGCCGGCAAGTTTGACGAAGAGATCGTCCCGGTGCTGATCCC<br>GCAGCGCAAGGGCGACCCGGTGGCCTTCAAGACCGACGAGTTCGTGCGCCAGGGCGCCACGCTGGACAGCATGTCCGGCC<br>TCAAGCCCGCCTTCGACAAGGCCGGCACGGTGACCGCGGCCAACGCCTCGGGCCTGAACGACGGCGCCGCCGCGGTGGTG<br>GTGATGTCGGCGGCCAAGGCCAAGGAACTGGGCCTGACCCCGCTGGCCACGATCAAGAGCTATGCCAACGCCGGTGTCGA<br>TCCCAAGGTGATGGGCATGGGCCCGGTGCCGGCCTCCAAGCGCGCCCTGTCGCGCGCCGAGTGGACCCCGCAAGACCTGG<br>ACCTGATGGAGATCAACGAGGCCTTTGCCGCGCAGGCGCTGGCGGTGCACCAGCAGATGGGCTGGGACACCTCCAAGGTC<br>AATGTGAACGGCGGCGCCATCGCCATCGGCCACCCGATCGGCGCGTCGGGCTGCCGTATCCTGGTGACGCTGCTGCACGA |

TABLE 4-continued

Nucleic Acid Sequences: Plasmids

| SEQ ID NO | Nucleotide Sequence |
|---|---|
| | GATGAAGCGCCGTGACGCGAAGAAGGGCCTGGCCTCGCTGTGCATCGGCGGCGGCATGGGCGTGGCGCTGGCAGTCGAG<br>CGCAAATAAGGAAGGGGTTTTCCGGGGCCGCGCGCGGTTGGCGCGGACCCGGCGACGATAACGAAGCCAATCAAGGAGT<br>GGACATGACTCAGCGCATTGCGTATGTGACCGGCGGCATGGGTGGTATCGGAACCGCCATTTGCCAGCGGCTGGCCAAGG<br>ATGGCTTTCGTGTGGTGGCCGGTTGCGGCCCCAACTCGCCGCGCCGCGAAAAGTGGCTGGAGCAGCAGAAGGCCCTGGGC<br>TTCGATTTCATTGCCTCGGAAGGCAATGTGGCTGACTGGGACTCGACCAAGACCGCATTCGACAAGGTCAAGTCCGAGGT<br>CGGCGAGGTTGATGTGCTGATCAACAACGCCGGTATCACCCGCGACGTGGTGTTCCGCAAGATGACCCGCGCCGACTGGG<br>ATGCGGTGATCGACACCAACCTGACCTCGCTGTTCAACGTCACCAAGCAGGTGATCGACGGCATGGCCGACCGTGGCTGG<br>GGCCGCATCGTCAACATCTCGTCGGTGAACGGGCAGAAGGGCCAGTTCGGCCAGACCAACTACTCCACCGCCAAGGCCGG<br>CCTGCATGGCTTCACCATGGCACTGGCGCAGGAAGTGGCGACCAAGGGCGTGACCGTCAACACGGTCTCTCCGGGCTATA<br>TCGCCACCGACATGGTCAAGGCGATCCGCCAGGACGTGCTCGACAAGATCGTCGCGACGATCCCGGTCAAGCGCCTGGGC<br>CTGCCGGAAGAGATCGCCTCGATCTGCGCCTGGTTGTCGTCGGAGGAGTCCGGTTTCTCGACCGGCGCCGACTTCTCGCTC<br>AACGGCGGCCTGCATATGGGCTGAGCTAGCAAAGGAGGTAAAGATAATGAGAAAAGTAGAAATCATTACAGCTGAACAA<br>GCAGCTCAGCTCGTAAAAGACAACGACACGATTACGTCTATCGGCTTTGTCAGCAGCGCCCATCCGGAAGCACTGACCAA<br>AGCTTTGGAAAAACGGTTCCTGGACACGAACACCCCGCAGAACTTGACCTACATCTATGCAGGCTCTCAGGGCAAACGCG<br>ATGGCCGTGCCGCTGAACATCTGGCACACACAGGCCTTTTGAAACGCGCCATCATCGGTCACTGGCAGACTGTACCGGCT<br>ATCGGTAAACTGGCTGTCGAAAACAAGATTGAAGCTTACAACTTCTCGCAGGGCACGTTGGTCCACTGGTTCCGCGCCTTG<br>GCAGGTCATAAGCTCGGCGTCTTCACCGACATCGGTCTGGAAACTTTCCTCGATCCCCGTCAGCTCGGCGGCAAGCTCAAT<br>GACGTAACCAAAGAAGACCTCGTCAAACTGATCGAAGTCGATGGTCATGAACAGCTTTTCTACCCGACCTTCCCGGTCAA<br>CGTAGCTTTCCTCCGCGGTACGTATGCTGATGAATCCGGCAATATCACCATGGACGAAGAAATCGGGCCTTTCGAAAGCA<br>CTTCCGTAGCCCAGGCCGTTCACAACTGTGGCGGTAAAGTCGTCGTCCAGGTCAAAGACGTCGTCGCTCACGGCAGCCTCG<br>ACCCGCGCATGGTCAAGATCCCTGGCATCTATGTCGACTACGTCGTCGTAGCAGCTCCGGAAGACCATCAGCAGACGTAT<br>GACTGCGAATACGATCCGTCCCTCAGCGGTGAACATCGTGCTCCTGAAGGCGCTACCGATGCAGCTCTCCCCATGAGCGCT<br>AAGAAAATCATCGGCCGCCGCGGCGCTTTGGAATTGACTGAAAACGCTGTCGTCAACCTCGGCGTCGGTGCTCCGGAATA<br>CGTTGCTTCTGTTGCCGGTGAAGAAGGTATCGCCGATACCATTACCCTGACCGTCGAAGGTGGCGCCATCGGTGGCGTACC<br>GCAGGGCGGTGCCCGCTTCGGTTCGTCCCGCAATGCCGATGCCATCATCGACCACACCTATCAGTTCGACTTCTACGATGG<br>CGGCGGTCTGGACATCGCTTACCTCGGCCTGGCCCAGTGCGATGGCTCGGGCAACATCAACGTCAGCAAGTTCGGTACTA<br>ACGTTGCCGGCTGCGGCGGTTTCCCCAACATTTCCCAGCAGACACCGAATGTTTACTTCTGCGGCACCTTCACGGCTGGCG<br>GCTTGAAAATCGCTGTCGAAGACGGCAAAGTCAAGATCCTCCAGGAAGGCAAAGCCAAGAAGTTCATCAAAGCTGTCGA<br>CCAGATCACTTTCAACGGTTCCTATGCAGCCCGCAACGGCAAACACGTTCTCTACATCACAGAACGCTGCGTATTTGAACT<br>GACCAAAGAAGGCTTGAAACTCATCGAAGTCGCACCGGGCATCGATATTGAAAAAGATATCCTCGCTCACATGGACTTCA<br>AGCCGATCATTGATAATCCGAAACTCATGGATGCCCGCCTCTTCCAGGACGGTCCCATGGGACTGAAAAAATAAGCGAGA<br>GTAGGGAACTGCCAGGCATCAAATAAAACGAAAGGCTCAGTCGAAAGACTGGGCCTTTCGTTTTATCTGTTGTTTGTCGGT<br>GAACGCTCTCCTGAGTAGGACAAATCCGCCGGGAGCGGATTTGAACGTTGCGAAGCAACGGCCCGGAGGGTGGCGGGCA<br>GGACGCCCGCCATAAACTGCCAGGCATCAAATTAAGCAGAAGGCCATCCTGACGGATGGCCTTTTTGCGTTTCTACAAACT<br>CTTTTTGTTTATTTTTCTAAATACATTCAAATATGTATCCGCTCATGAGACAATAACCCTGATAAATGCTTCAATAATATTG<br>AAAAAGGAAGAGTATGAGTATTCAACATTTCCGTGTCGCCCTTATTCCCTTTTTTGCGGCATTTTGCCTTCCTGTTTTTGCTC<br>ACCCAGAAACGCTGGTGAAAGTAAAAGATGCTGAAGATCAGTTGGGTGCACGAGTGGGTTACATCGAACTGGATCTCAAC<br>AGCGGTAAGATCCTTGAGAGTTTTCGCCCCGAAGAACGTTTTCCAATGATGAGCACTTTTAAAGTTCTGCTATGTGGCGCG<br>GTATTATCCCGTGTTGACGCCGGGCAAGAGCAACTCGGTCGCCGCATACACTATTCTCAGAATGACTTGGTTGAGTACTCA<br>CCAGTCACAGAAAAGCATCTTACGGATGGCATGACAGTAAGAGAATTATGCAGTGCTGCCATAACCATGAGTGATAACAC<br>TGCGGCCAACTTACTTCTGACAACGATCGGAGGACCGAAGGAGCTAACCGCTTTTTTGCACAACATGGGGGATCATGTAA<br>CTCGCCTTGATCGTTGGGAACCGGAGCTGAATGAAGCCATACCAAACGACGAGCGTGACACCACGATGCCTACAGCAATG<br>GCAACAACGTTGCGCAAACTATTAACTGGCGAACTACTTACTCTAGCTTCCCGGCAACAATTAATAGACTGGATGGAGGC<br>GGATAAAGTTGCAGGACCACTTCTGCGCTCGGCCCTTCCGGCTGGCTGGTTTATTGCTGATAAATCTGGAGCCGGTGAGCG<br>TGGGTCTCGCGGTATCATTGCAGCACTGGGGCCAGATGGTAAGCCCTCCCGTATCGTAGTTATCTACACGACGGGGAGTCA<br>GGCAACTATGGATGAACGAAATAGACAGATCGCTGAGATAGGTGCCTCACTGATTAAGCATTGGTAACTGTCAGACCAAG<br>TTTACTCATATATACTTTAGATTGATTTAAAACTTCATTTTTAATTTAAAAGGATCTAGGTGAAGATCCTTTTTGATAATCT<br>CATGACCAAAATCCCTTAACGTGAGTTTTCGTTCCACTGAGCGTCAGACCCCGTAGAAAAGATCAAAGGATCTTCTTGAGA<br>TCCTTTTTTTCTGCGCGTAATCTGCTGCTTGCAAACAAAAAAACCACCGCTACCAGCGGTGGTTTGTTTGCCGGATCAAGA<br>GCTACCAACTCTTTTTCCGAAGGTAACTGGCTTCAGCAGAGCGCAGATACCAAATACTGTCCTTCTAGTGTAGCCGTAGTT<br>AGGCCACCACTTCAAGAACTCTGTAGCACCGCCTACATACCTCGCTCTGCTAATCCTGTTACCAGTGGCTGCTGCCAGTGG<br>CGATAAGTCGTGTCTTACCGGGTTGGACTCAAGACGATAGTTACCGGATAAGGCGCAGCGGTCGGGCTGAACGGGGGGTT<br>CGTGCACACAGCCCAGCTTGGAGCGAACGACCTACACCGAACTGAGATACCTACAGCGTGAGCTATGAGAAAGCGCCAC<br>GCTTCCCGAAGGGAGAAAGGCGGACAGGTATCCGGTAAGCGGCAGGGTCGGAACAGGAGAGCGCACGAGGGAGCTTCCA<br>GGGGGAAACGCCTGGTATCTTTATAGTCCTGTCGGGTTTCGCCACCTCTGACTTGAGCGTCGATTTTTGTGATGCTCGTCAG<br>GGGGGCGGAGCCTATGGAAAAACGCCAGCAACGCGGCCTTTTTACGGTTCCTGGCCTTTTGCTGGCCTTTTGCTCACATGT<br>TCTTTCCTGCGTTATCCCCTGATTCTGTGGATAACCGTATTACCGCCTTTGAGTGAGCTGATACCGCTCGCCGCAGCCGAAC<br>GACCGAGCGCAGCGAGTCAGTGAGCGAGGAAGCGGAAGAGCGCCTGATGCGGTATTTTCTCCTTACGCATCTGTGCGGTA<br>TTTCACACCGCATATGGTGCACTCTCAGTACAATCTGCTCTGATGCCGCATAGTTAAGCCAGTATACACTCCGCTATCGCT<br>ACGTGACTGGGTCATGGCTGCGCCCCGACACCCGCCAACACCCGCTGACGCGCCCTGACGGGCTTGTCTGCTCCCGGCATC<br>CGCTTACAGACAAGCTGTGACCGTCTCCGGGAGCTGCATGTGTCAGAGGTTTTCACCGTCATCACCGAAACGCGCGAGGC<br>AGCAGATCAATTCGCGCGCGAAGGCGAAGCGGCATGCATTTACGTTGACACCATCGAATGGTGCAAAACCTTTCGCGGTA<br>TGGCATGATAGCGCCCGGAAGAGAGTCAATTCAGGGTGGTGAATGTGAAACCAGTAACGTTATACGATGTCGCAGAGTAT<br>GCCGGTGTCTCTTATCAGACCGTTTCCCGCGTGGTGAACCAGGCCAGCCACGTTTCTGCGAAAACGCGGGAAAAAGTGGA<br>AGCGGCGATGGCGGAGCTGAATTACATTCCCAACCGCGTGGCACAACAACTGGCGGGCAAACAGTCGTTGCTGATTGGCG<br>TTGCCACCTCCAGTCTGGCCCTGCACGCGCCGTCGCAAATTGTCGCGGCGATTAAATCTCGCGCCGATCAACTGGGTGCCA<br>GCGTGGTGGTGTCGATGGTAGAACGAAGCGGCGTCGAAGCCTGTAAAGCGGCGGTGCACAATCTTCTCGCGCAACGCGTC<br>AGTGGGCTGATCATTAACTATCCGCTGGATGACCAGGATGCCATTGCTGTGGAAGCTGCCTGCACTAATGTTCCGGCGTTA<br>TTTCTTGATGTCTCTGACCAGACACCCATCAACAGTATTATTTTCTCCCATGAAGACGGTACGCGACTGGGCGTGGAGCAT<br>CTGGTCGCATTGGGTCACCAGCAAATCGCGCTGTTAGCGGGCCCATTAAGTTCTGTCTCGGCGCGTCTGCGTCTGGCTGGC<br>TGGCATAAATATCTCACTCGCAATCAAATTCAGCCGATAGCGGAACGGGAAGGCGACTGGAGTGCCATGTCCGGTTTTCA<br>ACAAACCATGCAAATGCTGAATGAGGGCATCGTTCCCACTGCGATGCTGGTTGCCAACGATCAGATGGCGCTGGGCGCAA<br>TGCGCGCCATTACCGAGTCCGGGCTGCGCGTTGGTGCGGATATCTCGGTAGTGGGATACGACGATACCGAAGACAGCTCA<br>TGTTATATCCCGCCGTTAACCACCATCAAACAGGATTTTCGCCTGCTGGGGCAAACCAGCGTGGACCGCTTGCTGCAACTC<br>TCTCAGGGCCAGGCGGTGAAGGGCAATCAGCTGTTGCCCGTCTCACTGGTGAAAAGAAAAACCACCCTGGCGCCCAATAC |

TABLE 4-continued

| Nucleic Acid Sequences: Plasmids | |
|---|---|
| SEQ ID NO | Nucleotide Sequence |
| | GCAAACCGCCTCTCCCCGCGCGTTGGCCGATTCATTAATGCAGCTGGCACGACAGGTTTCCCGACTGGAAAGCGGGCAGT<br>GAGCGCAACGCAATTAATGTGAGTTAGCGCGAATTGATCTG |
| SEQ ID NO: 164 nucleic acid sequence for the plasmid pK-lvaE:tesB | ATGATGGTTCCAACCCTCGAACACGAGCTTGCTCCCAACGAAGCCAACCATGTCCCGCTGTCGCCGCTGTCGTTCCTCAAG<br>CGTGCCGCGCAGGTGTACCCGCAGCGCGATGCGGTGATCTATGGCGCAAGGCGCTACAGCTACCGTCAGTTGCACGAGCG<br>CAGCCGCGCCCTGGCCAGTGCCTTGGAGCGGGTCGGTGTTCAGCCGGGCGAGCGGGTGGCGATATTGGCGCCGAACATCC<br>CGGAAATGCTCGAGGCCCACTATGGCGTGCCCGGTGCCGGGGCGGTGCTGGTGTGCATCAACATCCGCCTGGAGGGGCGC<br>AGCATTGCCTTCATCCTGCGTCACTGCGCGGCCAAGGTATTGATCTGCGATCGTGAGTTCGGTGCCGTGGCCAATCAGGCG<br>CTGGCCATGCTCGATGCGCCGCCCTTGCTGGTGGGCATCGACGATGATCAGGCCGAGCGCGCCGATTTGGCCCACGACCT<br>GGACTACGAAGCGTTCTTGGCCCAGGGCGACCCCGCGCGGCCGTTGAGTGCGCCACAGAACGAATGGCAGTCGATCGCCA<br>TCAACTACACCTCCGGCACCACGGGGGACCCCAAGGGCGTGGTGCTGCATCACCGCGGCGCCTACCTCAACGCCTGCGCC<br>GGGGCGCTGATCTTCCAGTTGGGGCCGCGCAGCGTCTACTTGTGGACCTTGCCGATGTTCCACTGCAACGGCTGGAGCCAT<br>ACCTGGGCGGTGACGTTGTCCGGTGGCACCCACGTGTGTCTGCGCAAGGTCCAGCCTGATGCGATCAACGCCGCCATCGC<br>CGAGCATGCCGTGACTCACCTGAGCGCCGCCCCAGTGGTGATGTCGATGCTGATCCACGCCGAGCATGCCAGCGCCCCTC<br>CGGTGCCGGTTTCGGTGATCACTGGCGGTGCCGCCCCGCCCAGTGCGGTCATCGCGGCGATGGAGGCGCGTGGCTTCAAC<br>ATCACCCATGCCTATGGCATGACCGAAAGCTACGGTCCCAGCACATTGTGCCTGTGGCAGCCGGGTGTCGACGAGTTGCC<br>GCTGGAGGCCCGGGCCCAGTTCATGAGCCGCCAGGGCGTCGCCCACCCGCTGCTCGAGGAGGCCACGGTGCTGGATACCG<br>ACACCGGCCGCCCGGTCCCGGCCGACGGCCTTACCCTCGGCGAGCTGGTGGTGCGGGGCAACACTGTGATGAAAGGCTAC<br>CTGCACAACCCAGAGGCTACCCGTGCCGCGTTGGCCAACGGCTGGCTGCACACGGGCGACCTGGCCGTGCTGCACCTGGA<br>CGGCTATGTGGAAATCAAGGACCGAGCCAAGGACATCATCATTTCTGGCGGCGAGAACATCAGTTCGCTGGAGATAGAAG<br>AAGTGCTCTACCAGCACCCCGAGGTGGTCGAGGCTGCGGTGGTGGCGCGTCCGGATTCGCGCTGGGGCGAGACACCTCAC<br>GCTTTCGTCACGCTGCGCGCTGATGCACTGGCCAGCGGGGACGACCTGGTCCGCTGGTGCCGTGAGCGTCTGGCGCACTTC<br>AAGGCGCCGCGCCATGTGTCGCTCGTGGACCTGCCCAAGACCGCCACTGGAAAAATACAGAAGTTCGTCCTGCGTGAGTG<br>GGCCCGGCAACAGGAGGCGCAGATCGCCGACGCCGAGCATTGACTCGAGAAAGGAGGATAAGATAATGAGTCAGGCGCT<br>AAAAAATTTACTGACATTGTTAAATCTGGAAAAAATTGAGGAAGGACTCTTTCGCGGCCAGAGTGAAGATTTAGGTTTAC<br>GCCAGGTGTTTGGCGGCCAGGTCGTGGGTCAGGCCTTGTATGCTGCAAAAGAGACCGTCCCTGAAGAGCGGCTGGTACAT<br>TCGTTTCACAGCTACTTTCTTCGCCCTGGCGATAGTAAGAAGCCGATTATTTATGATGTCGAAACGCTGCGTGACGGTAAC<br>AGCTTCAGCGCCCGCCGGGTTGCTGCTATTCAAAACGGCAAACCGATTTTTTATATGACTGCCTCTTTCCAGGCACCAGAA<br>GCGGGTTTCGAACATCAAAAAACAATGCCGTCCGCGCCAGCGCCTGATGGCCTCCCTTCGGAAACGCAAATCGCCCAATC<br>GCTGGCGCACCTGCTGCCGCCAGTGCTGAAAGATAAATTCATCTGCGATCGTCCGCTGGAAGTCCGTCCGGTGGAGTTTCA<br>TAACCCACTGAAAGGTCACGTCGCAGAACCACATCGTCAGGTGTGGATCCGCGCAAATGGTAGCGTGCCGGATGACCTGC<br>GCGTTCATCAGTATCTGCTCGGTTACGCTTCTGATCTTAACTTCCTGCCGGTAGCTCTACAGCCGCACGGCATCGGTTTTCT<br>CGAACCGGGGATTCAGATTGCCACCATTGACCATTCCATGTGGTTCCATCGCCCGTTTAATTTGAATGAATGGCTGCTGTA<br>TAGCGTGGAGAGCACCTCGGCGTCCAGCGCACGTGGCTTTGTGCGCGGTGAGTTTTATACCCAAGACGGCGTACTGGTTGC<br>CTCGACCGTTCAGGAAGGGGTGATGCGTAATCACAATTAATGATTACGAATTCGAGCTCGGTACCCGGGGATCCTCTAGA<br>GTCGACCTGCAGGCATGCAAGCTTGGCACTGGCCGTCGTTTTACAACGTCGTGACTGGGAAAACCCTGGCGTTACCCAACT<br>TAATCGCCTTGCAGCACATCCCCCTTTCGCCAGCTGGCGTAATAGCGAAGAGGCCCGCACCGATCGCCCTTCCCAACAGTT<br>GCGCAGCCTGAATGGCGAATGGCGCGATAAGCTAGCTTCACGCTGCCGCAAGCACTCAGGGCGCAAGGGCTGCTAAAGG<br>AAGCGGAACACGTAGAAAGCCAGTCCGCAGAAACGGTGCTGACCCCGGATGAATGTCAGCTACTGGGCTATCTGGACAA<br>GGGAAAACGCAAGCGCAAAGAGAAAGCAGGTAGCTTGCAGTGGGCTTACATGGCGATAGCTAGACTGGGCGGTTTTATG<br>GACAGCAAGCGAACCGGAATTGCCAGCTGGGGCGCCCTCTGGTAAGGTTGGGAAGCCCTGCAAAGTAAACTGGATGGCTT<br>TCTTGCCGCCAAGGATCTGATGGCGCAGGGGATCAAGATCTGATCAAGAGACAGGATGAGGATCGTTTCGCATGATTGAA<br>CAAGATGGATTGCACGCAGGTTCTCCGGCCGCTTGGGTGGAGAGGCTATTCGGCTATGACTGGGCACAACAGACAATCGG<br>CTGCTCTGATGCCGCCGTGTTCCGGCTGTCAGCGCAGGGGCGCCCGGTTCTTTTTGTCAAGACCGACCTGTCCGGTGCCCT<br>GAATGAACTCCAAGACGAGGCAGCGCGGCTATCGTGGCTGGCCACGACGGGCGTTCCTTGCGCAGCTGTGCTCGACGTTG<br>TCACTGAAGCGGGAAGGGACTGGCTGCTATTGGGCGAAGTGCCGGGGCAGGATCTCCTGTCATCTCACCTTGCTCCTGCCG<br>AGAAAGTATCCATCATGGCTGATGCAATGCGGCGGCTGCATACGCTTGATCCGGCTACCTGCCCATTCGACCACCAAGCG<br>AAACATCGCATCGAGCGAGCACGTACTCGGATGGAAGCCGGTCTTGTCGATCAGGATGATCTGGACGAAGAGCATCAGGG<br>GCTCGCGCCAGCCGAACTGTTCGCCAGGCTCAAGGCGCGGATGCCCGACGGCGAGGATCTCGTCGTGACCCATGGCGATG<br>CCTGCTTGCCGAATATCATGGTGGAAAATGGCCGCTTTTCTGGATTCATCGACTGTGGCCGGCTGGGTGTGGCGGACCGCT<br>ATCAGGACATAGCGTTGGCTACCCGTGATATTGCTGAAGAGCTTGGCGGCGAATGGGCTGACCGCTTCCTCGTGCTTTACG<br>GTATCGCCGCTCCCGATTCGCAGCGCATCGCCTTCTATCGCCTTCTTGACGAGTTCTTCTGAGCGGGACTCTGGGGTTCGCG<br>ATGATAAGCTGTCAAACATGAGAATTACAACTTATATCGTATGGGGCTGACTTCAGGTGCTACATTTGAAGAGATAAATTG<br>CACTGAAATCTAGAAATATTTTATCTGATTAATAAGATGATCTTCTTGAGATCGTTTTGGTCTGCGCGTAATCTCTTGCTCT<br>GAAAACGAAAAAACCGCCTTGCAGGGCGGTTTTTCGAAGGTTCTCTGAGCTACCAACTCTTTGAACCGAGGTAACTGGCTT<br>GGAGGAGCGCAGTCACCAAAACTTGTCCTTTCAGTTTAGCCTTAACCGGCGCATGACTTCAAGACTAACTCCTCTAAATCA<br>ATTACCAGTGGCTGCTGCCAGTGGTGCTTTTGCATGTCTTTCCGGGTTGGACTCAAGACGATAGTTACCGGATAAGGCGCA<br>GCGGTCGGACTGAACGGGGGGTTCGTGCATACAGTCCAGCTTGGAGCGAACTGCCTACCCGGAACTGAGTGTCAGGCGTG<br>GAATGAGACAAACGCGGCCATAACAGCGGAATGACACCGGTAAACCGAAAGGCAGGAACAGGAGAGCGCACGAGGGAG<br>CCGCCAGGGGAAACGCCTGGTATCTTTATAGTCCTGTCGGGTTTCGCCACCACTGATTTGAGCGTCAGATTTCGTGATGCT<br>TGTCAGGGGGGCGGAGCCTATGGAAAAACGGCTTTGCCTTCTTTCCTGCGTTATCCCCTGATTCTGTGGATAACCGTATTA<br>CCGCCTTTGAGTGAGCTGATACCGCTCGCCGCAGCCGAACGACCGAGCGCAGCGAGTCAGTGAGCGAGGAAGCGGAAGA<br>GCGCCCAATACGCAAACCGCCTCTCCCCGCGCGTTGGCCGATTCATTAATGCAGCTGGCACGACAGGTTTCCCGACTGGAA<br>AGCGGGCAGTGAGCGCAACGCAATTAATGTGAGTTAGCTCACTCATTAGGCACCCCAGGCTTTACACTTTATGCTTCCGGC<br>TCGTATGTTGTGTGGAATTGTGAGCGGATAACAATTTCACACAGGAGGAATCAAAA |
| SEQ ID NO: 165 nucleic acid sequence for the plasmid pTrc-PP_2216:H16_RS27940 | GTTTGACAGCTTATCATCGACTGCACGGTGCACCAATGCTTCTGGCGTCAGGCAGCCATCGGAAGCTGTGGTATGGCTGTG<br>CAGGTCGTAAATCACTGCATAATTCGTGTCGCTCAAGGCGCACTCCCGTTCTGGATAATGTTTTTTGCGCCGACATCATAA<br>CGGTTCTGGCAAATATTCTGAAATGAGCTGTTGACAATTAATCATCCGGCTCGTATAATGTGTGGAATTGTGAGCGGATAA<br>CAATTTCACACAGGAGGAATCAAAAATGCTGGTAAATGACGAGCAACAACAGATCGCCGACGCGGTACGTGCGTTCGCCC<br>AGGAACGCCTGAAGCCGTTTGCCGAGCAATGGGACAAGGACCATCGCTTCCCGAAAGAGGCCATCGACGAGATGGCCGA<br>ACTGGGCCTGTTCGGCATGCTGGTGCCGGAGCAGTGGGGCGGTAGCGACACCGGTTATGTGGCCTATGCCATGGCCTTGG<br>AGGAAATCGCTGCGGGCGATGGCGCCTGCTCGACCATCATGAGCGTGCACAACTCGGTGGGTTGCGTGCCGATCCTGCGC<br>TTCGGCAACGAGCAGCAGAAAGAGCAGTTCCTCACCCCGCTGGCGACAGGTGCGATGCTCGGTGCTTTCGCCCTGACCGA<br>GCCGCAGGCTGGCTCCGATGCCAGCAGCCTGAAGACCCGCGCACGCCTGGAAGGCGACCATTACGTGCTCAATGGCAGCA |

TABLE 4-continued

| Nucleic Acid Sequences: Plasmids | |
|---|---|
| SEQ ID NO | Nucleotide Sequence |
| | AGCAGTTCATTACCTCGGGGCAGAACGCCGGCGTAGTGATCGTGTTTGCGGTCACCGACCCGGAGGCCGGCAAGCGTGGC<br>ATCAGCGCCTTCATCGTGCCGACCGATTCGCCGGGCTACCAGGTAGCGCGGGTGGAGGACAAACTCGGCCAGCACGCCTC<br>CGACACCTGCCAGATCGTTTTCGACAATGTGCAAGTGCCAGTGGCCAACCGGCTGGGGGCGGAGGGTGAAGGCTACAAGA<br>TCGCCCTGGCCAACCTTGAAGGCGGCCGTATCGGCATCGCCTCGCAAGCGGTGGGTATGGCCCGCGCGGCGTTCGAAGTG<br>GCGCGGGACTATGCCAACGAGCGCCAGAGCTTTGGCAAACCGCTGATCGAGCACCAGGCCGTGGCGTTTCGCCTGGCCGA<br>CATGGCAACGAAAATTTCCGTTGCCCGGCAGATGGTATTGCACGCCGCTGCCCTTCGTGATGCGGGGCGCCCGGCGCTGGT<br>GGAAGCGTCGATGGCCAAGCTGTTCGCCTCGGAAATGGCCGAAAAGGTCTGTTCGGACGCCTTGCAGACCCTGGGCGGTT<br>ATGGCTATCTGAGTGACTTCCCGCTGGAGCGGATCTACCGCGACGTTCGGGTTTGCCAGATCTACGAAGGCACCAGCGAC<br>ATTCAGCGCATGGTCATTGCGCGCAATCTTTGAGCTAGCAAAGGAGGTAAAGATAATGTACGCAGCTAAGGACATCACCG<br>TGGAGGAGCGCGCCGGCGGCGCGCTATGGATCACGATCGACCGGGCGCAGAAACACAATGCGCTGGCCCGCCACGTGCT<br>GGCGGGATTGGCGCAGGTGGTGAGCGCCGCGGCGGCGCAGCCCGGGGTGCGCTGCATCGTGCTGACCGGCGCCGGCCAG<br>CGCTTCTTTGCGGCAGGCGGCGATCTGGTCGAGCTGTCCGGCGTGCGCGACCGGGAGGCTACGCTGGCCATGAGCGAGCA<br>GGCGCGCGGTGCCCTGGATGCGGTGCGCGACTGCCCGCTGCCGGTGCTGGCCTACCTGAACGGCGATGCCATCGGCGGCG<br>GCGCCGAGCTGGCATTGGCCTGCGACATGCGGCTGCAGTCGGCGAGCGCGCGCATCGGCTTTATCCAGGCGCGGCTGGCC<br>ATCACCTCGGCCTGGGGCGGCGGCCCCGACCTGTGCCGGATCGTCGGCGCGGCGCGGGCCATGCGCATGATGAGCCGTTG<br>CGAGCTTGTCGATGCGCAGCAGGCGCTGCAGTGGGGCTTGGCCGATGCGGTGGTCACGGACGGACCCGCCGGCAAGGAC<br>ATCCACGCCTTCCTGCAACCGCTGCTGGGCTGCGCCCCGCAGGTGCTGCGCGGCATCAAGGCGCAGACCGCGGCCAGCCG<br>GCGCGGCGAGTCGCATGACGCTGCCCGCACCATCGAGCAGCAGCAACTGTTGCATACCTGGCTCCATGCGGACCATTGGA<br>ACGCTGCCGAGGGCATCCTCTCCAGGAGGGCCCAATGAGGCTGTTTTGGCGGATGAGAGAAGATTTTCAGCCTGATACAG<br>ATTAAATCAGAACGCAGAAGCGGTCTGATAAAACAGAATTTGCCTGGCGGCAGTAGCGCGGTGGTCCCACCTGACCCCAT<br>GCCGAACTCAGAAGTGAAACGCCGTAGCGCCGATGGTAGTGTGGGGTCTCCCCATGCGAGAGTAGGGAACTGCCAGGCAT<br>CAAATAAAACGAAAGGCTCAGTCGAAAGACTGGGCCTTTCGTTTTATCTGTTGTTTGTCGGTGAACGCTCTCCTGAGTAGG<br>ACAAATCCGCCGGGAGCGGATTTGAACGTTGCGAAGCAACGGCCCGGAGGGTGGCGGGCAGGACGCCCGCCATAAACTG<br>CCAGGCATCAAATTAAGCAGAAGGCCATCCTGACGGATGGCCTTTTTGCGTTTCTACAAACTCTTTTTGTTTATTTTTCTAA<br>ATACATTCAAATATGTATCCGCTCATGAGACAATAACCCTGATAAATGCTTCAATAATATTGAAAAAGGAAGAGTATGAG<br>TATTCAACATTTCCGTGTCGCCCTTATTCCCTTTTTTGCGGCATTTTGCCTTCCTGTTTTTGCTCACCCAGAAACGCTGGTGA<br>AAGTAAAAGATGCTGAAGATCAGTTGGGTGCACGAGTGGGTTACATCGAACTGGATCTCAACAGCGGTAAGATCCTTGAG<br>AGTTTTCGCCCCGAAGAACGTTTTCCAATGATGAGCACTTTTAAAGTTCTGCTATGTGGCGCGGTATTATCCCGTGTTGACG<br>CCGGGCAAGAGCAACTCGGTCGCCGCATACACTATTCTCAGAATGACTTGGTTGAGTACTCACCAGTCACAGAAAAGCAT<br>CTTACGGATGGCATGACAGTAAGAGAATTATGCAGTGCTGCCATAACCATGAGTGATAACACTGCGGCCAACTTACTTCT<br>GACAACGATCGGAGGACCGAAGGAGCTAACCGCTTTTTTGCACAACATGGGGGATCATGTAACTCGCCTTGATCGTTGGG<br>AACCGGAGCTGAATGAAGCCATACCAAACGACGAGCGTGACACCACGATGCCTACAGCAATGGCAACAACGTTGCGCAA<br>ACTATTAACTGGCGAACTACTTACTCTAGCTTCCCGGCAACAATTAATAGACTGGATGGAGGCGGATAAAGTTGCAGGAC<br>CACTTCTGCGCTCGGCCCTTCCGGCTGGCTGGTTTATTGCTGATAAATCTGGAGCCGGTGAGCGTGGGTCTCGCGGTATCA<br>TTGCAGCACTGGGGCCAGATGGTAAGCCCTCCCGTATCGTAGTTATCTACACGACGGGGAGTCAGGCAACTATGGATGAA<br>CGAAATAGACAGATCGCTGAGATAGGTGCCTCACTGATTAAGCATTGGTAACTGTCAGACCAAGTTTACTCATATATACTT<br>TAGATTGATTTAAAACTTCATTTTTAATTTAAAAGGATCTAGGTGAAGATCCTTTTTGATAATCTCATGACCAAAATCCCTT<br>AACGTGAGTTTTCGTTCCACTGAGCGTCAGACCCCGTAGAAAAGATCAAAGGATCTTCTTGAGATCCTTTTTTTCTGCGCG<br>TAATCTGCTGCTTGCAAACAAAAAAACCACCGCTACCAGCGGTGGTTTGTTTGCCGGATCAAGAGCTACCAACTCTTTTTC<br>CGAAGGTAACTGGCTTCAGCAGAGCGCAGATACCAAATACTGTCCTTCTAGTGTAGCCGTAGTTAGGCCACCACTTCAAG<br>AACTCTGTAGCACCGCCTACATACCTCGCTCTGCTAATCCTGTTACCAGTGGCTGCTGCCAGTGGCGATAAGTCGTGTCTT<br>ACCGGGTTGGACTCAAGACGATAGTTACCGGATAAGGCGCAGCGGTCGGGCTGAACGGGGGGTTCGTGCACACAGCCCA<br>GCTTGGAGCGAACGACCTACACCGAACTGAGATACCTACAGCGTGAGCTATGAGAAAGCGCCACGCTTCCCGAAGGGAG<br>AAAGGCGGACAGGTATCCGGTAAGCGGCAGGGTCGGAACAGGAGAGCGCACGAGGGAGCTTCCAGGGGGAAACGCCTG<br>GTATCTTTATAGTCCTGTCGGGTTTCGCCACCTCTGACTTGAGCGTCGATTTTTGTGATGCTCGTCAGGGGGGCGGAGCCTA<br>TGGAAAAACGCCAGCAACGCGGCCTTTTTACGGTTCCTGGCCTTTTGCTGGCCTTTTGCTCACATGTTCTTTCCTGCGTTAT<br>CCCCTGATTCTGTGGATAACCGTATTACCGCCTTTGAGTGAGCTGATACCGCTCGCCGCAGCCGAACGACCGAGCGCAGCG<br>AGTCAGTGAGCGAGGAAGCGGAAGAGCGCCTGATGCGGTATTTTCTCCTTACGCATCTGTGCGGTATTTCACACCGCATAT<br>GGTGCACTCTCAGTACAATCTGCTCTGATGCCGCATAGTTAAGCCAGTATACACTCCGCTATCGCTACGTGACTGGGTCAT<br>GGCTGCGCCCCGACACCCGCCAACACCCGCTGACGCGCCCTGACGGGCTTGTCTGCTCCCGGCATCCGCTTACAGACAAG<br>CTGTGACCGTCTCCGGGAGCTGCATGTGTCAGAGGTTTTCACCGTCATCACCGAAACGCGCGAGGCAGCAGATCAATTCG<br>CGCGCGAAGGCGAAGCGGCATGCATTTACGTTGACACCATCGAATGGTGCAAAACCTTTCGCGGTATGGCATGATAGCGC<br>CCGGAAGAGAGTCAATTCAGGGTGGTGAATGTGAAACCAGTAACGTTATACGATGTCGCAGAGTATGCCGGTGTCTCTTA<br>TCAGACCGTTTCCCGCGTGGTGAACCAGGCCAGCCACGTTTCTGCGAAAACGCGGGAAAAAGTGGAAGCGGCGATGGCG<br>GAGCTGAATTACATTCCCAACCGCGTGGCACAACAACTGGCGGGCAAACAGTCGTTGCTGATTGGCGTTGCCACCTCCAG<br>TCTGGCCCTGCACGCGCCGTCGCAAATTGTCGCGGCGATTAAATCTCGCGCCGATCAACTGGGTGCCAGCGTGGTGGTGTC<br>GATGGTAGAACGAAGCGGCGTCGAAGCCTGTAAAGCGGCGGTGCACAATCTTCTCGCGCAACGCGTCAGTGGGCTGATCA<br>TTAACTATCCGCTGGATGACCAGGATGCCATTGCTGTGGAAGCTGCCTGCACTAATGTTCCGGCGTTATTTCTTGATGTCTC<br>TGACCAGACACCCATCAACAGTATTATTTTCTCCCATGAAGACGGTACGCGACTGGGCGTGGAGCATCTGGTCGCATTGGG<br>TCACCAGCAAATCGCGCTGTTAGCGGGCCCATTAAGTTCTGTCTCGGCGCGTCTGCGTCTGGCTGGCTGGCATAAATATCT<br>CACTCGCAATCAAATTCAGCCGATAGCGGAACGGGAAGGCGACTGGAGTGCCATGTCCGGTTTTCAACAAACCATGCAAA<br>TGCTGAATGAGGGCATCGTTCCCACTGCGATGCTGGTTGCCAACGATCAGATGGCGCTGGGCGCAATGCGCGCCATTACC<br>GAGTCCGGGCTGCGCGTTGGTGCGGATATCTCGGTAGTGGGATACGACGATACCGAAGACAGCTCATGTTATATCCCGCC<br>GTTAACCACCATCAAACAGGATTTTCGCCTGCTGGGGCAAACCAGCGTGGACCGCTTGCTGCAACTCTCTCAGGGCCAGG<br>CGGTGAAGGGCAATCAGCTGTTGCCCGTCTCACTGGTGAAAAGAAAAACCACCCTGGCGCCCAATACGCAAACCGCCTCT<br>CCCCGCGCGTTGGCCGATTCATTAATGCAGCTGGCACGACAGGTTTCCCGACTGGAAAGCGGGCAGTGAGCGCAACGCAA<br>TTAATGTGAGTTAGCGCGAATTGATCTG |
| SEQ ID NO: 166 nucleic acid sequence for the plasmid pTrc- | GTTTGACAGCTTATCATCGACTGCACGGTGCACCAATGCTTCTGGCGTCAGGCAGCCATCGGAAGCTGTGGTATGGCTGTG<br>CAGGTCGTAAATCACTGCATAATTCGTGTCGCTCAAGGCGCACTCCCGTTCTGGATAATGTTTTTTGCGCCGACATCATAA<br>CGGTTCTGGCAAATATTCTGAAATGAGCTGTTGACAATTAATCATCCGGCTCGTATAATGTGTGGAATTGTGAGCGGATAA<br>CAATTTCACACAGGAGGAATCAAAAATGCATTTTAAACTATCAGAAGAACATGAAATGATAAGAAAAATGGTTCGAGATT<br>TTGCTAAAAATGAAGTGGCACCAACAGCAGCTGAGCGTGATGAGGAAGAGCGATTTGATCGAGAATTATTTGATCAAATG<br>GCAGAGCTTGGTTTAACCGGTATTCCGTGGCCTGAAGAGTACGGTGGAATTGGAAGCGATTACTTAGCGTACGTAATCGCT<br>ATTGAAGAATTATCCCGCGTTTGTGCTTCAACAGGCGTAACACTGTCCGCGCATACTTCACTTGCAGGATGGCCAATTTTT |

TABLE 4-continued

Nucleic Acid Sequences: Plasmids

| SEQ ID NO | Nucleotide Sequence |
|---|---|
| BC_5341:H16_RS27940 | AAATTTGGGACGGAAGAGCAAAAGCAAAAGTTTTTACGACCGATGGCTGAAGGAAAGAAAATTGGTGCATACGGCTTAA<br>CGGAGCCAGGATCTGGATCGGATGCTGGTGGAATGAAGACAATCGCAAAGAGAGATGGAGACCATTATATTTTAAATGG<br>ATCAAAAATTTTCATTACAAATGGCGGTATTGCTGATATTTACGTTGTTTTGCGCTAACTGATCCTGAATCAAAGCAGCG<br>CGGTACGAGTGCATTTATTGTAGAAAGTGATACACCGGGATTTTCAGTTGGGAAGAAGGAGAGCAAGCTAGGGATTCGCT<br>CTTCACCAACGACTGAAATTATGTTTGAAGATTGCCGTATTCCTGTAGAGAATCTACTTGGAGAAGAGGGGCAAGGGTTTA<br>AAGTTGCGATGCAAACATTAGATGGAGGTCGTAACGGTATTGCGGCGCAAGCTGTTGGTATTGCACAAGGGGCTTTAGAT<br>GCTTCTGTAGAATATGCAAGGGAGCGCCATCAATTTGGAAAACCAATTGCGGCGCAGCAAGGGATTGGCTTTAAACTTGC<br>GGATATGGCAACAGATGTAGAAGCGGCACGCCTTTTAACATATCAAGCGGCTTGGCTTGAATCAGAAGGGCTTCCGTATG<br>GAAAAGAGTCAGCGATGTCAAAAGTATTTGCAGGAGATACAGCGATGAGGGTGACGACTGAAGCGGTGCAAGTATTTGG<br>TGGTTACGGTTATACGAAAGATTATCCAGTAGAGCGTTATATGCGAGATGCAAAAATTACACAAATATATGAAGGAACAC<br>AAGAGATTCAGAGGCTTGTAATTTCTCGTATGTTAACGAAGTAGGCTAGCAAAGGAGGTAAAGATAATGTACGCAGCTAA<br>GGACATCACCGTGGAGGAGCGCGCCGGCGGCGCGCTATGGATCACGATCGACCGGGCGCAGAAACACAATGCGCTGGCC<br>CGCCACGTGCTGGCGGGATTGGCGCAGGTGGTGAGCGCCGCGGCGGCGCAGCCCGGGGTGCGCTGCATCGTGCTGACCGG<br>CGCCGGCCAGCGCTTCTTTGCGGCAGGCGGCGATCTGGTCGAGCTGTCCGGCGTGCGCGACCGGGAGGCTACGCTGGCCA<br>TGAGCGAGCAGGCGCGCGGTGCCCTGGATGCGGTGCGCGACTGCCCGCTGCCGGTGCTGGCCTACCTGAACGGCGATGCC<br>ATCGGCGGCGGCGCCGAGCTGGCATTGGCCTGCGACATGCGGCTGCAGTCGGCGAGCGCGCGCATCGGCTTTATCCAGGC<br>GCGGCTGGCCATCACCTCGGCCTGGGGCGGCGGCCCCGACCTGTGCCGGATCGTCGGCGCGGCGCGGGCCATGCGCATGA<br>TGAGCCGTTGCGAGCTTGTCGATGCGCAGCAGGCGCTGCAGTGGGGCTTGGCCGATGCGGTGGTCACGGACGGACCCGCC<br>GGCAAGGACATCCACGCCTTCCTGCAACCGCTGCTGGGCTGCGCCCCGCAGGTGCTGCGCGGCATCAAGGCGCAGACCGC<br>GGCCAGCCGGCGCGGCGAGTCGCATGACGCTGCCCGCACCATCGAGCAGCAGCAACTGTTGCATACCTGGCTCCATGCGG<br>ACCATTGGAACGCTGCCGAGGGCATCCTCTCCAGGAGGGCCCAATGAGGCTGTTTTGGCGGATGAGAGAAGATTTTCAGC<br>CTGATACAGATTAAATCAGAACGCAGAAGCGGTCTGATAAAACAGAATTTGCCTGGCGGCAGTAGCGCGGTGGTCCCACC<br>TGACCCCATGCCGAACTCAGAAGTGAAACGCCGTAGCGCCGATGGTAGTGTGGGGTCTCCCCATGCGAGAGTAGGGAACT<br>GCCAGGCATCAAATAAAACGAAAGGCTCAGTCGAAAGACTGGGCCTTTCGTTTTATCTGTTGTTTGTCGGTGAACGCTCTC<br>CTGAGTAGGACAAATCCGCCGGGAGCGGATTTGAACGTTGCGAAGCAACGGCCCGGAGGGTGGCGGGCAGGACGCCCGC<br>CATAAACTGCCAGGCATCAAATTAAGCAGAAGGCCATCCTGACGGATGGCCTTTTTGCGTTTCTACAAACTCTTTTTGTTT<br>ATTTTTCTAAATACATTCAAATATGTATCCGCTCATGAGACAATAACCCTGATAAATGCTTCAATAATATTGAAAAAGGAA<br>GAGTATGAGTATTCAACATTTCCGTGTCGCCCTTATTCCCTTTTTTGCGGCATTTTGCCTTCCTGTTTTTGCTCACCCAGAAA<br>CGCTGGTGAAAGTAAAAGATGCTGAAGATCAGTTGGGTGCACGAGTGGGTTACATCGAACTGGATCTCAACAGCGGTAAG<br>ATCCTTGAGAGTTTTCGCCCCGAAGAACGTTTTCCAATGATGAGCACTTTTAAAGTTCTGCTATGTGGCGCGGTATTATCCC<br>GTGTTGACGCCGGGCAAGAGCAACTCGGTCGCCGCATACACTATTCTCAGAATGACTTGGTTGAGTACTCACCAGTCACA<br>GAAAAGCATCTTACGGATGGCATGACAGTAAGAGAATTATGCAGTGCTGCCATAACCATGAGTGATAACACTGCGGCCAA<br>CTTACTTCTGACAACGATCGGAGGACCGAAGGAGCTAACCGCTTTTTTGCACAACATGGGGGATCATGTAACTCGCCTTGA<br>TCGTTGGGAACCGGAGCTGAATGAAGCCATACCAAACGACGAGCGTGACACCACGATGCCTACAGCAATGGCAACAACG<br>TTGCGCAAACTATTAACTGGCGAACTACTTACTCTAGCTTCCCGGCAACAATTAATAGACTGGATGGAGGCGGATAAAGTT<br>GCAGGACCACTTCTGCGCTCGGCCCTTCCGGCTGGCTGGTTTATTGCTGATAAATCTGGAGCCGGTGAGCGTGGGTCTCGC<br>GGTATCATTGCAGCACTGGGGCCAGATGGTAAGCCCTCCCGTATCGTAGTTATCTACACGACGGGGAGTCAGGCAACTAT<br>GGATGAACGAAATAGACAGATCGCTGAGATAGGTGCCTCACTGATTAAGCATTGGTAACTGTCAGACCAAGTTTACTCAT<br>ATATACTTTAGATTGATTTAAAACTTCATTTTTAATTTAAAAGGATCTAGGTGAAGATCCTTTTTGATAATCTCATGACCAA<br>AATCCCTTAACGTGAGTTTTCGTTCCACTGAGCGTCAGACCCCGTAGAAAAGATCAAAGGATCTTCTTGAGATCCTTTTTTT<br>CTGCGCGTAATCTGCTGCTTGCAAACAAAAAAACCACCGCTACCAGCGGTGGTTTGTTTGCCGGATCAAGAGCTACCAACT<br>CTTTTTCCGAAGGTAACTGGCTTCAGCAGAGCGCAGATACCAAATACTGTCCTTCTAGTGTAGCCGTAGTTAGGCCACCAC<br>TTCAAGAACTCTGTAGCACCGCCTACATACCTCGCTCTGCTAATCCTGTTACCAGTGGCTGCTGCCAGTGGCGATAAGTCG<br>TGTCTTACCGGGTTGGACTCAAGACGATAGTTACCGGATAAGGCGCAGCGGTCGGGCTGAACGGGGGGTTCGTGCACACA<br>GCCCAGCTTGGAGCGAACGACCTACACCGAACTGAGATACCTACAGCGTGAGCTATGAGAAAGCGCCACGCTTCCCGAAG<br>GGAGAAAGGCGGACAGGTATCCGGTAAGCGGCAGGGTCGGAACAGGAGAGCGCACGAGGGAGCTTCCAGGGGGAAACG<br>CCTGGTATCTTTATAGTCCTGTCGGGTTTCGCCACCTCTGACTTGAGCGTCGATTTTTGTGATGCTCGTCAGGGGGGCGGAG<br>CCTATGGAAAAACGCCAGCAACGCGGCCTTTTTACGGTTCCTGGCCTTTTGCTGGCCTTTTGCTCACATGTTCTTTCCTGCG<br>TTATCCCCTGATTCTGTGGATAACCGTATTACCGCCTTTGAGTGAGCTGATACCGCTCGCCGCAGCCGAACGACCGAGCGC<br>AGCGAGTCAGTGAGCGAGGAAGCGGAAGAGCGCCTGATGCGGTATTTTCTCCTTACGCATCTGTGCGGTATTTCACACCG<br>CATATGGTGCACTCTCAGTACAATCTGCTCTGATGCCGCATAGTTAAGCCAGTATACACTCCGCTATCGCTACGTGACTGG<br>GTCATGGCTGCGCCCCGACACCCGCCAACACCCGCTGACGCGCCCTGACGGGCTTGTCTGCTCCCGGCATCCGCTTACAGA<br>CAAGCTGTGACCGTCTCCGGGAGCTGCATGTGTCAGAGGTTTTCACCGTCATCACCGAAACGCGCGAGGCAGCAGATCAA<br>TTCGCGCGCGAAGGCGAAGCGGCATGCATTTACGTTGACACCATCGAATGGTGCAAAACCTTTCGCGGTATGGCATGATA<br>GCGCCCGGAAGAGAGTCAATTCAGGGTGGTGAATGTGAAACCAGTAACGTTATACGATGTCGCAGAGTATGCCGGTGTCT<br>CTTATCAGACCGTTTCCCGCGTGGTGAACCAGGCCAGCCACGTTTCTGCGAAAACGCGGGAAAAAGTGGAAGCGGCGATG<br>GCGGAGCTGAATTACATTCCCAACCGCGTGGCACAACAACTGGCGGGCAAACAGTCGTTGCTGATTGGCGTTGCCACCTC<br>CAGTCTGGCCCTGCACGCGCCGTCGCAAATTGTCGCGGCGATTAAATCTCGCGCCGATCAACTGGGTGCCAGCGTGGTGGT<br>GTCGATGGTAGAACGAAGCGGCGTCGAAGCCTGTAAAGCGGCGGTGCACAATCTTCTCGCGCAACGCGTCAGTGGGCTGA<br>TCATTAACTATCCGCTGGATGACCAGGATGCCATTGCTGTGGAAGCTGCCTGCACTAATGTTCCGGCGTTATTTCTTGATGT<br>CTCTGACCAGACACCCATCAACAGTATTATTTTCTCCCATGAAGACGGTACGCGACTGGGCGTGGAGCATCTGGTCGCATT<br>GGGTCACCAGCAAATCGCGCTGTTAGCGGGCCCATTAAGTTCTGTCTCGGCGCGTCTGCGTCTGGCTGGCTGGCATAAATA<br>TCTCACTCGCAATCAAATTCAGCCGATAGCGGAACGGGAAGGCGACTGGAGTGCCATGTCCGGTTTTCAACAAACCATGC<br>AAATGCTGAATGAGGGCATCGTTCCCACTGCGATGCTGGTTGCCAACGATCAGATGGCGCTGGGCGCAATGCGCGCCATT<br>ACCGAGTCCGGGCTGCGCGTTGGTGCGGATATCTCGGTAGTGGGATACGACGATACCGAAGACAGCTCATGTTATATCCC<br>GCCGTTAACCACCATCAAACAGGATTTTCGCCTGCTGGGGCAAACCAGCGTGGACCGCTTGCTGCAACTCTCTCAGGGCCA<br>GGCGGTGAAGGGCAATCAGCTGTTGCCCGTCTCACTGGTGAAAAGAAAAACCACCCTGGCGCCCAATACGCAAACCGCCT<br>CTCCCCGCGCGTTGGCCGATTCATTAATGCAGCTGGCACGACAGGTTTCCCGACTGGAAAGCGGGCAGTGAGCGCAACGC<br>AATTAATGTGAGTTAGCGCGAATTGATCTG |
| SEQ ID NO: 167 nucleic acid sequence for the | CGGTGTATGCAAGAGGGATAAAAAATGAAAACAAAATTGATGACATTACAAGACGCCACCGGCTTCTTTCGTGACGGCAT<br>GACCATCATGGTGGGCGGATTTATGGGGATTGGCACTCCATCCCGCCTGGTTGAAGCATTACTGGAATCTGGTGTTCGCGA<br>CCTGACATTGATAGCCAATGATACCGCGTTTGTTGATACCGGCATCGGTCCGCTCATCGTCAATGGTCGAGTCCGCAAAGT<br>GATTGCTTCACATATCGGCACCAACCCGGAAACAGGTCGGCGCATGATATCTGGTGAGATGGACGTCGTTCTGGTGCCGC<br>AAGGTACGCTAATCGAGCAAATTCGCTGTGGTGGAGCTGGACTTGGTGGTTTTCTCACCCCAACGGGTGTCGGCACCGTCG |

TABLE 4-continued

| Nucleic Acid Sequences: Plasmids | |
|---|---|
| SEQ ID NO | Nucleotide Sequence |
| plasmid pk- | TAGAGGAAGGCAAACAGACACTGACACTCGACGGTAAAACCTGGCTGCTCGAACGCCCACTGCGCGCCGACCTGGCGCTA |
| atoDAE:tesB | ATTCGCGCTCATCGTTGCGACACACTTGGCAACCTGACCTATCAACTTAGCGCCCGCAACTTTAACCCCCTGATAGCCCTT |
| | GCGGCTGATATCACGCTGGTAGAGCCAGATGAACTGGTCGAAACCGGCGAGCTGCAACCTGACCATATTGTCACCCCTGG |
| | TGCCGTTATCGACCACATCATCGTTTCACAGGAGAGCAAATAATGGATGCGAAACAACGTATTGCGCGCCGTGTGGCGCA |
| | AGAGCTTCGTGATGGTGACATCGTTAACTTAGGGATCGGTTTACCCACAATGGTCGCCAATTATTTACCGGAGGGTATTCA |
| | TATCACTCTGCAATCGGAAAACGGCTTCCTCGGTTTAGGCCCGGTCACGACAGCGCATCCAGATCTGGTGAACGCTGGCG |
| | GGCAACCGTGCGGTGTTTTACCCGGTGCAGCCATGTTTGATAGCGCCATGTCATTTGCGCTAATCCGTGGCGGTCATATTG |
| | ATGCCTGCGTGCTCGGCGGTTTGCAAGTAGACGAAGAAGCAAACCTCGCGAACTGGGTAGTGCCTGGGAAAATGGTGCCC |
| | GGTATGGGTGGCGCGATGGATCTGGTGACCGGGTCGCGCAAAGTGATCATCGCCATGGAACATTGCGCCAAAGATGGTTC |
| | AGCAAAAATTTTGCGCCGCTGCACCATGCCACTCACTGCGCAACATGCGGTGCATATGCTGGTTACTGAACTGGCTGTCTT |
| | TCGTTTTATTGACGGCAAAATGTGGCTCACCGAAATTGCCGACGGGTGTGATTTAGCCACCGTGCGTGCCAAAACAGAAG |
| | CTCGGTTTGAAGTCGCCGCCGATCTGAATACGCAACGGGGTGATTTATGATTGGTCGCATATCGCGTTTTATGACGCGTTT |
| | TGTCAGCCGGTGGCTTCCCGATCCACTGATCTTTGCCATGTTGCTGACATTGCTAACATTCGTGATCGCGCTTTGGTTAACA |
| | CCACAAACGCCGATCAGCATGGTGAAAATGTGGGGTGACGGTTTCTGGAACTTGCTGGCGTTTGGTATGCAGATGGCGCT |
| | TATCATCGTTACCGGTCATGCCCTTGCCAGCTCTGCTCCGGTGAAAAGTTTGCTGCGTACTGCCGCCTCCGCCGCAAAGAC |
| | GCCCGTACAGGGCGTCATGCTGGTCACTTTCTTCGGTTCAGTCGCTTGTGTCATCAACTGGGGATTTGGTTTGGTTGTCGGC |
| | GCAATGTTTGCCCGTGAAGTCGCCCGGCGAGTCCCCGGTTCTGATTATCCGTTGCTCATTGCCTGCGCCTACATTGGTTTTC |
| | TCACCTGGGGTGGCGGCTTCTCTGGATCAATGCCTCTGTTGGCTGCAACACCGGGCAACCCGGTTGAGCATATCGCCGGGC |
| | TGATCCCGGTGGGCGATACTCTGTTCAGTGGTTTTAACATTTTCATCACTGTGGCGTTGATTGTGGTGATGCCATTTATCAC |
| | CCGCATGATGATGCCAAAACCGTCTGACGTGGTGAGTATCGATCCAAAACTACTCATGGAAGAGGCTGATTTTCAAAAGC |
| | AGCTACCGAAAGATGCCCCACCATCCGAGCGACTGGAAGAAAGCCGCATTCTGACGTTGATCATCGGCGCACTCGGTATC |
| | GCTTACCTTGCGATGTACTTCAGCGAACATGGCTTCAACATCACCATCAATACCGTCAACCTGATGTTTATGATTGCGGGT |
| | CTGCTGCTACATAAAACGCCAATGGCTTATATGCGTGCTATCAGCGCGGCAGCACGCAGTACTGCCGGTATTCTGGTGCAA |
| | TTCCCCTTCTACGCTGGGATCCAACTGATGATGGAGCATTCCGGTCTGGGCGGACTCATTACCGAATTCTTCATCAATGTTG |
| | CGAACAAAGACACCTTCCCGGTAATGACCTTTTTTAGTTCTGCACTGATTAACTTCGCCGTTCCGTCTGGCGGCGGTCACTG |
| | GGTTATTCAGGGACCTTTCGTGATACCCGCAGCCCAGGCGCTGGGCGCTGATCTCGGTAAATCGGTAATGGCGATCGCCTA |
| | CGGCGAGCAATGGATGAACATGGCACAACCATTCTGGGCGCTGCCAGCACTGGCAATCGCCGGACTCGGTGTCCGCGACA |
| | TCATGGGCTACTGCATCACTGCCCTGCTCTTCTCCGGTGTCATTTTCGTCATTGGTTTAACGCTGTTCTGACTCGAGAAAGG |
| | AGGATAAGATAATGAGTCAGGCGCTAAAAAATTTACTGACATTGTTAAATCTGGAAAAAATTGAGGAAGGACTCTTTCGC |
| | GGCCAGAGTGAAGATTTAGGTTTACGCCAGGTGTTTGGCGGCCAGGTCGTGGGTCAGGCCTTGTATGCTGCAAAAGAGAC |
| | CGTCCCTGAAGAGCGGCTGGTACATTCGTTTCACAGCTACTTTCTTCGCCCTGGCGATAGTAAGAAGCCGATTATTTATGA |
| | TGTCGAAACGCTGCGTGACGGTAACAGCTTCAGCGCCCGCCGGGTTGCTGCTATTCAAAACGGCAAACCGATTTTTTATAT |
| | GACTGCCTCTTTCCAGGCACCAGAAGCGGGTTTCGAACATCAAAAAACAATGCCGTCCGCGCCAGCGCCTGATGGCCTCC |
| | CTTCGGAAACGCAAATCGCCCAATCGCTGGCGCACCTGCTGCCGCCAGTGCTGAAAGATAAATTCATCTGCGATCGTCCGC |
| | TGGAAGTCCGTCCGGTGGAGTTTCATAACCCACTGAAAGGTCACGTCGCAGAACCACATCGTCAGGTGTGGATCCGCGCA |
| | AATGGTAGCGTGCCGGATGACCTGCGCGTTCATCAGTATCTGCTCGGTTACGCTTCTGATCTTAACTTCCTGCCGGTAGCTC |
| | TACAGCCGCACGGCATCGGTTTTCTCGAACCGGGGATTCAGATTGCCACCATTGACCATTCCATGTGGTTCCATCGCCCGT |
| | TTAATTTGAATGAATGGCTGCTGTATAGCGTGGAGAGCACCTCGGCGTCCAGCGCACGTGGCTTTGTGCGCGGTGAGTTTT |
| | ATACCCAAGACGGCGTACTGGTTGCCTCGACCGTTCAGGAAGGGGTGATGCGTAATCACAATTAATGATTACGAATTCGA |
| | GCTCGGTACCCGGGGATCCTCTAGAGTCGACCTGCAGGCATGCAAGCTTGGCACTGGCCGTCGTTTTACAACGTCGTGACT |
| | GGGAAAACCCTGGCGTTACCCAACTTAATCGCCTTGCAGCACATCCCCCTTTCGCCAGCTGGCGTAATAGCGAAGAGGCC |
| | CGCACCGATCGCCCTTCCCAACAGTTGCGCAGCCTGAATGGCGAATGGCGCGATAAGCTAGCTTCACGCTGCCGCAAGCA |
| | CTCAGGGCGCAAGGGCTGCTAAAGGAAGCGGAACACGTAGAAAGCCAGTCCGCAGAAACGGTGCTGACCCCGGATGAAT |
| | GTCAGCTACTGGGCTATCTGGACAAGGGAAAACGCAAGCGCAAAGAGAAAGCAGGTAGCTTGCAGTGGGCTTACATGGC |
| | GATAGCTAGACTGGGCGGTTTTATGGACAGCAAGCGAACCGGAATTGCCAGCTGGGGCGCCCTCTGGTAAGGTTGGGAAG |
| | CCCTGCAAAGTAAACTGGATGGCTTTCTTGCCGCCAAGGATCTGATGGCGCAGGGGATCAAGATCTGATCAAGAGACAGG |
| | ATGAGGATCGTTTCGCATGATTGAACAAGATGGATTGCACGCAGGTTCTCCGGCCGCTTGGGTGGAGAGGCTATTCGGCT |
| | ATGACTGGGCACAACAGACAATCGGCTGCTCTGATGCCGCCGTGTTCCGGCTGTCAGCGCAGGGGCGCCCGGTTCTTTTTG |
| | TCAAGACCGACCTGTCCGGTGCCCTGAATGAACTCCAAGACGAGGCAGCGCGGCTATCGTGGCTGGCCACGACGGGCGTT |
| | CCTTGCGCAGCTGTGCTCGACGTTGTCACTGAAGCGGGAAGGGACTGGCTGCTATTGGGCGAAGTGCCGGGGCAGGATCT |
| | CCTGTCATCTCACCTTGCTCCTGCCGAGAAAGTATCCATCATGGCTGATGCAATGCGGCGGCTGCATACGCTTGATCCGGC |
| | TACCTGCCCATTCGACCACCAAGCGAAACATCGCATCGAGCGAGCACGTACTCGGATGGAAGCCGGTCTTGTCGATCAGG |
| | ATGATCTGGACGAAGAGCATCAGGGGCTCGCGCCAGCCGAACTGTTCGCCAGGCTCAAGGCGCGGATGCCCGACGGCGA |
| | GGATCTCGTCGTGACCCATGGCGATGCCTGCTTGCCGAATATCATGGTGGAAAATGGCCGCTTTTCTGGATTCATCGACTG |
| | TGGCCGGCTGGGTGTGGCGGACCGCTATCAGGACATAGCGTTGGCTACCCGTGATATTGCTGAAGAGCTTGGCGGCGAAT |
| | GGGCTGACCGCTTCCTCGTGCTTTACGGTATCGCCGCTCCCGATTCGCAGCGCATCGCCTTCTATCGCCTTCTTGACGAGTT |
| | CTTCTGAGCGGGACTCTGGGGTTCGCGATGATAAGCTGTCAAACATGAGAATTACAACTTATATCGTATGGGGCTGACTTC |
| | AGGTGCTACATTTGAAGAGATAAATTGCACTGAAATCTAGAAATATTTTATCTGATTAATAAGATGATCTTCTTGAGATCG |
| | TTTTGGTCTGCGCGTAATCTCTTGCTCTGAAAACGAAAAAACCGCCTTGCAGGGCGGTTTTTCGAAGGTTCTCTGAGCTAC |
| | CAACTCTTTGAACCGAGGTAACTGGCTTGGAGGAGCGCAGTCACCAAAACTTGTCCTTTCAGTTTAGCCTTAACCGGCGCA |
| | TGACTTCAAGACTAACTCCTCTAAATCAATTACCAGTGGCTGCTGCCAGTGGTGCTTTTGCATGTCTTTCCGGGTTGGACTC |
| | AAGACGATAGTTACCGGATAAGGCGCAGCGGTCGGACTGAACGGGGGGTTCGTGCATACAGTCCAGCTTGGAGCGAACT |
| | GCCTACCCGGAACTGAGTGTCAGGCGTGGAATGAGACAAACGCGGCCATAACAGCGGAATGACACCGGTAAACCGAAAG |
| | GCAGGAACAGGAGAGCGCACGAGGGAGCCGCCAGGGGAAACGCCTGGTATCTTTATAGTCCTGTCGGGTTTCGCCACCAC |
| | TGATTTGAGCGTCAGATTTCGTGATGCTTGTCAGGGGGGCGGAGCCTATGGAAAAACGGCTTTGCCTTCTTTCCTGCGTTA |
| | TCCCCTGATTCTGTGGATAACCGTATTACCGCCTTTGAGTGAGCTGATACCGCTCGCCGCAGCCGAACGACCGAGCGCAGC |
| | GAGTCAGTGAGCGAGGAAGCGGAAGAGCGCCCAATACGCAAACCGCCTCTCCCCGCGCGTTGGCCGATTCATTAATGCAG |
| | CTGGCACGACAGGTTTCCCGACTGGAAAGCGGGCAGTGAGCGCAACGCAATTAATGTGAGTTAGCTCACTCATTAGGCAC |
| | CCCAGGCTTTACACTTTATGCTTCCGGCTCGTATGTTGTGTGGAATTGTGAGCGGATAACAATTT |
| | GTTTGACAGCTTATCATCGACTGCACGGTGCACCAATGCTTCTGGCGTCAGGCAGCCATCGGAAGCTGTGGTATGGCTGTG |
| | CAGGTCGTAAATCACTGCATAATTCGTGTCGCTCAAGGCGCACTCCCGTTCTGGATAATGTTTTTTGCGCCGACATCATAA |
| SEQ ID | CGGTTCTGGCAAATATTCTGAAATGAGCTGTTGACAATTAATCATCCGGCTCGTATAATGTGTGGAATTGTGAGCGGATAA |
| NO: 168 | CAATTTCACACAGGAGGAATCAAAAATGCTGGTAAATGACGAGCAACAACAGATCGCCGACGCGGTACGTGCGTTCGCCC |
| nucleic acid | AGGAACGCCTGAAGCCGTTTGCCGAGCAATGGGACAAGGACCATCGCTTCCCGAAAGAGGCCATCGACGAGATGGCCGA |

TABLE 4-continued

| Nucleic Acid Sequences: Plasmids | |
|---|---|
| SEQ ID NO | Nucleotide Sequence |
| sequence for the plasmid pTrc-PP_2216:phaJ | ACTGGGCCTGTTCGGCATGCTGGTGCCGGAGCAGTGGGGCGGTAGCGACACCGGTTATGTGGCCTATGCCATGGCCTTGG<br>AGGAAATCGCTGCGGGCGATGGCGCCTGCTCGACCATCATGAGCGTGCACAACTCGGTGGGTTGCGTGCCGATCCTGCGC<br>TTCGGCAACGAGCAGCAGAAAGAGCAGTTCCTCACCCCGCTGGCGACAGGTGCGATGCTCGGTGCTTTCGCCCTGACCGA<br>GCCGCAGGCTGGCTCCGATGCCAGCAGCCTGAAGACCCGCGCACGCCTGGAAGGCGACCATTACGTGCTCAATGGCAGCA<br>AGCAGTTCATTACCTCGGGGCAGAACGCCGGCGTAGTGATCGTGTTTGCGGTCACCGACCCGGAGGCCGGCAAGCGTGGC<br>ATCAGCGCCTTCATCGTGCCGACCGATTCGCCGGGCTACCAGGTAGCGCGGGTGGAGGACAAACTCGGCCAGCACGCCTC<br>CGACACCTGCCAGATCGTTTTCGACAATGTGCAAGTGCCAGTGGCCAACCGGCTGGGGGCGGAGGGTGAAGGCTACAAGA<br>TCGCCCTGGCCAACCTTGAAGGCGGCCGTATCGGCATCGCCTCGCAAGCGGTGGGTATGGCCCGCGCGGCGTTCGAAGTG<br>GCGCGGGACTATGCCAACGAGCGCCAGAGCTTTGGCAAACCGCTGATCGAGCACCAGGCCGTGGCGTTTCGCCTGGCCGA<br>CATGGCAACGAAAATTTCCGTTGCCCGGCAGATGGTATTGCACGCCGCTGCCCTTCGTGATGCGGGGCGCCCGGCGCTGGT<br>GGAAGCGTCGATGGCCAAGCTGTTCGCCTCGGAAATGGCCGAAAAGGTCTGTTCGGACGCCTTGCAGACCCTGGGCGGTT<br>ATGGCTATCTGAGTGACTTCCCGCTGGAGCGGATCTACCGCGACGTTCGGGTTTGCCAGATCTACGAAGGCACCAGCGAC<br>ATTCAGCGCATGGTCATTGCGCGCAATCTTTGAGCTAGCAAAGGAGGTAAAGATAATGAGTACACAAACCCTTGCCGTGG<br>GCCAGAAGGCTCGCCTGACCAAGCGCTTCGGCCCGGCCGAGGTGGCGGCCTTCGCCGGCCTCTCGGAGGATTTCAATCCC<br>CTGCACCTGGACCCGGACTTCGCCGCCACGACGGTGTTCGAGCGCCCCATCGTCCACGGCATGCTGCTGGCGAGCCTCTTC<br>TCCGGGCTCCTCGGGCAGCAACTGCCCGGGAAAGGGAGCATCTATCTGGGCCAGAGCCTCGGCTTCAAACTGCCGGTGTT<br>CGTGGGGGACGAGGTGACGGCGGAGGTGGAGGTGATTGCCCTTCGAAGCGACAAGCCCATCGCCACCCTGGCCACCCGC<br>ATCTTCACCCAGGGCGGCGCCCTCGCCGTGACGGGGGAAGCGGTGGTAAAACTCCCTTGAGGCTGTTTTGGCGGATGAGA<br>GAAGATTTTCAGCCTGATACAGATTAAATCAGAACGCAGAAGCGGTCTGATAAAACAGAATTTGCCTGGCGGCAGTAGCG<br>CGGTGGTCCCACCTGACCCCATGCCGAACTCAGAAGTGAAACGCCGTAGCGCCGATGGTAGTGTGGGGTCTCCCCATGCG<br>AGAGTAGGGAACTGCCAGGCATCAAATAAAACGAAAGGCTCAGTCGAAAGACTGGGCCTTTCGTTTTATCTGTTGTTTGTC<br>GGTGAACGCTCTCCTGAGTAGGACAAATCCGCCGGGAGCGGATTTGAACGTTGCGAAGCAACGGCCCGGAGGGTGGCGG<br>GCAGGACGCCCGCCATAAACTGCCAGGCATCAAATTAAGCAGAAGGCCATCCTGACGGATGGCCTTTTTGCGTTTCTACA<br>AACTCTTTTTGTTTATTTTTCTAAATACATTCAAATATGTATCCGCTCATGAGACAATAACCCTGATAAATGCTTCAATAAT<br>ATTGAAAAAGGAAGAGTATGAGTATTCAACATTTCCGTGTCGCCCTTATTCCCTTTTTTGCGGCATTTTGCCTTCCTGTTTTT<br>GCTCACCCAGAAACGCTGGTGAAAGTAAAAGATGCTGAAGATCAGTTGGGTGCACGAGTGGGTTACATCGAACTGGATCT<br>CAACAGCGGTAAGATCCTTGAGAGTTTTCGCCCCGAAGAACGTTTTCCAATGATGAGCACTTTTAAAGTTCTGCTATGTGG<br>CGCGGTATTATCCCGTGTTGACGCCGGGCAAGAGCAACTCGGTCGCCGCATACACTATTCTCAGAATGACTTGGTTGAGTA<br>CTCACCAGTCACAGAAAAGCATCTTACGGATGGCATGACAGTAAGAGAATTATGCAGTGCTGCCATAACCATGAGTGATA<br>ACACTGCGGCCAACTTACTTCTGACAACGATCGGAGGACCGAAGGAGCTAACCGCTTTTTTGCACAACATGGGGGATCAT<br>GTAACTCGCCTTGATCGTTGGGAACCGGAGCTGAATGAAGCCATACCAAACGACGAGCGTGACACCACGATGCCTACAGC<br>AATGGCAACAACGTTGCGCAAACTATTAACTGGCGAACTACTTACTCTAGCTTCCCGGCAACAATTAATAGACTGGATGG<br>AGGCGGATAAAGTTGCAGGACCACTTCTGCGCTCGGCCCTTCCGGCTGGCTGGTTTATTGCTGATAAATCTGGAGCCGGTG<br>AGCGTGGGTCTCGCGGTATCATTGCAGCACTGGGGCCAGATGGTAAGCCCTCCCGTATCGTAGTTATCTACACGACGGGG<br>AGTCAGGCAACTATGGATGAACGAAATAGACAGATCGCTGAGATAGGTGCCTCACTGATTAAGCATTGGTAACTGTCAGA<br>CCAAGTTTACTCATATATACTTTAGATTGATTTAAAACTTCATTTTTAATTTAAAAGGATCTAGGTGAAGATCCTTTTTGAT<br>AATCTCATGACCAAAATCCCTTAACGTGAGTTTTCGTTCCACTGAGCGTCAGACCCCGTAGAAAAGATCAAAGGATCTTCT<br>TGAGATCCTTTTTTTCTGCGCGTAATCTGCTGCTTGCAAACAAAAAAACCACCGCTACCAGCGGTGGTTTGTTTGCCGGAT<br>CAAGAGCTACCAACTCTTTTTCCGAAGGTAACTGGCTTCAGCAGAGCGCAGATACCAAATACTGTCCTTCTAGTGTAGCCG<br>TAGTTAGGCCACCACTTCAAGAACTCTGTAGCACCGCCTACATACCTCGCTCTGCTAATCCTGTTACCAGTGGCTGCTGCC<br>AGTGGCGATAAGTCGTGTCTTACCGGGTTGGACTCAAGACGATAGTTACCGGATAAGGCGCAGCGGTCGGGCTGAACGGG<br>GGGTTCGTGCACACAGCCCAGCTTGGAGCGAACGACCTACACCGAACTGAGATACCTACAGCGTGAGCTATGAGAAAGCG<br>CCACGCTTCCCGAAGGGAGAAAGGCGGACAGGTATCCGGTAAGCGGCAGGGTCGGAACAGGAGAGCGCACGAGGGAGCT<br>TCCAGGGGGAAACGCCTGGTATCTTTATAGTCCTGTCGGGTTTCGCCACCTCTGACTTGAGCGTCGATTTTTGTGATGCTCG<br>TCAGGGGGGCGGAGCCTATGGAAAAACGCCAGCAACGCGGCCTTTTTACGGTTCCTGGCCTTTTGCTGGCCTTTTGCTCAC<br>ATGTTCTTTCCTGCGTTATCCCCTGATTCTGTGGATAACCGTATTACCGCCTTTGAGTGAGCTGATACCGCTCGCCGCAGCC<br>GAACGACCGAGCGCAGCGAGTCAGTGAGCGAGGAAGCGGAAGAGCGCCTGATGCGGTATTTTCTCCTTACGCATCTGTGC<br>GGTATTTCACACCGCATATGGTGCACTCTCAGTACAATCTGCTCTGATGCCGCATAGTTAAGCCAGTATACACTCCGCTAT<br>CGCTACGTGACTGGGTCATGGCTGCGCCCCGACACCCGCCAACACCCGCTGACGCGCCCTGACGGGCTTGTCTGCTCCCGG<br>CATCCGCTTACAGACAAGCTGTGACCGTCTCCGGGAGCTGCATGTGTCAGAGGTTTTCACCGTCATCACCGAAACGCGCGA<br>GGCAGCAGATCAATTCGCGCGCGAAGGCGAAGCGGCATGCATTTACGTTGACACCATCGAATGGTGCAAAACCTTTCGCG<br>GTATGGCATGATAGCGCCCGGAAGAGAGTCAATTCAGGGTGGTGAATGTGAAACCAGTAACGTTATACGATGTCGCAGAG<br>TATGCCGGTGTCTCTTATCAGACCGTTTCCCGCGTGGTGAACCAGGCCAGCCACGTTTCTGCGAAAACGCGGGAAAAAGT<br>GGAAGCGGCGATGGCGGAGCTGAATTACATTCCCAACCGCGTGGCACAACAACTGGCGGGCAAACAGTCGTTGCTGATTG<br>GCGTTGCCACCTCCAGTCTGGCCCTGCACGCGCCGTCGCAAATTGTCGCGGCGATTAAATCTCGCGCCGATCAACTGGGTG<br>CCAGCGTGGTGGTGTCGATGGTAGAACGAAGCGGCGTCGAAGCCTGTAAAGCGGCGGTGCACAATCTTCTCGCGCAACGC<br>GTCAGTGGGCTGATCATTAACTATCCGCTGGATGACCAGGATGCCATTGCTGTGGAAGCTGCCTGCACTAATGTTCCGGCG<br>TTATTTCTTGATGTCTCTGACCAGACACCCATCAACAGTATTATTTTCTCCCATGAAGACGGTACGCGACTGGGCGTGGAG<br>CATCTGGTCGCATTGGGTCACCAGCAAATCGCGCTGTTAGCGGGCCCATTAAGTTCTGTCTCGGCGCGTCTGCGTCTGGCT<br>GGCTGGCATAAATATCTCACTCGCAATCAAATTCAGCCGATAGCGGAACGGGAAGGCGACTGGAGTGCCATGTCCGGTTT<br>TCAACAAACCATGCAAATGCTGAATGAGGGCATCGTTCCCACTGCGATGCTGGTTGCCAACGATCAGATGGCGCTGGGCG<br>CAATGCGCGCCATTACCGAGTCCGGGCTGCGCGTTGGTGCGGATATCTCGGTAGTGGGATACGACGATACCGAAGACAGC<br>TCATGTTATATCCCGCCGTTAACCACCATCAAACAGGATTTTCGCCTGCTGGGGCAAACCAGCGTGGACCGCTTGCTGCAA<br>CTCTCTCAGGGCCAGGCGGTGAAGGGCAATCAGCTGTTGCCCGTCTCACTGGTGAAAAGAAAAACCACCCTGGCGCCCAA<br>TACGCAAACCGCCTCTCCCCGCGCGTTGGCCGATTCATTAATGCAGCTGGCACGACAGGTTTCCCGACTGGAAAGCGGGC<br>AGTGAGCGCAACGCAATTAATGTGAGTTAGCGCGAATTGATCTG |
| SEQ ID NO: 169 nucleic acid sequence for the plasmid pK-lvaE:gadAe | ATGATGGTTCCAACCCTCGAACACGAGCTTGCTCCCAACGAAGCCAACCATGTCCCGCTGTCGCCGCTGTCGTTCCTCAAG<br>CGTGCCGCGCAGGTGTACCCGCAGCGCGATGCGGTGATCTATGGCGCAAGGCGCTACAGCTACCGTCAGTTGCACGAGCG<br>CAGCCGCGCCCTGGCCAGTGCCTTGGAGCGGGTCGGTGTTCAGCCGGGCGAGCGGGTGGCGATATTGGCGCCGAACATCC<br>CGGAAATGCTCGAGGCCCACTATGGCGTGCCCGGTGCCGGGGCGGTGCTGGTGTGCATCAACATCCGCCTGGAGGGGCGC<br>AGCATTGCCTTCATCCTGCGTCACTGCGCGGCCAAGGTATTGATCTGCGATCGTGAGTTCGGTGCCGTGGCCAATCAGGCG<br>CTGGCCATGCTCGATGCGCCGCCCTTGCTGGTGGGCATCGACGATGATCAGGCCGAGCGCGCCGATTTGGCCCACGACCT<br>GGACTACGAAGCGTTCTTGGCCCAGGGCGACCCCGCGCGGCCGTTGAGTGCGCCACAGAACGAATGGCAGTCGATCGCCA<br>TCAACTACACCTCCGGCACCACGGGGGACCCCAAGGGCGTGGTGCTGCATCACCGCGGCGCCTACCTCAACGCCTGCGCC |

TABLE 4-continued

Nucleic Acid Sequences: Plasmids

| SEQ ID NO | Nucleotide Sequence |
|---|---|
| | GGGGCGCTGATCTTCCAGTTGGGGCCGCGCAGCGTCTACTTGTGGACCTTGCCGATGTTCCACTGCAACGGCTGGAGCCAT ACCTGGGCGGTGACGTTGTCCGGTGGCACCCACGTGTGTCTGCGCAAGGTCCAGCCTGATGCGATCAACGCCGCCATCGC CGAGCATGCCGTGACTCACCTGAGCGCCGCCCCAGTGGTGATGTCGATGCTGATCCACGCCGAGCATGCCAGCGCCCCTC CGGTGCCGGTTTCGGTGATCACTGGCGGTGCCGCCCCGCCCAGTGCGGTCATCGCGGCGATGGAGGCGCGTGGCTTCAAC ATCACCCATGCCTATGGCATGACCGAAAGCTACGGTCCCAGCACATTGTGCCTGTGGCAGCCGGGTGTCGACGAGTTGCC GCTGGAGGCCCGGGCCCAGTTCATGAGCCGCCAGGGCGTCGCCCACCCGCTGCTCGAGGAGGCCACGGTGCTGGATACCG ACACCGGCCGCCCGGTCCCGGCCGACGGCCTTACCCTCGGCGAGCTGGTGGTGCGGGGCAACACTGTGATGAAAGGCTAC CTGCACAACCCAGAGGCTACCCGTGCCGCGTTGGCCAACGGCTGGCTGCACACGGGCGACCTGGCCGTGCTGCACCTGGA CGGCTATGTGGAAATCAAGGACCGAGCCAAGGACATCATCATTTCTGGCGGCGAGAACATCAGTTCGCTGGAGATAGAAG AAGTGCTCTACCAGCACCCCGAGGTGGTCGAGGCTGCGGTGGTGGCGCGTCCGGATTCGCGCTGGGGCGAGACACCTCAC GCTTTCGTCACGCTGCGCGCTGATGCACTGGCCAGCGGGGACGACCTGGTCCGCTGGTGCCGTGAGCGTCTGGCGCACTTC AAGGCGCCGCGCCATGTGTCGCTCGTGGACCTGCCCAAGACCGCCACTGGAAAAATACAGAAGTTCGTCCTGCGTGAGTG GGCCCGGCAACAGGAGGCGCAGATCGCCGACGCCGAGCATTGACTCGAGAAAGGAGGATAAGATAATGGACCAGAAGCT GTTAACGGATTTCCGCTCAGAACTACTCGATTCACGTTTTGGCGCAAAGGCCATTTCTACTATCGCGGAGTCAAAACGATT TCCGCTGCACGAAATGCGCGATGATGTCGCATTTCAGATTATCAATGATGAATTATATCTTGATGGCAACGCTCGTCAGAA CCTGGCCACTTTCTGCCAGACCTGGGACGACGAAAACGTCCATAAATTGATGGATTTGTCGATCAATAAAAACTGGATCG ACAAAGAACAGTATCCGCAATCCGCAGCCATCGACCTGCGTTGCGTAAATATGGTTGCCGATCTGTGGCATGCGCCTGCG CCGAAAAATGGTCAGGCCGTTGGCACCAACACCATTGGTTCTTCCGAGGCCTGTATGCTCGGCGGGATGGCGATGAAATG GCGTTGGCGCAAGCGTATGGAAGCTGCAGGCAAACCAACGGATAAACCAAACCTGGTGTGCGGTCCGGTACAAATCTGCT GGCATAAATTCGCCCGCTACTGGGATGTGGAGCTGCGTGAGATCCCTATGCGCCCCGGTCAGTTGTTTATGGACCCGAAAC GCATGATTGAAGCCTGTGACGAAAACACCATCGGCGTGGTGCCGACTTTCGGCGTGACCTACACCGGTAACTATGAGTTC CCACAACCGCTGCACGATGCGCTGGATAAATTCCAGGCCGACACCGGTATCGACATCGACATGCACATCGACGCTGCCAG CGGTGGCTTCCTGGCACCGTTCGTCGCCCCGGATATCGTCTGGGACTTCCGCCTGCCGCGTGTGAAATCGATCAGTGCTTC AGGCCATAAATTCGGTCTGGCTCCGCTGGGCTGCGGCTGGGTTATCTGGCGTGACGAAGAAGCGCTGCCGCAGGAACTGG TGTTCAACGTTGACTACCTGGGTGGTCAAATTGGTACTTTTGCCATCAACTTCTCCCGCCCGGCGGGTCAGGTAATTGCAC AGTACTATGAATTCCTGCGCCTCGGTCGTGAAGGCTATACCAAAGTACAGAACGCCTCTTACCAGGTTGCCGCTTATCTGG CGGATGAAATCGCCAAACTGGGGCCGTATGAGTTCATCTGTACGGGTCGCCCGGACGAAGGCATCCCGGCGGTTTGCTTC AAACTGAAAGATGGTGAAGATCCGGGATACACCCTGTACGACCTCTCTGAACGTCTGCGTCTGCGCGGCTGGCAGGTTCC GGCCTTCACTCTCGGCGGTGAAGCCACCGACATCGTGGTGATGCGCATTATGTGTCGTCGCGGCTTCGAAATGGACTTTGC TGAACTGTTGCTGGAAGACTACAAAGCCTCCCTGAAATATCTCAGCGATCACTAAAGGAAGCGGAACACGTAGAAAGCCA GTCCGCAGAAACGGTGCTGACCCCGGATGAATGTCAGCTACTGGGCTATCTGGACAAGGGAAAACGCAAGCGCAAAGAG AAAGCAGGTAGCTTGCAGTGGGCTTACATGGCGATAGCTAGACTGGGCGGTTTTATGGACAGCAAGCGAACCGGAATTGC CAGCTGGGGCGCCCTCTGGTAAGGTTGGGAAGCCCTGCAAAGTAAACTGGATGGCTTTCTTGCCGCCAAGGATCTGATGG CGCAGGGGATCAAGATCTGATCAAGAGACAGGATGAGGATCGTTTCGCATGATTGAACAAGATGGATTGCACGCAGGTTC TCCGGCCGCTTGGGTGGAGAGGCTATTCGGCTATGACTGGGCACAACAGACAATCGGCTGCTCTGATGCCGCCGTGTTCCG GCTGTCAGCGCAGGGGCGCCCGGTTCTTTTTGTCAAGACCGACCTGTCCGGTGCCCTGAATGAACTCCAAGACGAGGCAG CGCGGCTATCGTGGCTGGCCACGACGGGCGTTCCTTGCGCAGCTGTGCTCGACGTTGTCACTGAAGCGGGAAGGGACTGG CTGCTATTGGGCGAAGTGCCGGGGCAGGATCTCCTGTCATCTCACCTTGCTCCTGCCGAGAAAGTATCCATCATGGCTGAT GCAATGCGGCGGCTGCATACGCTTGATCCGGCTACCTGCCCATTCGACCACCAAGCGAAACATCGCATCGAGCGAGCACG TACTCGGATGGAAGCCGGTCTTGTCGATCAGGATGATCTGGACGAAGAGCATCAGGGGCTCGCGCCAGCCGAACTGTTCG CCAGGCTCAAGGCGCGGATGCCCGACGGCGAGGATCTCGTCGTGACCCATGGCGATGCCTGCTTGCCGAATATCATGGTG GAAAATGGCCGCTTTTCTGGATTCATCGACTGTGGCCGGCTGGGTGTGGCGGACCGCTATCAGGACATAGCGTTGGCTACC CGTGATATTGCTGAAGAGCTTGGCGGCGAATGGGCTGACCGCTTCCTCGTGCTTTACGGTATCGCCGCTCCCGATTCGCAG CGCATCGCCTTCTATCGCCTTCTTGACGAGTTCTTCTGAGCGGGACTCTGGGGTTCGCGATGATAAGCTGTCAAACATGAG AATTACAACTTATATCGTATGGGGCTGACTTCAGGTGCTACATTTGAAGAGATAAATTGCACTGAAATCTAGAAATATTTT ATCTGATTAATAAGATGATCTTCTTGAGATCGTTTTGGTCTGCGCGTAATCTCTTGCTCTGAAAACGAAAAAACCGCCTTG CAGGGCGGTTTTTCGAAGGTTCTCTGAGCTACCAACTCTTTGAACCGAGGTAACTGGCTTGGAGGAGCGCAGTCACCAAA ACTTGTCCTTTCAGTTTAGCCTTAACCGGCGCATGACTTCAAGACTAACTCCTCTAAATCAATTACCAGTGGCTGCTGCCAG TGGTGCTTTTGCATGTCTTTCCGGGTTGGACTCAAGACGATAGTTACCGGATAAGGCGCAGCGGTCGGACTGAACGGGGG GTTCGTGCATACAGTCCAGCTTGGAGCGAACTGCCTACCCGGAACTGAGTGTCAGGCGTGGAATGAGACAAACGCGGCCA TAACAGCGGAATGACACCGGTAAACCGAAAGGCAGGAACAGGAGAGCGCACGAGGGAGCCGCCAGGGGAAACGCCTGG TATCTTTATAGTCCTGTCGGGTTTCGCCACCACTGATTTGAGCGTCAGATTTCGTGATGCTTGTCAGGGGGGCGGAGCCTAT GGAAAAACGGCTTTGCCTTCTTTCCTGCGTTATCCCCTGATTCTGTGGATAACCGTATTACCGCCTTTGAGTGAGCTGATAC CGCTCGCCGCAGCCGAACGACCGAGCGCAGCGAGTCAGTGAGCGAGGAAGCGGAAGAGCGCCCAATACGCAAACCGCCT CTCCCCGCGCGTTGGCCGATTCATTAATGCAGCTGGCACGACAGGTTTCCCGACTGGAAAGCGGGCAGTGAGCGCAACGC AATTAATGTGAGTTAGCTCACTCATTAGGCACCCCAGGCTTTACACTTTATGCTTCCGGCTCGTATGTTGTGTGGAATTGTG AGCGGATAACAATTTCACACAGGAGGAATCAAAA |
| SEQ ID NO: 170 nucleic acid sequence for the plasmid pTrc-FG99_15380: pduP(Se):gabD | GTTTGACAGCTTATCATCGACTGCACGGTGCACCAATGCTTCTGGCGTCAGGCAGCCATCGGAAGCTGTGGTATGGCTGTG CAGGTCGTAAATCACTGCATAATTCGTGTCGCTCAAGGCGCACTCCCGTTCTGGATAATGTTTTTTGCGCCGACATCATAA CGGTTCTGGCAAATATTCTGAAATGAGCTGTTGACAATTAATCATCCGGCTCGTATAATGTGTGGAATTGTGAGCGGATAA CAATTTCACACAGGAGGAATCAAAAATGAATCAACAGGTAAATGTGGCCCCCAGCGCGGCAGCAGACTTAAATCTGAAA GCGCATTGGATGCCTTTTAGCGCCAACCGCAACTTCCACAAGGACCCCCGCATCATCGTAGCTGCCGAAGGATCGTGGCTG GTAGACGATAAGGGACGCCGTATCTACGACTCATTGAGTGGCTTGTGGACCTGCGGCGCGGGTCACTCTCGTAAGGAAAT TGCCGACGCAGTGGCGAAACAGATTGGGACCCTGGACTACTCGCCAGGGTTTCAATATGGCCACCCTCTGTCGTTTCAGCT TGCAGAGAAGATTGCGCAAATGACGCCTGGCACGCTGGATCATGTCTTCTTTACAGGAAGTGGGAGTGAATGCGCGGACA CATCTATCAAAATGGCTCGCGCCTACTGGCGCATCAAGGGCCAAGCGCAGAAGACCAAGTTGATCGGCCGTGCTCGCGGA TATCACGGCGTCAACGTGGCCGGAACATCGCTTGGAGGTATTGGGGGAAACCGTAAAATGTTCGGACCCCTGATGGATGT CGATCATTTGCCTCACACATTACAACCTGGAATGGCATTCACTAAGGGCGCAGCAGAAACAGGTGGGGTGGAGCTTGCCA ATGAATTGCTGAAGTTAATTGAGTTACATGATGCTTCGAATATCGCCGCAGTGATTGTGGAGCCTATGTCTGGCAGTGCCG GTGTGATTGTGCCACCAAAAGGTTATCTTCAGCGTTTACGTGAGATTTGCGACGCTAACGATATCCTGTTAATCTTCGACG AGGTGATTACAGCTTTTGGCCGTATGGGCAAAGCAACGGGTGCCGAGTATTTTGGAGTAACTCCCGATATCATGAACGTG GCTAAGCAAGTAACCAACGGGGCCGTTCCGATGGGAGCCGTTATCGCCTCCTCTGAAATTTATGACACCTTCATGAACCAA AACTTGCCCGAATACGCCGTGGAATTTGGACATGGTTATACTTACAGCGCTCATCCAGTGGCATGTGCCGCCGGCATCGCG GCGCTGGATCTGCTTCAAAAAGAGAATTTAATCCAGCAGTCGGCCGAGCTTGCACCTCACTTCGAAAAGGCCTTACATGG |

TABLE 4-continued

Nucleic Acid Sequences: Plasmids

| SEQ ID NO | Nucleotide Sequence |
|---|---|
| | CTTAAAGGGCACTAAAAACGTTATCGATATCCGCAACTGTGGCCTTGCTGGAGCGATTCAAATCGCGGCGCGCGACGGAG<br>ACGCGATCGTGCGCCCCTTTGAGGCGAGCATGAAGTTGTGGAAGGAAGGCTTCTACGTGCGTTTCGGCGGTGATACCCTG<br>CAATTTGGCCCTACTTTCAACGCCAAACCGGAAGACTTAGATCGCCTTTTCGATGCAGTTGGAGAGGCACTGAACGGGGTC<br>GCTTAAGCTAGCAAAGGAGGTAAAGATAATGAATACTTCTGAACTCGAAACCCTGATTCGCACCATTCTTAGCGAGCAAT<br>TAACCACGCCGGCGCAAACGCCGGTCCAGCCTCAGGGCAAAGGGATTTTCCAGTCCGTGAGCGAGGCCATCGACGCCGCG<br>CACCAGGCGTTCTTACGTTATCAGCAGTGCCCGCTAAAAACCCGCAGCGCCATTATCAGCGCGATGCGTCAGGAGCTGAC<br>GCCGCTGCTGGCGCCCCTGGCGGAAGAGAGCGCCAATGAAACGGGGATGGGCAACAAAGAAGATAAATTTCTCAAAAAC<br>AAGGCTGCGCTGGACAACACGCCGGGCGTAGAAGATCTCACCACCACGCGCTGACCGGCGACGGCGGCATGGTGCTGTT<br>TGAATACTCACCGTTTGGCGTTATCGGTTCGGTCGCCCCAAGCACCAACCCGACGGAAACCATCATCAACAACAGTATCA<br>GCATGCTGGCGGCGGGCAACAGTATCTACTTTAGCCCGCATCCGGGAGCGAAAAAGGTCTCTCTGAAGCTGATTAGCCTG<br>ATTGAAGAGATTGCCTTCCGCTGCTGCGGCATCCGCAATCTGGTGGTGACCGTGGCGGAACCCACCTTCGAAGCGACCCA<br>GCAGATGATGGCCCACCCGCGAATCGCAGTACTGGCCATTACCGGCGGCCCGGGCATTGTGGCAATGGGCATGAAGAGCG<br>GTAAGAAGGTGATTGGCGCTGGCGCGGGTAACCCGCCCTGCATCGTTGATGAAACGGCGGACCTGGTGAAAGCGGCGGA<br>AGATATCATCAACGGCGCGTCATTCGATTACAACCTGCCCTGCATTGCCGAGAAGAGCCTGATCGTAGTGGAGAGTGTCG<br>CCGAACGTCTGGTGCAGCAAATGCAAACCTTCGGCGCGCTGCTGTTAAGCCCTGCCGATACCGACAAACTCCGCGCCGTCT<br>GCCTGCCTGAAGGCCAGGCGAATAAAAAACTGGTCGGCAAGAGCCCATCGGCCATGCTGGAAGCCGCCGGGATCGCTGTC<br>CCTGCAAAAGCGCCGCGTCTGCTGATTGCGCTGGTTAACGCTGACGATCCGTGGGTCACCAGCGAACAGTTGATGCCGAT<br>GCTGCCAGTGGTAAAAGTCAGCGATTTCGATAGCGCGCTGGCGCTGGCCCTGAAGGTTGAAGAGGGGCTGCATCATACCG<br>CCATTATGCACTCGCAGAACGTGTCACGCCTGAACCTCGCGGCCCGCACGCTGCAAACCTCGATATTCGTCAAAAACGGC<br>CCCTCTTATGCCGGGATCGGCGTCGGCGGCGAAGGCTTTACCACCTTCACTATCGCCACACCAACCGGTGAAGGGACCAC<br>GTCAGCGCGTACTTTTGCCCGTTCCCGGCGCTGCGTACTGACCAACGGCTTTTCTATTCGCTAACTCGAGAAAGGAGGATA<br>ACTAAATGAAACTTAACGACAGTAACTTATTCCGCCAGCAGGCGTTGATTAACGGGGAATGGCTGGACGCCAACAATGGT<br>GAAGCCATCGACGTCACCAATCCGGCGAACGGCGACAAGCTGGGTAGCGTGCCGAAAATGGGCGCGGATGAAACCCGCG<br>CCGCTATCGACGCCGCCAACCGCGCCCTGCCCGCCTGGCGCGCGCTCACCGCCAAAGAACGCGCCACCATTCTGCGCAAC<br>TGGTTCAATTTGATGATGGAGCATCAGGACGATTTAGCGCGCCTGATGACCCTCGAACAGGGTAAACCACTGGCCGAAGC<br>GAAAGGCGAAATCAGCTACGCCGCCTCCTTTATTGAGTGGTTTGCCGAAGAAGGCAAACGCATTTATGGCGACACCATTC<br>CTGGTCATCAGGCCGATAAACGCCTGATTGTTATCAAGCAGCCGATTGGCGTCACCGCGGCTATCACGCCGTGGAACTTCC<br>CGGCGGCGATGATTACCCGCAAAGCCGGTCCGGCGCTGGCAGCAGGCTGCACCATGGTGCTGAAGCCCGCCAGTCAGACG<br>CCGTTCTCTGCGCTGGCGCTGGCGGAGCTGGCGATCCGCGCGGGCGTTCCGGCTGGGGTATTTAACGTGGTCACCGGTTCG<br>GCGGGCGCGGTCGGTAACGAACTGACCAGTAACCCGCTGGTGCGCAAACTGTCGTTTACCGGTTCGACCGAAATTGGCCG<br>CCAGTTAATGGAACAGTGCGCGAAAGACATCAAGAAAGTGTCGCTGGAGCTGGGCGGTAACGCGCCGTTTATCGTCTTTG<br>ACGATGCCGACCTCGACAAAGCCGTGGAAGGCGCGCTGGCCTCGAAATTCCGCAACGCCGGGCAAACCTGCGTCTGCGCC<br>AACCGCCTGTATGTGCAGGACGGCGTGTATGACCGTTTTGCCGAAAAATTGCAGCAGGCAGTGAGCAAACTGCACATCGG<br>CGACGGGCTGGATAACGGCGTCACCATCGGGCCGCTGATCGATGAAAAAGCGGTAGCAAAAGTGGAAGAGCATATTGCC<br>GATGCGCTGGAGAAAGGCGCGCGCGTGGTTTGCGGCGGTAAAGCGCACGAACGCGGCGGCAACTTCTTCCAGCCGACCAT<br>TCTGGTGGACGTTCCGGCCAACGCCAAAGTGTCGAAAGAAGAGACGTTCGGCCCCCTCGCCCCGCTGTTCCGCTTTAAAG<br>ATGAAGCTGATGTGATTGCGCAAGCCAATGACACCGAGTTTGGCCTTGCCGCCTATTTCTACGCCCGTGATTTAAGCCGCG<br>TCTTCCGCGTGGGCGAAGCGCTGGAGTACGGCATCGTCGGCATCAATACCGGCATTATTTCCAATGAAGTGGCCCCGTTCG<br>GCGGCATCAAAGCCTCGGGTCTGGGTCGTGAAGGTTCGAAGTATGGCATCGAAGATTACTTAGAAATCAAATATATGTGC<br>ATCGGTCTTTAAGGCTGTTTTGGCGGATGAGAGAAGATTTTCAGCCTGATACAGATTAAATCAGAACGCAGAAGCGGTCT<br>GATAAAACAGAATTTGCCTGGCGGCAGTAGCGCGGTGGTCCCACCTGACCCCATGCCGAACTCAGAAGTGAAACGCCGTA<br>GCGCCGATGGTAGTGTGGGGTCTCCCCATGCGAGAGTAGGGAACTGCCAGGCATCAAATAAAACGAAAGGCTCAGTCGA<br>AAGACTGGGCCTTTCGTTTTATCTGTTGTTTGTCGGTGAACGCTCTCCTGAGTAGGACAAATCCGCCGGGAGCGGATTTGA<br>ACGTTGCGAAGCAACGGCCCGGAGGGTGGCGGGCAGGACGCCCGCCATAAACTGCCAGGCATCAAATTAAGCAGAAGGC<br>CATCCTGACGGATGGCCTTTTTGCGTTTCTACAAACTCTTTTTGTTTATTTTTCTAAATACATTCAAATATGTATCCGCTCAT<br>GAGACAATAACCCTGATAAATGCTTCAATAATATTGAAAAAGGAAGAGTATGAGTATTCAACATTTCCGTGTCGCCCTTAT<br>TCCCTTTTTTGCGGCATTTTGCCTTCCTGTTTTTGCTCACCCAGAAACGCTGGTGAAAGTAAAAGATGCTGAAGATCAGTTG<br>GGTGCACGAGTGGGTTACATCGAACTGGATCTCAACAGCGGTAAGATCCTTGAGAGTTTTCGCCCCGAAGAACGTTTTCCA<br>ATGATGAGCACTTTTAAAGTTCTGCTATGTGGCGCGGTATTATCCCGTGTTGACGCCGGGCAAGAGCAACTCGGTCGCCGC<br>ATACACTATTCTCAGAATGACTTGGTTGAGTACTCACCAGTCACAGAAAAGCATCTTACGGATGGCATGACAGTAAGAGA<br>ATTATGCAGTGCTGCCATAACCATGAGTGATAACACTGCGGCCAACTTACTTCTGACAACGATCGGAGGACCGAAGGAGC<br>TAACCGCTTTTTTGCACAACATGGGGGATCATGTAACTCGCCTTGATCGTTGGGAACCGGAGCTGAATGAAGCCATACCAA<br>ACGACGAGCGTGACACCACGATGCCTACAGCAATGGCAACAACGTTGCGCAAACTATTAACTGGCGAACTACTTACTCTA<br>GCTTCCCGGCAACAATTAATAGACTGGATGGAGGCGGATAAAGTTGCAGGACCACTTCTGCGCTCGGCCCTTCCGGCTGG<br>CTGGTTTATTGCTGATAAATCTGGAGCCGGTGAGCGTGGGTCTCGCGGTATCATTGCAGCACTGGGGCCAGATGGTAAGCC<br>CTCCCGTATCGTAGTTATCTACACGACGGGGAGTCAGGCAACTATGGATGAACGAAATAGACAGATCGCTGAGATAGGTG<br>CCTCACTGATTAAGCATTGGTAACTGTCAGACCAAGTTTACTCATATATACTTTAGATTGATTTAAAACTTCATTTTTAATT<br>TAAAAGGATCTAGGTGAAGATCCTTTTTGATAATCTCATGACCAAAATCCCTTAACGTGAGTTTTCGTTCCACTGAGCGTC<br>AGACCCCGTAGAAAAGATCAAAGGATCTTCTTGAGATCCTTTTTTTCTGCGCGTAATCTGCTGCTTGCAAACAAAAAAACC<br>ACCGCTACCAGCGGTGGTTTGTTTGCCGGATCAAGAGCTACCAACTCTTTTTCCGAAGGTAACTGGCTTCAGCAGAGCGCA<br>GATACCAAATACTGTCCTTCTAGTGTAGCCGTAGTTAGGCCACCACTTCAAGAACTCTGTAGCACCGCCTACATACCTCGC<br>TCTGCTAATCCTGTTACCAGTGGCTGCTGCCAGTGGCGATAAGTCGTGTCTTACCGGGTTGGACTCAAGACGATAGTTACC<br>GGATAAGGCGCAGCGGTCGGGCTGAACGGGGGGTTCGTGCACACAGCCCAGCTTGGAGCGAACGACCTACACCGAACTG<br>AGATACCTACAGCGTGAGCTATGAGAAAGCGCCACGCTTCCCGAAGGGAGAAAGGCGGACAGGTATCCGGTAAGCGGCA<br>GGGTCGGAACAGGAGAGCGCACGAGGGAGCTTCCAGGGGGAAACGCCTGGTATCTTTATAGTCCTGTCGGGTTTCGCCAC<br>CTCTGACTTGAGCGTCGATTTTTGTGATGCTCGTCAGGGGGGCGGAGCCTATGGAAAAACGCCAGCAACGCGGCCTTTTTA<br>CGGTTCCTGGCCTTTTGCTGGCCTTTTGCTCACATGTTCTTTCCTGCGTTATCCCCTGATTCTGTGGATAACCGTATTACCGC<br>CTTTGAGTGAGCTGATACCGCTCGCCGCAGCCGAACGACCGAGCGCAGCGAGTCAGTGAGCGAGGAAGCGGAAGAGCGC<br>CTGATGCGGTATTTTCTCCTTACGCATCTGTGCGGTATTTCACACCGCATATGGTGCACTCTCAGTACAATCTGCTCTGATG<br>CCGCATAGTTAAGCCAGTATACACTCCGCTATCGCTACGTGACTGGGTCATGGCTGCGCCCCGACACCCGCCAACACCCGC<br>TGACGCGCCCTGACGGGCTTGTCTGCTCCCGGCATCCGCTTACAGACAAGCTGTGACCGTCTCCGGGAGCTGCATGTGTCA<br>GAGGTTTTCACCGTCATCACCGAAACGCGCGAGGCAGCAGATCAATTCGCGCGCGAAGGCGAAGCGGCATGCATTTACGT<br>TGACACCATCGAATGGTGCAAAACCTTTCGCGGTATGGCATGATAGCGCCCGGAAGAGAGTCAATTCAGGGTGGTGAATG<br>TGAAACCAGTAACGTTATACGATGTCGCAGAGTATGCCGGTGTCTCTTATCAGACCGTTTCCCGCGTGGTGAACCAGGCCA<br>GCCACGTTTCTGCGAAAACGCGGGAAAAAGTGGAAGCGGCGATGGCGGAGCTGAATTACATTCCCAACCGCGTGGCACA |

TABLE 4-continued

| Nucleic Acid Sequences: Plasmids | |
|---|---|
| SEQ ID NO | Nucleotide Sequence |
| | ACAACTGGCGGGCAAACAGTCGTTGCTGATTGGCGTTGCCACCTCCAGTCTGGCCCTGCACGCGCCGTCGCAAATTGTCGC<br>GGCGATTAAATCTCGCGCCGATCAACTGGGTGCCAGCGTGGTGGTGTCGATGGTAGAACGAAGCGGCGTCGAAGCCTGTA<br>AAGCGGCGGTGCACAATCTTCTCGCGCAACGCGTCAGTGGGCTGATCATTAACTATCCGCTGGATGACCAGGATGCCATT<br>GCTGTGGAAGCTGCCTGCACTAATGTTCCGGCGTTATTTCTTGATGTCTCTGACCAGACACCCATCAACAGTATTATTTTCT<br>CCCATGAAGACGGTACGCGACTGGGCGTGGAGCATCTGGTCGCATTGGGTCACCAGCAAATCGCGCTGTTAGCGGGCCCA<br>TTAAGTTCTGTCTCGGCGCGTCTGCGTCTGGCTGGCTGGCATAAATATCTCACTCGCAATCAAATTCAGCCGATAGCGGAA<br>CGGGAAGGCGACTGGAGTGCCATGTCCGGTTTTCAACAAACCATGCAAATGCTGAATGAGGGCATCGTTCCCACTGCGAT<br>GCTGGTTGCCAACGATCAGATGGCGCTGGGCGCAATGCGCGCCATTACCGAGTCCGGGCTGCGCGTTGGTGCGGATATCT<br>CGGTAGTGGGATACGACGATACCGAAGACAGCTCATGTTATATCCCGCCGTTAACCACCATCAAACAGGATTTTCGCCTGC<br>TGGGGCAAACCAGCGTGGACCGCTTGCTGCAACTCTCTCAGGGCCAGGCGGTGAAGGGCAATCAGCTGTTGCCCGTCTCA<br>CTGGTGAAAAGAAAAACCACCCTGGCGCCCAATACGCAAACCGCCTCTCCCCGCGCGTTGGCCGATTCATTAATGCAGCT<br>GGCACGACAGGTTTCCCGACTGGAAAGCGGGCAGTGAGCGCAACGCAATTAATGTGAGTTAGCGCGAATTGATCTG |

In embodiments, the recombinant bacterial cell for producing PHBV comprises at least one nucleic acid molecule having a nucleic acid sequence having at least 75%, 80%, 85%, 90%, 91%, 92%, 93%, 94%, 95%, 96%, 97%, 98%, 99%, 99.1%, 99.2%, 99.3% 99.4% 99.5% 99.6%, 99.7%, 99.8%, 99.9%, or 100% sequence identity to any one of SEQ ID NO: 60-118, 174-175, 185-193, 204-213, 218-220, 227-229, and 231, or a complementary sequence thereof, or a segment thereof. In embodiments, the at least one nucleic acid molecule described herein is optionally a heterologous nucleic acid molecule having a nucleic acid sequence encoding a recombinant polypeptide described herein. In embodiments, the acyl-CoA synthetase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 85 or 86, the acetate CoA-transferase polypeptides are encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 63 and 64 or 174 and 175, the propionate-CoA transferase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 89 or 90. In embodiments, the PutP polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 205. In embodiments, the AtoE polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 65. In embodiments, the first β-ketothiolase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 67. In embodiments, the NADPH-dependent acetoacetyl-CoA reductase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 94. In embodiments, the NADH-dependent acetoacetyl-CoA reductase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 228. In embodiments, the short-chain polyhydroxyalkanoate synthase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 95, 229, or 231. In embodiments, the CoA-dependent propanal dehydrogenase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 91 or 92, the β-alanine transaminase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 74 or 75, or the NADP+-dependent succinate semialdehyde dehydrogenase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 76. In embodiments, the short-chain acyl-CoA dehydrogenase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 97, 98, 66, 87, or 72, and the enoyl-CoA hydratase/isomerase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 81, 96, or 206. In embodiments, the propionyl-CoA synthetase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 102, 103, or 104. In embodiments, the glutamate decarboxylase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 78, 79, 204, 219, 220, or 227. In embodiments, the glutamate dehydrogenase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 218. In embodiments, the second β-ketothiolase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 93. In embodiments, the succinyl-CoA transferase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 69. In embodiments, the succinyl-CoA synthetase polypeptides are encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 109 and 110. In embodiments, the CoA-acylating aldehyde dehydrogenase polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 193. In embodiments, the bifunctional protein polypeptide is encoded by a nucleic acid molecule, optionally a heterologous nucleic acid molecule, having a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to SEQ ID NO: 88. In embodiments, the at least one heterologous nucleic acid molecule encoding a polypeptide is operably linked to a promoter capable of expressing a heterologous nucleic acid sequence encoding the recombinant polypeptide in a bacterial cell.

Also provided is a plasmid comprising nucleic acid sequence described herein. In embodiments, the plasmid comprises a nucleic acid sequence having at least 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to any one of SEQ ID NO: 162-171.

In an aspect, the heterologous nucleic acid molecule or plasmid is codon-optimized for expression in a bacterial cell described herein. In embodiments, the bacterial cell is selected from the group consisting of *Escherichia coli*, optionally strain K-12 or a derivative thereof, optionally CPC-Sbm or a derivative thereof, *Bacillus subtilis, Bacillus megaterium, Corynebacterium glutamicum, Salmonella enterica, Klebsiella pneumoniae, Klebsiella oxytoca, Lactococcus lactis, Pseudomonas putida, Cupriavidus necator, Cupriavidus gilardii, Cupriavidus* sp. S-6, and *Lactobacillus reuteri.*

In embodiments, the nucleic acid molecule comprises an isolated and/or purified nucleic acid molecule. In embodiments, a nucleic acid molecule, a plasmid, or an expression system comprising these isolated and/or purified nucleic acid molecules, may be used to create a recombinant bacterial cell that produces polypeptides which catalyze the synthesis of PHBV. Therefore, some embodiments relate to a recombinant bacterial cell comprising a nucleic acid molecule, a plasmid, or an expression system having at least one of SEQ ID NO: 60-118, 162-170, 185-193, 204-213, 218-220, 227-229, and 231, or having at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9% sequence identity to at least one of SEQ ID NO: 60-118, 162-170, 185-193, 204-213, 218-220, 227-229, and 231.

A person of ordinary skill in the art would readily understand that the disclosed polypeptide amino acid and nucleic acid sequences may be used interchangeably with any of their corresponding homologs. For example, In embodiments, the recombinant bacterial cell for producing PHBV comprises at least one nucleic acid molecule encoding a polypeptide corresponding to any of the homologs listed in Table 6. In embodiments, a homolog of AckA comprises a polypeptide having an accession no. WP_151250307.1, WP_025758333.1, WP_000095714.1, WP_094316684.1, WP_000095699.1, WP_059270696.1, WP_160523843.1, WP_108188758.1, WP_000095694.1, WP_079781741.1, WP_000095691.1, WP_162383091.1, WP_110248734.1, WP_016529145.1, or WP_064543869.1. In embodiments, a homolog of Acs comprises a polypeptide having an accession no. WP_094321046.1, WP_134796521.1, WP_000078234.1, WP_000078255.1, WP_160523940.1, WP_130258462.1, WP_135490640.1, WP_000078187.1, WP_000078188.1, WP_105283185.1, WP_079225661.1, WP_151218054.1, EAX3726079.1, WP_061075561.1, or WP_087051807.1. In embodiments, a homolog of Ald comprises a polypeptide having an accession no. WP_077830381.1, WP_065419149.1, WP_017211959.1, WP_077844109.1, AAD31841.1, WP_087702529.1, WP_077868466.1, WP_077366605.1, WP_026888070.1, WP_077860531.1, WP_022747467.1, WP_077863550.1, WP_009171375.1, WP_128214949.1, WP_160679606.1, WP_012059995.1, WP_041898834.1, or WP_015395720.1. In embodiments, a homolog of AcsA comprises a polypeptide having an accession no. WP_047183033.1, WP_144459203.1, WP_071577026.1, WP_061186774.1, WP_075747112.1, WP_010329597.1, WP_024714615.1, WP_162101126.1, WP_105990205.1, WP_061572550.1, WP_109567131.1, WP_061523123.1, or WP_103526694.1. In embodiments, a homolog of AtoA comprises a polypeptide having an accession no. WP_103053735.1, WP_137325583.1, WP_050899668.1, WP_000339071.1, WP_128880225.1, WP_047462387.1, WP_135321227.1, WP_090049661.1, WP_004184955.1, WP_151219893.1, WP_100682748.1, WP_013365500.1, WP_000339048.1, or WP_087857377.1. In embodiments, a homolog of AtoD comprises a polypeptide having an accession no. WP_053001645.1, QGU62017.1, WP_155555734.1, WP_038355059.1, MLY49728.1, WP_105269001.1, WP_105284960.1, WP_149476985.1, WP_108188772.1, WP_000850520.1, WP_138957179.1, WP_123267594.1, WP_114680602.1, WP_047500919.1, or WP_004184954.1. In embodiments, a homolog of BC_5341 comprises a polypeptide having an accession no. WP_088022147.1, WP_098448816.1, WP_149216716.1, WP_101167410.1, WP_143881711.1, WP_085450733.1, WP_144504985.1, BCA34359.1, WP_098299175.1, WP_071710801.1, CKE48212.1, WP_163095898.1, WP_071725959.1, WP_136445333.1, or WP_128975345.1. In embodiments, a homolog of BktB comprises a polypeptide having an accession no. WP_013956457.1, WP_035820088.1, WP_092317205.1, WP_115013782.1, WP_116382528.1, WP_018311404.1, WP_063238655.1, WP_116321050.1, AGW89814.1, WP_062798985.1, WP_133094381.1, AGW95651.1, WP_140952189.1, WP_144195740.1, or WP_011516125.1. In embodiments, a homolog of PhaC comprises a polypeptide having an accession no. ACZ57807.1, WP_010810133.1, WP_013956451.1, AAW65074.1, WP_018311399.1, AGW89808.1, WP_115678329.1, WP_062798976.1, WP_115013788.1, WP_115680054.1, or WP_112777370.1. In embodiments, a homolog of CKL_RS14680 comprises a polypeptide having an accession no. WP_073539834.1 or WP_010236491.1. In embodiments, a homolog of FadE comprises a polypeptide having an accession no. WP_094316844.1, WP_130224094.1, WP_135404353.1, WP_046076114.1, WP_011069257.1, WP_135489829.1, WP_085448671.1, WP_124782953.1, WP_153879457.1, EDR1571704.1, WP_103776898.1, WP_008783785.1, WP_087053141.1, WP_079225425.1, WP_137366593.1, or WP_000973041.1. In embodiments, a homolog of PhaJ(Aa) comprises a polypeptide having an accession no. WP_169200570.1, WP_053422493.1, WP_169118971.1, WP_169202263.1, AUL99438.1, WP_136349851.1, WP_136385326.1, WP_187719679.1, WP_107493682.1, or WP_169262136.1. In embodiments, a homolog of GabD comprises a polypeptide having an accession no. WP_105285925.1, WP_135494970.1, WP_094315749.1, WP_161983589.1, WP_000772895.1, WP_078167276.1, WP_016249103.1, WP_105267583.1, WP_149461599.1, WP_128880059.1, WP_149461599.1, WP_060773285.1, WP_153257801.1, WP_108418849.1, or WP_045446520.1. In embodiments, a homolog of Gad comprises a polypeptide having an accession no. XP_002871761.1, KFK41557.1, VVB14898.1, RID41892.1, XP_013661825.1, VDC86651.1, XP_006400267.1, XP_010420446.1, XP_010453919.1, CAA7061503.1, XP_006400266.1, ESQ41721.1, XP_013627326.1, or XP_031273023.1. In embodiments, a homolog of GadAe comprises a polypeptide having an accession no. WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, or EAB0955940.1. In embodiments, a homolog of GadBe(Ec) comprises a polypeptide having an accession no. WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, or EAB0955940.1. In embodiments, a homolog of GadBe(Lb) polypeptide comprises a polypeptide having an accession no. STX19016.1, QBY21422.1, ANN49747.1, KIO99344.1, ERK41051.1, KRN34776.1, KRL97822.1, WP_057717368.1, VDG20388.1, WP_165444417.1, or AHX56280.1. In embodiments, a homolog of GadB(Lp) polypeptide comprises a polypeptide having an accession no. BBA26472.1, SPD93437.1, KTF01778.1, RDF95564.1, AQY71158.1, KRL97822.1, AHX56280.1, TBX37968.1, AHX56282.1, AHX56281.1, AHX56283.1, or WP_048001054.1. In embodiments, a homolog of Gad(Ls) polypeptide comprises a polypeptide having an accession no. WP_125641322.1, WP_226457942.1, BAN05709.1, MBL3537851.1, WP_039105805.1, WP_052957185.1, KIR08754.1, WP_125574762.1, WP_063488771.1, or WP_017262688.1. In embodiments, a homolog of GdhA polypeptide comprises a polypeptide having an accession no. WP_077135411.1, EFY1585775.1, EFW0012466.1, WP_135489199.1, WP_105291250.1, EEW3328042.1, WP_105274563.1, AGB78530.1, WP_113858645.1, WP_181668454.1, or WP_203398179.1. In embodiments, a homolog of H16_RS27940 comprises a polypeptide having an accession no. WP_051591491.1, WP_114130480.1, WP_078200706.1, EON20731.1, PKO64515.1, WP_092007571.1, WP_162566377.1, WP_137921632.1, or WP_162591754.1. In embodiments, a homolog of KES23458 comprises a polypeptide having an accession no. WP_116425784.1, WP_069862932.1, WP_043315988.1, WP_009614288.1, WP_089392503.1, WP_109934365.1, WP_090268322.1, WP_138519936.1, WP_138213347.1, WP_015474919.1, WP_043256620.1, WP_084311461.1, WP_053816481.1, WP_070656248.1, or WP_077524299.1. In embodiments, a homolog of LvaE comprises a polypeptide having an accession no. WP_051095536.1, AGA73676.1, WP_054905284.1, OFQ86312.1, OFQ81524.1, WP_102880076.1, WP_092297027.1, WP_160291004.1, WP_081520035.1, WP_104443972.1, WP_046855848.1, WP_134690622.1, WP_103303932.1, WP_042129240.1, or BAV75244.1. In embodiments, a homolog of MELS_RS10970 comprises a polypeptide having an accession no. WP_020723925.1, WP_048514244.1, WP_074501184.1, KXB91325.1, WP_154877386.1, WP_107195291.1, WP_087477538.1, WP_095630133.1, WP_091647756.1, WP_023053225.1, WP_101912630.1, WP_075572446.1, WP_006790232.1, or WP_006942404.1. In embodiments, a homolog of PaaZ comprises a polypeptide having an accession no. WP_160599600.1, WP_152066042.1, WP_094316530.1, WP_032252644.1, WP_001186464.1, WP_125401136.1, WP_001186494.1, WP_119163289.1, WP_095281943.1, WP_045888522.1, WP_058840681.1, WP_095440732.1, WP_162382197.1, WP_059385322.1, or WP_045286529.1. In embodiments, a homolog of Pct(Cp) comprises a polypeptide having an accession no. WP_066087637.1, NCC15629.1, WP_054329786.1, WP_072853413.1, CDC28613.1, WP_016408311.1, WP_088107724.1, WP_160302233.1, or WP_004038625.1. In embodiments, a homolog of Pct(Me) comprises a polypeptide having an accession no. WP_054336166.1, WP_036203125.1, WP_044502862.1, WP_065360594.1, KXA66894.1, WP_095629974.1, WP_087478516.1, WP_107195767.1, WP_048515067.1, WP_101912966.1, WP_156208970.1, KXB92430.1, WP_023053187.1, WP_039891686.1, or KXB92214.1. In embodiments, a homolog of PduP(Kp) comprises a polypeptide having an accession no. WP_109231734.1, WP_109848747.1, WP_136028274.1, WP_100680758.1, WP_100631313.1, WP_049157539.1, WP_029884370.1, MXH33721.1, WP_144232363.1, WP_153679752.1, WP_148849915.1, EBS2830838.1, WP_112213940.1, or WP_064370270.1.

In embodiments, a homolog of PduP(Se) comprises a polypeptide having an accession no. WP_001097684.1, WP_001528442.1, WP_080203692.1, WP_108450871.1, WP_009652778.1, WP_142983670.1, WP_105274032.1, WP_070556870.1, WP_142502560.1, WP_012131760.1, WP_012906342.1, WP_006683971.1, WP_103775053.1, WP_060570657.1, or WP_135321437.1. In embodiments, a homolog of PhaA comprises a polypeptide having an accession no. WP_013956452.1, SCU96900.1, WP_035820078.1, 4O9C_A, WP_116382525.1, WP_092317196.1, WP_062798979.1, WP_116321054.1, AGW89809.1, WP_039016192.1, WP_063238652.1, WP_029049660.1, WP_011297518.1, WP_124684437.1, or WP_109580845.1. In embodiments, a homolog of PhaB comprises a polypeptide having an accession no. RWA53825.1, WP_042885115.1, WP_039016191.1, WP_116336746.1, WP_112777371.1, WP_006577377.1, WP_135705030.1, WP_133096842.1, WP_124684436.1, WP_116321053.1, WP_006155939.1, WP_045241722.1, WP_011297519.1, WP_144195744.1, or ODV43053.1. In embodiments, a homolog of PhaB(Hb) comprises a polypeptide having an accession no. WP_162219671.1, WP_126946472.1, WP_120385833.1, WP_030074446.1, WP_188637499.1, WP_058579713.1, WP_083023226.1, WP_039183428.1, WP_159340906.1, or WP_096653461.1. In embodiments, a homolog of PhaJ(Ac) comprises a polypeptide having an accession no. WP_103260220.1, WP_104454254.1, OJW67134.1, WP_041998622.1, WP_043760202.1, WP_043129860.1, WP_042076944.1, WP_100860962.1, WP_163157368.1, WP_042638062.1, WP_106886672.1, WP_033131291.1, WP_025327110.1, WP_040094291.1, or WP_139745378.1. In embodiments, a homolog of PP_2216 comprises a polypeptide having an accession no. WP_003250094.1, WP_104887321.1, WP_039614175.1, WP_023662689.1, WP_085706434.1, WP_070087269.1, WP_060512757.1, WP_144171976.1, WP_054884005.1, WP_051100719.1, WP_099814118.1, WP_125859423.1, WP_125464833.1, WP_090345830.1, or WP_110994568.1. In embodiments, a homolog of PrpE(Cn) comprises a polypeptide having an accession no. WP_081623799.1, WP_115213214.1, WP_082818978.1, WP_116324638.1, WP_092309442.1, AMR79067.1, WP_151072146.1, WP_029046365.1, AGW91162.1, WP_116321975.1, WP_039006728.1, WP_092134378.1, WP_109580644.1, WP_035882297.1, or WP_149135646.1. In embodiments, a homolog of PrpE(Ec) comprises a polypeptide having an accession no. WP_024249411.1, WP_130258507.1, WP_000010307.1, WP_138159881.1, WP_105281240.1, WP_000010239.1, WP_000010244.1, WP_160524152.1, WP_105270931.1, WP_160530253.1, WP_016235155.1, WP_061090735.1, WP_103014998.1, WP_094761423.1, or ATX90159.1. In embodiments, a homolog of PrpE(Se) comprises a polypeptide having an accession no. WP_127836169.1, WP_103776706.1, WP_044259075.1, WP_012904755.1, WP_043015332.1, WP_008783866.1, WP_153690685.1, WP_058587683.1, WP_101700584.1, WP_042324663.1, WP_123268908.1, WP_137351112.1, WP_048219548.1, WP_160955604.1, or WP_012133646.1. In embodiments, a homolog of Pta comprises a polypeptide having an accession no. WP_119174868.1, WP_114414934.1, WP_112484304.1, WP_000086724.1, WP_135520103.1, WP_113650156.1, WP_105273752.1, WP_079788930.1, WP_000086702.1, WP_135520103.1, WP_038354606.1, WP_025714133.1, WP_071260224.1, WP_046483030.1, or WP_080924257.1. In embodiments, a homolog of Sbm comprises a polypeptide having an accession no. CDW60403.1, WP_096098300.1, QGU68683.1, WP_000073215.1, WP_024250007.1, WP_105273911.1, EBT2497755.1, WP_064198903.1, WP_105271628.1, CDZ86651.1, WP_130258050.1, WP_038355443.1, WP_142462060.1, WP_103769047.1, or WP_137649991.1. In embodiments, a homolog of SucC comprises a polypeptide having an accession no. WP_111780024.1, WP_105268114.1, WP_149508492.1, EBH0782533.1, WP_079789068.1, EAA0703253.1, WP_001048612.1, WP_103776364.1, HAC6539881.1, WP_139538723.1, WP_040076526.1, WP_152308781.1, WP_061708388.1, WP_159152251.1, or WP_159754306.1

In embodiments, a homolog of SucD comprises a polypeptide having an accession no. WP_148048643.1, WP_161983406.1, WP_128882005.1, SEK68167.1, WP_064567804.1, WP_090133347.1, EDS6037479.1, WP_015965312.1, WP_154777294.1, WP_108473875.1, WP_162082208.1, or WP_154158334.1. In embodiments, a homolog of YgfD comprises a polypeptide having an accession no. HBV28035.1, WP_094338169.1, EBT2497754.1, WP_105273912.1, WP_105271629.1, MJD64661.1, MVY25917.1, WP_152060700.1, CDZ86650.1, CDK74861.1, WP_138183055.1, WP_138158389.1, WP_138158874.1, WP_137651359.1, or WP_038355444.1. In embodiments, a homolog of YgfG comprises a polypeptide having an accession no. WP_105273913.1, WP_011069498.1, WP_095785007.1, KAE9894204.1, WP_128881119.1, WP_105287397.1, EBT2497753.1, WP_112366200.1, CDZ86649.1, WP_137653935.1, WP_103750818.1, WP_135521100.1, EFE06586.1, WP_080626129.1, or WP_079226013.1. In embodiments, a homolog of YgfH comprises a polypeptide having an accession no. WP_094321963.1, WP_075331646.1, WP_105271630.1, WP_128881120.1, WP_075328602.1, WP_128861696.1, ECA1898152.1, WP_105273914.1, CDZ86648.1, WP_130221450.1, WP_135519865.1, WP_001027665.1, WP_135407775.1, WP_130221450.1, or WP_135492970.1.

Cultivation Medium

Strains were maintained as glycerol stocks at −80° C., and were revived on non-selective lysogeny broth (LB) agar containing 5 g/L NaCl, 5 g/L yeast extract, 10 g/L tryptone, 15 g/L agar, and antibiotics as required, and incubated overnight at 30-37° C. LB also served as the medium for starter and seed cultures and was supplemented with antibiotics as required. The performance of *E. coli* strains was evaluated in shake flask cultures in a base medium of the following composition: M9 salts (12.8 g/L $Na_2HPO_4 \cdot H_2O$, 3 g/L $KH_2PO_4$, 0.5 g/L NaCl, and 1 g/L $NH_4Cl$), yeast extract (5 g/L), $NaHCO_3$ (10 mM), trace elements (2.86 g/L $H_3BO_3$, 1.81 g/L $MnCl_2·4H_2O$, 0.22 g/L $ZnSO_4·7H_2O$, 0.39 g/L $Na_2MoO_4·2H_2O$, 79 μg/L $CuSO_4·5H_2O$, and 49.4 μg/L $Co(NO_3)_2·6H_2O$) as a 1000× concentrate), $MgSO_4$ (1 mM), and isopropyl beta-D-1-thiogalactopyranoside (IPTG), with antibiotics added as required. Cultures can be supplemented with sodium acetate, sodium propionate, and/or sodium butyrate at respective concentrations of up to 20 g/L, 10 g/L, and 8 g/L, or a VFA feedstock at up to 75% by volume to facilitate (R)-HB-CoA and (R)-HV-CoA production (to produce PHBV). Additional carbon sources, for example, but not limited to, glucose, glycerol, pretreated biomass, and cheese whey can be used to augment PHBV production and growth. Additionally, nitrogen sources, for example, but not limited to, ammonium salts and corn steep liquor can be used in place of yeast extract. Inducer (i.e. IPTG) concentration may vary between 0 mM and 1 mM to tune expression of pathway enzymes. Cyanocobalamin (vitamin $B_{12}$) is added to the medium at a concentration of 0.1-2 μM to facilitate the functional expression of Sbm as required. Pyridoxal 5'-phosphate (PLP), the active form of vitamin $B_6$, can be added to the medium at a concentration of 0.1-2 mM to facilitate the conversion of L-glutamate to 4-aminobutyrate via a glutamate decarboxylase polypeptide. The same range of medium compositions can be used for bioreactor cultures.

In embodiments, the method comprises culturing a recombinant bacterial cell in a culture medium comprising at least one carbon source. In embodiments, the carbon source comprises at least one of VFA, optionally sodium acetate, sodium propionate, sodium butyrate, and glucose, glycerol, biomass, optionally pretreated biomass, and cheese whey. In embodiments, the method comprises culturing a recombinant bacterial cell in a culture medium comprising at least one of about 0.01 to 20 g/L sodium acetate, about 0.01 to 10 g/L sodium propionate, about 0.01 to 8 g/L sodium butyrate, about 1-10 g/L butyraldehyde, about 1-10 g/L L-glutamate, about 1-10 g/L 4-aminobutyrate, and about 1-10 g/L succinate. In embodiments, the method comprises culturing a recombinant bacterial cell in a culture medium comprising at least one of about 0.01 to 20 g/L sodium acetate, about 0.01 to 10 g/L sodium propionate, and about 0.01 to 8 g/L sodium butyrate. In embodiments, the method comprises culturing a recombinant bacterial cell in a culture medium further comprising at least one of about 1-10 g/L butyraldehyde, about 1-10 g/L L-glutamate, about 1-10 g/L 4-aminobutyrate, and about 1-10 g/L succinate. In embodiments, the method comprises culturing a recombinant bacterial cell in a culture medium comprising between about 20 VFA mmol/L and about 5 VFA mol/L, optionally between about 20 VFA mmol/L and about 90 VFA mmol/L, optionally between about 90 VFA mmol/L land about 180 mmol/L, optionally about or at least 400, 450, 500, 550, 600, 650, 700, 750, or 800 VFA mmol/L, optionally about or up to 1 VFA mol/L. In embodiments, the VFA comprises at least one of about 10-70 mol % acetic acid, about 10-80 mol % propionic acid, and about 10-70 mol % butyric acid. In embodiments, the method comprises culturing a recombinant bacterial cell in a culture medium containing VFA comprising of at least one of about 20-60 mol % acetic acid, about 5-30 mol % propionic acid, and about 20-60 mol % butyric acid. In embodiments, the method comprises culturing a recombinant bacterial cell in a culture medium comprising about at least one of about 0.1-20% (w/v) glucose, optionally about 0.1%-15% (w/v) glucose, optionally about 0.1%-10% glucose, about 0.1-20% (w/v) glycerol, optionally about 0.1%-10% (w/v) glycerol, optionally about 0.1%-5% glycerol, about 0.1-50% (w/v) biomass, optionally about 0.1%-25% (w/v) biomass, optionally about 0.1%-10% biomass, optionally about 50% (w/v) pretreated biomass, optionally about 0.1%-25% (w/v) pretreated biomass, optionally about 0.1%-10% pretreated biomass and about 0.1-50% (w/v) cheese whey, optionally about 0.1%-25% (w/v) cheese whey, optionally about 0.1%-10% cheese whey.

In embodiments, the method comprises culturing a recombinant bacterial cell in a culture medium comprising at least one nitrogen source. In embodiments, the nitrogen source comprises at least one of yeast extract, an ammonium salt, and corn steep liquor. In embodiments, the method comprises culturing a recombinant bacterial cell in a culture media comprising at least one of about 0.1-20% (w/v) yeast extract, about 0.1-20% (w/v) ammonium salt, about 0.1-20% (w/v) casamino acids, and about 0.1-20% (w/v) corn steep liquors.

In embodiments, the method comprises culturing a recombinant bacterial cell in a culture media comprising about 0-2 mM isopropyl beta-D-1-thiogalactopyranoside (IPTG), optionally about 0.3 mM IPTG. In embodiments, the method comprises culturing a recombinant bacterial cell in a culture media comprising about 0.1-2 μM cyanocobalamin, optionally about 0.2 μM cyanocobalamin. In embodiments, the method comprises culturing a recombinant bacterial cell in a culture media comprising about 0.1-2 mM pyridoxal 5'-phosphate (PLP), optionally about 0.5 mM PLP.

In a specific embodiment, the method comprises culturing a recombinant bacterial cell in a culture medium comprising about 30 g/L glycerol, about 10 g/L yeast extract, about 10 mM $NaHCO_3$, about 0.4 μM vitamin $B_{12}$, trace elements, about 0.1 mM IPTG, about 0.23 g/L $K_2HPO_4$, about 0.51 g/L $NH_4Cl$, about 49.8 mg/L $MgCl_2$, about 48.1 mg/L $K_2SO_4$, about 2.78 mg/L $FeSO_4·7H_2O$, about 0.055 mg/L $CaCl_2$, about 2.93 g/L NaCl, and about 0.72 g/L tricine. In embodiments, the trace elements comprises $H_3BO_3$, $MnCl_2·4H_2O$, $ZnSO_4·7H_2O$, $Na_2MoO_4·2H_2O$, $CuSO_4·5H_2O$, $Co(NO_3)_2·6H_2O$. In embodiments, the culture medium comprises trace elements at about 2.86 mg/L $H_3BO_3$, about 1.81 mg/L $MnCl_2·4H_2O$, about 0.222 mg/L $ZnSO_4·7H_2O$, about 0.39 mg/L $Na_2MoO_4·2H_2O$, about 79 ng/L $CuSO_4·5H_2O$, about 49.4 ng/L $Co(NO_3)_2·6H_2O$). In embodiments, the volumetric mass transfer coefficient ($k_La$) is between 50 and 500 $h^{-1}$.

Cultivation Conditions

Shake flask and bioreactor cultures can be performed at temperatures between 25° C. and 42° C. The starting pH in shake flask cultures can be adjusted to pH 5-9, which is the same pH range that can be maintained in bioreactor cultures. The agitation rate in shake flask cultures may range between 50 and 400 revolutions per min (rpm) and can be adjusted between 100 and 1200 rpm in bioreactor cultures. The dissolved oxygen (DO) concentration will be maintained between 1% and 50% of saturation in bioreactor cultures. Various surfactants and perfluorocarbon- and hydrocarbon-based oxygen carriers can be used to improve PHBV production and growth via improved oxygen mass transfer and altered membrane fluidity.

Growth and PHBV production can be improved, for example, by repeated culturing to acclimate *E. coli* strains to higher concentrations of VFA. Such repeated culturing involves, for example, culturing the recombinant *E. coli* cells in a medium containing increasing concentrations of VFA. Culturing can begin in a medium such as a semi-defined medium containing VFA at 1-50 mmol/L, and one or more of, but not limited to, M9 salts, yeast extract, glycerol, $MgSO_4$, $MgCl_2$, $K_2SO_4$, tricine, thiamine, $(NH_4)_2HPO_4$, sodium citrate, $CaCl_2$, $FeSO_4$, $K_2HPO_4$, and trace elements such as $H_3BO_3$, $MnCl_2 \cdot 4H_2O$, $ZnSO_4 \cdot 7H_2O$, $Na_2MoO_4 \cdot 2H_2O$, $CuSO_4 \cdot 5H_2O$, and $Co(NO_3)_2 \cdot 6H_2O$ (i.e. the starting medium). The strains can be cultured for 1-7 days in the starting medium, after which time 5-100% of the culture is centrifuged and the resulting cell pellet is resuspended into a fresh medium containing VFA at a concentration of 101-200% of the starting medium. For example, if the starting medium contains 40 mmol/L VFA, the subsequent (second) round of culturing can occur in a medium containing 40.4-80 mmol/L VFA. Similarly, the second round of culturing can occur for 1-7 days, after which time 5-100% of the culture is centrifuged and the resulting cell pellet is resuspended into a fresh medium containing VFA at a concentration of 101-200% of the medium from the second round of culturing. For example, if the second round of culturing occurred in a medium containing 60 mmol/L VFA, the fresh medium can contain 60.6-120 mmol/L VFA. This process can be repeated until the strains can consume all VFA in cultures supplemented with up to 300 mmol/L VFA, with PHBV yields reaching at least 30% of dry cell weight, assuming that VFA that has not been converted to PHBV can be converted to biomass at a concentration of up to 100 g dry cell weight/L.

In embodiments, the method comprises culturing a recombinant bacterial cell in a culture medium comprising maintaining a temperature of about 20-42° C., optionally about 25-42° C., optionally about 25-37° C. In embodiments, the method comprises culturing a recombinant bacterial cell in a culture medium comprising maintaining a pH of about 4-10, optionally about 5-9, optionally about 6-8. In embodiments, the method comprises culturing a recombinant bacterial cell in a culture medium comprising maintaining an agitation rate of about 50-1200 rpm, optionally about 50-600 rpm, optionally about 100-1200 rpm, optionally about 100-600 rpm. In embodiments, the method comprises culturing a recombinant bacterial cell in a culture medium comprising maintaining dissolved oxygen of about 1-100% of saturation, optionally about 1-5% of saturation, optionally about 6-10% of saturation, optionally about 11-15% of saturation, optionally about 16-20% of saturation, optionally about 21-25% of saturation, optionally about 26-30% of saturation, optionally about 31-35% of saturation, optionally about 36-40% of saturation, optionally about 41-45% of saturation, optionally about 46-50% of saturation, optionally about 51-55% of saturation, optionally about 56-60% of saturation, optionally about 61-65% of saturation, optionally about 66-70% of saturation, optionally about 71-75% of saturation, optionally about 76-80% of saturation, optionally about 81-85% of saturation, optionally about 86-90% of saturation, optionally about 91-95% of saturation, optionally about 96-100% of saturation.

In embodiments, the method comprises culturing a recombinant bacterial cell in a culture media comprising at least one of a surfactant, optionally an anionic surfactant, a cationic surfactant, an amphoteric surfactants, or a non-ionic surfactant, a perfluorocarbon-based oxygen carrier, optionally n-perfluorooctane, perfluorodecalin, perfluoromethyldecalin, or perfluoro-1,3-dimethylcyclohexane) and a hydrocarbon-based oxygen carrier, optionally n-heptane, n-hexadecane, and n-dodecane.

In embodiments, the method described herein comprises producing PHBV in about 1-10 days, optionally about 1-9 days, optionally about 1-8 days, optionally about 1-7 days, optionally about 1-6 days, optionally about 1-5 days, optionally about 1-4 days, optionally about 1-3 days, optionally about 1-2 days, optionally less than 10, 9, 8, 7, 6, 5, 4, 3, or 2, optionally about 1, 2, 3, 4, 5, 6, 7, 8, 9, or 10 days.

In embodiments, the feedstock comprises VFA composition of about: 20-60 mol % acetic acid, 5-30 mol % propionic acid, and 20-60 mol % butyric acid.

In embodiments, the culturing condition for producing intracellular PHBV granules by the recombinant bacterial cell is under pH conditions of 6-9, optionally 6-7 or 7-8, or 8-9, temperature conditions of 20-40° C., optionally 20-25° C., or 25-30° C., or 30-35° C., or 35-40° C. and incubation times of 1 hour to 2 weeks, optionally 1 h to 1 week, optionally 1 h to 5 days, optionally 1 h to 4 days, optionally 1 h to 3 days, optionally 1 h to 2 days, optionally 1-24 h, optionally 1-3 h, or 3-6 h, or 6-9 h, or 9-12 h, or 12-18 h, or 18-24 h. Culturing of the recombinant bacterial cell for producing PHBV may use bubble column reactors, stirred tank reactors, airlift reactors, preferably airlift reactors, flasks such as polycarbonate flasks. PHBV production is done under aerobic condition, for example, when a flask for incubation is vented, or under microaerobic condition, when a flask for incubation is capped.

In embodiments, the method of culturing a recombinant bacterial cell for producing PHBV comprises, culturing the PHA producing bacteria in a culture medium comprising suitable nutrients, VFA at 30-60 mmol/L, 30-90 mmol/L, 30-240 mmol/L, or 30-720 mmol/L, a carbon source, and a nitrogen source maintaining pH at 6-9, optionally 6-7, 7-8, or 8-9, and maintaining a temperature of between about 20 and 40° C., optionally between about 20 and 25° C., 25 and 30° C., 30 and 35° C., or 35 and 40° C., for between about 1-24 h, optionally 1-3 h, 3-6 h, 6-9 h, 9-12 h, 12-18 h, or 18-24 h.

In embodiments, the method comprises culturing a recombinant bacterial cell by repeated culturing in a medium containing increasing concentrations of VFA. In embodiments, the repeated culturing comprises i) culturing in a medium comprising VFA at 1-50 mmol/L, and one or more of M9 salts, yeast extract, glycerol, trace elements, and $MgSO_4$, for 1-7 days; ii) centrifuging 5-100% of the culture and resuspending the resulting cell pellet into a fresh medium comprising VFA at a concentration of 101-200% of the medium of step i), and one or more of M9 salts, yeast extract, glycerol, trace elements, and $MgSO_4$, for 1-7 days; and iii) repeating step ii) until the recombinant bacterial cell is capable of consuming all VFA up to 300 mmol/L VFA in the medium, and the recombinant bacterial cell produces PHBV at a minimum of 30% (w/w) of dry cell weight. In embodiments, the trace elements comprises $H_3BO_3$, $MnCl_2 \cdot 4H_2O$, $ZnSO_4 \cdot 7H_2O$, $Na_2MoO_4 \cdot 2H_2O$, $CuSO_4 \cdot 5H_2O$, and $Co(NO_3)_2 \cdot 6H_2O$.

The PHBV accumulates in the form of granules. The PHBV polymers are stored inside of the cells as discrete granules that are water-insoluble. In embodiments, the accumulation of PHBV granules is monitored, optionally by fluorescence spectroscopy analysis of the PHBV producing culture. In embodiments, the cells are fixed by heating a smear of the PHBV producing culture, which is the liquid mixture that contains the PHBV producing bacteria, on a glass slide. The heat-fixed cells can then be stained with 1% (v/v) aqueous Nile Blue A solution, or another appropriate staining solution and washed with sequences of water, acetic acid and water again. Afterward, the fixed culture can be analyzed using fluorescence microscopy as PHBV granules will fluoresce under these conditions. Optionally, a high throughput Nile Red assay may be used to monitor and quantify the intracellular PHBV granules in a liquid culture using fluorescence spectroscopy.

In an aspect, PHBV polymers are extracted with sequential washes for up to 3 times and lyophilized with a lyophilizer. In embodiments, the PHBV polymers are extracted with sequential washes for up to 3 times and lyophilized with a lyophilizer for about 48 h at temperatures of −20 to −80° C., optionally −30 to −35° C., −35 to −40° C., −40 to −45° C., or −45 to −50° C. Centrifugation or microfiltration with an appropriate centrifuge and microfilter for purification, may also be used during PHBV granule extraction. The skilled person can readily recognize the appropriate centrifuge and microfilter.

In embodiments, the method for producing PHBV from a recombinant bacterial cell comprises:

- transforming a bacterial cell to express a recombinant nucleic acid molecule encoding at least one of an acyl-CoA synthetase polypeptide, optionally a short chain acyl-CoA synthetase polypeptide, optionally LvaE polypeptide, an acetate-CoA transferase polypeptide, optionally a MELS_RS00170 polypeptide and MELS_RS00175 polypeptide, optionally an AtoD polypeptide and an AtoA polypeptide, and a propionate-CoA transferase polypeptide, optionally Pet polypeptide to obtain a recombinant bacterial cell; and
- culturing the recombinant bacterial cell in a culture medium under conditions effective to produce PHBV.

In embodiments. the culture medium comprises cyanocobalamin, optionally at a concentration of 0.1-2 μM.

In embodiments, the conditions comprise maintaining a temperature of about 20-42° C., optionally about 25-42° C., optionally about 25-37° C. In embodiments, the conditions comprise maintaining a pH of about 4-10, optionally about 5-9, optionally about 6-8.

In embodiments, the culture medium comprises at least one carbon source. In embodiments, the carbon source comprises at least one of VFA, optionally sodium acetate, sodium propionate, sodium butyrate, and glucose, glycerol, biomass, optionally pretreated biomass, and cheese whey. In embodiments, the culture media comprises at least one of about 0.01 to 20 g/L sodium acetate, about 0.01 to 10 g/L sodium propionate, and about 0.01 to 8 g/L sodium butyrate. In embodiments, the VFA comprises at least one of about 10-70 mol % acetic acid, about 10-80 mol % propionic acid, and about 10-70 mol % butyric acid.

In embodiments, the culture medium comprises at least one nitrogen source. In embodiments, the at least one nitrogen source is at least one of an ammonium salt, corn steep liquor, casamino acids, and yeast extract.

In embodiments, PHBV has a hydroxyvaleric acid (HV) content of about 1-20 mol %, about 1-30 mol %, about 1-40 mol %, or about 1-50 mol %.

In embodiments, the method further comprising extracting the PHBV from the bacterial cell and/or isolating PHBV from the culture medium.

Figure 2:
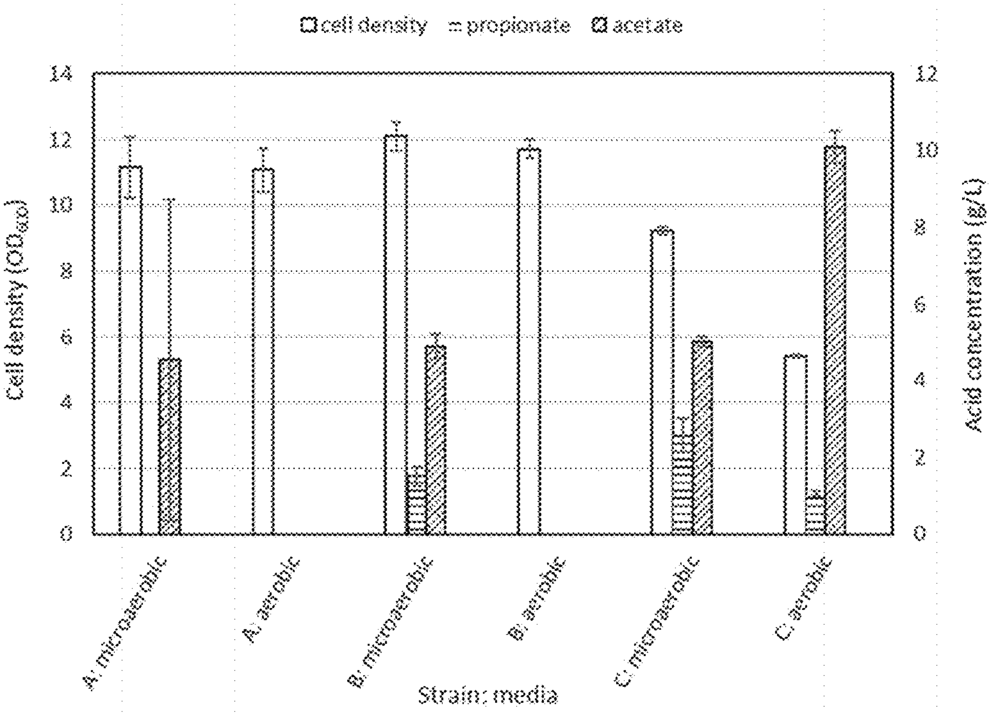
FIG. 2 shows cultivation results for acetate consumption in strains engineered for high Sbm pathway carbon flux.
Figure 3:
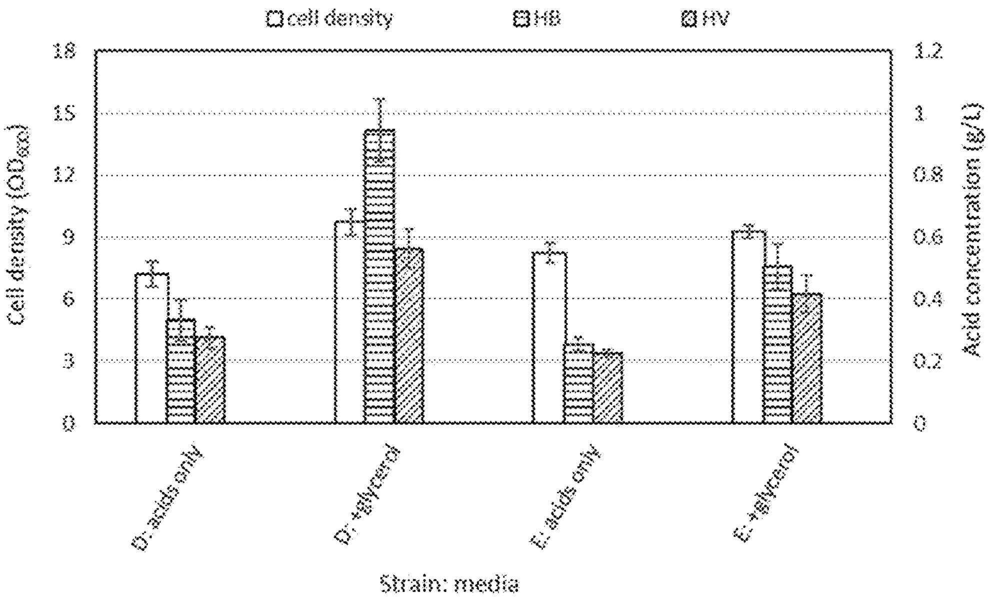
FIG. 3 shows cultivation results for acetate and propionate co-utilization for HB and HV co-production.
Figure 4:
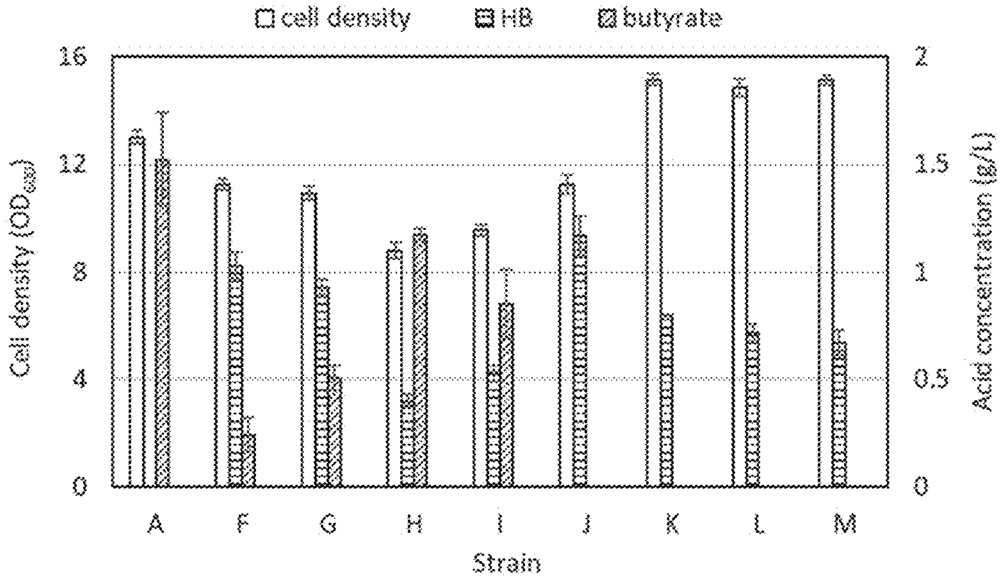
FIG. 4 shows cultivation results for the conversion of butyrate to HB or succinate.

List of strains and corresponding labels used in FIGS. 2-4 is shown in Table 5.

TABLE 5

List of strains and corresponding labels used in FIGS. 2-4.

| Label | Strain |
|---|---|
| A | CPC-Sbm |
| B | CPC-Sbm(ΔiclR) |
| C | CPC-Sbm(ΔiclR ΔsdhA) |
| D | CPC-Sbm(pK-bktB:hbd:tesB, Ptrc-phaAB:pct(Cp)) |
| E | CPC-Sbm(pK-bktB:hbd:tesB, Ptrc-phaAB:pct(Me)) |
| F | CPC-Sbm(pK-lvaE:tesB, pTrc-PP_2216:H16_RS27940) |
| G | CPC-Sbm(pK-lvaE:tesB, pTrc-BC_5341:H16_RS27940) |
| H | CPC-Sbm(pK-atoDAE:tesB, pTrc-PP_2216:H16_RS27940) |
| I | CPC-Sbm(pK-atoDAE:tesB, pTrc-BC5341:H16_RS27940) |
| J | CPC-Sbm(pK-lvaE:tesB, pTrc-PP_2216:phaJ) |
| K | CPC-Sbm(pK-lvaE:gadAe, Ptrc-FG99_15380:pduP(Se):gabD) |
| L | CPC-Sbm(pK-lvaE:gadAe, Ptrc-FG99_15380:pduP(Kp):gabD) |
| M | CPC-Sbm(pK-lvaE:gadAe) |

TABLE 6

Examples of polypeptide homologs.

| Polypeptide | Homolog Accession Numbers |
|---|---|
| AckA (SEQ ID NO: 1) | WP_151250307.1, WP_025758333.1, WP_000095714.1, WP_094316684.1, WP_000095699.1, WP_059270696.1, WP_160523843.1, WP_108188758.1, WP_000095694.1, WP_079781741.1, WP_000095691.1, WP_162383091.1, WP_110248734.1, WP_016529145.1, WP_064543869.1 |
| Acs (SEQ ID NO: 2) | WP_094321046.1, WP_134796521.1, WP_000078234.1, WP_000078255.1, WP_160523940.1, WP_130258462.1, WP_135490640.1, WP_000078187.1, WP_000078188.1, WP_105283185.1, WP_079225661.1, WP_151218054.1, EAX3726079.1, WP_061075561.1, WP_087051807.1 |
| AcsA (SEQ ID NO: 3) | WP_047183033.1, WP_144459203.1, WP_071577026.1, WP_061186774.1, WP_075747112.1, WP_010329597.1, WP_024714615.1, WP_162101126.1, WP_105990205.1, WP_061572550.1, WP_109567131.1, WP_061523123.1, WP_103526694.1 |
| Ald (SEQ ID NO: 184) | WP_077830381.1, WP_065419149.1, WP_017211959.1, WP_077844109.1, AAD31841.1, WP_087702529.1, WP_077868466.1, WP_077366605.1, WP_026888070.1, WP_077860531.1, WP_022747467.1, WP_077863550.1, WP_009171375.1, WP_128214949.1, WP_160679606.1, WP_012059995.1, WP_041898834.1, WP_015395720.1 |
| AtoA ((SEQ ID NO: 4) | WP_103053735.1, WP_137325583.1, WP_050899668.1, WP_000339071.1, WP_128880225.1, WP_047462387.1, WP_135321227.1, WP_090049661.1, WP_004184955.1, WP_151219893.1, WP_100682748.1, WP_013365500.1, WP_000339048.1, WP_087857377.1 |

TABLE 6-continued

| Examples of polypeptide homologs. | |
|---|---|
| Polypeptide | Homolog Accession Numbers |
| AtoD (SEQ ID NO: 5) | WP_053001645.1, QGU62017.1, WP_155555734.1, WP_038355059.1, MLY49728.1, WP_105269001.1, WP_105284960.1, WP_149476985.1, WP_108188772.1, WP_000850520.1, WP_138957179.1, WP_123267594.1, WP_114680602.1, WP_047500919.1, WP_004184954.1 |
| BC_5341 (SEQ ID NO: 7) | WP_088022147.1, WP_098448816.1, WP_149216716.1, WP_101167410.1, WP_143881711.1, WP_085450733.1, WP_144504985.1, BCA34359.1, WP_098299175.1, WP_071710801.1, CKE48212.1, WP_163095898.1, WP_071725959.1, WP_136445333.1, WP_128975345.1 |
| BktB (SEQ ID NO: 8) | WP_013956457.1, WP_035820088.1, WP_092317205.1, WP_115013782.1, WP_116382528.1, WP_018311404.1, WP_063238655.1, WP_116321050.1, AGW89814.1, WP_062798985.1, WP_133094381.1, AGW95651.1, WP_140952189.1, WP_144195740.1, WP_011516125.1 |
| CKL_RS14680 (SEQ ID NO: 10) | WP_073539834.1, WP_010236491.1 |
| FadE (SEQ ID NO: 13) | WP_094316844.1, WP_130224094.1, WP_135404353.1, WP_046076114.1, WP_011069257.1, WP_135489829.1, WP_085448671.1, WP_124782953.1, WP_153879457.1, EDR1571704.1, WP_103776898.1, WP_008783785.1, WP_087053141.1, WP_079225425.1, WP_137366593.1, WP_000973041.1 |
| GabD (SEQ ID NO: 17) | WP_105285925.1, WP_135494970.1, WP_094315749.1, WP_161983589.1, WP_000772895.1, WP_078167276.1, WP_016249103.1, WP_105267583.1, WP_149461599.1, WP_128880059.1, WP_149461599.1, WP_060773285.1, WP_153257801.1, WP_108418849.1, WP_045446520.1 |
| Gad (SEQ ID NO: 19) | XP_002871761.1, KFK41557.1, VVB14898.1, RID41892.1, XP_013661825.1, VDC86651.1, XP_006400267.1, XP_010420446.1, XP_010453919.1, CAA7061503.1, XP_006400266.1, ESQ41721.1, XP_013627326.1, XP_031273023.1 |
| Gad(Ls) (SEQ ID NO: 224) | WP_125641322.1, WP_226457942.1, BAN05709.1, MBL3537851.1, WP_039105805.1, WP_052957185.1, KIR08754.1, WP_125574762.1, WP_063488771.1, WP_017262688.1 |
| GadAe (SEQ ID NO: 20) | WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, EAB0955940.1 |
| GadBe(Ec) (SEQ ID NO: 194) | WP_134806912.1, WP_052942456.1, WP_128881419.1, WP_135383171.1, WP_054518524.1, WP_138158972.1, WP_103194808.1, WP_000358851.1, WP_107164449.1, WP_000358937.1, WP_135385956.1, WP_113623060.1, EAB0955940.1 |
| H16_RS27940 (SEQ ID NO: 22) | WP_051591491.1, WP_114130480.1, WP_078200706.1, EON20731.1, PKO64515.1, WP_092007571.1, WP_162566377.1, WP_137921632.1, WP_162591754.1 |
| KES23458 (SEQ ID NO: 15) | WP_116425784.1, WP_069862932.1, WP_043315988.1, WP_009614288.1, WP_089392503.1, WP_109934365.1, WP_090268322.1, WP_138519936.1, WP_138213347.1, WP_015474919.1, WP_043256620.1, WP_084311461.1, WP_053816481.1, WP_070656248.1, WP_077524299.1 |
| LvaE (SEQ ID NO: 26) | WP_051095536.1, AGA73676.1, WP_054905284.1, OFQ86312.1, OFQ81524.1, WP_102880076.1, WP_092297027.1, WP_160291004.1, WP_081520035.1, WP_104443972.1, WP_046855848.1, WP_134690622.1, WP_103303932.1, WP_042129240.1, BAV75244.1 |
| MELS_RS10970 (SEQ ID NO: 28) | WP_020723925.1, WP_048514244.1, WP_074501184.1, KXB91325.1, WP_154877386.1, WP_107195291.1, WP_087477538.1, WP_095630133.1, WP_091647756.1, WP_023053225.1, WP_101912630.1, WP_075572446.1, WP_006790232.1, WP_006942404.1 |
| PaaZ ((SEQ ID NO: 29) | WP_160599600.1, WP_152066042.1, WP_094316530.1, WP_032252644.1, WP_001186464.1, WP_125401136.1, WP_001186494.1, WP_119163289.1, WP_095281943.1, WP_045888522.1, WP_058840681.1, WP_095440732.1, WP_162382197.1, WP_059385322.1, WP_045286529.1 |
| Pct(Cp) ((SEQ ID NO: 30) | WP_066087637.1, NCC15629.1, WP_054329786.1, WP_072853413.1, CDC28613.1, WP_016408311.1, WP_088107724.1, WP_160302233.1, WP_004038625.1 |
| Pct(Me) ((SEQ ID NO: 31) | WP_054336166.1, WP_036203125.1, WP_044502862.1, WP_065360594.1, KXA66894.1, WP_095629974.1, WP_087478516.1, WP_107195767.1, WP_048515067.1, WP_101912966.1, WP_156208970.1, KXB92430.1, WP_023053187.1, WP_039891686.1, KXB92214.1 |
| PduP(Kp) (SEQ ID NO: 32) | WP_109231734.1, WP_109848747.1, WP_136028274.1, WP_100680758.1, WP_100631313.1, WP_049157539.1, WP_029884370.1, MXH33721.1, WP_144232363.1, WP_153679752.1, WP_148849915.1, EBS2830838.1, WP_112213940.1, WP_064370270.1 |
| PduP(Se) (SEQ ID NO: 33) | WP_001097684.1, WP_001528442.1, WP_080203692.1, WP_108450871.1, WP_009652778.1, WP_142983670.1, WP_105274032.1, WP_070556870.1, WP_142502560.1, WP_012131760.1, WP_012906342.1, WP_006683971.1, WP_103775053.1, WP_060570657.1, WP_135321437.1 |
| PhaA (SEQ ID NO: 34) | WP_013956452.1, SCU96900.1, WP_035820078.1, 4O9C_A, WP_116382525.1, WP_092317196.1, WP_062798979.1, WP_116321054.1, AGW89809.1, WP_039016192.1, WP_063238652.1, WP_029049660.1, WP_011297518.1, WP_124684437.1, WP_109580845.1 |

TABLE 6-continued

Examples of polypeptide homologs.

| Polypeptide | Homolog Accession Numbers |
|---|---|
| PhaB (SEQ ID NO: 35) | RWA53825.1, WP_042885115.1, WP_039016191.1, WP_116336746.1, WP_112777371.1, WP_006577377.1, WP_135705030.1, WP_133096842.1, WP_124684436.1, WP_116321053.1, WP_006155939.1, WP_045241722.1, WP_011297519.1, WP_144195744.1, ODV43053.1 |
| PhaB(Hb) (SEQ ID NO: 225) | WP_162219671.1, WP_126946472.1, WP_120385833.1, WP_030074446.1, WP_188637499.1, WP_058579713.1, WP_083023226.1, WP_039183428.1, WP_159340906.1, WP_096653461.1 |
| PhaC (SEQ ID NO: 36) | ACZ57807.1, WP_010810133.1, WP_013956451.1, AAW65074.1, WP_018311399.1, AGW89808.1, WP_115678329.1, WP_062798976.1, WP_115013788.1, WP_115680054.1, WP_112777370.1 |
| PhaJ(Aa) (SEQ ID NO: 196) | WP_169200570.1, WP_053422493.1, WP_169118971.1, WP_169202263.1, AUL99438.1, WP_136349851.1, WP_136385326.1, WP_187719679.1, WP_107493682.1, WP_169262136.1 |
| PhaJ(Ac) (SEQ ID NO: 37) | WP_103260220.1, WP_104454254.1, OJW67134.1, WP_041998622.1, WP_043760202.1, WP_043129860.1, WP_042076944.1, WP_100860962.1, WP_163157368.1, WP_042638062.1, WP_106886672.1, WP_033131291.1, WP_025327110.1, WP_040094291.1, WP_139745378.1 |
| PP_2216 (SEQ ID NO: 38) | WP_003250094.1, WP_104887321.1, WP_039614175.1, WP_023662689.1, WP_085706434.1, WP_070087269.1, WP_060512757.1, WP_144171976.1, WP_054884005.1, WP_051100719.1, WP_099814118.1, WP_125859423.1, WP_125464833.1, WP_090345830.1, WP_110994568.1 |
| PrpE(Cn) (SEQ ID NO: 43) | WP_081623799.1, WP_115213214.1, WP_082818978.1, WP_116324638.1, WP_092309442.1, AMR79067.1, WP_151072146.1, WP_029046365.1, AGW91162.1, WP_116321975.1, WP_039006728.1, WP_092134378.1, WP_109580644.1, WP_035882297.1, WP_149135646.1 |
| PrpE(Ec) (SEQ ID NO: 44) | WP_024249411.1, WP_130258507.1, WP_000010307.1, WP_138159881.1, WP_105281240.1, WP_000010239.1, WP_000010244.1, WP_160524152.1, WP_105270931.1, WP_160530253.1, WP_016235155.1, WP_061090735.1, WP_103014998.1, WP_094761423.1, ATX90159.1 |
| PrpE(Se) (SEQ ID NO: 45) | WP_127836169.1, WP_103776706.1, WP_044259075.1, WP_012904755.1, WP_043015332.1, WP_008783866.1, WP_153690685.1, WP_058587683.1, WP_101700584.1, WP_042324663.1, WP_123268908.1, WP_137351112.1, WP_048219548.1, WP_160955604.1, WP_012133646.1 |
| Pta (SEQ ID NO: 46) | WP_119174868.1, WP_114414934.1, WP_112484304.1, WP_000086724.1, WP_135520103.1, WP_113650156.1, WP_105273752.1, WP_079788930.1, WP_000086702.1, WP_135520103.1, WP_038354606.1, WP_025714133.1, WP_071260224.1, WP_046483030.1, WP_080924257.1 |
| Sbm (SEQ ID NO: 48) | CDW60403.1, WP_096098300.1, QGU68683.1, WP_000073215.1, WP_024250007.1, WP_105273911.1, EBT2497755.1, WP_064198903.1, WP_105271628.1, CDZ86651.1, WP_130258050.1, WP_038355443.1, WP_142462060.1, WP_103769047.1, WP_137649991.1 |
| SucC (SEQ ID NO: 50) | WP_111780024.1, WP_105268114.1, WP_149508492.1, EBH0782533.1, WP_079789068.1, EAA0703253.1, WP_001048612.1, WP_103776364.1, HAC6539881.1, WP_139538723.1, WP_040076526.1, WP_152308781.1, WP_061708388.1, WP_159152251.1, WP_159754306.1 |
| SucD (SEQ ID NO: 51) | WP_148048643.1, WP_161983406.1, WP_128882005.1, SEK68167.1, WP_064567804.1, WP_090133347.1, EDS6037479.1, WP_015965312.1, WP_154777294.1, WP_108473875.1, WP_162082208.1, WP_154158334.1 |
| YgfD (SEQ ID NO: 55) | HBV28035.1, WP_094338169.1, EBT2497754.1, WP_105273912.1, WP_105271629.1, MJD64661.1, MVY25917.1, WP_152060700.1, CDZ86650.1, CDK74861.1, WP_138183055.1, WP_138158389.1, WP_138158874.1, WP_137651359.1, WP_038355444.1 |
| YgfG (SEQ ID NO: 56) | WP_105273913.1, WP_011069498.1, WP_095785007.1, KAE9894204.1, WP_128881119.1, WP_105287397.1, EBT2497753.1, WP_112366200.1, CDZ86649.1, WP_137653935.1, WP_103750818.1, WP_135521100.1, EFE06586.1, WP_080626129.1, WP_079226013.1 |
| YgfH (SEQ ID NO: 57) | WP_094321963.1, WP_075331646.1, WP_105271630.1, WP_128881120.1, WP_075328602.1, WP_128861696.1, ECA1898152.1, WP_105273914.1, CDZ86648.1, WP_130221450.1, WP_135519865.1, WP_001027665.1, WP_135407775.1, WP_130221450.1, WP_135492970.1 |

PHBV Recovery and Analysis

PHBV can be recovered by any methods known in the art. The method can be an extraction method recovering PHBV from within bacterial cells, or a method recovering PHBV from culture media. A range of parameters (i.e. temperature, treatment time, pH and concentrations) for surfactant (for example SDS or non-ionic surfactant Triton X-100) and hypochlorite can be used to extract PHBV. The purity of PHBV can be determined by methods known in the art, for example, by gas chromatography mass spectroscopy (GC-MS). The recombinant bacterial cells and methods described herein produce PHBV with a mass yield of 5-80% of dry cell weight. The HV content of PHBV can also be determined by methods known in the art, for example, PHBV can be treated in a reflux at 100° C. for 150 min in the presence of chloroform, methanol, and sulfuric acid, and the PHBV is then converted into methyl esters which facilitates the separation of different hydroxyalkanoates present in the copolymer structure for further analysis, for example, by GC-MS. The monomer composition of PHBV can also be determined via proton-nuclear magnetic resonance (1H-NMR). The polymer sample can be solubilized in an appropriate deuterated solvent such as deuterated methylene chloride ($CDCl_2$) at a concentration of 1-10 mg/mL. The analysis can be conducted in a spectrometer operating at 300-600 MHz, and the molar ratio of HB and HV monomers can be taken as the ratio of integrals of the chemical shifts at 1.25 ppm (corresponding to the CH3- group of HB) and at 0.85 ppm (corresponding to the CH3-CH2- group of HV). Dry cell weight (DCW) can be determined by centrifuging culture samples at 2000-6000×g for 10-30 min, followed by at least one wash step using distilled water, and subsequent lyophilization of the cell paste overnight. In embodiments, PHBV composition is analyzed by GC-MS and/or 1H-NMR.

Applications of PHBV with Varying HV Content

The PHBV produced by the recombinant bacterial cell described herein has a defined HV content, which affects properties such as melting point, water permeability, glass transition temperature, and tensile strength of the biopolymer. PHBV with different HV contents thus has different applications.

For example, PHBV with 0-5 mol % HV has properties that are comparable to polylactic acid (PLA) or polystyrene (PS), and it is useful as, for example, 3D printing filament, golf tees, writing utensils, cutlery, and coffee cup lids, which can be manufactured by injection moulding or extrusion of the PHBV with this amount of HV content.

For example, PHBV with 5-10 mol % HV has properties that are comparable to acrylonitrile butadiene styrene (ABS), and it is useful as, for example, building blocks (in toys) and clamshells, which can be manufactured by injection moulding or extrusion of the PHBV with this amount of HV content.

For example, PHBV with 10-20 mol % HV has properties that are comparable to polypropylene (PP) or polyethylene terephthalate (PET), and it is useful as, for example, bioplastic bottles, clothing, straws, electrical insulation, baby wipes, bottle caps, sanitary applicators, yogurt containers, which can be manufactured by blow moulding, injection moulding, profile, extrusion, or textile spinning of the PHBV with this amount of HV content.

For example, PHBV with at least 20 mol % HV has properties that are comparable to polyethylene (PE), and it is useful as, for example, shopping bags, agricultural wrap, paper cup liners, plastic wrap, banners, labels, cigarette filters, which can be manufactured by blow moulding or spray coating of the PHBV with this amount of HV content.

Further, the PHBV produced by the recombinant bacterial cell described herein has applications in the field of biomaterials.

For example, PHBV with at least 20 mol % HV is useful as a flexible porous sheet, for example, for tissue separation to enable healing of pericardiac defect in sheep (see WO1990000067A1, herein incorporated by reference in its entirety).

For example, PHBV with at least 8.25 mol % HV is useful as a film, for example, to immobilize antimicrobial peptide tachyplesin I tagged with PHA-granule-associated protein (PhaP).

For example, PHBV with at least 5 mol % HV, optionally at least 8 mol % HV, is useful as a scaffold, for example, for tissue engineering, such as neural tissue engineering.

For example, PHBV is useful as nanoparticles, for example, PHBV with at least 12 wt % HV is useful to encapsulate photosensitizer 5,10,15,20-Tetrakis(4-hydroxyphenyl)-21H, 23H-porphine, for example, for photodynamic therapy for cancer treatment, and PHBV with at least 15% mol % is useful to encapsulate drug, for example, anticancer drug such as Ellipticine.

For example, PHBV with at least 11.3 mol % HV is useful as carrier rods for local antibiotic delivery.

Further details are provided in Xue Q et al., *Biomaterials* 2018, 178:351-362, Rathbone S, et al., *Journal of biomedical materials research Part A* 2010, 93:1391-1403, Chen W, et al., *Acta biomaterialia* 2012, 8:540-548, Pramual S, *Journal of Materials Science: Materials in Medicine* 2016, 27:40-40, Masood F, *Materials science & engineering C, Materials for biological applications* 2013, 33:1054-1060, and Türesin F, et al., *Journal of Biomaterials Science, Polymer Edition* 2001, 12:195-207, the contents of which are incorporated herein by reference in its entirety for all purposes.

For example, 10-30 wt % PHBV, where the PHBV has at least 5-25% wt % HV is useful as a PHBV/polylactic acid absorbable suture, for example, for nerve and vascular repair (see CN105063790A, herein incorporated by reference in its entirety).

The recombinant bacterial cells and methods described herein produce PHBV with a HV content of about 0-50 mol %, about 1-50 mol %, about 0-40 mol %, about 1-40 mol %, about 0-30 mol %, about 1-30 mol %, about 0-20 mol %, about 1-20 mol %, about 20-50 mol %, about 10-20 mol %, about 5-10 mol %, or about 0-5 mol %. In embodiments, the recombinant bacterial cells and methods described herein produce PHBV with a HV content of about 0-50 mol %, about 5-25 mol %, about 1-50 mol %, about 0-40 mol %, about 1-40 mol %, about 0-30 mol %, about 1-30 mol %, about 0-20 mol %, about 1-20 mol %, about 20-50 mol %, about 10-20 mol %, about 5-10 mol %, or about 0-5 mol %. In embodiments, the recombinant bacterial cells and methods described herein produce PHBV with a HV content of at least about 5 mol %, at least about 6 mol %, at least about 7 mol %, at least about 8 mol %, at least about 8.25 mol %, at least about 8.5 mol %, at least about 8.75 mol %, at least about 9 mol %, at least about 10 mol %, at least about 11 mol %, at least about 11 mol %, at least about 11.1 mol %, at least about 11.2 mol %, at least about 11.3 mol %, at least about 11.4 mol %, at least about 11.5 mol %, at least about 11.6 mol %, at least about 11.7 mol %, at least about 11.8 mol %, at least about 11.9 mol %, at least about 12 mol %, at least about 13 mol %, at least about 14 mol %, at least about 15 mol %, at least about 16 mol %, at least about 17 mol %, at least about 18 mol %, at least about 19 mol %, at least about 20 mol %, at least about 25 mol %, at least about 30 mol %, or at least about 35 mol %, and optionally at most about 40 mol %, at most about 45 mol %, or at most about 50 mol %. In embodiments, the recombinant bacterial cell comprises nucleic acid molecule having the sequence of SEQ ID NO: 239 and SEQ ID NO: 240, and the recombinant bacterial cell produces PHBV with a HV content of up to about 40 mol %. In embodiments, the recombinant bacterial cell comprising nucleic acid molecule having the sequence of SEQ ID NO: 239 and SEQ ID NO: 240 produces PHBV by culturing the bacterial cell in a culture medium comprising at least one carbon source. In embodiments, the carbon source comprises glycerol. In embodiments the carbon source comprises at least one VFA. In embodiments, the recombinant bacterial cell comprises nucleic acid molecule having the sequence of SEQ ID NO: 239 and SEQ ID NO: 240, and the recombinant bacterial cell produces PHBV with a HV content from about 15 mol % to about 40 mol %. In embodiments, the recombinant bacterial strain is CPC-Sbm(bcsA::($P_{gracmax2}$::(T7.RBS)bktB:(RBS1)phaB), intF::($P_{gracmax2}$::

(T7.RBS)phaC:(RBS1)phaA) and the bacterial strain produces PHBV with a HV content of up to about 40 mol %. In embodiments, the recombinant bacterial strain is CPC-Sbm(bcsA::($P_{gracmax2}$::(T7.RBS)bktB:(RBS1)phaB), intF::($P_{gracmax2}$::(T7.RBS)phaC:(RBS1)phaA) and the bacterial strain produces PHBV with a HV content from about 15 mol % to about 40 mol %. In embodiments, the recombinant bacterial cell produces PHBV at a mass yield of up to about 80% of dry cell weight. In embodiments, the HV content of PHBV is adjustable by expression, overexpression, under-expression, attenuation, silencing and/or inactivation of genes or enzymes described herein, optionally the gene is a nonessential gene.

Embodiments of the disclosure will be described in a non-limiting manner by reference to the examples below.

EXAMPLES

Example 1: Production of HV and HB—Case A

A two-plasmid system was employed to assess the potential of *E. coli* to co-produce the monomers of PHBV, i.e. HV and HB, respectively derived from (R)-HV-CoA and (R)-HB-CoA, from propionate and acetate as HV and HB can be readily measured via high performance liquid chromatography (HPLC). The first plasmid contained bktB, hbd (encoding hydroxybutyryl-CoA dehydrogenase Hbd polypeptide that converts 3-ketovaleryl-CoA to (S)-HV-CoA and acetoacetyl-CoA to (S)-HB-CoA), and tesB (encoding acyl-CoA thioesterase II TesB polypeptide that converts (S)-HV-CoA and (R)-HV-CoA to HV, and (S)-HB-CoA and (R)-HB-CoA to HB), i.e. plasmid pK-bktB-hbd-tesB. The second plasmid contained phaA, phaB (PhaB polypeptide converts 3-ketovaleryl-CoA to (R)-HV-CoA and acetoacetyl-CoA to (R)-HB-CoA), and pct(Cp) (from *C. propionicum*), i.e. plasmid pTrc-phaAB:pct(Cp), which was constructed by amplifying the $P_{trc}$::phaAB fragment (including the plasmid backbone) from plasmid pTrc-phaAB-crt-ter with primers P01 and P02 (SEQ ID NO: 119 and 120), and pct(Cp) from *C. propionicum* DSM 1682 genomic DNA (gDNA) with primer P03 and P04 (SEQ ID NO: 121 and 122), followed by subsequent assembly of the two fragments via the NEBuilder HiFi DNA Assembly Master Mix (New England Biolabs; USA) as per the manufacturers' instructions and readily undertaken by the skilled person. The host cell is *E. coli* strain CPC-Sbm, which is derived from strain K-12. It is understood that any K-12 derived strain may be useful and the skilled person can readily identify the relevant derivatives of K-12 strain. Plasmids pK-bktB-hbd-tesB and pTrc-phaAB:pct(Cp) (SEQ ID NO: 162) were co-transformed into the host *E. coli* strain CPC-Sbm [14], resulting in strain CPC-Sbm(pK-bktB-hbd-tesB, pTrc-phaAB:pct(Cp)), and its ability to produce HV and HB was evaluated in shake flask cultures (see FIG. 3)

Example 2: Production of HV and HB—Case B

A two-plasmid system was employed to assess the potential of *E. coli* to co-produce the monomers of PHBV, i.e. HV and HB, respectively derived from (R)-HV-CoA and (R)-HB-CoA, from propionate and acetate as HV and HB can be readily measured via HPLC. Plasmid pK-bktB-hbd-tesB was the same as in Example 1, and the second plasmid contained phaA, phaB, and pct(Me) (from *M. elsdenii*), i.e. plasmid pTrc-phaAB:pct(Me) (SEQ ID NO: 163), which was constructed by amplifying the $P_{trc}$::phaAB fragment (including the plasmid backbone) from plasmid pTrc-phaAB-crt-ter with primers P05 and P02 (SEQ ID NO: 123 and 120), and pct(Me) from *M. elsdenii* DSM 20460 gDNA with primer P06 and P07 (SEQ ID NO: 124 and 125), followed by subsequent assembly of the two fragments via the NEBuilder HiFi DNA Assembly Master Mix as per the manufacturers' instructions. Plasmids pK-bktB-hbd-tesB and pTrc-phaAB:pct(Me) (SEQ ID NO: 163) were co-transformed into strain CPC-Sbm [14], resulting in strain CPC-Sbm(pK-bktB-hbd-tesB, pTrc-phaAB:pct(Me)), and its ability to produce HV and HB was evaluated in shake flask cultures (see FIG. 3)

Example 3: Production of HV and HB—Case C

A two-plasmid system is employed to assess the potential of *E. coli* to co-produce the monomers of PHBV, i.e. HV and HB, respectively derived from (R)-HV-CoA and (R)-HB-CoA, from propionate and acetate as HV and HB can be readily measured via HPLC. Plasmid pK-bktB-hbd-tesB was the same as in Example 1, and the second plasmid contains phaA, phaB, and prpE(Ec) (from *E. coli*), i.e. plasmid pTrc-phaAB:prpE(Ec), which is constructed by amplifying the $P_{trc}$::phaAB fragment (including the plasmid backbone) from plasmid pTrc-phaAB-crt-ter, and prpE(Ec) from *E. coli* MG1655 gDNA, followed by subsequent assembly of the two fragments via the NEBuilder HiFi DNA Assembly Master Mix as per the manufacturers' instructions. Plasmids pK-bktB-hbd-tesB and pTrc-phaAB:prpE(Ec) were co-transformed into strain CPC-Sbm, resulting in strain CPC-Sbm(pK-bktB-hbd-tesB, pTrc-phaAB:prpE(Ec)). This strain produces HV and HB in comparable quantities as strains described in Examples 1 and 2 (FIG. 3). Further details are provided at Miscevic D et al., *Applied microbiology and biotechnology* 2019, 103:5215-5230, and Srirangan K et al., *Applied Microbiology and Biotechnology* 2014, 98:9499-9515, the contents of which are incorporated herein by reference in its entirety for all purposes.

Example 4: Production of HV and HB—Case D

A two-plasmid system is employed to assess the potential of *E. coli* to co-produce the monomers of PHBV, i.e. HV and HB, respectively derived from (R)-HV-CoA and (R)-HB-CoA, from propionate and acetate as HV and HB can be readily measured via HPLC. Plasmid pK-bktB-hbd-tesB was previously disclosed [13], and the second plasmid contains phaA, phaB, and prpE(Se) (from *S. enterica*), i.e. plasmid pTrc-phaAB:prpE(Se), which is constructed by amplifying the $P_{trc}$::phaAB fragment (including the plasmid backbone) from plasmid pTrc-phaAB-crt-ter [13], and prpE(Se) from *S. enterica* DSM 18522 gDNA, followed by subsequent assembly of the two fragments via the NEBuilder HiFi DNA Assembly Master Mix as per the manufacturers' instructions. Plasmids pK-bktB-hbd-iesB and pTrc-phaAB:prpE(Se) were co-transformed into strain CPC-Sbm [14], resulting in strain CPC-Sbm(pK-bktB-hbd-tesB, pTrc-phaAB:prpE(Se)). This strain produces HV and HB in comparable quantities as strains described in Examples 1 and 2 (FIG. 3).

Example 5: Production of HB—Case A

A two-plasmid system was employed to assess the potential of *E. coli* to produce the monomer of PHBV, i.e. HB, derived from (R)-HB-CoA, from butyrate as HB can be readily measured via HPLC. The first plasmid contained lvaE and tesB, i.e. plasmid pK-lvaE:tesB, and was constructed by amplifying lvaE from *P. putida* KT2440 gDNA with primers P08 and P09 (SEQ ID NO: 116 and 117), and the $P_{lac}$-tesB fragment (including plasmid backbone) from pK-bktB-hbd-tesB with primers P10 and P11 (SEQ ID NO: 128 and 129), followed by subsequent assembly of the two fragments via the NEBuilder HiFi DNA Assembly Master Mix as per the manufacturers' instructions. The second plasmid contained PP_2216 (gene encoding a short-chain acyl-CoA dehydrogenase polypeptide) and H16_RS27940, i.e. plasmid pTrc-PP_2216:H16_RS27940, and was constructed by amplifying PP_2216 from *P. putida* KT2440 gDNA with primers P12 and P13 (SEQ ID NO: 130 and 131), H16_RS27940 from *C. necator* H16 gDNA with primers P14 and P15 (SEQ ID NO: 122 and 123), and $P_{trc}$ (including plasmid backbone) from Ptrc99a (as detailed in Amann E et al., *Gene* 1988, 69:301-315, the contents of which are incorporated herein by reference in its entirety for all purposes) with primers P16 and P17 (SEQ ID NO: 124 and 125), followed by subsequent assembly of the three fragments via the NEBuilder HiFi DNA Assembly Master Mix as per the manufacturers' instructions. lvaE and PP_2216 that have been codon optimized for expression in *E. coli* can also be used. Plasmids pK-lvaE:tesB and pTrc-PP_2216:H16_RS27940 (SEQ ID NO: 165) were co-transformed into strain CPC-Sbm, resulting in strain CPC-Sbm (pK-lvaE:tesB, pTrc-PP_2216:H16_RS27940), and its ability to produce HB was evaluated in shake flask cultures (FIG. 4).

Example 6: Production of HB—Case B

A two-plasmid system was employed to assess the potential of *E. coli* to produce the monomer of PHBV, i.e. HB, derived from (R)-HB-CoA, from butyrate as HB can be readily measured via HPLC. The first plasmid contained lvaE and tesB, i.e. plasmid pK-lvaE:tesB, and its construction was described in Example 5. The second plasmid contained BC_5341 (gene encoding a short-chain acyl-CoA dehydrogenase polypeptide) and H16_RS27940, i.e. plasmid pTrc-BC_5341:H16_RS27940, and was constructed by amplifying BC_5341 from *B. cereus* DSM 31 gDNA with primers P18 and P19 (SEQ ID NO: 136 and 137), and the $P_{trc}$-H16_RS27940 fragment (including plasmid backbone) from plasmid pTrc-PP_2216:H16_RS27940 with primers P20 and P21 (SEQ ID NO: 138 and 139), followed by subsequent assembly of the two fragments via the NEBuilder HiFi DNA Assembly Master Mix as per the manufacturers' instructions. Plasmids pK-lvaE:tesB and pTrc-BC_5341:H16_RS27940 were co-transformed into strain CPC-Sbm [14], resulting in strain CPC-Sbm(pK-lvaE:tesB, pTrc-BC_5341:H16_RS27940), and its ability to produce HB was evaluated in shake flask cultures (FIG. 4).

Example 7: Production of HB—Case C

A two-plasmid system was employed to assess the potential of *E. coli* to produce the monomer of PHBV, i.e. HB, derived from (R)-HB-CoA, from butyrate as HB can be readily measured via HPLC. The first plasmid contained atoDAE (atoE encodes putative short-chain fatty acid transporter AtoE) and tesB, i.e. plasmid pK-atoDAE:tesB, and was constructed by amplifying atoDAE from *E. coli* MG1655 gDNA with primers P22 and P23 (SEQ ID NO: 140 and 141), and the $P_{lac}$-tesB fragment (including plasmid backbone) from pK-bktB-hbd-tesB with primers P10 and P24 (SEQ ID NO: 128 and 142), followed by subsequent assembly of the two fragments via the NEBuilder HiFi DNA Assembly Master Mix as per the manufacturers' instructions. The second plasmid contained PP_2216 and H16_RS27940, i.e. plasmid pTrc-PP_2216:H16_RS27940, and its construction was described in Example 5. Plasmids pK-atoDAE:tesB and pTrc-PP_2216:H16_RS27940 were co-transformed into strain CPC-Sbm [14], resulting in strain CPC-Sbm(pK-atoDAE:tesB, pTrc-PP_2216:H16_RS27940), and its ability to produce HB was evaluated in shake flask cultures (FIG. 4).

Example 8: Production of HB—Case D

A two-plasmid system was employed to assess the potential of *E. coli* to produce the monomer of PHBV, i.e. HB, derived from (R)-HB-CoA, from butyrate as HB can be readily measured via HPLC. The first plasmid contained atoDAE (atoE encodes putative short-chain fatty acid transporter AtoE) and tesB, i.e. plasmid pK-atoDAE:tesB, and was described in Example 7. The second plasmid contained BC_5341 and H16_RS27940, i.e. plasmid pTrc-BC_5341:H16_RS27940, and its construction was described in Example 6. Plasmids pK-atoDAE:tesB and pTrc-BC_5341:H16_RS27940 were co-transformed into strain CPC-Sbm [14], resulting in strain CPC-Sbm(pK-atoDAE:tesB, pTrc-BC_5341:H16_RS27940), and its ability to produce HB was evaluated in shake flask cultures (FIG. 4).

Example 9: Production of HB—Case E

A two-plasmid system was employed to assess the potential of *E. coli* to produce the monomer of PHBV, i.e. HB, derived from (R)-HB-CoA, from butyrate as HB can be readily measured via HPLC. The first plasmid contained lvaE and tesB, i.e. plasmid pK-lvaE:tesB, and its construction was described in Example 5. The second plasmid contained PP_2216 and phaJ(Ac), i.e. plasmid pTrc-PP_2216:phaJ(Ac), and was constructed by amplifying the $P_{trc}$::PP_2216 fragment (including plasmid backbone) from plasmid pTrc-PP_2216:H16_RS27940 with primers P25 and P26 (SEQ ID NO: 143 and 144), and phaJ(Ac) from *A. caviae* DSM 7323 gDNA with primers P27 and P28 (SEQ ID NO: 145 and 146), followed by subsequent assembly of the two fragments via the NEBuilder HiFi DNA Assembly Master Mix as per the manufacturers' instructions. Plasmids pK-lvaE:tesB and pTrc-PP_2216:phaJ(Ac) were co-transformed into strain CPC-Sbm [14], resulting in strain CPC-Sbm(pK-lvaE:tesB, pTrc-PP_2216:phaJ(Ac)), and its ability to produce HB was evaluated in shake flask cultures (FIG. 4).

Example 10: Production of HB—Case F

A two-plasmid system is employed to assess the potential of *E. coli* to produce the monomer of PHBV, i.e. HB, derived from (R)-HB-CoA, from butyrate as HB can be readily measured via HPLC. The first plasmid contains lvaE and tesB, i.e. plasmid pK-lvaE:tesB, and its construction was described in Example 5. The second plasmid contains fadE and phaJ(Ac), i.e. plasmid pTrc-fadE:phaJ(Ac), and is constructed by amplifying fadE from *E. coli* MG1655 gDNA and the $P_{trc}$-phaJ(Ac) fragment (including plasmid backbone) from plasmid pTrc-PP_2216:phaJ(Ac), followed by subsequent assembly of the two fragments via the NEBuilder HiFi DNA Assembly Master Mix as per the manufacturers' instructions. Plasmids pK-lvaE:tesB and pTrc-fadE:phaJ(Ac) are co-transformed into strain CPC-Sbm [14], resulting in strain CPC-Sbm(pK-lvaE:tesB, pTrcfadE:phaJ(Ac)). This strain produces HB in comparable quantities as strains listed in Examples 5-8 (FIG. 4).

Example 11: Production of Succinate—Case A

A two-plasmid system was employed to assess the potential of *E. coli* to produce succinate, i.e. an intermediate in the biosynthesis of (R)-HV-CoA from butyrate. The first plasmid contained lvaE and gadAe, i.e. plasmid pK-lvaE:gadAe, and was constructed by amplifying lvaE from *P. putida* KT2440 gDNA with primers P08 and P09 (SEQ ID NO: 116 and 117), gadAe from a gBlock® gene fragment synthesized by Integrated DNA Technologies (USA) with primers P29 and P30 (SEQ ID NO: 147 and 148), and the $P_{lac}$ fragment (including plasmid backbone) from pK184 (further details in Jobling M G et al., *Nucleic Acids Research* 1990, 18:5315, the contents of which are incorporated herein by reference in its entirety for all purposes) with primers P31 and P11 (SEQ ID NO: 149 and 129), followed by subsequent assembly of the three fragments via the NEBuilder HiFi DNA Assembly Master Mix as per the manufacturers' instructions. The second plasmid contained FG99_15380, pduP(Se), and gabD, i.e. plasmid pTrc-FG99_15380:pduP(Se):gabD, and was constructed by amplifying FG99_15380 from a gBlock® gene fragment synthesized by Integrated DNA Technologies (FG99_15380 was codon optimized for expression in *E. coli*) with primers P32 and P33 (SEQ ID NO: 150 and 151), pduP(Se) from *S. enterica* DSM 18522 gDNA with primers P34 and P35 (SEQ ID NO: 152 and 153), gabD from *E. coli* MG1655 gDNA with primers P36 and P37 (SEQ ID NO: 154 and 155), and $P_{trc}$ (including plasmid backbone) from Ptrc99a [15] with primers P38 and P39 (SEQ ID NO: 156 and 157), followed by subsequent assembly of the four fragments via the NEBuilder HiFi DNA Assembly Master Mix as per the manufacturers' instructions. Plasmids pK-lvaE:gadAe and pTrc-FG99_15380:pduP(Se):gabD were co-transformed into strain CPC-Sbm [14], resulting in strain CPC-Sbm(pK-lvaE:gadAe, pTrc-FG99_15380:pduP(Se):gabD), and its ability to produce succinate was evaluated in shake flask cultures (FIG. 4).

Example 12: Production of Succinate—Case B

A two-plasmid system was employed to assess the potential of *E. coli* to produce succinate, i.e. an intermediate in the biosynthesis of (R)-HV-CoA from butyrate. The first plasmid contained lvaE and gadAe, i.e. plasmid pK-lvaE:gadAe (SEQ ID NO: 169), and its construction was described in Example 11. The second plasmid contained FG99_15380, pduP(Kp), and gabD, i.e. plasmid pTrc-FG99_15380:pduP(Kp):gabD, and was constructed by amplifying the $P_{trc}$::FG99_15380-gabD fragment (including plasmid backbone) from pTrc-FG99_15380:pduP(Se):gabD with primers P40 and P41 (SEQ ID NO: 158 and 159), and pduP(Kp) from *K. pneumoniae* DSM 2026 gDNA with primers P42 and P43 (SEQ ID NO: 160 and 161), followed by subsequent assembly of the two fragments via the NEBuilder HiFi DNA Assembly Master Mix as per the manufacturers' instructions. Plasmids pK-lvaE:gadAe (SEQ ID NO: 169) and pTrc-FG99_15380:pduP(Kp):gabD (SEQ ID NO:171) were co-transformed into strain CPC-Sbm [14], resulting in strain CPC-Sbm(pK-lvaE:gadAe, pTrc-FG99_15380:pduP(Kp):gabD), and its ability to produce succinate was evaluated in shake flask cultures (FIG. 4).

Example 13: Production of PHBV—Case A

Genes that encode enzymes that convert propionate to propionyl-CoA, or comprise a pathway for the conversion of butyrate to (R)-HB-CoA are stably integrated into the genome of *E. coli* to avoid the use of antibiotics for plasmid maintenance and chemical inducers of protein expression, and plasmid instability (i.e. plasmid loss from the engineered cell). The expression of pct(Cp), is controlled by any one of a plethora of synthetic promoters that have been previously disclosed, for example but not limited to those described in Puigbo et al (2007), Nakamura et al (2000), and Jobling et al (1990), herein incorporated by reference. For instance, synthetic promoters can be derived by altering the upstream, −35 or −10, or spacer (i.e. the sequence between the −35 and −10) (further details in Hwang H J et al., *Biotechnology for Biofuels* 2018, 11:103, the contents of which are incorporated herein by reference in its entirety for all purposes) sequences of promoters recognized by $\sigma^{70}$ (a protein that initiates the transcription of most genes in *E. coli*). Constitutive promoters with activities spanning at least one order of magnitude are also tested to determine the required promoter activity for each genomically integrated expression cassette to achieve the desired HV content and/or PHBV yield. The Design of Experiment (DoE) approach can be used to reduce the number promoters that must be tested for each genomically integrated expression cassette, and the number of experiments to be conducted, while identifying important interactions that may be observed upon altering the promoter activities of multiple expression cassettes simultaneously. Inducible promoters, for example, but not limited to, IPTG-inducible promoter $P_{trc}$, arabinose-inducible promoter $P_{BAD}$, and tetracycline-inducible promoter $P_{tetA}$ can also be employed to tune the expression of genomically integrated operons, but without wishing to be bound by theory, are considered a less favorable option due to the cost associated with inducer chemicals.

To facilitate the conversion of propionate to propionyl-CoA, the constitutive expression cassette consisting of pct (Cp) and synthetic promoter is integrated into the genome of strain CPC-Sbm, or any strain derived from it, at a locus corresponding to a nonessential gene, i.e. genes that can be silenced or inactivated, or its activity attenuated, without significantly affecting cell viability. Examples of nonessential genes include but are not limited to, cadA (encoding lysine decarboxylase 1 polypeptide), yjcS (encoding linear primary-alkylsulfatase polypeptide), endA (encoding DNA-specific endonuclease I polypeptide), intF (encoding putative phage integrase), bcsA (encoding cellulose synthase catalytic subunit), bcsC (encoding cellulose synthase outer membrane channel), and lacI (encoding the transcriptional repressor of the lac operon). In addition, nonessential genes that encode enzymes that inhibit or reduce the dissimilation of VFAs and/or PHBV production can be used as genomic integration sites, or can be silenced or inactivated for the purpose of improving VFA dissimilation and/or PHBV production. Examples of such nonessential genes can include but are not limited to ghrB (encoding glyoxylate reductase polypeptide that consumes both glyoxylate needed for growth on acetate and NADPH, a cofactor required by PhaB); gcl (encoding glyoxylate carboligase polypeptide that consumes glyoxylate); gabT and puuE (encoding 4-aminobutyrate aminotransferase polypeptides that consume 4-aminobutyrate needed to produce succinate semialdehyde by KES23458); gadC (encoding L-glutamate:4-aminobutyrate antiporter that exports 4-aminobutyrate out of the cell); sad (encoding NAD(+)-dependent succinate semialdehyde dehydrogenase polypeptide); atoB and yqeF (encoding acetyl-CoA acetyltransferase polypeptides that consume acetyl-CoA); fadA (encoding 3-ketoacyl-CoA thiolase polypeptide that may consume butyryl-CoA and acetyl-CoA);

fadB, fadJ, and paaZ (encoding enzymes with significant 3-hydroxyacyl-CoA dehydrogenase activity that can consume crotonyl-CoA and/or (R)-HB-CoA); fadE (encoding acyl-CoA dehydrogenase polypeptide that can consume butyryl-CoA and/or crotonyl-CoA); fadR (encoding DNA-binding transcriptional dual regulator that represses transcription of fadA, fadB, fadE, etc.), ybgC, yigI, tesA, tesB, and yciA (encoding thioesterase polypeptides that can consume HB-CoA and HV-CoA); arcA and fnr (encoding global regulatory protein polypeptides that can regulate carbon flux through the TCA cycle); prpBCD (encoding enzymes that comprise the 2-methylcitrate cycle that converts propionyl-CoA to succinate); and yqhD (encoding NADPH-dependent aldehyde reductase that can convert butyraldehyde to butanol). Subsequently, one or more constitutive expression cassettes consisting of lvaE and phaJ(Ac) and one or more synthetic promoters are integrated into the genome of a derivative of strain CPC-Sbm that contains the genomically-integrated pct(Cp) expression cassette at one or more loci corresponding to one or more nonessential genes to facilitate the conversion of butyrate to (R)-HB-CoA as previously outlined. In this case, however, fadR is inactivated by inventor through fadR gene knockout to derepress expression of fadE to facilitate the conversion of butyryl-CoA to crotonyl-CoA. In addition, atoC (encoding DNA-binding transcriptional activator/ornithine decarboxylase inhibitor that activates transcription of the atoDAEB operon for enhanced VFA uptake and conversion to acyl-CoAs) is mutated to confer constitutive expression of the atoDAEB operon by introducing the amino acid substitution I129S, yielding atoC(Con). The resulting strain containing genomically-integrated pct(Cp), lvaE, and phaJ(Ac) expression cassettes, and constitutively expressed fadE and atoDAEB are subsequently co-transformed with plasmids pPhaCAB (encoding phaA, phaB, and phaC) and pKBktB (encoding bktB) [18], and the resulting strain is evaluated for PHBV production in shake flask and/or bioreactor cultures. The strain produces PHBV with a HV content of 1-30 mol % at a mass yield of 5-80% of dry cell weight.

Example 14: Production of PHBV—Case B

Genes that encode enzymes that 1) convert propionate to propionyl-CoA, 2) comprise a pathway for the conversion of butyrate to (R)-HB-CoA, or 3) comprise a pathway for the conversion of butyrate to succinate are stably integrated into the genome of *E. coli*. The expression of pct(Cp) is controlled by a synthetic promoter and the corresponding constitutive expression cassette is integrated into the genome of strain CPC-Sbm, or any strain derived from it, at a locus corresponding to a nonessential gene to facilitate the conversion of propionate to propionyl-CoA as outlined in Example 13. Subsequently, one or more constitutive expression cassettes consisting of lvaE, PP_2216, and phaJ(Ac) and one or more synthetic promoters are integrated into the genome of a derivative of strain CPC-Sbm that contains the genomically-integrated pct(Cp) expression cassette at one or more loci corresponding to one or more nonessential genes to facilitate the conversion of butyrate to (R)-HB-CoA. Subsequently, one or more constitutive expression cassettes consisting of gadAe, FG99_15380, pduP(Se), and gabD and one or more synthetic promoters are integrated into the genome of a derivative of strain CPC-Sbm that contains the genomically-integrated pct(Cp), lvaE, PP_2216, and phaJ (Ac) expression cassettes at one or more loci corresponding to one or more nonessential genes to facilitate the conversion of butyryl-CoA to succinate. Finally, the resulting strain containing genomically-integrated pct(Cp), lvaE, PP_2216, phaJ(Ac), gadAe, FG99_15380, pduP(Se), and gabD expression cassettes are subsequently co-transformed with plasmids pPhaCAB (encoding phaA, phaB, and phaC) and pKBktB (encoding bktB) [18], and the resulting strain is evaluated for PHBV production in shake flask and/or bioreactor cultures in which cyanocobalamin has been added to activate the Sbm pathway for the conversion of succinyl-CoA to propionyl-CoA. The strain produces PHBV with a HV content of 1-30 mol % at a mass yield of 5-80% of dry cell weight.

Example 15: Production of PHBV—Case C

Genes that encode enzymes that 1) convert propionate to propionyl-CoA, 2) comprise a pathway for the conversion of butyrate to succinate, 3) comprise a pathway for the conversion of butyrate to acetyl-CoA, and 4) facilitate the conversion of succinate to succinyl-CoA are stably integrated into the genome of *E. coli*. The expression of lvaE and pct(Cp) is controlled by a synthetic promoter and the corresponding constitutive expression cassette is integrated into the genome of strain CPC-Sbm, or any strain derived from it, at a locus corresponding to a nonessential gene to facilitate the conversion of butyrate to butyryl-CoA and propionate to propionyl-CoA, respectively. Subsequently, a constitutive expression cassette consisting of fadE, fadB, and atoB and a synthetic promoter is integrated into a locus corresponding to a nonessential gene in the genome of a derivative of strain CPC-Sbm that contains the genomically-integrated lvaE:pct(Cp) expression cassette to facilitate the conversion of butyryl-CoA to acetyl-CoA. One or more constitutive expression cassettes consisting of gadAe, FG99_15380, pduP(Se), and gabD and one or more synthetic promoters are then integrated into the genome of a derivative of strain CPC-Sbm containing genomically-integrated lvaE:pct(Cp) and fadE:fadB:atoB expression cassettes at one or more loci corresponding to one or more nonessential genes to facilitate the conversion of butyryl-CoA to succinate. Subsequently, a constitutive expression cassette consisting of CKL_RS14680 and a synthetic promoter is integrated into the genome of a derivative of strain CPC-Sbm that contains the genomically-integrated lvaE:pct (Cp), fadE:fadB:atoB, gadAe, FG99_15380, pduP(Se), and gabD expression cassettes at a locus corresponding to a nonessential gene to facilitate the conversion of succinate to succinyl-CoA. Finally, the resulting strain containing genomically-integrated lvaE:pct(Cp), fadE:fadB:atoB, gadAe, FG99_15380, pduP(Se), gabD, and CKL_RS14680 expression cassettes are subsequently co-transformed with plasmids pPhaCAB (encoding phaA, phaB, and phaC) and pKBktB (encoding bktB) [18], and the resulting strain is evaluated for PHBV production in shake flask and/or bioreactor cultures in which cyanocobalamin has been added to activate the Sbm pathway for the conversion of succinyl-CoA to propionyl-CoA. The strain produces PHBV with a HV content of 1-40 mol % at a mass yield of 5-80% of dry cell weight.

Example 16: Production of PHBV—Case D

Genes that encode enzymes that 1) convert propionate to propionyl-CoA, 2) comprise a pathway for the conversion of butyrate to (R)-HB-CoA, 3) comprise a pathway for the conversion of butyrate to succinate, or 4) facilitate the conversion of succinate to succinyl-CoA are stably integrated into the genome of *E. coli*. Inventor has determined that inactivation of iclR, encoding a transcriptional repressor that regulates the glyoxylate shunt in *E. coli*, can stimulate propionyl-CoA production from acetate when the Sbm pathway is activated (FIG. 2). Moreover, over-transcription of small noncoding RNAs DsrA, RprA and ArcZ (encoded by dsrA, rprA, and arcZ, respectively; coding sequences shown in Table 3B; RNA sequences shown in Table 3C) significantly increased the tolerance of *E. coli* to acetate and butyrate. The expression of pct(Cp) is controlled by a synthetic promoter and the corresponding constitutive expression cassette is integrated into the genome of strain CPC-Sbm(ΔiclR), or any strain derived from it, at a locus corresponding to a nonessential gene to facilitate the conversion of propionate to propionyl-CoA as outlined in Example 13. Subsequently, one or more constitutive expression cassettes consisting of lvaE, PP_2216, and phaJ(Ac) and one or more synthetic promoters are integrated into the genome of a derivative of strain CPC-Sbm(ΔiclR) that contains the genomically-integrated pct(Cp) expression cassette at one or more loci corresponding to one or more nonessential genes to facilitate the conversion of butyrate to (R)-HB-CoA. Subsequently, one or more constitutive expression cassettes consisting of gadBe(Ec), FG99_15380, pduP(Se), and gabD and one or more synthetic promoters are integrated into the genome of a derivative of strain CPC-Sbm(ΔiclR) that contains the genomically-integrated pct(Cp), lvaE, PP_2216, and phaJ(Ac) expression cassettes at one or more loci corresponding to one or more nonessential genes to facilitate the conversion of butyryl-CoA to succinate. Subsequently, sdhA is inactivated and an expression cassette containing sdhA under control of the rhamnose-inducible promoter Prha from the rhaBAD operon of *E. coli* is integrated into the genome of a derivative of strain CPC-Sbm(ΔiclR) that contains the genomically-integrated pct(Cp), lvaE, PP_2216, phaJ(Ac), gadBe(Ec), FG99_15380, pduP(Se), and gabD expression cassettes at a locus corresponding to a nonessential gene. The purpose of making sdhA expression inducible is to reduce the conversion of succinate to fumarate in a tunable manner to enhance the conversion of succinate to succinyl-CoA as succinate levels increase due to reduced sdhA expression (compared to wild-type levels). Finally, the resulting ΔsdhA mutant containing genomically-integrated pct(Cp), lvaE, PP_2216, phaJ(Ac), gadBe(Ec), FG99_15380, pduP(Se), gabD, and Prha::sdhA expression cassettes are subsequently co-transformed with plasmids pPhaCAB (encoding phaA, phaB, and phaC) and pK-bktB-dsrA-rprA-arcZ (a derivative of plasmid pKBktB encoding bktB [18], and dsrA. rprA, and arcZ transcribed from their respective native promoters), and the resulting strain is evaluated for PHBV production in shake flask and/or bioreactor cultures in which cyanocobalamin has been added to activate the Sbm pathway for the conversion of succinyl-CoA to propionyl-CoA. The strain produces PHBV with a HV content of 1-50 mol % at a mass yield of 5-80% of dry cell weight.

Example 17: Production of PHBV—Case E

Genes that encode enzymes that 1) convert propionate to propionyl-CoA, 2) comprise a pathway for the conversion of butyrate to succinate, or 3) facilitate the conversion of succinate to succinyl-CoA are stably integrated into the genome of *E. coli*. The expression of pct(Cp) is controlled by a synthetic promoter and the corresponding constitutive expression cassette is integrated into the genome of strain CPC-Sbm, or any strain derived from it, at a locus corresponding to a nonessential gene to facilitate the conversion of propionate to propionyl-CoA as outlined in Example 13. Subsequently, a constitutive expression cassette consisting of lvaE and a synthetic promoter is integrated into the genome of a derivative of strain CPC-Sbm that contains the genomically-integrated pct(Cp) expression cassette at a locus corresponding to a nonessential gene to facilitate the conversion of butyrate to butyryl-CoA. Subsequently, the native fadR promoter is replaced with the rhamnose-inducible promoter Prha from the rhaBAD operon of *E. coli* in the genome of a derivative of strain CPC-Sbm that contains the genomically-integrated pct(Cp) and lvaE expression cassettes to facilitate inducible derepression of fadE, which will restrict the conversion of butyryl-CoA to crotonyl-CoA to reduce butyrate dissimilation for biomass accumulation in a tunable manner. In addition, an atoS:atoC(I129S) expression cassette containing the native promoter is integrated into the genome of a derivative of strain CPC-Sbm that contains the genomically-integrated pct(Cp), lvaE, and Prha::fadR expression cassettes to confer constitutive expression of the atoDAEB operon. Subsequently, one or more constitutive expression cassettes consisting of gad(Ls), FG99_15380, pduP(Se), and gabD and one or more synthetic promoters are integrated into the genome of a derivative of strain CPC-Sbm that contains the genomically-integrated pct(Cp), lvaE, Prha::fadR, and atoS:atoC(I129S) expression cassettes at a locus corresponding to one or more nonessential genes to facilitate the conversion of butyryl-CoA to succinate. Subsequently, a constitutive expression cassette consisting of CKL_RS14680 and a synthetic promoter is integrated into the genome of a derivative of strain CPC-Sbm that contains the genomically-integrated pct(Cp), lvaE, Prha::fadR, atoS:atoC(I129S), gad(Ls), FG99_15380, pduP(Se), and gabD expression cassettes at a locus corresponding to a nonessential gene to facilitate the conversion of succinate to succinyl-CoA. Finally, the resulting strain containing genomically-integrated pct(Cp), lvaE, Prha::fadR, atoS:atoC (I129S), gad(Ls), FG99_15380, pduP(Se), gabD, and CKL_RS14680 expression cassettes are subsequently co-transformed with plasmids pPhaCAB (encoding phaA, phaB, and phaC) and pKBktB (encoding bktB) [18], and the resulting strain is evaluated for PHBV production in shake flask and/or bioreactor cultures in which cyanocobalamin has been added to activate the Sbm pathway for the conversion of succinyl-CoA to propionyl-CoA. The strain produces PHBV with a HV content of 1-50 mol % at a mass yield of 5-80% of dry cell weight.

Example 18: Production of PHBV—Case F

Genes that encode enzymes that 1) convert propionate to propionyl-CoA, 2) comprise a pathway for the conversion of butyrate to (R)-HB-CoA, 3) comprise a pathway for the conversion of butyrate to succinate, 4) facilitate the conversion of succinate to succinyl-CoA, 5) comprise the pathways for the conversion of acetyl-CoA to (R)-HB-CoA, and acetyl-CoA and propionyl-CoA to (R)-HV-CoA, or 6) facilitate the polymerization of (R)-HB-CoA and (R)-HV-CoA to PHBV are stably integrated into the genome of *E. coli*. The construction of a strain containing genomically-integrated lvaE:pct(Cp), fadE:fadB:atoB, gadAe, FG99_15380, pduP (Se), gabD, and CKL_RS14680 expression cassettes was described in Example 15. A constitutive expression cassette consisting of phaC, phaB, bktB, phaA and one or more synthetic promoters is integrated into the genome of a derivative of strain CPC-Sbm that contains the genomically-integrated lvaE:pct(Cp), fadE:fadB:atoB, gadAe, FG99_15380, pduP(Se), gabD, and CKL_RS14680 expression cassettes at loci corresponding to nonessential genes to facilitate the conversion of acetyl-CoA to (R)-HB-CoA, acetyl-CoA and propionyl-CoA to (R)-HV-CoA, and the polymerization of (R)-HB-CoA and (R)-HV-CoA to PHBV. Finally, the resulting strain containing genomically-integrated lvaE:pct(Cp), fadE:fadB:atoB, gadAe, FG99_15380, pduP(Se), gabD, CKL_RS14680, phaC, phaB, bktB, and phaA expression cassettes is evaluated for PHBV production in shake flask and/or bioreactor cultures in which cyanocobalamin has been added to activate the Sbm pathway for the conversion of succinyl-CoA to propionyl-CoA. The strain produces PHBV with a HV content of 1-40 mol % at a mass yield of 5-80% of dry cell weight.

Example 19: Acetate Consumption in Strains Engineered for High Sbm Pathway Carbon Flux Carbon flux through the Sbm pathway primarily occurs through the reductive TCA cycle under low oxygenic conditions. However, high carbon flux through the Sbm pathway was achieved under aerobic conditions by simultaneously blocking the oxidative TCA cycle and deregulating the glyoxylate shunt through respective inactivation of sdhA and iclR. Accordingly, strains CPC-Sbm, CPC-Sbm(ΔiclR), and CPC-Sbm(ΔiclR ΔsdhA) were tested for their ability to consume acetate under aerobic and microaerobic conditions. These strains were cultivated in the base medium supplemented with 20 g/L sodium acetate, 0.3 mM IPTG, and 0.6 μM vitamin $B_{12}$ in capped (microaerobic) and vented (aerobic) 125 mL polycarbonate flasks (FIG. 2). The strains and corresponding labels are shown in Table 5. Cultivations were performed at 30° C. and 280 rpm over 48 hours. Strain CPC-Sbm achieved slightly lower cell densities than strain CPC-Sbm(ΔiclR) under aerobic ($OD_{600}$ 11.1 and 11.7, respectively) and microaerobic ($OD_{600}$ 11.2 and 12.1, respectively) conditions. Moreover, acetate consumption was similar between these strains under aerobic (100% of acetate consumed) and microaerobic (~70% acetate consumed) conditions, although strain CPC-Sbm(ΔiclR) produced 1.5 g/L propionate under microaerobic conditions indicating significant flux through the Sbm pathway. On the other hand, strain CPC-Sbm(ΔiclR ΔsdhA) exhibited significantly lower growth (cell density $OD_{600}$ 5.4) and acetate consumption (32% of acetate consumed) under aerobic conditions, although this strain produced propionate under both microaerobic (2.6 g/L) and aerobic (1.1 g/L) conditions. The relatively poor acetate consumption of strains CPC-Sbm and CPC-Sbm(ΔiclR) under microaerobic, compared to aerobic conditions, and the inability of strain CPC-Sbm(ΔiclR ΔsdhA) to effectively consume acetate under aerobic conditions indicates that the oxidative TCA cycle (which is highly active under aerobic conditions and inactive in strain CPC-Sbm(ΔiclR ΔsdhA)) is critical for effective dissimilation of acetate. In addition, inactivation of iclR can partially divert the flux of acetate from the oxidative TCA cycle into the Sbm pathway under low oxygenic conditions, such that altering dissolved oxygen (DO) levels can be useful for tuning the HV content of PHBV produced in cultures of iclR mutants. Similarly, reducing the expression of sdhA, or increasing the conversion of succinate to succinyl-CoA, can be useful for increasing HV content. Further details are provided in Miscevic D et al., *Biotechnology and Bioengineering* 2020, and Miscevic D, et al., *Metabolic Engineering* 2019, the contents of each of which are incorporated herein by reference in its entirety for all purposes.

Example 20: Acetate and Propionate Co-Utilization for HB and HV Co-Production

Strains CPC-Sbm(pK-bktB-hbd-tesB, pTrc-phaAB:pct (Cp)) and CPC-Sbm(pK-bktB-hbd-tesB, pTrc-phaAB:pct (Me)) were evaluated for their ability to co-produce HB and HV from acetate and propionate, with or without glycerol. These strains were cultivated in the base medium supplemented with 5 g/L sodium acetate, 4 g/L sodium propionate, 0.3 mM IPTG, 30 mg/L kanamycin, and 60 mg/L ampicillin, with or without 5 g/L glycerol in 125 mL Erlenmeyer flasks with foam stoppers (i.e. under aerobic conditions; FIG. 3). The strains and corresponding labels are shown in Table 5. Cultivations were performed at 30° C. and 280 rpm over 48 hours. The skilled person readily recognizes that the molar ratio of acetate to propionate can deviate from 1.46:1, for example, 4:3, or from 0.125:1 to 7:1. The Sbm pathway was not activated to accurately assess the ability of the strains to incorporate exogenous propionate into HV. Strains CPC-Sbm(pK-bktB-hbd-tesB, pTrc-phaAB:pct(Cp)) and CPC-Sbm(pK-bktB-hbd-tesB, pTrc-phaAB:pct(Me)) achieved similar cell densities in the medium with ($OD_{600}$ 9.8 and 9.3, respectively) or without ($OD_{600}$ 7.2 and 8.3, respectively) glycerol. Moreover, HV titers were higher in cultures of strain CPC-Sbm(pK-bktB-hbd-tesB, pTrc-phaAB:pct(Cp)) with (0.56 g/L compared to 0.42 g/L) or without (0.28 g/L compared to 0.22 g/L) glycerol. Surprisingly, HB titers were significantly higher in cultures of strain CPC-Sbm(pK-bktB-hbd-tesB, pTrc-phaAB:pct(Cp)), particularly when glycerol was present in the medium (0.94 g/L compared to 0.51 g/L). These results indicate that expression of pct(Cp) can result in greater incorporation of exogenous propionate into PHBV and improved HB production, compared to expression of pct(Me). On the other hand, expression of pct(Me) can result in the production of PHBV of higher HV content given the lower HB production observed in cultures of strain CPC-Sbm(pK-bktB-hbd-tesB, pTrc-phaAB:pct(Me)).

Example 21: Conversion of Butyrate to HB

Strains CPC-Sbm(pK-lvaE:tesB, Ptrc-PP_2216:H16_RS27940), CPC-Sbm(pK-lvaE:tesB, Ptrc-BC_5341:H16_RS27940), CPC-Sbm(pK-atoDAE:tesB, Ptrc-PP_2216:H16_RS27940), CPC-Sbm(pK-atoDAE:tesB, Ptrc-BC_5341:H16_RS27940), and CPC-Sbm(pK-lvaE:tesB, Ptrc-PP_2216:phaJ(Ac)) were evaluated for their ability to produce HB from butyrate. These strains were cultivated in the base medium supplemented with 3 g/L sodium butyrate, 10 g/L glucose (as carbon source for growth), 0.3 mM IPTG, 30 mg/L kanamycin, and 60 mg/L ampicillin in 125 mL Erlenmeyer flasks with foam stoppers (FIG. 4). The strains and corresponding labels are shown in Table 5. Cultivations were performed at 30° C. and 280 rpm over 48 hours. Strains CPC-Sbm(pK-lvaE:tesB, Ptrc-PP_2216:H16_RS27940), CPC-Sbm(pK-lvaE:tesB, Ptrc-BC_5341:H16_RS27940), and CPC-Sbm(pK-lvaE:tesB, Ptrc-PP_2216:phaJ(Ac)) achieved similar cell densities ($OD_{600}$ 11.3, 10.9, and 11.3, respectively) and HB titers (1.03, 0.93, and 1.17 g/L, respectively), and respectively consumed 90, 79, and 100% of the sodium butyrate. On the other hand, strains CPC-Sbm(pK-atoDAE:tesB, Ptrc-PP_2216:H16_RS27940) and CPC-Sbm(pK-atoDAE:tesB, Ptrc-BC_5341:H16_RS27940) achieved significantly lower cell densities ($OD_{600}$ 8.8 and 9.6, respectively) and HB titers (0.40 and 0.53 g/L, respectively), and consumed significantly less sodium butyrate (51 and 65% of sodium butyrate consumed, respectively) compared to the other three strains.

These results indicate that AtoD polypeptide and AtoA polypeptide, which are, without wishing to be bound by theory, thought to facilitate the conversion of butyrate to butyryl-CoA in atoC (Con) ΔfadR double mutants that can grow on butyrate as the sole carbon source [21, 22], is less effective at converting butyrate to butyryl-CoA, compared to LvaE. In addition, PP_2216 and BC_5341, and H16_RS27940 and PhaJ(Ac) were similarly effective at respectively converting butyryl-CoA to crotonyl-CoA, and crotonyl-CoA to (R)-HB-CoA.

Example 22: Conversion of Butyrate to Succinate

Strains CPC-Sbm(pK-lvaE:gadAe, PTrc-FG99_15380: pduP(Se):gabD) and CPC-Sbm(pK-lvaE:gadAe, PTrc-FG99_15380:pduP(Kp):gabD) were evaluated for their ability to produce succinate from butyrate. These strains were cultivated in the base medium supplemented with 3 g/L sodium butyrate, 10 g/L glucose, 0.3 mM IPTG, 30 mg/L kanamycin, and 60 mg/L ampicillin in 125 mL Erlenmeyer flasks with foam stoppers (FIG. 4). These strains achieved similar respective cell densities of $OD_{600}$ 15.2 and 14.9, and no succinate was detected in cultures of either strain. However, cell densities were approximately 35% higher compared to strains CPC-Sbm(pK-lvaE:tesB, Ptrc-PP_2216: H16_RS27940), CPC-Sbm(pK-lvaE:tesB, Ptrc-BC_5341: H16_RS27940), and CPC-Sbm(pK-lvaE:tesB, Ptrc-PP_2216:phaJ(Ac)) (i.e. strains engineered to convert butyrate to HB; FIG. 4), and both strains consumed all sodium butyrate, indicating that, without wishing to be bound by theory, sodium butyrate has been converted to succinate which, in turn, was metabolized through the TCA cycle. Succinate semialdehyde is another intermediate in the pathway for conversion of butyryl-CoA to succinate. Succinate semialdehyde can be converted to 4-hydroxybutyrate, a metabolite that is not naturally consumed by *E. coli*, via heterologous 4-hydroxybutyrate dehydrogenase polypeptide, without wishing to be bound by theory, as a means of evaluating the functionality of the pathway for the conversion of butyryl-CoA to succinate. Similar amounts of HB were detected in cultures of strains CPC-Sbm(pK-lvaE: gadAe, PTrc-FG99_15380:pduP(Se):gabD) and CPC-Sbm (pK-lvaE:gadAe, PTrc-FG99_15380:pduP(Kp):gabD) showing that *E. coli* can naturally convert butyrate and/or glucose to HB. Accordingly, two control strains were tested, i.e. CPC-Sbm and CPC-Sbm(pK-lvaE:gadAe) for their ability to produce HB under the same experimental conditions (See FIG. 4). While CPC-Sbm could not produce HB from butyrate or glucose, CPC-Sbm(pK-lvaE:gadAe) converted butyrate to HB, suggesting that *E. coli* can naturally convert butyryl-CoA to HB (i.e. LvaE was required to convert butyrate to butyryl-CoA)).

Example 23: Conversion of Glycerol to PHBV

An expression cassette containing 1) promoter $P_{gracmax2}$, a stronger derivative of promoter $P_{grac}$, 2) the strong RBS from gene 10 of Phage T7 (T7.RBS) that can significantly enhance translation efficiency relative to the consensus RBS of *E. coli,* 3) bktB, 4) a strong Gram-positive RBS coupled with a nine bp sequence derived from T7.RBS (i.e. TTAACTTTA) that facilitates base-pairing with the 16S rRNA of *E. coli* to enhance translation efficiency (RBS1), 5)phaB, and 6) a strong transcriptional terminator was genomically integrated into the bcsA locus of CPC-Sbm, resulting in strain CPC-Sbm(bcsA::($P_{gracmax2}$::(T7.RBS) bktB:(RBS1)phaB). An expression cassette containing the same elements as previously described, except that bktB and phaB were respectively replaced with phaC and phaA, was subsequently genomically integrated into the intF locus of CPC-Sbm(bcsA::($P_{gracmax2}$::(T7.RBS)bktB:(RBS1)phaB), resulting in strain CPC-Sbm(bcsA::($P_{gracmax2}$::(T7.RBS) bktB:(RBS1)phaB), intF::($P_{gracmax2}$::(T7.RBS)phaC: (RBS1)phaA). This strain was fermented in a medium containing 30 g/L glycerol, 10 g/L yeast extract, 10 mM $NaHCO_3$, 0.4 μM vitamin $B_{12}$, and $1000^{th}$ dilution (i.e. 1 mL/L) trace elements (2.86 g/L $H_3BO_3$, 1.81 g/L $MnCl_2 \cdot 4H_2O$, 0.222 g/L $ZnSO_4 \cdot 7H_2O$, 0.39 g/L $Na_2MoO_4 \cdot 2H_2O$, 79 μg/L $CuSO_4 \cdot 5H_2O$, 49.4 μg/L $Co(NO_3)_2 \cdot 6H_2O$), 0.1 mM IPTG, 0.23 g/L $K_2HPO_4$, 0.51 g/L $NH_4Cl$, 49.8 mg/L $MgCl_2$, 48.1 mg/L $K_2SO_4$, 2.78 mg/L $FeSO_4 \cdot 7H_2O$, 0.055 mg/L $CaCl_2$, 2.93 g/L NaCl, and 0.72 g/L tricine under different aeration conditions, resulting in the production of PHBV with a HV content of 15-40 mol % at a mass yield of up to 80% of dry cell weight. Further details are provided in Phan T T P et al., *Protein expression and purification* 2006, 46:189-195, the contents of which are incorporated herein by reference in its entirety for all purposes.

Example 24: Production of PHBV with a Weight Average Molecular Weight (Mw) of 1-1.5 MDa To analyze the factors that possibly contribute to the production of PHBV with a Mw of 1-1.5 MDa, the following experiments were performed to test the effect of different variables, such as, the use of thermostable enzymes, the order of the genes in an operon, ribosomal binding sites and genome integration sites.

Strains listed in Table 7 below were analyzed for their ability to produce PHBV using the methods described herein. While GEN-EC-GLY-01 strain was engineered to comprise nucleic acid molecules encoding the *Cupriavidus necator* PhaA protein, the *Cupriavidus necator* PhaB protein, the *Cupriavidus necator* PhaC protein and the *Cupriavidus necator* BtkB protein, the GEN-EC-GLY-17 strain was engineered to comprise nucleic acid molecules encoding the *Cupriavidus* sp. S-6 PhaA protein, the *Cupriavidus* sp. S-6 PhaB protein, the *Cupriavidus* sp. S-6 PhaC protein and the *Cupriavidus gilardii* QJ1 BtkB protein.

TABLE 7

| Strain Name | Strain Genotype |
| --- | --- |
| GEN-EC-GLY-01 | CPC-Sbm(endA::λ-Red, yjcS::(PtetA::spc.P279T-cas9), bcsA::(Pgracmax2::(RBS-T7)bktB(Cn):phaB(Cn)), intF::(Pgracmax2::(RBS-T7)phaC(Cn):phaA(Cn))) |
| GEN-EC-GLY-17 | CPC-Sbm(yjcS::(Pgracmax2::phaCAB(S-6))), bcsA::(Pgracmax2::(RBS-T7)bktB(QJ1):phaB(S-6))) |

Without being bound by a theory, it is thought that, because *Cupriavidus necator* is a mesophile, the *Cupriavidus necator* PhaA, PhaB, PhaC and BtkB proteins would be thermostable at a temperature of about 28° C. to about 30° C., and thereby be capable of promoting the production of PHBV in the bacterial host cell at this temperature range. On the other hand, it is thought that since *Cupriavidus* sp. S-6 and *Cupriavidus gilardii* QJ1 are moderate thermophiles, the PhaA, PhaB, PhaC and BtkB proteins of these organisms would be thermostable at temperature higher than 30° C. (such as, at a temperature in the range of about 37° C. to about 50° C.), and thereby be capable of promoting the production of PHBV in the bacterial host cell at this higher temperature range.

Figure 5:
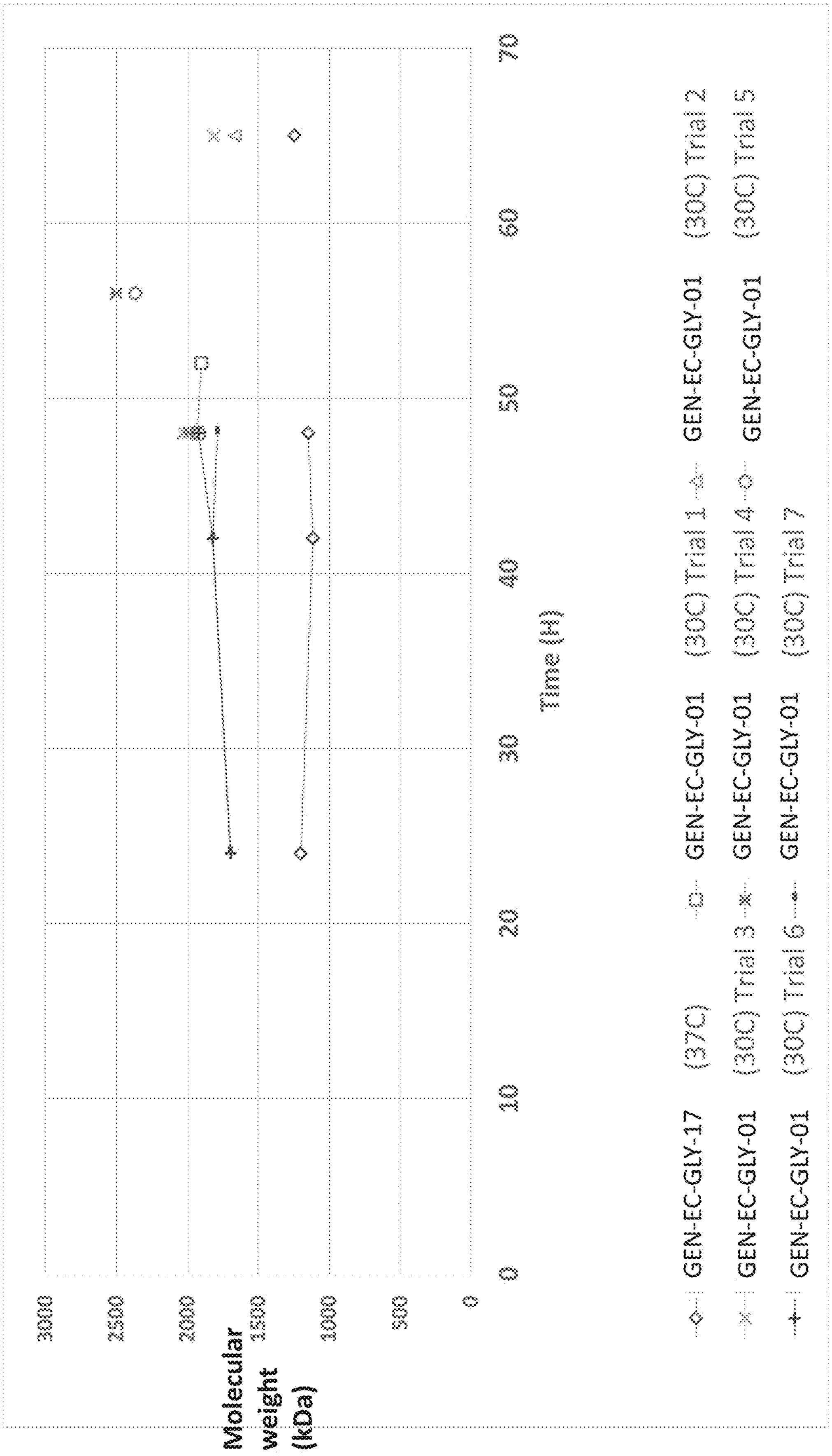
FIG. 5 is a line graph depicting the molecular weight of PHBV produced by the strains listed in Table 7.

Analysis of PHBV produced by the strains listed in Table 7 shows that GEN-EC-GLY-17 is indeed capable of producing PHBV at 37° C. However, surprisingly, it was seen that the molecular weight of PHBV produced varied based on the strain (FIG. 5). While GEN-EC-GLY-17 produced PHBV having a weight average molecular weight of about 1-1.5 MDa at 37° C., GEN-EC-GLY-1 produced PHBV having a weight average molecular weight of about 1.5-2 MDa at 30° C.

Next, the strains listed in Table 8 below, which differ in the order and combination of phaA, phaB and phaC genes in the operons, were analyzed for their ability to produce PHBV using the methods described herein.

TABLE 8

| Strain ID | Strain Genotype |
|---|---|
| Strain A (GEN-EC-GLY-19) | CPC-Sbm(bcsA::(Pgracmax2::(RBS-T7)bktB(QJ1):phaB(S-6)), yjcS::(Pgracmax2::phaA(S-6):(RBS-T7)phaC(S-6))) |
| Strain B (GEN-EC-GLY-17) | CPC-Sbm(yjcS::(Pgracmax2::phaCAB(S-6))), bcsA::(Pgracmax2::(RBS-T7)bktB(QJ1):phaB(S-6))) |

Figure 6:
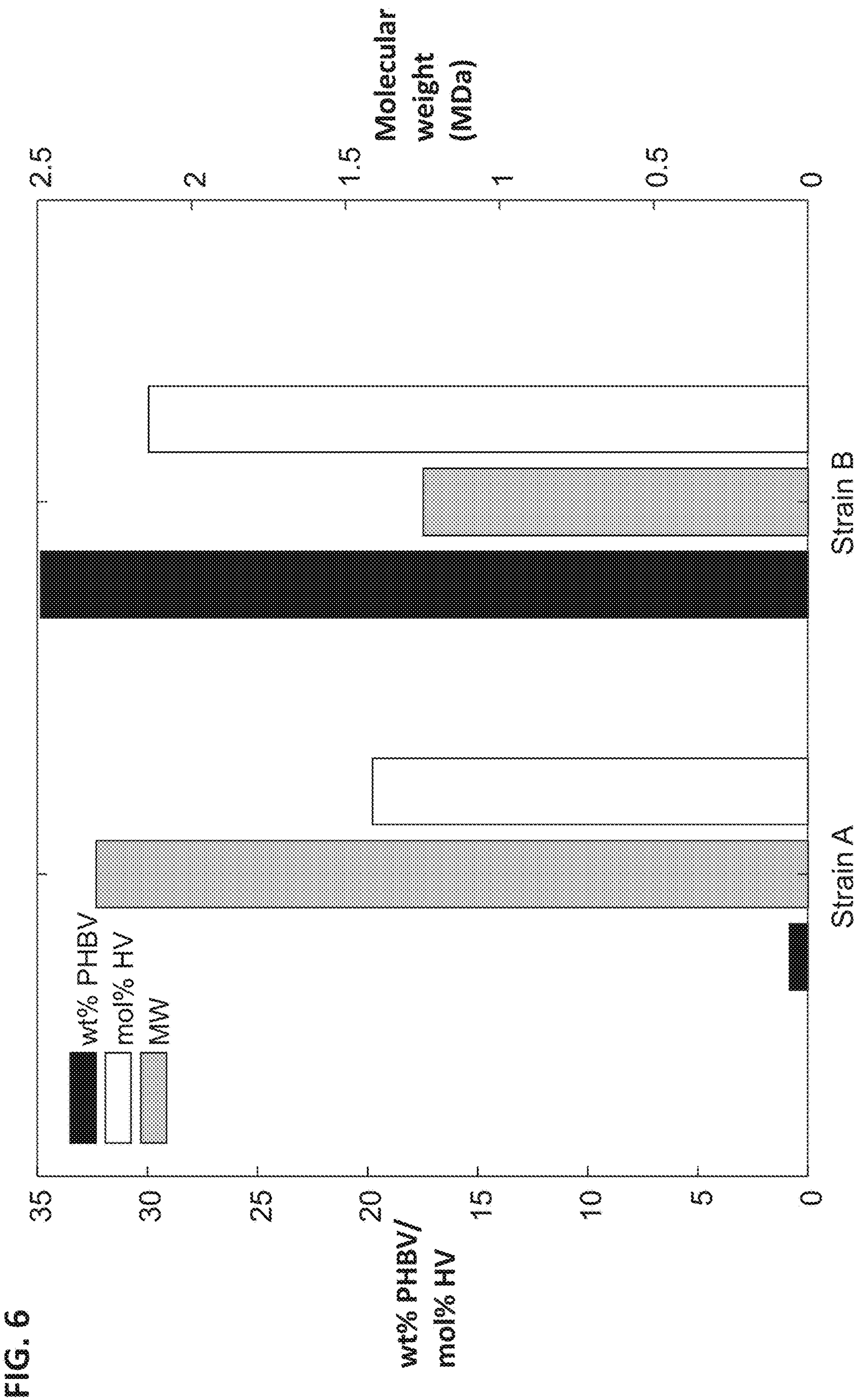
FIG. 6 is a bar graph depicting the wt % of PHBV, mol % of HV and the Mw of PHBV produced by the strains listed in Table 8.

As shown in FIG. 6, the production of PHBV from Strain B (GEN-EC-GLY-17) was significantly higher than from Strain A (GEN-EC-GLY-19) upon growth and fermentation under comparable conditions. Additionally, not only did Strain B produce more PHBV than Strain A, Strain B also produced PHBV of a different molecular weight than Strain A. While Strain B produced PHBV with a molecular weight of about 1-1.5 MDa, Strain A produced PHBV with a molecular weight of over 2 MDa. Since Strains A and B express the same heterologous genes (that is, phaA, phaB, phaC and BktB), a difference in the amount of PHBV produced and the molecular weight of PHBV was unexpected.

Next, the strains listed in Table 9 below, which differ in the ribosomal binding site (RBS) used in the phaCAB expression cassette, were analyzed for their ability to produce PHBV using the methods described herein.

TABLE 9

| Strain ID | Strain |
|---|---|
| Strain A (GEN-EC-GLY-13) | CPC-Sbm(yjcS::(Pgracmax2::(RBS-5)phaCAB(S-6))) |
| Strain B (GEN-EC-GLY-11) | CPC-Sbm(intF::(PtetA::spc.P279T-cas9), yjcS::(Pgracmax2::(RBS-T7)phaCAB(S-6))) |

Figure 7:
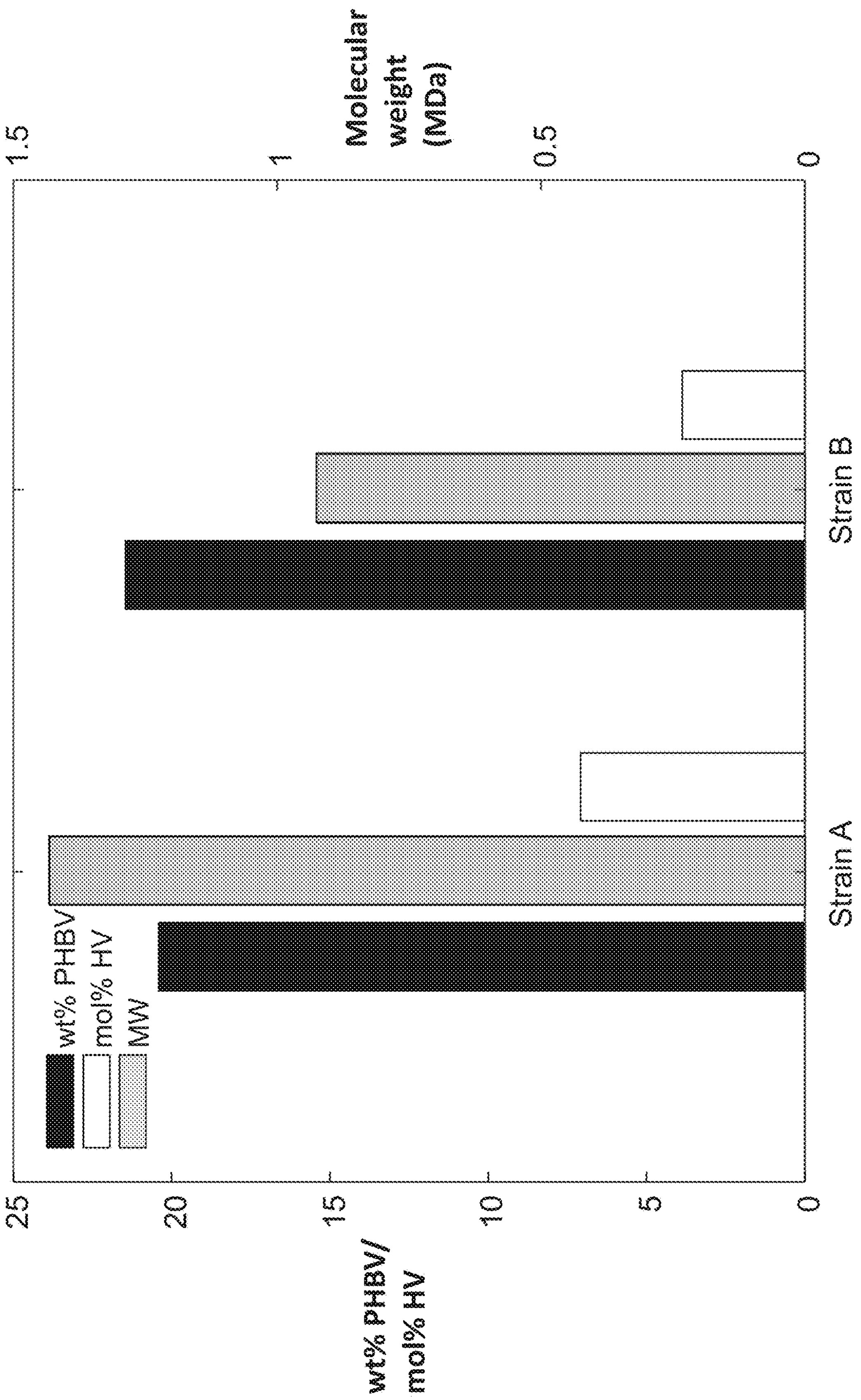
FIG. 7 is a bar graph depicting the wt % of PHBV, mol % of HV and the Mw of PHBV produced by the strains listed in Table 9.

While GEN-EC-GLY-13 comprises a nucleic acid molecule encoding PhaA, PhaB and PhaC proteins operably linked to a $P_{gracmax2}$ promoter and a RBS-5 ribosomal binding site, the GEN-EC-GLY-11 strain comprises a similar nucleic acid molecule encoding PhaA, PhaB and PhaC proteins operably linked to a $P_{gracmax2}$ promoter and a RBS-T7 ribosomal binding site. When the production of PHBV from glycerol by either of these strains was evaluated, the molecular weight of the PHBV produced was seen to differ. As shown in FIG. 7, the use of the RBS-T7 (SEQ ID NO: 256), a stronger ribosomal binding site than RBS-5 (SEQ ID NO: 255), resulted in the production of PHBV with lower molecular weight.

While the present disclosure has been described with reference to examples, it is to be understood that the scope of the claims should not be limited by the embodiments set forth in the examples but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety.

NUMBERED EMBODIMENTS—I

The following list of embodiments is included herein for illustration purposes only and is not intended to be comprehensive or limiting. The subject matter to be claimed is expressly not limited to the following embodiments.

Embodiment 1. A bacterial host cell, comprising one or more of the following nucleic acid molecules integrated into the bacterial host cell genome:

(a) a first operon, comprising:

(i) a nucleic acid molecule encoding a PhaC protein, wherein the PhaC protein is a *Cupriavidus* sp. S-6 PhaC protein, (ii) a nucleic acid molecule encoding a PhaA protein, wherein the PhaA protein is a *Cupriavidus* sp. S-6 PhaA protein, (iii) a nucleic acid molecule encoding a PhaB protein, wherein the PhaB protein is a *Cupriavidus* sp. S-6 PhaB protein, wherein the first operon comprises a first promoter; and (b) a second operon, comprising:

(iv) a nucleic acid molecule encoding a BktB protein, wherein the BktB protein is a *Cupriavidus* sp. QJ1 BktB protein and (v) a nucleic acid molecule encoding a PhaB protein, wherein the PhaB protein is a *Cupriavidus* sp. S-6 PhaB protein wherein the second operon comprises a second promoter, wherein the bacterial host cell comprises an activated sleeping beauty mutase (Sbm) pathway.

Embodiment 2. The bacterial host cell of embodiment 1, wherein the first promoter and the second promoter are the same, and wherein each of the first promoter and the second promoter comprises the nucleic acid sequence of SEQ ID NO: 233 ($P_{gracmax2}$).

Embodiment 3. The bacterial host cell of embodiment 1, wherein the PhaA protein comprises an amino acid sequence having at least 90% identity to SEQ ID NO: 241.

Embodiment 4. The bacterial host cell of embodiment 1, wherein the nucleic acid molecule encoding a PhaA protein comprises a nucleic acid sequence having at least 80% identity to SEQ ID NO: 248.

Embodiment 5. The bacterial host cell of embodiment 1, wherein the PhaB protein comprises an amino acid sequence having at least 90% identity to SEQ ID NO: 242.

Embodiment 6. The bacterial host cell of embodiment 1, wherein the nucleic acid molecule encoding a PhaB protein comprises a nucleic acid sequence having at least 80% identity to SEQ ID NO: 249.

Embodiment 7. The bacterial host cell of embodiment 1, wherein the PhaC protein comprises an amino acid sequence having at least 90% identity to SEQ ID NO: 243.

Embodiment 8. The bacterial host cell of embodiment 1, wherein the nucleic acid molecule encoding a PhaC protein comprises a nucleic acid sequence having at least 80% identity to SEQ ID NO: 250.

Embodiment 9. The bacterial host cell of embodiment 1, wherein the BtkB protein comprises an amino acid sequence having at least 90% identity to SEQ ID NO: 245.

Embodiment 10. The bacterial host cell of embodiment 1, wherein the nucleic acid molecule encoding a BtkB protein comprises a nucleic acid sequence having at least 80% identity to SEQ ID NO: 251.

Embodiment 11. The bacterial host cell of embodiment 1, wherein the bacterial host cell converts glycerol to poly(3-hydroxybutyrate-co-3-hydroxyvalerate) or PHBV.

Embodiment 12. The bacterial host cell of embodiment 1, wherein the bacterial host cell converts glycerol into poly (3-hydroxybutyrate-co-3-hydroxyvalerate) or PHBV at a temperature in the range of about 37° C. to about 50° C.

Embodiment 13. The bacterial host cell embodiment 1, wherein the bacterial host cell comprises a sleeping beauty mutase (Sbm) operon comprising a Ptrc promoter.

Embodiment 14. The bacterial host cell of embodiment 1, wherein the bacterial host cell is *Escherichia coli.*

Embodiment 15. A method of producing poly(3-hydroxybutyrate-co-3-hydroxyvalerate) (PHBV), the method comprising:

growing the bacterial host cell of embodiment 1 in a liquid medium containing glycerol, wherein the method results in the conversion of glycerol to PHBV by the bacterial host cell.

Embodiment 16. A method of producing poly(3-hydroxybutyrate-co-3-hydroxyvalerate) (PHBV), the method comprising:

(a) growing the bacterial host cell of embodiment 1 in a liquid medium containing glycerol at a first temperature in a range of about 30° C. to about 37° C. for a first period to form a bacterial culture, and (b) incubating the bacterial culture at a second temperature in a range of about 37° C. to about 50° C. for a second period, wherein the method results in the conversion of glycerol to PHBV by the bacterial host cell.

Embodiment 17. The method of embodiment 16, wherein the first temperature is about 37° C.

Embodiment 18. The method of embodiment 16, wherein the second temperature is in a range of about 37° C. to about 45° C.

Embodiment 19. The method of embodiment 16, wherein the method comprises producing PHBV with a molecular weight of about 1 mDa to about 1.5 mDa.

Embodiment 20. The method of embodiment 16, wherein the first period is in the range of about 1 hour to about 24 hours.

Embodiment 21. The method of embodiment 16, wherein the second period is in the range of about 24 hours to about 44 hours.

Embodiment 22. A method of metabolizing glycerol using a bacterial host cell, the method comprising:

growing the bacterial host cell of embodiment 1 in a liquid medium containing glycerol, wherein the method results in the conversion of glycerol to one or more metabolic products by the bacterial host cell.

Embodiment 23. A bacterial host cell, comprising:

a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, (c) a nucleic acid molecule encoding a PhaB protein, wherein the nucleic acid molecule comprises a sequence having at least 90% identity to SEQ ID NO: 249;

a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249; and a sleeping beauty mutase (Sbm) operon comprises a Ptrc promoter, wherein each of the first and the second operons comprises a promoter comprising the nucleic acid sequence of SEQ ID NO: 233 ($P_{gracmax2}$).

Embodiment 24. A method of producing poly(3-hydroxybutyrate-co-3-hydroxyvalerate) (PHBV), the method comprising:

growing the bacterial host cell of embodiment 23 in a liquid medium containing glycerol, wherein the method results in the conversion of glycerol to PHBV by the bacterial host cell.

Embodiment 25. The method of embodiment 24, wherein the method comprises producing PHBV with a molecular weight of about 1 mDa to about 1.5 mDa.

Embodiment 26. A method of producing poly(3-hydroxybutyrate-co-3-hydroxyvalerate) (PHBV), the method comprising:

(a) growing the bacterial host cell of embodiment 23 in a liquid medium containing glycerol at a first temperature in a range of about 30° C. to about 37° C. for a first period to form a bacterial culture, and (b) incubating the bacterial culture at a second temperature in a range of about 37° C. to about 50° C. for a second period, wherein the method results in the conversion of glycerol to PHBV by the bacterial host cell.

Embodiment 27. The method of embodiment 26, wherein the method comprises producing PHBV with a molecular weight of about 1 mDa to about 1.5 mDa.

Embodiment 28. The bacterial host cell of embodiment 1, wherein the first operon comprises the following nucleic acid molecules in the order (i) through (iii): (i) the nucleic acid molecule encoding a PhaC protein, (ii) the nucleic acid molecule encoding a PhaA protein, and (iii) a nucleic acid molecule encoding a PhaB protein.

NUMBERED EMBODIMENTS—II

The following list of embodiments is included herein for illustration purposes only and is not intended to be comprehensive or limiting. The subject matter to be claimed is expressly not limited to the following embodiments.

Embodiment 1. A bacterial host cell, comprising one or more of the following nucleic acid molecules integrated into the bacterial host cell genome:

a first operon comprising (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, and (c) a nucleic acid molecule encoding a PhaB protein, wherein the PhaB protein is a *Cupriavidus* sp. S-6 PhaB protein, wherein the first operon comprises a first promoter;

a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein, wherein the second operon comprises a second promoter;

a third operon, comprising: (a) a nucleic acid molecule encoding a FadE protein, and (b) a nucleic acid molecule encoding a FadB protein, wherein the third operon comprises a third promoter;

a fourth operon, comprising: (a) a nucleic acid molecule encoding a LvaE protein, wherein the LvaE protein is a *Pseudomonas putida* LvaE protein, and (b) a nucleic acid molecule encoding a propionate-CoA transferase, wherein the propionate-CoA transferase is a *Clostridium propionicum* propionate-CoA transferase (Pct(Cp)), wherein the fourth operon comprises a fourth promoter, and wherein the bacterial host cell comprises an activated sleeping beauty mutase (Sbm) pathway.

Embodiment 2. The bacterial host cell of embodiment 1, wherein each of the first, second and fourth operons comprises a promoter comprising the nucleic acid sequence of SEQ ID NO: 233 ($P_{gracmax2}$), and the third operon comprises a promoter comprising the nucleic acid sequence of SEQ ID NO: 254 ($P_{trc}$).

Embodiment 3. The bacterial host cell of embodiment 1, wherein the PhaA protein comprises an amino acid sequence having at least 90% identity to SEQ ID NO: 241.

Embodiment 4. The bacterial host cell of embodiment 1, wherein the nucleic acid molecule encoding a PhaA protein comprises a nucleic acid sequence having at least 80% identity to SEQ ID NO: 248.

Embodiment 5. The bacterial host cell of embodiment 1, wherein the PhaB protein comprises an amino acid sequence having at least 90% identity to SEQ ID NO: 242.

Embodiment 6. The bacterial host cell of embodiment 1, wherein the nucleic acid molecule encoding a PhaB protein comprises a nucleic acid sequence having at least 80% identity to SEQ ID NO: 249.

Embodiment 7. The bacterial host cell of embodiment 1, wherein the PhaC protein comprises an amino acid sequence having at least 90% identity to SEQ ID NO: 243.

Embodiment 8. The bacterial host cell of embodiment 1, wherein the nucleic acid molecule encoding a PhaC protein comprises a nucleic acid sequence having at least 80% identity to SEQ ID NO: 250.

Embodiment 9. The bacterial host cell of embodiment 1, wherein the BtkB protein comprises an amino acid sequence having at least 90% identity to SEQ ID NO: 245.

Embodiment 10. The bacterial host cell of embodiment 1, wherein the nucleic acid molecule encoding a BtkB protein comprises a nucleic acid sequence having at least 80% identity to SEQ ID NO: 251.

Embodiment 11. The bacterial host cell of embodiment 1, wherein the LvaE protein comprises an amino acid sequence having at least 90% identity to SEQ ID NO: 247.

Embodiment 12. The bacterial host cell of embodiment 1, wherein the nucleic acid molecule encoding a LvaE protein comprises a nucleic acid sequence having at least 80% identity to SEQ ID NO: 253.

Embodiment 13. The bacterial host cell of embodiment 1, wherein the FadE protein comprises an amino acid sequence having at least 90% identity to SEQ ID NO: 13.

Embodiment 14. The bacterial host cell of embodiment 1, wherein the nucleic acid molecule encoding a FadE protein comprises a nucleic acid sequence having at least 80% identity to SEQ ID NO: 72.

Embodiment 15. The bacterial host cell of embodiment 1, wherein the FadB protein comprises an amino acid sequence having at least 90% identity to SEQ ID NO: 12.

Embodiment 16. The bacterial host cell of embodiment 1, wherein the nucleic acid molecule encoding a FadB protein comprises a nucleic acid sequence having at least 80% identity to SEQ ID NO: 71.

Embodiment 17. The bacterial host cell of embodiment 1, wherein the third operon comprises a nucleic acid molecule encoding a AtoB protein, and wherein the AtoB protein comprises an amino acid sequence having at least 90% identity to SEQ ID NO: 182.

Embodiment 18. The bacterial host cell of embodiment 17, wherein the nucleic acid molecule encoding a AtoB protein comprises a nucleic acid sequence having at least 80% identity to SEQ ID NO: 191.

Embodiment 19. The bacterial host cell of embodiment 1, wherein the bacterial host cell comprises a deletion of the nucleic acid sequence encoding a endogenous lacI repressor.

Embodiment 20. The bacterial host cell of embodiment 1, wherein the bacterial host cell converts one or more volatile fatty acids (VFAs) to poly(3-hydroxybutyrate-co-3-hydroxyvalerate) or PHBV.

Embodiment 21. The bacterial host cell of embodiment 1, wherein the bacterial host cell is capable of growing in a medium containing more than 100 mM VFAs.

Embodiment 22. The bacterial host cell embodiment 1, wherein the bacterial host cell comprises a sleeping beauty mutase (Sbm) operon comprising a $P_{trc}$ promoter.

Embodiment 23. The bacterial host cell of embodiment 1, wherein the bacterial host cell is *Escherichia coli.*

Embodiment 24. A method of producing poly(3-hydroxybutyrate-co-3-hydroxyvalerate) (PHBV), the method comprising:

growing the bacterial host cell of embodiment 1 in a medium containing one or more volatile fatty acids (VFAs), wherein the method results in the conversion of VFAs to PHBV by the bacterial host cell.

Embodiment 25. A method of metabolizing volatile fatty acids (VFAs) in a bacterial medium, the method comprising:

growing the bacterial host cell of embodiment 1 in a medium containing one or more volatile fatty acids (VFAs), wherein the method results in the conversion of VFAs to one or more metabolic products by the bacterial host cell.

Embodiment 26. The method of embodiment 24, wherein the one or more volatile fatty acids comprises a mixture of acetate, propionate, and butyrate.

Embodiment 27. The method of embodiment 26, wherein the mixture of acetate, propionate, and butyrate comprises about 50 mol % acetate, about 20 mol % propionate, and about 30 mol % butyrate.

Embodiment 28. A bacterial host cell, comprising:

a first operon comprising (a) a nucleic acid molecule encoding a PhaC protein, wherein the nucleic acid molecule comprises a sequence having at least 80% identity to SEQ ID NO: 250, (b) a nucleic acid molecule encoding a PhaA protein, wherein the nucleic acid molecule comprises a sequence having at least 80% identity to SEQ ID NO: 248, (c) a nucleic acid molecule encoding a PhaB protein, wherein the nucleic acid molecule comprises a sequence having at least 80% identity to SEQ ID NO: 249;

a second operon comprising: (i) a nucleic acid molecule encoding a BktB protein, wherein the nucleic acid molecule comprises a sequence having at least 80% identity to SEQ ID NO: 251, and (ii) a nucleic acid molecule encoding a PhaB protein, wherein the nucleic acid molecule comprises a sequence having at least 80% identity to SEQ ID NO: 249;

a third operon, comprising: (a) a nucleic acid molecule encoding a FadE protein, wherein the nucleic acid molecule comprises a sequence having at least 80% identity to SEQ ID NO: 72, and (b) a nucleic acid molecule encoding a FadB protein, wherein the nucleic acid molecule comprises a sequence having at least 80% identity to SEQ ID NO: 71;

a fourth operon, comprising: (a) a nucleic acid molecule encoding a LvaE protein, wherein the nucleic acid molecule comprises a sequence having at least 80% identity to SEQ ID NO: 253 and (b) a nucleic acid molecule encoding a propionate CoA-transferase, wherein the nucleic acid molecule comprises a sequence having at least 80% identity to SEQ ID NO: 89, and a sleeping beauty mutase (Sbm) operon comprises a $P_{trc}$ promoter, wherein each of the first, second and fourth operons comprises a promoter comprising the nucleic acid sequence of SEQ ID NO: 233 ($P_{gracmax2}$), and the third operon comprises a promoter comprising the nucleic acid sequence of SEQ ID NO: 254 ($P_{trc}$).

Embodiment 29. A method of producing poly(3-hydroxybutyrate-co-3-hydroxyvalerate) (PHBV), the method comprising:

growing the bacterial host cell of embodiment 28 in a medium containing one or more volatile fatty acids (VFAs), wherein the method results in the conversion of VFAs to PHBV by the bacterial host cell.

Embodiment 30. A method of metabolizing volatile fatty acids (VFAs) in a bacterial medium, the method comprising:

growing the bacterial host cell of embodiment 28 in a medium containing one or more volatile fatty acids (VFAs), wherein the method results in the conversion of VFAs to one or more metabolic products by the bacterial host cell.

NUMBERED EMBODIMENTS—III

Embodiment 1. A bacterial host cell, comprising one or more of the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway.

Embodiment 2. The bacterial host cell of embodiment 1, comprising the following nucleic acid molecules: (a) a nucleic acid molecule encoding a PhaC protein, (b) a nucleic acid molecule encoding a PhaA protein, (c) a nucleic acid molecule encoding a PhaB protein, and (d) a nucleic acid molecule encoding a BktB protein, wherein the bacterial host cell comprises an activated sleeping beauty mutase (Sbm) pathway.

Embodiment 3. The bacterial host cell of embodiment 1 or 2, wherein the PhaA protein is a *Cupriavidus* sp. S-6 PhaA protein, a *Cupriavidus gilardii* QJ1 PhaA protein, or a *Cupriavidus necator* PhaA protein.

Embodiment 4. The bacterial host cell of any one of embodiments 1-3, wherein the PhaA protein comprises an amino acid sequence having at least 90% identity to SEQ ID NO: 241.

Embodiment 5. The bacterial host cell of any one of embodiments 1-4, wherein the nucleic acid molecule encoding a PhaA protein comprises a nucleic acid sequence having at least 80% identity to SEQ ID NO: 248.

Embodiment 6. The bacterial host cell of any one of embodiments 1-5, wherein the PhaB protein is a *Cupriavidus* sp. S-6 PhaB protein, a *Cupriavidus gilardii* QJ1 PhaB protein, or a *Cupriavidus necator* PhaB protein.

Embodiment 7. The bacterial host cell of any one of embodiments 1-6, wherein the PhaB protein comprises an amino acid sequence having at least 90% identity to SEQ ID NO: 242.

Embodiment 8. The bacterial host cell of any one of embodiments 1-7, wherein the nucleic acid molecule encoding a PhaB protein comprises a nucleic acid sequence having at least 80% identity to SEQ ID NO: 249.

Embodiment 9. The bacterial host cell of any one of embodiments 1-8, wherein the PhaC protein is a *Cupriavidus* sp. S-6 PhaC protein, a *Cupriavidus gilardii* QJ1 PhaC protein, or a *Cupriavidus necator* PhaC protein.

Embodiment 10. The bacterial host cell of any one of embodiments 1-9, wherein the PhaC protein comprises an amino acid sequence having at least 90% identity to SEQ ID NO: 243.

Embodiment 11. The bacterial host cell of any one of embodiments 1-10, wherein the nucleic acid molecule encoding a PhaC protein comprises a nucleic acid sequence having at least 80% identity to SEQ ID NO: 250.

Embodiment 12. The bacterial host cell of any one of embodiments 1-11, wherein the BtkB protein is a *Cupriavidus* sp. S-6 BtkB protein, a *Cupriavidus gilardii* QJ1 BtkB protein, or a *Cupriavidus necator* BtkB protein.

Embodiment 13. The bacterial host cell of any one of embodiments 1-12, wherein the BtkB protein comprises an amino acid sequence having at least 90% identity to SEQ ID NO: 245.

Embodiment 14. The bacterial host cell of any one of embodiments 1-13, wherein the nucleic acid molecule encoding a BtkB protein comprises a nucleic acid sequence having at least 80% identity to SEQ ID NO: 251.

Embodiment 15. The bacterial host cell of any one of embodiments 1-14, wherein the bacterial host cell comprises a sleeping beauty mutase (Sbm) operon comprising a Ptrc promoter.

Embodiment 16. The bacterial host cell of any one of embodiments 1-15, wherein the bacterial host cell comprises: a first operon, comprising: (a) a nucleic acid molecule encoding a PhaC protein, (b) a nucleic acid molecule encoding a PhaA protein, and (c) a nucleic acid molecule encoding a PhaB protein.

Embodiment 17. The bacterial host cell of any one of embodiments 1-16, wherein the bacterial host cell comprises: a second operon comprising: (i) a nucleic acid molecule encoding a BktB protein and (ii) a nucleic acid molecule encoding a PhaB protein.

Embodiment 18. The bacterial host cell of any one of embodiments 1-17, wherein the bacterial host cell comprises: a first operon, comprising: (a) a nucleic acid molecule encoding a PhaC protein, (b) a nucleic acid molecule encoding a PhaA protein, (c) a nucleic acid molecule encoding a PhaB protein; and a second operon comprising: (i) a nucleic acid molecule encoding a BktB protein and (ii) a nucleic acid molecule encoding a PhaB protein.

Embodiment 19. The bacterial host cell of embodiment 18, wherein the first and/or second operons comprise a promoter.

Embodiment 20. The bacterial host cell of embodiment 19, wherein the promoter comprises the nucleic acid sequence of SEQ ID NO: 233 ($P_{gracmax2}$) or the nucleic acid sequence of SEQ ID NO: 254 ($P_{trc}$).

Embodiment 21. A bacterial host cell, comprising:

a first operon comprising: (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, and (c) a nucleic acid molecule encoding a PhaB protein, wherein the PhaB protein is a *Cupriavidus* sp. S-6 PhaB protein;

a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein; and a sleeping beauty mutase (Sbm) operon comprising a promoter, wherein each of the first and the second operons comprises a promoter comprising the nucleic acid sequence of SEQ ID NO: 233 ($P_{gracmax2}$).

Embodiment 22. A bacterial host cell, comprising:

a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, (c) a nucleic acid molecule encoding a PhaB protein, wherein the nucleic acid molecule comprises a sequence having at least 90% identity to SEQ ID NO: 249;

a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249; and a sleeping beauty mutase (Sbm) operon comprises a promoter, wherein each of the first and the second operons comprises a promoter comprising the nucleic acid sequence of SEQ ID NO: 233 ($P_{gracmax2}$).

Embodiment 23. The bacterial host cell of any one of embodiments 1-22, wherein the bacterial host cell converts glycerol to poly(3-hydroxybutyrate-co-3-hydroxyvalerate) or PHBV.

Embodiment 24. The bacterial host cell of any one of embodiments 1-23, wherein the bacterial host cell converts glycerol into poly(3-hydroxybutyrate-co-3-hydroxyvalerate) or PHBV at a temperature in the range of about 37° C. to about 50° C.

Embodiment 25. The bacterial host cell of any one of embodiments 1-24, wherein the bacterial host cell exhibits reduced or eliminated succinate dehydrogenase (sdhA) function.

Embodiment 26. The bacterial host cell of embodiment 25, wherein the bacterial host cell comprises a nucleic acid molecule encoding a fusion protein, comprising sdhA and a protease degradation tag, wherein the expression of the fusion protein is regulated by a EsaR quorum sensing system.

Embodiment 27. The bacterial host cell of any one of embodiments 1-26, wherein the bacterial host cell comprises a nucleic acid molecule encoding sulA, wherein the nucleic acid molecule is operably linked to an inducible promoter.

Embodiment 28. The bacterial host cell of embodiment 27, wherein the inducible promoter is a temperature-inducible promoter.

Embodiment 29. A method of producing poly(3-hydroxybutyrate-co-3-hydroxyvalerate) (PHBV), the method comprising:

growing the bacterial host cell of any one of embodiments 1-28 in a medium containing glycerol, wherein the method results in the conversion of glycerol to PHBV by the bacterial host cell.

Embodiment 30. A method of metabolizing glycerol using a bacterial host cell, the method comprising:

growing the bacterial host cell of any one of embodiments 1-28 in a medium containing glycerol, wherein the method results in the conversion of glycerol to one or more metabolic products by the bacterial host cell.

Embodiment 31. A method of producing poly(3-hydroxybutyrate-co-3-hydroxyvalerate) (PHBV), the method comprising:

(a) growing the bacterial host cell of any one of embodiments 1-28 in a medium containing glycerol at a first temperature in a range of about 30° C. to about 37° C. for a first period to form a bacterial culture, and (b) incubating the bacterial culture at a second temperature in a range of about 37° C. to about 50° C. for a second period, wherein the method results in the conversion of glycerol to PHBV by the bacterial host cell.

Embodiment 32. The method of embodiment 31, wherein the first temperature is about 37° C.

Embodiment 33. The method of embodiment 31 or embodiment 32, wherein the second temperature is in a range of about 37° C. to about 45° C.

Embodiment 34. The method of any one of embodiments 29-33, wherein the method comprises producing PHBV with a weight average molecular weight (Mw) of about 1 MDa to about 1.5 MDa.

Embodiment 35. The method of any one of embodiments 29-34, wherein the medium contains more than about 0.7 g/g glycerol.

Embodiment 36. The method of any one of embodiments 29-35, wherein the first period is in the range of about 1 hour to about 24 hours.

Embodiment 37. The method of any one of embodiments 29-36, wherein the second period is in the range of about 24 hours to about 44 hours.

Embodiment 38. The bacterial host cell of any one of embodiments 1-28, wherein the bacterial host cell comprises one or more of the following: (a) a nucleic acid molecule encoding a LvaE protein, (b) a nucleic acid molecule encoding a propionate-CoA transferase, (c) a nucleic acid molecule encoding a FadE protein, (d) a nucleic acid molecule encoding a FadB protein, and (e) a nucleic acid molecule encoding a AtoB protein.

Embodiment 39. The bacterial host cell of embodiment 38, wherein the bacterial host cell comprises: a third operon, comprising: (a) a nucleic acid molecule encoding a FadE protein, and (b) a nucleic acid molecule encoding a FadB protein.

Embodiment 40. The bacterial host cell of embodiment 38 or embodiment 39, wherein the bacterial host cell comprises: a third operon, comprising: (a) a nucleic acid molecule encoding a FadE protein, (b) a nucleic acid molecule encoding a FadB protein, and (c) a nucleic acid molecule encoding a AtoB protein.

Embodiment 41. The bacterial host cell of any one of embodiments 38-40, wherein the bacterial host cell comprises: a fourth operon, comprising: (a) a nucleic acid molecule encoding a LvaE protein, and (b) a nucleic acid molecule encoding a propionate-CoA transferase.

Embodiment 42. The bacterial host cell of any one of embodiments 38-41, wherein the bacterial host cell comprises: a third operon, comprising: (a) a nucleic acid molecule encoding a FadE protein, and (b) a nucleic acid molecule encoding a FadB protein; and a fourth operon, comprising: (a) a nucleic acid molecule encoding a LvaE protein, and (b) a nucleic acid molecule encoding a propionate-CoA transferase.

Embodiment 43. The bacterial host cell of any one of embodiments 38-42, wherein the bacterial host cell comprises: a third operon, comprising: (a) a nucleic acid molecule encoding a FadE protein, (b) a nucleic acid molecule encoding a FadB protein, and (c) a nucleic acid molecule encoding a AtoB protein; and a fourth operon, comprising: (a) a nucleic acid molecule encoding a LvaE protein, and (b) a nucleic acid molecule encoding a propionate-CoA transferase.

Embodiment 44. The bacterial host cell of any one of embodiments 38-43, wherein the propionate CoA-transferase is a *Clostridium propionicum* propionate CoA-transferase (Pct(Cp)) or a *Megasphaera elsdenii* propionate CoA-transferase (Pct(Me)).

Embodiment 45. The bacterial host cell of embodiment 44, wherein the propionate CoA-transferase is a *Clostridium propionicum* (Pct(Cp)).

Embodiment 46. The bacterial host cell of embodiment 45, wherein the Pct(Cp) protein comprises an amino acid sequence having at least 90% identity to SEQ ID NO: 30.

Embodiment 47. The bacterial host cell of embodiment 45 or 46, wherein the nucleic acid molecule encoding a Pct(Cp) protein comprises a nucleic acid sequence having at least 80% identity to SEQ ID NO: 89.

Embodiment 48. The bacterial host cell of any one of embodiments 38-47, wherein LvaE protein is a *Pseudomonas putida* LvaE protein.

Embodiment 49. The bacterial host cell of embodiment 48, wherein the LvaE protein comprises an amino acid sequence having at least 90% identity to SEQ ID NO: 247.

Embodiment 50. The bacterial host cell of embodiment 48 or embodiment 49, wherein the nucleic acid molecule encoding a LvaE protein comprises a nucleic acid sequence having at least 80% identity to SEQ ID NO: 253.

Embodiment 51. The bacterial host cell of any one of embodiments 38-50, wherein the FadE protein comprises an amino acid sequence having at least 90% identity to SEQ ID NO: 13.

Embodiment 52. The bacterial host cell of embodiment 51, wherein the nucleic acid molecule encoding a FadE protein comprises a nucleic acid sequence having at least 80% identity to SEQ ID NO: 72.

Embodiment 53. The bacterial host cell of any one of embodiments 38-52, wherein the FadB protein comprises an amino acid sequence having at least 90% identity to SEQ ID NO: 12.

Embodiment 54. The bacterial host cell of embodiment 53, wherein the nucleic acid molecule encoding a FadB protein comprises a nucleic acid sequence having at least 80% identity to SEQ ID NO: 71.

Embodiment 55. The bacterial host cell of any one of embodiments 38-54, wherein the AtoB protein comprises an amino acid sequence having at least 90% identity to SEQ ID NO: 182.

Embodiment 56. The bacterial host cell of embodiment 55, wherein the nucleic acid molecule encoding a AtoB protein comprises a nucleic acid sequence having at least 80% identity to SEQ ID NO: 191.

Embodiment 57. The bacterial host cell of any one of embodiments 40-56, wherein each of the first, second, third and fourth operons comprises a promoter.

Embodiment 58. The bacterial host cell of embodiment 57, wherein the promoter comprises the nucleic acid sequence of SEQ ID NO: 233 ($P_{gracmax2}$) or the nucleic acid sequence of SEQ ID NO: 254 ($P_{trc}$).

Embodiment 59. The bacterial host cell of any one of embodiments 40-58, wherein each of the first, second, third and fourth operons comprises an inducible promoter or a constitutive promoter.

Embodiment 60. A bacterial host cell, comprising:

a first operon comprising (a) a nucleic acid molecule encoding a PhaC protein, wherein the PhaC protein is a *Cupriavidus* sp. S-6 PhaC protein, (b) a nucleic acid molecule encoding a PhaA protein, wherein the PhaA protein is a *Cupriavidus* sp. S-6 PhaA protein, (c) a nucleic acid molecule encoding a PhaB protein, wherein the PhaB protein is a *Cupriavidus* sp. S-6 PhaB protein;

a second operon comprising: (i) a nucleic acid molecule encoding a BktB protein, wherein the BktB protein is a *Cupriavidus gilardii* QJ1 BktB protein, and (ii) a nucleic acid molecule encoding a PhaB protein, wherein the PhaB protein is a *Cupriavidus* sp. S-6 PhaB protein;

a third operon, comprising: (a) a nucleic acid molecule encoding a FadE protein, (b) a nucleic acid molecule encoding a FadB protein, and (c) a nucleic acid molecule encoding a AtoB protein;

a fourth operon, comprising: (a) a nucleic acid molecule encoding a LvaE protein, wherein the LvaE protein is a *Pseudomonas putida* LvaE protein, and (b) a nucleic acid molecule encoding a propionate-CoA transferase, wherein the propionate CoA-transferase is a *Clostridium propionicum* propionate CoA-transferase (Pct(Cp)), and a sleeping beauty mutase (Sbm) operon comprises a ($P_{trc}$) promoter, wherein each of the first, second and fourth operons comprises a promoter comprising the nucleic acid sequence of SEQ ID NO: 233 ($P_{gracmax2}$), and the third operon comprises a promoter comprising the nucleic acid sequence of SEQ ID NO: 254 ($P_{trc}$).

Embodiment 61. A bacterial host cell, comprising:

a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, (c) a nucleic acid molecule encoding a PhaB protein, wherein the nucleic acid molecule comprises a sequence having at least 90% identity to SEQ ID NO: 249;

a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249;

a third operon, comprising: (a) a nucleic acid molecule encoding a FadE protein, wherein the nucleic acid molecule comprises a sequence having at least 80% identity to SEQ ID NO: 72, (b) a nucleic acid molecule encoding a FadB protein, wherein the nucleic acid molecule comprises a sequence having at least 80% identity to SEQ ID NO: 71, and (c) a nucleic acid molecule encoding a AtoB protein, and wherein the nucleic acid molecule comprises a sequence having at least 80% identity to SEQ ID NO: 191;

a fourth operon, comprising: (a) a nucleic acid molecule encoding a LvaE protein, wherein the nucleic acid molecule comprises a sequence having at least 80% identity to SEQ ID NO: 253 and (b) a nucleic acid molecule encoding a propionate CoA-transferase, wherein the nucleic acid molecule comprises a sequence having at least 80% identity to SEQ ID NO: 89, and a sleeping beauty mutase (Sbm) operon comprising a promoter, wherein each of the first, second and fourth operons comprise a promoter comprising the nucleic acid sequence of SEQ ID NO: 233 ($P_{gracmax2}$), and the third operon comprises a promoter comprising the nucleic acid sequence of SEQ ID NO: 254 ($P_{trc}$).

Embodiment 62. The bacterial host cell of any one of embodiments 38-61, wherein the bacterial host cell exhibits reduced or eliminated function of an endogenous lacI repressor.

Embodiment 63. The bacterial host cell of embodiment 62, wherein the bacterial host cell comprises a deletion of the nucleic acid sequence encoding an endogenous lacI repressor.

Embodiment 64. The bacterial host cell of any one of embodiments 38-63, wherein the bacterial host cell comprises a nucleic acid molecule encoding an enoyl-CoA hydratase/isomerase PhaJ.

Embodiment 65. The bacterial host cell of embodiment 64, wherein the enoyl-CoA hydratase/isomerase PhaJ is a *Aeromonas caviae* PhaJ, or a homolog thereof.

Embodiment 66. The bacterial host cell of any one of embodiments 38-65, wherein the bacterial host cell comprises one or more of the following nucleic acid molecules: (a) a nucleic acid molecule encoding an CoA-acylating aldehyde dehydrogenase (Ald); (b) a nucleic acid molecule encoding an glutamate decarboxylase GadB; and (c) β-alanine transaminase KES23458.

Embodiment 67. The bacterial host cell of embodiment 66, wherein the CoA-acylating aldehyde dehydrogenase (Ald) is a *Clostridium beijerinckii* Ald, or a homolog thereof.

Embodiment 68. The bacterial host cell of embodiment 66 or embodiment 67, wherein the glutamate decarboxylase GadB is a *E. coli* GadB or a *Lactobacillus senmaizukei* GadB.

Embodiment 69. The bacterial host cell of any one of embodiments 66-68, wherein the (3-alanine transaminase KES23458 is a *Pseudomonas* sp. strain AAC β-alanine transaminase KES23458.

Embodiment 70. The bacterial host cell of any one of embodiments 38-69, wherein the bacterial host cell converts one or more volatile fatty acids (VFAs) to poly(3-hydroxybutyrate-co-3-hydroxyvalerate) or PHBV.

Embodiment 71. The bacterial host cell of any one of embodiments 38-70, wherein the bacterial host cell is capable of growing in a medium containing more than 100 mM VFAs.

Embodiment 72. The bacterial host cell of embodiment 38-71, wherein the bacterial host cell is capable of growing in a medium containing more than 225 mM VFAs.

Embodiment 73. A method of producing poly(3-hydroxybutyrate-co-3-hydroxyvalerate) (PHBV), the method comprising:

growing the bacterial host cell of any one of embodiments 38-72 in a medium containing one or more volatile fatty acids (VFAs), wherein the method results in the conversion of VFAs to PHBV by the bacterial host cell.

Embodiment 74. A method of metabolizing volatile fatty acids (VFAs) in a bacterial medium, the method comprising:

growing the bacterial host cell of any one of embodiments 38-72 in a medium containing one or more volatile fatty acids (VFAs), wherein the method results in the conversion of VFAs to one or more metabolic products by the bacterial host cell.

Embodiment 75. The bacterial host cell of any one of embodiments 70-72, or the method of embodiment 73 or 74, wherein the one or more volatile fatty acids comprises a mixture of acetate, propionate, and butyrate.

Embodiment 76. The bacterial host cell of embodiment 75, wherein the mixture of acetate, propionate, and butyrate comprises about 50 mol % acetate, about 20 mol % propionate, and about 30 mol % butyrate.

Embodiment 77. The bacterial host cell of any one of embodiments 1-28, 38-72, and 75-76, or the method of any one of embodiments 29-37, 73 and 74, wherein the bacterial host cell is *Escherichia coli.*

Embodiment 78. The bacterial host cell of any one of embodiments 1-28, 38-72, and 75-77, or the method of any one of embodiments 29-37, 73 and 74, wherein at least one of the one or more nucleic acid molecules is integrated into the bacterial host cell genome.

Embodiment 79. The bacterial host cell of any one of embodiments 1-28, 38-72, and 75-77, or the method of any one of embodiments 29-37, 73 and 74, wherein all of the one or more nucleic acid molecules are integrated into the bacterial host cell genome.

Embodiment 80. The bacterial host cell of any one of embodiments 1-28, 38-72, and 75-77, or the method of any one of embodiments 29-37, 73 and 74, wherein the bacterial host cell comprises at least one plasmid, wherein the at least one plasmid comprises at least one of the one or more nucleic acid molecules.

Embodiment 81. The method of any one of embodiments 29-37, 73 and 74, wherein the medium is a liquid medium.

What is claimed is:

1. A bacterial host cell, comprising the following nucleic acid molecules integrated into the bacterial host cell genome:

(a) a first operon, comprising:

(i) a nucleic acid molecule encoding a PhaC protein, wherein the PhaC protein is a *Cupriavidus* sp. S-6 PhaC protein, (ii) a nucleic acid molecule encoding a PhaA protein, wherein the PhaA protein is a *Cupriavidus* sp. S-6 PhaA protein, (iii) a nucleic acid molecule encoding a PhaB protein, wherein the PhaB protein is a *Cupriavidus* sp. S-6 PhaB protein, wherein the first operon comprises a first promoter; and (b) a second operon, comprising:

(iv) a nucleic acid molecule encoding a BktB protein, wherein the BktB protein is a *Cupriavidus* sp. QJ1 BktB protein and (v) a nucleic acid molecule encoding a PhaB protein, wherein the PhaB protein is a *Cupriavidus* sp. S-6 PhaB protein wherein the second operon comprises a second promoter, wherein the bacterial host cell comprises an activated sleeping beauty mutase (Sbm) pathway; and wherein the first promoter and the second promoter are the same, and wherein each of the first promoter and the second promoter comprises the nucleic acid sequence of SEQ ID NO: 233.

2. The bacterial host cell of claim 1, wherein the PhaA protein comprises an amino acid sequence having at least 90% identity to SEQ ID NO: 241.

3. The bacterial host cell of claim 1, wherein the nucleic acid molecule encoding the PhaA protein comprises a nucleic acid sequence having at least 80% identity to SEQ ID NO: 248.

4. The bacterial host cell of claim 1, wherein one of the PhaB proteins comprises an amino acid sequence having at least 90% identity to SEQ ID NO: 242.

5. The bacterial host cell of claim 1, wherein one of the nucleic acid molecules encoding the PhaB protein comprises a nucleic acid sequence having at least 80% identity to SEQ ID NO: 249.

6. The bacterial host cell of claim 1, wherein the PhaC protein comprises an amino acid sequence having at least 90% identity to SEQ ID NO: 243.

7. The bacterial host cell of claim 1, wherein the nucleic acid molecule encoding the PhaC protein comprises a nucleic acid sequence having at least 80% identity to SEQ ID NO: 250.

8. The bacterial host cell of claim 1, wherein the BtkB protein comprises an amino acid sequence having at least 90% identity to SEQ ID NO: 245.

9. The bacterial host cell of claim 1, wherein the nucleic acid molecule encoding the BtkB protein comprises a nucleic acid sequence having at least 80% identity to SEQ ID NO: 251.

10. The bacterial host cell of claim 1, wherein the bacterial host cell converts glycerol to poly(3-hydroxybutyrate-co-3-hydroxyvalerate).

11. The bacterial host cell of claim 1, wherein the bacterial host cell converts glycerol into poly(3-hydroxybutyrate-co-3-hydroxyvalerate) at a temperature in the range of about 37° C. to about 50° C.

12. The bacterial host cell claim 1, wherein the bacterial host cell comprises a sleeping beauty mutase (Sbm) operon comprising a Ptrc promoter.

13. The bacterial host cell of claim 1, wherein the bacterial host cell is *Escherichia coli.*

14. The bacterial host cell of claim 1, wherein the first operon comprises the following nucleic acid molecules in the order (i) through (iii): (i) the nucleic acid molecule encoding the PhaC protein, (ii) the nucleic acid molecule encoding the PhaA protein, and (iii) the nucleic acid molecule encoding the PhaB protein.

15. The bacterial host cell of claim 1, wherein both of the PhaB proteins comprise an amino acid sequence having at least 90% identity to SEQ ID NO: 242.

16. The bacterial host cell of claim 1, wherein both of the nucleic acid molecules encoding the PhaB protein comprise a nucleic acid sequence having at least 80% identity to SEQ ID NO: 249.

17. A method of producing poly(3-hydroxybutyrate-co-3-hydroxyvalerate) (PHBV), the method comprising:

growing the bacterial host cell of claim 1 in a liquid medium containing glycerol, wherein the method results in the conversion of glycerol to PHBV by the bacterial host cell.

18. A method of producing poly(3-hydroxybutyrate-co-3-hydroxyvalerate) (PHBV), the method comprising:

(a) growing the bacterial host cell of claim 1 in a liquid medium containing glycerol at a first temperature in a range of about 30° ° C. to about 37°C for a first period to form a bacterial culture, and (b) incubating the bacterial culture at a second temperature in a range of about 37° C. to about 50°C for a second period, wherein the method results in the conversion of glycerol to PHBV by the bacterial host cell.

19. The method of claim 18, wherein the first temperature is about 37° C.

20. The method of claim 18, wherein the second temperature is in a range of about 37° ° C. to about 45°C.

21. The method of claim 18, wherein the method comprises producing PHBV with a molecular weight of about 1 MDa to about 1.5 MDa.

22. The method of claim 18, wherein the first period is in the range of about 1 hour to about 24 hours.

23. The method of claim 18, wherein the second period is in the range of about 24 hours to about 44 hours.

24. A method of metabolizing glycerol using a bacterial host cell, the method comprising:

growing the bacterial host cell of claim 1 in a liquid medium containing glycerol, wherein the method results in the conversion of glycerol to one or more metabolic products by the bacterial host cell.

25. A bacterial host cell, comprising:

a first operon comprising (a) a nucleic acid molecule encoding a PhaC protein, wherein the nucleic acid molecule comprises a sequence having at least 90% identity to SEQ ID NO: 250, (b) a nucleic acid molecule encoding a PhaA protein, wherein the nucleic acid molecule comprises a sequence having at least 90% identity to SEQ ID NO: 248, (c) a nucleic acid molecule encoding a PhaB protein, wherein the nucleic acid molecule comprises a sequence having at least 90% identity to SEQ ID NO: 249;

a second operon comprising: (i) a nucleic acid molecule encoding a BktB protein, wherein the nucleic acid molecule comprises a sequence having at least 90% identity to SEQ ID NO: 251, and (ii) a nucleic acid molecule encoding a PhaB protein, wherein the nucleic acid molecule comprises a sequence having at least 90% identity to SEQ ID NO: 249; and a sleeping beauty mutase (Sbm) operon comprises a Ptrc promoter, wherein each of the first and the second operons comprises a promoter comprising the nucleic acid sequence of SEQ ID NO: 233.

26. A method of producing poly(3-hydroxybutyrate-co-3-hydroxyvalerate) (PHBV), the method comprising:

growing the bacterial host cell of claim 25 in a liquid medium containing glycerol, wherein the method results in the conversion of glycerol to PHBV by the bacterial host cell.

27. The method of claim 26, wherein the method comprises producing PHBV with a molecular weight of about 1 MDa to about 1.5 MDa.

28. A method of producing poly(3-hydroxybutyrate-co-3-hydroxyvalerate) (PHBV), the method comprising:

(a) growing the bacterial host cell of claim 25 in a liquid medium containing glycerol at a first temperature in a range of about 30° ° C. to about 37°C for a first period to form a bacterial culture, and (b) incubating the bacterial culture at a second temperature in a range of about 37° C. to about 50° C. for a second period, wherein the method results in the conversion of glycerol to PHBV by the bacterial host cell.

29. The method of claim 28, wherein the method comprises producing PHBV with a molecular weight of about 1 MDa to about 1.5 MDa.

* * * * *

SEQUENCE LISTING

```
Sequence total quantity: 258
SEQ ID NO: 1          moltype = AA  length = 400
FEATURE               Location/Qualifiers
source                1..400
                      mol_type = protein
                      organism = Escherichia coli
```

-continued

```
SEQUENCE: 1
MSSKLVLVLN CGSSSLKFAI IDAVNGEEYL SGLAECFHLP EARIKWKMDG NKQEAALGAG  60
AAHSEALNFI VNTILAQKPE LSAQLTAIGH RIVHGGEKYT SSVVIDESVI QGIKDAASFA  120
PLHNPAHLIG IEEALKSFPQ LKDKNVAVFD TAFHQTMPEE SYLYALPYNL YKEHGIRRYG  180
AHGTSHFYVT QEAAKMLNKP VEELNIITCH LGNGGSVSAI RNGKCVDTSM GLTPLEGLVM  240
GTRSGDIDPA IIFHLHDTLG MSVDAINKLL TKESGLLGLT EVTSDCRYVE DNYATKEDAK  300
RAMDVYCHRL AKYIGAYTAL MDGRLDAVVF TGGIGENAAM VRELSLGKLG VLGFEVDHER  360
NLAARFGKSG FINKEGTRPA VVIPTNEELV IAQDASRLTA                       400

SEQ ID NO: 2           moltype = AA  length = 652
FEATURE                Location/Qualifiers
source                 1..652
                       mol_type = protein
                       organism = Escherichia coli
SEQUENCE: 2
MSQIHKHTIP ANIADRCLIN PQQYEAMYQQ SINVPDTFWG EQGKILDWIK PYQKVKNTSF  60
APGNVSIKWY EDGTLNLAAN CLDRHLQENG DRTAIIWEGD DASQSKHISY KELHRDVCRF  120
ANTLLELGIK KGDVVAIYMP MVPEAAVAML ACARIGAVHS VIFGGFSPEA VAGRIIDSNS  180
RLVITSDEGV RAGRSIPLKK NVDDALKNPN VTSVEHVVVL KRTGGKIDWQ EGRDLWWHDL  240
VEQASDQHQA EEMNAEDPLF ILYTSGSTGK PKGVLHTTGG YLVYAALTFK YVFDYHPGDI  300
YWCTADVGWV TGHSYLLYGP LACGATTLMF EGVPNWPTPA RMAQVVDKHQ VNILYTAPTA  360
IRALMAEGDK AIEGTDRSSL RILGSVGEPI NPEAWEWYWK KIGNEKCPVV DTWWQTETGG  420
FMITPLPGAT ELKAGSATRP FFGVQPALVD NEGNPLEGAT EGSLVITDSW PGQARTLFGD  480
HERFEQTYFS TFKNMYFSGD GARRDEDGYY WITGRVDDVL NVSGHRLGTA EIESALVAHP  540
KIAEAAVVGI PHNIKGQAIY AYVTLNHGEE PSPELYAEVR NWVRKEIGPL ATPDVLHWTD  600
SLPKTRSGKI MRRILRKIAA GDTSNLGDTS TLADPGVVEK LLEEKQAIAM PS          652

SEQ ID NO: 3           moltype = AA  length = 572
FEATURE                Location/Qualifiers
source                 1..572
                       mol_type = protein
                       organism = Bacillus subtilis
SEQUENCE: 3
MNLKALPAIE GDHNLKNYEE TYRHFDWAEA EKHFSWHETG KLNAAYEAID RHAESFRKNK  60
VALYYKDAKR DEKYTFKEMK EESNRAGNVL RRYGNVEKGD RVFIFMPRSP ELYFIMLGAI  120
KIGAIAGPLF EAFMEGAVKD RLENSEAKVV VTTPELLERI PVDKLPHLQH VFVVGGEAES  180
GTNIINYDEA AKQESTRLDI EWMDKKDGFL LHYTSGSTGT PKGVLHVHEA MIQQYQTGKW  240
VLDLKEEDIY WCTADPGWVT GTVYGIFAPW LNGATNVIVG GRFSPESWYG TIEQLGVNVW  300
YSAPTAFRML MGAGDEMAAK YDLTSLRHVL SVGEPLNPEV IRWGHKVFNK RIHDTWWMTE  360
TGSQLICNYP CMDIKPGSMG KPIPGVEAAI VDNQGNELPP YRMGNLAIKK GWPSMMHTIW  420
NNPEKYESYF MPGGWYVSGD SAYMDEEGYF WFQGRVDDVI MTSGERVGPF EVESKLVEHP  480
AIAEAGVIGK PDPVRGEIIK AFIALREGFE PSDKLKEEIR LFVKQGLAAH AAPREIEFKD  540
KLPKTRSGKI MRRVLKAWEL NLPAGDLSTM ED                               572

SEQ ID NO: 4           moltype = AA  length = 216
FEATURE                Location/Qualifiers
source                 1..216
                       mol_type = protein
                       organism = Escherichia coli
SEQUENCE: 4
MDAKQRIARR VAQELRDGDI VNLGIGLPTM VANYLPEGIH ITLQSENGFL GLGPVTTAHP  60
DLVNAGGQPC GVLPGAAMFD SAMSFALIRG GHIDACVLGG LQVDEEANLA NWVVPGKMVP  120
GMGGAMDLVT GSRKVIIAME HCAKDGSAKI LRRCTMPLTA QHAVHMLVTE LAVFRFIDGK  180
MWLTEIADGC DLATVRAKTE ARFEVAADLN TQRGDL                           216

SEQ ID NO: 5           moltype = AA  length = 220
FEATURE                Location/Qualifiers
source                 1..220
                       mol_type = protein
                       organism = Escherichia coli
SEQUENCE: 5
MKTKLMTLQD ATGFFRDGMT IMVGGFMGIG TPSRLVEALL ESGVRDLTLI ANDTAFVDTG  60
IGPLIVNGRV RKVIASHIGT NPETGRRMIS GEMDVVLVPQ GTLIEQIRCG GAGLGGFLTP  120
TGVGTVVEEG KQTLTLDGKT WLLERPLRAD LALIRAHRCD TLGNLTYQLS ARNFNPLIAL  180
AADITLVEPD ELVETGELQP DHIVTPGAVI DHIIVSQESK                       220

SEQ ID NO: 6           moltype = AA  length = 440
FEATURE                Location/Qualifiers
source                 1..440
                       mol_type = protein
                       organism = Escherichia coli
SEQUENCE: 6
MIGRISRFMT RFVSRWLPDP LIFAMLLTLL TFVIALWLTP QTPISMVKMW GDGFWNLLAF  60
GMQMALIIVT GHALASSAPV KSLLRTAASA AKTPVQGVML VTFFGSVACV INWGFGLVVG  120
AMFAREVARR VPGSDYPLLI ACAYIGFLTW GGGFSGSMPL LAATPGNPVE HIAGLIPVGD  180
TLFSGFNIFI TVALIVVMPF ITRMMMPKPS DVVSIDPKLL MEEADFQKQL PKDAPPSERL  240
EESRILTLII GALGIAYLAM YFSEHGFNIT INTVNLMFMI AGLLLHKTPM AYMRAISAAA  300
RSTAGILVQF PFYAGIQLMM EHSGLGGLIT EFFINVANKD TFPVMTFFSS ALINFAVPSG  360
GGHWVIQGPF VIPAAQALGA DLGKSVMAIA YGEQWMNMAQ PFWALPALAI AGLGVRDIMG  420
```

-continued

```
YCITALLFSG VIFVIGLTLF                                         440

SEQ ID NO: 7           moltype = AA  length = 379
FEATURE                Location/Qualifiers
source                 1..379
                       mol_type = protein
                       organism = Bacillus cereus
SEQUENCE: 7
MHFKLSEEHE MIRKMVRDFA KNEVAPTAAE RDEEERFDRE LFDQMAELGL TGIPWPEEYG  60
GIGSDYLAYV IAIEELSRVC ASTGVTLSAH TSLAGWPIFK FGTEEQKQKF LRPMAEGKKI  120
GAYGLTEPGS GSDAGGMKTI AKRDGDHYIL NGSKIFITNG GIADIYVVFA LTDPESKQRG  180
TSAFIVESDT PGFSVGKKES KLGIRSSPTT EIMFEDCRIP VENLLGEEGQ GFKVAMQTLD  240
GGRNGIAAQA VGIAQGALDA SVEYARERHQ FGKPIAAQQG IGFKLADMAT DVEAARLLTY  300
QAAWLESEGL PYGKESAMSK VFAGDTAMRV TTEAVQVFGG YGYTKDYPVE RYMRDAKITQ  360
IYEGTQEIQR LVISRMLTK                                          379

SEQ ID NO: 8           moltype = AA  length = 394
FEATURE                Location/Qualifiers
source                 1..394
                       mol_type = protein
                       organism = Cupriavidus necator
SEQUENCE: 8
MTREVVVVSG VRTAIGTFGG SLKDVAPAEL GALVVREALA RAQVSGDDVG HVVFGNVIQT  60
EPRDMYLGRV AAVNGGVTIN APALTVNRLC GSGLQAIVSA AQTILLGDTD VAIGGGAESM  120
SRAPYLAPAA RWGARMGDAG LVDMMLGALH DPFHRIHMGV TAENVAKEYD ISRAQQDEAA  180
LESHRRASAA IKAGYFKDQI VPVVSKGRKG DVTFDTDEHV RHDATIDDMT KLRPVFVKEN  240
GTVTAGNASG LNDAAAAVVM MERAEAERRG LKPLARLVSY GHAGVDPKAM GIGPVPATKI  300
ALERAGLQVS DLDVIEANEA FAAQACAVTK ALGLDPAKVN PNGSGISLGH PIGATGALIT  360
VKALHELNRV QGRYALVTMC IGGGQGIAAI FERI                         394

SEQ ID NO: 9           moltype = AA  length = 715
FEATURE                Location/Qualifiers
source                 1..715
                       mol_type = protein
                       organism = Escherichia coli
SEQUENCE: 9
MNVIAILNHM GVYFKEEPIR ELHRALERLN FQIVYPNDRD DLLKLIENNA RLCGVIFDWD  60
KYNLELCEEI SKMNENLPLY AFANTYSTLD VSLNDLRLQI SFFEYALGAA EDIANKIKQT  120
TDEYINTILP PLTKALFKYV REGKYTFCTP GHMGGTAFQK SPVGSLFYDF FGPNTMKSDI  180
SISVSELGSL LDHSGPHKEA EQYIARVFNA DRSYMVTNGT STANKIVGMY SAPAGSTILI  240
DRNCHKSLTH LMMMSDVTPI YFRPTRNAYG ILGGIPQSEF QHATIAKRVK ETPNATWPVH  300
AVITNSTYDG LLYNTDFIKK TLDVKSIHFD SAWVPYTNFS PIYEGKCGMS GGRVEGKVIY  360
ETQSTHKLLA AFSQASMIHV KGDVNEETFN EAYMMHTTTS PHYGIVASTE TAAAMMKGNA  420
GKRLINGSIE RAIKFRKEIK RLRTESDGWF FDVWQPDHID TTECWPLRSD STWHGFKNID  480
NEHMYLDPIK VTLLTPGMEK DGTMSDFGIP ASIVAKYLDE HGIVVEKTGP YNLLFLFSIG  540
IDKTKALSLL RALTDFKRAF DLNLRVKNML PSLYREDPEF YENMRIQELA QNIHKLIVHH  600
NLPDLMYRAF EVLPTMVMTP YAAFQKELHG MTEEVYLDEM VGRINANMIL PYPPGVPLVM  660
PGEMITEESR PVLEFLQMLC EIGAHYPGFE TDIHGAYRQA DGRYTVKVLK EESKK   715

SEQ ID NO: 10          moltype = AA  length = 538
FEATURE                Location/Qualifiers
source                 1..538
                       mol_type = protein
                       organism = Clostridium kluyveri
SEQUENCE: 10
MSKGIKNSQL KKKNVKASNV AEKIEEKVEK TDKVVEKAAE VTEKRIRNLK LQEKVVTADV  60
AADMIENGMI VAISGFTPSG YPKEVPKALT KKVNALEEEF KVTLYTGSST GADIDGEWAK  120
AGIIERRIPY QTNSDMRKKI NDGSIKYADM HLSHMAQYIN YSVIPKVDIA IIEAVAITEE  180
GDIIPSTGIG NTATFVENAD KVIVEINEAQ PLELEGMADI YTLKNPPRRE PIPIVNAGNR  240
IGTTYVTCGS EKICAIVMTN TQDKTRPLTE VSPVSQAISD NLIGFLNKEV EEGKLPKNLL  300
PIQSGVGSVA NAVLAGLCES NFKNLSCYTE VIQDSMLKLI KCGKADVVSG TSISPSPEML  360
PEFIKDINFF REKIVLRPQE ISNNPEIARR IGVISINTAL EVDIYGNVNS THVMGSKMMN  420
GIGGSGDFAR NAYLTIFTTE SIAKKGDISS IVPMVSHVDH TEHDVMVIVT EQGVADLRGL  480
SPREKAVAII ENCVHPDYKD MLMEYFEEAC KSSGGNTPHN LEKALSWHTK FIKTGSMK   538

SEQ ID NO: 11          moltype = AA  length = 235
FEATURE                Location/Qualifiers
source                 1..235
                       mol_type = protein
                       organism = Escherichia coli
SEQUENCE: 11
MYRYLSIAAV VLSAAFSGPA LAEGINSFSQ AKAAAVKVHA DAPGTFYCGC KINWQGKKGV  60
VDLQSCGYQV RKNENRASRV EWEHVVPAWQ FGHQRQCWQD GGRKNCAKDP VYRKMESDMH  120
NLQPSVGEVN GDRGNFMYSQ WNGGEGQYGQ CAMKVDFKEK AAEPPARARG AIARTYFYMR  180
DQYNLTLSRQ QTQLFNAWNK MYPVTDWECE RDERIAKVQG NHNPYVQRAC QARKS      235

SEQ ID NO: 12          moltype = AA  length = 729
FEATURE                Location/Qualifiers
source                 1..729
```

```
                         mol_type = protein
                         organism = Escherichia coli
SEQUENCE: 12
MLYKGDTLYL DWLEDGIAEL VFDAPGSVNK LDTATVASLG EAIGVLEQQS DLKGLLLRSN  60
KAAFIVGADI TEFLSLFLVP EEQLSQWLHF ANSVFNRLED LPVPTIAAVN GYALGGGCEC  120
VLATDYRLAT PDLRIGLPET KLGIMPGFGG SVRMPRMLGA DSALEIIAAG KDVGADQALK  180
IGLVDGVVKA EKLVEGAKAV LRQAINGDLD WKAKRQPKLE PLKLSKIEAT MSFTIAKGMV  240
AQTAGKHYPA PITAVKTIEA AARFGREEAL NLENKSFVPL AHTNEARALV GIFLNDQYVK  300
GKAKKLTKDV ETPKQAAVLG AGIMGGGIAY QSAWKGVPVV MKDINDKSLT LGMTEAAKLL  360
NKQLERGKID GLKLAGVIST IHPTLDYAGF DRVDIVVEAV VENPKVKKAV LAETEQKVRQ  420
DTVLASNTST IPISELANAL ERPENFCGMH FFNPVHRMPL VEIIRGEKSS DETIAKVVAW  480
ASKMGKTPIV VNDCPGFFVN RVLFPYFAGF SQLLRDGADF RKIDKVMEKQ FGWPMGPAYL  540
LDVVGIDTAH HAQAVMAAGF PQRMQKDYRD AIDALFDANR FGQKNGLGFW RYKEDSKGKP  600
KKEEDAAVED LLAEVSQPKR DFSEEEIIAR MMIPMVNEVV RCLEEGIIAT PAEADMALVY  660
GLGFPPFHGG AFRWLDTLGS AKYLDMAQQY QHLGPLYEVP EGLRNKARHN EPYYPPVEPA  720
RPVGDLKTA                                                         729

SEQ ID NO: 13            moltype = AA  length = 814
FEATURE                  Location/Qualifiers
source                   1..814
                         mol_type = protein
                         organism = Escherichia coli
SEQUENCE: 13
MMILSILATV VLLGALFYHR VSLFISSLIL LAWTAALGVA GLWSAWVLVP LAIILVPFNF  60
APMRKSMISA PVFRGFRKVM PPMSRTEKEA IDAGTTWWEG DLFQGKPDWK KLHNYPQPRL  120
TAEEQAFLDG PVEEACRMAN DFQITHELAD LPPELWAYLK EHRFFAMIIK KEYGGLEFSA  180
YAQSRVLQKL SGVSGILAIT VGVPNSLGPG ELLQHYGTDE QKDHYLPRLA RGQEIPCFAL  240
TSPEAGSDAG AIPDTGIVCM GEWQGQQVLG MRLTWNKRYI TLAPIATVLG LAFKLSDPEK  300
LLGGAEDLGI TCALIPTTTP GVEIGRRHFP LNVPFQNGPT RGKDVFVPID YIIGGPKMAG  360
QGWRMLVECL SVGRGITLPS NSTGGVKSVA LATGAYAHIR RQFKISIGKM EGIEEPLARI  420
AGNAYVMDAA ASLITYGIML GEKPAVLSAI VKYHCTHRGQ QSIIDAMDIT GGKGIMLGQS  480
NFLARAYQGA PIAITVEGAN ILTRSMMIFG QGAIRCHPYV LEEMEAAKNN DVNAFDKLLF  540
KHIGHVGSNK VRSFWLGLTR GLTSSTPTGD ATKRYYQHLN RLSANLALLS DVSMAVLGGS  600
LKRRERISAR LGDILSQLYL ASAVLKRYDD EGRNEADLPL VHWGVQDALY QAEQAMDDLL  660
QNFPNRVVAG LLNVVIFPTG RHYLAPSDKL DHKVAKILQV PNATRSRIGR GQYLTPSEHN  720
PVGLLEEALV DVIAADPIHQ RICKELGKNL PFTRLDELAH NALVKGLIDK DEAAILVKAE  780
ESRLRSINVD DFDPEELATK PVKLPEKVRK VEAA                             814

SEQ ID NO: 14            moltype = AA  length = 714
FEATURE                  Location/Qualifiers
source                   1..714
                         mol_type = protein
                         organism = Escherichia coli
SEQUENCE: 14
MEMTSAFTLN VRLDNIAVIT IDVPGEKMNT LKAEFASQVR AIIKQLRENK ELRGVVFVSA  60
KPDNFIAGAD INMIGNCKTA QEAEALARQG QQLMAEIHAL PIQVIAAIHG ACLGGGLELA  120
LACHGRVCTD DPKTVLGLPE VQLGLLPGSG GTQRLPRLIG VSTALEMILT GKQLRAKQAL  180
KLGLVDDVVP HSILLEAAVE LAKKERPSSR PLPVRERILA GPLGRALLFK MVGKKTEHKT  240
QGNYPATERI LEVVETGLAQ GTSSGYDAEA RAFGELAMTP QSQALRSIFF ASTDVKKDPG  300
SDAPPAPLNS VGILGGGLMG GGIAYVTACK AGIPVRIKDI NPQGINHALK YSWDQLEGKV  360
RRRHLKASER DKQLALISGT TDYRGFAHRD LIIEAVFENL ELKQQMVAEV EQNCAAHTIF  420
ASNTSSLPIG DIAAHATRPE QVIGLHFFSP VEKMPLVEII PHAGTSAQTI ATTVKLAKKQ  480
GKTPIVVRDK AGFYVNRILA PYINEAIRML TQGERVEHID AALVKFGFPV GPIQLLDEVG  540
IDTGTKIIPV LEAAYGERFS APANVVSSIL NDDRKGRKNG RGFYLYGQKG RKSKKQVDPA  600
IYPLIGTQGQ GRISAPQVAE RCVMLMLNEA VRCVDEQVIR SVRDGDIGAV FGIGFPPFLG  660
GPFRYIDSLG AGEVVAIMQR LATQYGSRFT PCERLVEMGA RGESFWKTTA TDLQ       714

SEQ ID NO: 15            moltype = AA  length = 448
FEATURE                  Location/Qualifiers
source                   1..448
                         mol_type = protein
                         organism = Pseudomonas sp.
SEQUENCE: 15
MNQQVNVAPS AAADLNLKAH WMPFSANRNF HKDPRIIVAA EGSWLVDDKG RRIYDSLSGL  60
WTCGAGHSRK EIADAVAKQI GTLDYSPGFQ YGHPLSFQLA EKIAQMTPGT LDHVFFTGSG  120
SECADTSIKM ARAYWRIKGQ AQKTKLIGRA RGYHGVNVAG TSLGGIGGNR KMFGPLMDVD  180
HLPHTLQPGM AFTKGAAETG GVELANELLK LIELHDASNI AAVIVEPMSG SAGVIVPPKG  240
YLQRLREICD ANDILLIFDE VITAFGRMGK ATGAEYFGVT PDIMNVAKQV TNGAVPMGAV  300
IASSEIYDTF MNQNLPEYAV EFGHGYTYSA HPVACAAGIA ALDLLQKENL IQQSAELAPH  360
FEKALHGLKG TKNVIDIRNC GLAGAIQIAA RDGDAIVRPF EASMKLWKEG FYVRFGGDTL  420
QFGPTFNAKP EDLDRLFDAV GEALNGVA                                    448

SEQ ID NO: 16            moltype = AA  length = 448
FEATURE                  Location/Qualifiers
source                   1..448
                         mol_type = protein
                         organism = synthetic construct
SEQUENCE: 16
MNQQVNVAPS AAADLNLKAH WMPFSANRNF HKDPRIIVAA EGSWLVDDKG RRIYDSLSGL  60
```

-continued

```
WTCGAGHSRK EIADAVAKQI GTLDYSPGFQ YGHPLSFQLA EKIAQMTPGT LDHVFFTGSG  120
SECADTSIKM ARAYWRIKGQ AQKTKLIGRA RGYHGVNVAG TSLGGIGGNR KMFGPLMDVD  180
HLPHTLQPGM AFTKGAAETG GVELANELLK LIELHDASNI AAVIVEPMSG SAGVIVPPKG  240
YLQRLREICD ANDILLIFDE VITAFGRMGK ATGAEYFGVT PDIMNVAKQV TNGAVPMGAV  300
IASSEIYDTF MNQNLPEYAV EFGHGYTYSA HPVACAAGIA ALDLLQKENL IQQSAELAPH  360
FEKALHGLKG TKNVIDIRNC GLAGAIQIAA RDGDAIVRPF EASMKLWKEG FYVRFGGDTL  420
QFGPTFNAKP EDLDRLFDAV GEALNGVA                                   448

SEQ ID NO: 17          moltype = AA  length = 482
FEATURE                Location/Qualifiers
source                 1..482
                       mol_type = protein
                       organism = Escherichia coli
SEQUENCE: 17
MKLNDSNLFR QQALINGEWL DANNGEAIDV TNPANGDKLG SVPKMGADET RAAIDAANRA  60
LPAWRALTAK ERATILRNWF NLMMEHQDDL ARLMTLEQGK PLAEAKGEIS YAASFIEWFA  120
EEGKRIYGDT IPGHQADKRL IVIKQPIGVT AAITPWNFPA AMITRKAGPA LAAGCTMVLK  180
PASQTPFSAL ALAELAIRAG VPAGVFNVVT GSAGAVGNEL TSNPLVRKLS FTGSTEIGRQ  240
LMEQCAKDIK KVSLELGGNA PFIVFDDADL DKAVEGALAS KFRNAGQTCV CANRLYVQDG  300
VYDRFAEKLQ QAVSKLHIGD GLDNGVTIGP LIDEKAVAKV EEHIADALEK GARVVCGGKA  360
HERGGNFFQP TILVDVPANA KVSKEETFGP LAPLFRFKDE ADVIAQANDT EFGLAAYFYA  420
RDLSRVFRVG EALEYGIVGI NTGIISNEVA PFGGIKASGL GREGSKYGIE DYLEIKYMCI  480
GL                                                               482

SEQ ID NO: 18          moltype = AA  length = 426
FEATURE                Location/Qualifiers
source                 1..426
                       mol_type = protein
                       organism = Escherichia coli
SEQUENCE: 18
MNSNKELMQR RSQAIPRGVG QIHPIFADRA ENCRVWDVEG REYLDFAGGI AVLNTGHLHP  60
KVVAAVEAQL KKLSHTCFQV LAYEPYLELC EIMNQKVPGD FAKKTLLVTT GSEAVENAVK  120
IARAATKRSG TIAFSGAYHG RTHYTLALTG KVNPYSAGMG LMPGHVYRAL YPCPLHGISE  180
DDAIASIHRI FKNDAAPEDI AAIVIEPVQG EGGFYASSPA FMQRLRALCD EHGIMLIADE  240
VQSGAGRTGT LFAMEQMGVA PDLTTFAKSI AGGFPLAGVT GRAEVMDAVA PGGLGGTYAG  300
NPIACVAALE VLKVFEQENL LQKANDLGQK LKDGLLAIAE KHPEIGDVRG LGAMIAIELF  360
EDGDHNKPDA KLTAEIVARA RDKGLILLSC GPYYNVLRIL VPLTIEDAQI RQGLEIISQC  420
FDEAKQ                                                           426

SEQ ID NO: 19          moltype = AA  length = 502
FEATURE                Location/Qualifiers
source                 1..502
                       mol_type = protein
                       organism = Arabidopsis thaliana
SEQUENCE: 19
MVLSHAVSES DVSVHSTFAS RYVRTSLPRF KMPENSIPKE AAYQIINDEL MLDGNPRLNL  60
ASFVTTWMEP ECDKLIMSSI NKNYVDMDEY PVTTELQNRC VNMIAHLFNA PLEEAETAVG  120
VGTVGSSEAI MLAGLAFKRK WQNKRKAEGK PVDKPNIVTG ANVQVCWEKF ARYFEVELKE  180
VKLSEGYYVM DPQQAVDMVD ENTICVADIL GSTLNGEFED VKLLNDLLVE KNKETGWDTP  240
IHVDAASGGF IAPFLYPELE WDFRLPLVKS INVSGHKYGL VYAGIGWVIW RNKEDLPEEL  300
IFHINYLGAD QPTFTLNFSK GSSQVIAQYY QLIRLGHEGY RNVMENCREN MIVLREGLEK  360
TERFNIVSKD EGVPLVAFSL KDSSCHTEFE ISDMLRRYGW IVPAYTMPPN AQHITVLRVV  420
IREDFSRTLA ERLVIDIEKV MRELDELPSR VIHKISLGQE KSESNSDNLM VTVKKSDIDK  480
QRDIITGWKK FVADRKKTSG IC                                         502

SEQ ID NO: 20          moltype = AA  length = 451
FEATURE                Location/Qualifiers
source                 1..451
                       mol_type = protein
                       organism = Escherichia coli
SEQUENCE: 20
MDQKLLTDFR SELLDSRFGA KAISTIAESK RFPLHEMRDD VAFQIINDEL YLDGNARQNL  60
ATFCQTWDDE NVHKLMDLSI NKNWIDKEQY PQSAAIDLRC VNMVADLWHA PAPKNGQAVG  120
TNTIGSSEAC MLGGMAMKWR WRKRMEAAGK PTDKPNLVCG PVQICWHKFA RYWDVELREI  180
PMRPGQLFMD PKRMIEACDE NTIGVVPTFG VTYTGNYEFP QPLHDALDKF QADTGIDIDM  240
HIDAASGGFL APFVAPDIVW DFRLPRVKSI SASGHKFGLA PLGCGWVIWR DEEALPQELV  300
FNVDYLGGQI GTFAINFSRP AGQVIAQYYE FLRLGREGYT KVQNASYQVA AYLADEIAKL  360
GPYEFICTGR PDEGIPAVCF KLKDGEDPGY TLYDLSERLR LRGWQVPAFT LGGEATDIVV  420
MRIMCRRGFE MDFAELLLED YKASLKYLSD H                               451

SEQ ID NO: 21          moltype = AA  length = 324
FEATURE                Location/Qualifiers
source                 1..324
                       mol_type = protein
                       organism = Escherichia coli
SEQUENCE: 21
MKPSVILYKA LPDDLLQRLQ EHFTVHQVAN LSPQTVEQNA AIFAEAEGLL GSNENVNAAL  60
LEKMPKLRAT STISVGYDNF DVDALTARKI LLMHTPTVLT ETVADTLMAL VLSTARRVVE  120
VAERVKAGEW TASIGPDWYG TDVHHKTLGI VGMGRIGMAL AQRAHFGFNM PILYNARRHH  180
```

```
KEAEERFNAR YCDLDTLLQE SDFVCLILPL TDETHHLFGA EQFAKMKSSA IFINAGRGPV    240
VDENALIAAL QKGEIHAAGL DVFEQEPLSV DSPLLSMANV VAVPHIGSAT HETRYGMAAC    300
AVDNLIDALQ GKVEKNCVNP HVAD                                          324

SEQ ID NO: 22          moltype = AA   length = 259
FEATURE                Location/Qualifiers
source                 1..259
                       mol_type = protein
                       organism = Escherichia coli
SEQUENCE: 22
MYAAKDITVE ERAGGALWIT IDRAQKHNAL ARHVLAGLAQ VVSAAAAQPG VRCIVLTGAG     60
QRFFAAGGDL VELSGVRDRE ATLAMSEQAR GALDAVRDCP LPVLAYLNGD AIGGGAELAL    120
ACDMRLQSAS ARIGFIQARL AITSAWGGGP DLCRIVGAAR AMRMMSRCEL VDAQQALQWG    180
LADAVVTDGP AGKDIHAFLQ PLLGCAPQVL RGIKAQTAAS RRGESHDAAR TIEQQQLLHT    240
WLHADHWNAA EGILSRRAQ                                                 259

SEQ ID NO: 23          moltype = AA   length = 282
FEATURE                Location/Qualifiers
source                 1..282
                       mol_type = protein
                       organism = Clostridium acetobutylicum
SEQUENCE: 23
MKKVCVIGAG TMGSGIAQAF AAKGFEVVLR DIKDEFVDRG LDFINKNLSK LVKKGKIEEA     60
TKVEILTRIS GTVDLNMAAD CDLVIEAAVE RMDIKKQIFA DLDNICKPET ILASNTSSLS    120
ITEVASATKR PDKVIGMHFF NPAPVMKLVE VIRGIATSQE TFDAVKETSI AIGKDPVEVA    180
EAPGFVVNRI LIPMINEAVG ILAEGIASVE DIDKAMKLGA NHPMGPLELG DFIGLDICLA    240
IMDVLYSETG DSKYRPHTLL KKYVRAGWLG RKSGKGFYDY SK                       282

SEQ ID NO: 24          moltype = AA   length = 274
FEATURE                Location/Qualifiers
source                 1..274
                       mol_type = protein
                       organism = Escherichia coli
SEQUENCE: 24
MVAPIPAKRG RKPAVATAPA TGQVQSLTRG LKLLEWIAES NGSVALTELA QQAGLPNSTT     60
HRLLTTMQQQ GFVRQVGELG HWAIGAHAFM VGSSFLQSRN LLAIVHPILR NLMEESGETV    120
NMAVLDQSDH EAIIIDQVQC THLMRMSAPI GGKLPMHASG AGKAFLAQLS EEQVTKLLHR    180
KGLHAYTHAT LVSPVHLKED LAQTRKRGYS FDDEEHALGL RCLAACIFDE HREPFAAISI    240
SGPISRITDD RVTEFGAMVI KAAKEVTLAY GGMR                                274

SEQ ID NO: 25          moltype = AA   length = 360
FEATURE                Location/Qualifiers
source                 1..360
                       mol_type = protein
                       organism = Escherichia coli
SEQUENCE: 25
MKPVTLYDVA EYAGVSYQTV SRVVNQASHV SAKTREKVEA AMAELNYIPN RVAQQLAGKQ     60
SLLIGVATSS LALHAPSQIV AAIKSRADQL GASVVVSMVE RSGVEACKAA VHNLLAQRVS    120
GLIINYPLDD QDAIAVEAAC TNVPALFLDV SDQTPINSII FSHEDGTRLG VEHLVALGHQ    180
QIALLAGPLS SVSARLRLAG WHKYLTRNQI QPIAEREGDW SAMSGFQQTM QMLNEGIVPT    240
AMLVANDQMA LGAMRAITES GLRVGADISV VGYDDTEDSS CYIPPLTTIK QDFRLLGQTS    300
VDRLLQLSQG QAVKGNQLLP VSLVKRKTTL APNTQTASPR ALADSLMQLA RQVSRLESGQ    360

SEQ ID NO: 26          moltype = AA   length = 548
FEATURE                Location/Qualifiers
source                 1..548
                       mol_type = protein
                       organism = Pseudomonas putida
SEQUENCE: 26
MMVPTLEHEL APNEANHVPL SPLSFLKRAA QVYPQRDAVI YGARRYSYRQ LHERSRALAS     60
ALERVGVQPG ERVAILAPNI PEMLEAHYGV PGAGAVLVCI NIRLEGRSIA FILRHCAAKV    120
LICDREFGAV ANQALAMLDA PPLLVGIDDD QAERADLAHD LDYEAFLAQG DPARPLSAPQ    180
NEWQSIAINY TSGTTGDPKG VVLHHRGAYL NACAGALIFQ LGPRSVYLWT LPMFHCNGWS    240
HTWAVTLSGG THVCLRKVQP DAINAAIAEH AVTHLSAAPV VMSMLIHAEH ASAPPVPVSV    300
ITGGAAPPSA VIAAMEARGF NITHAYGMTE SYGPSTLCLW QPGVDELPLE ARAQFMSRQG    360
VAHPLLEEAT VLDTDTGRPV PADGLTLGEL VVRGNTVMKG YLHNPEATRA ALANGWLHTG    420
DLAVLHLDGY VEIKDRAKDI IISSGENISS LEIEEVLYQH PEVVEAAVVA RPDSRWGETP    480
HAFVTLRADA LASGDDLVRW CRERLAHFKA PRHVSLVDLP KTATGKIQKF VLREWARQQE    540
AQIADAEH                                                            548

SEQ ID NO: 27          moltype = DNA   length = 87
FEATURE                Location/Qualifiers
source                 1..87
                       mol_type = genomic DNA
                       organism = Escherichia coli
SEQUENCE: 27
aacacatcag atttcctggt gtaacgaatt ttttaagtgc ttcttgctta agcaagtttc     60
atcccgaccc cctcagggtc gggattt                                        87
```

```
SEQ ID NO: 28          moltype = AA  length = 383
FEATURE                Location/Qualifiers
source                 1..383
                       mol_type = protein
                       organism = Megasphaera sp.
SEQUENCE: 28
MDFNLTDIQQ DFLKLAHDFG EKKLAPTVTE RDHKGIYDKE LIDELLSLGI TGAYFEEKYG  60
GSGDDGGDVL SYILAVEELA KYDAGVAITL SATVSLCANP IWQFGTEAQK EKFLVPLVEG  120
TKLGAFGLTE PNAGTDASGQ QTIATKNDDG TYTLNGSKIF ITNGGAADIY IVFAMTDKSK  180
GNHGITAFIL EDGTPGFTYG KKEDKMGIHT SQTMELVFQD VKVPAENMLG EEGKGFKIAM  240
MTLDGGRIGV AAQALGIAEA ALADAVEYSK QRVQFGKPLC KFQSISFKLA DMKMQIEAAR  300
NLVYKAACKK QEGKPFTVDA AIAKRVASDV AMRVTTEAVQ IFGGYGYSEE YPVARHMRDA  360
KITQIYEGTN EVQLMVTGGA LLR                                         383

SEQ ID NO: 29          moltype = AA  length = 681
FEATURE                Location/Qualifiers
source                 1..681
                       mol_type = protein
                       organism = Escherichia coli
SEQUENCE: 29
MQQLASFLSG TWQSGRGRSR LIHHAISGEA LWEVTSEGLD MAAARQFAIE KGAPALRAMT  60
FIERAAMLKA VAKHLLSEKE RFYALSAQTG ATRADSWVDI EGGIGTLFTY ASLGSRELPD  120
DTLWPEDELI PLSKEGGFAA RHLLTSKSGV AVHINAFNFP CWGMLEKLAP TWLGGMPAII  180
KPATATAQLT QAMVKSIVDS GLVPEGAISL ICGSAGDLLD HLDSQDVVTF TGSAATGQML  240
RVQPNIVAKS IPFTMEADSL NCCVLGEDVT PDQPEFALFI REVVREMTTK AGQKCTAIRR  300
IIVPQALVNA VSDALVARLQ KVVVGDPAQE GVKMGALVNA EQRADVQEKV NILLAAGCEI  360
RLGGQADLSA AGAFFPPTLL YCPQPDETPA VHATEAFGPV ATLMPAQNQR HALQLACAGG  420
GSLAGTLVTA DPQIARQFIA DAARTHGRIQ ILNEESAKES TGHGSPLPQL VHGGPGRAGG  480
GEELGGLRAV KHYMQRTAVQ GSPTMLAAIS KQWVRGAKVE EDRIHPFRKY FEELQPGDSL  540
LTPRRTMTEA DIVNFACLSG DHFYAHMDKI AAAESIFGER VVHGYFVLSA AAGLFVDAGV  600
GPVIANYGLE SLRFIEPVKP GDTIQVRLTC KRKTLKKQRS AEEKPTGVVE WAVEVFNQHQ  660
TPVALYSILT LVARQHGDFV D                                           681

SEQ ID NO: 30          moltype = AA  length = 524
FEATURE                Location/Qualifiers
source                 1..524
                       mol_type = protein
                       organism = Anaerotignum propionicum
SEQUENCE: 30
MRKVPIITAD EAAKLIKDGD TVTTSGFVGN AIPEALDRAV EKRFLETGEP KNITYVYCGS  60
QGNRDGRGAE HFAHEGLLKR YIAGHWATVP ALGKMAMENK MEAYNVSQGA LCHLFRDIAS  120
HKPGVFTKVG IGTFIDPRNG GGKVNDITKE DIVELVEIKG QEYLFYPAFP IHVALIRGTY  180
ADESGNITFE KEVAPLEGTS VCQAVKNSGG IVVVQVERVV KAGTLDPRHV KVPGIYVDYV  240
VVADPEDHQQ SLDCEYDPAL SGEHRRPEVV GEPLPLSAKK VIGRRGAIEL EKDVAVNLGV  300
GAPEYVASVA DEEGIVDFMT LTAESGAIGG VPAGGVRFGA SYNADALIDQ GYQFDYYDGG  360
GLDLCYLGLA ECDEKGNINV SRFGPRIAGC GGFINITQNT PKVFFCGTFT AGGLKVKIED  420
GKVIIVQEGK QKKFLKAVEQ ITFNGDVALA NKQQVTYITE RCVFLLKEDG LHLSEIAPGI  480
DLQTQILDVM DFAPIIDRDA NGQIKLMDAA LFAEGLMGLK EMKS                  524

SEQ ID NO: 31          moltype = AA  length = 517
FEATURE                Location/Qualifiers
source                 1..517
                       mol_type = protein
                       organism = Megasphaera elsdenii
SEQUENCE: 31
MRKVEIITAE QAAQLVKDND TITSIGFVSS AHPEALTKAL EKRFLDTNTP QNLTYIYAGS  60
QGKRDGRAAE HLAHTGLLKR AIIGHWQTVP AIGKLAVENK IEAYNFSQGT LVHWFRALAG  120
HKLGVFTDIG LETFLDPRQL GGKLNDVTKE DLVKLIEVDG HEQLFYPTFP VNVAFLRGTY  180
ADESGNITMD EEIGPFESTS VAQAVHNCGG KVVVQVKDVV AHGSLDPRMV KIPGIYVDYV  240
VVAAPEDHQQ TYDCEYDPSL SGEHRAPEGA TDAALPMSAK KIIGRRGALE LTENAVVNLG  300
VGAPEYVASV AGEEGIADTI TLTVEGGAIG GVPQGGARFG SSRNADAIID HTYQFDFYDG  360
GGLDIAYLGL AQCDGSGNIN VSKFGTNVAG CGGFPNISQQ TPNVYFCGTF TAGGLKIAVE  420
DGKVKILQEG KAKKFIKAVD QITFNGSYAA RNGKHVLYIT ERCVFELTKE GLKLIEVAPG  480
IDIEKDILAH MDFKPIIDNP KLMDARLFQD GPMGLKK                          517

SEQ ID NO: 32          moltype = AA  length = 462
FEATURE                Location/Qualifiers
source                 1..462
                       mol_type = protein
                       organism = Klebsiella pneumoniae
SEQUENCE: 32
MNTAELETLI RTILSEKLAP TPPAPQQEQG IFCDVGSAID AAHQAFLRYQ QCPLKTRSAI  60
ISALRETLAP ELATLAEESA TETGMGNKED KYLKNKAALE NTPGIEDLTT SALTGDGGMV  120
LFEYSPFGVI GAVAPSTNPT ETIINNSISM LAAGNSVYFS PHPGAKKVSL KLIARIEEIA  180
YRCSGIRNLV VTVAEPTFEA TQQMMSHPLI AVLAITGGPG IVAMGMKSGK KVIGAGAGNP  240
PCIVDETADL VKAAEDIISG AAFDYNLPCI AEKSLIVVAS VADRLIQQMQ DFDALLLSRQ  300
EADTLRTVCL PDGAANKKLV GKSPAALLAA AGLAVPPRPP RLLIAEVEAN DPWVTCEQLM  360
PVLPIVRVAD FDSALALALR VEEGLHHTAI MHSQNVSRLN LAARTLQTSI FVKNGPSYAG  420
IGVGGEGFTT FTIATPTGEG TTSARTFARL RRCVLTNGFS IR                    462
```

-continued

```
SEQ ID NO: 33          moltype = AA  length = 464
FEATURE                Location/Qualifiers
source                 1..464
                       mol_type = protein
                       organism = Salmonella enterica
SEQUENCE: 33
MNTSELETLI RTILSEQLTT PAQTPVQPQG KGIFQSVSEA IDAAHQAFLR YQQCPLKTRS  60
AIISAMRQEL TPLLAPLAEE SANETGMGNK EDKFLKNKAA LDNTPGVEDL TTTALTGDGG  120
MVLFEYSPFG VIGSVAPSTN PTETIINNSI SMLAAGNSIY FSPHPGAKKV SLKLISLIEE  180
IAFRCCGIRN LVVTVAEPTF EATQQMMAHP RIAVLAITGG PGIVAMGMKS GKKVIGAGAG  240
NPPCIVDETA DLVKAAEDII NGASFDYNLP CIAEKSLIVV ESVAERLVQQ MQTFGALLLS  300
PADTDKLRAV CLPEGQANKK LVGKSPSAML EAAGIAVPAK APRLLIALVN ADDPWVTSEQ  360
LMPMLPVVKV SDFDSALALA LKVEEGLHHT AIMHSQNVSR LNLAARTLQT SIFVKNGPSY  420
AGIGVGGEGF TTFTIATPTG EGTTSARTFA RSRRCVLTNG FSIR                  464

SEQ ID NO: 34          moltype = AA  length = 393
FEATURE                Location/Qualifiers
source                 1..393
                       mol_type = protein
                       organism = Cupriavidus sp.
SEQUENCE: 34
MTDVVIVSAA RTAVGKFGGS LAKIPAPELG AVVIKAALER AGVKPEQVSE VIMGQVLTAG  60
SGQNPARQAA IKAGLPAMVP AMTINKVCGS GLKAVMLAAN AIMAGDAEIV VAGGQENMSA  120
APHVLPGSRD GFRMGDAKLV DTMIVDGLWD VYNQYHMGIT AENVAKEYGI TREAQDEFAV  180
GSQNKAEAAQ KAGKFDEEIV PVLIPQRKGD PVAFKTDEFV RQGATLDSMS GLKPAFDKAG  240
TVTAANASGL NDGAAAVVVM SAAKAKELGL TPLATIKSYA NAGVDPKVMG MGPVPASKRA  300
LSRAEWTPQD LDLMEINEAF AAQALAVHQQ MGWDTSKVNV NGGAIAIGHP IGASGCRILV  360
TLLHEMKRRD AKKGLASLCI GGGMGVALAV ERK                              393

SEQ ID NO: 35          moltype = AA  length = 246
FEATURE                Location/Qualifiers
source                 1..246
                       mol_type = protein
                       organism = Cupriavidus sp.
SEQUENCE: 35
MTQRIAYVTG GMGGIGTAIC QRLAKDGFRV VAGCGPNSPR REKWLEQQKA LGFDFIASEG  60
NVADWDSTKT AFDKVKSEVG EVDVLINNAG ITRDVVFRKM TRADWDAVID TNLTSLFNVT  120
KQVIDGMADR GWGRIVNISS VNGQKGQFGQ TNYSTAKAGL HGFTMALAQE VATKGVTVNT  180
VSPGYIATDM VKAIRQDVLD KIVATIPVKR LGLPEEIASI CAWLSSEESG FSTGADFSLN  240
GGLHMG                                                            246

SEQ ID NO: 36          moltype = AA  length = 589
FEATURE                Location/Qualifiers
source                 1..589
                       mol_type = protein
                       organism = Cupriavidus necator
SEQUENCE: 36
MATGKGAAAS TQEGKSQPFK VTPGPFDPAT WLEWSRQWQG TEGNGHAAAS GIPGLDALAG  60
VKIAPAQLGD IQQRYMKDFS ALWQAMAEGK AEATGPLHDR RFAGDAWRTN LPYRFAAAFY  120
LLNARALTEL ADAVEADAKT RQRIRFAISQ WVDAMSPANF LATNPEAQRL LIESGGESLR  180
AGVRNMMEDL TRGKISQTDE SAFEVGRNVA VTEGAVVFEN EYFQLLQYKP LTDKVHARPL  240
LMVPPCINKY YILDLQPESS LVRHVVEQGH TVFLVSWRNP DASMAGSTWD DYIEHAAIRA  300
IEVARDISGQ DKINVLGFCV GGTIVSTALA VLAARGEHPA ASVTLLTTLL DFADTGILDV  360
FVDEGHVQLR EATLGGGAGA PCALLRGLEL ANTFSFLRPN DLVWNYVVDN YLKGNTPVPF  420
DLLFWNGDAT NLPGPWYCWY LRHTYLQNEL KVPGKLTVCG VPVDLASIDV PTYIYGSRED  480
HIVPWTAAYA STALLANKLR FVLGASGHIA GVINPPAKNK RSHWTNDALP ESPQQWLAGA  540
IEHHGSWWPD WTAWLAGQAG AKRAAPANYG NARYRAIEPA PGRYVKAKA                589

SEQ ID NO: 37          moltype = AA  length = 134
FEATURE                Location/Qualifiers
source                 1..134
                       mol_type = protein
                       organism = Aeromonas caviae
SEQUENCE: 37
MSTQTLAVGQ KARLTKRFGP AEVAAFAGLS EDFNPLHLDP DFAATTVFER PIVHGMLLAS  60
LFSGLLGQQL PGKGSIYLGQ SLGFKLPVFV GDEVTAEVEV IALRSDKPIA TLATRIFTQG  120
GALAVTGEAV VKLP                                                   134

SEQ ID NO: 38          moltype = AA  length = 375
FEATURE                Location/Qualifiers
source                 1..375
                       mol_type = protein
                       organism = Pseudomonas putida
SEQUENCE: 38
MLVNDEQQQI ADAVRAFAQE RLKPFAEQWD KDHRFPKEAI DEMAELGLFG MLVPEQWGGS  60
DTGYVAYAMA LEEIAAGDGA CSTIMSVHNS VGCVPILRFG NEQQKEQFLT PLATGAMLGA  120
FALTEPQAGS DASSLKTRAR LEGDHYVLNG SKQFITSGQN AGVVIVFAVT DPEAGKRGIS  180
AFIVPTDSPG YQVARVEDKL GQHASDTCQI VFDNVQVPVA NRLGAEGEGY KIALANLEGG  240
```

```
RIGIASQAVG MARAAFEVAR DYANERQSFG KPLIEHQAVA FRLADMATKI SVARQMVLHA  300
AALRDAGRPA LVEASMAKLF ASEMAEKVCS DALQTLGGYG YLSDFPLERI YRDVRVCQIY  360
EGTSDIQRMV IARNL                                                  375

SEQ ID NO: 39          moltype = DNA  length = 105
FEATURE                Location/Qualifiers
source                 1..105
                       mol_type = genomic DNA
                       organism = Escherichia coli
SEQUENCE: 39
acggttataa atcaacatat tgatttataa gcatggaaat cccctgagtg aaacaacgaa  60
ttgctgtgtg tagtctttgc ccatctccca cgatgggctt ttttt                 105

SEQ ID NO: 40          moltype = AA  length = 296
FEATURE                Location/Qualifiers
source                 1..296
                       mol_type = protein
                       organism = Escherichia coli
SEQUENCE: 40
MSLHSPGKAF RAALTKENPL QIVGTINANH ALLAQRAGYQ AIYLSGGGVA AGSLGLPDLG  60
ISTLDDVLTD IRRITDVCSL PLLVDADIGF GSSAFNVART VKSMIKAGAA GLHIEDQVGA  120
KRCGHRPNKA IVSKEEMVDR IRAAVDAKTD PDFVIMARTD ALAVEGLDAA IERAQAYVEA  180
GAEMLFPEAI TELAMYRQFA DAVQVPILAN ITEFGATPLF TTDELRSAHV AMALYPLSAF  240
RAMNRAAEHV YNVLRQEGTQ KSVIDTMQTR NELYESINYY QYEEKLDNLF ARSQVK     296

SEQ ID NO: 41          moltype = AA  length = 389
FEATURE                Location/Qualifiers
source                 1..389
                       mol_type = protein
                       organism = Escherichia coli
SEQUENCE: 41
MSDTTILQNS THVIKPKKSV ALSGVPAGNT ALCTVGKSGN DLHYRGYDIL DLAKHCEFEE  60
VAHLLIHGKL PTRDELAAYK TKLKALRGLP ANVRTVLEAL PAASHPMDVM RTGVSALGCT  120
LPEKEGHTVS GARDIADKLL ASLSSILLYW YHYSHNGERI QPETDDDSIG GHFLHLLHGE  180
KPSQSWEKAM HISLVLYAEH EFNASTFTSR VIAGTGSDMY SAIIGAIGAL RGPKHGGANE  240
VSLEIQQRYE TPDEAEADIR KRVENKEVVI GFGHPVYTIA DPRHQVIKRV AKQLSQEGGS  300
LKMYNIADRL ETVMWESKKM FPNLDWFSAV SYNMMGVPTE MFTPLFVIAR VTGWAAHIIE  360
QRQDNKIIRP SANYVGPEDR PFVALDKRQ                                   389

SEQ ID NO: 42          moltype = AA  length = 483
FEATURE                Location/Qualifiers
source                 1..483
                       mol_type = protein
                       organism = Escherichia coli
SEQUENCE: 42
MSAQINNIRP EFDREIVDIV DYVMNYEISS KVAYDTAHYC LLDTLGCGLE ALEYPACKKL  60
LGPIVPGTVV PNGVRVPGTQ FQLDPVQAAF NIGAMIRWLD FNDTWLAAEW GHPSDNLGGI  120
LATADWLSRN AVASGKAPLT MKQVLTAMIK AHEIQGCIAL ENSFNRVGLD HVLLVKVAST  180
AVVAEMLGLT REEILNAVSL AWVDGQSLRT YRHAPNTGTR KSWAAGDATS RAVRLALMAK  240
TGEMGYPSAL TAPVWGFYDV SFKGESFRFQ RPYGSYVMEN VLFKISFPAE FHSQTAVEAA  300
MTLYEQMQAA GKTAADIEKV TIRTHEACIR IIDKKGPLNN PADRDHCIQY MVAIPLLFGR  360
LTAADYEDNV AQDKRIDALR EKINCFEDPA FTADYHDPEK RAIANAITLE FTDGTRFEEV  420
VVEYPIGHAR RRQDGIPKLV DKFKINLARQ FPTRQQQRIL EVSLDRARLE QMPVNEYLDL  480
YVI                                                               483

SEQ ID NO: 43          moltype = AA  length = 639
FEATURE                Location/Qualifiers
source                 1..639
                       mol_type = protein
                       organism = Cupriavidus sp.
SEQUENCE: 43
MTADAEETDM TASHAVHARS LADPEGFWAE QAARIDWETP FGQVLDNSRA PFTRWFVGGR  60
TNLCHNAVDR HLAARASQPA LHWVSTETDQ ARTFTYAELH DEVSRMAAIL QGLDVQKGDR  120
VLIYMPMIPE AAFAMLACAR IGAIHSVVFG GFASVSLAAR IEDARPRVVV SADAGSRAGK  180
VVPYKPLLDE AIRLSSHQPG KVLLVDRQLA QMPRTEGRDE DYAAWRERVA GVQVPCVWLE  240
SSEPSYVLYT SGTTGKPKGV QRDTGGYAVA LATSMEYIFC GKPGDTMFTA SDIGWVVGHS  300
YIVYGPLLAG MATLMYEGTP IRPDGGILWR LVEQYKVNLM FSAPTAIRVL KKQDPAWLTR  360
YDLSSLRLLF LAGEPLDEPT ARWIQDGLGK PVVDNYWQTE SGWPILAIQR GIEALPPKLG  420
SPGVPAYGYD LKIVDENTGA ECPPGQKGVV AIDGPLPPGC MSTVWGDDDR FVRTYWQAVP  480
NRLCYSTFDW GVRDADGYVF ILGRTDDVIN VAGHRLGTRE IEESLSSNAA VAEVAVVGVQ  540
DALKGQVAMA FCIARDPART ATAEARLALE GELMKTVEQQ LGAVARPARV FFVNALPKTR  600
SGKLLRRAMQ AVAEGRDPGD LTTIEDPGAL EQLQAALKG                        639

SEQ ID NO: 44          moltype = AA  length = 628
FEATURE                Location/Qualifiers
source                 1..628
                       mol_type = protein
                       organism = Escherichia coli
SEQUENCE: 44
```

```
MSFSEFYQRS INEPEQFWAE QARRIDWQTP FTQTLDHSNP PFARWFCEGR TNLCHNAIDR  60
WLEKQPEALA LIAVSSETEE ERTFTFRQLH DEVNAVASML RSLGVQRGDR VLVYMPMIAE  120
AHITLLACAR IGAIHSVVFG GFASHSVAAR IDDAKPVLIV SADAGARGGK IIPYKKLLDD  180
AISQAQHQPR HVLLVDRGLA KMARVSGRDV DFASLRHQHI GARVPVAWLE SNETSCILYT  240
SGTTGKPKGV QRDVGGYAVA LATSMDTIFG GKAGSVFFCA SDIGWVVGHS YIVYAPLLAG  300
MATIVYEGLP TWPDCGVWWT IVEKYQVSRM FSAPTAIRVL KKFPTAEIRK HDLSSLEVLY  360
LAGEPLDEPT ASWVSNTLDV PVIDNYWQTE SGWPIMAIAR GLDDRPTRLG SPGVPMYGYN  420
VQLLNEVTGE PCGVNEKGML VVEGPLPPGC IQTIWGDDGR FVKTYWSLFS RPVYATFDWG  480
IRDADGYHFI LGRTDDVINV AGHRLGTREI EESISSHPGV AEVAVVGVKD ALKGQVAVAF  540
VIPKESDSLE DRDVAHSQEK AIMALVDSQI GNFGRPAHVW FVSQLPKTRS GKMLRRTIQA  600
ICEGRDPGDL TTIDDPASLD QIRQAMEE                                    628

SEQ ID NO: 45          moltype = AA  length = 628
FEATURE                Location/Qualifiers
source                 1..628
                       mol_type = protein
                       organism = Salmonella enterica
SEQUENCE: 45
MSFSEFYQRS INEPEAFWAE QARRIDWRQP FTQTLDHSRP PFARWFCGGT TNLCHNAVDR  60
WRDKQPEALA LIAVSSETDE ERTFTFSQLH DEVNIVAAML LSLGVQRGDR VLVYMPMIAE  120
AQITLLACAR IGAIHSVVFG GFASHSVAAR IDDARPALIV SADAGARGGK ILPYKKLLDD  180
AIAQAQHQPK HVLLVDRGLA KMAWVDGRDL DFATLRQQHL GASVPVAWLE SNETSCILYT  240
SGTTGKPKGV QRDVGGYAVA LATSMDTIFG GKAGGVFFCA SDIGWVVGHS YIVYAPLLAG  300
MATIVYEGLP TYPDCGVWWK IVEKYQVNRM FSAPTAIRVL KKFPTAQIRN HDLSSLEALY  360
LAGEPLDEPT ASWVTETLGV PVIDNYWQTE SGWPIMALAR ALDDRPSRLG SPGVPMYGYN  420
VQLLNEVTGE PCGINEKGML VIEGPLPPGC IQTIWGDDAR FVKTYWSLFN RQVYATFDWG  480
IRDAEGYYFI LGRTDDVINI AGHRLGTREI EESISSYPNV AEVAVVGIKD ALKGQVAVAF  540
VIPKQSDTLA DREAARDEEN AIMALVDNQI GHFGRPAHVW FVSQLPKTRS GKMLRRTIQA  600
ICEGRDPGDL TTIDDPASLQ QIRQAIEE                                    628

SEQ ID NO: 46          moltype = AA  length = 714
FEATURE                Location/Qualifiers
source                 1..714
                       mol_type = protein
                       organism = Escherichia coli
SEQUENCE: 46
MSRIIMLIPT GTSVGLTSVS LGVIRAMERK GVRLSVFKPI AQPRTGGDAP DQTTTIVRAN  60
SSTTTAAEPL KMSYVEGLLS SNQKDVLMEE IVANYHANTK DAEVVLVEGL VPTRKHQFAQ  120
SLNYEIAKTL NAEIVFVMSQ GTDTPEQLKE RIELTRNSFG GAKNTNITGV IVNKLNAPVD  180
EQGRTRPDLS EIFDDSSKAK VNNVDPAKLQ ESSPLPVLGA VPWSFDLIAT RAIDMARHLN  240
ATIINEGDIN TRRVKSVTFC ARSIPHMLEH FRAGSLLVTS ADRPDVLVAA CLAAMNGVEI  300
GALLLTGGYE MDARISKLCE RAFATGLPVF MVNTNTWQTS LSLQSFNLEV PVDDHERIEK  360
VQEYVANYIN ADWIESLTAT SERSRRLSPP AFRYQLTELA RKAGKRIVLP EGDEPRTVKA  420
AAICAERGIA TCVLLGNPAE INRVAASQGV ELGAGIEIVD PEVVRESYVG RLVELRKNKG  480
MTETVAREQL EDNVVLGTLM LEQDEVDGLV SGAVHTTANT IRPPLQLIKT APGSSLVSSV  540
FFMLLPEQVY VYGDCAINPD PTAEQLAEIA IQSADSAAAF GIEPRVAMLS YSTGTSGAGS  600
DVEKVREATR LAQEKRPDLM IDGPLQYDAA VMADVAKSKA PNSPVAGRAT VFIFPDLNTG  660
NTTYKAVQRS ADLISIGPML QGMRKPVNDL SRGALVDDIV YTIALTAIQS AQQQ        714

SEQ ID NO: 47          moltype = AA  length = 421
FEATURE                Location/Qualifiers
source                 1..421
                       mol_type = protein
                       organism = Escherichia coli
SEQUENCE: 47
MSNNEFHQRR LSATPRGVGV MCNFFAQSAE NATLKDVEGN EYIDFAAGIA VLNTGHRHPD  60
LVAAVEQQLQ QFTHTAYQIV PYESYVTLAE KINALAPVSG QAKTAFFTTG AEAVENAVKI  120
ARAHTGRPGV IAFSGGFHGR TYMTMALTGK VAPYKIGFGP FPGSVYHVPY PSDLHGISTQ  180
DSLDAIERLF KSDIEAKQVA AIIFEPVQGE GGFNVAPKEL VAAIRRLCDE HGIVMIADEV  240
QSGFARTGKL FAMDHYADKP DLMTMAKSLA GGMPLSGVVG NANIMDAPAP GGLGGTYAGN  300
PLAVAAAHAV LNIIDKESLC ERANQLGQRL KNTLIDAKES VPAIAAVRGL GSMIAVEFND  360
PQTGEPSAAI AQKIQQRALA QGLLLLTCGA YGNVIRFLYP LTIPDAQFDA AMKILQDALS  420
D                                                                 421

SEQ ID NO: 48          moltype = AA  length = 714
FEATURE                Location/Qualifiers
source                 1..714
                       mol_type = protein
                       organism = Escherichia coli
SEQUENCE: 48
MSNVQEWQQL ANKELSRREK TVDSLVHQTA EGIAIKPLYT EADLDNLEVT GTLPGLPPYV  60
RGPRATMYTA QPWTIRQYAG FSTAKESNAF YRRNLAAGQK GLSVAFDLAT HRGYDSDNPR  120
VAGDVGKAGV AIDTVEDMKV LFDQIPLDKM SVSMTMNGAV LPVLAFYIVA AEEQGVTPDK  180
LTGTIQNDIL KEYLCRNTYI YPPKPSMRII ADIIAWCSGN MPRFNTISIS GYHMGEAGAN  240
CVQQVAFTLA DGIEYIKAAI SAGLKIDDFA PRLSFFFGIG MDLFMNVAML RAARYLWSEA  300
VSGFGAQDPK SLALRTHCQT SGWSLTEQDP YNNVIRTTIE ALAATLGGTQ SLHTNAFDEA  360
LGLPTDFSAR IARNTQIIIQ EESELCRTVD PLAGSYYIES LTDQIVKQAR AIIQQIDEAG  420
GMAKAIEAGL PKRMIEEASA REQSLIDQGK RVIVGVNKYK LDHEDETDVL EIDNVMVRNE  480
QIASLERIRA TRDDAAVTAA LNALTHAAQH NENLLAAAVN AARVRATLGE ISDALEVAFD  540
```

-continued

```
RYLVPSQCVT GVIAQSYHQS EKSASEFDAI VAQTEQFLAD NGRRPRILIA KMGQDGHDRG  600
AKVIASAYSD LGFDVDLSPM FSTPEEIARL AVENDVHVVG ASSLAAGHKT LIPELVEALK  660
KWGREDICVV AGGVIPPQDY AFLQERGVAA IYGPGTPMLD SVRDVLNLIS QHHD        714

SEQ ID NO: 49          moltype = AA  length = 588
FEATURE                Location/Qualifiers
source                 1..588
                       mol_type = protein
                       organism = Escherichia coli
SEQUENCE: 49
MKLPVREFDA VVIGAGGAGM RAALQISQSG QTCALLSKVF PTRSHTVSAQ GGITVALGNT  60
HEDNWEWHMY DTVKGSDYIG DQDAIEYMCK TGPEAILELE HMGLPFSRLD DGRIYQRPFG  120
GQSKNFGGEQ AARTAAAADR TGHALLHTLY QQNLKNHTTI FSEWYALDLV KNQDGAVVGC  180
TALCIETGEV VYFKARATVL ATGGAGRIYQ STTNAHINTG DGVGMAIRAG VPVQDMEMWQ  240
FHPTGIAGAG VLVTEGCRGE GGYLLNKHGE RFMERYAPNA KDLAGRDVVA RSIMIEIREG  300
RGCDGPWGPH AKLKLDHLGK EVLESRLPGI LELSRTFAHV DPVKEPIPVI PTCHYMMGGI  360
PTKVTGQALT VNEKGEDVVV PGLFAVGEIA CVSVHGANRL GGNSLLDLVV FGRAAGLHLQ  420
ESIAEQGALR DASESDVEAS LDRLNRWNNN RNGEDPVAIR KALQECMQHN FSVFREGDAM  480
AKGLEQLKVI RERLKNARLD DTSSEFNTQR VECLELDNLM ETAYATAVSA NFRTESRGAH  540
SRFDFPDRDD ENWLCHSLYL PESESMTRRS VNMEPKLRPA FPPKIRTY               588

SEQ ID NO: 50          moltype = AA  length = 388
FEATURE                Location/Qualifiers
source                 1..388
                       mol_type = protein
                       organism = Escherichia coli
SEQUENCE: 50
MNLHEYQAKQ LFARYGLPAP VGYACTTPRE AEEAASKIGA GPWVVKCQVH AGGRGKAGGV  60
KVVNSKEDIR AFAENWLGKR LVTYQTDANG QPVNQILVEA ATDIAKELYL GAVVDRSSRR  120
VVFMASTEGG VEIEKVAEET PHLIHKVALD PLTGPMPYQG RELAFKLGLE GKLVQQFTKI  180
FMGLATIFLE RDLALIEINP LVITKQGDLI CLDGKLGADG NALFRQPDLR EMRDQSQEDP  240
REAQAAQWEL NYVALDGNIG CMVNGAGLAM GTMDIVKLHG GEPANFLDVG GGATKERVTE  300
AFKIILSDDK VKAVLVNIFG GIVRCDLIAD GIIGAVAEVG VNVPVVVRLE GNNAELGAKK  360
LADSGLNIIA AKGLTDAAQQ VVAAVEGK                                     388

SEQ ID NO: 51          moltype = AA  length = 289
FEATURE                Location/Qualifiers
source                 1..289
                       mol_type = protein
                       organism = Escherichia coli
SEQUENCE: 51
MSILIDKNTK VICQGFTGSQ GTFHSEQAIA YGTKMVGGVT PGKGGTTHLG LPVFNTVREA  60
VAATGATASV IYVPAPFCKD SILEAIDAGI KLIITITEGI PTLDMLTVKV KLDEAGVRMI  120
GPNCPGVITP GECKIGIQPG HIHKPGKVGI VSRSGTLTYE AVKQTTDYGF GQSTCVGIGG  180
DPIPGSNFID ILEMFEKDPQ TEAIVMIGEI GGSAEEEAAA YIKEHVTKPV VGYIAGVTAP  240
KGKRMGHAGA IIAGGKGTAD EKFAALEAAG VKTVRSLADI GEALKTVLK              289

SEQ ID NO: 52          moltype = AA  length = 286
FEATURE                Location/Qualifiers
source                 1..286
                       mol_type = protein
                       organism = Escherichia coli
SEQUENCE: 52
MSQALKNLLT LLNLEKIEEG LFRGQSEDLG LRQVFGGQVV GQALYAAKET VPEERLVHSF  60
HSYFLRPGDS KKPIIYDVET LRDGNSFSAR RVAAIQNGKP IFYMTASFQA PEAGFEHQKT  120
MPSAPAPDGL PSETQIAQSL AHLLPPVLKD KFICDRPLEV RPVEFHNPLK GHVAEPHRQV  180
WIRANGSVPD DLRVHQYLLG YASDLNFLPV ALQPHGIGFL EPGIQIATID HSMWFHRPFN  240
LNEWLLYSVE STSASSARGF VRGEFYTQDG VLVASTVQEG VMRNHN                 286

SEQ ID NO: 53          moltype = AA  length = 134
FEATURE                Location/Qualifiers
source                 1..134
                       mol_type = protein
                       organism = Escherichia coli
SEQUENCE: 53
MNTTLFRWPV RVYYEDTDAG GVVYHASYVA FYERARTEML RHHHFSQQAL MAERVAFVVR  60
KMTVEYYAPA RLDDMLEIQT EITSMRGTSL VFTQRIVNAE NTLLNEAEVL VVCVDPLKMK  120
PRALPKSIVA EFKQ                                                    134

SEQ ID NO: 54          moltype = AA  length = 132
FEATURE                Location/Qualifiers
source                 1..132
                       mol_type = protein
                       organism = Escherichia coli
SEQUENCE: 54
MSTTHNVPQG DLVLRTLAMP ADTNANGDIF GGWLMSQMDI GGAILAKEIA HGRVVTVRVE  60
GMTFLRPVAV GDVVCCYARC VQKGTTSVSI NIEVWVKKVA SEPIGQRYKA TEALFKYVAV  120
DPEGKPRALP VE                                                      132
```

-continued

```
SEQ ID NO: 55          moltype = AA  length = 331
FEATURE                Location/Qualifiers
source                 1..331
                       mol_type = protein
                       organism = Escherichia coli
SEQUENCE: 55
MINEATLAES IRRLRQGERA TLAQAMTLVE SRHPRHQALS TQLLDAIMPY CGNTLRLGVT  60
GTPGAGKSTF LEAFGMLLIR EGLKVAVIAV DPSSPVTGGS ILGDKTRMND LARAEAAFIR  120
PVPSSGHLGG ASQRARELML LCEAAGYDVV IVETVGVGQS ETEVARMVDC FISLQIAGGG  180
DDLQGIKKGL MEVADLIVIN KDDGDNHTNV AIARHMYESA LHILRRKYDE WQPRVLTCSA  240
LEKRGIDEIW HAIIDFKTAL TASGRLQQVR QQQSVEWLRK QTEEEVLNHL FANEDFDRYY  300
RQTLLAVKNN TLSPRTGLRQ LSEFIQTQYF D                                331

SEQ ID NO: 56          moltype = AA  length = 261
FEATURE                Location/Qualifiers
source                 1..261
                       mol_type = protein
                       organism = Escherichia coli
SEQUENCE: 56
MSYQYVNVVT INKVAVIEFN YGRKLNALSK VFIDDLMQAL SDLNRPEIRC IILRAPSGSK  60
VFSAGHDIHE LPSGGRDPLS YDDPLRQITR MIQKFPKPII SMVEGSVWGG AFEMIMSSDL  120
IIAASTSTFS MTPVNLGVPY NLVGIHNLTR DAGFHIVKEL IFTASPITAQ RALAVGILNH  180
VVEVEELEDF TLQMAHHISE KAPLAIAVIK EELRVLGEAH TMNSDEFERI QGMRRAVYDS  240
EDYQEGMNAF LEKRKPNFVG H                                          261

SEQ ID NO: 57          moltype = AA  length = 492
FEATURE                Location/Qualifiers
source                 1..492
                       mol_type = protein
                       organism = Escherichia coli
SEQUENCE: 57
METQWTRMTA NEAAEIIQHN DMVAFSGFTP AGSPKALPTA IARRANEQHE AKKPYQIRLL  60
TGASISAAAD DVLSDADAVS WRAPYQTSSG LRKKINQGAV SFVDLHLSEV AQMVNYGFFG  120
DIDVAVIEAS ALAPDGRVWL TSGIGNAPTW LLRAKKVIIE LNHYHDPRVA ELADIVIPGA  180
PPRRNSVSIF HAMDRVGTRY VQIDPKKIVA VVETNLPDAG NMLDKQNPMC QQIADNVVTF  240
LLQEMAHGRI PPEFLPLQSG VGNINNAVMA RLGENPVIPP FMMYSEVLQE SVVHLLETGK  300
ISGASASSLT ISADSLRKIY DNMDYFASRI VLRPQEISNN PEIIRRLGVI ALNVGLEFDI  360
YGHANSTHVA GVDLMNGIGG SGDFERNAYL SIFMAPSIAK EGKISTVVPM CSHVDHSEHS  420
VKVIITEQGI ADLRGLSPLQ RARTIIDNCA HPMYRDYLHR YLENAPGGHI HHDLSHVFDL  480
HRNLIATGSM LG                                                    492

SEQ ID NO: 58          moltype = AA  length = 155
FEATURE                Location/Qualifiers
source                 1..155
                       mol_type = protein
                       organism = Escherichia coli
SEQUENCE: 58
MSAVLTAEQA LKLVGEMFVY HMPFNRALGM ELERYEKEFA QLAFKNQPMM VGNWAQSILH  60
GGVIASALDV AAGLVCVGST LTRHETISED ELRQRLSRMG TIDLRVDYLR PGRGERFTAT  120
SSLLRAGNKV AVARVELHNE EQLYIASATA TYMVG                            155

SEQ ID NO: 59          moltype = AA  length = 661
FEATURE                Location/Qualifiers
source                 1..661
                       mol_type = protein
                       organism = Escherichia coli
SEQUENCE: 59
MNNSRLFRLS RIVIALTAAS GMMVNTANAK EEAKAATQYT QQVNQNYAKS LPFSDRQDFD  60
DAQRGFIAPL LDEGILRDAN GKVYYRADDY KFDINAAAPE TVNPSLWRQS QINGISGLFK  120
VTDKMYQVRG QDISNITFVE GEKGIIVIDP LVTPPAAKAA LDLYFQHRPQ KPIVAVIYTH  180
SHTDHYGGVK GIISEADVKS GKVQVIAPAG FMDEAISENV LAGNIMSRRA LYSYGLLLPH  240
NAQGNVGNGL GVTLATGDPS IIAPTKTIVR TGEKMIIDGL EFDFLMTPGS EAPAEMHFYI  300
PALKALCTAE NATHTLHNFY TLRGAKTRDT SKWTEYLNET LDMWGNDAEV LFMPHTWPVW  360
GNKHINDYIG KYRDTIKYIH DQTLHLANQG YTMNEIGDMI KLPPALANNW ASRGYYGSVS  420
HNARAVYNFY LGYYDGNPAN LHPYGQVEMG KRYVQALGGS ARVINLAQEA NKQGDYRWSA  480
ELLKQVIAAN PGDQVAKNLQ ANNFEQLGYQ AESATWRGFY LTGAKELREG VHKFSHGTTG  540
SPDTIRGMSV EMLFDFMAVR LDSAKAAGKN ISLNFNMSNG DNLNLTLNDS VLNYRKTLQP  600
QADASFYISR EDLHAVLTGQ AKMADLVKAK KAKIIGNGAK LEEIIACLDN FDLWVNIVTP  660
N                                                                661

SEQ ID NO: 60          moltype = DNA  length = 1203
FEATURE                Location/Qualifiers
source                 1..1203
                       mol_type = genomic DNA
                       organism = Escherichia coli
SEQUENCE: 60
atgtcgagta agttagtact ggttctgaac tgcggtagtt cttcactgaa atttgccatc  60
atcgatgcag taaatggtga agagtacctt tctggtttag ccgaatgttt ccacctgccc  120
gaagcacgta tcaaatggaa aatggacggc aataaacagg aagcggcttt aggtgcaggc  180
```

-continued

```
gccgctcaca gcgaagcgct caactttatc gttaatacta ttctggcaca aaaaccagaa  240
ctgtctgcgc agctgactgc tatcggtcac cgtatcgtac acggcggcga aaagtatacc  300
agctccgtag tgatcgatga gtctgttatt cagggtatca aagatgcagc ttcttttgca  360
ccgctgcaca acccggctca cctgatcggt atcgaagaag ctctgaaatc tttcccacag  420
ctgaaagaca aaaacgttgc tgtatttgac accgcgttcc accagactat gccggaagag  480
tcttacctct acgccctgcc ttacaacctg tacaaagagc acggcatccg tcgttacggc  540
gcgcacggca ccagccactt ctatgtaacc caggaagcgg caaaaatgct gaacaaaccg  600
gtagaagaac tgaacatcat cacctgccac ctgggcaacg gtggttccgt ttctgctatc  660
cgcaacggta aatgcgttga cacctctatg ggcctgaccc cgctggaagg tctggtcatg  720
ggtacccgtt ctggtgatat cgatccggcg atcatcttcc acctgcacga caccctgggc  780
atgagcgttg acgcaatcaa caaactgctg accaaagagt ctggcctgct gggtctgacc  840
gaagtgacca gcgactgccg ctatgttgaa gacaactacg cgacgaaaga agacgcgaag  900
cgcgcaatgg acgtttactg ccaccgcctg gcgaaataca tcggtgccta cactgcgctg  960
atggatggtc gtctggacgc tgttgtattc actggtggta tcggtgaaaa tgccgcaatg  1020
gttcgtgaac tgtctctggg caaactgggc gtgctgggct ttgaagttga tcatgaacgc  1080
aacctggctg cacgtttcgg caaatctggt ttcatcaaca aagaaggtac ccgtcctgcg  1140
gtggttatcc caaccaacga agaactggtt atcgcgcaag acgcgagccg cctgactgcc  1200
tga                                                                1203
```

```
SEQ ID NO: 61          moltype = DNA  length = 1959
FEATURE                Location/Qualifiers
source                 1..1959
                       mol_type = genomic DNA
                       organism = Escherichia coli
SEQUENCE: 61
atgagccaaa ttcacaaaca caccattcct gccaacatcg cagaccgttg cctgataaac  60
cctcagcagt acgaggcgat gtatcaacaa tctattaacg tacctgatac cttctggggc  120
gaacagggaa aaattcttga ctggatcaaa ccttaccaga aggtgaaaaa cacctccttt  180
gcccccggta atgtgtccat taaatggtac gaggacggca cgctgaatct ggcggcaaac  240
tgccttgacc gccatctgca agaaaacggc gatcgtaccg ccatcatctg ggaaggcgac  300
gacgccagcc agagcaaaca tatcagctat aaagagctgc accgcgacgt ctgccgcttc  360
gccaataccc tgctcgagct gggcattaaa aaaggtgatg tggtggcgat ttatatgccg  420
atggtgccgg aagccgcggt tgcgatgctg gcctgcgccc gcattggcgc ggtgcattcg  480
gtgattttcg gcggcttctc gccggaagcc gttgccgggc gcattattga ttccaactca  540
cgactggtga tcacttccga cgaaggtgtg cgtgccgggc gcagtattcc gctgaagaaa  600
aacgttgatg acgcgctgaa aaacccgaac gtcaccagcg tagagcatgt ggtggtactg  660
aagcgtactg gcgggaaaat tgactggcag gaagggcgcg acctgtggtg gcacgacctg  720
gttgagcaag cgagcgatca gcaccaggcg gaagagatga acgccgaaga tccgctgttt  780
attctctaca cctccggttc taccggtaag ccaaaaggtg tgctgcatac taccggcggt  840
tatctggtgt acgcggcgct gacctttaaa tatgtctttg attatcatcc gggtgatatc  900
tactggtgca ccgccgatgt gggctgggtg accggacaca gttacttgct gtacggcccg  960
ctggcctgcg gtgcgaccac gctgatgttt gaaggcgtac ccaactggcc gacgcctgcc  1020
cgtatggcgc aggtggtgga caagcatcag gtcaatattc tctataccgc acccacggcg  1080
atccgcgcgc tgatggcgga aggcgataaa gcgatcgaag gcaccgaccg ttcgtcgctg  1140
cgcattctcg gttccgtggg cgagccaatt aacccggaag cgtgggagtg gtactggaaa  1200
aaaatcggca acgagaaatg tccggtggtc gatacctggt ggcagaccga aaccggcggt  1260
ttcatgatca ccccgctgcc tggcgctacc gagctgaaag ccggttcggc aacacgtccg  1320
ttcttcggcg tgcaaccggc gctggtcgat aacgaaggta acccgctgga gggggccacc  1380
gaaggtagcc tggtaatcac cgactcctgg ccgggtcagg cgcgtacgct gtttggcgat  1440
cacgaacgtt ttgaacagac ctacttctcc accttcaaaa atatgtattt cagcggcgac  1500
ggcgcgcgtc gcgatgaaga tggctattac tggataaccg ggcgtgtgga cgacgtgctg  1560
aacgtctccg gtcaccgtct ggggacggca gagattgagt cggcgctggt ggcgcatccg  1620
aagattgccg aagccgccgt agtaggtatt ccgcacaata ttaaaggtca ggcgatctac  1680
gcctacgtca cgcttaatca cggggaggaa ccgtcaccag aactgtacgc agaagtccgc  1740
aactgggtgc gtaaagagat tggcccgctg gcgacgccag acgtgctgca ctggaccgac  1800
tccctgccta aaacccgctc cggcaaaatt atgcgccgta ttctgcgcaa aattgcggcg  1860
ggcgatacca gcaacctggg cgatacctcg acgcttgccg atcctggcgt agtcgagaag  1920
ctgcttgaag agaagcaggc tatcgcgatg ccatcgtaa                         1959
```

```
SEQ ID NO: 62          moltype = DNA  length = 1719
FEATURE                Location/Qualifiers
source                 1..1719
                       mol_type = genomic DNA
                       organism = Bacillus subtilis
SEQUENCE: 62
atgaacttga aagcgttacc agcaatagag gggatcata acttaaaaaa ctatgaagaa  60
acgtaccggc attttgattg ggccgaggca gagaaacatt tctcttggca tgagacaggg  120
aaactgaatg cggcgtatga agcgattgac cgccatgccg aatcgtttcg aaaaaacaaa  180
gtagcgcttt attataaaga cgcaaaaagg gatgaaaaat acacatttaa agaaatgaag  240
gaagaatcaa acagagccgg gaatgtgctg agacggtatg gaaatgtgga aaaaggggac  300
cgcgtttta tttttatgcc gagatcaccc gagctttatt ttattatgct tggcgcaatc  360
aaaattggcg ccatcgccgg gccgctgttc gaagcattta tggagggagc ggtgaaagac  420
cggcttgaaa acagtgaggc aaaggttgtt gtcacaacgc ctgagctgct ggagagaata  480
ccggtagaca aactgcctca cttgcagcat gtcttcgtag tcgggggaga ggctgagagc  540
ggcacgaata tcatcaatta tgatgaagca gcgaaacagg aaagcacaag attggatatc  600
gaatggatgg ataaaaaaga cggctttctg cttcactata catcaggttc cactggtacg  660
ccaaagggcg tgttgcatgt ccatgaagcg atgattcagc aatatcaaac aggaaagtgg  720
gtccttgatt taaaggaaga agacatttat tggtgcacgg ctgatccagg ctgggtgaca  780
ggtacggtat acggcatttt tgcaccgtgg ctgaacggag cgacaaatgt catcgtcggc  840
```

-continued

```
ggacgtttca gcccggaaag ctggtatgga acgattgaac agcttggcgt caatgtctgg  900
tacagcgcgc cgacagcttt tcggatgctg atgggagcgg gagatgaaat ggctgcgaaa  960
tatgatctaa cttcactccg gcatgtgctc agtgtcggtg agccgctaaa tccggaagtc  1020
atcagatggg gacataaagt ttttaacaaa cgaatccatg atacctggtg gatgaccgaa  1080
acgggcagtc agctcatctg caactatcct tgcatggata ttaaaccggg ttcaatgggt  1140
aagccgattc caggagtgga ggcagcgatc gttgacaatc aaggcaacga gctaccgccg  1200
taccgaatgg gcaatctcgc catcaaaaag ggctggcctt ccatgatgca taccatttgg  1260
aataaccctg aaaagtatga atcgtatttc atgccgggcg gctggtatgt gtctggggat  1320
tctgcttaca tggatgaaga gggatacttt tggttccaag gcagagttga tgacgtcatc  1380
atgacctccg gtgagcgcgt cggcccattt gaagtggaaa gcaagcttgt cgaacatccg  1440
gctattgcag aagcaggcgt tatcggaaag cctgacccgg tgcgtggaga aatcattaaa  1500
gcctttattg cactcaggga aggatttgag ccgtctgata aactgaaaga agagatccgc  1560
ctatttgtaa agcagggtct tgcagcccat gcggctccgc gtgagatcga atttaaagat  1620
aagcttccga aaaccagaag cggaaagatc atgaggcgcg tgctgaaggc atgggagctt  1680
aatctgccgg ctggagatct gtcaacaatg gaggattaa                         1719

SEQ ID NO: 63           moltype = DNA  length = 651
FEATURE                 Location/Qualifiers
source                  1..651
                        mol_type = genomic DNA
                        organism = Escherichia coli
SEQUENCE: 63
atggatgcga aacaacgtat tgcgcgccgt gtggcgcaag agcttcgtga tggtgacatc  60
gttaacttag ggatcggttt acccacaatg gtcgccaatt atttaccgga gggtattcat  120
atcactctgc aatcggaaaa cggcttcctc ggtttaggcc cggtcacgac agcgcatcca  180
gatctggtga acgctggcgg gcaaccgtgc ggtgtttttac ccggtgcagc catgtttgat  240
agcgccatgt catttgcgct aatccgtggc ggtcatattg atgcctgcgt gctcggcggt  300
ttgcaagtag acgaagaagc aaacctcgcg aactgggtag tgcctgggaa aatggtgccc  360
ggtatgggtg gcgcgatgga tctggtgacc gggtcgcgca aagtgatcat cgccatggaa  420
cattgcgcca aagatggttc agcaaaaatt ttgcgccgct gcaccatgcc actcactgcg  480
caacatgcgg tgcatatgct ggttactgaa ctggctgtct ttcgttttat tgacggcaaa  540
atgtggctca ccgaaattgc cgacgggtgt gatttagcca ccgtgcgtgc caaaacagaa  600
gctcggtttg aagtcgccgc cgatctgaat acgcaacggg gtgatttatg a           651

SEQ ID NO: 64           moltype = DNA  length = 663
FEATURE                 Location/Qualifiers
source                  1..663
                        mol_type = genomic DNA
                        organism = Escherichia coli
SEQUENCE: 64
atgaaaacaa aattgatgac attacaagac gccaccggct tctttcgtga cggcatgacc  60
atcatggtgg gcggatttat ggggattggc actccatccc gcctggttga agcattactg  120
gaatctggtg ttcgcgacct gacattgata gccaatgata ccgcgtttgt tgataccggc  180
atcggtccgc tcatcgtcaa tggtcgagtc cgcaaagtga ttgcttcaca tatcggcacc  240
aacccggaaa caggtcggcg catgatatct ggtgagatgg acgtcgttct ggtgccgcaa  300
ggtacgctaa tcgagcaaat tcgctgtggt ggagctggac ttggtggttt tctcacccca  360
acgggtgtcg gcaccgtcgt agaggaaggc aaacagacac tgacactcga cggtaaaacc  420
tggctgctcg aacgcccact gcgcgccgac ctggcgctaa ttcgcgctca tcgttgcgac  480
acacttggca acctgaccta tcaacttagc gcccgcaact ttaacccccct gatagccctt  540
gcggctgata tcacgctggt agagccagat gaactggtcg aaaccggcga gctgcaacct  600
gaccatattg tcacccctgg tgccgttatc gaccacatca tcgtttcaca ggagagcaaa  660
taa                                                                663

SEQ ID NO: 65           moltype = DNA  length = 1323
FEATURE                 Location/Qualifiers
source                  1..1323
                        mol_type = genomic DNA
                        organism = Escherichia coli
SEQUENCE: 65
atgattggtc gcatatcgcg ttttatgacg cgttttgtca gccggtggct tcccgatcca  60
ctgatctttg ccatgttgct gacattgcta acattcgtga tcgcgctttg gttaacacca  120
caaacgccga tcagcatggt gaaaatgtgg ggtgacggtt tctggaactt gctggcgttt  180
ggtatgcaga tggcgcttat catcgttacc ggtcatgccc ttgccagctc tgctccggtg  240
aaaagtttgc tgcgtactgc cgcctccgcc gcaaagacgc ccgtacaggg cgtcatgctg  300
gtcactttct tcggttcagt cgcttgtgtc atcaactggg gatttggttt ggttgtcggc  360
gcaatgtttg cccgtgaagt cgcccggcga gtccccggtt ctgattatcc gttgctcatt  420
gcctgcgcct acattggttt tctcacctgg ggtggcggct tctctggatc aatgcctctg  480
ttggctgcaa caccgggcaa cccggttgag catatcgccg ggctgatccc ggtgggcgat  540
actctgttca gtggttttaa cattttcatc actgtggcgt tgattgtggt gatgccattt  600
atcacccgca tgatgatgcc aaaaccgtct gacgtggtga gtatcgatcc aaaactactc  660
atggaagagg ctgattttca aaagcagcta ccgaaagatg ccccaccatc cgagcgactg  720
gaagaaagcc gcattctgac gttgatcatc ggcgcactcg gtatcgctta ccttgcgatg  780
tacttcagcg aacatggctt caacatcacc atcaataccg tcaacctgat gtttatgatt  840
gcgggtctgc tgctacataa aacgccaatg gcttatatgc gtgctatcag cgcggcagca  900
cgcagtactg ccggtattct ggtgcaattc cccttctacg ctgggatcca actgatgatg  960
gagcattccg gtctgggcgg actcattacc gaattcttca tcaatgttgc gaacaaagac  1020
accttcccgg taatgacctt ttttagttct gcactgatta acttcgccgt tccgtctggc  1080
ggcggtcact gggttattca gggacctttc gtgataccgc cagcccaggc gctgggcgct  1140
gatctcggta aatcggtaat ggcgatcgcc tacggcgagc aatggatgaa catggcacaa  1200
```

-continued

```
ccattctggg cgctgccagc actggcaatc gccggactcg gtgtccgcga catcatgggc  1260
tactgcatca ctgccctgct cttctccggt gtcattttcg tcattggttt aacgctgttc  1320
tga                                                                1323

SEQ ID NO: 66          moltype = DNA  length = 1140
FEATURE                Location/Qualifiers
source                 1..1140
                       mol_type = genomic DNA
                       organism = Bacillus cereus
SEQUENCE: 66
atgcatttta aactatcaga agaacatgaa atgataagaa aaatggttcg agattttgct  60
aaaaatgaag tggcaccaac agcagctgag cgtgatgagg aagagcgatt tgatcgagaa  120
ttatttgatc aaatggcaga gcttggttta accggtattc cgtggcctga agagtacggt  180
ggaattggaa gcgattactt agcgtacgta atcgctattg aagaattatc ccgcgtttgt  240
gcttcaacag gcgtaacact gtccgcgcat acttcacttg caggatggcc aatttttaaa  300
tttgggacgg aagagcaaaa gcaaaagttt ttacgaccga tggctgaagg aaagaaaatt  360
ggtgcatacg gcttaacgga gccaggatct ggatcggatg ctggtggaat gaagacaatc  420
gcaaagagag atggagacca ttatatttta aatggatcaa aaattttcat tacaaatggc  480
ggtattgctg atatttacgt tgtttttgcg ctaactgatc ctgaatcaaa gcagcgcggt  540
acgagtgcat ttattgtaga aagtgataca ccgggatttt cagttgggaa gaaggagagc  600
aagctaggga ttcgctcttc accaacgact gaaattatgt ttgaagattg ccgtattcct  660
gtagagaatc tacttggaga agaggggcaa gggtttaaag ttgcgatgca aacattagat  720
ggaggtcgta acggtattgc ggcgcaagct gttggtattg cacaaggggc tttagatgct  780
tctgtagaat atgcaaggga gcgccatcaa tttggaaaac caattgcggc gcagcaaggg  840
attggcttta aacttgcgga tatggcaaca gatgtagaag cggcacgcct tttaacatat  900
caagcggctt ggcttgaatc agaagggctt ccgtatggaa aagagtcagc gatgtcaaaa  960
gtatttgcag gagatacagc gatgagggtg acgactgaag cggtgcaagt atttggtggt  1020
tacggttata cgaaagatta tccagtagag cgttatatgc gagatgcaaa aattacacaa  1080
atatatgaag gaacacaaga gattcagagg cttgtaattt ctcgtatgtt aacgaagtag  1140

SEQ ID NO: 67          moltype = DNA  length = 1185
FEATURE                Location/Qualifiers
source                 1..1185
                       mol_type = genomic DNA
                       organism = Cupriavidus necator
SEQUENCE: 67
atgacgcgtg aagtggtagt ggtaagcggt gtccgtaccg cgatcgggac ctttggcggc  60
agcctgaagg atgtggcacc ggcggagctg ggcgcactgg tggtgcgcga ggcgctggcg  120
cgcgcgcagg tgtcgggcga cgatgtcggc cacgtggtat tcggcaacgt gatccagacc  180
gagccgcgcg acatgtatct gggccgcgtc gcggccgtca acggcggggt gacgatcaac  240
gcccccgcgc tgaccgtgaa ccgcctgtgc ggctcgggcc tgcaggccat tgtcagcgcc  300
gcgcagacca tcctgctggg cgataccgac gtcgccatcg gcggcggcgc ggaaagcatg  360
agccgcgcac cgtacctggc gccggcagcg cgctggggcg cacgcatggg cgacgccggc  420
ctggtcgaca tgatgctggg tgcgctgcac gatcccttcc atcgcatcca catgggcgtg  480
accgccgaga atgtcgccaa ggaatacgac atctcgcgcg cgcagcagga cgaggccgcg  540
ctggaatcgc accgccgcgc ttcggcagcg atcaaggccg gctacttcaa ggaccagatc  600
gtcccggtgg tgagcaaggg ccgcaagggc gacgtgacct tcgacaccga cgagcacgtg  660
cgccatgacg ccaccatcga cgacatgacc aagctcaggc cggtcttcgt caaggaaaac  720
ggcacggtca cggccggcaa tgcctcgggc ctgaacgacg ccgccgccgc ggtggtgatg  780
atggagcgcg ccgaagccga gcgccgcggc ctgaagccgc tggcccgcct ggtgtcgtac  840
ggccatgccg gcgtggaccc gaaggccatg ggcatcggcc cggtgccggc gacgaagatc  900
gcgctggagc gcgccggcct gcaggtgtcg gacctggacg tgatcgaagc caacgaagcc  960
tttgccgcac aggcgtgcgc cgtgaccaag gcgctcggtc tggacccggc caaggttaac  1020
ccgaacggct cgggcatctc gctgggccac ccgatcggcg ccaccggtgc cctgatcacg  1080
gtgaaggcgc tgcatgagct gaaccgcgtg cagggccgct acgcgctggt gacgatgtgc  1140
atcggcggcg ggcagggcat tgccgccatc ttcgagcgta tctga                  1185

SEQ ID NO: 68          moltype = DNA  length = 2148
FEATURE                Location/Qualifiers
source                 1..2148
                       mol_type = genomic DNA
                       organism = Escherichia coli
SEQUENCE: 68
atgaacgtta ttgcaatatt gaatcacatg gggggtttatt ttaaagaaga acccatccgt  60
gaacttcatc gcgcgcttga acgtctgaac ttccagattg tttacccgaa cgaccgtgac  120
gacttattaa aactgatcga aaacaatgcg cgtctgtgcg gcgttatttt tgactgggat  180
aaatataatc tcgagctgtg cgaagaaatt agcaaaatga acgagaacct gccgttgtac  240
gcgttcgcta atacgtattc cactctcgat gtaagcctga atgacctgcg tttacagatt  300
agcttctttg aatatgcgct gggtgctgct gaagatattg ctaataagat caagcagacc  360
actgacgaat atatcaacac tattctgcct ccgctgacta aagcactgtt taaatatgtt  420
cgtgaaggta aatatacttt ctgtactcct ggtcacatgg gcggtactgc attccagaaa  480
agcccggtag gtagcctgtt ctatgatttc tttggtccga ataccatgaa atctgatatt  540
tccatttcag tatctgaact gggttctctg ctggatcaca gtggtccaca caaagaagca  600
gaacagtata tcgctcgcgt ctttaacgca gaccgcagct acatggtgac caacggtact  660
tccactgcga acaaaattgt tggtatgtac tctgctccag caggcagcac cattctgatt  720
gaccgtaact gccacaaatc gctgacccac ctgatgatga tgagcgatgt tacgccaatc  780
tatttccgcc cgacccgtaa cgcttacggt attcttggtg gtatcccaca gagtgaattc  840
cagcacgcta ccattgctaa gcgcgtgaaa gaaacaccaa acgcaacctg gccggtacat  900
gctgtaatta ccaactctac ctatgatggt ctgctgtaca acaccgactt catcaagaaa  960
```

-continued

```
acactggatg tgaaatccat ccactttgac tccgcgtggg tgccttacac caacttctca  1020
ccgatttacg aaggtaaatg cggtatgagc ggtggccgtg tagaagggaa agtgatttac  1080
gaaacccagt ccactcacaa actgctggcg gcgttctctc aggcttccat gatccacgtt  1140
aaaggtgacg taaacgaaga aacctttaac gaagcctaca tgatgcacac caccacttct  1200
ccgcactacg gtatcgtggc gtccactgaa accgctgcgg cgatgatgaa aggcaatgca  1260
ggtaagcgtc tgatcaacgg ttctattgaa cgtgcgatca aattccgtaa agagatcaaa  1320
cgtctgagaa cggaatctga tggctggttc tttgatgtat ggcagccgga tcatatcgat  1380
acgactgaat gctggccgct gcgttctgac agcacctggc acggcttcaa aaacatcgat  1440
aacgagcaca tgtatcttga cccgatcaaa gtcaccctgc tgactccggg gatggaaaaa  1500
gacggcacca tgagcgactt tggtattccg gccagcatcg tggcgaaata cctcgacgaa  1560
catggcatcg ttgttgagaa aaccggtccg tataacctgc tgttcctgtt cagcatcggt  1620
atcgataaga ccaaagcact gagcctgctg cgtgctctga ctgactttaa acgtgcgttc  1680
gacctgaacc tgcgtgtgaa aaacatgctg ccgtctctgt atcgtgaaga tcctgaattc  1740
tatgaaaaca tgcgtattca ggaactggct cagaatatcc acaaactgat tgttcaccac  1800
aatctgccgg atctgatgta tcgcgcattt gaagtgctgc cgacgatggt aatgactccg  1860
tatgctgcat tccagaaaga gctgcacggt atgaccgaag aagtttacct cgacgaaatg  1920
gtaggtcgta ttaacgccaa tatgatcctt ccgtacccgc cgggagttcc tctggtaatg  1980
ccgggtgaaa tgatcaccga agaaagccgt ccggttctgg agttcctgca gatgctgtgt  2040
gaaatcggcg ctcactatcc gggctttgaa accgatattc acggtgcata ccgtcaggct  2100
gatggccgct ataccgttaa ggtattgaaa gaagaaagca aaaaataa              2148
```

```
SEQ ID NO: 69           moltype = DNA  length = 1617
FEATURE                 Location/Qualifiers
source                  1..1617
                        mol_type = genomic DNA
                        organism = Clostridium kluyveri
SEQUENCE: 69
atgagtaaag ggataaagaa ttcacaattg aaaaaaaaga atgtaaaggc tagtaatgtg  60
gcagaaaaga ttgaagagaa agttgaaaaa acagataagg ttgttgaaaa ggcagctgag  120
gttacagaaa aacgaattag aaacttgaag cttcaggaaa aagttgtaac agcagatgtg  180
gcagctgata tgatagaaaa cggtatgatt gttgcaatta gcggatttac tccttccggg  240
tatcctaaag aagtacctaa agcattgact aaaaaagtta atgccttaga ggaagaattc  300
aaggtaacac tttatacagg ttcatctaca ggagccgata tagacggaga atgggcaaaa  360
gcaggaataa tagaaagaag aattccatat cagacaaatt ctgatatgag gaaaaaaata  420
aatgatggtt ctattaagta tgctgatatg catttaagcc atatggctca atatattaat  480
tattctgtaa ttcctaaagt agatatagct ataatagagg cagtagctat tacagaagaa  540
ggggatatta ttccttcaac aggaattgga aatacagcta cttttgtgga aaatgcagat  600
aaggtaatag tggaaattaa tgaggctcaa ccgcttgaat tggaaggtat ggcagatata  660
tatacattaa aaaaccctcc aagaagagag cccataccta tagttaatgc aggcaatagg  720
atagggacca catatgtgac ctgtggttct gaaaaaatat gcgctatagt gatgacaaat  780
acccaggata aaacaagacc tcttacagaa gtgtctcctg tatctcaggc tatatccgat  840
aatcttatag gatttttaaa taaagaggtt gaagagggaa aattacctaa gaacctgctt  900
cctatacagt caggagttgg aagtgtagca aatgcagttt tggccggact ttgtgaatca  960
aattttaaaa atttgagttg ttatacagaa gttatacagg attctatgct gaagcttata  1020
aaatgtggta aagcagatgt ggtgtcaggc acttccataa gtccttcacc ggagatgttg  1080
cctgagttca taaaggacat aaatttcttt agagaaaaga tagtattaag accacaggaa  1140
ataagtaata atccagagat agcaagaaga ataggagtta tatccataaa cactgctttg  1200
gaagtagata tatatggtaa tgtaaactcc actcatgtta tgggaagcaa aatgatgaat  1260
ggtataggcg gttctggaga ctttgccaga aatgcatatt tgactatatt cactacagag  1320
tctatcgcca aaaaaggaga tatatcatct atagttccta tggtatccca tgtggatcat  1380
acagaacatg atgtaatggt aattgttaca gaacagggag tagcagattt aagaggtctt  1440
tctcctaggg aaaaggccgt ggctataata gaaaattgtg ttcatcctga ttacaaggat  1500
atgcttatgg aatattttga agaggcttgt aagtcatcag gtggaaatac accacataat  1560
cttgaaaaag ctctttcctg gcatacaaaa tttataaaaa ctggtagtat gaaataa     1617
```

```
SEQ ID NO: 70           moltype = DNA  length = 708
FEATURE                 Location/Qualifiers
source                  1..708
                        mol_type = genomic DNA
                        organism = Escherichia coli
SEQUENCE: 70
atgtaccgtt atttgtctat tgctgcggtg gtactgagcg cagcattttc cggcccggcg  60
ttggccgaag gtatcaatag tttttctcag gcgaaagccg cggcggtaaa agtccacgct  120
gacgcgcccg gtacgtttta ttgcggatgt aaaattaact ggcagggcaa aaaaggcgtt  180
gttgatctgc aatcgtgcgg ctatcaggtg cgcaaaaatg aaaaccgcgc cagccgcgta  240
gagtgggaac atgtcgttcc cgcctggcag ttcggtcacc agcgccagtg ctggcaggac  300
ggtggacgta aaaactgcgc taaagatccg gtctatcgca agatggaaag cgatatgcat  360
aacctgcagc cgtcagtcgg tgaggtgaat ggcgatcgcg gcaactttat gtacagccag  420
tggaatggcg gtgaaggcca gtacggtcaa tgcgccatga aggtcgattt caaagaaaaa  480
gctgccgaac caccagcgcg tgcacgcggt gccattgcgc gcacctactt ctatatgcgc  540
gaccaataca acctgacact ctctcgccag caaacgcagc tgttcaacgc atggaacaag  600
atgtatccgg ttaccgactg ggagtgcgag cgcgatgaac gcatcgcgaa ggtgcagggc  660
aatcataacc cgtatgtgca acgcgcttgc caggcgcgaa agagctaa              708
```

```
SEQ ID NO: 71           moltype = DNA  length = 2190
FEATURE                 Location/Qualifiers
source                  1..2190
                        mol_type = genomic DNA
                        organism = Escherichia coli
```

```
SEQUENCE: 71
atgctttaca aaggcgacac cctgtacctt gactggctgg aagatggcat tgccgaactg  60
gtatttgatg ccccaggttc agttaataaa ctcgacactg cgaccgtcgc cagcctcggc  120
gaggccatcg gcgtgctgga acagcaatca gatctaaaag ggctgctgct gcgttcgaac  180
aaagcagcct ttatcgtcgg tgctgatatc accgaatttt tgtccctgtt cctcgttcct  240
gaagaacagt taagtcagtg gctgcacttt gccaatagcg tgtttaatcg cctggaagat  300
ctgccggtgc cgaccattgc tgccgtcaat ggctatgcgc tgggcggtgg ctgcgaatgc  360
gtgctggcga ccgattatcg tctggcgacg ccggatctgc gcatcggtct gccggaaacc  420
aaactgggca tcatgcctgg ctttggcggt tctgtacgta tgccacgtat gctgggcgct  480
gacagtgcgc tggaaatcat tgccgccggt aaagatgtcg gcgcggatca ggcgctgaaa  540
atcggtctgg tggatggcgt agtcaaagca gaaaaactgg ttgaaggcgc aaaggcggtt  600
ttacgccagg ccattaacgg cgacctcgac tggaaagcaa aacgtcagcc gaagctggaa  660
ccactaaaac tgagcaagat tgaagccacc atgagcttca ccatcgctaa agggatggtc  720
gcacaaacag cggggaaaca ttatccggcc cccatcaccg cagtaaaaac cattgaagct  780
gcggcccgtt ttggtcgtga agaagcctta aacctggaaa acaaaagttt tgtcccgctg  840
gcgcatacca acgaagcccg cgcactggtc ggcattttcc ttaacgatca atatgtaaaa  900
ggcaaagcga agaaactcac caaagacgtt gaaaccccga aacaggccgc ggtgctgggt  960
gcaggcatta tgggcggcgg catcgcttac cagtctgcgt ggaaaggcgt gccggttgtc  1020
atgaaagata tcaacgacaa gtcgttaacc ctcggcatga ccgaagccgc gaaactgctg  1080
aacaagcagc ttgagcgcgg caagatcgat ggtctgaaac tggctggcgt gatctccaca  1140
atccacccaa cgctcgacta cgccggattt gaccgcgtgg atattgtggt agaagcggtt  1200
gttgaaaacc cgaaagtgaa aaaagccgta ctggcagaaa ccgaacaaaa agtacgccag  1260
gataccgtgc tggcgtctaa cacttcaacc attcctatca gcgaactggc caacgcgctg  1320
gaacgcccgg aaaacttctg cgggatgcac ttctttaacc cggtccaccg aatgccgttg  1380
gtagaaatta ttcgcggcga gaaaagctcc gacgaaacca tcgcgaaagt tgtcgcctgg  1440
gcgagcaaga tgggcaagac gccgattgtg gttaacgact gccccggctt ctttgttaac  1500
cgcgtgctgt tcccgtattt cgccggtttc agccagctgc tgcgcgacgg cgcggatttc  1560
cgcaagatcg acaaagtgat ggaaaaacag tttggctggc cgatgggccc ggcatatctg  1620
ctggacgttg tgggcattga taccgcgcat cacgctcagg ctgtcatggc agcaggcttc  1680
ccgcagcgga tgcagaaaga ttaccgcgat gccatcgacg cgctgtttga tgccaaccgc  1740
tttggtcaga agaacggcct cggtttctgg cgttataaag aagacagcaa aggtaagccg  1800
aagaaagaag aagacgccgc cgttgaagac ctgctggcag aagtgagcca gccgaagcgc  1860
gatttcagcg aagaagagat tatcgcccgc atgatgatcc cgatggtcaa cgaagtggtg  1920
cgctgtctgg aggaaggcat tatcgccact ccggcggaag cggatatggc gctggtctac  1980
ggcctgggct tccctccgtt ccacggcggc gcgttccgct ggctggacac cctcggtagc  2040
gcaaaatacc tcgatatggc acagcaatat cagcacctcg gcccgctgta tgaagtgccg  2100
gaaggtctgc gtaataaagc gcgtcataac gaaccgtact atcctccggt tgagccagcc  2160
cgtccggttg gcgacctgaa aacggcttaa                                   2190

SEQ ID NO: 72           moltype = DNA  length = 2445
FEATURE                 Location/Qualifiers
source                  1..2445
                        mol_type = genomic DNA
                        organism = Escherichia coli
SEQUENCE: 72
atgatgattt tgagtattct cgctacggtt gtcctgctcg gcgcgttgtt ctatcaccgc  60
gtgagcttat ttatcagcag tctgattttg ctcgcctgga cagccgccct cggcgttgct  120
ggtctgtggt cggcgtgggt actggtgcct ctggccatta tcctcgtgcc atttaacttt  180
gcgcctatgc gtaagtcgat gatttccgcg ccggtatttc gcggtttccg taaggtgatg  240
ccgccgatgt cgcgcactga gaaagaagcg attgatgcgg gcaccacctg gtgggagggc  300
gacttgttcc agggcaagcc ggactggaaa aagctgcata actatccgca gccgcgcctg  360
accgccgaag agcaagcgtt tctcgacggc ccggtagaag aagcctgccg gatggcgaat  420
gatttccaga tcacccatga gctggcggat ctgccgccgg agttgtgggc gtaccttaaa  480
gagcatcgtt tcttcgcgat gatcatcaaa aaagagtacg gcgggctgga gttctcggct  540
tatgcccagt ctcgcgtgct gcaaaaactc tccggcgtga gcgggatcct ggcgattacc  600
gtcggcgtgc caaactcatt aggcccgggc gaactgttgc aacattacgg cactgacgag  660
cagaaagatc actatctgcc gcgtctggcg cgtggtcagg agatcccctg ctttgcactg  720
accagcccgg aagcgggttc cgatgcgggc gcgattccgg acaccgggat tgtctgcatg  780
ggcgaatggc agggccagca ggtgctgggg atgcgtctga cctggaacaa acgctacatt  840
acgctggcac cgattgcgac cgtgcttggg ctggcgttta aactctccga cccggaaaaa  900
ttactcggcg gtgcagaaga tttaggcatt acctgtgcgc tgatcccaac caccacgccg  960
ggcgtggaaa ttggtcgtcg ccacttcccg ctgaacgtac cgttccagaa cggaccgacg  1020
cgcggtaaag atgtcttcgt gccgatcgat tacatcatcg gcgggccgaa aatggccggg  1080
caaggctggc ggatgctggt ggagtgcctc tcggtaggcc gcggcatcac cctgccttcc  1140
aactcaaccg gcggcgtgaa atcggtagcg ctggcaaccg gcgcgtatgc tcacattcgc  1200
cgtcagttca aaatctctat tggtaagatg gaagggattg aagagccgct ggcgcgtatt  1260
gccggtaatg cctacgtgat ggatgctgcg gcatcgctga ttacctacgg cattatgctc  1320
ggcgaaaaac ctgccgtgct gtcggctatc gttaagtatc actgtaccca ccgcgggcag  1380
cagtcgatta ttgatgcgat ggatattacc ggcggtaaag gcattatgct cgggcaaagc  1440
aacttcctgg cgcgtgctta ccagggcgca ccgattgcca tcaccgttga aggggctaac  1500
attctgaccc gcagcatgat gatcttcgga caaggagcga ttcgttgcca tccgtacgtg  1560
ctggaagaga tggaagcggc gaagaacaat gacgtcaacg cgttcgataa actgttgttc  1620
aaacatatcg gtcacgtcgg tagcaacaaa gttcgcagct tctggctggg cctgacgcgc  1680
ggtttaacca gcagcacgcc aaccggcgat gccactaaac gctactatca gcacctgaac  1740
cgcctgagcg ccaacctcgc cctgctttct gatgtctcga tggcagtgct gggcggcagc  1800
ctgaaacgtc gcgagcgcat ctcggcccgt ctgggggata ttttaagcca gctctacctc  1860
gcctctgccg tgctgaagcg ttatgacgac gaaggccgta atgaagccga cctgccgctg  1920
gtgcactggg gcgtacaaga tgcgctgtat caggctgaac aggcgatgga tgatttactg  1980
caaaacttcc cgaaccgcgt ggttgccggg ctgctgaatg tggtgatctt cccgaccgga  2040
```

-continued

```
cgtcattatc tggcaccttc tgacaagctg gatcataaag tggcgaagat tttacaagtg  2100
ccgaacgcca cccgttcccg cattggtcgc ggtcagtacc tgacgccgag cgagcataat  2160
ccggttggct tgctggaaga ggcgctggtg gatgtgattg ccgccgaccc aattcatcag  2220
cggatctgta aagagctggg taaaaacctg ccgtttaccc gtctggatga actggcgcac  2280
aacgcgctgg tgaaggggct gattgataaa gatgaagccg ctattctggt gaaagctgaa  2340
gaaagccgtc tgcgcagtat taacgttgat gactttgatc cggaagagct ggcgacgaag  2400
ccggtaaagt tgccggagaa agtgcggaaa gttgaagccg cgtaa                    2445

SEQ ID NO: 73          moltype = DNA  length = 2145
FEATURE                Location/Qualifiers
source                 1..2145
                       mol_type = genomic DNA
                       organism = Escherichia coli
SEQUENCE: 73
atggaaatga catcagcgtt taccettaat gttcgtctgg acaacattgc cgttatcacc  60
atcgacgtac cgggtgagaa aatgaatacc ctgaaggcgg agtttgcctc gcaggtgcgc  120
gccattatta agcaactccg tgaaaacaaa gagttgcgag gcgtggtgtt tgtctccgct  180
aaaccggaca acttcattgc tggcgcagac atcaacatga tcggcaactg caaaacggcg  240
caagaagcgg aagctctggc gcggcagggc caacagttga tggcggagat tcatgctttg  300
cccattcagg ttatcgcggc tattcatggc gcttgcctgg gtggtgggct ggagttggcg  360
ctggcgtgcc acggtcgcgt ttgtactgac gatcctaaaa cggtgctcgg tttgcctgaa  420
gtacaacttg gattgttacc cggttcaggc ggcacccagc gtttaccgcg tctgataggc  480
gtcagcacag cattagagat gatcctcacc ggaaaacaac ttcgggcgaa acaggcatta  540
aagctggggc tggtggatga cgttgttccg cactccattc tgctggaagc cgctgttgag  600
ctggcaaaga aggagcgccc atcttcccgc cctctacctg tacgcgagcg tattctggcg  660
gggccgttag gtcgtgcgct gctgttcaaa atggtcggca agaaaacaga acacaaaact  720
caaggcaatt atccggcgac agaacgcatc ctggaggttg ttgaaacggg attagcgcag  780
ggcaccagca gcggttatga cgccgaagct cgggcgtttg gcgaactggc gatgacgcca  840
caatcgcagg cgctgcgtag tatctttttt gccagtacgg acgtgaagaa agatcccggc  900
agtgatgcgc cgcctgcgcc attaaacagc gtggggattt taggtggtgg cttgatgggc  960
ggcggtattg cttatgtcac tgcttgtaaa gcggggattc cggtcagaat taaagatatc  1020
aacccgcagg gcataaatca tgcgctgaag tacagttggg atcagctgga gggcaaagtt  1080
cgccgtcgtc atctcaaagc cagcgaacgt gacaaacagc tggcattaat ctccggaacg  1140
acggactatc gcggctttgc ccatcgcgat ctgattattg aagcggtgtt tgaaaatctc  1200
gaattgaaac aacagatggt ggcggaagtt gagcaaaatt gcgccgctca taccatcttt  1260
gcttcgaata cgtcatcttt accgattggt gatatcgccg ctcacgccac gcgacctgag  1320
caagttatcg gcctgcattt cttcagtccg gtggaaaaaa tgccgctggt ggagattatt  1380
cctcatgcgg ggacatcggc gcaaaccatc gctaccacag taaaactggc gaaaaaacag  1440
ggtaaaacgc caattgtcgt gcgtgacaaa gccggttttt acgtcaatcg catcttagcg  1500
ccttacatta atgaagctat ccgcatgttg acccaaggtg aacgggtaga gcacattgat  1560
gccgcgctag tgaaatttgg ttttccggta ggcccaatcc aacttttgga tgaggtagga  1620
atcgacaccg ggactaaaat tattcctgta ctggaagccg cttatggaga acgttttagc  1680
gcgcctgcaa atgttgtttc ttcaattttg aacgacgatc gcaaaggcag aaaaaatggc  1740
cggggtttct atctttatgg tcagaaaggg cgtaaaagca aaaaacaggt cgatcccgcc  1800
atttaccccgc tgattggcac acaagggcag gggcgaatct ccgcaccgca ggttgctgaa  1860
cggtgtgtga tgttgatgct gaatgaagca gtacgttgtg ttgatgagca ggttatccgt  1920
agcgtgcgtg acggggatat tggcgcggta tttggcattg gttttccgcc atttctcggt  1980
ggaccgttcc gctatatcga ttctctcggc gcgggcgaag tggttgcaat aatgcaacga  2040
cttgccacgc agtatggttc ccgttttacc ccttgcgagc gtttggtcga gatgggcgcg  2100
cgtggggaaa gtttttggaa aacaactgca actgacctgc aataa                    2145

SEQ ID NO: 74          moltype = DNA  length = 1347
FEATURE                Location/Qualifiers
source                 1..1347
                       mol_type = genomic DNA
                       organism = Pseudomonas citronellolis
SEQUENCE: 74
atgaaccagc aagtgaacgt agcgccgtcg gccgccgccg acctgaacct gaaggcccac  60
tggatgccct tcagcgccaa ccgcaacttc cacaaggacc cgcgcatcat cgtggccgcc  120
gagggcagct ggctggtgga cgacaagggc cggcgcatct acgacagcct gtccggcctg  180
tggacctgcg gcgccggtca ctcgcgcaag gaaatcgccg acgcggtggc caagcagatt  240
ggcaccctcg actactcccc gggcttccag tacggccacc cgctgtcctt ccagctggcc  300
gagaagatcg cccagatgac ccccggcacc ctcgaccacg tgttcttcac cggctccggt  360
tccgagtgcg ccgacacctc gatcaagatg gcccgcgcct actggcgcat caaaggccag  420
gcgcagaaga ccaagctgat cggccgcgcc cgtggctacc acggcgtgaa cgtcgccggc  480
acctccctgg gcggcatcgg cggcaaccgc aagatgttcg gcccgctgat ggacgtcgac  540
cacctgccgc acaccctgca gccgggcatg gcctttacca agggtgcggc cgagaccggc  600
ggcgtcgagc tggccaacga actgctgaag ctgatcgagc tgcacgacgc ctccaacatc  660
gccgcggtga tcgtcgagcc gatgtccggc tccgccggcg tgatcgtgcc gccgaagggc  720
tacctgcagc gcctgcggga aatctgcgac gccaacgaca tcctgctgat cttcgacgaa  780
gtcatcaccg ccttcggccg catgggcaag gccaccggcg ccgaatactt cggcgtgacc  840
ccggacatca tgaacgtcgc caagcaggtc accaacggcg ccgtgcccat gggcgcggtg  900
atcgccagca gcgaaatcta cgacaccttc atgaaccaga acctgccgga atacgcggtg  960
gagttcggcc atggctacac ctactccgcg cacccggtcg cctgcgccgc cggcatcgcc  1020
gcgctggacc tgctgcagaa ggaaaacctg atccagcagt ccgccgaact ggcgccgcac  1080
ttcgagaagg ccctgcacgg cctcaagggc acgaagaacg tcatcgacat ccgcaactgc  1140
ggcctggccg gcgccatcca gatcgccgcc cgcgacggcg acgccatcgt ccgccccgttc  1200
gaagccagca tgaagctgtg gaaggaaggc ttctacgtgc gcttcggcgg cgacaccctg  1260
cagttcgggc cgaccttcaa cgccaagccc gaagacctcg accgcctgtt cgacgcggtc  1320
```

```
ggcgaagccc tcaacggggt ggcgtaa                                        1347

SEQ ID NO: 75          moltype = DNA  length = 1347
FEATURE                Location/Qualifiers
source                 1..1347
                       mol_type = other DNA
                       organism = synthetic construct
SEQUENCE: 75
atgaatcaac aggtaaatgt ggcccccagc gcggcagcag acttaaatct gaaagcgcat  60
tggatgcctt ttagcgccaa ccgcaacttc cacaaggacc cccgcatcat cgtagctgcc  120
gaaggatcgt ggctggtaga cgataaggga cgccgtatct acgactcatt gagtggcttg  180
tggacctgcg gcgcgggtca ctctcgtaag gaaattgccg acgcagtggc gaaacagatt  240
gggaccctgg actactcgcc agggtttcaa tatggccacc ctctgtcgtt tcagcttgca  300
gagaagattg cgcaaatgac gcctggcacg ctggatcatg tcttctttac aggaagtggg  360
agtgaatgcg cggacacatc tatcaaaatg gctcgcgcct actggcgcat caagggccaa  420
gcgcagaaga ccaagttgat cggccgtgct cgcggatatc acggcgtcaa cgtggccgga  480
acatcgcttg gaggtattgg gggaaaccgt aaaatgttcg gacccctgat ggatgtcgat  540
catttgcctc acacattaca acctggaatg gcattcacta agggcgcagc agaaacaggt  600
ggggtggagc ttgccaatga attgctgaag ttaattgagt tacatgatgc ttcgaatatc  660
gccgcagtga ttgtggagcc tatgtctggc agtgccggtg tgattgtgcc accaaaaggt  720
tatcttcagc gtttacgtga gatttgcgac gctaacgata tcctgttaat cttcgacgag  780
gtgattacag cttttggccg tatgggcaaa gcaacgggtg ccgagtattt tggagtaact  840
cccgatatca tgaacgtggc taagcaagta accaacgggg ccgttccgat gggagccgtt  900
atcgcctcct ctgaaattta tgacaccttc atgaaccaaa acttgcccga atacgccgtg  960
gaatttggac atggttatac ttacagcgct catccagtgg catgtgccgc cggcatcgcg  1020
gcgctggatc tgcttcaaaa agagaattta atccagcagt cggccgagct tgcacctcac  1080
ttcgaaaagg ccttacatgg cttaaagggc actaaaaacg ttatcgatat ccgcaactgt  1140
ggccttgctg gagcgattca aatcgcggcg cgcgacggag acgcgatcgt gcgccccttt  1200
gaggcgagca tgaagttgtg gaaggaaggc ttctacgtgc gtttcggcgg tgataccctg  1260
caatttggcc ctactttcaa cgccaaaccg gaagacttag atcgcctttt cgatgcagtt  1320
ggagaggcac tgaacggggt cgcttaa                                        1347

SEQ ID NO: 76          moltype = DNA  length = 1449
FEATURE                Location/Qualifiers
source                 1..1449
                       mol_type = genomic DNA
                       organism = Escherichia coli
SEQUENCE: 76
atgaaactta acgacagtaa cttattccgc cagcaggcgt tgattaacgg ggaatggctg  60
gacgccaaca atggtgaagc catcgacgtc accaatccgg cgaacggcga caagctgggt  120
agcgtgccga aaatgggcgc ggatgaaacc cgcgccgcta tcgacgccgc caaccgcgcc  180
ctgcccgcct ggcgcgcgct caccgccaaa gaacgcgcca ccattctgcg caactggttc  240
aatttgatga tggagcatca ggacgattta gcgcgcctga tgaccctcga acagggtaaa  300
ccactggccg aagcgaaagg cgaaatcagc tacgccgcct cctttattga gtggtttgcc  360
gaagaaggca aacgcattta tggcgacacc attcctggtc atcaggccga taaacgcctg  420
attgttatca agcagccgat tggcgtcacc gcggctatca cgccgtggaa cttcccggcg  480
gcgatgatta cccgcaaagc cggtccggcg ctggcagcag gctgcaccat ggtgctgaag  540
cccgccagtc agacgccgtt ctctgcgctg gcgctggcgg agctggcgat ccgcgcgggc  600
gttccggctg gggtatttaa cgtggtcacc ggttcggcgg gcgcggtcgg taacgaactg  660
accagtaacc cgctggtgcg caaactgtcg tttaccggtt cgaccgaaat tggccgccag  720
ttaatggaac agtgcgcgaa agacatcaag aaagtgtcgc tggagctggg cggtaacgcg  780
ccgtttatcg tctttgacga tgccgacctc gacaaagccg tggaaggcgc gctggcctcg  840
aaattccgca acgccgggca aacctgcgtc tgcgccaacc gcctgtatgt gcaggacggc  900
gtgtatgacc gttttgccga aaaattgcag caggcagtga gcaaactgca catcggcgac  960
gggctggata acggcgtcac catcgggccg ctgatcgatg aaaaagcggt agcaaaagtg  1020
gaagagcata ttgccgatgc gctggagaaa ggcgcgcgcg tggtttgcgg cggtaaagcg  1080
cacgaacgcg gcggcaactt cttccagccg accattctgg tggacgttcc ggccaacgcc  1140
aaagtgtcga aagaagagac gttcggcccc ctcgccccgc tgttccgctt taaagatgaa  1200
gctgatgtga ttgcgcaagc caatgacacc gagtttggcc ttgccgccta tttctacgcc  1260
cgtgatttaa gccgcgtctt ccgcgtgggc gaagcgctgg agtacggcat cgtcggcatc  1320
aataccggca ttatttccaa tgaagtggcc ccgttcggcg gcatcaaagc ctcgggtctg  1380
ggtcgtgaag gttcgaagta tggcatcgaa gattacttag aaatcaaata tatgtgcatc  1440
ggtctttaa                                                            1449

SEQ ID NO: 77          moltype = DNA  length = 1281
FEATURE                Location/Qualifiers
source                 1..1281
                       mol_type = genomic DNA
                       organism = Escherichia coli
SEQUENCE: 77
atgaacagca ataaagagtt aatgcagcgc cgcagtcagg cgattccccg tggcgttggg  60
caaattcacc cgattttcgc tgaccgcgcg gaaaactgcc gggtgtggga cgttgaaggc  120
cgtgagtatc ttgatttcgc gggcgggatt gcggtgctca ataccgggca cctgcatccg  180
aaggtggtgg ccgcggtgga agcgcagttg aaaaaactgt cgcacacctg cttccaggtg  240
ctggcttacg agccgtatct ggagctgtgc gagattatga atcagaaggt gccgggcgat  300
ttcgccaaga aaacgctgct ggttacgacc ggttccgaag cggtggaaaa cgcggtaaaa  360
atcgcccgcg ccgccaccaa acgtagcggc accatcgctt ttagcggcgc gtatcacggg  420
cgcacgcatt acacgctggc gctgaccggc aaggtgaatc cgtactctgc gggcatgggg  480
ctgatgccgg gtcatgttta tcgcgcgctt tatccttgcc cgctgcacgg cataagcgag  540
```

-continued

```
gatgacgcta tcgccagcat ccaccggatc ttcaaaaatg atgccgcgcc ggaagatatc  600
gccgccatcg tgattgagcc ggttcagggc gaaggcggtt tctacgcctc gtcgccagcc  660
tttatgcagc gtttacgcgc tctgtgtgac gagcacggga tcatgctgat tgccgatgaa  720
gtgcagagcg gcgcggggcg taccggcacg ctgtttgcga tggagcagat gggcgttgcg  780
ccggatctta ccacctttgc gaaatcgatc gcgggcggct tcccgctggc gggcgtcacc  840
gggcgcgcgg aagtaatgga tgccgtcgct ccaggcggtc tgggcggcac ctatgcgggt  900
aacccgattg cctgcgtggc tgcgctggaa gtgttgaagg tgtttgagca ggaaaatctg  960
ctgcaaaaag ccaacgatct ggggcagaag ttgaaagacg gattgctggc gatagccgaa  1020
aaacacccgg agatcggcga cgtacgcggg ctgggggcga tgatcgccat tgagctgttt  1080
gaagacggcg atcacaacaa gccggacgcc aaactcaccg ccgagatcgt ggctcgcgcc  1140
cgcgataaag gcctgattct tctctcctgc ggcccgtatt acaacgtgct gcgcatcctt  1200
gtaccgctca ccattgaaga cgctcagatc cgtcagggtc tggagatcat cagccagtgt  1260
tttgatgagg cgaagcagta g                                            1281

SEQ ID NO: 78          moltype = DNA  length = 1509
FEATURE                Location/Qualifiers
source                 1..1509
                       mol_type = genomic DNA
                       organism = Arabidopsis thaliana
SEQUENCE: 78
atggtgctct cccacgccgt atcggagtcg gacgtctccg tccactccac attcgcatca  60
cgttacgtcc gtacttcact tcctaggttc aagatgccgg aaaactcgat tcctaaggaa  120
gcggcgtatc agatcatcaa cgacgagctg atgcttgacg ggaatccacg gttgaactta  180
gcctcctttg tgacgacatg gatggagcct gagtgtgata aactcatcat gtcctccatc  240
aacaagaact atgttgacat ggacgagtac cccgtcacca ccgaacttca gaaccgatgt  300
gtgaacatga ttgcacatct attcaatgca ccgttagaag aggcggagac cgccgtcgga  360
gtaggaaccg ttggatcatc ggaggccata atgttggccg gtttggcctt caagcgtaaa  420
tggcagaaca agcgcaaagc tgaaggcaaa cccgtcgata aacccaacat tgtcaccgga  480
gccaatgttc aagtgtgttg ggagaaattc gctaggtact ttgaggttga acttaaggaa  540
gtgaaattga gtgaaggata ctatgtgatg gaccctcaac aagctgttga tatggttgat  600
gagaacacca tttgtgttgc ggacattctt ggttccactc ttaatggaga attcgaagat  660
gttaaactct tgaacgatct cttggtcgaa aagaacaaag aaaccggatg ggatacacca  720
atccacgtgg atgcggcaag tggaggattc attgcaccgt ttttgtatcc ggaattggaa  780
tgggacttta gacttccctt ggtgaagagt atcaatgtga gtggtcacaa gtatggactt  840
gtgtacgcag ggattggttg ggtgatctgg agaaacaaag aggatttgcc tgaggaactc  900
atcttccata tcaattatct tggtgctgac caacccacct ttactctcaa tttctccaaa  960
ggttcaagtc aagtcattgc tcaatactac caacttatcc gattgggcca cgagggttac  1020
agaaatgtga tggagaattg cagagagaat atgatcgtcc taagggaagg acttgagaag  1080
acagaaaggt tcaacatcgt ctcaaaggac gagggagtgc cacttgtcgc tttctccttg  1140
aaagatagca gctgtcacac tgagttcgaa atctccgaca tgcttcgcag gtatggatgg  1200
atagtgccgg cctacacaat gcctccaaat gcacaacaca tcactgttct tcgtgtggtt  1260
atcagagaag atttctcgag aacactcgct gagagacttg tgatcgatat agagaaagtg  1320
atgcgtgagc tcgatgagct tccttcgaga gtgattcaca aaatatcact tggacaagag  1380
aagagtgaat ctaacagcga taacttgatg gtcacggtga agaagagcga tatcgacaag  1440
cagagagata tcatcactgg ctggaagaag tttgtcgccg acaggaagaa gacgagtggt  1500
atctgctaa                                                          1509

SEQ ID NO: 79          moltype = DNA  length = 1356
FEATURE                Location/Qualifiers
source                 1..1356
                       mol_type = genomic DNA
                       organism = Escherichia coli
SEQUENCE: 79
atggaccaga agctgttaac ggatttccgc tcagaactac tcgattcacg ttttggcgca  60
aaggccattt ctactatcgc ggagtcaaaa cgatttccgc tgcacgaaat gcgcgatgat  120
gtcgcatttc agattatcaa tgatgaatta tatcttgatg gcaacgctcg tcagaacctg  180
gccactttct gccagacctg ggacgacgaa aacgtccata aattgatgga tttgtcgatc  240
aataaaaact ggatcgacaa agaacagtat ccgcaatccg cagccatcga cctgcgttgc  300
gtaaatatgg ttgccgatct gtggcatgcg cctgcgccga aaaatggtca ggccgttggc  360
accaacacca ttggttcttc cgaggcctgt atgctcggcg ggatggcgat gaaatggcgt  420
tggcgcaagc gtatggaagc tgcaggcaaa ccaacggata aaccaaacct ggtgtgcggt  480
ccggtacaaa tctgctggca taaattcgcc cgctactggg atgtggagct gcgtgagatc  540
cctatgcgcc ccggtcagtt gtttatggac ccgaaacgca tgattgaagc ctgtgacgaa  600
aacaccatcg gcgtggtgcc gactttcggc gtgacctaca ccggtaacta tgagttccca  660
caaccgctgc acgatgcgct ggataaattc caggccgaca ccggtatcga catcgacatg  720
cacatcgacg ctgccagcgg tggcttcctg gcaccgttcg tcgccccgga tatcgtctgg  780
gacttccgcc tgccgcgtgt gaaatcgatc agtgcttcag gccataaatt cggtctggct  840
ccgctgggct gcggctgggt tatctggcgt gacgaagaag cgctgccgca ggaactggtg  900
ttcaacgttg actacctggg tggtcaaatt ggtacttttg ccatcaactt ctcccgcccg  960
gcgggtcagg taattgcaca gtactatgaa ttcctgcgcc tcggtcgtga aggctatacc  1020
aaagtacaga acgcctctta ccaggttgcc gcttatctgg cggatgaaat cgccaaactg  1080
gggccgtatg agttcatctg tacgggtcgc ccggacgaag gcatcccggc ggtttgcttc  1140
aaactgaaag atggtgaaga tccgggatac accctgtacg acctctctga acgtctgcgt  1200
ctgcgcggct ggcaggttcc ggccttcact ctcggcggtg aagccaccga catcgtggtg  1260
atgcgcatta tgtgtcgtcg cggcttcgaa atggactttg ctgaactgtt gctggaagac  1320
tacaaagcct ccctgaaata tctcagcgat cactaa                            1356

SEQ ID NO: 80          moltype = DNA  length = 975
FEATURE                Location/Qualifiers
```

```
source                  1..975
                        mol_type = genomic DNA
                        organism = Escherichia coli
SEQUENCE: 80
atgaagccgt ccgttatcct ctacaaagcc ttacctgatg atttactgca acgcctgcaa  60
gagcatttca ccgttcacca ggtggcaaac ctcagcccac aaaccgtcga acaaaatgca  120
gcaatttttg ccgaagctga aggtttactg ggttcaaacg agaatgtaaa tgccgcattg  180
ctggaaaaaa tgccgaaact gcgtgccaca tcaacgatct ccgtcggcta tgacaatttt  240
gatgtcgatg cgcttaccgc ccgaaaaatt ctgctgatgc acacgccaac cgtattaaca  300
gaaaccgtcg ccgatacgct gatggcgctg gtgttgtcta ccgctcgtcg ggttgtggag  360
gtagcagaac gggtaaaagc aggcgaatgg accgcgagca taggcccgga ctggtacggc  420
actgacgttc accataaaac actgggcatt gtcgggatgg gacggatcgg catggcgctg  480
gcacaacgtg cgcactttgg cttcaacatg cccatcctct ataacgcgcg ccgccaccat  540
aaagaagcag aagaacgctt caacgcccgc tactgcgatt tggatactct gttacaagag  600
tcagatttcg tttgcctgat cctgccgtta actgatgaga cgcatcatct gtttggcgca  660
gaacaattcg ccaaaatgaa atcctccgcc attttcatta atgccggacg tggcccggtg  720
gttgacgaaa atgcactgat cgcagcattg cagaaaggcg aaattcacgc tgccgggctg  780
gatgtcttcg aacaagagcc actgtccgta gattcgccgt tgctctcaat ggccaacgtc  840
gtcgcagtac cgcatattgg atctgccacc catgagacgc gttatggcat ggccgcctgt  900
gccgtggata atttgattga tgcgttacaa ggaaaggttg agaagaactg tgtgaatccg  960
cacgtcgcgg actaa                                                   975

SEQ ID NO: 81           moltype = DNA  length = 780
FEATURE                 Location/Qualifiers
source                  1..780
                        mol_type = genomic DNA
                        organism = Cupriavidus necator
SEQUENCE: 81
gtgtacgcag ctaaggacat caccgtggag gagcgcgccg gcggcgcgct atggatcacg  60
atcgaccggg cgcagaaaca caatgcgctg gcccgccacg tgctggcggg attggcgcag  120
gtggtgagcg ccgcggcggc gcagcccggg gtgcgctgca tcgtgctgac cggcgccggc  180
cagcgcttct ttgcggcagg cggcgatctg gtcgagctgt ccggcgtgcg cgaccgggag  240
gctacgctgg ccatgagcga gcaggcgcgc ggtgccctgg atgcggtgcg cgactgcccg  300
ctgccggtgc tggcctacct gaacggcgat gccatcggcg gcggcgccga gctggcattg  360
gcctgcgaca tgcggctgca gtcggcgagc gcgcgcatcg gctttatcca ggcgcggctg  420
gccatcacct cggcctgggg cggcggcccc gacctgtgcc ggatcgtcgg cgcggcgcgg  480
gccatgcgca tgatgagccg ttgcgagctt gtcgatgcgc agcaggcgct gcagtggggc  540
ttggccgatg cggtggtcac ggacggaccc gccggcaagg acatccacgc cttcctgcaa  600
ccgctgctgg gctgcgcccc gcaggtgctg cgcggcatca aggcgcagac cgcggccagc  660
cggcgcggcg agtcgcatga cgctgcccgc accatcgagc agcagcaact gttgcatacc  720
tggctccatg cggaccattg gaacgctgcc gagggcatcc tctccaggag ggcccaatga  780

SEQ ID NO: 82           moltype = DNA  length = 849
FEATURE                 Location/Qualifiers
source                  1..849
                        mol_type = genomic DNA
                        organism = Clostridium acetobutylicum
SEQUENCE: 82
atgaaaaagg tatgtgttat aggtgcaggt actatgggtt caggaattgc tcaggcattt  60
gcagctaaag gatttgaagt agtattaaga gatattaaag atgaatttgt tgatagagga  120
ttagatttta tcaataaaaa tctttctaaa ttagttaaaa aaggaaagat agaagaagct  180
actaaagttg aaatcttaac tagaatttcc ggaacagttg accttaatat ggcagctgat  240
tgcgatttag ttatagaagc agctgttgaa agaatggata ttaaaaagca gatttttgct  300
gacttagaca atatatgcaa gccagaaaca attcttgcat caaatacatc atcactttca  360
ataacagaag tggcatcagc aactaaaact aatgataagg ttataggtat gcatttcttt  420
aatccagctc ctgttatgaa gcttgtagag gtaataagag gaatagctac atcacaagaa  480
acttttgatg cagttaaaga gacatctata gcaataggaa aagatcctgt agaagtagca  540
gaagcaccag gatttgttgt aaatagaata ttaataccaa tgattaatga agcagttggt  600
atattagcag aaggaatagc ttcagtagaa gacatagata aagctatgaa acttggagct  660
aatcacccaa tgggaccatt agaattaggt gattttatag gtcttgatat atgtcttgct  720
ataatggatg ttttatactc agaaactgga gattctaagt atagaccaca tacattactt  780
aagaagtatg taagagcagg atggcttgga agaaaatcag gaaaaggttt ctacgattat  840
tcaaaataa                                                          849

SEQ ID NO: 83           moltype = DNA  length = 825
FEATURE                 Location/Qualifiers
source                  1..825
                        mol_type = genomic DNA
                        organism = Escherichia coli
SEQUENCE: 83
atggtcgcac ccattcccgc gaaacgcggc agaaaacccg ccgttgccac cgcaccagcg  60
actggacagg ttcagtcttt aacgcgtggc ctgaaattac tggagtggat tgccgaatcc  120
aatggcagtg tggcactcac ggaactggcg caacaagccg ggttacccaa ttccacgacc  180
caccgcctgc taaccacgat gcaacagcag ggtttcgtgc gtcaggttgg cgaactggga  240
cattgggcaa tcggcgcaca tgcctttatg gtcggcagca gctttctcca gagccgtaat  300
ttgttagcga ttgttcaccc tatcctgcgc aatctaatgg aagagtctgg cgaaacggtc  360
aatatggcgg tgcttgatca aagcgatcac gaagcgatta ttatcgacca ggtacagtgt  420
acgcatctga tgcgaatgtc cgcgcctatc ggcggtaaat tgccgatgca cgcttccggt  480
gcgggtaaag cctttttagc ccaactgagc gaagaacagg tgacgaagct gctgcaccgc  540
```

```
aaagggttac atgcctatac ccacgcaacg ctggtgtctc ctgtgcattt aaaagaagat  600
ctcgcccaaa cgcgcaaacg gggttattca tttgacgatg aggaacatgc actggggcta  660
cgttgccttg cagcgtgtat tttcgatgag caccgtgaac cgtttgccgc aatttctatt  720
tccggaccga tttcacgtat taccgatgac cgcgtgaccg agtttggcgc gatggtgatt  780
aaagcggcga aggaagtgac gctggcgtac ggtggaatgc gctga                    825

SEQ ID NO: 84          moltype = DNA  length = 1083
FEATURE                Location/Qualifiers
source                 1..1083
                       mol_type = genomic DNA
                       organism = Escherichia coli
SEQUENCE: 84
gtgaaaccag taacgttata cgatgtcgca gagtatgccg gtgtctctta tcagaccgtt  60
tcccgcgtgg tgaaccaggc cagccacgtt tctgcgaaaa cgcgggaaaa agtggaagcg  120
gcgatggcgg agctgaatta cattcccaac cgcgtggcac aacaactggc gggcaaacag  180
tcgttgctga ttggcgttgc cacctccagt ctggccctgc acgcgccgtc gcaaattgtc  240
gcggcgatta aatctcgcgc cgatcaactg ggtgccagcg tggtggtgtc gatggtagaa  300
cgaagcggcg tcgaagcctg taaagcggcg gtgcacaatc ttctcgcgca acgcgtcagt  360
gggctgatca ttaactatcc gctggatgac caggatgcca ttgctgtgga agctgcctgc  420
actaatgttc cggcgttatt tcttgatgtc tctgaccaga cacccatcaa cagtattatt  480
ttctcccatg aagacggtac gcgactgggc gtggagcatc tggtcgcatt gggtcaccag  540
caaatcgcgc tgttagcggg cccattaagt tctgtctcgg cgcgtctgcg tctggctggc  600
tggcataaat atctcactcg caatcaaatt cagccgatag cggaacggga aggcgactgg  660
agtgccatgt ccggttttca acaaaccatg caaatgctga atgagggcat cgttcccact  720
gcgatgctgg ttgccaacga tcagatggcg ctgggcgcaa tgcgcgccat taccgagtcc  780
gggctgcgcg ttggtgcgga tatctcggta gtgggatacg acgataccga agacagctca  840
tgttatatcc cgccgttaac caccatcaaa caggattttc gcctgctggg gcaaaccagc  900
gtggaccgct tgctgcaact ctctcagggc caggcggtga agggcaatca gctgttgccc  960
gtctcactgg tgaaaagaaa aaccaccctg gcgcccaata cgcaaaccgc ctctccccgc  1020
gcgttggccg attcattaat gcagctggca cgacaggttt cccgactgga aagcgggcag  1080
tga                                                               1083

SEQ ID NO: 85          moltype = DNA  length = 1647
FEATURE                Location/Qualifiers
source                 1..1647
                       mol_type = genomic DNA
                       organism = Pseudomonas putida
SEQUENCE: 85
atgatggttc caaccctcga acacgagctt gctcccaacg aagccaacca tgtcccgctg  60
tcgccgctgt cgttcctcaa gcgtgccgcg caggtgtacc cgcagcgcga tgcggtgatc  120
tatggcgcaa ggcgctacag ctaccgtcag ttgcacgagc gcagccgcgc cctggccagt  180
gccttggagc gggtcggtgt tcagccgggc gagcgggtgg cgatattggc gccgaacatc  240
ccggaaatgc tcgaggccca ctatggcgtg cccggtgccg gggcggtgct ggtgtgcatc  300
aacatccgcc tggaggggcg cagcattgcc ttcatcctgc gtcactgcgc ggccaaggta  360
ttgatctgcg atcgtgagtt cggtgccgtg gccaatcagg cgctggccat gctcgatgcg  420
ccgcccttgc tggtgggcat cgacgatgat caggccgagc gcgccgattt ggcccacgac  480
ctggactacg aagcgttctt ggcccagggc gaccccgcgc ggccgttgag tgcgccacag  540
aacgaatggc agtcgatcgc catcaactac acctccggca ccacggggga ccccaagggc  600
gtggtgctgc atcaccgcgg cgcctacctc aacgcctgcg ccggggcgct gatcttccag  660
ttggggccgc gcagcgtcta cttgtggacc ttgccgatgt tccactgcaa cggctggagc  720
catacctggg cggtgacgtt gtccggtggc acccacgtgt gtctgcgcaa ggtccagcct  780
gatgcgatca acgccgccat cgccgagcat gccgtgactc acctgagcgc cgccccagtg  840
gtgatgtcga tgctgatcca cgccgagcat gccagcgccc ctccggtgcc ggtttcggtg  900
atcactggcg gtgccgcccc gcccagtgcg gtcatcgcgg cgatggaggc gcgtggcttc  960
aacatcaccc atgcctatgg catgaccgaa agctacggtc ccagcacatt gtgcctgtgg  1020
cagccgggtg tcgacgagtt gccgctggag gcccgggccc agttcatgag ccgccagggc  1080
gtcgcccacc cgctgctcga ggaggccacg gtgctggata ccgacaccgg ccgcccggtc  1140
ccggccgacg gccttaccct cggcgagctg gtggtgcggg gcaacactgt gatgaaaggc  1200
tacctgcaca acccagaggc tacccgtgcc gcgttggcca acggctggct gcacacgggc  1260
gacctggccg tgctgcacct ggacggctat gtggaaatca aggaccgagc caaggacatc  1320
atcatttctg gcggcgagaa catcagttcg ctggagatag aagaagtgct ctaccagcac  1380
cccgaggtgg tcgaggctgc ggtggtggcg cgtccggatt cgcgctgggg cgagacacct  1440
cacgctttcg tcacgctgcg cgctgatgca ctggccagcg gggacgacct ggtccgctgg  1500
tgccgtgagc gtctggcgca cttcaaggcg ccgcgccatg tgtcgctcgt ggacctgccc  1560
aagaccgcca ctggaaaaat acagaagttc gtcctgcgtg agtgggcccg gcaacaggag  1620
gcgcagatcg ccgacgccga gcattga                                    1647

SEQ ID NO: 86          moltype = DNA  length = 1647
FEATURE                Location/Qualifiers
source                 1..1647
                       mol_type = other DNA
                       organism = synthetic construct
SEQUENCE: 86
atgatggttc cgaccctgga gcatgaactg gcgccgaatg aagcgaacca tgtgccgtta  60
agcccgctga gctttctgaa acgtgccgcc caggtctatc ctcagcgtga tgccgtgatt  120
tacggcgccc gtcgttatag ctatcgtcag ctgcacgaac gcagccgcgc cctggcttcc  180
gccttagagc gtgtgggtgt gcagcctggt gagcgcgttg caattcttgc cccgaacatt  240
ccggaaatgc tggaggcgca ctacggcgtg cctggcgccg gtgcggtgct ggtttgcatt  300
aacatccgcc tggagggccg cagcattgcc ttcattttac gccattgtgc ggcgaaggtg  360
```

-continued

```
ctgatttgtg atcgtgaatt cggtgccgtt gctaatcaag cgctggcgat gctggatgcg  420
ccgccgctgc tggtgggtat cgatgatgac caggcggagc gcgcggatct ggcacatgat  480
ctggactatg aggccttttt agcgcagggc gatccggccc gtccgttgtc agcgccgcag  540
aatgaatggc agagcattgc gattaactat acctcgggca ccaccggtga tccaaaaggt  600
gtagtgctgc atcaccgtgg tgcgtatctg aatgcatgcg caggcgcctt aatctttcag  660
ttaggccctc gctcggtcta tctttggacg ctgccgatgt ttcactgtaa cggttggagc  720
cacacgtggg cggttaccct gtcaggtggt acgcacgttt gcttacgcaa agttcagccg  780
gacgcgatta acgcagcaat cgccgagcat gccgtgactc atctgtctgc agccccggtg  840
gtgatgtcta tgctgattca cgccgagcat gctagcgcgc cgccggtgcc tgtgtctgtg  900
atcaccggcg gtgcagcccc gcctagcgcc gtgattgcgg caatggaagc tcgtggcttc  960
aatatcacgc acgcgtatgg tatgaccgaa tcctacggtc caagcaccct gtgcctgtgg  1020
caaccaggtg tggatgaact gccgttagaa gcacgtgcgc agtttatgag ccgtcagggt  1080
gtcgcgcatc cgttactgga agaagcgacc gttttagata ccgatactgg ccgtccggta  1140
ccggcggacg gtctgaccct gggcgaactg gttgtgcgtg gtaataccgt tatgaaaggg  1200
tacttacaca atccggaagc gacgcgcgca gcactggcga acggttggtt acataccggc  1260
gatctggccg tattgcatct ggatggctac gttgaaatta aagatcgtgc aaaagatatt  1320
atcatttcgg gcggcgaaaa catttctagc ctggaaatcg aagaagtcct gtatcagcac  1380
ccggaggttg tggaggcagc cgtcgtggca cgcccggaca gccgttgggg cgagaccccg  1440
cacgcctttg ttactctgcg tgccgacgcc cttgcgtctg gtgacgatct ggtgcgttgg  1500
tgccgtgagc gtcttgccca cttcaaagcg ccgcgccatg ttagccttgt ggatctgccg  1560
aaaaccgcca cgggcaaaat tcagaaattt gtattacgtg aatgggcacg ccagcaggag  1620
gcccagattg ccgacgcaga acactaa                                   1647

SEQ ID NO: 87          moltype = DNA  length = 1152
FEATURE                Location/Qualifiers
source                 1..1152
                       mol_type = genomic DNA
                       organism = Megasphaera elsdenii
SEQUENCE: 87
atggatttta acttaacaga tattcaacag gacttcttaa aactcgctca tgatttcggc  60
gaaaagaaat tagcaccgac cgttacggaa cgcgaccaca aaggtattta tgacaaagaa  120
ctcatcgacg aattgctcag cctcggtatt accggcgctt acttcgaaga aaaatacggc  180
ggttccggcg atgacggcgg cgacgttttg agctacatcc tcgctgttga agaattggct  240
aaatacgacg ctggtgttgc tatcaccttg tcggcaacgg tttccctttg cgctaacccg  300
atttggcagt tcggtacaga agctcagaaa gaaaaattcc tcgttccttt ggttgaaggc  360
actaaactcg gcgctttcgg cttgaccgaa ccgaacgcag gtactgatgc ttccggccag  420
cagaccattg ctacgaagaa cgatgacggc acttacacgt tgaacggctc caagatcttc  480
atcaccaacg gcggcgctgc tgacatctac attgtcttcg ctatgaccga taagagcaaa  540
ggcaaccacg gcattacagc cttcatcctc gaagacggta ctccgggctt tacttacggc  600
aagaaagaag acaagatggg catccatact tcgcagacca tggaactcgt attccaggac  660
gtcaaagttc cggctgaaaa catgctcggc gaagaaggca aaggcttcaa gattgctatg  720
atgaccttgg acggcggccg tatcggcgtt gctgctcagg ctctcggcat tgcagaagct  780
gctttggcag atgctgttga atactccaaa cagcgtgtac agttcggcaa accgctctgc  840
aaattccagt ccatttcctt caaactggct gacatgaaga tgcagatcga agctgctcgt  900
aacctcgttt acaaagctgc ttgcaagaaa caggaaggca aaccccttcac cgttgacgct  960
gctatcgcaa aacgcgttgc ttccgacgtc gctatgcgcg taacgaccga agctgtccag  1020
atcttcggcg gctatggcta cagcgaagaa tatccggttg ctcgtcacat gcgcgatgct  1080
aagattactc agatctacga aggcacgaac gaagttcagc tcatggttac aggcggtgct  1140
ctgttaagat aa                                                   1152

SEQ ID NO: 88          moltype = DNA  length = 2046
FEATURE                Location/Qualifiers
source                 1..2046
                       mol_type = genomic DNA
                       organism = Escherichia coli
SEQUENCE: 88
atgcagcagt tagccagttt cttatccggt acctggcagt ctggccgggg ccgtagccgt  60
ttgattcacc acgctattag cggcgaggcg ttatgggaag tgaccagtga aggtcttgat  120
atggcggctg cccgccagtt tgccattgaa aaaggtgccc ccgcccttcg cgctatgacc  180
tttatcgaac gtgcggcgat gcttaaagcg gtcgctaaac atctgctgag tgaaaaagag  240
cgtttctatg ctctttctgc gcaaacaggc gcaacgcggg cagacagttg ggttgatatt  300
gaaggtggca ttgggacgtt atttacttac gccagcctcg gtagccggga gctgcctgac  360
gatacgctgt ggccggaaga tgaattgatc cccttatcga aagaaggtgg atttgccgcg  420
cgccatttac tgacctcaaa gtcaggcgtg gcagtgcata ttaacgcctt taacttcccc  480
tgctggggaa tgctggaaaa gctggcacca acgtggctgg gcggaatgcc agccatcatc  540
aaaccagcta ccgcgacggc ccaactgact caggcgatgg tgaaatcaat tgtcgatagt  600
ggtcttgttc ccgaaggcgc aattagtctg atctgcggta gtgctggcga cttgttggat  660
catctggaca gccaggatgt ggtgactttc acggggtcag cggcgaccgg acagatgctg  720
cgagttcagc caaatatcgt cgccaaatct atccccttca ctatggaagc tgattccctg  780
aactgctgcg tactgggcga agatgtcacc ccggatcaac cggagtttgc gctgtttatt  840
cgtgaagttg tgcgtgagat gaccacaaaa gccgggcaaa aatgtacggc aatccggcgg  900
attattgtgc cgcaggcatt ggttaatgct gtcagtgatg ctctggttgc gcgattacag  960
aaagtcgtgg tcggtgatcc tgctcaggaa ggcgtgaaaa tgggcgcact ggtaaatgct  1020
gagcagcgtg ccgatgtgca ggaaaaagtg aacatattgc tggctgcagg atgcgagatt  1080
cgcctcggtg gtcaggcgga tttatctgct gcgggtgcct tcttcccgcc aaccttattg  1140
tactgtccgc agccggatga aacaccggcg gtacatgcaa cagaagcctt tggccctgtc  1200
gcaacgctga tgccagcaca aaaccagcga catgctctgc aactggcttg tgcaggcggc  1260
ggtagccttg cgggaacgct ggtgacggct gatccgcaaa ttgcgcgtca gtttattgcc  1320
gacgcggcac gtacgcatgg gcgaattcag atcctcaatg aagagtcggc aaaagaatcc  1380
```

-continued

```
accgggcatg gctccccact gccacaactg gtacatggtg ggcctggtcg cgcaggaggc  1440
ggtgaagaat taggcggttt acgagcggtg aaacattaca tgcagcgaac cgctgttcag  1500
ggtagtccga cgatgcttgc cgctatcagt aaacagtggg tgcgcggtgc gaaagtcgaa  1560
gaagatcgta ttcatccgtt ccgcaaatat tttgaggagc tacaaccagg cgacagcctg  1620
ttgactcccc gccgcacaat gacagaggcc gatattgtta actttgcttg cctcagcggc  1680
gatcatttct atgcacatat ggataagatt gctgctgccg aatctatttt cggtgagcgg  1740
gtggtgcatg ggtattttgt gctttctgcg gctgcgggtc tgtttgtcga tgccggtgtc  1800
ggtccggtca ttgctaacta cgggctggaa agcttgcgtt ttatcgaacc cgtaaagcca  1860
ggcgatacca tccaggtgcg tctcacctgt aagcgcaaga cgctgaaaaa acagcgtagc  1920
gcagaagaaa aaccaacagg tgtggtggaa tgggctgtag aggtattcaa tcagcatcaa  1980
accccggtgg cgctgtattc aattctgacg ctggtggcca ggcagcacgg tgattttgtc  2040
gattaa                                                              2046

SEQ ID NO: 89          moltype = DNA  length = 1575
FEATURE                Location/Qualifiers
source                 1..1575
                       mol_type = genomic DNA
                       organism = Anaerotignum propionicum
SEQUENCE: 89
atgagaaagg ttcccattat taccgcagat gaggctgcaa agcttattaa agacggtgat  60
acagttacaa caagtggttt cgttggaaat gcaatccctg aggctcttga tagagctgta  120
gaaaaaagat tcttagaaac aggcgaaccc aaaaacatta catatgttta ttgtggttct  180
caaggtaaca gagacggaag aggtgctgag cactttgctc atgaaggcct tttaaaacgt  240
tacatcgctg gtcactgggc tacagttcct gctttgggta aaatggctat ggaaaataaa  300
atggaagcat ataatgtatc tcagggtgca ttgtgtcatt tgttccgtga tatagcttct  360
cataagccag gcgtatttac aaaggtaggt atcggtactt tcattgaccc cagaaatggc  420
ggcggtaaag taaatgatat taccaaagaa gatattgttg aattggtaga gattaagggt  480
caggaatatt tattctaccc tgcttttcct attcatgtag ctcttattcg tggtacttac  540
gctgatgaaa gcggaaatat cacatttgag aaagaagttg ctcctctgga aggaacttca  600
gtatgccagg ctgttaaaaa cagtggcggt atcgttgtag ttcaggttga aagagtagta  660
aaagctggta ctcttgaccc tcgtcatgta aaagttccag gaatttatgt tgactatgtt  720
gttgttgctg acccagaaga tcatcagcaa tctttagatt gtgaatatga tcctgcatta  780
tcaggcgagc atagaagacc tgaagttgtt ggagaaccac ttcctttgag tgcaaagaaa  840
gttattggtc gtcgtggtgc cattgaatta gaaaaagatg ttgctgtaaa tttaggtgtt  900
ggtgcgcctg aatatgtagc aagtgttgct gatgaagaag gtatcgttga ttttatgact  960
ttaactgctg aaagtggtgc tattggtggt gttcctgctg gtggcgttcg ctttggtgct  1020
tcttataatg cggatgcatt gatcgatcaa ggttatcaat tcgattacta tgatggcggc  1080
ggcttagacc tttgctattt aggcttagct gaatgcgatg aaaaaggcaa tatcaacgtt  1140
tcaagatttg gccctcgtat cgctggttgt ggtggtttca tcaacattac acagaataca  1200
cctaaggtat tcttctgtgg tactttcaca gcaggtggct taaaggttaa aattgaagat  1260
ggcaaggtta ttattgttca agaaggcaag cagaaaaaat tcttgaaagc tgttgagcag  1320
attacattca atggtgacgt tgcacttgct aataagcaac aagtaactta tattacagaa  1380
agatgcgtat tccttttgaa ggaagatggt ttgcacttat ctgaaattgc acctggtatt  1440
gatttgcaga cacagattct tgacgttatg gattttgcac ctattattga cagagatgca  1500
aacggccaaa tcaaattgat ggacgctgct ttgtttgcag aaggcttaat gggtctgaag  1560
gaaatgaagt cctga                                                    1575

SEQ ID NO: 90          moltype = DNA  length = 1554
FEATURE                Location/Qualifiers
source                 1..1554
                       mol_type = genomic DNA
                       organism = Megasphaera elsdenii
SEQUENCE: 90
atgagaaaag tagaaatcat tacagctgaa caagcagctc agctcgtaaa agacaacgac  60
acgattacgt ctatcggctt tgtcagcagc gcccatccgg aagcactgac caaagctttg  120
gaaaaacggt tcctggacac gaacaccccg cagaacttga cctacatcta tgcaggctct  180
cagggcaaac gcgatggccg tgccgctgaa catctggcac acacaggcct tttgaaacgc  240
gccatcatcg gtcactggca gactgtaccg gctatcggta aactggctgt cgaaaacaag  300
attgaagctt acaacttctc gcagggcaca ttggtccact ggttccgcgc cttggcaggt  360
cataagctcg gcgtcttcac cgacatcggt ctggaaactt tcctcgatcc ccgtcagctc  420
ggcggcaagc tcaatgacgt aaccaaagaa gacctcgtca aactgatcga agtcgatggt  480
catgaacagc ttttctaccc gaccttcccg gtcaacgtag ctttcctccg cggtacgtat  540
gctgatgaat ccggcaatat caccatggac gaagaaatcg ggcctttcga aagcacttcc  600
gtagcccagg ccgttcacaa ctgtggcggt aaagtcgtcg tccaggtcaa agacgtcgtc  660
gctcacggca gcctcgaccc gcgcatggtc aagatccctg gcatctatgt cgactacgtc  720
gtcgtagcag ctccggaaga ccatcagcag acgtatgact gcgaatacga tccgtccctc  780
agcggtgaac atcgtgctcc tgaaggcgct accgatgcag ctctccccat gagcgctaag  840
aaaatcatcg gccgccgcgg cgctttggaa ttgactgaaa acgctgtcgt caacctcggc  900
gtcggtgctc cggaatacgt tgcttctgtt gccggtgaag aaggtatcgc cgataccatt  960
accctgaccg tcgaaggtgg cgccatcggt ggcgtaccgc agggcggtgc ccgcttcggt  1020
tcgtcccgca atgccgatgc catcatcgac cacacctatc agttcgactt ctacgatggc  1080
ggcggtctgg acatcgctta cctcggcctg gcccagtgcg atggctcggg caacatcaac  1140
gtcagcaagt tcggtactaa cgttgccggc tgcggcggtt tccccaacat ttcccagcag  1200
acaccgaatg tttacttctg cggcaccttc acggctggcg gcttgaaaat cgctgtcgaa  1260
gacggcaaag tcaagatcct ccaggaaggc aaagccaaga agttcatcaa agctgtcgac  1320
cagatcactt tcaacggttc ctatgcagcc cgcaacggca aacacgttct ctacatcaca  1380
gaacgctgcg tatttgaact gaccaaagaa ggcttgaaac tcatcgaagt cgcaccgggc  1440
atcgatattg aaaaagatat cctcgctcac atggacttca agccgatcat tgataatccg  1500
aaactcatgg atgcccgcct cttccaggac ggtcccatgg gactgaaaaa ataa        1554
```

-continued

```
SEQ ID NO: 91          moltype = DNA  length = 1389
FEATURE                Location/Qualifiers
source                 1..1389
                       mol_type = genomic DNA
                       organism = Klebsiella pneumoniae
SEQUENCE: 91
atgaatacag cagaactgga aacccttatc cgcaccatcc tcagtgaaaa gctcgcgccg  60
acgcccccctg cccctcagca agagcagggc attttctgcg atgtcggcag cgccatcgac  120
gccgctcatc aggcttttct ccgctatcag cagtgtccgc taaaaacccg cagcgccatt  180
atcagcgccc tgcgggagac gctggccccc gagctggcga cgctggcgga agagagcgcc  240
acggaaaccg gcatgggcaa caaagaagat aaatatctga aaaataaagc cgctcttgaa  300
aacacgccgg gcatagagga tctcactacc agcgccctca ccggcgatgg cgggatggtg  360
ctgtttgagt actcgccgtt cggggttatt ggcgccgtgg cgcccagcac caacccaacg  420
gaaaccatta tcaacaacag tatcagcatg ctggcggcgg gtaacagcgt ctatttcagc  480
ccccatcccg gcgcgaaaaa ggtctcgttg aagcttatcg ccaggatcga agagatcgcc  540
taccgctgca gcgggatccg taacctggtg gtgaccgttg ccgagccgac ctttgaagcc  600
acccagcaaa tgatgtccca cccgctgatt gccgttctgg ctatcaccgg cggccctggc  660
attgtggcga tgggcatgaa aagcggtaaa aaagtgatcg gcgctggcgc cggcaatccg  720
ccgtgcatcg ttgatgaaac cgccgatctc gtcaaagccg ccgaagatat tatcagcggc  780
gccgccttcg attacaacct gccctgtatc gccgaaaaaa gcctgatcgt cgtcgcctcc  840
gtcgctgacc gcctgatcca gcagatgcag gattttgacg cgctgctgtt gagccgacag  900
gaggccgata ccctgcgtac cgtctgcctg cccgacggcg cggcgaataa aaaactggtc  960
ggtaaaagcc cggctgcgct gctggcggcg gcgggtctcg ccgttccgcc tcgccccccct  1020
cgcctgctga tagccgaggt ggaggcgaac gacccctggg tgacctgcga gcagctgatg  1080
ccggtgctgc cgatcgtcag ggtcgccgac tttgacagcg ccctggcgct ggccctgcgc  1140
gtagaggagg gtctgcacca caccgccatt atgcactcgc agaatgtctc gcggctcaat  1200
ctggcggcac gcaccctgca gacctccatt tttgtcaaaa atggcccgtc ttacgcggga  1260
atcggcgtcg gcggcgaagg gtttaccacc ttcaccatcg ccacgccaac cggagaaggc  1320
accacctccg cgcggacgtt cgcccgcctg cggcgctgcg tgttgaccaa cggtttttcc  1380
attcgctaa                                                          1389

SEQ ID NO: 92          moltype = DNA  length = 1395
FEATURE                Location/Qualifiers
source                 1..1395
                       mol_type = genomic DNA
                       organism = Salmonella enterica
SEQUENCE: 92
atgaatactt ctgaactcga aaccctgatt cgcaccattc ttagcgagca attaaccacg  60
ccggcgcaaa cgccggtcca gcctcagggc aaagggattt tccagtccgt gagcgaggcc  120
atcgacgccg cgcaccaggc gttcttacgt tatcagcagt gcccgctaaa aacccgcagc  180
gccattatca gcgcgatgcg tcaggagctg acgccgctgc tggcgcccct ggcggaagag  240
agcgccaatg aaacggggat gggcaacaaa gaagataaat ttctcaaaaa caaggctgcg  300
ctggacaaca cgccgggcgt agaagatctc accaccaccg cgctgaccgg cgacggcggc  360
atggtgctgt ttgaatactc accgtttggc gttatcggtt cggtcgcccc aagcaccaac  420
ccgacggaaa ccatcatcaa caacagtatc agcatgctgg cggcgggcaa cagtatctac  480
tttagcccgc atccgggagc gaaaaaggtc tctctgaagc tgattagcct gattgaagag  540
attgccttcc gctgctgcgg catccgcaat ctggtggtga ccgtggcgga acccaccttc  600
gaagcgaccc agcagatgat ggcccacccg cgaatcgcag tactggccat taccggcggc  660
ccgggcattg tggcaatggg catgaagagc ggtaagaagg tgattggcgc tggcgcgggt  720
aacccgccct gcatcgttga tgaaacggcg gacctggtga aagcggcgga agatatcatc  780
aacggcgcgt cattcgatta caacctgccc tgcattgccg agaagagcct gatcgtagtg  840
gagagtgtcg ccgaacgtct ggtgcagcaa atgcaaacct tcggcgcgct gctgttaagc  900
cctgccgata ccgacaaact ccgcgccgtc tgcctgcctg aaggccaggc gaataaaaaa  960
ctggtcggca agagcccatc ggccatgctg gaagccgccg ggatcgctgt ccctgcaaaa  1020
gcgccgcgtc tgctgattgc gctggttaac gctgacgatc cgtgggtcac cagcgaacag  1080
ttgatgccga tgctgccagt ggtaaaagtc agcgatttcg atagcgcgct ggcgctggcc  1140
ctgaaggttg aagaggggct gcatcatacc gccattatgc actcgcagaa cgtgtcacgc  1200
ctgaacctcg cggcccgcac gctgcaaacc tcgatattcg tcaaaaacgg cccctcttat  1260
gccgggatcg gcgtcggcgg cgaaggcttt accaccttca ctatcgccac accaaccggt  1320
gaagggacca cgtcagcgcg tacttttgcc cgttcccggc gctgcgtact gaccaacggc  1380
ttttctattc gctaa                                                   1395

SEQ ID NO: 93          moltype = DNA  length = 1182
FEATURE                Location/Qualifiers
source                 1..1182
                       mol_type = genomic DNA
                       organism = Cupriavidus necator
SEQUENCE: 93
atgactgacg ttgtcatcgt atccgccgcc cgcaccgcgg tcggcaagtt tggcggctcg  60
ctggccaaga tcccggcacc ggaactgggt gccgtggtca tcaaggccgc gctggagcgc  120
gccggcgtca agccggagca ggtgagcgaa gtcatcatgg gccaggtgct gaccgccggt  180
tcgggccaga accccgcacg ccaggccgcg atcaaggccg gcctgccggc gatggtgccg  240
gccatgacca tcaacaaggt gtgcggctcg ggcctgaagg ccgtgatgct ggccgccaac  300
gcgatcatgg cgggcgacgc cgagatcgtg gtggccggcg gccaggaaaa catgagcgcc  360
gccccgcacg tgctgccggg ctcgcgcgat ggtttccgca tgggcgatgc caagctggtc  420
gacaccatga tcgtcgacgg cctgtgggac gtgtacaacc agtaccacat gggcatcacc  480
gccgagaacg tggccaagga atacggcatc acacgcgagg cgcaggatga gttcgccgtc  540
ggctcgcaga acaaggccga agccgcgcag aaggccggca agtttgacga agagatcgtc  600
```

```
ccggtgctga tcccgcagcg caagggcgac ccggtggcct tcaagaccga cgagttcgtg  660
cgccagggcg ccacgctgga cagcatgtcc ggcctcaagc ccgccttcga caaggccggc  720
acggtgaccg cggccaacgc ctcgggcctg aacgacggcg ccgccgcggt ggtggtgatg  780
tcggcggcca aggccaagga actgggcctg accccgctgg ccacgatcaa gagctatgcc  840
aacgccggtg tcgatcccaa ggtgatgggc atgggcccgg tgccggcctc caagcgcgcc  900
ctgtcgcgcg ccgagtggac cccgcaagac ctggacctga tggagatcaa cgaggccttt  960
gccgcgcagg cgctggcggt gcaccagcag atgggctggg acacctccaa ggtcaatgtg  1020
aacggcggcg ccatcgccat cggccacccg atcggcgcgt cgggctgccg tatcctggtg  1080
acgctgctgc acgagatgaa gcgccgtgac gcgaagaagg gcctggcctc gctgtgcatc  1140
ggcggcggca tgggcgtggc gctggcagtc gagcgcaaat aa                    1182
```

```
SEQ ID NO: 94          moltype = DNA  length = 741
FEATURE                Location/Qualifiers
source                 1..741
                       mol_type = genomic DNA
                       organism = Cupriavidus necator
SEQUENCE: 94
atgactcagc gcattgcgta tgtgaccggc ggcatgggtg gtatcggaac cgccatttgc  60
cagcggctgg ccaaggatgg ctttcgtgtg gtggccggtt gcggccccaa ctcgccgcgc  120
cgcgaaaagt ggctggagca gcagaaggcc ctgggcttcg atttcattgc ctcggaaggc  180
aatgtggctg actgggactc gaccaagacc gcattcgaca aggtcaagtc cgaggtcggc  240
gaggttgatg tgctgatcaa caacgccggt atcacccgcg acgtggtgtt ccgcaagatg  300
acccgcgccg actgggatgc ggtgatcgac accaacctga cctcgctgtt caacgtcacc  360
aagcaggtga tcgacggcat ggccgaccgt ggctggggcc gcatcgtcaa catctcgtcg  420
gtgaacgggc agaagggcca gttcggccag accaactact ccaccgccaa ggccggcctg  480
catggcttca ccatggcact ggcgcaggaa gtggcgacca agggcgtgac cgtcaacacg  540
gtctctccgg gctatatcgc caccgacatg gtcaaggcga tccgccagga cgtgctcgac  600
aagatcgtcg cgacgatccc ggtcaagcgc ctgggcctgc cggaagagat cgcctcgatc  660
tgcgcctggt tgtcgtcgga ggagtccggt ttctcgaccg gcgccgactt ctcgctcaac  720
ggcggcctgc atatgggctg a                                          741
```

```
SEQ ID NO: 95          moltype = DNA  length = 1770
FEATURE                Location/Qualifiers
source                 1..1770
                       mol_type = genomic DNA
                       organism = Cupriavidus necator
SEQUENCE: 95
atggcgaccg gcaaaggcgc ggcagcttcc acgcaggaag gcaagtccca accattcaag  60
gtcacgccgg ggccattcga tccagccaca tggctggaat ggtcccgcca gtggcagggc  120
actgaaggca acggccacgc ggccgcgtcc ggcattccgg gcctggatgc gctggcaggc  180
gtcaagatcg cgccggcgca gctgggtgat atccagcagc gctacatgaa ggacttctca  240
gcgctgtggc aggccatggc cgagggcaag gccgaggcca ccggtccgct gcacgaccgg  300
cgcttcgccg gcgacgcatg gcgcaccaac ctcccatatc gcttcgctgc cgcgttctac  360
ctgctcaatg cgcgcgcctt gaccgagctg gccgatgccg tcgaggccga tgccaagacc  420
cgccagcgca tccgcttcgc gatctcgcaa tgggtcgatg cgatgtcgcc cgccaacttc  480
cttgccacca atcccgaggc gcagcgcctg ctgatcgagt cgggcggcga atcgctgcgt  540
gccggcgtgc gcaacatgat ggaagacctg acacgcggca agatctcgca gaccgacgag  600
agcgcgtttg aggtcggccg caatgtcgcg gtgaccgaag gcgccgtggt cttcgagaac  660
gagtacttcc agctgttgca gtacaagccg ctgaccgaca aggtgcacgc gcgcccgctg  720
ctgatggtgc cgccgtgcat caacaagtac tacatcctgg acctgcagcc ggagagctcg  780
ctggtgcgcc atgtggtgga gcagggacat acggtgtttc tggtgtcgtg gcgcaatccg  840
gacgccagca tggccggcag cacctgggac gactacatcg agcacgcggc catccgcgcc  900
atcgaagtcg cgcgcgacat cagcggccag gacaagatca acgtgctcgg cttctgcgtg  960
ggcggcacca ttgtctcgac cgcgctggcg gtgctggccg cgcgcggcga gcacccggcc  1020
gccagcgtca cgctgctgac cacgctgctg gactttgccg acacgggcat cctcgacgtc  1080
tttgtcgacg agggccatgt gcagttgcgc gaggccacgc tgggcggcgg cgccggcgcg  1140
ccgtgcgcgc tgctgcgcgg ccttgagctg gccaatacct tctcgttctt gcgcccgaac  1200
gacctggtgt ggaactacgt ggtcgacaac tacctgaagg gcaacacgcc ggtgccgttc  1260
gacctgctgt tctggaacgg cgacgccacc aacctgccgg ggccgtggta ctgctggtac  1320
ctgcgccaca cctacctgca gaacgagctc aaggtaccgg gcaagctgac cgtgtgcggc  1380
gtgccggtgg acctggccag catcgacgtg ccgacctata tctacggctc gcgcgaagac  1440
catatcgtgc cgtggaccgc ggcctatgcc tcgaccgcgc tgctggcgaa caagctgcgc  1500
ttcgtgctgg gtgcgtcggg ccatatcgcc ggtgtgatca acccgccggc caagaacaag  1560
cgcagccact ggactaacga tgcgctgccg gagtcgccgc agcaatggct ggccggcgcc  1620
atcgagcatc acggcagctg gtggccggac tggaccgcat ggctggccgg gcaggccggc  1680
gcgaaacgcg ccgcgcccgc caactatggc aatgcgcgct atcgcgcaat cgaacccgcg  1740
cctgggcgat acgtcaaagc caaggcatga                                  1770
```

```
SEQ ID NO: 96          moltype = DNA  length = 405
FEATURE                Location/Qualifiers
source                 1..405
                       mol_type = genomic DNA
                       organism = Aeromonas caviae
SEQUENCE: 96
atgagtacac aaacccttgc cgtgggccag aaggctcgcc tgaccaagcg cttcggcccg  60
gccgaggtgg cggccttcgc cggcctctcg gaggatttca atcccctgca cctggacccg  120
gacttcgccg ccacgacggt gttcgagcgc cccatcgtcc acggcatgct gctggcgagc  180
ctcttctccg ggctcctcgg gcagcaactg cccgggaaag ggagcatcta tctgggccag  240
agcctcggct tcaaactgcc ggtgttcgtg ggggacgagg tgacggcgga ggtggaggtg  300
```

-continued

```
attgcccttc gaagcgacaa gcccatcgcc accctggcca cccgcatctt cacccagggc  360
ggcgccctcg ccgtgacggg ggaagcggtg gtaaaactcc cttga                  405

SEQ ID NO: 97          moltype = DNA  length = 1128
FEATURE                Location/Qualifiers
source                 1..1128
                       mol_type = genomic DNA
                       organism = Pseudomonas putida
SEQUENCE: 97
atgctggtaa atgacgagca acaacagatc gccgacgcgg tacgtgcgtt cgcccaggaa  60
cgcctgaagc cgtttgccga gcaatgggac aaggaccatc gcttccccga agaggccatc  120
gacgagatgg ccgaactggg cctgttcggc atgctggtgc cggagcagtg gggcggtagc  180
gacaccggtt atgtggccta tgccatggcc ttggaggaaa tcgctgcggg cgatggcgcc  240
tgctcgacca tcatgagcgt gcacaactcg gtgggttgcg tgccgatcct gcgcttcggc  300
aacgagcagc agaaagagca gttcctcacc ccgctggcga caggtgcgat gctcggtgct  360
ttcgccctga ccgagccgca ggctggctcc gatgccagca gcctgaagac ccgcgcacgc  420
ctggaaggcg accattacgt gctcaatggc agcaagcagt tcattacctc ggggcagaac  480
gccggcgtag tgatcgtgtt tgcggtcacc gacccggagg ccggcaagcg tggcatcagc  540
gccttcatcg tgccgaccga ttcgccgggc taccaggtag cgcgggtgga ggacaaactc  600
ggccagcacg cctccgacac ctgccagatc gttttcgaca atgtgcaagt gccagtggcc  660
aaccggctgg gggcggaggg tgaaggctac aagatcgccc tggccaacct tgaaggcggc  720
cgtatcggca tcgcctcgca agcggtgggt atggcccgcg cggcgttcga agtggcgcgg  780
gactatgcca acgagcgcca gagctttggc aaaccgctga tcgagcacca ggccgtggcg  840
tttcgcctgg ccgacatggc aacgaaaatt tccgttgccc ggcagatggt attgcacgcc  900
gctgcccttc gtgatgcggg gcgcccggcg ctggtggaag cgtcgatggc caagctgttc  960
gcctcggaaa tggccgaaaa ggtctgttcg gacgccttgc agaccctggg cggttatggc  1020
tatctgagtg acttcccgct ggagcggatc taccgcgacg ttcgggtttg ccagatctac  1080
gaaggcacca gcgacattca gcgcatggtc attgcgcgca atctttga                1128

SEQ ID NO: 98          moltype = DNA  length = 1128
FEATURE                Location/Qualifiers
source                 1..1128
                       mol_type = other DNA
                       organism = synthetic construct
SEQUENCE: 98
atgctggtga acgacgaaca gcagcaaatt gccgatgctg tgcgcgcctt tgctcaagag  60
cgtttaaaac cgttcgcgga gcagtgggac aaagaccacc gtttccccgaa agaagcgatt  120
gatgagatgg cagaactggg cctgtttggc atgttagtcc cggagcaatg gggcggctcg  180
gacaccggtt atgtggcata tgcgatggcg ctggaagaga ttgcggccgg tgatggcgct  240
tgtagcacca ttatgagcgt ccacaattcg gtgggttgcg tgccgattct gcgctttggt  300
aacgaacagc agaaagaaca gttcctgacc cctttagcaa cgggtgcgat gctgggcgcg  360
tttgccttaa ccgaacctca ggcgggctcg gacgcaagct cgttgaaaac ccgtgcgcgc  420
ctggaaggtg atcactacgt gttgaatggc agtaagcaat tcattaccag cggccaaaat  480
gccggtgtgg tgatcgtgtt tgcggtgact gacccggaag cgggcaaacg cggcattagt  540
gcgttcatcg tgccgaccga tagcccgggc tatcaggtcg cccgtgttga agataagctt  600
ggtcagcatg cgagcgatac ctgtcaaatc gtgtttgaca acgtacaagt tccggtagcc  660
aatcgcctgg gtgctgaagg tgaaggttat aaaatcgcac tggcaaacct tgaaggtggc  720
cgcattggca tcgcgagtca ggccgttggc atggcacgcg ccgcgtttga agttgcgcgc  780
gattacgcaa acgaacgtca gagcttcggc aaaccgctca ttgaacatca ggcggttgcc  840
tttcgtctgg ccgatatggc cacgaaaatc agcgtggcgc gccagatggt tctgcatgcg  900
gctgccctgc gtgatgcggg ccgtccggcg ctggttgaag catcaatggc gaagctgttc  960
gcctcagaaa tggctgaaaa agtctgctca gatgcgctgc agacgctggg cggttacggt  1020
tacctgagcg attttccact ggaacgtatt tatcgtgatg ttcgcgtatg ccagatctat  1080
gagggtacta gcgacattca gcgcatggta atcgcccgta acctgtaa                1128

SEQ ID NO: 99          moltype = DNA  length = 891
FEATURE                Location/Qualifiers
source                 1..891
                       mol_type = genomic DNA
                       organism = Escherichia coli
SEQUENCE: 99
atgtctctac actctccagg taaagcgttt cgcgctgcac tgactaaaga aaatccattg  60
cagattgttg gcaccatcaa cgctaatcat gcgctgttgg cgcagcgtgc cggatatcag  120
gcaatttatc tttctggcgg tggcgtggcg gcaggttcgc tggggctgcc cgatctcggt  180
atttctaccc ttgatgatgt gctgaccgac attcgccgta tcaccgacgt ttgttcgctg  240
ccgctgctgg tggatgcgga tatcggtttt ggttcttcgg cctttaacgt ggcgcgcacc  300
gtgaaatcga tgattaaagc cggtgcggca ggattgcata ttgaagatca ggttggtgcg  360
aaacgctgcg gtcatcgtcc gaataaagcg atcgtctcga aagaagagat ggtggatcgg  420
atccgcgcgg cggtggatgc gaaaaccgat cctgattttg tgatcatggc gcgcaccgat  480
gctctggcgg tagaggggct ggatgcggcg atcgagcgtg cgcaggccta tgttgaagcg  540
ggtgccgaga tgttgttccc ggaggcgatt accgaactcg ccatgtaccg ccagtttgcc  600
gatgcggtgc aggtgccgat cctcgccaac atcaccgaat ttggtgccac gccgctgttt  660
accaccgacg aattacgcag cgcccatgtc gcaatggcgc tgtacccact ttcagcgttc  720
cgcgccatga accgcgccgc tgaacatgtc tacaacgtcc tgcgccagga aggcacgcag  780
aaaagcgtca tcgacaccat gcagacccgc aacgagctgt acgaaagcat caactactac  840
cagtacgaag agaagctcga caacctgttt gcccgtagcc aggtgaaata a            891

SEQ ID NO: 100         moltype = DNA  length = 1170
FEATURE                Location/Qualifiers
```

-continued

```
source                  1..1170
                        mol_type = genomic DNA
                        organism = Escherichia coli
SEQUENCE: 100
atgagcgaca caacgatcct gcaaaacagt acccatgtca ttaaaccgaa aaaatctgtg  60
gcactttctg gcgttccggc gggcaatacg gcgctctgca ccgtgggtaa aagtggcaat  120
gacctgcatt accgcggcta cgatattctt gatctggcga aacattgcga atttgaagaa  180
gtggcgcatc tgctgatcca cggcaaactg ccgacccgtg acgaactcgc cgcttacaaa  240
acgaaactga aagccctgcg cggtttaccg gctaacgtgc gtaccgtgct ggaagcctta  300
ccggcggcgt cgcacccgat ggatgttatg cgcaccggtg tttccgcgct cggctgcacg  360
ctgccagaaa aagaggggca taccgtctct ggcgcgcggg atattgccga caaactgctg  420
gcgtcgctta gctcgattct cctttattgg tatcactaca gccacaacgg cgaacgcatc  480
caaccggaaa ccgatgacga ctccatcggc ggtcacttcc tgcatctgct gcacggcgaa  540
aagccatcgc aaagctggga aaaggcgatg catatctcgc tggtgctgta cgccgaacac  600
gagtttaacg cctccacctt taccagtcgg gtgattgcgg gcaccggctc tgatatgtat  660
tccgcgatta ttggcgcgat tggcgcactg cgcgggccaa aacacggcgg ggcgaatgaa  720
gtgtcgctgg agatccagca acgctacgaa acgccggacg aagccgaagc agatatccgc  780
aagcgcgtgg aaaacaaaga agtggtcatt ggttttggtc atccggttta caccatcgct  840
gacccgcgcc accaggtgat taaacgtgtg gcgaagcagc tctcgcagga aggcggctcg  900
ctgaagatgt acaacatcgc cgatcgcctg gaaacggtga tgtgggagag caaaaagatg  960
ttccccaatc tcgactggtt ctctgctgtt tcctacaaca tgatgggcgt tcccaccgag  1020
atgttcacac cactgtttgt tatcgcccgc gtcaccggct gggcggcgca cattatcgaa  1080
caacgtcagg acaacaaaat tatccgtcct tccgccaatt atgttggacc ggaagaccgc  1140
ccgtttgtcg cgctggataa gcgccagtaa                                  1170

SEQ ID NO: 101          moltype = DNA  length = 1452
FEATURE                 Location/Qualifiers
source                  1..1452
                        mol_type = genomic DNA
                        organism = Escherichia coli
SEQUENCE: 101
atgtcagctc aaatcaacaa catccgcccg gaatttgatc gtgaaatcgt tgatatcgtc  60
gattacgtca tgaactacga aatcagctct aaagtggcct acgacaccgc acattactgc  120
ctgctcgaca cgctcggctg cggtctggaa gctctcgaat acccggcctg taaaaaactg  180
ctggggccaa ttgttcccgg caccgtcgta cccaacggcg tgcgcgtccc cggaactcag  240
ttccagctcg accccgtcca ggcggcattt aacatcggcg cgatgatccg ctggctcgat  300
ttcaacgata cctggctggc ggcggagtgg ggccatcctt ccgacaacct cggcggcatt  360
ctggcaacgg cggactggct ttcgcgcaac gcggtcgcca gcggcaaagc gccgttgacc  420
atgaaacagg tgctgaccgc aatgatcaaa gcccatgaaa ttcagggctg catcgcgctg  480
gaaaactcct ttaaccgcgt cggcctcgac cacgttctgt tagtgaaagt ggcttccacc  540
gccgtggtcg ccgaaatgct cggcctgacc cgcgaggaaa ttctcaacgc cgtttcgctg  600
gcgtgggtgg acggtcagtc gctgcgcacc tatcgccatg cgccgaacac cggcacgcgt  660
aaatcctggg cggcgggcga tgccacttcc cgcgcggtac gtctggcact gatggcgaaa  720
acgggcgaaa tgggttaccc gtcagccctg actgcgccgg tgtggggctt ctacgacgtc  780
tcctttaaag gtgaatcgtt ccgcttccag cgcccgtacg gttcctacgt tatggaaaat  840
gtgctgttca aaatctcctt cccggcggag ttccactccc agacggcagt tgaagcagcg  900
atgacgctct atgaacagat gcaggcagca ggcaaaacgg cggcggatat cgaaaaagtg  960
accattcgca cccacgaagc ctgtattcgc atcatcgaca aaaaagggcc gctcaataac  1020
ccggcagacc gcgatcactg cattcagtac atggtggcga tcccgctgct attcgggcgc  1080
ttaacggcgg cagattacga ggacaacgtt gcgcaagata aacgcattga cgccctgcgc  1140
gagaagatca attgctttga agatccggca tttaccgctg actaccacga cccggaaaaa  1200
cgcgccatcg ccaatgccat taccttgag ttcaccgacg gcacacgatt tgaagaagtg  1260
gtggtggagt accccattgg tcatgctcgc cgccgtcagg atggtattcc gaaactggtc  1320
gataaattca aaatcaatct cgcgcgccag ttcccgactc gccaacagca gcgcattctg  1380
gaggtttctc tcgacagagc tcgcctggaa cagatgccgg tcaatgagta tctcgacctg  1440
tacgtcattt aa                                                     1452

SEQ ID NO: 102          moltype = DNA  length = 1920
FEATURE                 Location/Qualifiers
source                  1..1920
                        mol_type = genomic DNA
                        organism = Cupriavidus necator
SEQUENCE: 102
atgaccgcag acgcggagga gacagacatg acggcaagcc atgccgtgca tgcccgttcg  60
ctggccgacc ccgaggggtt ctgggccgaa caggcggcgc gcatcgactg ggaaaccccg  120
ttcggccagg tgctcgacaa cagccgcgcg ccctttacgc gctggttcgt cggcgggcgc  180
accaacctgt gccacaacgc ggtcgaccgc cacctggcgg cccgcgccag ccagccggcg  240
ctgcactggg tctcgaccga gaccgaccag gcccgcacct ttacctacgc cgagctgcac  300
gacgaagtca gccgcatggc cgcgatcctg cagggcctgg acgtgcagaa gggcgaccgc  360
gtgctgatct acatgccgat gatcccggaa gccgcctttg ccatgctggc ctgcgcgcgc  420
atcggcgcga tccattcggt ggtgttcggc ggctttgcct cggtcagcct ggccgcgcgc  480
atcgaggatg cccggccgcg cgtggtggtc agcgccgacg ccggctcgcg tgccggcaag  540
gtggtgccct acaagccgct gctggacgag gccatccggc tctcgtcgca ccagcccggg  600
aaggtgctgc tggtggaccg gcaactggcg caaatgcccc gtaccgaggg ccgcgatgag  660
gactacgccg cctggcgcga acgcgtggcc ggcgtgcagg tgccgtgcgt gtggctggaa  720
tcgagcgagc cgtcgtacgt gctatacacc tccggcacca ccggcaagcc caagggcgtg  780
cagcgcgata ccggcggcta cgcggtggcg ctggccacct cgatggaata catcttctgc  840
ggcaagcccg gcgacaccat gttcaccgcg tcggacatcg gctgggtggt ggggcacagc  900
tatatcgtct acggcccgct gctggccggc atggccacgc tgatgtatga aggcacgccg  960
```

-continued

```
atccgccccg acggtggcat cctgtggcgg ctggtggagc aatacaaggt caacctgatg  1020
ttcagcgcgc cgaccgcgat ccgcgtgctg aagaagcagg acccggcctg gctgacccgc  1080
tacgacctgt ccagcctgcg cctgctgttc ctggccggcg agccgctgga cgagcccacc  1140
gcgcgctgga tccaggacgg cctgggcaag cccgtggtcg acaactactg gcagaccgaa  1200
tccggctggc cgatcctcgc gatccagcgc ggcatcgagg cgctgccgcc caagctgggc  1260
tcgcccggcg tgcccgccta cggctatgac ctgaagatcg tcgacgagaa caccggcgct  1320
gaatgcccgc cggggcagaa gggtgtggtc gccatcgacg gcccgctgcc gccgggatgc  1380
atgagcacgg tctggggcga cgacgaccgc ttcgtgcgca cctactggca ggcggtgccg  1440
aaccggctgt gctattcgac cttcgactgg ggcgtgcgcg acgccgacgg ctatgttttt  1500
atcctgggcc gcaccgacga cgtgatcaac gttgccggcc accggctggg cacccgcgag  1560
atcgaggaaa gcctgtcgtc caacgctgcc gtggccgagg tggcggtggt gggcgtgcag  1620
gacgcgctca aggggcaggt ggcgatggcc ttctgcatcg cccgcgatcc ggcgcgcacg  1680
gccacggccg aagcgcggct ggcattggag ggcgagttga tgaagacggt ggagcagcaa  1740
ctgggtgccg tggcgcggcc ggcgcgcgta ttctttgtca atgcactgcc caagacccgc  1800
tccggcaagt tgctgcggcg cgccatgcag gcggtggccg aagggcgcga tccgggcgac  1860
ctgaccacga tcgaggaccc gggtgcgctg gaacagttgc aggcagcgct gaaaggctag  1920
```

```
SEQ ID NO: 103          moltype = DNA  length = 1887
FEATURE                 Location/Qualifiers
source                  1..1887
                        mol_type = genomic DNA
                        organism = Escherichia coli
SEQUENCE: 103
atgtctttta gcgaatttta tcagcgttcg attaacgaac cggagcagtt ctgggccgag  60
caggcccggc gtattgactg gcagacgccc tttacgcaaa cgctcgatca cagcaatccg  120
ccgtttgccc gttggttttg tgaaggccga accaacttgt gccacaacgc catcgaccgc  180
tggctggaga aacagccaga ggcgctggcg ctgattgccg tctcttcgga aacagaagaa  240
gagcgcacct ttacctttcg tcagctgcat gacgaagtga acgcggtggc ctcaatgttg  300
cgttcattgg gtgtgcagcg cggcgatcgg gtgctggtgt atatgccgat gattgccgaa  360
gcgcatatta ctctgctggc ctgcgcgcgc attggcgcta ttcactcggt ggtgtttggt  420
ggatttgcct cgcacagcgt ggcggcgcga attgatgacg ctaaaccggt gctgattgtc  480
tcggctgatg ccggagcgcg cggtggcaaa atcattccct ataaaaaatt gctcgacgat  540
gcgataagtc aggcgcagca ccagccacgc catgttttgc tggtggatcg cgggctggcg  600
aaaatggcgc gcgtcagcgg gcgggatgtc gatttcgcgt cgttgcgcca tcaacacatc  660
ggcgcgcggg taccggtggc gtggctggaa tccaacgaaa cctcctgcat tctctacact  720
tccggcacga ccggcaaacc taaaggcgtg cagcgtgacg tcggcggata tgcggtggcg  780
ctggcgacct cgatggacac catttttggc ggcaaagcgg gcagcgtgtt cttttgcgca  840
tcggatatcg gctgggtggt ggggcattcg tatatcgttt acgcgccgct gctggcgggg  900
atggcgacta tcgtttacga aggattgccg acctggccgg actgcggcgt gtggtggaca  960
atcgtcgaga aatatcaggt tagccggatg ttctcagcgc cgaccgccat tcgcgtgctg  1020
aaaaaattcc ctaccgctga aattcgcaaa cacgatctct cgtcgctgga agtgctctat  1080
ctggctggag aaccgctgga cgagccgacc gccagttggg tgagcaatac gctggatgtg  1140
ccggtcatcg acaactactg gcagaccgaa tccggctggc cgattatggc gattgctcgc  1200
ggtctggacg acaggccgac gcgtctggga agcccccggtg tgccgatgta tggctataac  1260
gtgcagttgc ttaatgaagt caccggcgaa ccgtgtggcg tcaacgagaa agggatgctg  1320
gtggtggaag ggccgctgcc gccggggtgt attcagacca tctggggcga cgacggccgc  1380
tttgtgaaga cttactggtc gctgttttcc cgcccggtgt acgccacctt tgactggggc  1440
atccgtgacg ctgacggtta tcactttatt ctcgggcgca ctgacgatgt aattaacgtt  1500
gccgggcatc ggctggggac gcgcgagatt gaagagagta tctccagcca tccgggcgtt  1560
gccgaagtgg cggtggttgg ggtgaaagat gcgctgaaag ggcaggtggc ggtggcgttt  1620
gtcattccga aagagagcga cagtctggaa gatcgtgatg tggcgcactc gcaagagaag  1680
gcgattatgg cgctggtgga cagccagatt ggcaactttg gccgcccggc gcacgtctgg  1740
tttgtctcgc aattgccaaa aacgcgatcc ggaaaaatgc tgcgccgcac gatccaggcg  1800
atttgcgaag gacgcgatcc tggagatctg acgaccattg atgatcctgc gtcgttggat  1860
cagatccgcc aggcgatgga agagtag                                    1887
```

```
SEQ ID NO: 104          moltype = DNA  length = 1887
FEATURE                 Location/Qualifiers
source                  1..1887
                        mol_type = genomic DNA
                        organism = Salmonella enterica
SEQUENCE: 104
atgtctttta gcgaatttta tcagcgttcc attaacgaac cggaggcgtt ctgggccgag  60
caggcccggc gtatcgactg gcgacagccg tttacgcaga cgctggatca tagccgtcca  120
ccgtttgccc gctggttttg cggcggcacc actaacttat gtcataacgc cgtcgaccgc  180
tggcgggata aacagccgga ggcgctggcg ctgattgccg tctcatcaga gaccgatgaa  240
gagcgcacat ttaccttcag ccagttgcat gatgaagtca acattgtggc cgccatgttg  300
ctgtcgctgg gcgtgcagcg tggcgatcgc gtattggtct atatgccgat gattgccgaa  360
gcgcagataa ccctgctggc ctgcgcgcgc attggcgcga tccattcggt ggtctttggc  420
ggttttgcct cgcacagcgt ggcggcgcgc attgacgatg ccagaccggc gctgattgtg  480
tcggcggatg ccggagcgcg gggcggtaaa atcctgccgt ataaaaagct gctcgatgac  540
gctattgcgc aggcgcagca tcagccgaaa cacgttctgc tggtggacag agggctggcg  600
aaaatggcat gggtggatgg gcgcgatctg gattttgcca cgttgcgcca gcagcatctc  660
ggcgcgagcg tgccggtggc gtggctggaa tccaacgaaa cctcgtgcat tctttacacc  720
tccggcacta ccggcaaacc gaaaggcgtc cagcgcgacg tcggcggtta tgcggtggcg  780
ctggcaacct cgatggacac catttttggc ggcaaggcgg gcggcgtatt cttttgcgca  840
tcggatatcg gctgggtcgt cggccactcc tatatcgttt acgcgccgtt gctggcaggc  900
atggcgacta ttgtttacga aggactgccg acgtacccgg actgcggggt ctggtggaaa  960
attgtcgaga aataccaggt taaccggatg ttttccgccc cgaccgcgat tcgcgtgctg  1020
```

-continued

```
aaaaaattcc cgacggcgca aatccgcaat cacgatctct cctcgctgga ggcgctttat  1080
ctggccggtg agccgctgga cgagccgacg gccagttggg taacggagac gctgggcgta  1140
ccggtcatcg acaattattg gcagacggag tccggctggc cgatcatggc gctggcccgc  1200
gcgctggacg acaggccgtc gcgtctggga agtcccggcg tgccgatgta cggttataac  1260
gtccagctac tcaatgaagt caccggcgaa ccttgcggca taaatgaaaa ggggatgctg  1320
gtgatcgaag ggccgctgcc gccgggctgt attcagacta tttggggcga cgatgcgcgt  1380
tttgtgaaga cttactggtc gctgtttaac cgtcaggttt atgccacttt cgactgggga  1440
atccgcgacg ccgaggggta ttactttatt ctgggccgta ccgatgatgt gattaatatt  1500
gcgggtcatc ggctggggac gcgagaaata gaagaaagta tctccagcta cccgaacgta  1560
gcggaagtgg cggtagtggg gataaaagac gctctgaaag ggcaggtagc ggtggcgttt  1620
gtcattccga agcagagcga tacgctggcg gatcgcgagg cggcgcgcga cgaggaaaac  1680
gcgattatgg cgctggtgga caaccagatc ggtcactttg gtcgtccggc gcatgtctgg  1740
tttgtttcgc agctccccaa aacgcgttcc ggaaagatgc ttcgccgcac gatccaggcg  1800
atctgcgaag gccgcgatcc gggcgatctg acaaccattg acgatcccgc gtcgttgcag  1860
caaattcgcc aggcgatcga agaatag                                      1887
```

```
SEQ ID NO: 105         moltype = DNA  length = 2145
FEATURE                Location/Qualifiers
source                 1..2145
                       mol_type = genomic DNA
                       organism = Escherichia coli
SEQUENCE: 105
gtgtcccgta ttattatgct gatccctacc ggaaccagcg tcggtctgac cagcgtcagc  60
cttggcgtga tccgtgcaat ggaacgcaaa ggcgttcgtc tgagcgtttt caaacctatc  120
gctcagccgc gtaccggtgg cgatgcgccc gatcagacta cgactatcgt gcgtgcgaac  180
tcttccacca cgacggccgc tgaaccgctg aaaatgagct acgttgaagg tctgctttcc  240
agcaatcaga aagatgtgct gatggaagag atcgtcgcaa actaccacgc taacaccaaa  300
gacgctgaag tcgttctggt tgaaggtctg gtcccgacac gtaagcacca gtttgcccag  360
tctctgaact acgaaatcgc taaaacgctg aatgcggaaa tcgtcttcgt tatgtctcag  420
ggcactgaca ccccggaaca gctgaaagag cgtatcgaac tgacccgcaa cagcttcggc  480
ggtgccaaaa acaccaacat caccggcgtt atcgttaaca aactgaacgc accggttgat  540
gaacagggtc gtactcgccc ggatctgtcc gagattttcg acgactcttc caaagctaaa  600
gtaaacaatg ttgatccggc gaagctgcaa gaatccagcc cgctgccggt tctcggcgct  660
gtgccgtgga gctttgacct gatcgcgact cgtgcgatcg atatggctcg ccacctgaat  720
gcgaccatca tcaacgaagg cgacatcaat actcgccgcg ttaaatccgt cactttctgc  780
gcacgcagca ttccgcacat gctggagcac ttccgtgccg gttctctgct ggtgacttcc  840
gcagaccgtc ctgacgtgct ggtggccgct tgcctggcag ccatgaacgg cgtagaaatc  900
ggtgccctgc tgctgactgg cggttacgaa atggacgcgc gcatttctaa actgtgcgaa  960
cgtgctttcg ctaccggcct gccggtattt atggtgaaca ccaacacctg gcagacctct  1020
ctgagcctgc agagcttcaa cctggaagtt ccggttgacg atcacgaacg tatcgagaaa  1080
gttcaggaat acgttgctaa ctacatcaac gctgactgga tcgaatctct gactgccact  1140
tctgagcgca gccgtcgtct gtctccgcct gcgttccgtt atcagctgac tgaacttgcg  1200
cgcaaagcgg gcaaacgtat cgtactgccg gaaggtgacg aaccgcgtac cgttaaagca  1260
gccgctatct gtgctgaacg tggtatcgca acttgcgtac tgctgggtaa tccggcagag  1320
atcaaccgtg ttgcagcgtc tcagggtgta gaactgggtg cagggattga aatcgttgat  1380
ccagaagtgg ttcgcgaaag ctatgttggt cgtctggtcg aactgcgtaa gaacaaaggc  1440
atgaccgaaa ccgttgcccg cgaacagctg gaagacaacg tggtgctcgg tacgctgatg  1500
ctggaacagg atgaagttga tggtctggtt tccggtgctg ttcacactac cgcaaacacc  1560
atccgtccgc cgctgcagct gatcaaaact gcaccgggca gctccctggt atcttccgtg  1620
ttcttcatgc tgctgccgga acaggtttac gtttacggtg actgtgcgat caacccggat  1680
ccgaccgctg aacagctggc agaaatcgcg attcagtccg ctgattccgc tgcggccttc  1740
ggtatcgaac cgcgcgttgc tatgctctcc tactccaccg gtacttctgg tgcaggtagc  1800
gacgtagaaa aagttcgcga agcaactcgt ctggcgcagg aaaaacgtcc tgacctgatg  1860
atcgacggtc cgctgcagta cgacgctgcg gtaatggctg acgttgcgaa atccaaagcg  1920
ccgaactctc cggttgcagg tcgcgctacc gtgttcatct tcccggatct gaacaccggt  1980
aacaccacct acaaagcggt acagcgttct gccgacctga tctccatcgg gccgatgctg  2040
cagggtatgc gcaagccggt taacgacctg tcccgtggcg cactggttga cgatatcgtc  2100
tacaccatcg cgctgactgc gattcagtct gcacagcagc agtaa                 2145
```

```
SEQ ID NO: 106         moltype = DNA  length = 1266
FEATURE                Location/Qualifiers
source                 1..1266
                       mol_type = genomic DNA
                       organism = Escherichia coli
SEQUENCE: 106
atgagcaaca atgaattcca tcagcgtcgt ctttctgcca ctccgcgcgg ggttggcgtg  60
atgtgtaact tcttcgccca gtcggctgaa aacgccacgc tgaaggatgt tgagggcaac  120
gagtacatcg atttcgccgc aggcattgcg gtgctgaata ccggacatcg ccaccctgat  180
ctggtcgcgg cggtggagca gcaactgcaa cagtttaccc acaccgcgta tcagattgtg  240
ccgtatgaaa gctacgtcac cctggcggag aaaatcaacg cccttgcccc ggtgagcggg  300
caggccaaaa ccgcgttctt caccaccggt gcggaagcgg tggaaaacgc ggtgaaaatt  360
gctcgcgccc ataccggacg ccctggcgtg attgcgttta gcggcggctt tcacggtcgt  420
acgtatatga ccatggcgct gaccggaaaa gttgcgccgt acaaaatcgg cttcggcccg  480
ttccctggtt cggtgtatca cgtaccttat ccgtcagatt tacacggcat ttcaacacag  540
gactccctcg acgccatcga acgcttgttt aaatcagaca tcgaagcgaa gcaggtggcg  600
gcgattattt tcgaaccggt gcagggcgag ggcggtttca acgttgcgcc aaaagagctg  660
gttgccgcta ttcgccgcct gtgcgacgag cacggtattg tgatgattgc tgatgaagtg  720
caaagcggct ttgcgcgtac cggtaagctg tttgccatgg atcattacgc cgataagccg  780
gatttaatga cgatggcgaa aagcctcgcg ggcgggatgc cgctttcggg cgtggtcggt  840
```

```
aacgcgaata ttatggacgc acccgcgccg ggcgggcttg gcggcaccta cgccggtaac  900
ccgctggcgg tggctgccgc gcacgcggtg ctcaacatta tcgacaaaga atcactctgc  960
gaacgcgcga atcaactggg ccagcgtctc aaaaacacgt tgattgatgc caaagaaagc  1020
gttccggcca ttgctgcggt acgcggcctg ggtcgatga ttgcggtaga gtttaacgat  1080
ccgcaaacgg gcgagccgtc agcggcgatt gcacagaaaa tccagcaacg cgcgctggcg  1140
caggggctgc tcctgctgac ctgtggcgca tacggcaacg tgattcgctt cctgtatccg  1200
ctgaccatcc cggatgcgca attcgatgcg gcaatgaaaa ttttgcagga tgcgctgagc  1260
gattaa                                                             1266
```

```
SEQ ID NO: 107          moltype = DNA  length = 2145
FEATURE                 Location/Qualifiers
source                  1..2145
                        mol_type = genomic DNA
                        organism = Escherichia coli
SEQUENCE: 107
atgtctaacg tgcaggagtg gcaacagctt gccaacaagg aattgagccg tcgggagaaa  60
actgtcgact cgctggttca tcaaaccgcg gaagggatcg ccatcaagcc gctgtatacc  120
gaagccgatc tcgataatct ggaggtgaca ggtacccttc ctggtttgcc gccctacgtt  180
cgtggcccgc gtgccactat gtataccgcc caaccgtgga ccatccgtca gtatgctggt  240
ttttcaacag caaaagagtc caacgctttt tatcgccgta acctggccgc cgggcaaaaa  300
ggtctttccg ttgcgtttga ccttgccacc caccgtggct acgactccga taacccgcgc  360
gtggcgggcg acgtcggcaa agcgggcgtc gctatcgaca ccgtggaaga tatgaaagtc  420
ctgttcgacc agatcccgct ggataaaatg tcggtttcga tgaccatgaa tggcgcagtg  480
ctaccagtac tggcgtttta tatcgtcgcc gcagaagagc aaggtgttac acctgataaa  540
ctgaccggca ccattcaaaa cgatattctc aaagagtacc tctgccgcaa cacctatatt  600
tacccaccaa aaccgtcaat gcgcattatc gccgacatca tcgcctggtg ttccggcaac  660
atgccgcgat ttaataccat cagtatcagc ggttaccaca tgggtgaagc gggtgccaac  720
tgcgtgcagc aggtagcatt tacgctcgct gatgggattg agtacatcaa agcagcaatc  780
tctgccggac tgaaaattga tgacttcgct cctcgcctgt cgttcttctt cggcatcggc  840
atggatctgt ttatgaacgt cgccatgttg cgtgcggcac gttatttatg gagcgaagcg  900
gtcagtggat ttggcgcaca ggacccgaaa tcactggcgc tgcgtaccca ctgccagacc  960
tcaggctgga gcctgactga acaggatccg tataacaacg ttatccgcac caccattgaa  1020
gcgctggctg cgacgctggg cggtactcag tcactgcata ccaacgcctt tgacgaagcg  1080
cttggtttgc ctaccgattt ctcagcacgc attgcccgca acacccagat catcatccag  1140
gaagaatcag aactctgccg caccgtcgat ccactggccg gatcctatta cattgagtcg  1200
ctgaccgatc aaatcgtcaa acaagccaga gctattatcc aacagatcga cgaagccggt  1260
ggcatggcga aagcgatcga agcaggtctg ccaaaacgaa tgatcgaaga ggcctcagcg  1320
cgcgaacagt cgctgatcga ccagggcaag cgtgtcatcg ttggtgtcaa caagtacaaa  1380
ctggatcacg aagacgaaac cgatgtactt gagatcgaca acgtgatggt gcgtaacgag  1440
caaattgctt cgctggaacg cattcgcgcc acccgtgatg atgccgccgt aaccgccgcg  1500
ttgaacgccc tgactcacgc cgcacagcat aacgaaaacc tgctggctgc cgctgttaat  1560
gccgctcgcg ttcgcgccac cctgggtgaa atttccgatg cgctggaagt cgctttcgac  1620
cgttatctgg tgccaagcca gtgtgttacc ggcgtgattg cgcaaagcta tcatcagtct  1680
gagaaatcgg cctccgagtt cgatgccatt gttgcgcaaa cggagcagtt ccttgccgac  1740
aatggtcgtc gcccgcgcat tctgatcgct aagatgggcc aggatggaca cgatcgcggc  1800
gcgaaagtga tcgccagcgc ctattccgat ctcggtttcg acgtagattt aagcccgatg  1860
ttctctacac ctgaagagat cgcccgcctg gccgtagaaa acgacgttca cgtagtgggc  1920
gcatcctcac tggctgccgg tcataaaacg ctgatcccgg aactggtcga agcgctgaaa  1980
aaatggggac gcgaagatat ctgcgtggtc gcgggtggcg tcattccgcc gcaggattac  2040
gccttcctgc aagagcgcgg cgtggcggcg atttatggtc caggtacacc tatgctcgac  2100
agtgtgcgcg acgtactgaa tctgataagc cagcatcatg attaa                   2145
```

```
SEQ ID NO: 108          moltype = DNA  length = 1767
FEATURE                 Location/Qualifiers
source                  1..1767
                        mol_type = genomic DNA
                        organism = Escherichia coli
SEQUENCE: 108
atgaaattgc cagtcagaga atttgatgca gttgtgattg gtgccggtgg cgcaggtatg  60
cgcgcggcgc tgcaaatttc ccagagcggc cagacctgtg cgctgctctc taaagtcttc  120
ccgacccgtt cccataccgt ttctgcgcaa ggcggcatta ccgttgcgct gggtaatacc  180
catgaagata actgggaatg gcatatgtac gacaccgtga aagggtcgga ctatatcggt  240
gaccaggacg cgattgaata tatgtgtaaa accgggccgg aagcgattct ggaactcgaa  300
cacatgggcc tgccgttctc gcgtctcgat gatggtcgta tctatcaacg tccgtttggc  360
ggtcagtcga aaaacttcgg cggcgagcag gcggcacgca ctgcggcagc agctgaccgt  420
accggtcacg cactgttgca cacgctttat cagcagaacc tgaaaaacca caccaccatt  480
ttctccgagt ggtatgcgct ggatctggtg aaaaaccagg atggcgcggt ggtgggttgt  540
accgcactgt gcatcgaaac cggtgaagtg gtttatttca aagcccgcgc taccgtgctg  600
gcgactggcg gagcagggcg tatttatcag tccaccacca acgcccacat taacaccggc  660
gacggtgtcg gcatggctat ccgtgccggc gtaccggtgc aggatatgga aatgtggcag  720
ttccacccga ccggcattgc cggtgcgggc gtactggtca ccgaaggttg ccgtggtgaa  780
ggcggttatc tgctgaacaa acatggcgaa cgttttatgg agcgttatgc gccgaacgcc  840
aaagacctgg cgggccgtga cgtggttgcg cgttccatca tgatcgaaat ccgtgaaggt  900
cgcggctgtg atggtccgtg ggggccacac gcgaaactga aactcgatca cctgggtaaa  960
gaagttctcg aatcccgtct gccgggtatc ctggagcttt cccgtacctt cgctcacgtc  1020
gatccggtga aagagccgat tccggttatc ccaacctgtc actacatgat gggcggtatt  1080
ccgaccaaag ttaccggtca ggcactgact gtgaatgaga aaggcgaaga tgtggttgtt  1140
ccgggactgt ttgccgttgg tgaaatcgct tgtgtatcgg tacacggcgc taaccgtctg  1200
ggcggcaact cgctgctgga cctggtggtc tttggtcgcg cggcaggtct gcatctgcaa  1260
```

-continued

```
gagtctatcg ccgagcaggg cgcactgcgc gatgccagcg agtctgatgt tgaagcgtct  1320
ctggatcgcc tgaaccgctg gaacaataat cgtaacggtg aagatccggt ggcgatccgt  1380
aaagcgctgc aagaatgtat gcagcataac ttctcggtct tccgtgaagg tgatgcgatg  1440
gcgaaagggc ttgagcagtt gaaagtgatc cgcgagcgtc tgaaaaatgc ccgtctggat  1500
gacacttcca gcgagttcaa cacccagcgc gttgagtgcc tggaactgga taacctgatg  1560
gaaacggcgt atgcaacggc tgtttctgcc aacttccgta ccgaaagccg tggcgcgcat  1620
agccgcttcg acttcccgga tcgtgatgat gaaaactggc tgtgccactc cctgtatctg  1680
ccagagtcgg aatccatgac gcgccgaagc gtcaacatgg aaccgaaact gcgcccggca  1740
ttcccgccga agattcgtac ttactaa                                       1767

SEQ ID NO: 109         moltype = DNA  length = 1167
FEATURE                Location/Qualifiers
source                 1..1167
                       mol_type = genomic DNA
                       organism = Escherichia coli
SEQUENCE: 109
atgaacttac atgaatatca ggcaaaacaa ctttttgccc gctatggctt accagcaccg  60
gtgggttatg cctgtactac tccgcgcgaa gcagaagaag ccgcttcaaa aatcggtgcc  120
ggtccgtggg tagtgaaatg tcaggttcac gctggtggcc gcggtaaagc gggcggtgtg  180
aaagttgtaa acagcaaaga agacatccgt gcttttgcag aaaactggct gggcaagcgt  240
ctggtaacgt atcaaacaga tgccaatggc caaccggtta accagattct ggttgaagca  300
gcgaccgata tcgctaaaga gctgtatctc ggtgccgttg ttgaccgtag ttcccgtcgt  360
gtggtcttta tggcctccac cgaaggcggc gtggaaatcg aaaaagtggc ggaagaaact  420
ccgcacctga tccataaagt tgcgcttgat ccgctgactg gcccgatgcc gtatcaggga  480
cgcgagctgg cgttcaaact gggtctggaa ggtaaactgg ttcagcagtt caccaaaatc  540
ttcatgggcc tggcgaccat tttcctggag cgcgacctgg cgttgatcga aatcaacccg  600
ctggtcatca ccaaacaggg cgatctgatt tgcctcgacg gcaaactggg cgctgacggc  660
aacgcactgt tccgccagcc tgatctgcgc gaaatgcgtg accagtcgca ggaagatccg  720
cgtgaagcac aggctgcaca gtgggaactg aactacgttg cgctggacgg taacatcggt  780
tgtatggtta acggcgcagg tctggcgatg ggtacgatgg acatcgttaa actgcacggc  840
ggcgaaccgg ctaacttcct tgacgttggc ggcggcgcaa ccaaagaacg tgtaaccgaa  900
gcgttcaaaa tcatcctctc tgacgacaaa gtgaaagccg ttctggttaa catcttcggc  960
ggtatcgttc gttgcgacct gatcgctgac ggtatcatcg gcgcggtagc agaagtgggt  1020
gttaacgtac cggtcgtggt acgtctggaa ggtaacaacg ccgaactcgg cgcgaagaaa  1080
ctggctgaca gcggcctgaa tattattgca gcaaaaggtc tgacggatgc agctcagcag  1140
gttgttgccg cagtggaggg gaaataa                                       1167

SEQ ID NO: 110         moltype = DNA  length = 870
FEATURE                Location/Qualifiers
source                 1..870
                       mol_type = genomic DNA
                       organism = Escherichia coli
SEQUENCE: 110
atgtccattt taatcgataa aaacaccaag gttatctgcc agggctttac cggtagccag  60
gggactttcc actcagaaca ggccattgca tacggcacta aaatggttgg cggcgtaacc  120
ccaggtaaag gcggcaccac ccacctcggc ctgccggtgt tcaacaccgt gcgtgaagcc  180
gttgctgcca ctggcgctac cgcttctgtt atctacgtac cagcaccgtt ctgcaaagac  240
tccattctgg aagccatcga cgcaggcatc aaactgatta tcaccatcac tgaaggcatc  300
ccgacgctgg atatgctgac cgtgaaagtg aagctggatg aagcaggcgt tcgtatgatc  360
ggcccgaact gcccaggcgt tatcactccg ggtgaatgca aaatcggtat ccagcctggt  420
cacattcaca aaccgggtaa agtgggtatc gtttcccgtt ccggtacact gacctatgaa  480
gcggttaaac agaccacgga ttacggtttc ggtcagtcga cctgtgtcgg tatcggcggt  540
gacccgatcc cgggctctaa ctttatcgac attctcgaaa tgttcgaaaa agatccgcag  600
accgaagcga tcgtgatgat cggtgagatc ggcggtagcg ctgaagaaga agcagctgcg  660
tacatcaaag agcacgttac caagccagtt gtgggttaca tcgctggtgt gactgcgccg  720
aaaggcaaac gtatgggcca cgcgggtgcc atcattgccg gtgggaaagg gactgcggat  780
gagaaattcg ctgctctgga agccgcaggc gtgaaaaccg ttcgcagcct ggcggatatc  840
ggtgaagcac tgaaaactgt tctgaaataa                                    870

SEQ ID NO: 111         moltype = DNA  length = 861
FEATURE                Location/Qualifiers
source                 1..861
                       mol_type = genomic DNA
                       organism = Escherichia coli
SEQUENCE: 111
atgagtcagg cgctaaaaaa tttactgaca ttgttaaatc tggaaaaaat tgaggaagga  60
ctctttcgcg gccagagtga agatttaggt ttacgccagg tgtttggcgg ccaggtcgtg  120
ggtcaggcct tgtatgctgc aaaagagacc gtccctgaag agcggctggt acattcgttt  180
cacagctact ttcttcgccc tggcgatagt aagaagccga ttatttatga tgtcgaaacg  240
ctgcgtgacg gtaacagctt cagcgcccgc cgggttgctg ctattcaaaa cggcaaaccg  300
atttttttata tgactgcctc tttccaggca ccagaagcgg gtttcgaaca tcaaaaaaca  360
atgccgtccg cgccagcgcc tgatggcctc ccttcggaaa cgcaaatcgc ccaatcgctg  420
gcgcacctgc tgccgccagt gctgaaagat aaattcatct gcgatcgtcc gctggaagtc  480
cgtccggtgg agtttcataa cccactgaaa ggtcacgtcg cagaaccaca tcgtcaggtg  540
tggatccgcg caaatggtag cgtgccggat gacctgcgcg ttcatcagta tctgctcggt  600
tacgcttctg atcttaactt cctgccggta gctctacagc cgcacggcat cggttttctc  660
gaaccgggga ttcagattgc caccattgac cattccatgt ggttccatcg cccgtttaat  720
ttgaatgaat ggctgctgta tagcgtggag agcacctcgg cgtccagcgc acgtggcttt  780
gtgcgcggtg agttttatac ccaagacggc gtactggttg cctcgaccgt tcaggaaggg  840
```

```
gtgatgcgta atcacaatta a                                          861

SEQ ID NO: 112         moltype = DNA  length = 405
FEATURE                Location/Qualifiers
source                 1..405
                       mol_type = genomic DNA
                       organism = Escherichia coli
SEQUENCE: 112
gtgaatacaa cgctgtttcg atggccggtt cgcgtctact atgaagatac cgatgccggt  60
ggtgtggtgt accacgccag ttacgtcgct ttttatgaaa gagcacgcac agagatgctg  120
cgtcatcatc acttcagtca gcaggcgctg atggctgaac gcgttgcctt tgtggtacgt  180
aaaatgacgg tggaatatta cgcacctgcg cggctcgacg atatgctcga aatacagact  240
gaaataacat caatgcgtgg cacctctttg gttttcacgc aacgtattgt caacgccgag  300
aatactttgc tgaatgaagc agaggttctg gttgtttgcg ttgacccact caaaatgaag  360
cctcgtgcgc ttcccaagtc tattgtcgcg gagtttaagc agtga                405

SEQ ID NO: 113         moltype = DNA  length = 399
FEATURE                Location/Qualifiers
source                 1..399
                       mol_type = genomic DNA
                       organism = Escherichia coli
SEQUENCE: 113
atgtctacaa cacataacgt ccctcagggc gatcttgttt tacgtacttt agccatgccc  60
gccgatacca atgccaatgg tgacatcttt ggtggttggt taatgtcaca aatggatatt  120
ggcggcgcta ttctggcaaa agaaattgcc cacggtcgcg tagtgactgt gcgggttgaa  180
ggaatgactt tcttacggcc ggttgcggtc ggcgatgtgg tgtgctgcta tgcacgctgt  240
gtccagaaag ggacgacatc ggtcagcatt aatattgaag tgtgggtgaa aaaagtagcg  300
tctgaaccaa ttgggcaacg ctataaagcg acagaagcat tatttaagta tgtcgcggtt  360
gatcctgaag gaaaacctcg cgccttacct gttgagtaa                       399

SEQ ID NO: 114         moltype = DNA  length = 996
FEATURE                Location/Qualifiers
source                 1..996
                       mol_type = genomic DNA
                       organism = Escherichia coli
SEQUENCE: 114
atgattaatg aagccacgct ggcagaaagt attcgccgct tacgtcaggg tgagcgtgcc  60
acactcgccc aggccatgac gctggtggaa agccgtcacc cgcgtcatca ggcactaagt  120
acgcagctgc ttgatgccat tatgccgtac tgcggtaaca ccctgcgact gggcgttacc  180
ggcacccccg gcgcggggaa aagtaccttt cttgaggcct ttggcatgtt gttgattcga  240
gagggattaa aggtcgcggt tattgcggtc gatcccagca gcccggtcac tggcggtagc  300
attctcgggg ataaaacccg catgaatgac ctggcgcgtg ccgaagcggc gtttattcgc  360
ccggtaccat cctccggtca tctgggcggt gccagtcagc gagcgcggga attaatgctg  420
ttatgcgaag cagcgggtta tgacgtagtg attgtcgaaa cggttggcgt cgggcagtcg  480
gaaacagaag tcgcccgcat ggtggactgt tttatctcgt tgcaaattgc cggtggcggc  540
gatgatctgc agggcattaa aaaagggctg atggaagtgg ctgatctgat cgttatcaac  600
aaagacgatg gcgataacca taccaatgtc gccattgccc ggcatatgta cgagagtgcc  660
ctgcatattc tgcgacgtaa atacgacgaa tggcagccac gggttctgac ttgtagcgca  720
ctggaaaaac gtggaatcga tgagatctgg cacgccatca tcgacttcaa aaccgcgcta  780
actgccagtg gtcgtttaca acaagtgcgg caacaacaat cggtggaatg gctgcgtaag  840
cagaccgaag aagaagtact gaatcacctg ttcgcgaatg aagatttcga tcgctattac  900
cgccagacgc ttttagcggt caaaaacaat acgctctcac cgcgcaccgg cctgcggcag  960
ctcagtgaat ttatccagac gcaatatttt gattaa                          996

SEQ ID NO: 115         moltype = DNA  length = 786
FEATURE                Location/Qualifiers
source                 1..786
                       mol_type = genomic DNA
                       organism = Escherichia coli
SEQUENCE: 115
atgtcttatc agtatgttaa cgttgtcact atcaacaaag tggcggtcat tgagtttaac  60
tatggccgaa aacttaatgc cttaagtaaa gtctttattg atgatcttat gcaggcgtta  120
agcgatctca accggccgga aattcgctgt atcattttgc gcgcaccgag tggatccaaa  180
gtcttctccg caggtcacga tattcacgaa ctgccgtctg gcggtcgcga tccgctctcc  240
tatgatgatc cattgcgtca aatcacccgc atgatccaaa aattcccgaa accgatcatt  300
tcgatggtgg aaggtagtgt ttggggtggc gcatttgaaa tgatcatgag ttccgatctg  360
atcatcgccg ccagtacctc aaccttctca atgacgcctg taaacctcgg cgtcccgtat  420
aacctggtcg gcattcacaa cctgacccgc gacgcgggct tccacattgt caaagagctg  480
atttttaccg cttcgccaat caccgcccag cgcgcgctgg ctgtcggcat cctcaaccat  540
gttgtggaag tggaagaact ggaagatttc accttacaaa tggcgcacca catctctgag  600
aaagcgccgt tagccattgc cgttatcaaa gaagagctgc gtgtactggg cgaagcacac  660
accatgaact ccgatgaatt tgaacgtatt caggggatgc gccgcgcggt gtatgacagc  720
gaagattacc aggaagggat gaacgctttc ctcgaaaaac gtaaacctaa tttcgttggt  780
cattaa                                                           786

SEQ ID NO: 116         moltype = DNA  length = 1479
FEATURE                Location/Qualifiers
source                 1..1479
                       mol_type = genomic DNA
```

```
                         organism = Escherichia coli
SEQUENCE: 116
atggaaactc agtggacaag gatgaccgcc aatgaagcgg cagaaattat ccagcataac  60
gacatggtgg catttagcgg ctttaccccg gcgggttcgc cgaaagccct acccaccgcg  120
attgcccgca gagctaacga acagcatgag gccaaaaagc cgtatcaaat tcgccttctg  180
acgggtgcgt caatcagcgc cgccgctgac gatgtacttt ctgacgccga tgctgtttcc  240
tggcgtgcgc catatcaaac atcgtccggt ttacgtaaaa agatcaatca gggcgcggtg  300
agtttcgttg acctgcattt gagcgaagtg gcgcaaatgg tcaattacgg tttcttcggc  360
gacattgatg ttgccgtcat tgaagcatcg gcactggcac cggatggtcg agtctggtta  420
accagcggga tcggtaatgc gccgacctgg ctgctgcggg cgaagaaagt gatcattgaa  480
ctcaatcact atcacgatcc gcgcgttgca gaactggcgg atattgtgat tcctggcgcg  540
ccaccgcggc gcaatagcgt gtcgatcttc catgcaatgg atcgcgtcgg tacccgctat  600
gtgcaaatcg atccgaaaaa gattgtcgcc gtcgtggaaa ccaacttgcc cgacgccggt  660
aatatgctgg ataagcaaaa tcccatgtgc cagcagattg ccgataacgt ggtcacgttc  720
ttattgcagg aaatggcgca tgggcgtatt ccgccggaat ttctgccgct gcaaagtggc  780
gtgggcaata tcaataatgc ggtaatggcg cgtctggggg aaaacccggt aattcctccg  840
tttatgatgt attcggaagt gctacaggaa tcggtggtgc atttactgga aaccggcaaa  900
atcagcgggg ccagcgcctc cagcctgaca atctcggccg attccctgcg caagatttac  960
gacaatatgg attactttgc cagccgcatt gtgttgcgtc cgcaggagat ttccaataac  1020
ccggaaatca tccgtcgtct gggcgtcatc gctctgaacg tcggcctgga gtttgatatt  1080
tacgggcatg ccaactcaac acacgtagcc ggggtcgatc tgatgaacgg catcggcggc  1140
agcggtgatt ttgaacgcaa cgcgtatctg tcgatcttta tggccccgtc gattgctaaa  1200
gaaggcaaga tctcaaccgt cgtgccaatg tgcagccatg ttgatcacag cgaacacagc  1260
gtcaaagtga tcatcaccga acaagggatc gccgatctgc gcggtctttc cccgcttcaa  1320
cgcgcccgca ctatcattga taattgtgca catcctatgt atcgggatta tctgcatcgc  1380
tatctggaaa atgcgcctgg cggacatatt caccacgatc ttagccacgt cttcgactta  1440
caccgtaatt taattgcaac cggctcgatg ctgggttaa                         1479

SEQ ID NO: 117           moltype = DNA  length = 468
FEATURE                  Location/Qualifiers
source                   1..468
                         mol_type = genomic DNA
                         organism = Escherichia coli
SEQUENCE: 117
atgtctgccg tactgaccgc tgaacaagcc ctgaaattag tgggtgagat gtttgtttat  60
cacatgccat ttaaccgcgc attggggatg gaactggagc gttacgaaaa agagttcgca  120
cagctggcct ttaaaaatca gccaatgatg gtgggcaact gggcgcaaag cattttgcac  180
ggcggggtca ttgcgtcggc gctggatgtc gccgccggtc tggtgtgcgt gggaagtacc  240
ttaacccgcc acgaaaccat cagtgaagat gaactacgcc agcggctatc gcggatgggg  300
accattgatc ttcgcgttga ttatctgcgc ccaggcaggg gcgagcgttt tactgctact  360
agtagcctgt tgcgtgcagg caataaagtc gccgtcgccc gcgttgaatt acacaatgaa  420
gaacagcttt atattgccag tgccaccgcc acctatatgg taggttga               468

SEQ ID NO: 118           moltype = DNA  length = 1986
FEATURE                  Location/Qualifiers
source                   1..1986
                         mol_type = genomic DNA
                         organism = Escherichia coli
SEQUENCE: 118
atgaataact ctcggttatt ccgtttgagc aggattgtta ttgcgttaac tgccgccagc  60
ggcatgatgg taaataccgc taacgcgaaa gaggaagcga aagccgccac tcaatatacc  120
caacaggtta atcagaatta cgccaaatca ttaccgttta gcgatcgtca ggattttgac  180
gatgcccagc gtggatttat cgccccgctg ctggatgaag gtattctgcg tgatgcgaac  240
ggtaaagttt actaccgcgc ggacgattac aaatttgata ttaatgccgc agcgccggaa  300
accgtaaacc ccagcctgtg gcgtcagtcg caaatcaacg gtatttctgg cctgttcaaa  360
gtcaccgata aaatgtatca ggtgcgcggc caggatatct ctaacattac gttcgttgag  420
ggcgagaaag gcattattgt tatcgacccg ctggtgacgc cgcctgccgc aaaagccgca  480
cttgaccttt acttccagca tcgtccgcaa aaaccgattg ttgccgttat ctacactcac  540
agccacaccg accactatgg tggcgtgaaa ggcattatct ctgaagccga tgttaaatcc  600
ggcaaagttc aggtgattgc ccctgcaggc tttatggacg aagccatcag cgaaaacgtg  660
ctggcgggta acatcatgag ccgccgtgcg ctctactctt acggtctgtt actgccgcac  720
aacgcgcaag gcaatgtggg taatggcctt ggcgtgacgc tggcaacggg cgacccgagc  780
attattgcac cgacgaaaac tatcgtcaga actggcgaga agatgattat cgacggcctg  840
gagtttgact tcctgatgac cccaggtagc gaagcgccag ccgaaatgca cttctatatt  900
ccggccctga aagccctgtg taccgccgag aacgccacgc ataccctgca caacttctac  960
actctgcgcg gcgcgaaaac ccgcgacacc agcaagtgga ccgagtatct gaacgaaacg  1020
ctggatatgt ggggtaacga cgcggaagtg ctgtttatgc cgcacacctg gccggtctgg  1080
ggcaataagc atatcaatga ttatattggt aaataccgcg ataccatcaa gtacattcac  1140
gaccagaccc tgcacctggc gaaccagggc tacaccatga atgaaatcgg cgacatgatt  1200
aagctgccgc ctgcacttgc caataactgg gccagccgcg gctattacgg ttctgtcagc  1260
cacaacgccc gcgcggtgta taacttctat cttggctatt acgacggtaa cccggctaac  1320
ctgcatccgt atggtcaggt ggagatgggt aaacgttacg tgcaggcgct gggcggttct  1380
gcccgtgtca tcaacctggc gcaagaagcg aacaagcaag gtgattaccg ctggtcggca  1440
gaactgctga aacaggtgat tgccgccaac ccgggtgacc aggtcgcgaa gaatctgcaa  1500
gcgaataact ttgaacagct gggctatcag gccgagtccg ccacatggcg cggtttctac  1560
ctgaccggcg cgaaagagct gcgcgaaggg gtgcataagt tcagccacgg caccaccggt  1620
tccccggaca ccattcgcgg gatgtcggtc gaaatgctgt tcgactttat ggccgttcgc  1680
ctcgatagcg cgaaagctgc gggtaaaaat atcagcctga acttcaatat gagcaacggc  1740
gataacctca acctgacgct gaacgatagc gtgcttaact accggaaaac gctgcaaccg  1800
```

```
caagccgacg cctctttcta catcagccgt gaagatctgc acgccgtgct gaccggacaa  1860
gccaaaatgg cggatctggt aaaagcgaag aaagccaaaa ttattggcaa tggcgcgaaa  1920
ctggaagaaa ttatcgcctg tctggataat ttcgatttgt gggtgaatat cgtaacccca  1980
aattaa                                                             1986

SEQ ID NO: 119          moltype = DNA  length = 39
FEATURE                 Location/Qualifiers
source                  1..39
                        mol_type = other DNA
                        organism = synthetic construct
SEQUENCE: 119
tgaaggaaat gaagtcctga gcgagagtag ggaactgcc                       39

SEQ ID NO: 120          moltype = DNA  length = 41
FEATURE                 Location/Qualifiers
source                  1..41
                        mol_type = other DNA
                        organism = synthetic construct
SEQUENCE: 120
tatctttacc tcctttgcta gctcagccca tatgcaggcc g                    41

SEQ ID NO: 121          moltype = DNA  length = 46
FEATURE                 Location/Qualifiers
source                  1..46
                        mol_type = other DNA
                        organism = synthetic construct
SEQUENCE: 121
gctagcaaag gaggtaaaga taatgagaaa ggttcccatt attacc               46

SEQ ID NO: 122          moltype = DNA  length = 23
FEATURE                 Location/Qualifiers
source                  1..23
                        mol_type = other DNA
                        organism = synthetic construct
SEQUENCE: 122
tcaggacttc atttccttca gac                                        23

SEQ ID NO: 123          moltype = DNA  length = 39
FEATURE                 Location/Qualifiers
source                  1..39
                        mol_type = other DNA
                        organism = synthetic construct
SEQUENCE: 123
ccatgggact gaaaaaataa gcgagagtag ggaactgcc                       39

SEQ ID NO: 124          moltype = DNA  length = 48
FEATURE                 Location/Qualifiers
source                  1..48
                        mol_type = other DNA
                        organism = synthetic construct
SEQUENCE: 124
gctagcaaag gaggtaaaga taatgagaaa agtagaaatc attacagc             48

SEQ ID NO: 125          moltype = DNA  length = 23
FEATURE                 Location/Qualifiers
source                  1..23
                        mol_type = other DNA
                        organism = synthetic construct
SEQUENCE: 125
ttattttttc agtcccatgg gac                                        23

SEQ ID NO: 126          moltype = DNA  length = 49
FEATURE                 Location/Qualifiers
source                  1..49
                        mol_type = other DNA
                        organism = synthetic construct
SEQUENCE: 126
caatttcaca caggaggaat caaaaatgat ggttccaacc ctcgaacac            49

SEQ ID NO: 127          moltype = DNA  length = 47
FEATURE                 Location/Qualifiers
source                  1..47
                        mol_type = other DNA
                        organism = synthetic construct
SEQUENCE: 127
cattatctta tcctcctttc tcgagtcaat gctcggcgtc ggcgatc              47

SEQ ID NO: 128          moltype = DNA  length = 54
FEATURE                 Location/Qualifiers
```

```
source                  1..54
                        mol_type = other DNA
                        organism = synthetic construct
SEQUENCE: 128
tgactcgaga aaggaggata agataatgag tcaggcgcta aaaaatttac tgac        54

SEQ ID NO: 129          moltype = DNA  length = 58
FEATURE                 Location/Qualifiers
source                  1..58
                        mol_type = other DNA
                        organism = synthetic construct
SEQUENCE: 129
ggttggaacc atcatttttg attcctcctg tgtgaaattg ttatccgctc acaattcc    58

SEQ ID NO: 130          moltype = DNA  length = 47
FEATURE                 Location/Qualifiers
source                  1..47
                        mol_type = other DNA
                        organism = synthetic construct
SEQUENCE: 130
caatttcaca caggaggaat caaaaatgct ggtaaatgac gagcaac                47

SEQ ID NO: 131          moltype = DNA  length = 47
FEATURE                 Location/Qualifiers
source                  1..47
                        mol_type = other DNA
                        organism = synthetic construct
SEQUENCE: 131
cattatcttt acctcctttg ctagctcaaa gattgcgcgc aatgacc                47

SEQ ID NO: 132          moltype = DNA  length = 49
FEATURE                 Location/Qualifiers
source                  1..49
                        mol_type = other DNA
                        organism = synthetic construct
SEQUENCE: 132
tgagctagca aaggaggtaa agataatgta cgcagctaag gacatcacc              49

SEQ ID NO: 133          moltype = DNA  length = 43
FEATURE                 Location/Qualifiers
source                  1..43
                        mol_type = other DNA
                        organism = synthetic construct
SEQUENCE: 133
tctctcatcc gccaaaacag cctcattggg ccctcctgga gag                    43

SEQ ID NO: 134          moltype = DNA  length = 41
FEATURE                 Location/Qualifiers
source                  1..41
                        mol_type = other DNA
                        organism = synthetic construct
SEQUENCE: 134
tctccaggag ggcccaatga ggctgttttg gcggatgaga g                      41

SEQ ID NO: 135          moltype = DNA  length = 50
FEATURE                 Location/Qualifiers
source                  1..50
                        mol_type = other DNA
                        organism = synthetic construct
SEQUENCE: 135
gtcatttacc agcatttttg attcctcctg tgtgaaattg ttatccgctc             50

SEQ ID NO: 136          moltype = DNA  length = 46
FEATURE                 Location/Qualifiers
source                  1..46
                        mol_type = other DNA
                        organism = synthetic construct
SEQUENCE: 136
ttcacacagg aggaatcaaa aatgcatttt aaactatcag aagaac                 46

SEQ ID NO: 137          moltype = DNA  length = 49
FEATURE                 Location/Qualifiers
source                  1..49
                        mol_type = other DNA
                        organism = synthetic construct
SEQUENCE: 137
tatctttacc tcctttgcta gcctacttcg ttaacatacg agaaattac              49

SEQ ID NO: 138          moltype = DNA  length = 45
```

-continued

```
FEATURE                Location/Qualifiers
source                 1..45
                       mol_type = other DNA
                       organism = synthetic construct
SEQUENCE: 138
ctcgtatgtt aacgaagtag gctagcaaag gaggtaaaga taatg                 45

SEQ ID NO: 139         moltype = DNA  length = 46
FEATURE                Location/Qualifiers
source                 1..46
                       mol_type = other DNA
                       organism = synthetic construct
SEQUENCE: 139
ttctgatagt ttaaaatgca tttttgattc ctcctgtgtg aaattg                46

SEQ ID NO: 140         moltype = DNA  length = 47
FEATURE                Location/Qualifiers
source                 1..47
                       mol_type = other DNA
                       organism = synthetic construct
SEQUENCE: 140
ttgtgagcgg ataacaattt cggtgtatgc aagagggata aaaaatg               47

SEQ ID NO: 141         moltype = DNA  length = 44
FEATURE                Location/Qualifiers
source                 1..44
                       mol_type = other DNA
                       organism = synthetic construct
SEQUENCE: 141
tcttatcctc ctttctcgag tcagaacagc gttaaaccaa tgac                  44

SEQ ID NO: 142         moltype = DNA  length = 46
FEATURE                Location/Qualifiers
source                 1..46
                       mol_type = other DNA
                       organism = synthetic construct
SEQUENCE: 142
tatccctctt gcatacaccg aaattgttat ccgctcacaa ttccac                46

SEQ ID NO: 143         moltype = DNA  length = 39
FEATURE                Location/Qualifiers
source                 1..39
                       mol_type = other DNA
                       organism = synthetic construct
SEQUENCE: 143
cggtggtaaa actcccttga ggctgttttg gcggatgag                        39

SEQ ID NO: 144         moltype = DNA  length = 42
FEATURE                Location/Qualifiers
source                 1..42
                       mol_type = other DNA
                       organism = synthetic construct
SEQUENCE: 144
gcaagggttt gtgtactcat tatctttacc tcctttgcta gc                    42

SEQ ID NO: 145         moltype = DNA  length = 41
FEATURE                Location/Qualifiers
source                 1..41
                       mol_type = other DNA
                       organism = synthetic construct
SEQUENCE: 145
tagcaaagga ggtaaagata atgagtacac aaacccttgc c                     41

SEQ ID NO: 146         moltype = DNA  length = 41
FEATURE                Location/Qualifiers
source                 1..41
                       mol_type = other DNA
                       organism = synthetic construct
SEQUENCE: 146
tctcatccgc caaaacagcc tcaagggagt tttaccaccg c                     41

SEQ ID NO: 147         moltype = DNA  length = 47
FEATURE                Location/Qualifiers
source                 1..47
                       mol_type = other DNA
                       organism = synthetic construct
SEQUENCE: 147
tgactcgaga aaggaggata agataatgga ccagaagctg ttaacgg               47
```

```
SEQ ID NO: 148          moltype = DNA  length = 47
FEATURE                 Location/Qualifiers
source                  1..47
                        mol_type = other DNA
                        organism = synthetic construct
SEQUENCE: 148
ctttctacgt gttccgcttc ctttagtgat cgctgagata tttcagg              47

SEQ ID NO: 149          moltype = DNA  length = 43
FEATURE                 Location/Qualifiers
source                  1..43
                        mol_type = other DNA
                        organism = synthetic construct
SEQUENCE: 149
aatatctcag cgatcactaa aggaagcgga acacgtagaa agc                  43

SEQ ID NO: 150          moltype = DNA  length = 49
FEATURE                 Location/Qualifiers
source                  1..49
                        mol_type = other DNA
                        organism = synthetic construct
SEQUENCE: 150
caatttcaca caggaggaat caaaaatgaa tcaacaggta aatgtggcc            49

SEQ ID NO: 151          moltype = DNA  length = 46
FEATURE                 Location/Qualifiers
source                  1..46
                        mol_type = other DNA
                        organism = synthetic construct
SEQUENCE: 151
cattatcttt acctcctttg ctagcttaag cgaccccgtt cagtgc               46

SEQ ID NO: 152          moltype = DNA  length = 50
FEATURE                 Location/Qualifiers
source                  1..50
                        mol_type = other DNA
                        organism = synthetic construct
SEQUENCE: 152
taagctagca aaggaggtaa agataatgaa tacttctgaa ctcgaaaccc           50

SEQ ID NO: 153          moltype = DNA  length = 48
FEATURE                 Location/Qualifiers
source                  1..48
                        mol_type = other DNA
                        organism = synthetic construct
SEQUENCE: 153
catttagtta tcctcctttc tcgagttagc gaatagaaaa gccgttgg             48

SEQ ID NO: 154          moltype = DNA  length = 53
FEATURE                 Location/Qualifiers
source                  1..53
                        mol_type = other DNA
                        organism = synthetic construct
SEQUENCE: 154
taactcgaga aaggaggata actaaatgaa acttaacgac agtaacttat tcc        53

SEQ ID NO: 155          moltype = DNA  length = 56
FEATURE                 Location/Qualifiers
source                  1..56
                        mol_type = other DNA
                        organism = synthetic construct
SEQUENCE: 155
tctctcatcc gccaaaacag ccttaaagac cgatgcacat atatttgatt tctaag     56

SEQ ID NO: 156          moltype = DNA  length = 41
FEATURE                 Location/Qualifiers
source                  1..41
                        mol_type = other DNA
                        organism = synthetic construct
SEQUENCE: 156
atatgtgcat cggtctttaa ggctgttttg gcggatgaga g                    41

SEQ ID NO: 157          moltype = DNA  length = 50
FEATURE                 Location/Qualifiers
source                  1..50
                        mol_type = other DNA
                        organism = synthetic construct
SEQUENCE: 157
tacctgttga ttcatttttg attcctcctg tgtgaaattg ttatccgctc           50
```

```
SEQ ID NO: 158         moltype = DNA  length = 25
FEATURE                Location/Qualifiers
source                 1..25
                       mol_type = other DNA
                       organism = synthetic construct
SEQUENCE: 158
ctcgagaaag gaggataact aaatg                                        25

SEQ ID NO: 159         moltype = DNA  length = 25
FEATURE                Location/Qualifiers
source                 1..25
                       mol_type = other DNA
                       organism = synthetic construct
SEQUENCE: 159
cattatcttt acctcctttg ctagc                                        25

SEQ ID NO: 160         moltype = DNA  length = 44
FEATURE                Location/Qualifiers
source                 1..44
                       mol_type = other DNA
                       organism = synthetic construct
SEQUENCE: 160
tagcaaagga ggtaaagata atgaatacag cagaactgga aacc                   44

SEQ ID NO: 161         moltype = DNA  length = 44
FEATURE                Location/Qualifiers
source                 1..44
                       mol_type = other DNA
                       organism = synthetic construct
SEQUENCE: 161
agttatcctc ctttctcgag ttagcgaatg gaaaaaccgt tggt                   44

SEQ ID NO: 162         moltype = DNA  length = 7531
FEATURE                Location/Qualifiers
source                 1..7531
                       mol_type = other DNA
                       organism = synthetic construct
SEQUENCE: 162
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gtttttttgcg ccgacatcat aacggttctg gcaaatattc  180
tgaaatgagc tgttgacaat taatcatccg gctcgtataa tgtgtggaat tgtgagcgga  240
taacaatttc acacaggaaa cagactgact gacgttgtca tcgtatccgc cgcccgcacc  300
gcggtcggca agtttggcgg ctcgctggcc aagatcccgg caccggaact gggtgccgtg  360
gtcatcaagg ccgcgctgga gcgcgccggc gtcaagccgg agcaggtgag cgaagtcatc  420
atgggccagg tgctgaccgc cggttcgggc cagaaccccg cacgccaggc cgcgatcaag  480
gccggcctgc cggcgatggt gccggccatg accatcaaca aggtgtgcgg ctcgggcctg  540
aaggccgtga tgctggccgc caacgcgatc atggcgggcg acgccgagat cgtggtggcc  600
ggcggccagg aaaacatgag cgccgccccg cacgtgctgc cgggctcgcg cgatggtttc  660
cgcatgggcg atgccaagct ggtcgacacc atgatcgtcg acggcctgtg ggacgtgtac  720
aaccagtacc acatgggcat caccgccgag aacgtggcca aggaatacgg catcacacgc  780
gaggcgcagg atgagttcgc cgtcggctcg cagaacaagg ccgaagccgc gcagaaggcc  840
ggcaagtttg acgaagagat cgtcccggtg ctgatcccgc agcgcaaggg cgacccggtg  900
gccttcaaga ccgacgagtt cgtgcgccag ggcgccacgc tggacagcat gtccggcctc  960
aagcccgcct tcgacaaggc cggcacggtg accgcggcca acgcctcggg cctgaacgac  1020
ggcgccgccg cggtggtggt gatgtcggcg gccaaggcca aggaactggg cctgaccccg  1080
ctggccacga tcaagagcta tgccaacgcc ggtgtcgatc ccaaggtgat gggcatgggc  1140
ccggtgccgg cctccaagcg cgccctgtcg cgcgccgagt ggaccccgca agacctggac  1200
ctgatggaga tcaacgaggc ctttgccgcg caggcgctgg cggtgcacca gcagatgggc  1260
tgggacacct ccaaggtcaa tgtgaacggc ggcgccatcg ccatcggcca cccgatcggc  1320
gcgtcgggct gccgtatcct ggtgacgctg ctgcacgaga tgaagcgccg tgacgcgaag  1380
aagggcctgg cctcgctgtg catcggcggc ggcatgggcg tggcgctggc agtcgagcgc  1440
aaataaggaa ggggttttcc ggggccgcgc gcggttggcg cggacccggc gacgataacg  1500
aagccaatca aggagtggac atgactcagc gcattgcgta tgtgaccggc ggcatgggtg  1560
gtatcggaac cgccatttgc cagcggctgg ccaaggatgg ctttcgtgtg gtggccggtt  1620
gcggccccaa ctcgccgcgc cgcgaaaagt ggctggagca gcagaaggcc ctgggcttcg  1680
atttcattgc ctcggaaggc aatgtggctg actgggactc gaccaagacc gcattcgaca  1740
aggtcaagtc cgaggtcggc gaggttgatg tgctgatcaa caacgccggt atcacccgcg  1800
acgtggtgtt ccgcaagatg acccgcgccg actgggatgc ggtgatcgac accaacctga  1860
cctcgctgtt caacgtcacc aagcaggtga tcgacggcat ggccgaccgt ggctggggcc  1920
gcatcgtcaa catctcgtcg gtgaacgggc agaagggcca gttcggccag accaactact  1980
ccaccgccaa ggccggcctg catggcttca ccatggcact ggcgcaggaa gtggcgacca  2040
agggcgtgac cgtcaacacg gtctctccgg gctatatcgc caccgacatg gtcaaggcga  2100
tccgccagga cgtgctcgac aagatcgtcg cgacgatccc ggtcaagcgc ctgggcctgc  2160
cggaagagat cgcctcgatc tgcgcctggt tgtcgtcgga ggagtccggt ttctcgaccg  2220
gcgccgactt ctcgctcaac ggcggcctgc atatgggctg agctagcaaa ggaggtaaag  2280
ataatgagaa aggttcccat tattaccgca gatgaggctg caaagcttat taaagacggt  2340
gatacagtta caacaagtgg tttcgttgga aatgcaatcc ctgaggctct tgatagagct  2400
```

-continued

```
gtagaaaaaa gattcttaga aacaggcgaa cccaaaaaca ttacatatgt ttattgtggt  2460
tctcaaggta acagagacgg aagaggtgct gagcactttg ctcatgaagg cctttttaaaa  2520
cgttacatcg ctggtcactg ggctacagtt cctgctttgg gtaaaatggc tatggaaaat  2580
aaaatggaag catataatgt atctcagggt gcattgtgtc atttgttccg tgatatagct  2640
tctcataagc caggcgtatt tacaaaggta ggtatcggta ctttcattga ccccagaaat  2700
ggcggcggta aagtaaatga tattaccaaa gaagatattg ttgaattggt agagattaag  2760
ggtcaggaat atttattcta ccctgctttt cctattcatg tagctcttat tcgtggtact  2820
tacgctgatg aaagcggaaa tatcacattt gagaaagaag ttgctcctct ggaaggaact  2880
tcagtatgcc aggctgttaa aaacagtggc ggtatcgttg tagttcaggt tgaaagagta  2940
gtaaaagctg gtactcttga ccctcgtcat gtaaaagttc caggaattta tgttgactat  3000
gttgttgttg ctgacccaga agatcatcag caatctttag attgtgaata tgatcctgca  3060
ttatcaggcg agcatagaag acctgaagtt gttggagaac cacttccttt gagtgcaaag  3120
aaagttattg gtcgtcgtgg tgccattgaa ttagaaaaag atgttgctgt aaatttaggt  3180
gttggtgcgc ctgaatatgt agcaagtgtt gctgatgaag aaggtatcgt tgattttatg  3240
actttaactg ctgaaagtgg tgctattggt ggtgttcctg ctggtggcgt tcgctttggt  3300
gcttcttata atgcggatgc attgatcgat caaggttatc aattcgatta ctatgatggc  3360
ggcggcttag acctttgcta tttaggctta gctgaatgcg atgaaaaagg caatatcaac  3420
gtttcaagat ttggccctcg tatcgctggt tgtggtggtt tcatcaacat tacacagaat  3480
acacctaagg tattcttctg tggtactttc acagcaggtg gcttaaaggt taaaattgaa  3540
gatggcaagg ttattattgt tcaagaaggc aagcagaaaa aattcttgaa agctgttgag  3600
cagattacat tcaatggtga cgttgcactt gctaataagc aacaagtaac ttatattaca  3660
gaaagatgcg tattcctttt gaaggaagat ggtttgcact tatctgaaat tgcacctggt  3720
attgatttgc agacacagat tcttgacgtt atggattttg cacctattat tgacagagat  3780
gcaaacggcc aaatcaaatt gatggacgct gctttgtttg cagaaggctt aatgggtctg  3840
aaggaaatga agtcctgagc gagagtaggg aactgccagg catcaaataa aacgaaaggc  3900
tcagtcgaaa gactgggcct ttcgttttat ctgttgtttg tcggtgaacg ctctcctgag  3960
taggacaaat ccgccgggag cggatttgaa cgttgcgaag caacggcccg gagggtggcg  4020
ggcaggacgc ccgccataaa ctgccaggca tcaaattaag cagaaggcca tcctgacgga  4080
tggccttttt gcgtttctac aaactctttt tgtttatttt tctaaataca ttcaaatatg  4140
tatccgctca tgagacaata accctgataa atgcttcaat aatattgaaa aaggaagagt  4200
atgagtattc aacatttccg tgtcgccctt attccctttt ttgcggcatt ttgccttcct  4260
gtttttgctc acccagaaac gctggtgaaa gtaaaagatg ctgaagatca gttgggtgca  4320
cgagtgggtt acatcgaact ggatctcaac agcggtaaga tccttgagag ttttcgcccc  4380
gaagaacgtt ttccaatgat gagcactttt aaagttctgc tatgtggcgc ggtattatcc  4440
cgtgttgacg ccgggcaaga gcaactcggt cgccgcatac actattctca gaatgacttg  4500
gttgagtact caccagtcac agaaaagcat cttacggatg gcatgacagt aagagaatta  4560
tgcagtgctg ccataaccat gagtgataac actgcggcca acttacttct gacaacgatc  4620
ggaggaccga aggagctaac cgcttttttg cacaacatgg gggatcatgt aactcgcctt  4680
gatcgttggg aaccggagct gaatgaagcc ataccaaacg acgagcgtga caccacgatg  4740
cctacagcaa tggcaacaac gttgcgcaaa ctattaactg gcgaactact tactctagct  4800
tcccggcaac aattaataga ctggatggag gcggataaag ttgcaggacc acttctgcgc  4860
tcggcccttc cggctggctg gtttattgct gataaatctg gagccggtga gcgtgggtct  4920
cgcggtatca ttgcagcact ggggccagat ggtaagccct cccgtatcgt agttatctac  4980
acgacgggga gtcaggcaac tatggatgaa cgaaatagac agatcgctga gataggtgcc  5040
tcactgatta agcattggta actgtcagac caagtttact catatatact ttagattgat  5100
ttaaaacttc atttttaatt taaaaggatc taggtgaaga tcctttttga taatctcatg  5160
accaaaatcc cttaacgtga gttttcgttc cactgagcgt cagaccccgt agaaaagatc  5220
aaaggatctt cttgagatcc tttttttctg cgcgtaatct gctgcttgca aacaaaaaaa  5280
ccaccgctac cagcggtggt ttgtttgccg gatcaagagc taccaactct ttttccgaag  5340
gtaactggct tcagcagagc gcagatacca aatactgtcc ttctagtgta gccgtagtta  5400
ggccaccact tcaagaactc tgtagcaccg cctacatacc tcgctctgct aatcctgtta  5460
ccagtggctg ctgccagtgg cgataagtcg tgtcttaccg ggttggactc aagacgatag  5520
ttaccggata aggcgcagcg gtcgggctga acggggggtt cgtgcacaca gcccagcttg  5580
gagcgaacga cctacaccga actgagatac ctacagcgtg agctatgaga aagcgccacg  5640
cttcccgaag ggagaaaggc ggacaggtat ccggtaagcg gcagggtcgg aacaggagag  5700
cgcacgaggg agcttccagg gggaaacgcc tggtatcttt atagtcctgt cgggtttcgc  5760
cacctctgac ttgagcgtcg atttttgtga tgctcgtcag gggggcggag cctatggaaa  5820
aacgccagca acgcggcctt tttacggttc ctggcctttt gctggccttt tgctcacatg  5880
ttctttcctg cgttatcccc tgattctgtg gataaccgta ttaccgcctt tgagtgagct  5940
gataccgctc gccgcagccg aacgaccgag cgcagcgagt cagtgagcga ggaagcggaa  6000
gagcgcctga tgcggtattt tctccttacg catctgtgcg gtatttcaca ccgcatatgg  6060
tgcactctca gtacaatctg ctctgatgcc gcatagttaa gccagtatac actccgctat  6120
cgctacgtga ctgggtcatg gctgcgcccc gacacccgcc aacacccgct gacgcgccct  6180
gacgggcttg tctgctcccg gcatccgctt acagacaagc tgtgaccgtc tccgggagct  6240
gcatgtgtca gaggttttca ccgtcatcac cgaaacgcgc gaggcagcag atcaattcgc  6300
gcgcgaaggc gaagcggcat gcatttacgt tgacaccatc gaatggtgca aaacctttcg  6360
cggtatggca tgatagcgcc cggaagagag tcaattcagg gtggtgaatg tgaaaccagt  6420
aacgttatac gatgtcgcag agtatgccgg tgtctcttat cagaccgttt cccgcgtggt  6480
gaaccaggcc agccacgttt ctgcgaaaac gcgggaaaaa gtggaagcgg cgatggcgga  6540
gctgaattac attcccaacc gcgtggcaca acaactggcg ggcaaacagt cgttgctgat  6600
tggcgttgcc acctccagtc tggccctgca cgcgccgtcg caaattgtcg cggcgattaa  6660
atctcgcgcc gatcaactgg gtgccagcgt ggtggtgtcg atggtagaac gaagcggcgt  6720
cgaagcctgt aaagcggcgg tgcacaatct tctcgcgcaa cgcgtcagtg ggctgatcat  6780
taactatccg ctggatgacc aggatgccat tgctgtggaa gctgcctgca ctaatgttcc  6840
ggcgttattt cttgatgtct ctgaccagac acccatcaac agtattattt tctcccatga  6900
agacggtacg cgactgggcg tggagcatct ggtcgcattg ggtcaccagc aaatcgcgct  6960
gttagcgggc ccattaagtt ctgtctcggc gcgtctgcgt ctggctggct ggcataaata  7020
tctcactcgc aatcaaattc agccgatagc ggaacgggaa ggcgactgga gtgccatgtc  7080
cggttttcaa caaaccatgc aaatgctgaa tgagggcatc gttcccactg cgatgctggt  7140
```

```
tgccaacgat cagatggcgc tgggcgcaat gcgcgccatt accgagtccg ggctgcgcgt  7200
tggtgcggat atctcggtag tgggatacga cgataccgaa gacagctcat gttatatccc  7260
gccgttaacc accatcaaac aggattttcg cctgctgggg caaaccagcg tggaccgctt  7320
gctgcaactc tctcagggcc aggcggtgaa gggcaatcag ctgttgcccg tctcactggt  7380
gaaaagaaaa accaccctgg cgcccaatac gcaaaccgcc tctccccgcg cgttggccga  7440
ttcattaatg cagctggcac gacaggtttc ccgactggaa agcgggcagt gagcgcaacg  7500
caattaatgt gagttagcgc gaattgatct g                                7531

SEQ ID NO: 163         moltype = DNA  length = 7510
FEATURE                Location/Qualifiers
source                 1..7510
                       mol_type = other DNA
                       organism = synthetic construct
SEQUENCE: 163
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gtttttttgcg ccgacatcat aacggttctg gcaaatattc  180
tgaaatgagc tgttgacaat taatcatccg gctcgtataa tgtgtggaat tgtgagcgga  240
taacaatttc acacaggaaa cagactgact gacgttgtca tcgtatccgc cgcccgcacc  300
gcggtcggca agtttggcgg ctcgctggcc aagatcccgg caccggaact gggtgccgtg  360
gtcatcaagg ccgcgctgga gcgcgccggc gtcaagccgg agcaggtgag cgaagtcatc  420
atgggccagg tgctgaccgc cggttcgggc cagaaccccg cacgccaggc cgcgatcaag  480
gccggcctgc cggcgatggt gccggccatg accatcaaca aggtgtgcgg ctcgggcctg  540
aaggccgtga tgctggccgc caacgcgatc atggcgggcg acgccgagat cgtggtggcc  600
ggcggccagg aaaacatgag cgccgccccg cacgtgctgc cgggctcgcg cgatggtttc  660
cgcatgggcg atgccaagct ggtcgacacc atgatcgtcg acggcctgtg ggacgtgtac  720
aaccagtacc acatgggcat caccgccgag aacgtggcca aggaatacgg catcacacgc  780
gaggcgcagg atgagttcgc cgtcggctcg cagaacaagg ccgaagccgc gcagaaggcc  840
ggcaagtttg acgaagagat cgtcccggtg ctgatcccgc agcgcaaggg cgacccggtg  900
gccttcaaga ccgacgagtt cgtgcgccag ggcgccacgc tggacagcat gtccggcctc  960
aagcccgcct tcgacaaggc cggcacggtg accgcggcca acgcctcggg cctgaacgac  1020
ggcgccgccg cggtggtggt gatgtcggcg gccaaggcca aggaactggg cctgaccccg  1080
ctggccacga tcaagagcta tgccaacgcc ggtgtcgatc ccaaggtgat gggcatgggc  1140
ccggtgccgg cctccaagcg cgccctgtcg cgcgccgagt ggaccccgca agacctggac  1200
ctgatggaga tcaacgaggc ctttgccgcg caggcgctgg cggtgcacca gcagatgggc  1260
tgggacacct ccaaggtcaa tgtgaacggc ggcgccatcg ccatcggcca cccgatcggc  1320
gcgtcgggct gccgtatcct ggtgacgctg ctgcacgaga tgaagcgccg tgacgcgaag  1380
aagggcctgg cctcgctgtg catcggcggc ggcatgggcg tggcgctggc agtcgagcgc  1440
aaataaggaa ggggttttcc ggggccgcgc gcggttggcg cggacccggc gacgataacg  1500
aagccaatca aggagtggac atgactcagc gcattgcgta tgtgaccggc ggcatgggtg  1560
gtatcggaac cgccatttgc cagcggctgg ccaaggatgg ctttcgtgtg gtggccggtt  1620
gcggccccaa ctcgccgcgc cgcgaaaagt ggctggagca gcagaaggcc ctgggcttcg  1680
atttcattgc ctcggaaggc aatgtggctg actgggactc gaccaagacc gcattcgaca  1740
aggtcaagtc cgaggtcggc gaggttgatg tgctgatcaa caacgccggt atcacccgcg  1800
acgtggtgtt ccgcaagatg acccgcgccg actgggatgc ggtgatcgac accaacctga  1860
cctcgctgtt caacgtcacc aagcaggtga tcgacggcat ggccgaccgt ggctggggcc  1920
gcatcgtcaa catctcgtcg gtgaacgggc agaagggcca gttcggccag accaactact  1980
ccaccgccaa ggccggcctg catggcttca ccatggcact ggcgcaggaa gtggcgacca  2040
agggcgtgac cgtcaacacg gtctctccgg gctatatcgc caccgacatg gtcaaggcga  2100
tccgccagga cgtgctcgac aagatcgtcg cgacgatccc ggtcaagcgc ctgggcctgc  2160
cggaagagat cgcctcgatc tgcgcctggt tgtcgtcgga ggagtccggt ttctcgaccg  2220
gcgccgactt ctcgctcaac ggcggcctgc atatgggctg agctagcaaa ggaggtaaag  2280
ataatgagaa aagtagaaat cattacagct gaacaagcag ctcagctcgt aaaagacaac  2340
gacacgatta cgtctatcgg ctttgtcagc agcgcccatc cggaagcact gaccaaagct  2400
ttggaaaaac ggttcctgga cacgaacacc ccgcagaact tgacctacat ctatgcaggc  2460
tctcagggca aacgcgatgg ccgtgccgct gaacatctgg cacacacagg cctttttgaaa  2520
cgcgccatca tcggtcactg gcagactgta ccggctatcg gtaaactggc tgtcgaaaac  2580
aagattgaag cttacaactt ctcgcagggc acgttggtcc actggttccg cgccttggca  2640
ggtcataagc tcggcgtctt caccgacatc ggtctggaaa ctttcctcga tccccgtcag  2700
ctcggcggca agctcaatga cgtaaccaaa gaagacctcg tcaaactgat cgaagtcgat  2760
ggtcatgaac agcttttcta cccgaccttc ccggtcaacg tagctttcct ccgcggtacg  2820
tatgctgatg aatccggcaa tatcaccatg gacgaagaaa tcgggccttt cgaaagcact  2880
tccgtagccc aggccgttca caactgtggc ggtaaagtcg tcgtccaggt caaagacgtc  2940
gtcgctcacg gcagcctcga cccgcgcatg gtcaagatcc ctggcatcta tgtcgactac  3000
gtcgtcgtag cagctccgga agaccatcag cagacgtatg actgcgaata cgatccgtcc  3060
ctcagcggtg aacatcgtgc tcctgaaggc gctaccgatg cagctctccc catgagcgct  3120
aagaaaatca tcggccgccg cggcgctttg gaattgactg aaaacgctgt cgtcaacctc  3180
ggcgtcggtg ctccggaata cgttgcttct gttgccggtg aagaaggtat cgccgatacc  3240
attaccctga ccgtcgaagg tggcgccatc ggtggcgtac cgcagggcgg tgcccgcttc  3300
ggttcgtccc gcaatgccga tgccatcatc gaccacacct atcagttcga cttctacgat  3360
ggcggcggtc tggacatcgc ttacctcggc ctggcccagt gcgatggctc gggcaacatc  3420
aacgtcagca agttcggtac taacgttgcc ggctgcggcg gtttccccaa catttcccag  3480
cagacaccga atgtttactt ctgcggcacc ttcacggctg gcggcttgaa aatcgctgtc  3540
gaagacggca aagtcaagat cctccaggaa ggcaaagcca agaagttcat caaagctgtc  3600
gaccagatca ctttcaacgg ttcctatgca gcccgcaacg gcaaacacgt tctctacatc  3660
acagaacgct gcgtatttga actgaccaaa gaaggcttga aactcatcga agtcgcaccg  3720
ggcatcgata ttgaaaaaga tatcctcgct cacatggact tcaagccgat cattgataat  3780
ccgaaactca tggatgcccg cctcttccag gacggtccca tgggactgaa aaaataagcg  3840
agagtaggga actgccaggc atcaaataaa acgaaaggct cagtcgaaag actgggcctt  3900
```

```
tcgttttatc tgttgtttgt cggtgaacgc tctcctgagt aggacaaatc cgccgggagc  3960
ggatttgaac gttgcgaagc aacggcccgg agggtggcgg gcaggacgcc cgccataaac  4020
tgccaggcat caaattaagc agaaggccat cctgacggat ggcctttttg cgtttctaca  4080
aactcttttt gtttattttt ctaaatacat tcaaatatgt atccgctcat gagacaataa  4140
ccctgataaa tgcttcaata atattgaaaa aggaagagta tgagtattca acatttccgt  4200
gtcgccctta ttcccttttt tgcggcattt tgccttcctg tttttgctca cccagaaacg  4260
ctggtgaaag taaaagatgc tgaagatcag ttgggtgcac gagtgggtta catcgaactg  4320
gatctcaaca gcggtaagat ccttgagagt tttcgccccg aagaacgttt tccaatgatg  4380
agcactttta aagttctgct atgtggcgcg gtattatccc gtgttgacgc cgggcaagag  4440
caactcggtc gccgcataca ctattctcag aatgacttgg ttgagtactc accagtcaca  4500
gaaaagcatc ttacggatgg catgacagta agagaattat gcagtgctgc cataaccatg  4560
agtgataaca ctgcggccaa cttacttctg acaacgatcg gaggaccgaa ggagctaacc  4620
gcttttttgc acaacatggg ggatcatgta actcgccttg atcgttggga accggagctg  4680
aatgaagcca taccaaacga cgagcgtgac accacgatgc ctacagcaat ggcaacaacg  4740
ttgcgcaaac tattaactgg cgaactactt actctagctt cccggcaaca attaatagac  4800
tggatggagg cggataaagt tgcaggacca cttctgcgct cggcccttcc ggctggctgg  4860
tttattgctg ataaatctgg agccggtgag cgtgggtctc gcggtatcat tgcagcactg  4920
gggccagatg gtaagccctc ccgtatcgta gttatctaca cgacggggag tcaggcaact  4980
atggatgaac gaaatagaca gatcgctgag ataggtgcct cactgattaa gcattggtaa  5040
ctgtcagacc aagtttactc atatatactt tagattgatt taaaacttca tttttaattt  5100
aaaaggatct aggtgaagat cctttttgat aatctcatga ccaaaatccc ttaacgtgag  5160
ttttcgttcc actgagcgtc agaccccgta gaaaagatca aaggatcttc ttgagatcct  5220
ttttttctgc gcgtaatctg ctgcttgcaa acaaaaaaac caccgctacc agcggtggtt  5280
tgtttgccgg atcaagagct accaactctt tttccgaagg taactggctt cagcagagcg  5340
cagataccaa atactgtcct tctagtgtag ccgtagttag gccaccactt caagaactct  5400
gtagcaccgc ctacatacct cgctctgcta atcctgttac cagtggctgc tgccagtggc  5460
gataagtcgt gtcttaccgg gttggactca agacgatagt taccggataa ggcgcagcgg  5520
tcgggctgaa cggggggttc gtgcacacag cccagcttgg agcgaacgac ctacaccgaa  5580
ctgagatacc tacagcgtga gctatgagaa agcgccacgc ttcccgaagg gagaaaggcg  5640
gacaggtatc cggtaagcgg cagggtcgga acaggagagc gcacgaggga gcttccaggg  5700
ggaaacgcct ggtatcttta tagtcctgtc gggtttcgcc acctctgact tgagcgtcga  5760
tttttgtgat gctcgtcagg ggggcggagc ctatggaaaa acgccagcaa cgcggccttt  5820
ttacggttcc tggccttttg ctggcctttt gctcacatgt tctttcctgc gttatcccct  5880
gattctgtgg ataaccgtat taccgccttt gagtgagctg ataccgctcg ccgcagccga  5940
acgaccgagc gcagcgagtc agtgagcgag gaagcggaag agcgcctgat gcggtatttt  6000
ctccttacgc atctgtgcgg tatttcacac cgcatatggt gcactctcag tacaatctgc  6060
tctgatgccg catagttaag ccagtataca ctccgctatc gctacgtgac tgggtcatgg  6120
ctgcgccccg acacccgcca acacccgctg acgcgccctg acgggcttgt ctgctcccgg  6180
catccgctta cagacaagct gtgaccgtct ccgggagctg catgtgtcag aggttttcac  6240
cgtcatcacc gaaacgcgcg aggcagcaga tcaattcgcg cgcgaaggcg aagcggcatg  6300
catttacgtt gacaccatcg aatggtgcaa aacctttcgc ggtatggcat gatagcgccc  6360
ggaagagagt caattcaggg tggtgaatgt gaaaccagta acgttatacg atgtcgcaga  6420
gtatgccggt gtctcttatc agaccgtttc ccgcgtggtg aaccaggcca gccacgtttc  6480
tgcgaaaacg cgggaaaaag tggaagcggc gatggcggag ctgaattaca ttcccaaccg  6540
cgtggcacaa caactggcgg gcaaacagtc gttgctgatt ggcgttgcca cctccagtct  6600
ggccctgcac gcgccgtcgc aaattgtcgc ggcgattaaa tctcgcgccg atcaactggg  6660
tgccagcgtg gtggtgtcga tggtagaacg aagcggcgtc gaagcctgta aagcggcggt  6720
gcacaatctt ctcgcgcaac gcgtcagtgg gctgatcatt aactatccgc tggatgacca  6780
ggatgccatt gctgtggaag ctgcctgcac taatgttccg gcgttatttc ttgatgtctc  6840
tgaccagaca cccatcaaca gtattatttt ctcccatgaa gacggtacgc gactgggcgt  6900
ggagcatctg gtcgcattgg gtcaccagca aatcgcgctg ttagcgggcc cattaagttc  6960
tgtctcggcg cgtctgcgtc tggctggctg gcataaatat ctcactcgca atcaaattca  7020
gccgatagcg gaacgggaag gcgactggag tgccatgtcc ggttttcaac aaaccatgca  7080
aatgctgaat gagggcatcg ttcccactgc gatgctggtt gccaacgatc agatggcgct  7140
gggcgcaatg cgcgccatta ccgagtccgg gctgcgcgtt ggtgcggata tctcggtagt  7200
gggatacgac gataccgaag acagctcatg ttatatcccg ccgttaacca ccatcaaaca  7260
ggattttcgc ctgctggggc aaaccagcgt ggaccgcttg ctgcaactct ctcagggcca  7320
ggcggtgaag ggcaatcagc tgttgcccgt ctcactggtg aaaagaaaaa ccaccctggc  7380
gcccaatacg caaaccgcct ctccccgcgc gttggccgat tcattaatgc agctggcacg  7440
acaggtttcc cgactggaaa gcgggcagtg agcgcaacgc aattaatgtg agttagcgcg  7500
aattgatctg                                                         7510
```

```
SEQ ID NO: 164          moltype = DNA  length = 4958
FEATURE                 Location/Qualifiers
source                  1..4958
                        mol_type = other DNA
                        organism = synthetic construct
SEQUENCE: 164
atgatggttc caaccctcga acacgagctt gctcccaacg aagccaacca tgtcccgctg  60
tcgccgctgt cgttcctcaa gcgtgccgcg caggtgtacc cgcagcgcga tgcggtgatc  120
tatggcgcaa ggcgctacag ctaccgtcag ttgcacgagc gcagccgcgc cctggccagt  180
gccttggagc gggtcggtgt tcagccgggc gagcgggtgg cgatattggc gccgaacatc  240
ccggaaatgc tcgaggccca ctatggcgtg cccggtgccg gggcggtgct ggtgtgcatc  300
aacatccgcc tggagggggcg cagcattgcc ttcatcctgc gtcactgcgc ggccaaggta  360
ttgatctgcg atcgtgagtt cggtgccgtg gccaatcagg cgctggccat gctcgatgcg  420
ccgcccttgc tggtgggcat cgacgatgat caggccgagc gcgccgattt ggcccacgac  480
ctggactacg aagcgttctt ggcccagggc gaccccgcgc ggccgttgag tgcgccacag  540
aacgaatggc agtcgatcgc catcaactac acctccggca ccacggggga ccccaagggc  600
gtggtgctgc atcaccgcgg cgcctacctc aacgcctgcg ccggggcgct gatcttccag  660
```

-continued

```
ttggggccgc gcagcgtcta cttgtggacc ttgccgatgt tccactgcaa cggctggagc  720
catacctggg cggtgacgtt gtccggtggc acccacgtgt gtctgcgcaa ggtccagcct  780
gatgcgatca acgccgccat cgccgagcat gccgtgactc acctgagcgc cgccccagtg  840
gtgatgtcga tgctgatcca cgccgagcat gccagcgccc ctccggtgcc ggtttcggtg  900
atcactggcg gtgccgcccc gcccagtgcg gtcatcgcgg cgatggaggc gcgtggcttc  960
aacatcaccc atgcctatgg catgaccgaa agctacggtc ccagcacatt gtgcctgtgg  1020
cagccgggtg tcgacgagtt gccgctggag gcccgggccc agttcatgag ccgccagggc  1080
gtcgcccacc cgctgctcga ggaggccacg gtgctggata ccgacaccgg ccgcccggtc  1140
ccggccgacg gccttaccct cggcgagctg gtggtgcggg gcaacactgt gatgaaaggc  1200
tacctgcaca acccagaggc tacccgtgcc gcgttggcca acggctggct gcacacgggc  1260
gacctggccg tgctgcacct ggacggctat gtggaaatca aggaccgagc caaggacatc  1320
atcatttctg gcggcgagaa catcagttcg ctggagatag aagaagtgct ctaccagcac  1380
cccgaggtgg tcgaggctgc ggtggtggcg cgtccggatt cgcgctgggg cgagacacct  1440
cacgctttcg tcacgctgcg cgctgatgca ctggccagcg gggacgacct ggtccgctgg  1500
tgccgtgagc gtctggcgca cttcaaggcg ccgcgccatg tgtcgctcgt ggacctgccc  1560
aagaccgcca ctggaaaaat acagaagttc gtcctgcgtg agtgggcccg gcaacaggag  1620
gcgcagatcg ccgacgccga gcattgactc gagaaaggag gataagataa tgagtcaggc  1680
gctaaaaaat ttactgacat tgttaaatct ggaaaaaatt gaggaaggac tctttcgcgg  1740
ccagagtgaa gatttaggtt tacgccaggt gtttggcggc caggtcgtgg gtcaggcctt  1800
gtatgctgca aaagagaccg tccctgaaga gcggctggta cattcgtttc acagctactt  1860
tcttcgccct ggcgatagta agaagccgat tatttatgat gtcgaaacgc tgcgtgacgg  1920
taacagcttc agcgcccgcc gggttgctgc tattcaaaac ggcaaaccga tttttatat  1980
gactgcctct ttccaggcac cagaagcggg tttcgaacat caaaaaacaa tgccgtccgc  2040
gccagcgcct gatggcctcc cttcggaaac gcaaatcgcc caatcgctgg cgcacctgct  2100
gccgccagtg ctgaaagata aattcatctg cgatcgtccg ctggaagtcc gtccggtgga  2160
gtttcataac ccactgaaag gtcacgtcgc agaaccacat cgtcaggtgt ggatccgcgc  2220
aaatggtagc gtgccggatg acctgcgcgt tcatcagtat ctgctcggtt acgcttctga  2280
tcttaacttc ctgccggtag ctctacagcc gcacggcatc ggttttctcg aaccggggat  2340
tcagattgcc accattgacc attccatgtg gttccatcgc ccgtttaatt tgaatgaatg  2400
gctgctgtat agcgtggaga gcacctcggc gtccagcgca cgtggctttg tgcgcggtga  2460
gttttatacc caagacggcg tactggttgc ctcgaccgtt caggaagggg tgatgcgtaa  2520
tcacaattaa tgattacgaa ttcgagctcg gtacccgggg atcctctaga gtcgacctgc  2580
aggcatgcaa gcttggcact ggccgtcgtt ttacaacgtc gtgactggga aaaccctggc  2640
gttacccaac ttaatcgcct tgcagcacat ccccctttcg ccagctggcg taatagcgaa  2700
gaggcccgca ccgatcgccc ttcccaacag ttgcgcagcc tgaatggcga atggcgcgat  2760
aagctagctt cacgctgccg caagcactca gggcgcaagg gctgctaaag gaagcggaac  2820
acgtagaaag ccagtccgca gaaacggtgc tgaccccgga tgaatgtcag ctactgggct  2880
atctggacaa gggaaaacgc aagcgcaaag agaaagcagg tagcttgcag tgggcttaca  2940
tggcgatagc tagactgggc ggttttatgg acagcaagcg aaccggaatt gccagctggg  3000
gcgccctctg gtaaggttgg gaagccctgc aaagtaaact ggatggcttt cttgccgcca  3060
aggatctgat ggcgcagggg atcaagatct gatcaagaga caggatgagg atcgtttcgc  3120
atgattgaac aagatggatt gcacgcaggt tctccggccg cttgggtgga gaggctattc  3180
ggctatgact gggcacaaca gacaatcggc tgctctgatg ccgccgtgtt ccggctgtca  3240
gcgcaggggc gcccggttct ttttgtcaag accgacctgt ccggtgccct gaatgaactc  3300
caagacgagg cagcgcggct atcgtggctg gccacgacgg gcgttccttg cgcagctgtg  3360
ctcgacgttg tcactgaagc gggaagggac tggctgctat tgggcgaagt gccggggcag  3420
gatctcctgt catctcacct tgctcctgcc gagaaagtat ccatcatggc tgatgcaatg  3480
cggcggctgc atacgcttga tccggctacc tgcccattcg accaccaagc gaaacatcgc  3540
atcgagcgag cacgtactcg gatggaagcc ggtcttgtcg atcaggatga tctggacgaa  3600
gagcatcagg ggctcgcgcc agccgaactg ttcgccaggc tcaaggcgcg gatgcccgac  3660
ggcgaggatc tcgtcgtgac ccatggcgat gcctgcttgc cgaatatcat ggtggaaaat  3720
ggccgctttt ctggattcat cgactgtggc cggctgggtg tggcggaccg ctatcaggac  3780
atagcgttgg ctacccgtga tattgctgaa gagcttggcg gcgaatgggc tgaccgcttc  3840
ctcgtgcttt acggtatcgc cgctcccgat tcgcagcgca tcgccttcta tcgccttctt  3900
gacgagttct tctgagcggg actctggggt tcgcgatgat aagctgtcaa acatgagaat  3960
tacaacttat atcgtatggg gctgacttca ggtgctacat ttgaagagat aaattgcact  4020
gaaatctaga aatattttat ctgattaata agatgatctt cttgagatcg ttttggtctg  4080
cgcgtaatct cttgctctga aaacgaaaaa accgccttgc agggcggttt ttcgaaggtt  4140
ctctgagcta ccaactcttt gaaccgaggt aactggcttg gaggagcgca gtcaccaaaa  4200
cttgtccttt cagtttagcc ttaaccggcg catgacttca agactaactc ctctaaatca  4260
attaccagtg gctgctgcca gtggtgcttt tgcatgtctt tccgggttgg actcaagacg  4320
atagttaccg gataaggcgc agcggtcgga ctgaacgggg ggttcgtgca tacagtccag  4380
cttggagcga actgcctacc cggaactgag tgtcaggcgt ggaatgagac aaacgcggcc  4440
ataacagcgg aatgacaccg gtaaaccgaa aggcaggaac aggagagcgc acgagggagc  4500
cgccagggga aacgcctggt atctttatag tcctgtcggg tttcgccacc actgatttga  4560
gcgtcagatt tcgtgatgct tgtcaggggg gcggagccta tggaaaaacg gctttgcctt  4620
ctttcctgcg ttatcccctg attctgtgga taaccgtatt accgcctttg agtgagctga  4680
taccgctcgc cgcagccgaa cgaccgagcg cagcgagtca gtgagcgagg aagcggaaga  4740
gcgcccaata cgcaaaccgc ctctccccgc gcgttggccg attcattaat gcagctggca  4800
cgacaggttt cccgactgga aagcgggcag tgagcgcaac gcaattaatg tgagttagct  4860
cactcattag gcaccccagg ctttacactt tatgcttccg gctcgtatgt tgtgtggaat  4920
tgtgagcgga taacaatttc acacaggagg aatcaaaa                          4958
```

SEQ ID NO: 165 moltype = DNA length = 6048
FEATURE Location/Qualifiers
source 1..6048
mol_type = other DNA
organism = synthetic construct

SEQUENCE: 165

-continued

```
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gttttttgcg ccgacatcat aacggttctg gcaaatattc  180
tgaaatgagc tgttgacaat taatcatccg gctcgtataa tgtgtggaat tgtgagcgga  240
taacaatttc acacaggagg aatcaaaaat gctggtaaat gacgagcaac aacagatcgc  300
cgacgcggta cgtgcgttcg cccaggaacg cctgaagccg tttgccgagc aatgggacaa  360
ggaccatcgc ttcccgaaag aggccatcga cgagatggcc gaactgggcc tgttcggcat  420
gctggtgccg gagcagtggg gcggtagcga caccggttat gtggcctatg ccatggcctt  480
ggaggaaatc gctgcgggcg atggcgcctg ctcgaccatc atgagcgtgc acaactcggt  540
gggttgcgtg ccgatcctgc gcttcggcaa cgagcagcag aaagagcagt tcctcacccc  600
gctggcgaca ggtgcgatgc tcggtgcttt cgccctgacc gagccgcagg ctggctccga  660
tgccagcagc ctgaagaccc gcgcacgcct ggaaggcgac cattacgtgc tcaatggcag  720
caagcagttc attacctcgg ggcagaacgc cggcgtagtg atcgtgtttg cggtcaccga  780
cccggaggcc ggcaagcgtg gcatcagcgc cttcatcgtg ccgaccgatt cgccgggcta  840
ccaggtagcg cgggtggagg acaaactcgg ccagcacgcc tccgacacct gccagatcgt  900
tttcgacaat gtgcaagtgc cagtggccaa ccggctgggg gcggagggtg aaggctacaa  960
gatcgccctg gccaaccttg aaggcggccg tatcggcatc gcctcgcaag cggtgggtat  1020
ggcccgcgcg gcgttcgaag tggcgcggga ctatgccaac gagcgccaga gctttggcaa  1080
accgctgatc gagcaccagg ccgtggcgtt tcgcctggcc gacatggcaa cgaaaatttc  1140
cgttgcccgg cagatggtat tgcacgccgc tgcccttcgt gatgcggggc gcccggcgct  1200
ggtggaagcg tcgatggcca agctgttcgc ctcggaaatg gccgaaaagg tctgttcgga  1260
cgccttgcag accctgggcg gttatggcta tctgagtgac ttcccgctgg agcggatcta  1320
ccgcgacgtt cgggtttgcc agatctacga aggcaccagc gacattcagc gcatggtcat  1380
tgcgcgcaat ctttgagcta gcaaaggagg taaagataat gtacgcagct aaggacatca  1440
ccgtggagga gcgcgccggc ggcgcgctat ggatcacgat cgaccgggcg cagaaacaca  1500
atgcgctggc ccgccacgtg ctggcgggat tggcgcaggt ggtgagcgcc gcggcggcgc  1560
agcccggggt gcgctgcatc gtgctgaccg gcgccggcca gcgcttcttt gcggcaggcg  1620
gcgatctggt cgagctgtcc ggcgtgcgcg accgggaggc tacgctggcc atgagcgagc  1680
aggcgcgcgg tgccctggat gcggtgcgcg actgcccgct gccggtgctg gcctacctga  1740
acggcgatgc catcggcggc ggcgccgagc tggcattggc ctgcgacatg cggctgcagt  1800
cggcgagcgc gcgcatcggc tttatccagg cgcggctggc catcacctcg gcctggggcg  1860
gcggccccga cctgtgccgg atcgtcggcg cggcgcgggc catgcgcatg atgagccgtt  1920
gcgagcttgt cgatgcgcag caggcgctgc agtggggctt ggccgatgcg gtggtcacgg  1980
acggacccgc cggcaaggac atccacgcct tcctgcaacc gctgctgggc tgcgcccccgc  2040
aggtgctgcg cggcatcaag gcgcagaccg cggccagccg gcgcggcgag tcgcatgacg  2100
ctgcccgcac catcgagcag cagcaactgt tgcatacctg gctccatgcg gaccattgga  2160
acgctgccga gggcatcctc tccaggaggg cccaatgagg ctgttttggc ggatgagaga  2220
agattttcag cctgatacag attaaatcag aacgcagaag cggtctgata aaacagaatt  2280
tgcctggcgg cagtagcgcg gtggtcccac ctgaccccat gccgaactca gaagtgaaac  2340
gccgtagcgc cgatggtagt gtggggtctc cccatgcgag agtagggaac tgccaggcat  2400
caaataaaac gaaaggctca gtcgaaagac tgggcctttc gttttatctg ttgtttgtcg  2460
gtgaacgctc tcctgagtag gacaaatccg ccgggagcgg atttgaacgt tgcgaagcaa  2520
cggcccggag ggtggcgggc aggacgcccg ccataaactg ccaggcatca aattaagcag  2580
aaggccatcc tgacggatgg cctttttgcg tttctacaaa ctctttttgt ttatttttct  2640
aaatacattc aaatatgtat ccgctcatga gacaataacc ctgataaatg cttcaataat  2700
attgaaaaag gaagagtatg agtattcaac atttccgtgt cgcccttatt cccttttttg  2760
cggcattttg ccttcctgtt tttgctcacc cagaaacgct ggtgaaagta aaagatgctg  2820
aagatcagtt gggtgcacga gtgggttaca tcgaactgga tctcaacagc ggtaagatcc  2880
ttgagagttt tcgccccgaa gaacgttttc caatgatgag cacttttaaa gttctgctat  2940
gtggcgcggt attatcccgt gttgacgccg ggcaagagca actcggtcgc cgcatacact  3000
attctcagaa tgacttggtt gagtactcac cagtcacaga aaagcatctt acggatggca  3060
tgacagtaag agaattatgc agtgctgcca taaccatgag tgataacact gcggccaact  3120
tacttctgac aacgatcgga ggaccgaagg agctaaccgc ttttttgcac aacatggggg  3180
atcatgtaac tcgccttgat cgttgggaac cggagctgaa tgaagccata ccaaacgacg  3240
agcgtgacac cacgatgcct acagcaatgg caacaacgtt gcgcaaacta ttaactggcg  3300
aactacttac tctagcttcc cggcaacaat taatagactg gatggaggcg gataaagttg  3360
caggaccact tctgcgctcg gcccttccgg ctggctggtt tattgctgat aaatctggag  3420
ccggtgagcg tgggtctcgc ggtatcattg cagcactggg gccagatggt aagccctccc  3480
gtatcgtagt tatctacacg acggggagtc aggcaactat ggatgaacga aatagacaga  3540
tcgctgagat aggtgcctca ctgattaagc attggtaact gtcagaccaa gtttactcat  3600
atatacttta gattgattta aaacttcatt tttaatttaa aaggatctag gtgaagatcc  3660
tttttgataa tctcatgacc aaaatccctt aacgtgagtt ttcgttccac tgagcgtcag  3720
accccgtaga aaagatcaaa ggatcttctt gagatccttt ttttctgcgc gtaatctgct  3780
gcttgcaaac aaaaaaacca ccgctaccag cggtggtttg tttgccggat caagagctac  3840
caactctttt tccgaaggta actggcttca gcagagcgca gataccaaat actgtccttc  3900
tagtgtagcc gtagttaggc caccacttca agaactctgt agcaccgcct acatacctcg  3960
ctctgctaat cctgttacca gtggctgctg ccagtggcga taagtcgtgt cttaccgggt  4020
tggactcaag acgatagtta ccggataagg cgcagcggtc gggctgaacg gggggttcgt  4080
gcacacagcc cagcttggag cgaacgacct acaccgaact gagataccta cagcgtgagc  4140
tatgagaaag cgccacgctt cccgaaggga gaaaggcgga caggtatccg gtaagcggca  4200
gggtcggaac aggagagcgc acgagggagc ttccaggggg aaacgcctgg tatctttata  4260
gtcctgtcgg gtttcgccac ctctgacttg agcgtcgatt tttgtgatgc tcgtcagggg  4320
ggcggagcct atggaaaaac gccagcaacg cggccttttt acggttcctg gccttttgct  4380
ggccttttgc tcacatgttc tttcctgcgt tatcccctga ttctgtggat aaccgtatta  4440
ccgcctttga gtgagctgat accgctcgcc gcagccgaac gaccgagcgc agcgagtcag  4500
tgagcgagga agcggaagag cgcctgatgc ggtattttct ccttacgcat ctgtgcggta  4560
tttcacaccg catatggtgc actctcagta caatctgctc tgatgccgca tagttaagcc  4620
agtatacact ccgctatcgc tacgtgactg ggtcatggct gcgccccgac acccgccaac  4680
acccgctgac gcgccctgac gggcttgtct gctcccggca tccgcttaca gacaagctgt  4740
```

-continued

```
gaccgtctcc gggagctgca tgtgtcagag gttttcaccg tcatcaccga aacgcgcgag  4800
gcagcagatc aattcgcgcg cgaaggcgaa gcggcatgca tttacgttga caccatcgaa  4860
tggtgcaaaa cctttcgcgg tatggcatga tagcgcccgg aagagagtca attcagggtg  4920
gtgaatgtga aaccagtaac gttatacgat gtcgcagagt atgccggtgt ctcttatcag  4980
accgtttccc gcgtggtgaa ccaggccagc cacgtttctg cgaaaacgcg ggaaaaagtg  5040
gaagcggcga tggcggagct gaattacatt cccaaccgcg tggcacaaca actggcgggc  5100
aaacagtcgt tgctgattgg cgttgccacc tccagtctgg ccctgcacgc gccgtcgcaa  5160
attgtcgcgg cgattaaatc tcgcgccgat caactgggtg ccagcgtggt ggtgtcgatg  5220
gtagaacgaa gcggcgtcga agcctgtaaa gcggcggtgc acaatcttct cgcgcaacgc  5280
gtcagtgggc tgatcattaa ctatccgctg gatgaccagg atgccattgc tgtggaagct  5340
gcctgcacta atgttccggc gttatttctt gatgtctctg accagacacc catcaacagt  5400
attattttct cccatgaaga cggtacgcga ctgggcgtgg agcatctggt cgcattgggt  5460
caccagcaaa tcgcgctgtt agcgggccca ttaagttctg tctcggcgcg tctgcgtctg  5520
gctggctggc ataaatatct cactcgcaat caaattcagc cgatagcgga acgggaaggc  5580
gactggagtg ccatgtccgg ttttcaacaa accatgcaaa tgctgaatga gggcatcgtt  5640
cccactgcga tgctggttgc caacgatcag atggcgctgg gcgcaatgcg cgccattacc  5700
gagtccgggc tgcgcgttgg tgcggatatc tcggtagtgg gatacgacga taccgaagac  5760
agctcatgtt atatcccgcc gttaaccacc atcaaacagg attttcgcct gctggggcaa  5820
accagcgtgg accgcttgct gcaactctct cagggccagg cggtgaaggg caatcagctg  5880
ttgcccgtct cactggtgaa aagaaaaacc accctggcgc ccaatacgca aaccgcctct  5940
ccccgcgcgt tggccgattc attaatgcag ctggcacgac aggtttcccg actggaaagc  6000
gggcagtgag cgcaacgcaa ttaatgtgag ttagcgcgaa ttgatctg              6048

SEQ ID NO: 166          moltype = DNA  length = 6060
FEATURE                 Location/Qualifiers
source                  1..6060
                        mol_type = other DNA
                        organism = synthetic construct
SEQUENCE: 166
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gtttttttgcg ccgacatcat aacggttctg gcaaatattc  180
tgaaatgagc tgttgacaat taatcatccg gctcgtataa tgtgtggaat tgtgagcgga  240
taacaatttc acacaggagg aatcaaaaat gcattttaaa ctatcagaag aacatgaaat  300
gataagaaaa atggttcgag attttgctaa aaatgaagtg gcaccaacag cagctgagcg  360
tgatgaggaa gagcgatttg atcgagaatt atttgatcaa atggcagagc ttggtttaac  420
cggtattccg tggcctgaag agtacggtgg aattggaagc gattacttag cgtacgtaat  480
cgctattgaa gaattatccc gcgtttgtgc ttcaacaggc gtaacactgt ccgcgcatac  540
ttcacttgca ggatggccaa tttttaaatt tgggacggaa gagcaaaagc aaaagttttt  600
acgaccgatg gctgaaggaa agaaaattgg tgcatacggc ttaacggagc caggatctgg  660
atcggatgct ggtggaatga agacaatcgc aaagagagat ggagaccatt atattttaaa  720
tggatcaaaa attttcatta caaatggcgg tattgctgat atttacgttg tttttgcgct  780
aactgatcct gaatcaaagc agcgcggtac gagtgcattt attgtagaaa gtgatacacc  840
gggattttca gttgggaaga aggagagcaa gctagggatt cgctcttcac caacgactga  900
aattatgttt gaagattgcc gtattcctgt agagaatcta cttggagaag aggggcaagg  960
gtttaaagtt gcgatgcaaa cattagatgg aggtcgtaac ggtattgcgg cgcaagctgt  1020
tggtattgca caaggggctt tagatgcttc tgtagaatat gcaagggagc gccatcaatt  1080
tggaaaacca attgcggcgc agcaagggat tggctttaaa cttgcggata tggcaacaga  1140
tgtagaagcg gcacgccttt taacatatca agcggcttgg cttgaatcag aagggcttcc  1200
gtatggaaaa gagtcagcga tgtcaaaagt atttgcagga gatacagcga tgagggtgac  1260
gactgaagcg gtgcaagtat ttggtggtta cggttatacg aaagattatc cagtagagcg  1320
ttatatgcga gatgcaaaaa ttacacaaat atatgaagga acacaagaga ttcagaggct  1380
tgtaatttct cgtatgttaa cgaagtaggc tagcaaagga ggtaaagata atgtacgcag  1440
ctaaggacat caccgtggag gagcgcgccg gcggcgcgct atggatcacg atcgaccggg  1500
cgcagaaaca caatgcgctg gcccgccacg tgctggcggg attggcgcag gtggtgagcg  1560
ccgcggcggc gcagcccggg gtgcgctgca tcgtgctgac cggcgccggc cagcgcttct  1620
ttgcggcagg cggcgatctg gtcgagctgt ccggcgtgcg cgaccgggag gctacgctgg  1680
ccatgagcga gcaggcgcgc ggtgccctgg atgcggtgcg cgactgcccg ctgccggtgc  1740
tggcctacct gaacggcgat gccatcggcg gcggcgccga gctggcattg gcctgcgaca  1800
tgcggctgca gtcggcgagc gcgcgcatcg gctttatcca ggcgcggctg gccatcacct  1860
cggcctgggg cggcggcccc gacctgtgcc ggatcgtcgg cgcggcgcgg gccatgcgca  1920
tgatgagccg ttgcgagctt gtcgatgcgc agcaggcgct gcagtggggc ttggccgatg  1980
cggtggtcac ggacggaccc gccggcaagg acatccacgc cttcctgcaa ccgctgctgg  2040
gctgcgcccc gcaggtgctg cgcggcatca aggcgcagac cgcggccagc cggcgcggcg  2100
agtcgcatga cgctgcccgc accatcgagc agcagcaact gttgcatacc tggctccatg  2160
cggaccattg gaacgctgcc gagggcatcc tctccaggag ggcccaatga ggctgttttg  2220
gcggatgaga gaagattttc agcctgatac agattaaatc agaacgcaga agcggtctga  2280
taaaacagaa tttgcctggc ggcagtagcg cggtggtccc acctgacccc atgccgaact  2340
cagaagtgaa acgccgtagc gccgatggta gtgtggggtc tccccatgcg agagtaggga  2400
actgccaggc atcaaataaa acgaaaggct cagtcgaaag actgggcctt tcgttttatc  2460
tgttgtttgt cggtgaacgc tctcctgagt aggacaaatc cgccgggagc ggatttgaac  2520
gttgcgaagc aacggcccgg agggtggcgg gcaggacgcc cgccataaac tgccaggcat  2580
caaattaagc agaaggccat cctgacggat ggcctttttg cgtttctaca aactcttttt  2640
gtttattttt ctaaatacat tcaaatatgt atccgctcat gagacaataa ccctgataaa  2700
tgcttcaata atattgaaaa aggaagagta tgagtattca acatttccgt gtcgccctta  2760
ttcccttttt tgcggcattt tgccttcctg tttttgctca cccagaaacg ctggtgaaag  2820
taaaagatgc tgaagatcag ttgggtgcac gagtgggtta catcgaactg gatctcaaca  2880
gcggtaagat ccttgagagt tttcgccccg aagaacgttt tccaatgatg agcactttta  2940
aagttctgct atgtggcgcg gtattatccc gtgttgacgc cgggcaagag caactcggtc  3000
```

-continued

```
gccgcataca ctattctcag aatgacttgg ttgagtactc accagtcaca gaaaagcatc  3060
ttacggatgg catgacagta agagaattat gcagtgctgc cataaccatg agtgataaca  3120
ctgcggccaa cttacttctg acaacgatcg gaggaccgaa ggagctaacc gcttttttgc  3180
acaacatggg ggatcatgta actcgccttg atcgttggga accggagctg aatgaagcca  3240
taccaaacga cgagcgtgac accacgatgc ctacagcaat ggcaacaacg ttgcgcaaac  3300
tattaactgg cgaactactt actctagctt cccggcaaca attaatagac tggatggagg  3360
cggataaagt tgcaggacca cttctgcgct cggcccttcc ggctggctgg tttattgctg  3420
ataaatctgg agccggtgag cgtgggtctc gcggtatcat tgcagcactg gggccagatg  3480
gtaagccctc ccgtatcgta gttatctaca cgacggggag tcaggcaact atggatgaac  3540
gaaatagaca gatcgctgag ataggtgcct cactgattaa gcattggtaa ctgtcagacc  3600
aagtttactc atatatactt tagattgatt taaaacttca tttttaattt aaaaggatct  3660
aggtgaagat cctttttgat aatctcatga ccaaaatccc ttaacgtgag ttttcgttcc  3720
actgagcgtc agaccccgta gaaaagatca aaggatcttc ttgagatcct ttttttctgc  3780
gcgtaatctg ctgcttgcaa acaaaaaaac caccgctacc agcggtggtt tgtttgccgg  3840
atcaagagct accaactctt tttccgaagg taactggctt cagcagagcg cagataccaa  3900
atactgtcct tctagtgtag ccgtagttag gccaccactt caagaactct gtagcaccgc  3960
ctacatacct cgctctgcta atcctgttac cagtggctgc tgccagtggc gataagtcgt  4020
gtcttaccgg gttggactca agacgatagt taccggataa ggcgcagcgg tcgggctgaa  4080
cggggggttc gtgcacacag cccagcttgg agcgaacgac ctacaccgaa ctgagatacc  4140
tacagcgtga gctatgagaa agcgccacgc ttcccgaagg gagaaaggcg gacaggtatc  4200
cggtaagcgg cagggtcgga acaggagagc gcacgaggga gcttccaggg ggaaacgcct  4260
ggtatcttta tagtcctgtc gggtttcgcc acctctgact tgagcgtcga tttttgtgat  4320
gctcgtcagg ggggcggagc ctatggaaaa acgccagcaa cgcggccttt ttacggttcc  4380
tggccttttg ctggcctttt gctcacatgt tctttcctgc gttatcccct gattctgtgg  4440
ataaccgtat taccgccttt gagtgagctg ataccgctcg ccgcagccga acgaccgagc  4500
gcagcgagtc agtgagcgag gaagcggaag agcgcctgat gcggtatttt ctccttacgc  4560
atctgtgcgg tatttcacac cgcatatggt gcactctcag tacaatctgc tctgatgccg  4620
catagttaag ccagtataca ctccgctatc gctacgtgac tgggtcatgg ctgcgccccg  4680
acacccgcca acacccgctg acgcgccctg acgggcttgt ctgctcccgg catccgctta  4740
cagacaagct gtgaccgtct ccgggagctg catgtgtcag aggttttcac cgtcatcacc  4800
gaaacgcgcg aggcagcaga tcaattcgcg cgcgaaggcg aagcggcatg catttacgtt  4860
gacaccatcg aatggtgcaa aacctttcgc ggtatggcat gatagcgccc ggaagagagt  4920
caattcaggg tggtgaatgt gaaaccagta acgttatacg atgtcgcaga gtatgccggt  4980
gtctcttatc agaccgtttc ccgcgtggtg aaccaggcca gccacgtttc tgcgaaaacg  5040
cgggaaaaag tggaagcggc gatggcggag ctgaattaca ttcccaaccg cgtggcacaa  5100
caactggcgg gcaaacagtc gttgctgatt ggcgttgcca cctccagtct ggccctgcac  5160
gcgccgtcgc aaattgtcgc ggcgattaaa tctcgcgccg atcaactggg tgccagcgtg  5220
gtggtgtcga tggtagaacg aagcggcgtc gaagcctgta aagcggcggt gcacaatctt  5280
ctcgcgcaac gcgtcagtgg gctgatcatt aactatccgc tggatgacca ggatgccatt  5340
gctgtggaag ctgcctgcac taatgttccg gcgttatttc ttgatgtctc tgaccagaca  5400
cccatcaaca gtattatttt ctcccatgaa gacggtacgc gactgggcgt ggagcatctg  5460
gtcgcattgg gtcaccagca aatcgcgctg ttagcgggcc cattaagttc tgtctcggcg  5520
cgtctgcgtc tggctggctg gcataaatat ctcactcgca atcaaattca gccgatagcg  5580
gaacgggaag gcgactggag tgccatgtcc ggttttcaac aaaccatgca aatgctgaat  5640
gagggcatcg ttcccactgc gatgctggtt gccaacgatc agatggcgct gggcgcaatg  5700
cgcgccatta ccgagtccgg gctgcgcgtt ggtgcggata tctcggtagt gggatacgac  5760
gataccgaag acagctcatg ttatatcccg ccgttaacca ccatcaaaca ggattttcgc  5820
ctgctggggc aaaccagcgt ggaccgcttg ctgcaactct ctcagggcca ggcggtgaag  5880
ggcaatcagc tgttgcccgt ctcactggtg aaaagaaaaa ccaccctggc gcccaatacg  5940
caaaccgcct ctccccgcgc gttggccgat tcattaatgc agctggcacg acaggtttcc  6000
cgactggaaa gcgggcagtg agcgcaacgc aattaatgtg agttagcgcg aattgatctg  6060
```

```
SEQ ID NO: 167          moltype = DNA  length = 5948
FEATURE                 Location/Qualifiers
source                  1..5948
                        mol_type = other DNA
                        organism = synthetic construct
SEQUENCE: 167
cggtgtatgc aagagggata aaaaatgaaa acaaaattga tgacattaca agacgccacc  60
ggcttctttc gtgacggcat gaccatcatg gtgggcggat ttatggggat tggcactcca  120
tcccgcctgg ttgaagcatt actggaatct ggtgttcgcg acctgacatt gatagccaat  180
gataccgcgt ttgttgatac cggcatcggt ccgctcatcg tcaatggtcg agtccgcaaa  240
gtgattgctt cacatatcgg caccaacccg gaaacaggtc ggcgcatgat atctggtgag  300
atggacgtcg ttctggtgcc gcaaggtacg ctaatcgagc aaattcgctg tggtggagct  360
ggacttggtg gttttctcac cccaacgggt gtcggcaccg tcgtagagga aggcaaacag  420
acactgacac tcgacggtaa aacctggctg ctcgaacgcc cactgcgcgc cgacctggcg  480
ctaattcgcg ctcatcgttg cgacacactt ggcaacctga cctatcaact tagcgcccgc  540
aactttaacc ccctgatagc ccttgcggct gatatcacgc tggtagagcc agatgaactg  600
gtcgaaaccg gcgagctgca acctgaccat attgtcaccc ctggtgccgt tatcgaccac  660
atcatcgttt cacaggagag caaataatgg atgcgaaaca acgtattgcg cgccgtgtgg  720
cgcaagagct tcgtgatggt gacatcgtta acttagggat cggtttaccc acaatggtcg  780
ccaattattt accggagggt attcatatca ctctgcaatc ggaaaacggc ttcctcggtt  840
taggcccggt cacgacagcg catccagatc tggtgaacgc tggcgggcaa ccgtgcggtg  900
ttttacccgg tgcagccatg tttgatagcg ccatgtcatt tgcgctaatc cgtggcggtc  960
atattgatgc ctgcgtgctc ggcggtttgc aagtagacga agaagcaaac ctcgcgaact  1020
gggtagtgcc tgggaaaatg gtgcccggta tgggtggcgc gatggatctg gtgaccgggt  1080
cgcgcaaagt gatcatcgcc atggaacatt gcgccaaaga tggttcagca aaaattttgc  1140
gccgctgcac catgccactc actgcgcaac atgcggtgca tatgctggtt actgaactgg  1200
ctgtctttcg ttttattgac ggcaaaatgt ggctcaccga aattgccgac gggtgtgatt  1260
```

```
tagccaccgt gcgtgccaaa acagaagctc ggtttgaagt cgccgccgat ctgaatacgc  1320
aacggggtga tttatgattg gtcgcatatc gcgttttatg acgcgttttg tcagccggtg  1380
gcttcccgat ccactgatct ttgccatgtt gctgacattg ctaacattcg tgatcgcgct  1440
ttggttaaca ccacaaacgc cgatcagcat ggtgaaaatg tggggtgacg gtttctggaa  1500
cttgctggcg tttggtatgc agatggcgct tatcatcgtt accggtcatg cccttgccag  1560
ctctgctccg gtgaaaagtt tgctgcgtac tgccgcctcc gccgcaaaga cgcccgtaca  1620
gggcgtcatg ctggtcactt tcttcggttc agtcgcttgt gtcatcaact ggggatttgg  1680
tttggttgtc ggcgcaatgt ttgcccgtga agtcgcccgg cgagtccccg gttctgatta  1740
tccgttgctc attgcctgcg cctacattgg ttttctcacc tggggtggcg gcttctctgg  1800
atcaatgcct ctgttggctg caacaccggg caacccggtt gagcatatcg ccgggctgat  1860
cccggtgggc gatactctgt tcagtggttt taacattttc atcactgtgg cgttgattgt  1920
ggtgatgcca tttatcaccc gcatgatgat gccaaaaccg tctgacgtgg tgagtatcga  1980
tccaaaacta ctcatggaag aggctgattt tcaaaagcag ctaccgaaag atgcccccac  2040
atccgagcga ctggaagaaa gccgcattct gacgttgatc atcggcgcac tcggtatcgc  2100
ttaccttgcg atgtacttca gcgaacatgg cttcaacatc accatcaata ccgtcaacct  2160
gatgtttatg attgcgggtc tgctgctaca taaaacgcca atggcttata tgcgtgctat  2220
cagcgcggca gcacgcagta ctgccggtat tctggtgcaa ttccccttct acgctgggat  2280
ccaactgatg atggagcatt ccggtctggg cggactcatt accgaattct tcatcaatgt  2340
tgcgaacaaa gacaccttcc cggtaatgac ctttttttagt tctgcactga ttaacttcgc  2400
cgttccgtct ggcggcggtc actgggttat tcagggacct ttcgtgatac ccgcagccca  2460
ggcgctgggc gctgatctcg gtaaatcggt aatggcgatc gcctacggcg agcaatggat  2520
gaacatggca caaccattct gggcgctgcc agcactggca atcgccggac tcggtgtccg  2580
cgacatcatg ggctactgca tcactgccct gctcttctcc ggtgtcattt tcgtcattgg  2640
tttaacgctg ttctgactcg agaaaggagg ataagataat gagtcaggcg ctaaaaaatt  2700
tactgacatt gttaaatctg gaaaaaattg aggaaggact ctttcgcggc cagagtgaag  2760
atttaggttt acgccaggtg tttggcggcc aggtcgtggg tcaggccttg tatgctgcaa  2820
aagagaccgt ccctgaagag cggctggtac attcgtttca cagctacttt cttcgccctg  2880
gcgatagtaa gaagccgatt atttatgatg tcgaaacgct gcgtgacggt aacagcttca  2940
gcgcccgccg ggttgctgct attcaaaacg gcaaaccgat tttttatatg actgcctctt  3000
tccaggcacc agaagcgggt ttcgaacatc aaaaaacaat gccgtccgcg ccagcgcctg  3060
atggcctccc ttcggaaacg caaatcgccc aatcgctggc gcacctgctg ccgccagtgc  3120
tgaaagataa attcatctgc gatcgtccgc tggaagtccg tccggtggag tttcataacc  3180
cactgaaagg tcacgtcgca gaaccacatc gtcaggtgtg gatccgcgca aatggtagcg  3240
tgccggatga cctgcgcgtt catcagtatc tgctcggtta cgcttctgat cttaacttcc  3300
tgccggtagc tctacagccg cacggcatcg gttttctcga accggggatt cagattgcca  3360
ccattgacca ttccatgtgg ttccatcgcc cgtttaattt gaatgaatgg ctgctgtata  3420
gcgtggagag cacctcggcg tccagcgcac gtggctttgt gcgcggtgag ttttataccc  3480
aagacggcgt actggttgcc tcgaccgttc aggaaggggt gatgcgtaat cacaattaat  3540
gattacgaat tcgagctcgg tacccgggga tcctctagag tcgacctgca ggcatgcaag  3600
cttggcactg gccgtcgttt tacaacgtcg tgactgggaa aaccctggcg ttacccaact  3660
taatcgcctt gcagcacatc ccccttttcgc cagctggcgt aatagcgaag aggcccgcac  3720
cgatcgccct tcccaacagt tgcgcagcct gaatggcgaa tggcgcgata agctagcttc  3780
acgctgccgc aagcactcag ggcgcaaggg ctgctaaagg aagcggaaca cgtagaaagc  3840
cagtccgcag aaacggtgct gaccccggat gaatgtcagc tactgggcta tctggacaag  3900
ggaaaacgca agcgcaaaga gaaagcaggt agcttgcagt gggcttacat ggcgatagct  3960
agactgggcg gttttatgga cagcaagcga accggaattg ccagctgggg cgccctctgg  4020
taaggttggg aagccctgca aagtaaactg gatggctttc ttgccgccaa ggatctgatg  4080
gcgcagggga tcaagatctg atcaagagac aggatgagga tcgtttcgca tgattgaaca  4140
agatggattg cacgcaggtt ctccggccgc ttgggtggag aggctattcg gctatgactg  4200
ggcacaacag acaatcggct gctctgatgc cgccgtgttc cggctgtcag cgcaggggcg  4260
cccggttctt tttgtcaaga ccgacctgtc cggtgccctg aatgaactcc aagacgaggc  4320
agcgcggcta tcgtggctgg ccacgacggg cgttccttgc gcagctgtgc tcgacgttgt  4380
cactgaagcg ggaagggact ggctgctatt gggcgaagtg ccggggcagg atctcctgtc  4440
atctcacctt gctcctgccg agaaagtatc catcatggct gatgcaatgc ggcggctgca  4500
tacgcttgat ccggctacct gcccattcga ccaccaagcg aaacatcgca tcgagcgagc  4560
acgtactcgg atggaagccg gtcttgtcga tcaggatgat ctggacgaag agcatcaggg  4620
gctcgcgcca gccgaactgt tcgccaggct caaggcgcgg atgcccgacg gcgaggatct  4680
cgtcgtgacc catggcgatg cctgcttgcc gaatatcatg gtggaaaatg gccgcttttc  4740
tggattcatc gactgtggcc ggctgggtgt ggcggaccgc tatcaggaca tagcgttggc  4800
tacccgtgat attgctgaag agcttggcgg cgaatgggct gaccgcttcc tcgtgcttta  4860
cggtatcgcc gctcccgatt cgcagcgcat cgccttctat cgccttcttg acgagttctt  4920
ctgagcggga ctctggggtt cgcgatgata agctgtcaaa catgagaatt acaacttata  4980
tcgtatgggg ctgacttcag gtgctacatt tgaagagata aattgcactg aaatctagaa  5040
atattttatc tgattaataa gatgatcttc ttgagatcgt tttggtctgc gcgtaatctc  5100
ttgctctgaa aacgaaaaaa ccgccttgca gggcggtttt tcgaaggttc tctgagctac  5160
caactctttg aaccgaggta actggcttgg aggagcgcag tcaccaaaac ttgtcctttc  5220
agtttagcct taaccggcgc atgacttcaa gactaactcc tctaaatcaa ttaccagtgg  5280
ctgctgccag tggtgctttt gcatgtcttt ccgggttgga ctcaagacga tagttaccgg  5340
ataaggcgca gcggtcggac tgaacggggg gttcgtgcat acagtccagc ttggagcgaa  5400
ctgcctaccc ggaactgagt gtcaggcgtg gaatgagaca aacgcggcca taacagcgga  5460
atgacaccgg taaaccgaaa ggcaggaaca ggagagcgca cgagggagcc gccaggggaa  5520
acgcctggta tctttatagt cctgtcgggt ttcgccacca ctgatttgag cgtcagattt  5580
cgtgatgctt gtcagggggg cggagcctat ggaaaaacgg ctttgccttc tttcctgcgt  5640
tatcccctga ttctgtggat aaccgtatta ccgcctttga gtgagctgat accgctcgcc  5700
gcagccgaac gaccgagcgc agcgagtcag tgagcgagga agcggaagag cgcccaatac  5760
gcaaaccgcc tctccccgcg cgttggccga ttcattaatg cagctggcac gacaggtttc  5820
ccgactggaa agcgggcagt gagcgcaacg caattaatgt gagttagctc actcattagg  5880
caccccaggc tttacacttt atgcttccgg ctcgtatgtt gtgtggaatt gtgagcggat  5940
aacaattt                                                            5948
```

```
SEQ ID NO: 168         moltype = DNA  length = 5673
FEATURE                Location/Qualifiers
source                 1..5673
                       mol_type = other DNA
                       organism = synthetic construct
SEQUENCE: 168
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gtttttttgcg ccgacatcat aacggttctg gcaaatattc  180
tgaaatgagc tgttgacaat taatcatccg gctcgtataa tgtgtggaat tgtgagcgga  240
taacaatttc acacaggagg aatcaaaaat gctggtaaat gacgagcaac aacagatcgc  300
cgacgcggta cgtgcgttcg cccaggaacg cctgaagccg tttgccgagc aatgggacaa  360
ggaccatcgc ttcccgaaag aggccatcga cgagatggcc gaactgggcc tgttcggcat  420
gctggtgccg gagcagtggg gcggtagcga caccggttat gtggcctatg ccatggcctt  480
ggaggaaatc gctgcgggcg atggcgcctg ctcgaccatc atgagcgtgc acaactcggt  540
gggttgcgtg ccgatcctgc gcttcggcaa cgagcagcag aaagagcagt tcctcacccc  600
gctggcgaca ggtgcgatgc tcggtgcttt cgccctgacc gagccgcagg ctggctccga  660
tgccagcagc ctgaagaccc gcgcacgcct ggaaggcgac cattacgtgc tcaatggcag  720
caagcagttc attacctcgg ggcagaacgc cggcgtagtg atcgtgtttg cggtcaccga  780
cccggaggcc ggcaagcgtg gcatcagcgc cttcatcgtg ccgaccgatt cgccgggcta  840
ccaggtagcg cgggtggagg acaaactcgg ccagcacgcc tccgacacct gccagatcgt  900
tttcgacaat gtgcaagtgc cagtggccaa ccggctgggg gcggagggtg aaggctacaa  960
gatcgccctg gccaaccttg aaggcggccg tatcggcatc gcctcgcaag cggtgggtat  1020
ggcccgcgcg gcgttcgaag tggcgcggga ctatgccaac gagcgccaga gctttggcaa  1080
accgctgatc gagcaccagg ccgtggcgtt tcgcctggcc gacatggcaa cgaaaatttc  1140
cgttgcccgg cagatggtat tgcacgccgc tgcccttcgt gatgcggggc gcccggcgct  1200
ggtggaagcg tcgatggcca agctgttcgc ctcggaaatg gccgaaaagg tctgttcgga  1260
cgccttgcag accctgggcg gttatggcta tctgagtgac ttcccgctgg agcggatcta  1320
ccgcgacgtt cgggtttgcc agatctacga aggcaccagc gacattcagc gcatggtcat  1380
tgcgcgcaat ctttgagcta gcaaaggagg taaagataat gagtacacaa acccttgccg  1440
tgggccagaa ggctcgcctg accaagcgct tcggcccggc cgaggtggcg gccttcgccg  1500
gcctctcgga ggatttcaat cccctgcacc tggacccgga cttcgccgcc acgacggtgt  1560
tcgagcgccc catcgtccac ggcatgctgc tggcgagcct cttctccggg ctcctcgggc  1620
agcaactgcc cgggaaaggg agcatctatc tgggccagag cctcggcttc aaactgccgg  1680
tgttcgtggg ggacgaggtg acggcggagg tggaggtgat tgcccttcga agcgacaagc  1740
ccatcgccac cctggccacc cgcatcttca cccagggcgg cgccctcgcc gtgacggggg  1800
aagcggtggt aaaactccct tgaggctgtt ttggcggatg agagaagatt ttcagcctga  1860
tacagattaa atcagaacgc agaagcggtc tgataaaaca gaatttgcct ggcggcagta  1920
gcgcggtggt cccacctgac cccatgccga actcagaagt gaaacgccgt agcgccgatg  1980
gtagtgtggg gtctccccat gcgagagtag ggaactgcca ggcatcaaat aaaacgaaag  2040
gctcagtcga aagactgggc ctttcgtttt atctgttgtt tgtcggtgaa cgctctcctg  2100
agtaggacaa atccgccggg agcggatttg aacgttgcga agcaacggcc cggagggtgg  2160
cgggcaggac gcccgccata aactgccagg catcaaatta agcagaaggc catcctgacg  2220
gatggccttt ttgcgtttct acaaactctt tttgtttatt tttctaaata cattcaaata  2280
tgtatccgct catgagacaa taaccctgat aaatgcttca ataatattga aaaaggaaga  2340
gtatgagtat tcaacatttc cgtgtcgccc ttattccctt ttttgcggca ttttgccttc  2400
ctgtttttgc tcacccagaa acgctggtga aagtaaaaga tgctgaagat cagttgggtg  2460
cacgagtggg ttacatcgaa ctggatctca acagcggtaa gatccttgag agttttcgcc  2520
ccgaagaacg ttttccaatg atgagcactt ttaaagttct gctatgtggc gcggtattat  2580
cccgtgttga cgccgggcaa gagcaactcg gtcgccgcat acactattct cagaatgact  2640
tggttgagta ctcaccagtc acagaaaagc atcttacgga tggcatgaca gtaagagaat  2700
tatgcagtgc tgccataacc atgagtgata acactgcggc caacttactt ctgacaacga  2760
tcggaggacc gaaggagcta accgcttttt tgcacaacat gggggatcat gtaactcgcc  2820
ttgatcgttg ggaaccggag ctgaatgaag ccataccaaa cgacgagcgt gacaccacga  2880
tgcctacagc aatggcaaca acgttgcgca aactattaac tggcgaacta cttactctag  2940
cttcccggca acaattaata gactggatgg aggcggataa agttgcagga ccacttctgc  3000
gctcggccct tccggctggc tggtttattg ctgataaatc tggagccggt gagcgtgggt  3060
ctcgcggtat cattgcagca ctggggccag atggtaagcc ctcccgtatc gtagttatct  3120
acacgacggg gagtcaggca actatggatg aacgaaatag acagatcgct gagataggtg  3180
cctcactgat taagcattgg taactgtcag accaagttta ctcatatata ctttagattg  3240
atttaaaact tcatttttaa tttaaaagga tctaggtgaa gatccttttt gataatctca  3300
tgaccaaaat cccttaacgt gagttttcgt tccactgagc gtcagacccc gtagaaaaga  3360
tcaaaggatc ttcttgagat cctttttttc tgcgcgtaat ctgctgcttg caaacaaaaa  3420
aaccaccgct accagcggtg gtttgtttgc cggatcaaga gctaccaact ctttttccga  3480
aggtaactgg cttcagcaga gcgcagatac caaatactgt ccttctagtg tagccgtagt  3540
taggccacca cttcaagaac tctgtagcac cgcctacata cctcgctctg ctaatcctgt  3600
taccagtggc tgctgccagt ggcgataagt cgtgtcttac cgggttggac tcaagacgat  3660
agttaccgga taaggcgcag cggtcgggct gaacgggggg ttcgtgcaca cagcccagct  3720
tggagcgaac gacctacacc gaactgagat acctacagcg tgagctatga gaaagcgcca  3780
cgcttcccga agggagaaag gcggacaggt atccggtaag cggcagggtc ggaacaggag  3840
agcgcacgag ggagcttcca gggggaaacg cctggtatct ttatagtcct gtcgggtttc  3900
gccacctctg acttgagcgt cgatttttgt gatgctcgtc aggggggcgg agcctatgga  3960
aaaacgccag caacgcggcc tttttacggt tcctggcctt ttgctggcct tttgctcaca  4020
tgttctttcc tgcgttatcc cctgattctg tggataaccg tattaccgcc tttgagtgag  4080
ctgataccgc tcgccgcagc cgaacgaccg agcgcagcga gtcagtgagc gaggaagcgg  4140
aagagcgcct gatgcggtat tttctcctta cgcatctgtg cggtatttca caccgcatat  4200
ggtgcactct cagtacaatc tgctctgatg ccgcatagtt aagccagtat acactccgct  4260
atcgctacgt gactgggtca tggctgcgcc ccgacacccg ccaacacccg ctgacgcgcc  4320
```

-continued

```
ctgacgggct tgtctgctcc cggcatccgc ttacagacaa gctgtgaccg tctccgggag  4380
ctgcatgtgt cagaggtttt caccgtcatc accgaaacgc gcgaggcagc agatcaattc  4440
gcgcgcgaag gcgaagcggc atgcatttac gttgacacca tcgaatggtg caaaaccttt  4500
cgcggtatgg catgatagcg cccggaagag agtcaattca gggtggtgaa tgtgaaacca  4560
gtaacgttat acgatgtcgc agagtatgcc ggtgtctctt atcagaccgt ttcccgcgtg  4620
gtgaaccagg ccagccacgt ttctgcgaaa acgcgggaaa aagtggaagc ggcgatggcg  4680
gagctgaatt acattcccaa ccgcgtggca caacaactgg cgggcaaaca gtcgttgctg  4740
attggcgttg ccacctccag tctggccctg cacgcgccgt cgcaaattgt cgcggcgatt  4800
aaatctcgcg ccgatcaact gggtgccagc gtggtggtgt cgatggtaga acgaagcggc  4860
gtcgaagcct gtaaagcggc ggtgcacaat cttctcgcgc aacgcgtcag tgggctgatc  4920
attaactatc cgctggatga ccaggatgcc attgctgtgg aagctgcctg cactaatgtt  4980
ccggcgttat ttcttgatgt ctctgaccag acacccatca acagtattat tttctcccat  5040
gaagacggta cgcgactggg cgtggagcat ctggtcgcat tgggtcacca gcaaatcgcg  5100
ctgttagcgg gcccattaag ttctgtctcg gcgcgtctgc gtctggctgg ctggcataaa  5160
tatctcactc gcaatcaaat tcagccgata gcggaacggg aaggcgactg gagtgccatg  5220
tccggttttc aacaaaccat gcaaatgctg aatgagggca tcgttcccac tgcgatgctg  5280
gttgccaacg atcagatggc gctgggcgca atgcgcgcca ttaccgagtc cgggctgcgc  5340
gttggtgcgg atatctcggt agtgggatac gacgataccg aagacagctc atgttatatc  5400
ccgccgttaa ccaccatcaa acaggatttt cgcctgctgg ggcaaaccag cgtggaccgc  5460
ttgctgcaac tctctcaggg ccaggcggtg aagggcaatc agctgttgcc cgtctcactg  5520
gtgaaaagaa aaaccaccct ggcgcccaat acgcaaaccg cctctccccg cgcgttggcc  5580
gattcattaa tgcagctggc acgacaggtt tcccgactgg aaagcgggca gtgagcgcaa  5640
cgcaattaat gtgagttagc gcgaattgat ctg                              5673
```

```
SEQ ID NO: 169          moltype = DNA  length = 5175
FEATURE                 Location/Qualifiers
source                  1..5175
                        mol_type = other DNA
                        organism = synthetic construct
SEQUENCE: 169
atgatggttc caaccctcga acacgagctt gctcccaacg aagccaacca tgtcccgctg  60
tcgccgctgt cgttcctcaa gcgtgccgcg caggtgtacc cgcagcgcga tgcggtgatc  120
tatggcgcaa ggcgctacag ctaccgtcag ttgcacgagc gcagccgcgc cctggccagt  180
gccttggagc gggtcggtgt tcagccgggc gagcgggtgg cgatattggc gccgaacatc  240
ccggaaatgc tcgaggccca ctatggcgtg cccggtgccg gggcggtgct ggtgtgcatc  300
aacatccgcc tggaggggcg cagcattgcc ttcatcctgc gtcactgcgc ggccaaggta  360
ttgatctgcg atcgtgagtt cggtgccgtg gccaatcagg cgctggccat gctcgatgcg  420
ccgcccttgc tggtgggcat cgacgatgat caggccgagc gcgccgattt ggcccacgac  480
ctggactacg aagcgttctt ggcccagggc gaccccgcgc ggccgttgag tgcgccacag  540
aacgaatggc agtcgatcgc catcaactac acctccggca ccacggggga ccccaagggc  600
gtggtgctgc atcaccgcgg cgcctacctc aacgcctgcg ccggggcgct gatcttccag  660
ttggggccgc gcagcgtcta cttgtggacc ttgccgatgt tccactgcaa cggctggagc  720
catacctggg cggtgacgtt gtccggtggc acccacgtgt gtctgcgcaa ggtccagcct  780
gatgcgatca acgccgccat cgccgagcat gccgtgactc acctgagcgc cgcccccagtg  840
gtgatgtcga tgctgatcca cgccgagcat gccagcgccc ctccggtgcc ggtttcggtg  900
atcactggcg gtgccgcccc gcccagtgcg gtcatcgcgg cgatggaggc gcgtggcttc  960
aacatcaccc atgcctatgg catgaccgaa agctacggtc ccagcacatt gtgcctgtgg  1020
cagccgggtg tcgacgagtt gccgctggag gcccgggccc agttcatgag ccgccagggc  1080
gtcgcccacc cgctgctcga ggaggccacg gtgctggata ccgacaccgg ccgcccggtc  1140
ccggccgacg gccttaccct cggcgagctg gtggtgcggg gcaacactgt gatgaaaggc  1200
tacctgcaca acccagaggc tacccgtgcc gcgttggcca acggctggct gcacacgggc  1260
gacctggccg tgctgcacct ggacggctat gtggaaatca aggaccgagc caaggacatc  1320
atcatttctg gcggcgagaa catcagttcg ctggagatag aagaagtgct ctaccagcac  1380
cccgaggtgg tcgaggctgc ggtggtggcg cgtccggatt cgcgctgggg cgagacacct  1440
cacgctttcg tcacgctgcg cgctgatgca ctggccagcg gggacgacct ggtccgctgg  1500
tgccgtgagc gtctggcgca cttcaaggcg ccgcgccatg tgtcgctcgt ggacctgccc  1560
aagaccgcca ctggaaaaat acagaagttc gtcctgcgtg agtggcccg gcaacaggag  1620
gcgcagatcg ccgacgccga gcattgactc gagaaaggag gataagataa tggaccagaa  1680
gctgttaacg gatttccgct cagaactact cgattcacgt tttggcgcaa aggccatttc  1740
tactatcgcg gagtcaaaac gatttccgct gcacgaaatg cgcgatgatg tcgcatttca  1800
gattatcaat gatgaattat atcttgatgg caacgctcgt cagaacctgg ccactttctg  1860
ccagacctgg gacgacgaaa acgtccataa attgatggat ttgtcgatca ataaaaactg  1920
gatcgacaaa gaacagtatc cgcaatccgc agccatcgac ctgcgttgcg taaatatggt  1980
tgccgatctg tggcatgcgc ctgcgccgaa aaatggtcag gccgttggca ccaacaccat  2040
tggttcttcc gaggcctgta tgctcggcgg gatggcgatg aaatggcgtt ggcgcaagcg  2100
tatggaagct gcaggcaaac caacggataa accaaacctg gtgtgcggtc cggtacaaat  2160
ctgctggcat aaattcgccc gctactggga tgtggagctg cgtgagatcc ctatgcgccc  2220
cggtcagttg tttatggacc cgaaacgcat gattgaagcc tgtgacgaaa acaccatcgg  2280
cgtggtgccg actttcggcg tgacctacac cggtaactat gagttcccac aaccgctgca  2340
cgatgcgctg gataaattcc aggccgacac cggtatcgac atcgacatgc acatcgacgc  2400
tgccagcggt ggcttcctgg caccgttcgt cgccccggat atcgtctggg acttccgcct  2460
gccgcgtgtg aaatcgatca gtgcttcagg ccataaattc ggtctggctc cgctgggctg  2520
cggctgggtt atctggcgtg acgaagaagc gctgccgcag gaactggtgt tcaacgttga  2580
ctacctgggt ggtcaaattg gtacttttgc catcaacttc tcccgcccgg cgggtcaggt  2640
aattgcacag tactatgaat tcctgcgcct cggtcgtgaa ggctatacca aagtacagaa  2700
cgcctcttac caggttgccg cttatctggc ggatgaaatc gccaaactgg ggccgtatga  2760
gttcatctgt acgggtcgcc cggacgaagg catcccggcg gtttgcttca aactgaaaga  2820
tggtgaagat ccgggataca ccctgtacga cctctctgaa cgtctgcgtc tgcgcggctg  2880
gcaggttccg gccttcactc tcggcggtga agccaccgac atcgtggtga tgcgcattat  2940
```

```
gtgtcgtcgc ggcttcgaaa tggactttgc tgaactgttg ctggaagact acaaagcctc  3000
cctgaaatat ctcagcgatc actaaaggaa gcggaacacg tagaaagcca gtccgcagaa  3060
acggtgctga ccccggatga atgtcagcta ctgggctatc tggacaaggg aaaacgcaag  3120
cgcaaagaga aagcaggtag cttgcagtgg gcttacatgg cgatagctag actgggcggt  3180
tttatggaca gcaagcgaac cggaattgcc agctggggcg ccctctggta aggttgggaa  3240
gccctgcaaa gtaaactgga tggctttctt gccgccaagg atctgatggc gcaggggatc  3300
aagatctgat caagagacag gatgaggatc gtttcgcatg attgaacaag atggattgca  3360
cgcaggttct ccggccgctt gggtggagag gctattcggc tatgactggg cacaacagac  3420
aatcggctgc tctgatgccg ccgtgttccg gctgtcagcg caggggcgcc cggttctttt  3480
tgtcaagacc gacctgtccg gtgccctgaa tgaactccaa gacgaggcag cgcggctatc  3540
gtggctggcc acgacgggcg ttccttgcgc agctgtgctc gacgttgtca ctgaagcggg  3600
aagggactgg ctgctattgg gcgaagtgcc ggggcaggat ctcctgtcat ctcaccttgc  3660
tcctgccgag aaagtatcca tcatggctga tgcaatgcgg cggctgcata cgcttgatcc  3720
ggctacctgc ccattcgacc accaagcgaa acatcgcatc gagcgagcac gtactcggat  3780
ggaagccggt cttgtcgatc aggatgatct ggacgaagag catcaggggc tcgcgccagc  3840
cgaactgttc gccaggctca aggcgcggat gcccgacggc gaggatctcg tcgtgaccca  3900
tggcgatgcc tgcttgccga atatcatggt ggaaaatggc cgcttttctg gattcatcga  3960
ctgtggccgg ctgggtgtgg cggaccgcta tcaggacata gcgttggcta cccgtgatat  4020
tgctgaagag cttggcggcg aatgggctga ccgcttcctc gtgctttacg gtatcgccgc  4080
tcccgattcg cagcgcatcg ccttctatcg ccttcttgac gagttcttct gagcgggact  4140
ctggggttcg cgatgataag ctgtcaaaca tgagaattac aacttatatc gtatggggct  4200
gacttcaggt gctacatttg aagagataaa ttgcactgaa atctagaaat attttatctg  4260
attaataaga tgatcttctt gagatcgttt tggtctgcgc gtaatctctt gctctgaaaa  4320
cgaaaaaacc gccttgcagg gcggtttttc gaaggttctc tgagctacca actctttgaa  4380
ccgaggtaac tggcttggag gagcgcagtc accaaaactt gtcctttcag tttagcctta  4440
accggcgcat gacttcaaga ctaactcctc taaatcaatt accagtggct gctgccagtg  4500
gtgcttttgc atgtctttcc gggttggact caagacgata gttaccggat aaggcgcagc  4560
ggtcggactg aacggggggt tcgtgcatac agtccagctt ggagcgaact gcctacccgg  4620
aactgagtgt caggcgtgga atgagacaaa cgcggccata acagcggaat gacaccggta  4680
aaccgaaagg caggaacagg agagcgcacg agggagccgc caggggaaac gcctggtatc  4740
tttatagtcc tgtcgggttt cgccaccact gatttgagcg tcagatttcg tgatgcttgt  4800
caggggggcg gagcctatgg aaaaacggct ttgccttctt tcctgcgtta tcccctgatt  4860
ctgtggataa ccgtattacc gcctttgagt gagctgatac cgctcgccgc agccgaacga  4920
ccgagcgcag cgagtcagtg agcgaggaag cggaagagcg cccaatacgc aaaccgcctc  4980
tccccgcgcg ttggccgatt cattaatgca gctggcacga caggtttccc gactggaaag  5040
cgggcagtga gcgcaacgca attaatgtga gttagctcac tcattaggca ccccaggctt  5100
tacactttat gcttccggct cgtatgttgt gtggaattgt gagcggataa caatttcaca  5160
caggaggaat caaaa                                                   5175

SEQ ID NO: 170          moltype = DNA  length = 8353
FEATURE                 Location/Qualifiers
source                  1..8353
                        mol_type = other DNA
                        organism = synthetic construct
SEQUENCE: 170
gtttgacagc ttatcatcga ctgcacggtg caccaatgct tctggcgtca ggcagccatc  60
ggaagctgtg gtatggctgt gcaggtcgta aatcactgca taattcgtgt cgctcaaggc  120
gcactcccgt tctggataat gtttttttgcg ccgacatcat aacggttctg gcaaatattc  180
tgaaatgagc tgttgacaat taatcatccg gctcgtataa tgtgtggaat tgtgagcgga  240
taacaatttc acacaggagg aatcaaaaat gaatcaacag gtaaatgtgg cccccagcgc  300
ggcagcagac ttaaatctga aagcgcattg gatgcctttt agcgccaacc gcaacttcca  360
caaggacccc cgcatcatcg tagctgccga aggatcgtgg ctggtagacg ataagggacg  420
ccgtatctac gactcattga gtggcttgtg gacctgcggc gcgggtcact ctcgtaagga  480
aattgccgac gcagtggcga aacagattgg gaccctggac tactcgccag ggtttcaata  540
tggccaccct ctgtcgtttc agcttgcaga gaagattgcg caaatgacgc ctggcacgct  600
ggatcatgtc ttctttacag gaagtgggag tgaatgcgcg gacacatcta tcaaaatggc  660
tcgcgcctac tggcgcatca agggccaagc gcagaagacc aagttgatcg gccgtgctcg  720
cggatatcac ggcgtcaacg tggccggaac atcgcttgga ggtattgggg gaaaccgtaa  780
aatgttcgga cccctgatgg atgtcgatca tttgcctcac acattacaac ctggaatggc  840
attcactaag ggcgcagcag aaacaggtgg ggtggagctt gccaatgaat tgctgaagtt  900
aattgagtta catgatgctt cgaatatcgc cgcagtgatt gtggagccta tgtctggcag  960
tgccggtgtg attgtgccac caaaaggtta tcttcagcgt ttacgtgaga tttgcgacgc  1020
taacgatatc ctgttaatct tcgacgaggt gattacagct tttggccgta tgggcaaagc  1080
aacgggtgcc gagtattttg gagtaactcc cgatatcatg aacgtggcta agcaagtaac  1140
caacggggcc gttccgatgg gagccgttat cgcctcctct gaaatttatg acaccttcat  1200
gaaccaaaac ttgcccgaat acgccgtgga atttggacat ggttatactt acagcgctca  1260
tccagtggca tgtgccgccg gcatcgcggc gctggatctg cttcaaaaag agaatttaat  1320
ccagcagtcg gccgagcttg cacctcactt cgaaaaggcc ttacatggct taaagggcac  1380
taaaaacgtt atcgatatcc gcaactgtgg ccttgctgga gcgattcaaa tcgcggcgcg  1440
cgacggagac gcgatcgtgc gcccctttga ggcgagcatg aagttgtgga aggaaggctt  1500
ctacgtgcgt ttcggcggtg ataccctgca atttggccct actttcaacg ccaaaccgga  1560
agacttagat cgcctttttcg atgcagttgg agaggcactg aacggggtcg cttaagctag  1620
caaaggaggt aaagataatg aatacttctg aactcgaaac cctgattcgc accattctta  1680
gcgagcaatt aaccacgccg gcgcaaacgc cggtccagcc tcagggcaaa gggatttttcc  1740
agtccgtgag cgaggccatc gacgccgcgc accaggcgtt cttacgttat cagcagtgcc  1800
cgctaaaaac ccgcagcgcc attatcagcg cgatgcgtca ggagctgacg ccgctgctgg  1860
cgcccctggc ggaagagagc gccaatgaaa cggggatggg caacaaagaa gataaatttc  1920
tcaaaaacaa ggctgcgctg gacaacacgc cgggcgtaga agatctcacc accaccgcgc  1980
tgaccggcga cggcggcatg gtgctgtttg aatactcacc gtttggcgtt atcggttcgg  2040
```

-continued

```
tcgccccaag caccaacccg acggaaacca tcatcaacaa cagtatcagc atgctggcgg  2100
cgggcaacag tatctacttt agcccgcatc cgggagcgaa aaaggtctct ctgaagctga  2160
ttagcctgat tgaagagatt gccttccgct gctgcggcat ccgcaatctg gtggtgaccg  2220
tggcggaacc caccttcgaa gcgacccagc agatgatggc ccacccgcga atcgcagtac  2280
tggccattac cggcggcccg ggcattgtgg caatgggcat gaagagcggt aagaaggtga  2340
ttggcgctgg cgcgggtaac ccgccctgca tcgttgatga aacggcggac ctggtgaaag  2400
cggcggaaga tatcatcaac ggcgcgtcat tcgattacaa cctgccctgc attgccgaga  2460
agagcctgat cgtagtggag agtgtcgccg aacgtctggt gcagcaaatg caaaccttcg  2520
gcgcgctgct gttaagccct gccgataccg acaaactccg cgccgtctgc ctgcctgaag  2580
gccaggcgaa taaaaaactg gtcggcaaga gcccatcggc catgctggaa gccgccggga  2640
tcgctgtccc tgcaaaagcg ccgcgtctgc tgattgcgct ggttaacgct gacgatccgt  2700
gggtcaccag cgaacagttg atgccgatgc tgccagtggt aaaagtcagc gatttcgata  2760
gcgcgctggc gctggccctg aaggttgaag aggggctgca tcataccgcc attatgcact  2820
cgcagaacgt gtcacgcctg aacctcgcgg cccgcacgct gcaaacctcg atattcgtca  2880
aaaacggccc ctcttatgcc gggatcggcg tcggcggcga aggctttacc accttcacta  2940
tcgccacacc aaccggtgaa gggaccacgt cagcgcgtac ttttgcccgt tcccggcgct  3000
gcgtactgac caacggcttt tctattcgct aactcgagaa aggaggataa ctaaatgaaa  3060
cttaacgaca gtaacttatt ccgccagcag gcgttgatta acggggaatg gctggacgcc  3120
aacaatggtg aagccatcga cgtcaccaat ccggcgaacg gcgacaagct gggtagcgtg  3180
ccgaaaatgg gcgcggatga aacccgcgcc gctatcgacg ccgccaaccg cgccctgccc  3240
gcctggcgcg cgctcaccgc caaagaacgc gccaccattc tgcgcaactg gttcaatttg  3300
atgatggagc atcaggacga tttagcgcgc ctgatgaccc tcgaacaggg taaaccactg  3360
gccgaagcga aaggcgaaat cagctacgcc gcctccttta ttgagtggtt tgccgaagaa  3420
ggcaaacgca tttatggcga caccattcct ggtcatcagg ccgataaacg cctgattgtt  3480
atcaagcagc cgattggcgt caccgcggct atcacgccgt ggaacttccc ggcggcgatg  3540
attacccgca aagccggtcc ggcgctggca gcaggctgca ccatggtgct gaagcccgcc  3600
agtcagacgc cgttctctgc gctggcgctg gcggagctgg cgatccgcgc gggcgttccg  3660
gctggggtat ttaacgtggt caccggttcg gcgggcgcgg tcggtaacga actgaccagt  3720
aacccgctgg tgcgcaaact gtcgtttacc ggttcgaccg aaattggccg ccagttaatg  3780
gaacagtgcg cgaaagacat caagaaagtg tcgctggagc tgggcggtaa cgcgccgttt  3840
atcgtctttg acgatgccga cctcgacaaa gccgtggaag gcgcgctggc ctcgaaattc  3900
cgcaacgccg ggcaaacctg cgtctgcgcc aaccgcctgt atgtgcagga cggcgtgtat  3960
gaccgttttg ccgaaaaatt gcagcaggca gtgagcaaac tgcacatcgg cgacgggctg  4020
gataacggcg tcaccatcgg gccgctgatc gatgaaaaag cggtagcaaa agtggaagag  4080
catattgccg atgcgctgga gaaaggcgcg cgcgtggttt gcggcggtaa agcgcacgaa  4140
cgcggcggca acttcttcca gccgaccatt ctggtggacg ttccggccaa cgccaaagtg  4200
tcgaaagaag agacgttcgg cccccctcgcc ccgctgttcc gctttaaaga tgaagctgat  4260
gtgattgcgc aagccaatga caccgagttt ggccttgccg cctatttcta cgcccgtgat  4320
ttaagccgcg tcttccgcgt gggcgaagcg ctggagtacg gcatcgtcgg catcaatacc  4380
ggcattattt ccaatgaagt ggccccgttc ggcggcatca aagcctcggg tctgggtcgt  4440
gaaggttcga agtatggcat cgaagattac ttagaaatca aatatatgtg catcggtctt  4500
taaggctgtt ttggcggatg agagaagatt ttcagcctga tacagattaa atcagaacgc  4560
agaagcggtc tgataaaaca gaatttgcct ggcggcagta gcgcggtggt cccacctgac  4620
cccatgccga actcagaagt gaaacgccgt agcgccgatg gtagtgtggg gtctccccat  4680
gcgagagtag ggaactgcca ggcatcaaat aaaacgaaag gctcagtcga aagactgggc  4740
ctttcgtttt atctgttgtt tgtcggtgaa cgctctcctg agtaggacaa atccgccggg  4800
agcggatttg aacgttgcga agcaacggcc cggagggtgg cgggcaggac gcccgccata  4860
aactgccagg catcaaatta agcagaaggc catcctgacg gatggccttt ttgcgtttct  4920
acaaactctt tttgtttatt tttctaaata cattcaaata tgtatccgct catgagacaa  4980
taaccctgat aaatgcttca ataatattga aaaaggaaga gtatgagtat tcaacatttc  5040
cgtgtcgccc ttattccctt ttttgcggca ttttgccttc ctgtttttgc tcacccagaa  5100
acgctggtga aagtaaaaga tgctgaagat cagttgggtg cacgagtggg ttacatcgaa  5160
ctggatctca acagcggtaa gatccttgag agttttcgcc ccgaagaacg ttttccaatg  5220
atgagcactt ttaaagttct gctatgtggc gcggtattat cccgtgttga cgccgggcaa  5280
gagcaactcg gtcgccgcat acactattct cagaatgact tggttgagta ctcaccagtc  5340
acagaaaagc atcttacgga tggcatgaca gtaagagaat tatgcagtgc tgccataacc  5400
atgagtgata acactgcggc caacttactt ctgacaacga tcggaggacc gaaggagcta  5460
accgcttttt tgcacaacat gggggatcat gtaactcgcc ttgatcgttg ggaaccggag  5520
ctgaatgaag ccataccaaa cgacgagcgt gacaccacga tgcctacagc aatggcaaca  5580
acgttgcgca aactattaac tggcgaacta cttactctag cttcccggca acaattaata  5640
gactggatgg aggcggataa agttgcagga ccacttctgc gctcggccct tccggctggc  5700
tggtttattg ctgataaatc tggagccggt gagcgtgggt ctcgcggtat cattgcagca  5760
ctggggccag atggtaagcc ctcccgtatc gtagttatct acacgacggg gagtcaggca  5820
actatggatg aacgaaatag acagatcgct gagataggtg cctcactgat taagcattgg  5880
taactgtcag accaagttta ctcatatata ctttagattg atttaaaact tcatttttaa  5940
tttaaaagga tctaggtgaa gatccttttt gataatctca tgaccaaaat cccttaacgt  6000
gagttttcgt tccactgagc gtcagacccc gtagaaaaga tcaaaggatc ttcttgagat  6060
cctttttttc tgcgcgtaat ctgctgcttg caaacaaaaa aaccaccgct accagcggtg  6120
gtttgtttgc cggatcaaga gctaccaact ctttttccga aggtaactgg cttcagcaga  6180
gcgcagatac caaatactgt ccttctagtg tagccgtagt taggccacca cttcaagaac  6240
tctgtagcac cgcctacata cctcgctctg ctaatcctgt taccagtggc tgctgccagt  6300
ggcgataagt cgtgtcttac cgggttggac tcaagacgat agttaccgga taaggcgcag  6360
cggtcgggct gaacgggggg ttcgtgcaca cagcccagct tggagcgaac gacctacacc  6420
gaactgagat acctacagcg tgagctatga gaaagcgcca cgcttcccga agggagaaag  6480
gcggacaggt atccggtaag cggcagggtc ggaacaggag agcgcacgag ggagcttcca  6540
gggggaaacg cctggtatct ttatagtcct gtcgggtttc gccacctctg acttgagcgt  6600
cgatttttgt gatgctcgtc aggggggcgg agcctatgga aaaacgccag caacgcggcc  6660
tttttacggt tcctggcctt ttgctggcct tttgctcaca tgttctttcc tgcgttatcc  6720
cctgattctg tggataaccg tattaccgcc tttgagtgag ctgataccgc tcgccgcagc  6780
```

-continued

```
cgaacgaccg agcgcagcga gtcagtgagc gaggaagcgg aagagcgcct gatgcggtat  6840
tttctcctta cgcatctgtg cggtatttca caccgcatat ggtgcactct cagtacaatc  6900
tgctctgatg ccgcatagtt aagccagtat acactccgct atcgctacgt gactgggtca  6960
tggctgcgcc ccgacacccg ccaacacccg ctgacgcgcc ctgacgggct tgtctgctcc  7020
cggcatccgc ttacagacaa gctgtgaccg tctccgggag ctgcatgtgt cagaggtttt  7080
caccgtcatc accgaaacgc gcgaggcagc agatcaattc gcgcgcgaag gcgaagcggc  7140
atgcatttac gttgacacca tcgaatggtg caaaaccttt cgcggtatgg catgatagcg  7200
cccggaagag agtcaattca gggtggtgaa tgtgaaacca gtaacgttat acgatgtcgc  7260
agagtatgcc ggtgtctctt atcagaccgt ttcccgcgtg gtgaaccagg ccagccacgt  7320
ttctgcgaaa acgcgggaaa aagtggaagc ggcgatggcg gagctgaatt acattcccaa  7380
ccgcgtggca caacaactgg cgggcaaaca gtcgttgctg attggcgttg ccacctccag  7440
tctggccctg cacgcgccgt cgcaaattgt cgcggcgatt aaatctcgcg ccgatcaact  7500
gggtgccagc gtggtggtgt cgatggtaga acgaagcggc gtcgaagcct gtaaagcggc  7560
ggtgcacaat cttctcgcgc aacgcgtcag tgggctgatc attaactatc cgctggatga  7620
ccaggatgcc attgctgtgg aagctgcctg cactaatgtt ccggcgttat ttcttgatgt  7680
ctctgaccag acacccatca acagtattat tttctcccat gaagacggta cgcgactggg  7740
cgtggagcat ctggtcgcat tgggtcacca gcaaatcgcg ctgttagcgg gcccattaag  7800
ttctgtctcg gcgcgtctgc gtctggctgg ctggcataaa tatctcactc gcaatcaaat  7860
tcagccgata gcggaacggg aaggcgactg gagtgccatg tccggttttc aacaaaccat  7920
gcaaatgctg aatgagggca tcgttcccac tgcgatgctg gttgccaacg atcagatggc  7980
gctgggcgca atgcgcgcca ttaccgagtc cgggctgcgc gttggtgcgg atatctcggt  8040
agtgggatac gacgataccg aagacagctc atgttatatc ccgccgttaa ccaccatcaa  8100
acaggatttt cgcctgctgg ggcaaaccag cgtggaccgc ttgctgcaac tctctcaggg  8160
ccaggcggtg aagggcaatc agctgttgcc cgtctcactg gtgaaaagaa aaaccaccct  8220
ggcgcccaat acgcaaaccg cctctccccg cgcgttggcc gattcattaa tgcagctggc  8280
acgacaggtt tcccgactgg aaagcgggca gtgagcgcaa cgcaattaat gtgagttagc  8340
gcgaattgat ctg                                                     8353

SEQ ID NO: 171         moltype =   length =
SEQUENCE: 171
000

SEQ ID NO: 172         moltype = AA  length = 220
FEATURE                Location/Qualifiers
source                 1..220
                       mol_type = protein
                       organism = Megasphaera sp.
SEQUENCE: 172
MVERKGRALI AWRCAQFFKN GDFVNLGIGL PLMCVNYLPE GVSLWLEAEI GTVGSGPSPD  60
WNHVDIDVID AGGQPASVIT GGSVYDHETS FAFIRGGHID ATVLGTLQVD QEGNIANWTI  120
PGKFVPGMGG AMDLCAGVKK IIVATDHCEK SGHSKILKKC TLPLTGARCV TDIVTERCYF  180
EVTPQGLVLR ELAPGYTVED IRACTEADFI VPETIAVMGE                        220

SEQ ID NO: 173         moltype = AA  length = 245
FEATURE                Location/Qualifiers
source                 1..245
                       mol_type = protein
                       organism = Megasphaera sp.
SEQUENCE: 173
MLSKVFSLQD ILEHIHDGQT IMFGDWHGQF AADEIIDGML EKGVKDIKAI AVSAGYPGQG  60
VGKLIVAHRV SSIVTTHIGL NPEALKQMLA GELAVEFVPQ GTWAERVRCG GAGLGGVLTP  120
TGVGTSVEEG KQKLVIDGKE YLLELPLHAD VALVKATKAD TAGNLYFRMN SRATNSTIAY  180
AADFVAAEVE EIVPVGQLLP EEIAIPAPVV DMVYERQGEK RFICPMWKKA RARAEAKARE  240
RQERG                                                              245

SEQ ID NO: 174         moltype = DNA  length = 663
FEATURE                Location/Qualifiers
source                 1..663
                       mol_type = genomic DNA
                       organism = Megasphaera sp.
SEQUENCE: 174
atggttgaac ggaaaggaag agctttgatt gcctggcgtt gtgcccaatt cttcaaaaat  60
ggggacttcg tcaacttagg gatcggcctg cccctgatgt gcgtcaacta tctgcccgaa  120
ggcgtatccc tctggctgga agctgaaatc ggcaccgttg gcagcggccc gtcgccggac  180
tggaatcatg tcgatatcga cgtcatcgat gctggcggcc agccggcttc ggtcattacc  240
ggcggcagtg tctacgacca cgaaacgtcc ttcgctttca tccgcggtgg ccatattgac  300
gcgactgtct tggggacgct gcaagtcgac caggaaggga atatcgccaa ctggaccatc  360
cccgggaaat tcgtgcccgg tatgggcggg gccatggacc tctgtgccgg tgtcaagaag  420
atcatcgtcg ccacggacca ttgcgaaaag agcggccatt ccaagatact gaagaaatgc  480
acgctgcccc tgacgggagc ccgttgcgtg accgacatcg taaccgaacg ctgctacttt  540
gaagtcacgc cgcaaggcct ggtcctgcgg gaactggccc cgggctatac cgtagaagat  600
atccgggcct gcaccgaagc ggacttcatc gtccccgaaa ccatcgccgt catgggcgag  660
tga                                                                663

SEQ ID NO: 175         moltype = DNA  length = 738
FEATURE                Location/Qualifiers
source                 1..738
                       mol_type = genomic DNA
                       organism = Megasphaera sp.
```

```
SEQUENCE: 175
gtgttatcga aggtattttc tctccaagat atcctggagc atatccatga cggacagacc  60
atcatgttcg gtgactggca tggccaattc gcggctgatg aaatcatcga cggcatgctg  120
gaaaaaggcg tcaaggatat caaagccatc gccgtatcgg ccggctatcc cggccagggc  180
gtaggcaagc tgatcgtggc tcatcgcgtg tcgtccatcg ttacgacgca tatcggcctc  240
aatccggaag cgctgaaaca gatgctggcc ggtgaactgg ccgtcgaatt cgtcccccag  300
gggacctggg ccgaacgcgt gcgctgcggc ggtgccggcc tgggcggcgt cctgacgccg  360
accggtgtcg gtacgagtgt cgaagaaggg aaacagaagc tggtcatcga tgggaaggaa  420
tatctcctgg aattaccgct ccatgccgac gtagccctgg tcaaggcgac caaagccgat  480
acggcaggga acctctattt ccgcatgaat tcgcgggcga cgaacagtac catcgcttat  540
gcggctgatt tcgtcgccgc cgaagtcgaa gaaatcgtcc ccgtcggcca gctcttgccg  600
gaagaaatcg ccatcccggc tcctgtcgtc gacatggtct atgaacggca gggcgaaaaa  660
cggtttatct gcccgatgtg gaaaaaggcc agggcccgtg ccgaagccaa ggcgcgggaa  720
cggcaggaaa ggggatga                                                738

SEQ ID NO: 176         moltype = AA  length = 238
FEATURE                Location/Qualifiers
source                 1..238
                       mol_type = protein
                       organism = Escherichia coli
SEQUENCE: 176
MQTPHILIVE DELVTRNTLK SIFEAEGYDV FEATDGAEMH QILSEYDINL VIMDINLPGK  60
NGLLLARELR EQANVALMFL TGRDNEVDKI LGLEIGADDY ITKPFNPREL TIRARNLLSR  120
TMNLGTVSEE RRSVESYKFN GWELDINSRS LIGPDGEQYK LPRSEFRAML HFCENPGKIQ  180
SRAELLKKMT GRELKPHDRT VDVTIRRIRK HFESTPDTPE IIATIHGEGY RFCGDLED    238

SEQ ID NO: 177         moltype = AA  length = 250
FEATURE                Location/Qualifiers
source                 1..250
                       mol_type = protein
                       organism = Escherichia coli
SEQUENCE: 177
MIPEKRIIRR IQSGGCAIHC QDCSISQLCI PFTLNEHELD QLDNIIERKK PIQKGQTLFK  60
AGDELKSLYA IRSGTIKSYT ITEQGDEQIT GFHLAGDLVG FDAIGSGHHP SFAQALETSM  120
VCEIPFETLD DLSGKMPNLR QQMMRLMSGE IKGDQDMILL LSKKNAEERL AAFIYNLSRR  180
FAQRGFSPRE FRLTMTRGDI GNYLGLTVET ISRLLGRFQK SGMLAVKGKY ITIENNDALA  240
QLAGHTRNVA                                                         250

SEQ ID NO: 178         moltype = AA  length = 462
FEATURE                Location/Qualifiers
source                 1..462
                       mol_type = protein
                       organism = Escherichia coli
SEQUENCE: 178
MTITPATHAI SINPATGEQL SVLPWAGADD IENALQLAAA GFRDWRETNI DYRAEKLRDI  60
GKALRARSEE MAQMITREMG KPINQARAEV AKSANLCDWY AEHGPAMLKA EPTLVENQQA  120
VIEYRPLGTI LAIMPWNFPL WQVMRGAVPI ILAGNGYLLK HAPNVMGCAQ LIAQVFKDAG  180
IPQGVYGWLN ADNDGVSQMI KDSRIAAVTV TGSVRAGAAI GAQAGAALKK CVLELGGSDP  240
FIVLNDADLE LAVKAAVAGR YQNTGQVCAA AKRFIIEEGI ASAFTERFVA AAAALKMGDP  300
RDEENALGPM ARFDLRDELH HQVEKTLAQG ARLLLGGEKM AGAGNYYPPT VLANVTPEMT  360
AFREEMFGPV AAITIAKDAE HALELANDSE FGLSATIFTT DETQARQMAA RLECGGVFIN  420
GYCASDARVA FGGVKKSGFG RELSHFGLHE FCNIQTVWKD RI                     462

SEQ ID NO: 179         moltype = AA  length = 393
FEATURE                Location/Qualifiers
source                 1..393
                       mol_type = protein
                       organism = Escherichia coli
SEQUENCE: 179
MKDVVIVGAL RTPIGCFRGA LAGHSAVELG SLVVKALIER TGVPAYAVDE VILGQVLTAG  60
AGQNPARQSA IKGGLPNSVS AITINDVCGS GLKALHLATQ AIQCGEADIV IAGGQENMSR  120
APHVLTDSRT GAQLGNSQLV DSLVHDGLWD AFNDYHIGVT AENLAREYGI SRQLQDAYAL  180
SSQQKARAAI DAGRFKDEIV PVMTQSNGQT LVVDTDEQPR TDASAEGLAR LNPSFDSLGS  240
VTAGNASSIN DGAAAVMMMS EAKARALNLP VLARIRAFAS VGVDPALMGI APVYATRRCL  300
ERVGWQLAEV DLIEANEAFA AQALSVGKML EWDERRVNVN GGAIALGHPI GASGCRILVS  360
LVHEMVKRNA RKGLATLCIG GGQGVALTIE RDE                                393

SEQ ID NO: 180         moltype = AA  length = 387
FEATURE                Location/Qualifiers
source                 1..387
                       mol_type = protein
                       organism = Escherichia coli
SEQUENCE: 180
MEQVVIVDAI RTPMGRSKGG AFRNVRAEDL SAHLMRSLLA RNPALEAAAL DDIYWGCVQQ  60
TLEQGFNIAR NAALLAEVPH SVPAVTVNRL CGSSMQALHD AARMIMTGDA QACLVGGVEH  120
MGHVPMSHGV DFHPGLSRNV AKAAGMMGLT AEMLARMHGI SREMQDAFAA RSHARAWAAT  180
QSAAFKNEII PTGGHDADGV LKQFNYDEVI RPETTVEALA TLRPAFDPVN GMVTAGTSSA  240
LSDGAAAMLV MSESRAHELG LKPRARVRSM AVVGCDPSIM GYGPVPASKL ALKKAGLSAS  300
DIGVFEMNEA FAAQILPCIK DLGLIEQIDE KINLNGGAIA LGHPLGCSGA RISTTLLNLM  360
```

```
ERKDVQFGLA TMCIGLGQGI ATVFERV                                  387

SEQ ID NO: 181          moltype = AA  length = 593
FEATURE                 Location/Qualifiers
source                  1..593
                        mol_type = protein
                        organism = Escherichia coli
SEQUENCE: 181
MAKMRAVDAA MYVLEKEGIT TAFGVPGAAI NPFYSAMRKH GGIRHILARH VEGASHMAEG  60
YTRATAGNIG VCLGTSGPAG TDMITALYSA SADSIPILCI TGQAPRARLH KEDFQAVDIE  120
AIAKPVSKMA VTVREAALVP RVLQQAFHLM RSGRPGPVLV DLPFDVQVAE IEFDPDMYEP  180
LPVYKPAASR MQIEKAVEML IQAERPVIVA GGGVINADAA ALLQQFAELT SVPVIPTLMG  240
WGCIPDDHEL MAGMVGLQTA HRYGNATLLA SDMVFGIGNR FANRHTGSVE KYTEGRKIVH  300
IDIEPTQIGR VLCPDLGIVS DAKAALTLLV EVAQEMQKAG RLPCRKEWVA DCQQRKRTLL  360
RKTHFDNVPV KPQRVYEEMN KAFGRDVCYV TTIGLSQIAA AQMLHVFKDR HWINCGQAGP  420
LGWTIPAALG VCAADPKRNV VAISGDFDFQ FLIEELAVGA QFNIPYIHVL VNNAYLGLIR  480
QSQRAFDMDY CVQLAFENIN SSEVNGYGVD HVKVAEGLGC KAIRVFKPED IAPAFEQAKA  540
LMAQYRVPVV VEVILERVTN ISMGSELDNV MEFEDIADNA ADAPTETCFM HYE         593

SEQ ID NO: 182          moltype = AA  length = 394
FEATURE                 Location/Qualifiers
source                  1..394
                        mol_type = protein
                        organism = Escherichia coli
SEQUENCE: 182
MKNCVIVSAV RTAIGSFNGS LASTSAIDLG ATVIKAAIER AKIDSQHVDE VIMGNVLQAG  60
LGQNPARQAL LKSGLAETVC GFTVNKVCGS GLKSVALAAQ AIQAGQAQSI VAGGMENMSL  120
APYLLDAKAR SGYRLGDGQV YDVILRDGLM CATHGYHMGI TAENVAKEYG ITREMQDELA  180
LHSQRKAAAA IESGAFTAEI VPVNVVTRKK TFVFSQDEFP KANSTAEALG ALRPAFDKAG  240
TVTAGNASGI NDGAAALVIM EESAALAAGL TPLARIKSYA SGGVPPALMG MGPVPATQKA  300
LQLAGLQLAD IDLIEANEAF AAQFLAVGKN LGFDSEKVNV NGGAIALGHP IGASGARILV  360
TLLHAMQARD KTLGLATLCI GGGQGIAMVI ERLN                          394

SEQ ID NO: 183          moltype = AA  length = 208
FEATURE                 Location/Qualifiers
source                  1..208
                        mol_type = protein
                        organism = Escherichia coli
SEQUENCE: 183
MMNFNNVFRW HLPFLFLVLL TFRAAAADTL LILGDSLSAG YRMSASAAWP ALLNDKWQSK  60
TSVVNASISG DTSQQGLARL PALLKQHQPR WVLVELGGND GLRGFQPQQT EQTLRQILQD  120
VKAANAEPLL MQIRLPANYG RRYNEAFSAI YPKLAKEFDV PLLPFFMEEV YLKPQWMQDD  180
GIHPNRDAQP FIADWMAKQL QPLVNHDS                                  208

SEQ ID NO: 184          moltype = AA  length = 468
FEATURE                 Location/Qualifiers
source                  1..468
                        mol_type = protein
                        organism = Clostridium beijerinckii
SEQUENCE: 184
MNKDTLIPTT KDLKVKTNGE NINLKNYKDN SSCFGVFENV ENAISSAVHA QKILSLHYTK  60
EQREKIITEI RKAALQNKEV LATMILEETH MGRYEDKILK HELVAKYTPG TEDLTTTAWS  120
GDNGLTVVEM SPYGVIGAIT PSTNPTETVI CNSIGMIAAG NAVVFNGHPC AKKCVAFAVE  180
MINKAIISCG GPENLVTTIK NPTMESLDAI IKHPSIKLLC GTGGPGMVKT LLNSGKKAIG  240
AGAGNPPVIV DDTADIEKAG RSIIEGCSFD NNLPCIAEKE VFVFENVADD LISNMLKNNA  300
VIINEDQVSK LIDLVLQKNN ETQEYFINKK WVGKDAKLFL DEIDVESPSN VKCIICEVNA  360
NHPFVMTELM MPILPIVRVK DIDEAIKYAK IAEQNRKHSA YIYSKNIDNL NRFEREIDTT  420
IFVKNAKSFA GVGYEAEGFT TFTIAGSTGE GITSARNFTR QRRCVLAG             468

SEQ ID NO: 185          moltype = DNA  length = 717
FEATURE                 Location/Qualifiers
source                  1..717
                        mol_type = genomic DNA
                        organism = Escherichia coli
SEQUENCE: 185
atgcagaccc cgcacattct tatcgttgaa gacgagttgg taacacgcaa cacgttgaaa  60
agtattttcg aagcggaagg ctatgatgtt ttcgaagcga cagatggcgc ggaaatgcat  120
cagatcctct ctgaatatga catcaacctg gtgatcatgg atatcaatct gccgggtaag  180
aacggtcttc tgttagcgcg tgaactgcgc gagcaggcga atgttgcgtt gatgttcctg  240
actggccgtg acaacgaagt cgataaaatt ctcggcctcg aaatcggtgc agatgactac  300
atcaccaaac cgttcaaccc gcgtgaactg acgattcgtg cacgcaacct actgtcccgt  360
accatgaatc tgggtactgt cagcgaagaa cgtcgtagcg ttgaaagcta caagttcaat  420
ggttgggaac tggacatcaa cagccgttcg ttgatcggcc ctgatggcga gcagtacaag  480
ctgccgcgca gcgagttccg cgccatgctt cacttctgtg aaaacccagg caaaattcag  540
tcccgtgctg aactgctgaa gaaaatgacc ggccgtgagc tgaaaccgca cgaccgtact  600
gtagacgtga cgatccgccg tattcgtaaa catttcgaat ctacgccgga tacgccggaa  660
atcatcgcca ccattcacgg tgaaggttat cgcttctgcg gtgatctgga agattaa     717

SEQ ID NO: 186          moltype = DNA  length = 753
```

```
FEATURE                Location/Qualifiers
source                 1..753
                       mol_type = genomic DNA
                       organism = Escherichia coli
SEQUENCE: 186
atgatcccgg aaaagcgaat tatacggcgc attcagtctg gcggttgtgc tatccattgc  60
caggattgca gcatcagcca gctttgcatc ccgttcacac tcaacgaaca tgagcttgat  120
cagcttgata atatcattga gcggaagaag cctattcaga aaggccagac gctgtttaag  180
gctggtgatg aacttaaatc gctttatgcc atccgctccg gtacgattaa aagttatacc  240
atcactgagc aaggcgacga gcaaatcact ggtttccatt tagcaggcga cctggtggga  300
tttgacgcca tcggcagcgg ccatcacccg agcttcgcgc aggcgctgga aacctcgatg  360
gtatgtgaaa tcccgttcga aacgctggac gatttgtccg gtaaaatgcc gaatctgcgt  420
cagcagatga tgcgtctgat gagcggtgaa atcaaaggcg atcaggacat gatcctgctg  480
ttgtcgaaga aaaatgccga ggaacgtctg gctgcattca tctacaacct gtcccgtcgt  540
tttgcccaac gcggcttctc ccctcgtgaa ttccgcctga cgatgactcg tggcgatatc  600
ggtaactatc tgggcctgac ggtagaaacc atcagccgtc tgctgggtcg cttccagaaa  660
agcggcatgc tggcagtcaa aggtaaatac atcaccatcg aaaataacga tgcgctggcc  720
cagcttgctg gtcatacgcg taacgttgcc tga                               753

SEQ ID NO: 187         moltype = DNA  length = 1389
FEATURE                Location/Qualifiers
source                 1..1389
                       mol_type = genomic DNA
                       organism = Escherichia coli
SEQUENCE: 187
atgaccatta ctccggcaac tcatgcaatt tcgataaatc ctgccacggg tgaacaactt  60
tctgtgctgc cgtgggctgg cgctgacgat atcgaaaacg cacttcagct ggcggcagca  120
ggctttcgcg actggcgcga gacaaatata gattatcgtg ctgaaaaact gcgtgatatc  180
ggtaaggctc tgcgcgctcg tagcgaagaa atggcgcaaa tgatcacccg cgaaatgggc  240
aaaccaatca accaggcgcg cgctgaagtg gcgaaatcgg cgaatttgtg tgactggtat  300
gcagaacatg gtccggcaat gctgaaggcg gaacctacgc tggtggaaaa tcagcaggcg  360
gttattgagt atcgaccgtt ggggacgatt ctggcgatta tgccgtggaa ttttccgtta  420
tggcaggtga tgcgtggcgc tgttcccatc attcttgcag gtaacggcta cttacttaaa  480
catgcgccga atgtgatggg ctgtgcacag ctcattgccc aggtgtttaa agatgcgggt  540
atcccacaag gcgtatatgg ctggctgaat gccgacaacg acggtgtcag tcagatgatt  600
aaagactcgc gcattgctgc tgtcacggtg accggaagtg ttcgtgcggg agcggctatt  660
ggcgcacagg ctggagcggc actgaaaaaa tgcgtactgg aactgggcgg ttcggatccg  720
tttattgtgc ttaacgatgc cgatctggaa ctggcggtga aagcggcggt agccggacgt  780
tatcagaata ccggacaggt atgtgcagcg gcaaaacgct ttattatcga agagggaatt  840
gcttcggcat ttaccgaacg ttttgtggca gctgcggcag ccttgaaaat gggcgatccc  900
cgtgacgaag agaacgctct cggaccaatg gctcgttttg atttacgtga tgagctgcat  960
catcaggtgg agaaaaccct ggcgcagggt gcgcgtttgt tactgggcgg ggaaaagatg  1020
gctggggcag gtaactacta tccgccaacg gttctggcga atgttacccc agaaatgacc  1080
gcgtttcggg aagaaatgtt tggccccgtt gcggcaatca ccattgcgaa agatgcagaa  1140
catgcactgg aactggctaa tgatagtgag ttcggccttt cagcgaccat tttaccact   1200
gacgaaacac aggccagaca gatggcggca cgtctggaat gcggtggggt gtttatcaat  1260
ggttattgtg ccagcgacgc gcgagtggcc tttggtggcg tgaaaaagag tggctttggt  1320
cgtgagcttt cccatttcgg cttacacgaa ttctgtaata tccagacggt gtggaaagac  1380
cggatctga                                                          1389

SEQ ID NO: 188         moltype = DNA  length = 1182
FEATURE                Location/Qualifiers
source                 1..1182
                       mol_type = genomic DNA
                       organism = Escherichia coli
SEQUENCE: 188
atgaaagacg ttgtgattgt cggggcgtta cggacaccta tcggctgctt tcgtggtgcg  60
ttagcgggtc attccgccgt ggaacttggt agtctggtcg tgaaagcgtt aatagaacgt  120
accggcgttc ctgcatatgc ggtggatgaa gtaattcttg gtcaggtgtt gactgcaggg  180
gcagggcaga atccggcaag gcaatcggct attaaaggtg gtctgcctaa tagcgtttct  240
gcaatcacta ttaatgacgt ttgcggttcc gggcttaaag cactgcatct ggctactcag  300
gcgatacagt gtggcgaggc tgatattgtc atcgccggtg gccaggaaaa catgagccgc  360
gcaccacatg ttctgactga tagccgcacc ggtgcacagc ttggcaatag ccagttggtt  420
gacagtcttg tgcatgatgg gttgtgggat gccttcaatg attatcatat tggtgtcacc  480
gccgaaaatc tggctcgcga atatggcatc agccgtcagt tgcaggatgc ttacgcactt  540
agctcgcaac aaaaagcgcg agcggcgatt gacgccggac gatttaaaga tgagatcgtc  600
ccggtaatga cccaaagtaa cggcagacg  ttggttgttg ataccgatga acagccacgc  660
actgacgcca gcgcagaagg cttagcccgt ttaaatcctt catttgatag tctcggttct  720
gtgacagcgg gtaatgcatc atccataaac gatggcgcag ctgcggtaat gatgatgagc  780
gaagccaaag cacgagcgtt gaatttaccc gtgctggccc gcattcgcgc atttgccagc  840
gttggtgtag atccggcatt gatgggaatt gcgccggtgt atgcgacccg ccgttgcctg  900
gagcgtgtag gctggcagtt ggctgaagtc gatcttatcg aggctaatga agcgtttgct  960
gcacaggcgc tttcggttgg caagatgctt gagtgggatg agcgtcgggt caatgtcaat  1020
ggtggcgcga tcgcactcgg tcacccgata ggcgcttccg gttgccgaat cctggtttct  1080
ctggttcatg aaatggtgaa acgtaatgcc cgcaaaggac tggcaacgct ttgtatcggc  1140
gggggccagg gtgtggcatt gaccattgaa cgtgacgaat ag                    1182

SEQ ID NO: 189         moltype = DNA  length = 1164
FEATURE                Location/Qualifiers
```

```
source                  1..1164
                        mol_type = genomic DNA
                        organism = Escherichia coli
SEQUENCE: 189
atggaacagg ttgtcattgt cgatgcaatt cgcaccccga tgggccgttc gaagggcggt  60
gcttttcgta acgtgcgtgc agaagatctc tccgctcatt taatgcgtag cctgctggcg  120
cgtaacccgg cgctggaagc ggcggccctc gacgatattt actggggttg tgtgcagcag  180
acgctggagc agggttttaa tatcgcccgt aacgcggcgc tgctggcaga agtaccacac  240
tctgtcccgg cggttaccgt taatcgcttg tgtggttcat ccatgcaggc actgcatgac  300
gcagcacgaa tgatcatgac tggcgatgcg caggcatgtc tggttggcgg cgtggagcat  360
atgggccatg tgccgatgag tcacggcgtc gattttcacc ccggcctgag ccgcaatgtc  420
gccaaagcgg cgggcatgat gggcttaacg gcagaaatgc tggcgcgtat gcacggtatc  480
agccgtgaaa tgcaggatgc ctttgccgcg cggtcacacg cccgcgcctg ggccgccacg  540
cagtcggccg catttaaaaa tgaaatcatc ccgaccggtg gtcacgatgc cgacggcgtc  600
ctgaagcagt ttaattacga cgaagtgatt cgcccggaaa ccaccgtgga agccctcgcc  660
acgctgcgtc cggcgtttga tccagtaaac ggtatggtaa cggcgggcac atcttctgca  720
ctttccgatg gcgcagctgc catgctggtg atgagtgaaa gccgcgccca tgaattaggt  780
cttaagccgc gcgctcgtgt gcgttcgatg gcggtcgttg gttgtgaccc atcgattatg  840
ggttacggcc cggttccggc ctcgaaactg gcgctgaaaa aagcggggct ttctgccagc  900
gatatcggcg tgtttgaaat gaacgaagcc tttgccgcgc agatcctgcc atgtattaaa  960
gatctgggac taattgagca gattgacgag aagatcaacc tcaacggtgg cgcgatcgcg  1020
ctgggtcatc cgctgggttg ttccggtgcg cgtatcagca ccacgctgct gaatctgatg  1080
gaacgcaaag acgttcagtt tggtctggcg acgatgtgta tcggtctggg tcagggtatt  1140
gcgacggtgt ttgagcgggt ttaa                                        1164

SEQ ID NO: 190          moltype = DNA  length = 1782
FEATURE                 Location/Qualifiers
source                  1..1782
                        mol_type = genomic DNA
                        organism = Escherichia coli
SEQUENCE: 190
atggcaaaaa tgagagccgt tgacgcggca atgtatgtgc tggagaaaga aggtatcact  60
accgccttcg gtgttccggg agctgcaatc aatccgttct actcagcgat gcgtaagcac  120
ggcggtattc gtcacattct ggcgcgtcat gtggaaggtg cttcgcacat ggcggaaggt  180
tatacccgcg caacggcagg gaatatcggc gtatgtctgg ggacttccgg tcctgcgggc  240
acggacatga tcaccgcgct ctattccgct tctgctgatt ccattcctat tctgtgcatt  300
accggccagg caccgcgcgc ccgtctgcat aaagaagatt ttcaggccgt agatattgaa  360
gcaattgcta aaccggtcag caaaatggcg gttacagttc gtgaagcggc gctggtgcct  420
cgcgtgctgc aacaggcatt tcacctgatg cgttctggtc gtccgggtcc ggtactggtg  480
gatttaccgt tcgacgttca ggttgcggaa atcgagtttg atcctgacat gtacgaaccg  540
ctgccggtct acaaacctgc tgccagccgt atgcagatcg aaaaagctgt agaaatgtta  600
atccaggccg aacgtccggt gattgttgcc gggggcgggg taattaatgc tgacgcagct  660
gcactgttac aacagtttgc tgaactgacc agcgttccgg tgatcccaac gctaatgggc  720
tggggctgta tcccggacga tcatgaactg atggccggga tggtgggtct gcaaaccgcg  780
catcgttacg gtaacgcaac gctgctggcg tctgacatgg tgtttggtat cggtaaccgt  840
tttgctaacc gtcataccgg ctcggtagag aaatacaccg aagggcgcaa aatcgttcat  900
attgatattg agccgacgca aattggtcgc gtgctgtgtc cggatctcgg tattgtctct  960
gatgctaaag cggcgctgac actgctggtt gaagtggcgc aggagatgca aaaagcgggt  1020
cgtctgccgt gtcgtaaaga atgggtcgcc gactgccagc agcgtaaacg cactttgctg  1080
cgcaaaaccc acttcgacaa cgtgccggtg aaaccgcagc gcgtgtatga agagatgaac  1140
aaagcctttg gtcgcgatgt ttgttatgtc accaccattg gtctgtcaca aatcgctgcg  1200
gcacaaatgc tgcatgtctt taaagaccgc cactggatca actgtggtca ggctggtccg  1260
ttaggctgga cgattccggc tgcgctaggg gtttgtgccg ctgatccgaa acgcaatgtg  1320
gtggcgattt ctggcgactt tgacttccag ttcctgattg aagagttagc tgttggcgcg  1380
cagttcaaca ttccgtacat ccatgtgctg gtcaacaacg cttatctggg gctgattcgt  1440
cagtcacaac gcgcttttga catggactac tgcgtgcaac tcgctttcga gaatatcaac  1500
tccagtgaag tgaatggcta cggtgttgac cacgtaaaag tagcggaagg tttaggttgt  1560
aaagctattc gggtcttcaa accggaagat attgcgccag cctttgaaca ggcgaaagcc  1620
ttaatggcgc aatatcgggt accggtagtc gtggaagtta ttctcgagcg tgtgaccaat  1680
atttcgatgg gcagcgaact ggataacgtc atggaatttg aagatatcgc cgataacgca  1740
gcggacgcac cgactgaaac ctgcttcatg cactatgaat aa                    1782

SEQ ID NO: 191          moltype = DNA  length = 1185
FEATURE                 Location/Qualifiers
source                  1..1185
                        mol_type = genomic DNA
                        organism = Escherichia coli
SEQUENCE: 191
atgaaaaatt gtgtcatcgt cagtgcggta cgtactgcta tcggtagttt taacggttca  60
ctcgcttcca ccagcgccat cgacctgggg gcgacagtaa ttaaagccgc cattgaacgt  120
gcaaaaatcg attcacaaca cgttgatgaa gtgattatgg gtaacgtgtt acaagccggg  180
ctggggcaaa atccggcgcg tcaggcactg ttaaaaagcg ggctggcaga aacggtgtgc  240
ggattcacgg tcaataaagt atgtggttcg ggtcttaaaa gtgtggcgct tgccgcccag  300
gccattcagg caggtcaggc gcagagcatt gtggcggggg gtatggaaaa tatgagttta  360
gccccctact tactcgatgc aaaagcacgc tctggttatc gtcttggaga cggacaggtt  420
tatgacgtaa tcctgcgcga tggcctgatg tgcgccaccc atggttatca tatggggatt  480
accgccgaaa acgtggctaa agagtacgga attacccgtg aaatgcagga tgaactggcg  540
ctacattcac agcgtaaagc ggcagccgca attgagtccg gtgcttttac agccgaaatc  600
gtcccggtaa atgttgtcac tcgaaagaaa accttcgtct tcagtcaaga cgaattcccg  660
```

```
aaagcgaatt caacggctga agcgttaggt gcattgcgcc cggccttcga taaagcagga  720
acagtcaccg ctgggaacgc gtctggtatt aacgacggtg ctgccgctct ggtgattatg  780
gaagaatctg cggcgctggc agcaggcctt acccccctgg ctcgcattaa aagttatgcc  840
agcggtggcg tgccccccgc attgatgggt atggggccag tacctgccac gcaaaaagcg  900
ttacaactgg cggggctgca actggcggat attgatctca ttgaggctaa tgaagcattt  960
gctgcacagt tccttgccgt tgggaaaaac ctgggctttg attctgagaa agtgaatgtc  1020
aacggcgggg ccatcgcgct cgggcatcct atcggtgcca gtggtgctcg tattctggtc  1080
acactattac atgccatgca ggcacgcgat aaaacgctgg ggctggcaac actgtgcatt  1140
ggcggcggtc agggaattgc gatggtgatt gaacggttga attaa                1185

SEQ ID NO: 192          moltype = DNA  length = 627
FEATURE                 Location/Qualifiers
source                  1..627
                        mol_type = genomic DNA
                        organism = Escherichia coli
SEQUENCE: 192
atgatgaact tcaacaatgt tttccgctgg catttgccct tcctgttcct ggtcctgtta  60
accttccgtg ccgccgcagc ggacacgtta ttgattctgg gtgatagcct gagcgccggg  120
tatcgaatgt ctgccagcgc ggcctggcct gccttgttga atgataagtg gcagagtaaa  180
acgtcggtag ttaatgccag catcagcggc gacacctcgc aacaaggact ggcgcgcctt  240
ccggctctgc tgaaacagca tcagccgcgt tgggtgctgg ttgaactggg cggcaatgac  300
ggtttgcgtg gttttcagcc acagcaaacc gagcaaacgc tgcgccagat tttgcaggat  360
gtcaaagccg ccaacgctga accattgtta atgcaaatac gtctgcctgc aaactatggt  420
cgccgttata atgaagcctt tagcgccatt taccccaaac tcgccaaaga gtttgatgtt  480
ccgctgctgc cctttttat ggaagaggtc tacctcaagc cacaatggat gcaggatgac  540
ggtattcatc ccaaccgcga cgcccagccg tttattgccg actggatggc gaagcagttg  600
cagcctttag taaatcatga ctcataa                                    627

SEQ ID NO: 193          moltype = DNA  length = 1407
FEATURE                 Location/Qualifiers
source                  1..1407
                        mol_type = genomic DNA
                        organism = Clostridium beijerinckii
SEQUENCE: 193
atgaataaag acacactaat acctacaact aaagatttaa aagtaaaaac aaatggtgaa  60
aacattaatt taaagaacta caaggataat tcttcatgtt tcggagtatt cgaaaatgtt  120
gaaaatgcta taagcagcgc tgtacacgca caaaagatat tatcccttca ttatacaaaa  180
gagcaaagag aaaaaatcat aactgagata agaaaggccg cattacaaaa taaagaggtc  240
ttggctacaa tgattctaga agaaacacat atgggaagat atgaggataa aatattaaaa  300
catgaattgg tagctaaata tactcctggt acagaagatt taactactac tgcttggtca  360
ggtgataatg gtcttacagt tgtagaaatg tctccatatg gtgttatagg tgcaataact  420
ccttctacga atccaactga aactgtaata tgtaatagca taggcatgat agctgctgga  480
aatgctgtag tatttaacgg acacccatgc gctaaaaaat gtgttgcctt tgctgttgaa  540
atgataaata aggcaattat ttcatgtggc ggtcctgaaa atctagtaac aactataaaa  600
aatccaacta tggagtctct agatgcaatt attaagcatc cttcaataaa acttctttgc  660
ggaactgggg gtccaggaat ggtaaaaacc ctcttaaatt ctggtaagaa agctataggt  720
gctggtgctg gaaatccacc agttattgta gatgatactg ctgatataga aaaggctggt  780
aggagcatca ttgaaggctg ttcttttgat aataatttac cttgtattgc agaaaaagaa  840
gtatttgttt ttgagaatgt tgcagatgat ttaatatcta acatgctaaa aaataatgct  900
gtaattataa atgaagatca agtatcaaaa ttaatagatt tagtattaca aaaaaataat  960
gaaactcaag aatactttat aaacaaaaaa tgggtaggaa aagatgcaaa attattctta  1020
gatgaaatag atgttgagtc tccttcaaat gttaaatgca taatctgcga agtaaatgca  1080
aatcatccat ttgttatgac agaactcatg atgccaatat tgccaattgt aagagttaaa  1140
gatatagatg aagctattaa atatgcaaag atagcagaac aaaatagaaa acatagtgcc  1200
tatatttatt ctaaaaatat agacaaccta aatagatttg aaagagaaat agatactact  1260
atttttgtaa agaatgctaa atcttttgct ggtgttggtt atgaagcaga aggatttaca  1320
actttcacta ttgctggatc tactggtgag ggaataacct ctgcaaggaa ttttacaaga  1380
caaagaagat gtgtacttgc cggctaa                                    1407

SEQ ID NO: 194          moltype = AA  length = 451
FEATURE                 Location/Qualifiers
source                  1..451
                        mol_type = protein
                        organism = Escherichia coli
SEQUENCE: 194
MDKKQVTDLR SELLDSRFGA KSISTIAESK RFPLHEMRDD VAFQIINDEL YLDGNARQNL  60
ATFCQTWDDE NVHKLMDLSI NKNWIDKEQY PQSAAIDLRC VNMVADLWHA PAPKNGQAVG  120
TNTIGSSEAC MLGGMAMKWR WRKRMEAAGK PTDKPNLVCG PVQICWHKFA RYWDVELREI  180
PMRPGQLFMD PKRMIEACDE NTIGVVPTFG VTYTGNYEFP QPLHDALDKF QADTGIDIDM  240
HIDAASGGFL APFVAPDIVW DFRLPRVKSI SASGHKFGLA PLGCGWVIWR DEEALPQELV  300
FNVDYLGGQI GTFAINFSRP AGQVIAQYYE FLRLGREGYT KVQNASYQVA AYLADEIAKL  360
GPYEFICTGR PDEGIPAVCF KLKDGEDPGY TLYDLSERLR LRGWQVPAFT LGGEATDIVV  420
MRIMCRRGFE MDFAELLLED YKASLKYLSD H                               451

SEQ ID NO: 195          moltype = AA  length = 502
FEATURE                 Location/Qualifiers
source                  1..502
                        mol_type = protein
                        organism = Escherichia coli
```

```
SEQUENCE: 195
MAISTPMLVT FCVYIFGMIL IGFIAWRSTK NFDDYILGGR SLGPFVTALS AGASDMSGWL  60
LMGLPGAVFL SGISESWIAI GLTLGAWINW KLVAGRLRVH TEYNNNALTL PDYFTGRFED  120
KSRILRIISA LVILLFFTIY CASGIVAGAR LFESTFGMSY ETALWAGAAA TILYTFIGGF  180
LAVSWTDTVQ ASLMIFALIL TPVIVIISVG GFGDSLEVIK QKSIENVDML KGLNFVAIIS  240
LMGWGLGYFG QPHILARFMA ADSHHSIVHA RRISMTWMIL CLAGAVAVGF FGIAYFNDHP  300
ALAGAVNQNA ERVFIELAQI LFNPWIAGIL LSAILAAVMS TLSCQLLVCS SAITEDLYKA  360
FLRKHASQKE LVWVGRVMVL VVALVAIALA ANPENRVLGL VSYAWAGFGA AFGPVVLFSV  420
MWSRMTRNGA LAGMIIGALT VIVWKQFGWL GLYEIIPGFI FGSIGIVVFS LLGKAPSAAM  480
QKRFAEADAH YHSAPPSRLQ ES                                           502

SEQ ID NO: 196         moltype = AA  length = 149
FEATURE                Location/Qualifiers
source                 1..149
                       mol_type = protein
                       organism = Aromatoleum aromaticum
SEQUENCE: 196
MSEAVRDFSQ CYGHDFEDLK VGMSAAIGRT VTEADIAIFA GISGDTNPVH LDAEFAASTM  60
FGERIAHGML SASFISAVFG TKLPGPGCIY LGQSLNFKAS VKVGETVVAR VTVRELVAHK  120
RRAFFDTVCT VAGKVVLEGH AEIYLPARQ                                    149

SEQ ID NO: 197         moltype = AA  length = 466
FEATURE                Location/Qualifiers
source                 1..466
                       mol_type = protein
                       organism = Escherichia coli
SEQUENCE: 197
MFIPSIYLHQ QLHYCKTAIL NWSRKMALSR QKFTFERLRR FTLPEGKKQT FLWDADVTTL  60
ACRATSGAKA FVFQSVYAGK TLRMTIGNIN DWKIDDARAE ARRLQTLIDT GIDPRIAKAV  120
KIAEAESLQA ESRKTKVTFS VAWEDYLQEL RTGISAKTKR PYSTRYIADH INLSSRGGES  180
KKRGQGPTSA GPLASLLNLP LSELTPDYIA AWLSTERQNR PTVTAHAYRL LRAFIKWSNY  240
QKKYQGIIPG DLAQDYNVRK MVPVSASKAD DCLQKEQLKS WFSAVRSLNN PIASAYLQVL  300
LLTGARREEI ASLRWSDVDF KWSSMRIKDK IEGERIIPLT PYVSELLNVL AQSPNSDVNK  360
EGWVFRSNSK SGKIIEPRSA HNRALVLAEL PHISLHGLRR SFGTLAEWVE VPTGIVAQIM  420
GHKPSALAEK HYRRRPLDLL RKWHEKIETW ILNEAGITIK NNVDMR                  466

SEQ ID NO: 198         moltype = AA  length = 872
FEATURE                Location/Qualifiers
source                 1..872
                       mol_type = protein
                       organism = Escherichia coli
SEQUENCE: 198
MSILTRWLLI PPVNARLIGR YRDYRRHGAS AFSATLGCFW MILAWIFIPL EHPRWQRIRA  60
EHKNLYPHIN ASRPRPLDPV RYLIQTCWLL IGASRKETPK PRRRAFSGLQ NIRGRYHQWM  120
NELPERVSHK TQHLDEKKEL GHLSAGARRL ILGIIVTFSL ILALICVTQP FNPLAQFIFL  180
MLLWGVALIV RRMPGRFSAL MLIVLSLTVS CRYIWWRYTS TLNWDDPVSL VCGLILLFAE  240
TYAWIVLVLG YFQVVWPLNR QPVPLPKDMS LWPSVDIFVP TYNEDLNVVK NTIYASLGID  300
WPKDKLNIWI LDDGGREEFR QFAQNVGVKY IARTTHEHAK AGNINNALKY AKGEFVSIFD  360
CDHVPTRSFL QMTMGWFLKE KQLAMMQTPH HFFSPDPFER NLGRFRKTPN EGTLFYGLVQ  420
DGNDMWDATF FCGSCAVIRR KPLDEIGGIA VETVTEDAHT SLRLHRRGYT SAYMRIPQAA  480
GLATESLSAH IGQRIRWARG MVQIFRLDNP LTGKGLKFAQ RLCYVNAMFH FLSGIPRLIF  540
LTAPLAFLLL HAYIIYAPAL MIALFVLPHM IHASLTNSKI QGKYRHSFWS EIYETVLAWY  600
IAPPTLVALI NPHKGKFNVT AKGGLVEEEY VDWVISRPYI FLVLLNLVGV AVGIWRYFYG  660
PPTEMLTVVV SMVWVFYNLI VLGGAVAVSV ESKQVRRSHR VEMTMPAAIA REDGHLFSCT  720
VQDFSDGGLG IKINGQAQIL EGQKVNLLLK RGQQEYVFPT QVARVMGNEV GLKLMPLTTQ  780
QHIDFVQCTF ARADTWALWQ DSYPEDKPLE SLLDILKLGF RGYRHLAEFA PSSVKGIFRV  840
LTSLVSWVVS FIPRRPERSE TAQPSDQALA QQ                                872

SEQ ID NO: 199         moltype = AA  length = 1157
FEATURE                Location/Qualifiers
source                 1..1157
                       mol_type = protein
                       organism = Escherichia coli
SEQUENCE: 199
MRKFTLNIFT LSLGLAVMPM VEAAPTAQQQ LLEQVRLGEA THREDLVQQS LYRLELIDPN  60
NPDVVAARFR SLLRQGDIDG AQKQLDRLSQ LAPSSNAYKS SRTTMLLSTP DGRQALQQAR  120
LQATTGHAEE AVASYNKLFN GAPPEGDIAV EYWSTVAKIP ARRGEAINQL KRINADAPGN  180
TGLQNNLALL LFSSDRRDEG FAVLEQMAKS NAGREGASKI WYGQIKDMPV SDASVSALKK  240
YLSIFSDGDS VAAAQSQLAE QQKQLADPAF RARAQGLAAV DSGMAGKAIP ELQQAVRANP  300
KDSEALGALG QAYSQKGDRA NAVANLEKAL ALDPHSSNND KWNSLLKVNR YWLAIQQGDA  360
ALKANNPDRA ERLFQQARNV DNTDSYAVLG LGDVAMARKD YPAAERYYQQ TLRMDSGNTN  420
AVRGLANIYR QQSPEKAEAF IASLSASQRR SIDDIERSLQ NDRLAQQAEA LENQGKWAQA  480
AALQRQRLAL DPGSVWITYR LSQDLWQAGQ RSQADTLMRN LAQQKSNDPE QVYAYGLYLS  540
GHDQDRAALA HINSLPRAQW NSNIQELVNR LQSDQVLETA NRLRESGKEA EAEAMLRQQP  600
PSTRIDLTLA DWAQQRRDYT AARAAYQNVL TREPANADAI LGLTEVDIAA GDKAAARSQL  660
AKLPATDNAS LNTQRRVALA QAQLGDTAAA QRTFNKLIPQ AKSQPPSMES AMVLRDGAKF  720
EAQAGDPTQA LETYKDAMVA SGVTTTRPQD NDTFTRLTRN DEKDDWLKRG VRSDAADLYR  780
QQDLNVTLEH DYWGSSGTGG YSDLKAHTTM LQVDAPYSDG RMFFRSDFVN MNVGSFSTNA  840
DGKWDDNWGT CTLQDCSGNR SQSDSGASVA VGWRNDVWSW DIGTTPMGFN VVDVVGGISY  900
```

```
SDDIGPLGYT VNAHRRPISS SLLAFGGQKD SPSNTGKKWG GVRADGVGLS LSYDKGEANG  960
VWASLSGDQL TGKNVEDNWR VRWMTGYYYK VINQNNRRVT IGLNNMIWHY DKDLSGYSLG  1020
QGGYYSPQEY LSFAIPVMWR ERTENWSWEL GASGSWSHSR TKTMPRYPLM NLIPTDWQEE  1080
AARQSNDGGS SQGFGYTARA LLERRVTSNW FVGTAIDIQQ AKDYAPSHFL LYVRYSAAGW  1140
QGDMDLPPQP LIPYADW                                                1157

SEQ ID NO: 200         moltype = AA  length = 511
FEATURE                Location/Qualifiers
source                 1..511
                       mol_type = protein
                       organism = Escherichia coli
SEQUENCE: 200
MATSVQTGKA KQLTLLGFFA ITASMVMAVY EYPTFATSGF SLVFFLLLGG ILWFIPVGLC  60
AAEMATVDGW EEGGVFAWVS NTLGPRWGFA AISFGYLQIA IGFIPMLYFV LGALSYILKW  120
PALNEDPITK TIAALIILWA LALTQFGGTK YTARIAKVGF FAGILLPAFI LIALAAIYLH  180
SGAPVAIEMD SKTFFPDFSK VGTLVVFVAF ILSYMGVEAS ATHVNEMSNP GRDYPLAMLL  240
LMVAAICLSS VGGLSIAMVI PGNEINLSAG VMQTFTVLMS HVAPEIEWTV RVISALLLLG  300
VLAEIASWIV GPSRGMYVTA QKNLLPAAFA KMNKNGVPVT LVISQLVITS IALIILTNTG  360
GGNNMSFLIA LALTVVIYLC AYFMLFIGYI VLVLKHPDLK RTFNIPGGKG VKLVVAIVGL  420
LTSIMAFIVS FLPPDNIQGD STDMYVELLV VSFLVVLALP FILYAVHDRK GKANTGVTLE  480
PINSQNAPKG HFFLHPRARS PHYIVMNDKK H                                511

SEQ ID NO: 201         moltype = AA  length = 239
FEATURE                Location/Qualifiers
source                 1..239
                       mol_type = protein
                       organism = Escherichia coli
SEQUENCE: 201
MVIKAQSPAG FAEEYIIESI WNNRFPPGTI LPAERELSEL IGVTRTTLRE VLQRLARDGW  60
LTIQHGKPTK VNNFWETSGL NILETLARLD HESVPQLIDN LLSVRTNIST IFIRTAFRQH  120
PDKAQEVLAT ANEVADHADA FAELDYNIFR GLAFASGNPI YGLILNGMKG LYTRIGRHYF  180
ANPEARSLAL GFYHKLSALC SEGAHDQVYE TVRRYGHESG EIWHRMQKNL PGDLAIQGR   239

SEQ ID NO: 202         moltype = AA  length = 387
FEATURE                Location/Qualifiers
source                 1..387
                       mol_type = protein
                       organism = Escherichia coli
SEQUENCE: 202
MNNFNLHTPT RILFGKGAIA GLREQIPHDA RVLITYGGGS VKKTGVLDQV LDALKGMDVL  60
EFGGIEPNPA YETLMNAVKL VREQKVTFLL AVGGGSVLDG TKFIAAAANY PENIDPWHIL  120
QTGGKEIKSA IPMGCVLTLP ATGSESNAGA VISRKTTGDK QAFHSAHVQP VFAVLDPVYT  180
YTLPPRQVAN GVVDAFVHTV EQYVTKPVDA KIQDRFAEGI LLTLIEDGPK ALKEPENYDV  240
RANVMWAATQ ALNGLIGAGV PQDWATHMLG HELTAMHGLD HAQTLAIVLP ALWNEKRDTK  300
RAKLLQYAER VWNITEGSDD ERIDAAIAAT RNFFEQLGVP THLSDYGLDG SSIPALLKKL  360
EEHGMTQLGE NHDITLDVSR RIYEAAR                                     387

SEQ ID NO: 203         moltype = AA  length = 461
FEATURE                Location/Qualifiers
source                 1..461
                       mol_type = protein
                       organism = Escherichia coli
SEQUENCE: 203
MTAINRILIV DDEDNVRRML STAFALQGFE THCANNGRTA LHLFADIHPD VVLMDIRMPE  60
MDGIKALKEM RSHETRTPVI LMTAYAEVET AVEALRCGAF DYVIKPFDLD ELNLIVQRAL  120
QLQSMKKESR HLHQALSTSW QWGHILTNSP AMMDICKDTA KIALSQASVL ISGESGTGKE  180
LIARAIHYNS RRAKGPFIKV NCAALPESLL ESELFGHEKG AFTGAQTLRQ GLFERANEGT  240
LLLDEIGEMP LVLQAKLLRI LQEREFERIG GHQTIKVDIR IIAATNRDLQ AMVKEGTFRE  300
DLFYRLNVIH LILPPLRDRR EDISLLANHF LQKFSSENQR DIIDIDPMAM SLLTAWSWPG  360
NIRELSNVIE RAVVMNSGPI IFSEDLPPQI RQPVCNAGEV KTAPVGERNL KEEIKRVEKR  420
IIMEVLEQQE GNRTRTALML GISRRALMYK LQEYGIDPAD V                     461

SEQ ID NO: 204         moltype = DNA  length = 1356
FEATURE                Location/Qualifiers
source                 1..1356
                       mol_type = genomic DNA
                       organism = Escherichia coli
SEQUENCE: 204
atggataaga agcaagtaac ggatttaagg tcggaactac tcgattcacg ttttggtgcg  60
aagtctattt ccactatcgc agaatcaaaa cgttttccgc tgcacgaaat gcgcgacgat  120
gtcgcattcc agattatcaa tgacgaatta tatcttgatg gcaacgctcg tcagaacctg  180
gccactttct gccagacctg ggacgacgaa aatgtccaca aattgatgga tttatccatt  240
aacaaaaact ggatcgacaa agaacagtat ccgcaatccg cagccatcga cctgcgttgc  300
gtaaatatgg ttgccgatct gtggcatgcg cctgcgccga aaaatggtca ggccgttggc  360
accaacacca ttggttcttc cgaggcctgt atgctcggcg ggatggcgat gaaatggcgt  420
tggcgcaagc gtatggaagc tgcaggcaaa ccaacggata aaccaaacct ggtgtgcggt  480
ccggtacaaa tctgctggca taaattcgcc cgctactggg atgtggagct gcgtgagatc  540
cctatgcgcc ccggtcagtt gtttatggac ccgaaacgca tgattgaagc ctgtgacgaa  600
aacaccatcg gcgtggtgcc gactttcggc gtgacctaca ctggtaacta tgagttccca  660
```

```
caaccgctgc acgatgcgct ggataaattc caggccgata ccggtatcga catcgacatg  720
cacatcgacg ctgccagcgg tggcttcctg gcaccgttcg tcgcccccgga tatcgtctgg  780
gacttccgcc tgccgcgtgt gaaatcgatc agtgcttcag gccataaatt cggtctggct  840
ccgctgggct gcggctgggt tatctggcgt gacgaagaag cgctgccgca ggaactggtg  900
ttcaacgttg actacctggg tggtcaaatt ggtacttttg ccatcaactt ctcccgcccg  960
gcgggtcagg taattgcaca gtactatgaa ttcctgcgcc tcggtcgtga aggctatacc  1020
aaagtacaga acgcctctta ccaggttgcc gcttatctgg cggatgaaat cgccaaactg  1080
gggccgtatg agttcatctg tacgggtcgc ccggacgaag gcatcccggc ggtttgcttc  1140
aaactgaaag atggtgaaga tccgggatac accctgtatg acctctctga acgtctgcgt  1200
ctgcgcggct ggcaggttcc ggccttcact ctcggcggtg aagccaccga catcgtggtg  1260
atgcgcatta tgtgtcgtcg cggcttcgaa atggactttg ctgaactgtt gctggaagac  1320
tacaaagcct ccctgaaata tctcagcgat cactaa                           1356

SEQ ID NO: 205          moltype = DNA  length = 1509
FEATURE                 Location/Qualifiers
source                  1..1509
                        mol_type = genomic DNA
                        organism = Escherichia coli
SEQUENCE: 205
atggctatta gcacaccgat gttggtgaca ttttgtgtct atatctttgg catgatattg  60
attgggttta tcgcctggcg atcaacgaaa aactttgacg actatattct gggcggtcgt  120
agtcttgggc cattcgtgac ggcattatcg gcgggtgcgt cggatatgag cggctggctg  180
ttaatggggt tgccgggcgc tgtttttctt tccgggattt ccgaaagctg gatcgccatt  240
ggcctgacat taggcgcgtg gattaactgg aagctggtgg ccgggcggtt gcgtgtgcat  300
accgaataca acaataacgc cttaacactg ccggattatt tcaccgggcg ctttgaagat  360
aaaagccgca ttttgcgcat tatctctgcg ctggttattt tgctgttctt caccatttat  420
tgcgcttcgg gcattgtggc aggcgcgcgt ctgtttgaaa gtacctttgg catgagctac  480
gaaacggctc tgtgggcggg cgctgcggcg acgatccttt acacctttat tggcggtttc  540
ctcgcggtga gctggactga cactgtacag gccagcctga tgatttttgc cctgatcctg  600
acgccggtta tcgtcattat cagtgtcggt ggctttggtg actcgctgga agtgatcaaa  660
caaaagagca tcgaaaacgt tgatatgctc aaaggtctga actttgttgc cattatctca  720
ctgatgggtt gggggctggg ttacttcggg cagccgcaca ttctggcgcg ttttatggcg  780
gcggattctc accacagcat tgtccatgcg cgtcgtatta gtatgacctg gatgatcctc  840
tgcctggcag ggcggtggc tgtcggcttc tttgggattg cttactttaa cgatcatccg  900
gcgttggctg gtgcggtaaa tcagaacgcc gagcgtgtgt ttatcgaact ggcgcaaatt  960
ctgtttaacc cgtggattgc cgggattctg ctgtcggcaa ttctggcggc ggtaatgtca  1020
accttaagtt gccagctgct ggtgtgctcc agtgcgatta ccgaagattt gtacaaagcg  1080
tttctgcgta aacatgccag ccagaaagag ctggtgtggg tagggcgtgt gatggtgctg  1140
gtggtggcgc tggtggcgat tgcgctggcg gcaaacccgg aaaaccgcgt gctgggctta  1200
gtgagctacg cgtgggcagg ctttggcgcg gcgtttggtc cagtggtgct gttctcggtg  1260
atgtggtcac gcatgacgcg taacggtgcg ctggcgggga tgatcatcgg tgcgctgacg  1320
gttatcgtct ggaaacagtt cggctggctg ggactgtacg aaattattcc gggctttatc  1380
ttcggcagta ttgggattgt agtgtttagt ttgctgggta aagcgccgtc agcggcgatg  1440
caaaaacgct ttgccgaggc cgatgcgcac tatcattcgg ctccgccgtc acggttgcag  1500
gaaagctaa                                                         1509

SEQ ID NO: 206          moltype = DNA  length = 450
FEATURE                 Location/Qualifiers
source                  1..450
                        mol_type = genomic DNA
                        organism = Aromatoleum aromaticum
SEQUENCE: 206
atgagtgaag cggtccgcga cttttcgcag tgctacggtc acgatttcga ggacctgaaa  60
gttggtatgt cagcggccat cgggcgcacc gtgacggagg cggatatcgc tattttcgct  120
ggcatttcgg gtgatacgaa tcccgttcac ctcgatgccg aatttgcggc gtcgacgatg  180
tttggcgaac gaatcgctca tgggatgctg tcggcgagct tcatttctgc agtgttcggt  240
acgaagctgc caggaccggg atgcatctat ctcgggcagt cgctgaactt caaggcctca  300
gtgaaagtcg gcgaaacggt cgtcgcccgt gtgacagtac gcgagctcgt ggctcacaag  360
cgcccgggcgt tctttgatac tgtctgtacg gtggccggaa aagtggtact cgaaggccat  420
gcggagatct accttcccgc caggcaataa                                  450

SEQ ID NO: 207          moltype = DNA  length = 1401
FEATURE                 Location/Qualifiers
source                  1..1401
                        mol_type = genomic DNA
                        organism = Escherichia coli
SEQUENCE: 207
atgtttattc cctccattta cttacaccag cagttacatt attgtaagac agcaattctc  60
aactggagcc gaaaaatggc gctttcaaga caaaaattta ccttcgaaag acttcgcaga  120
ttcaccttac cggaagggaa aaaacaaact tttctttggg atgcagatgt aacaaccctg  180
gcatgccgag caactagcgg agcaaaagcc tttgtattcc aaagcgtata tgcggggaaa  240
acccttcgca tgactattgg caacattaac gactggaaga ttgatgatgc gagagccgag  300
gcaagacggt tacaaacatt gatcgataca gggatagatc cacgaattgc taaggctgta  360
aaaatcgcag aagcagaatc cctgcaggca gaatcacgta aacaaaagt gactttctcc  420
gtcgcctggg aagactatct tcaagaattg agaaccggta tcagtgcaaa aactaaacgc  480
ccatattcta ctcgatacat tgccgatcac attaacttgt ccagtcgtgg aggcgaaagt  540
aaaaaaagag gccaaggccc gacttcggct ggaccattgg ctagtttgct caacctgccg  600
ttatcggagc taaccccaga ttacatagca gcgtggctga gtacagaaag gcaaaataga  660
cctaccgtca ctgctcacgc ttatcgccta ctacgtgctt tcatcaaatg gagtaattat  720
```

```
cagaaaaaat atcaagggat cattcctggc gatctggcac aagattacaa cgtaagaaaa  780
atggttcccg tgtcagcgag taaagctgat gattgcctgc aaaaggaaca actaaaaagc  840
tggtttagtg ccgtgcgtag cctcaataat cctattgcat cggcctatct ccaagtactt  900
ttgctcactg gtgctcggcg tgaagaaatt gcgtcgcttc gctggtcaga cgtagatttc  960
aaatggtcaa gcatgcgaat taaagacaag atcgaaggtg aacgtatcat ccctctcact  1020
ccttatgttt ctgaattgtt aaatgtacta gcgcaatccc caaattctga cgtaaataag  1080
gagggttggg ttttcagaag taacagtaaa agtggcaaaa ttattgagcc gcgttcagcg  1140
cacaacagag cattagtgct ggctgagtta ccacatatca gccttcacgg tttacgtcgt  1200
agttttggta ctttggccga gtgggttgaa gttcccactg gtattgttgc tcaaattatg  1260
ggacacaaac ccagcgctct tgccgaaaaa cactatcgcc gtcgtccgtt agatctgtta  1320
cgaaaatggc acgagaaaat tgagacatgg atcttaaatg aagcaggtat taccataaaa  1380
aacaacgttg atatgcgttg a                                            1401

SEQ ID NO: 208          moltype = DNA  length = 2619
FEATURE                 Location/Qualifiers
source                  1..2619
                        mol_type = genomic DNA
                        organism = Escherichia coli
SEQUENCE: 208
atgagtatcc tgacccggtg gttgcttatc ccgccggtca acgcgcggct tatcgggcgt  60
tatcgcgatt atcgtcgtca cggtgcgtcg gctttcagcg cgacgctcgg ctgtttctgg  120
atgatcctgg cctggatttt tattccgctg gagcacccgc gctggcagcg tattcgcgca  180
gaacataaaa acctgtatcc gcatatcaac gcctcgcgtc cgcgtccgct ggacccggtc  240
cgttatctca ttcaaacatg ctggttattg atcggtgcat cgcgcaaaga aacgccgaaa  300
ccgcgcaggc gggcattttc aggtctgcaa aatattcgtg gacgttacca tcaatggatg  360
aacgagctgc ctgagcgcgt tagccataaa acacagcatc tggatgagaa aaaagagctc  420
ggtcatttga gtgccggggc gcggcggttg atcctcggta tcatcgtcac cttctcgctg  480
attctggcgt taatctgcgt tactcagccg tttaacccgc tggcgcagtt tatcttcctg  540
atgctgctgt ggggggtagc gctgatcgta cggcggatgc cggggcgctt ctcggcgcta  600
atgttgattg tgctgtcgct gaccgtttct tgccgttata tctggtggcg ttacacctct  660
acgctgaact gggacgatcc ggtcagcctg gtgtgcgggc ttattctgct cttcgctgaa  720
acgtacgcgt ggattgtgct ggtgctcggc tacttccagg tagtatggcc gctgaatcgt  780
cagccggtgc cattgccgaa agatatgtcg ctgtggccgt cggtggatat ctttgtcccg  840
acttacaacg aagatctcaa cgtggtgaaa aataccattt acgcctcgct gggtatcgac  900
tggccgaaag ataagctgaa tatctggatc cttgatgacg gcggcaggga agagtttcgc  960
cagtttgcgc aaaacgtggg ggtgaaatat atcgcccgca ccactcatga acatgcgaaa  1020
gcaggcaaca tcaacaatgc gctgaaatat gccaaaggcg agttcgtgtc gattttcgac  1080
tgcgaccacg taccaacgcg atcgttcttg caaatgacca tgggctggtt cctgaaagaa  1140
aaacagctgg cgatgatgca gacgccgcac cacttcttct caccggaccc gtttgaacgc  1200
aacctggggc gtttccgtaa aacgccgaac gaaggcacgc tgttctatgg tctggtgcag  1260
gatggcaacg atatgtggga cgccactttc ttctgcggtt cctgtgcggt gattcgtcgt  1320
aagccgctgg atgaaattgg cggcattgct gtcgaaaccg tgactgaaga tgcgcatact  1380
tctctgcggt tgcaccgtcg tggctatacc tccgcgtata tgcgtattcc gcaggcggcg  1440
gggctggcga ccgaaagtct gtcggcgcat atcggtcagc gtattcgctg ggcgcgcggg  1500
atggtacaaa tcttccgtct cgataacccg ctcaccggta aagggctgaa gtttgctcag  1560
cggctatgtt acgtcaacgc catgttccac ttcttgtcgg gcattccacg gctgatcttc  1620
ctgactgcgc cgctggcgtt cctgctgctt catgcctaca tcatctatgc gccagcgttg  1680
atgatcgccc tattcgtgct gccgcatatg atccatgcca gcctgaccaa ctccaagatc  1740
cagggcaaat atcgccactc tttctggagt gaaatctacg aaacggtgct ggcgtggtat  1800
atcgcaccac cgacgctggt ggcgctgatt aacccgcaca aaggcaaatt taacgtcacc  1860
gccaaaggtg gactggtgga agaagagtac gtcgactggg tgatctcgcg gccctacatc  1920
ttccttgtcc tgctcaacct ggtgggcgtt gcggtaggca tctggcgcta cttctatggc  1980
ccgccaaccg agatgctcac cgtggtcgtc agtatggtgt gggtgttcta caacctgatt  2040
gttcttggcg gcgcagttgc ggtatcggta gaaagcaaac aggtacgccg atcgcaccgc  2100
gtggagatga cgatgcccgc ggcaattgcc cgcgaagatg gtcacctctt ctcgtgtacc  2160
gttcaggatt tctccgacgg tggtttgggg atcaagatca acggtcaggc gcagattctg  2220
gaagggcaga aagtgaatct gttgcttaaa cgcggtcagc aggaatacgt cttcccgacc  2280
caggtggcgc gcgtgatggg taatgaagtt gggctgaaat taatgccgct caccacccag  2340
caacatatcg attttgtgca gtgtacgttt gcccgtgcgg atacatgggc gctctggcag  2400
gacagctacc cggaagataa gccgctggaa agtctgctgg atattctgaa gctcggcttc  2460
cgtggctacc gccatctggc ggagtttgcg ccttcttcgg tgaagggcat attccgtgtg  2520
ctgacttctc tggtttcctg ggttgtatcg tttattccgc gccgcccgga gcggagcgaa  2580
acggcacaac catcggatca ggctttggct caacaatga                         2619

SEQ ID NO: 209          moltype = DNA  length = 3474
FEATURE                 Location/Qualifiers
source                  1..3474
                        mol_type = genomic DNA
                        organism = Escherichia coli
SEQUENCE: 209
atgcgcaaat tcacactaaa catattcacg ctttccctcg gtctggccgt catgccgatg  60
gtcgaggcag caccaaccgc tcagcaacag ttgctggagc aagttcggtt aggcgaagcg  120
acccatcgtg aagatctggt gcaacagtcg ttatatcggc tggaacttat tgatccgaat  180
aacccggacg tcgttgccgc ccgtttccgt tctttgttac gtcagggcga tattgatggc  240
gcgcaaaaac agctcgatcg gctgtcgcag ttagcgccga gttcaaatgc gtataaatcg  300
tcgcggacta cgatgctact ttccacgccg gatggtcgtc aggcactgca acaggcacga  360
ttgcaggcga cgaccggtca tgcagaagaa gctgtggcga gttacaacaa actgttcaac  420
ggtgcgccgc cggaaggtga cattgctgtc gagtactgga gtacggtggc gaaaattccg  480
gctcgccgtg gcgaagcgat taatcagtta aaacgcatca atgcggatgc accgggcaat  540
```

```
acgggcctgc aaaacaatct ggcgctattg ctgtttagta gcgatcgccg tgacgaaggt  600
tttgccgtcc tggaacagat ggcaaaatcg aacgccgggc gcgaaggggc ctctaaaatc  660
tggtacgggc agattaaaga catgcccgtc agtgatgcca gtgtgtcggc gctgaaaaaa  720
tatctctcga tctttagtga tggcgatagc gtggcggctg cgcaatcgca actggcagaa  780
cagcaaaaac agctggccga tcctgctttc cgcgctcgtg cgcaaggttt agcggcggtg  840
gactctggta tggcgggtaa agccattccc gaactacaac aggcggtgcg ggcgaacccg  900
aaagacagtg aagctctggg ggcgctgggc caggcgtatt ctcagaaagg cgatcgcgcc  960
aatgcagtgg cgaatctgga aaaagccctc gcactggacc cgcacagcag caacaacgac  1020
aaatggaaca gtctgctgaa agtaaaccgc tactggctgg cgatccagca gggcgatgct  1080
gcgctgaaag ccaataatcc tgaccgggca gaacgcctgt tccagcaggc gcgtaatgtc  1140
gataacaccg acagttatgc agtgctgggg ctgggcgatg tggcgatggc gcgaaaagat  1200
tatcccgccg ccgaacgtta ttatcagcag accttgcgta tggacagcgg caacactaac  1260
gccgtgcgcg ggctggcaaa tatttaccgc cagcaatcgc cagaaaaagc tgaagcgttt  1320
atcgcctcgc tctctgccag tcagcggcgt agcattgatg atatcgaacg cagcctgcaa  1380
aacgaccgtc tggcacagca ggcagaggca ctggaaaacc agggcaaatg ggcgcaggcg  1440
gcagcacttc agcggcaacg actggcgctg gaccccggca gcgtatggat tacttaccga  1500
ctttcgcagg atctctggca ggccggacaa cgcagccagg ccgatacgtt aatgcgcaat  1560
ctggcgcagc agaagtcgaa cgacccggag caggtttacg cttacgggct gtacctctct  1620
ggtcatgacc aggacagagc ggcgctggcg catatcaata gcctgccgcg tgcgcagtgg  1680
aacagcaata ttcaggagct ggttaatcga ctgcaaagcg atcaggtgct ggaaaccgct  1740
aaccgcctgc gagaaagcgg caaagaggca gaagcggaag cgatgctgcg ccagcaacca  1800
ccttccacgc gtattgacct cacgctggct gactgggcgc aacaacgacg tgattacacc  1860
gccgcccgcg ctgcatatca gaatgtcctg acgcgggagc cagctaacgc cgacgccatt  1920
cttggtctga cggaagtgga tattgctgcc ggtgacaaag cggcggcacg tagccagctg  1980
gcgaaactgc ccgctaccga taacgcctcg ctgaacacac agcggcgcgt ggcgctggca  2040
caggcgcagc ttggcgatac cgcagcagcg cagcggacgt ttaataagtt gatcccgcag  2100
gcaaaatctc agccaccgtc gatggaaagc gcgatggtgc tgcgtgatgg tgcgaagttt  2160
gaagcgcagg cgggcgatcc aacgcaggcg ctggaaacct acaaagacgc catggtcgca  2220
tccggtgtga ctacgacgcg tccgcaggat aacgacacct ttacccgact gacccgtaac  2280
gacgagaaag atgactggct gaaacgtggc gtgcgcagcg atgcggcgga cctctatcgc  2340
cagcaggatc ttaacgtcac ccttgagcac gattactggg gttcgagcgg caccggtggt  2400
tactccgatc tgaaagcgca cactaccatg ttgcaggtgg atgcgccgta ttctgacggg  2460
cggatgttct ttcgcagtga tttcgtcaat atgaacgtcg gcagtttctc cactaatgcc  2520
gatggcaaat gggatgacaa ctggggcacc tgtacattac aggactgtag cggcaaccgc  2580
agccagtcgg attccggtgc cagcgtggcg gtcggctggc gaaatgacgt ctggagctgg  2640
gatatcggta ccacgccgat gggcttcaac gtggtggatg tggtcggcgg catcagttac  2700
agcgatgata tcgggccgct gggttacacc gttaacgccc accgtcggcc catctccagt  2760
tctttgctgg cctttggtgg gcaaaaagac tccccgagca ataccgggaa aaaatggggt  2820
ggcgtacgtg ccgacggtgt ggggctaagt ctgagctacg ataaaggtga agcaaacggc  2880
gtctgggcat cgcttagtgg cgaccagtta accggtaaaa atgtcgaaga taactggcgc  2940
gtgcgctgga tgacgggcta ttactataag gtcattaacc agaacaatcg ccgcgtcaca  3000
atcggcctga acaacatgat ctggcattac gacaaagatc tgagtggcta ctcactcggt  3060
cagggcggtt actacagtcc gcaggaatac ctgtcgtttg ccataccggt gatgtggcgg  3120
gagcgcacgg aaaactggtc gtgggagctg ggtgcgtctg gctcgtggtc gcattcacgc  3180
accaaaacca tgccgcgtta tccgctgatg aatctgatcc cgaccgactg gcaggaagaa  3240
gctgcgcggc aatccaacga tggcggcagc agtcagggct tcggctacac ggcgcgggca  3300
ttacttgaac gacgtgttac ttccaactgg tttgttggca cggcaattga tatccagcag  3360
gcgaaagatt acgcacccag ccatttcctg ctctacgtac gttattccgc cgcccggatgg  3420
cagggtgaca tggatttacc gccgcagccg ctgatacctt acgccgactg gtaa        3474
```

```
SEQ ID NO: 210         moltype = DNA  length = 1536
FEATURE                Location/Qualifiers
source                 1..1536
                       mol_type = genomic DNA
                       organism = Escherichia coli
SEQUENCE: 210
atggctacat cagtacagac aggtaaagct aagcagctca cattacttgg attctttgcc  60
ataacggcat cgatggtaat ggctgtttat gaatacccta ccttcgcaac atcgggcttt  120
tcattagtct tcttcctgct attaggcggg attttatggt ttattcccgt gggactttgt  180
gctgcggaaa tggccaccgt cgacggctgg gaagaaggtg gtgtcttcgc ctgggtatca  240
aatactctgg ggccgagatg gggatttgca gcgatctcat ttggctatct gcaaatcgcc  300
attggtttta ttccgatgct ctatttcgtg ttaggggcac tctcctacat cctgaaatgg  360
ccagcgctga atgaagaccc cattaccaaa actattgcag cactcatcat tctttgggcg  420
ctggcattaa cgcagtttgg tggcacgaaa tacacggcgc gaattgctaa agttggcttc  480
ttcgccggta tcctgttacc tgcatttatt ttgatcgcat tagcggctat ttatctgcac  540
tccggtgccc ccgttgctat cgaaatggat tcgaagacct tcttccctga cttctctaaa  600
gtgggcaccc tggtagtatt tgttgccttc attttgagtt atatgggcgt agaagcatcc  660
gcaacccacg tcaatgaaat gagcaaccca gggcgcgact atccgttggc tatgttactg  720
ctgatggtgg cggcaatctg cttaagctct gttggtggtt tgtctattgc gatggtcatt  780
ccgggtaatg aaatcaacct ctccgcaggg gtaatgcaaa cctttaccgt tctgatgtcc  840
catgtggcac cagaaattga gtggacggtt cgcgtgatct ccgcactgct gttgctgggt  900
gttctggcgg aaatcgcctc ctggattgtt ggtccttctc gcgggatgta tgtaacagcg  960
cagaaaaacc tgctgccagc ggcattcgct aaaatgaaca aaaatggcgt accggtaacg  1020
ctggtcattt cgcagctggt gattacgtct atcgcgttga tcatcctcac caataccggt  1080
ggcggtaaca acatgtcctt cctgatcgca ctggcgctga cggtggtgat ttatctgtgt  1140
gcttatttca tgctgtttat tggctacatt gtgttggttc ttaaacatcc tgacttaaaa  1200
cgcacattta atatccctgg tggtaaaggg gtgaaactgg tcgtggcaat tgtcggtctg  1260
ctgacttcaa ttatggcgtt tattgtttcc ttcctgccgc cggataacat ccagggtgat  1320
tctaccgata tgtatgttga attactggtt gttagtttcc tggtggtact tgccctgccc  1380
```

-continued

```
tttattctct atgctgttca tgatcgtaaa ggcaaagcaa ataccggcgt cactctggag  1440
ccaatcaaca gtcagaacgc accaaaaggt cacttcttcc tgcacccgcg tgcacgttca  1500
ccacactata ttgtgatgaa tgacaagaaa cactaa                            1536

SEQ ID NO: 211         moltype = DNA  length = 720
FEATURE                Location/Qualifiers
source                 1..720
                       mol_type = genomic DNA
                       organism = Escherichia coli
SEQUENCE: 211
atggtcatta aggcgcaaag cccggcgggt ttcgcggaag agtacattat tgaaagtatc  60
tggaataacc gcttccctcc cgggactatt ttgcccgcag aacgtgaact ttcagaatta  120
attggcgtaa cgcgtactac gttacgtgaa gtgttacagc gtctggcacg agatggctgg  180
ttgaccattc aacatggcaa gccgacgaag gtgaataatt tctgggaaac ttccggttta  240
aatatccttg aaacactggc gcgactggat cacgaaagtg tgccgcagct tattgataat  300
ttgctgtcgg tgcgtaccaa tatttccact atttttattc gcaccgcgtt tcgtcagcat  360
cccgataaag cgcaggaagt gctggctacc gctaatgaag tggccgatca cgccgatgcc  420
tttgccgagc tggattacaa catattccgc ggcctggcgt ttgcttccgg caacccgatt  480
tacggtctga ttcttaacgg gatgaaaggg ctgtatacgc gtattggtcg tcactatttc  540
gccaatccgg aagcgcgcag tctggcgctg ggcttctacc acaaactgtc ggcgttgtgc  600
agtgaaggcg cgcacgatca ggtgtacgaa acagtgcgtc gctatgggca tgagagtggc  660
gagatttggc accggatgca gaaaaatctg ccgggtgatt tagccattca ggggcgataa  720

SEQ ID NO: 212         moltype = DNA  length = 1164
FEATURE                Location/Qualifiers
source                 1..1164
                       mol_type = genomic DNA
                       organism = Escherichia coli
SEQUENCE: 212
atgaacaact ttaatctgca caccccaacc cgcattctgt ttggtaaagg cgcaatcgct  60
ggtttacgcg aacaaattcc tcacgatgct cgcgtattga ttacctacgg cggcggcagc  120
gtgaaaaaaa ccggcgttct cgatcaagtt ctggatgccc tgaaaggcat ggacgtgctg  180
gaatttggcg gtattgagcc aaacccggct tatgaaacgc tgatgaacgc cgtgaaactg  240
gttcgcgaac agaaagtgac tttcctgctg gcggttggcg gcggttctgt actggacggc  300
accaaattta tcgccgcagc ggctaactat ccggaaaata tcgatccgtg gcacattctg  360
caaacgggcg gtaaagagat taaaagcgcc atcccgatgg gctgtgtgct gacgctgcca  420
gcaaccggtt cagaatccaa cgcaggcgcg gtgatctccc gtaaaaccac aggcgacaag  480
caggcgttcc attctgccca tgttcagccg gtatttgccg tgctcgatcc ggtttatacc  540
tacaccctgc cgccgcgtca ggtggctaac ggcgtagtgg acgcctttgt acacaccgtg  600
gaacagtatg ttaccaaacc ggttgatgcc aaaattcagg accgtttcgc agaaggcatt  660
ttgctgacgc taatcgaaga tggtccgaaa gccctgaaag agccagaaaa ctacgatgtg  720
cgcgccaacg tcatgtgggc ggcgactcag gcgctgaacg gtttgattgg cgctggcgta  780
ccgcaggact gggcaacgca tatgctgggc cacgaactga ctgcgatgca cggtctggat  840
cacgcgcaaa cactggctat cgtcctgcct gcactgtgga atgaaaaacg cgataccaag  900
cgcgctaagc tgctgcaata tgctgaacgc gtctggaaca tcactgaagg ttccgatgat  960
gagcgtattg acgccgcgat tgccgcaacc cgcaatttct ttgagcaatt aggcgtgccg  1020
acccacctct ccgactacgg tctggacggc agctccatcc cggctttgct gaaaaaactg  1080
gaagagcacg gcatgaccca actgggcgaa aatcatgaca ttacgttgga tgtcagccgc  1140
cgtatatacg aagccgcccg ctaa                                          1164

SEQ ID NO: 213         moltype = DNA  length = 1386
FEATURE                Location/Qualifiers
source                 1..1386
                       mol_type = genomic DNA
                       organism = Escherichia coli
SEQUENCE: 213
atgactgcta ttaatcgcat ccttattgtg gatgatgaag ataatgttcg ccgtatgctg  60
agcaccgctt ttgcactaca aggattcgaa acacattgtg cgaacaacgg acgcacagca  120
ttacacctgt ttgccgatat tcaccctgat gtggtgttga tggatatccg catgccagag  180
atggacggca tcaaggcact aaaggagatg cgcagccatg agacccggac acccgttatt  240
ctgatgacgg cctatgcgga agtggaaacc gccgtcgaag cgctacgctg cggagccttc  300
gactatgtta ttaaaccgtt tgatctcgat gagttgaatt taatcgttca gcgcgcttta  360
caactccagt caatgaaaaa agaatcgcgt catctgcacc aggcactgag caccagctgg  420
caatgggggc acattctcac caacagcccg gcgatgatgg acatctgcaa agacaccgcc  480
aaaattgccc tttctcaggc cagcgtcttg attagcggtg aaagcggcac cgggaaagag  540
ttgattgcca gagcgattca ctacaattcg cggcgggcaa aggggccgtt cattaaagtc  600
aactgcgcgg cgctgccgga atcgttgctc gaaagtgaac tgtttggtca tgaaaaaggt  660
gcatttactg gtgcacaaac cttgcgtcag ggattatttg aacgagccaa cgaaggtact  720
ctgctcctcg acgaaattgg cgaaatgccg ctggtactac aagccaaatt actacgcatt  780
ctacaggaac gggaatttga acggattggc ggccatcaga ccataaaagt tgatatccgc  840
atcattgctg ccaccaaccg cgacttgcag gcaatggtaa aagaaggcac cttccgtgaa  900
gatctctttt atcgccttaa cgttattcat ttaatactgc cgcctctgcg cgatcgccgg  960
gaagatattt ccctgttagc taatcacttt ttgcaaaaat tcagtagtga gaatcagcgc  1020
gatattatcg acatcgatcc gatggcaatg tcactgctta ccgcctggtc atggccggga  1080
aatattcgag agctttccaa cgttattgaa cgcgccgtcg tgatgaattc aggcccgatc  1140
attttttctg aggatcttcc gccacagatt cgtcagccag tctgtaatgc tggcgaggta  1200
aaaacagccc ctgtcggtga gcgtaattta aaagaggaaa ttaaacgcgt cgaaaaacgc  1260
atcattatgg aagtgctgga acaacaagaa ggaaaccgaa cccgcactgc tttaatgctg  1320
ggcatcagtc gccgtgcatt gatgtataaa ctccaggaat acggtatcga tccggcggat  1380
```

-continued

```
gtataa                                                           1386

SEQ ID NO: 214          moltype = DNA  length = 121
FEATURE                 Location/Qualifiers
source                  1..121
                        mol_type = genomic DNA
                        organism = Escherichia coli
SEQUENCE: 214
gtgcggcctg aaaaacagtg ctgtgccctt gtaactcatc ataataattt acggcgcagc  60
caagatttcc ctggtgttgg cgcagtattc gcgcaccccg gtctagccgg ggtcattttt  120
t                                                                  121

SEQ ID NO: 215          moltype = AA  length = 447
FEATURE                 Location/Qualifiers
source                  1..447
                        mol_type = protein
                        organism = Escherichia coli
SEQUENCE: 215
MDQTYSLESF LNHVQKRDPN QTEFAQAVRE VMTTLWPFLE QNPKYRQMSL LERLVEPERV  60
IQFRVVWVDD RNQIQVNRAW RVQFSSAIGP YKGGMRFHPS VNLSILKFLG FEQTFKNALT  120
TLPMGGGKGG SDFDPKGKSE GEVMRFCQAL MTELYRHLGA DTDVPAGDIG VGGREVGFMA  180
GMMKKLSNNT ACVFTGKGLS FGGSLIRPEA TGYGLVYFTE AMLKRHGMGF EGMRVSVSGS  240
GNVAQYAIEK AMEFGARVIT ASDSSGTVVD ESGFTKEKLA RLIEIKASRD GRVADYAKEF  300
GLVYLEGQQP WSLPVDIALP CATQNELDVD AAHQLIANGV KAVAEGANMP TTIEATELFQ  360
QAGVLFAPGK AANAGGVATS GLEMAQNAAR LGWKAEKVDA RLHHIMLDIH HACVEHGGEG  420
EQTNYVQGAN IAGFVKVADA MLAQGVI                                      447

SEQ ID NO: 216          moltype = AA  length = 468
FEATURE                 Location/Qualifiers
source                  1..468
                        mol_type = protein
                        organism = Levilactobacillus brevis
SEQUENCE: 216
MAMLYGKHTH ETDETLIPIF GASAERHDLP KYKLAKHALE PREADRLVRD QLLDEGNSRL  60
NLATFCQTYM EPEAVELMKD TLEKNAIDKS EYPRTAEIEN RCVNIIANLW HAPEAESFTG  120
TSTIGSSEAC MLAGLAMKFA WRKRAKANGL DLTAHQPNIV ISAGYQVCWE KFCVYWDIDM  180
HVVPMDDDHM SLNVDHVLDY VDDYTIGIVG IMGITYTGQY DDLARLDAVV ERYNRTTKFP  240
VYIHVDAASG GFYTPFIEPE LKWDFRLNNV ISINASGHKY GLVYPGVGWV IWRGQQYLPK  300
ELVFKVSYLG GSLPTMAINF SHSASQLIGQ YYNFIRFGFD GYREIHEKTH DVARYLAKSL  360
TKLGGFSLIN DGHELPLICY ELTADSDREW TLYDLSDRLL MKGWQVPTYP LPKNMTDRVI  420
QRIVVRADFG MSMAHDFIDD LTQAIHDLDQ AHIVFHSDPQ PKKYGFTH              468

SEQ ID NO: 217          moltype = AA  length = 469
FEATURE                 Location/Qualifiers
source                  1..469
                        mol_type = protein
                        organism = Lactiplantibacillus plantarum
SEQUENCE: 217
MAMLYGKHNH EAEEYLEPVF GAPSEQHDLP KYRLPKHSLS PREADRLVRD ELLDEGNSRL  60
NLATFCQTYM EPEAVELMKD TLAKNAIDKS EYPRTAEIEN RCVNIIANLW HAPDDEHFTG  120
TSTIGSSEAC MLGGLAMKFA WRKRAQAAGL DLNAHRPNLV ISAGYQVCWE KFCVYWDVDM  180
HVVPMDEQHM ALDVNHVLDY VDEYTIGIVG IMGITYTGQY DDLAALDKVV THYNHQHPKL  240
PVYIHVDAAS GGFYTPFIEP QLIWDFRLAN VVSINASGHK YGLVYPGVGW VVWRDRQFLP  300
PELVFKVSYL GGELPTMAIN FSHSAAQLIG QYYNFIRFGM DGYREIQTKT HDVARYLAAA  360
LDKVGEFKMI NNGHQLPLIC YQLAPREDRE WTLYDLSDRL LMNGWQVPTY PLPANLEQQV  420
IQRIVVRADF GMNMAHDFMD DLTKAVHDLN HAHIVYHHDA APKKYGFTH              469

SEQ ID NO: 218          moltype = DNA  length = 1344
FEATURE                 Location/Qualifiers
source                  1..1344
                        mol_type = genomic DNA
                        organism = Escherichia coli
SEQUENCE: 218
atggatcaga catattctct ggagtcattc ctcaaccatg tccaaaagcg cgacccgaat  60
caaaccgagt tcgcgcaagc cgttcgtgaa gtaatgacca cactctggcc ttttcttgaa  120
caaaatccaa aatatcgcca gatgtcatta ctggagcgtc tggttgaacc ggagcgcgtg  180
atccagtttc gcgtggtatg ggttgatgat cgcaaccaga tacaggtcaa ccgtgcatgg  240
cgtgtgcagt tcagctctgc catcggcccg tacaaaggcg gtatgcgctt ccatccgtca  300
gttaaccttt ccattctcaa attcctcggc tttgaacaaa ccttcaaaaa tgccctgact  360
actctgccga tgggcggtgg taaaggcggc agcgatttcg atccgaaagg aaaaagcgaa  420
ggtgaagtga tgcgtttttg ccaggcgctg atgactgaac tgtatcgcca cctgggcgcg  480
gataccgacg ttccggcagg tgatatcggg gttggtggtc gtgaagtcgg ctttatggcg  540
gggatgatga aaaagctctc caacaatacc gcctgcgtct tcaccggtaa gggcctttca  600
tttggcggca gtcttattcg cccggaagct accggctacg gtctggttta tttcacagaa  660
gcaatgctaa aacgccacgg tatgggtttt gaagggatgc gcgtttccgt ttctggctcc  720
ggcaacgtcg cccagtacgc tatcgaaaaa gcgatggaat ttggtgctcg tgtgatcact  780
gcgtcagact ccagcggcac tgtagttgat gaaagcggat tcacgaaaga gaaactggca  840
cgtcttatcg aaatcaaagc cagccgcgat ggtcgagtgg cagattacgc caaagaattt  900
ggtctggtct atctcgaagg ccaacagccg tggtctctac cggttgatat cgccctgcct  960
```

```
tgcgccaccc agaatgaact ggatgttgac gccgcgcatc agcttatcgc taatggcgtt  1020
aaagccgtcg ccgaaggggc aaatatgccg accaccatcg aagcgactga actgttccag  1080
caggcaggcg tactatttgc accgggtaaa gcggctaatg ctggtggcgt cgctacatcg  1140
ggcctggaaa tggcacaaaa cgctgcgcgc ctgggctgga aagccgagaa agttgacgca  1200
cgtttgcatc acatcatgct ggatatccac catgcctgtg ttgagcatgg tggtgaaggt  1260
gagcaaacca actacgtgca gggcgcgaac attgccggtt ttgtgaaggt tgccgatgcg  1320
atgctggcgc agggtgtgat ttaa                                         1344

SEQ ID NO: 219          moltype = DNA  length = 1407
FEATURE                 Location/Qualifiers
source                  1..1407
                        mol_type = genomic DNA
                        organism = Levilactobacillus brevis
SEQUENCE: 219
atggctatgt tgtatggaaa acacacgcat gaaacagatg agacgctcat tccaatcttc  60
ggggccagcg ctgaacgcca cgacctcccc aaatataaat tggcaaagca cgcgctcgag  120
ccccgtgaag ccgatcgatt ggttcgcgat caactattgg atgaaggaaa ctcgcggctg  180
aatctcgcca cgttctgtca gacttacatg gaaccggaag cggttgaact catgaaagat  240
acactggaga aaaacgccat cgataaatcc gagtatcctc ggaccgctga aattgaaaat  300
cgttgcgtta atatcattgc caacctctgg catgctccag aagctgagtc gttcactggc  360
acctcgacga ttggttcctc cgaggcctgc atgctggccg gtttggcgat gaagtttgct  420
tggcgtaagc gcgccaaagc gaacggtctt gacttaactg cccatcaacc taatattgtc  480
atctcagccg gttatcaagt ttgttgggaa aaattctgtg tctattggga catcgacatg  540
catgtcgttc ccatggacga tgaccacatg tccttgaatg tcgatcacgt gttagattac  600
gtggatgact acaccattgg tatcgttggc attatgggca tcacttatac tggacaatac  660
gacgatttag cccgattaga tgccgttgta gagcggtaca atcggacgac taagttcccg  720
gtatatatcc atgtcgatgc cgcttccggc ggattttaca cgccgtttat tgaacccgag  780
ctcaagtggg acttccgttt aaacaacgtg atttccatca atgcctccgg ccacaaatat  840
ggcttggttt atcccggagt cggctgggta atctggcgtg gccaacagta tctaccaaaa  900
gagctggtct ttaaggtcag ctacttgggt ggtagcctac ctacgatggc catcaacttc  960
tcccacagtg cctcccaatt aatcggtcag tattacaact ttattcgctt tggttttgat  1020
ggctatcgtg aaattcatga aaaaactcac gacgttgccc gctatctcgc gaaatcgctc  1080
actaaattag gggcttttc cctcattaat gacggccacg agttaccgct gatctgttat  1140
gaactcactg ccgattctga tcgcgaatgg accctctacg atttatccga tcggttatta  1200
atgaagggct ggcaggttcc cacctatccc ttaccaaaaa acatgacgga ccgcgttatt  1260
caacggatcg tggttcgggc tgactttggt atgagtatgg cccacgactt tattgatgat  1320
ctaacccaag ccattcacga tctcgaccaa gcacacatcg ttttccatag tgatccgcaa  1380
cctaaaaaat acgggttcac gcactaa                                      1407

SEQ ID NO: 220          moltype = DNA  length = 1410
FEATURE                 Location/Qualifiers
source                  1..1410
                        mol_type = genomic DNA
                        organism = Lactiplantibacillus plantarum
SEQUENCE: 220
atggcaatgt tatacggtaa acacaatcat gaagctgaag aatacttgga accagtcttt  60
ggtgcgcctt ctgaacaaca tgatcttcct aagtatcggt taccaaagca ttcattatcc  120
cctcgagaag ccgatcgctt agttcgtgat gaattattag atgaaggcaa ttcacgactg  180
aacctggcaa ctttttgtca gacctatatg gaacccgaag ccgttgaatt gatgaaggat  240
acgctggcta agaatgccat cgacaaatct gagtaccccc gcacggccga gattgaaaat  300
cggtgtgtga acattattgc caatctgtgg cacgcacctg atgacgaaca ctttacgggt  360
acctctacga ttggctcctc tgaagcttgt atgttaggcg gtttagcaat gaaattcgcc  420
tggcgtaaac gcgctcaagc ggcaggttta gatctgaatg cccatcgacc taacctcgtt  480
atttcggctg gctatcaagt ttgctgggaa aagttttgtg tctactggga cgttgacatg  540
cacgtggtcc caatggatga gcaacacatg gcccttgacg ttaaccacgt cttagactac  600
gtggacgaat acacaattgg tatcgtcggt atcatgggca tcacttatac cggtcaatat  660
gacgacctag ccgcactcga taaggtcgtt actcactaca atcatcagca tcccaaatta  720
ccagtctaca ttcacgttga cgcagcgtca ggtggcttct ataccccatt tattgagccg  780
caactcatct gggacttccg gttggctaac gtcgtttcga tcaacgcctc cgggcacaag  840
tacggtttag tttatcccgg ggtcggctgg gtcgtttggc gtgatcgtca gtttttaccg  900
ccagaattag tcttcaaagt tagttattta ggtggggagt tgccgacaat ggcgatcaac  960
ttctcacata gtgcagccca gctcattgga caatactata atttcattcg ctttggtatg  1020
gacggttacc gcgagattca aacaaagact cacgatgttg cccgctacct ggcagccgct  1080
ctggataaag ttggtgagtt taagatgatc aataacggac accaactccc cctgatttgt  1140
taccaactag ccccgcgcga agatcgtgaa tggacccttt atgatttatc ggatcgccta  1200
ttaatgaacg gttggcaagt accaacgtat cctttacctg ctaatctgga acaacaagtc  1260
atccaacgaa tcgtcgttcg ggctgacttt ggcatgaata tggcccacga tttcatggat  1320
gacctgacca aggctgtcca tgacttaaac cacgcccaca ttgtctatca tcatgacgcg  1380
gcacctaaga aatacggatt cacacactga                                   1410

SEQ ID NO: 221          moltype = RNA  length = 87
FEATURE                 Location/Qualifiers
source                  1..87
                        mol_type = genomic RNA
                        organism = Escherichia coli
SEQUENCE: 221
aacacatcag atttcctggt gtaacgaatt ttttaagtgc ttcttgctta agcaagtttc  60
atcccgaccc cctcagggtc gggattt                                      87
```

-continued

```
SEQ ID NO: 222         moltype = RNA  length = 105
FEATURE                Location/Qualifiers
source                 1..105
                       mol_type = genomic RNA
                       organism = Escherichia coli
SEQUENCE: 222
acggttataa atcaacatat tgatttataa gcatggaaat cccctgagtg aaacaacgaa  60
ttgctgtgtg tagtctttgc ccatctccca cgatgggctt ttttt                  105

SEQ ID NO: 223         moltype = RNA  length = 121
FEATURE                Location/Qualifiers
source                 1..121
                       mol_type = genomic RNA
                       organism = Escherichia coli
SEQUENCE: 223
gtgcggcctg aaaaacagtg ctgtgccctt gtaactcatc ataataattt acggcgcagc  60
caagatttcc ctggtgttgg cgcagtattc gcgcaccccg gtctagccgg ggtcattttt  120
t                                                                  121

SEQ ID NO: 224         moltype = AA  length = 478
FEATURE                Location/Qualifiers
source                 1..478
                       mol_type = protein
                       organism = Levilactobacillus senmaizukei
SEQUENCE: 224
MSKNDQETQQ MLDAAQLEKT FLGSTAAGES LPKNTMPAGP MAPDVAVEMV DHFRLNEAKA  60
NQNLATFCTT EMEPQADQLM MRTLNTNAID KSEYPKTSAM ENYCVSMIAH LWGIPDEEKF  120
GDDFIGTSTV GSSEGCMLGG LALLHTWKHR AKAAGLDIDD LHAHKPNLVI MSGNQVVWEK  180
FCTYWNVDFR QVPINGDQVS LDLDHVMDYV DENTIGIIGI EGITYTGSVD DIQGLDKLVT  240
EYNKTAALPV RIHVDAAFGG LFAPFVDGFK PWDFRLDNVV SINVSGHKYG MVYPGLGWIV  300
WRKNSYDILP KEMRFSVPYL GSSVDSIAIN FSHSGAHINA QYYNFLRFGL AGYKAIMNNV  360
RKVSLKLTDE LRKFGIFDIL VDGKELPINC WKLSDNANVS WSLYDMEDAL AKYGWQVPAY  420
PLPKNREETI TSRIVVRPGM TMAIADDFID DLKLAIADLN HSFGDVKDVN DKNKTTVR    478

SEQ ID NO: 225         moltype = AA  length = 248
FEATURE                Location/Qualifiers
source                 1..248
                       mol_type = protein
                       organism = Halomonas sp.
SEQUENCE: 225
MANQAPVAWV TGGTGGIGTS ICHSLADAGY LVVAGYHNPE KAKTWLETQQ AAGYDNIALS  60
GVDLSDHNAC LEGAREIQEK YGPVSVLVNC AGITRDGTMK KMSYEQWHQV IDTNLNSVFN  120
TCRSVIEMML EQGYGRIINI SSINGRKGQF GQVNYAAAKA GMHGLTMSLA QETATKGITV  180
NTVSPGYIAT DMIMKIPEQV REAIRETIPV KRYGTPEEIG RLVTFLADKE SGFITGANID  240
INGGQFMG                                                           248

SEQ ID NO: 226         moltype = AA  length = 589
FEATURE                Location/Qualifiers
source                 1..589
                       mol_type = protein
                       organism = synthetic construct
SEQUENCE: 226
MATGKGAAAS TQEGKSQPFK VTPGPFDPAT WLEWSRQWQG TEGNGHAAAS GIPGLDALAG  60
VKIAPAQLGD IQQRYMKDFS ALWQAMAEGK AEATGPLHDR RFAGDAWRTN LPYRFAAAFY  120
LLNARALTEL ADAVEADAKT RQRIRFAISQ WVDAMSPANF LATNPEAQRL LIESGGESLR  180
AGVRNMMEDL TRGKISQTDE SAFEVGRNVA VTEGAVVFEN EYFQLLQYKP LTDKVHARPL  240
LMVPPCINKY YILDLQPESS LVRHVVEQGH TVFLVSWRNP DASMAGSTWD DYIEHAAIRA  300
IEVARDISGQ DKINVLGFCV GGTIVSTALA VLAARGEHPA ASVTLLTTLL DFADTGILDV  360
FVDEGHVQLR EATLGGGAGA PCALLRGLEL ANTFSFLRPN DLVWNYVVDN YLKGNTPVPS  420
DLLFWNGDAT NLPGPWYCWY LRHTYLQNEL KVPGKLTVCG VPVDLASIDV PTYIYGSRED  480
HIVPWTAAYA STALLANKLR FVLGASGHIA GVINPPAKNK RSHWTNDALP ESPQQWLAGA  540
IEHHGSWWPD WTAWLAGQAG AKRAAPANYG NARYRAIEPA PGRYVKAKA                589

SEQ ID NO: 227         moltype = DNA  length = 1437
FEATURE                Location/Qualifiers
source                 1..1437
                       mol_type = other DNA
                       organism = synthetic construct
SEQUENCE: 227
atgagcaaaa acgatcagga gacgcagcag atgctggatg cagcacagct ggaaaaaacg  60
tttctgggaa gcaccgcagc cggggaatcg cttcccaaaa atacaatgcc ggcaggccca  120
atggccccag atgtagccgt agaaatggtg gaccactttc gcctgaacga ggcaaaagcg  180
aatcagaatc tggcgacctt ttgtaccact gagatggaac cgcaagcgga tcaactgatg  240
atgcgtaccc tgaacaccaa cgccattgat aagtccgaat accccaaaac gtccgcaatg  300
gaaaattatt gtgtgagtat gattgcgcat ctgtggggca ttccggacga agagaagttc  360
ggcgatgatt tcattgggac ctcaaccgtt gggtcttctg aaggatgcat gttaggagga  420
cttgcattgc tgcatacctg gaaacatcgc gcgaaagcgg cgggccttga tatcgatgat  480
ctgcacgcgc acaaacccaa tttagtgatt atgagcggca atcaggtggt gtgggaaaag  540
ttctgcacgt actggaacgt cgattttcgc caagtcccga ttaatggcga tcaggtgtcg  600
```

```
ctggacctcg accatgtgat ggactacgtc gatgagaaca ccattggcat cattggcatt  660
gaagggatta cctatactgg ttccgtcgat gatatccagg gcctggataa actggtgacc  720
gagtacaata agactgctgc tttgccggtc cgcattcatg tggatgctgc ctttggtggt  780
ttgtttgccc cgtttgttga cggcttcaaa ccgtgggatt tccgcctcga taacgtggtt  840
agcattaatg tttcgggcca caaatatggc atggtgtatc cgggtttagg ctggattgta  900
tggcgtaaaa acagctacga catcctcccg aaggaaatgc gtttcagcgt tccttatctt  960
ggttcaagtg tcgattcaat cgccatcaat ttctcgcatt ctggtgcgca cattaacgcc  1020
cagtactaca acttcctgcg ctttggttta gcaggctata aagcgatcat gaacaatgta  1080
cgcaaagtgt cactgaaact gacagacgaa ttacgtaagt ttggcatctt tgacatcctc  1140
gtggatggta aagaattacc gatcaactgc tggaaactga gcgacaatgc caatgtaagt  1200
tggagtctgt acgacatgga agatgctctg gcgaaatatg gctggcaagt acctgcgtat  1260
ccacttccga aaaaccgtga agagactatt accagccgca ttgttgttcg tcctggtatg  1320
acaatggcca ttgccgatga cttcatcgat gacttgaagc tggcgattgc ggatttgaat  1380
catagctttg gtgatgttaa agatgttaac gacaagaaca aaacgacggt gcgttaa     1437
```

```
SEQ ID NO: 228          moltype = DNA  length = 747
FEATURE                 Location/Qualifiers
source                  1..747
                        mol_type = other DNA
                        organism = synthetic construct
SEQUENCE: 228
atggcgaatc aggctccggt cgcttgggtt accggaggta cgggcggaat tggcacgtcg  60
atctgccact cactggccga tgccggttat cttgtggtag cgggttatca taaccctgaa  120
aaagcaaaga cttggttaga aacgcagcag gccgccggtt acgataacat tgcgctgtcc  180
ggtgtggact taagcgacca caacgcctgt ttggaaggag cgcgtgagat ccaggaaaaa  240
tacggaccgg ttagcgtgct ggtgaactgt gcgggtatca cccgtgatgg caccatgaaa  300
aagatgtcct acgaacaatg gcatcaagtt attgacacca acttgaactc ggtgtttaat  360
acctgccgta gtgtaattga aatgatgctg gaacaaggct atggccgtat cattaatatt  420
agctcaatta acggccgcaa aggccagttt gggcaggtca attatgcggc agccaaagca  480
ggcatgcatg gcctgaccat gagtcttgcg caagaaacgg cgaccaaggg cattacagtt  540
aataccgtgt ctccgggcta tattgcaacg gatatgatta tgaaaattcc cgaacaggtc  600
cgcgaggcca tccgcgaaac tatcccagtg aaacgctacg gcaccccgga agagattggt  660
cgcctggtaa cttttctcgc ggataaagag agcgggttca ttacaggcgc aaatatcgat  720
atcaatggtg gccagttcat ggggtaa                                     747
```

```
SEQ ID NO: 229          moltype = DNA  length = 1770
FEATURE                 Location/Qualifiers
source                  1..1770
                        mol_type = genomic DNA
                        organism = Cupriavidus necator
SEQUENCE: 229
atggcgaccg gcaaaggcgc ggcagcttcc acgcaggaag gcaagtccca accattcaag  60
gtcacgccgg ggccattcga tccagccaca tggctggaat ggtcccgcca gtggcagggc  120
actgaaggca acggccacgc ggccgcgtcc ggcattccgg gcctggatgc gctggcaggc  180
gtcaagatcg cgccggcgca gctgggtgat atccagcagc gctacatgaa ggacttctca  240
gcgctgtggc aggccatggc cgagggcaag gccgaggcca ccggtccgct gcacgaccgg  300
cgcttcgccg gcgacgcatg gcgcaccaac ctcccatatc gcttcgctgc cgcgttctac  360
ctgctcaatg cgcgcgcctt gaccgagctg gccgatgccg tcgaggccga tgccaagacc  420
cgccagcgca tccgcttcgc gatctcgcaa tgggtcgatg cgatgtcgcc cgccaacttc  480
cttgccacca atcccgaggc gcagcgcctg ctgatcgagt cgggcggcga atcgctgcgt  540
gccggcgtgc gcaacatgat ggaagacctg acacgcggca agatctcgca gaccgacgag  600
agcgcgtttg aggtcggccg caatgtcgcg gtgaccgaag gcgccgtggt cttcgagaac  660
gagtacttcc agctgttgca gtacaagccg ctgaccgaca aggtgcacgc gcgcccgctg  720
ctgatggtgc cgccgtgcat caacaagtac tacatcctgg acctgcagcc ggagagctcg  780
ctggtgcgcc atgtggtgga gcagggacat acggtgtttc tggtgtcgtg gcgcaatccg  840
gacgccagca tggccggcag cacctgggac gactacatcg agcacgcggc catccgcgcc  900
atcgaagtcg cgcgcgacat cagcggccag gacaagatca acgtgctcgg cttctgcgtg  960
ggcggcacca ttgtctcgac cgcgctggcg gtgctggccg cgcgcggcga gcacccggcc  1020
gccagcgtca cgctgctgac cacgctgctg gactttgccg acacgggcat cctcgacgtc  1080
tttgtcgacg agggccatgt gcagttgcgc gaggccacgc tgggcggcgg cgccggcgcg  1140
ccgtgcgcgc tgctgcgcgg ccttgagctg gccaatacct tctcgttctt gcgcccgaac  1200
gacctggtgt ggaactacgt ggtcgacaac tacctgaagg gcaacacgcc ggtgccgagc  1260
gacctgctgt tctggaacgg cgacgccacc aacctgccgg ggccgtggta ctgctggtac  1320
ctgcgccaca cctacctgca gaacgagctc aaggtaccgg gcaagctgac cgtgtgcggc  1380
gtgccggtgg acctggccag catcgacgtg ccgacctata tctacggctc gcgcgaagac  1440
catatcgtgc cgtggaccgc ggcctatgcc tcgaccgcgc tgctggcgaa caagctgcgc  1500
ttcgtgctgg gtgcgtcggg ccatatcgcc ggtgtgatca acccgccggc caagaacaag  1560
cgcagccact ggactaacga tgcgctgccg gagtcgccgc agcaatggct ggccggcgcc  1620
atcgagcatc acggcagctg gtggccggac tggaccgcat ggctggccgg gcaggccggc  1680
gcgaaacgcg ccgcgcccgc caactatggc aatgcgcgct atcgcgcaat cgaacccgcg  1740
cctgggcgat acgtcaaagc caaggcatga                                  1770
```

```
SEQ ID NO: 230          moltype = AA  length = 589
FEATURE                 Location/Qualifiers
source                  1..589
                        mol_type = protein
                        organism = Cupriavidus necator
SEQUENCE: 230
MATDKGAAAS TQEGKSQPFK VTPGPFDPAT WLEWSRQWQG TEGNGHAAAS GIPGLDALAG  60
```

-continued

```
VKIAPAQLGD IQQRYMKDFS ALWQAMAEGK AEATGPLHDR RFAGDAWRTN LPYRFAAAFY  120
LLNARALTEL ADAVEADAKT RQRIRFAISQ WVDAMSPANF LATNPEAQRL LIESGGESLR  180
AGVRNMMEDL TRGKISQTDE SAFEVGRNVA VTEGAVVFEN EYFQLLQYKP LTDKVHARPL  240
LMVPPCINKY YILDLQPESS LVRHVVEQGH TVFLVSWRNP DASMAGSTWD DYIEHAAIRA  300
IEVARDISGQ DKINVLGFCV GGTIVSTALA VLAARGEHPA ASVTLLTTLL DFADTGILDV  360
FVDEGHVQLR EATLGGGAGA PCALLRGLEL ANTFSFLRPN DLVWNYVVDN YLKGNTPVPF  420
DLLFWNGDAT NLPGPWYCWY LRHTYLQNEL KVPGKLTVCG VPVDLASIDV PTYIYGSRED  480
HIVPWTAAYA STALLANKLR FVLGASGHIA GVINPPAKNK RSHWTNDALP ESPQQWLAGA  540
IEHHGSWWPD WTAWLAGQAG AKRAAPANYG NARYRAIEPA PGRYVKAKA              589

SEQ ID NO: 231         moltype = DNA  length = 1770
FEATURE                Location/Qualifiers
source                 1..1770
                       mol_type = genomic DNA
                       organism = Cupriavidus necator
SEQUENCE: 231
atggcgaccg ataaaggcgc ggcagcttcc acgcaggaag gcaagtccca accattcaag  60
gtcacgccgg ggccattcga tccagccaca tggctggaat ggtcccgcca gtggcagggc  120
actgaaggca acggccacgc ggccgcgtcc ggcattccgg gcctggatgc gctggcaggc  180
gtcaagatcg cgccggcgca gctgggtgat atccagcagc gctacatgaa ggacttctca  240
gcgctgtggc aggccatggc cgagggcaag gccgaggcca ccggtccgct gcacgaccgg  300
cgcttcgccg gcgacgcatg gcgcaccaac ctcccatatc gcttcgctgc cgcgttctac  360
ctgctcaatg cgcgcgcctt gaccgagctg gccgatgccg tcgaggccga tgccaagacc  420
cgccagcgca tccgcttcgc gatctcgcaa tgggtcgatg cgatgtcgcc cgccaacttc  480
cttgccacca atcccgaggc gcagcgcctg ctgatcgagt cgggcggcga atcgctgcgt  540
gccggcgtgc gcaacatgat ggaagacctg acacgcggca agatctcgca gaccgacgag  600
agcgcgtttg aggtcggccg caatgtcgcg gtgaccgaag gcgccgtggt cttcgagaac  660
gagtacttcc agctgttgca gtacaagccg ctgaccgaca aggtgcacgc gcgcccgctg  720
ctgatggtgc cgccgtgcat caacaagtac tacatcctgg acctgcagcc ggagagctcg  780
ctggtgcgcc atgtggtgga gcagggacat acggtgtttc tggtgtcgtg gcgcaatccg  840
gacgccagca tggccggcag cacctgggac gactacatcg agcacgcggc catccgcgcc  900
atcgaagtcg cgcgcgacat cagcggccag gacaagatca acgtgctcgg cttctgcgtg  960
ggcggcacca ttgtctcgac cgcgctggcg gtgctggccg cgcgcggcga gcacccggcc  1020
gccagcgtca cgctgctgac cacgctgctg gactttgccg acacgggcat cctcgacgtc  1080
tttgtcgacg agggccatgt gcagttgcgc gaggccacgc tgggcggcgg cgccggcgcg  1140
ccgtgcgcgc tgctgcgcgg ccttgagctg gccaatacct tctcgttctt gcgcccgaac  1200
gacctggtgt ggaactacgt ggtcgacaac tacctgaagg gcaacacgcc ggtgccgttc  1260
gacctgctgt tctggaacgg cgacgccacc aacctgccgg ggccgtggta ctgctggtac  1320
ctgcgccaca cctacctgca gaacgagctc aaggtaccgg gcaagctgac cgtgtgcggc  1380
gtgccggtgg acctggccag catcgacgtg ccgacctata tctacggctc gcgcgaagac  1440
catatcgtgc cgtggaccgc ggcctatgcc tcgaccgcgc tgctggcgaa caagctgcgc  1500
ttcgtgctgg gtgcgtcggg ccatatcgcc ggtgtgatca acccgccggc caagaacaag  1560
cgcagccact ggactaacga tgcgctgccg gagtcgccgc agcaatggct ggccggcgcc  1620
atcgagcatc acggcagctg gtggccggac tggaccgcat ggctggccgg gcaggccggc  1680
gcgaaacgcg ccgcgcccgc caactatggc aatgcgcgct atcgcgcaat cgaacccgcg  1740
cctgggcgat acgtcaaagc caaggcatga                                    1770

SEQ ID NO: 232         moltype = DNA  length = 202
FEATURE                Location/Qualifiers
source                 1..202
                       mol_type = other DNA
                       organism = synthetic construct
SEQUENCE: 232
tgcctgaacg agaagctatc accgcccagc ctaaacggat atcatcatcg ctcatccgaa  60
aagaatgatg gatcactaga aaatttttta aaaaatctct tgacattgga agggagatat  120
gttataataa gaattgcgga attgtgagcg gataacaatt tctagaaata attttgttta  180
actttaagaa ggagatatac at                                            202

SEQ ID NO: 233         moltype = DNA  length = 103
FEATURE                Location/Qualifiers
source                 1..103
                       mol_type = other DNA
                       organism = synthetic construct
SEQUENCE: 233
gaaaagaatg atggatcact agaaaatttt ttaaaaaatc tcttgacatt ggaagggaga  60
tatgttataa taagaattgc ggaattgtga gcggataaca att                    103

SEQ ID NO: 234         moltype = DNA  length = 17
FEATURE                Location/Qualifiers
source                 1..17
                       mol_type = other DNA
                       organism = synthetic construct
SEQUENCE: 234
ttaactttaa gaaggag                                                  17

SEQ ID NO: 235         moltype =   length =
SEQUENCE: 235
000
```

```
SEQ ID NO: 236          moltype = DNA  length = 18
FEATURE                 Location/Qualifiers
source                  1..18
                        mol_type = other DNA
                        organism = synthetic construct
SEQUENCE: 236
ttaactttaa aaaggagg                                                 18

SEQ ID NO: 237          moltype =   length =
SEQUENCE: 237
000

SEQ ID NO: 238          moltype = DNA  length = 28
FEATURE                 Location/Qualifiers
source                  1..28
                        mol_type = other DNA
                        organism = synthetic construct
SEQUENCE: 238
gcagcccgcc taatgagcgg gctttttt                                      28

SEQ ID NO: 239          moltype = DNA  length = 2195
FEATURE                 Location/Qualifiers
source                  1..2195
                        mol_type = other DNA
                        organism = synthetic construct
SEQUENCE: 239
tgcctgaacg agaagctatc accgcccagc ctaaacggat atcatcatcg ctcatccgaa  60
aagaatgatg gatcactaga aaattttta aaaaatctct tgacattgga agggagatat  120
gttataataa gaattgcgga attgtgagcg gataacaatt tctagaaata attttgttta  180
actttaagaa ggagatatac atatgacgcg tgaagtggta gtggtaagcg gtgtccgtac  240
cgcgatcggg acctttggcg gcagcctgaa ggatgtggca ccggcggagc tgggcgcact  300
ggtggtgcgc gaggcgctgg cgcgcgcgca ggtgtcgggc gacgatgtcg gccacgtggt  360
attcggcaac gtgatccaga ccgagccgcg cgacatgtat ctgggccgcg tcgcggccgt  420
caacggcggg gtgacgatca acgcccccgc gctgaccgtg aaccgcctgt gcggctcggg  480
cctgcaggcc attgtcagcg ccgcgcagac catcctgctg ggcgataccg acgtcgccat  540
cggcggcggc gcggaaagca tgagccgcgc accgtacctg gcgccggcag cgcgctgggg  600
cgcacgcatg ggcgacgccg gcctggtcga catgatgctg ggtgcgctgc acgatccctt  660
ccatcgcatc cacatgggcg tgaccgccga gaatgtcgcc aaggaatacg acatctcgcg  720
cgcgcagcag gacgaggccg cgctggaatc gcaccgccgc gcttcggcag cgatcaaggc  780
cggctacttc aaggaccaga tcgtcccggt ggtgagcaag ggccgcaagg gcgacgtgac  840
cttcgacacc gacgagcacg tgcgccatga cgccaccatc gacgacatga ccaagctcag  900
gccggtcttc gtcaaggaaa acggcacggt cacggccggc aatgcctcgg gcctgaacga  960
cgccgccgcc gcggtggtga tgatggagcg cgccgaagcc gagcgccgcg gcctgaagcc  1020
gctggcccgc ctggtgtcgt acggccatgc cggcgtggac ccgaaggcca tgggcatcgg  1080
cccggtgccg gcgacgaaga tcgcgctgga gcgcgccggc ctgcaggtgt cggacctgga  1140
cgtgatcgaa gccaacgaag cctttgccgc acaggcgtgc gccgtgacca aggcgctcgg  1200
tctggacccg gccaaggtta acccgaacgg ctcgggcatc tcgctgggcc acccgatcgg  1260
cgccaccggt gccctgatca cggtgaaggc gctgcatgag ctgaaccgcg tgcagggccg  1320
ctacgcgctg gtgacgatgt gcatcggcgg cgggcagggc attgccgcca tcttcgagcg  1380
tatctgagct agcattaact ttaaaaagga ggaagaattc atgactcagc gcattgcgta  1440
tgtgaccggc ggcatgggtg gtatcggaac cgccatttgc cagcggctgg ccaaggatgg  1500
ctttcgtgtg gtggccggtt gcggccccaa ctcgccgcgc cgcgaaaagt ggctggagca  1560
gcagaaggcc ctgggcttcg atttcattgc ctcggaaggc aatgtggctg actgggactc  1620
gaccaagacc gcattcgaca aggtcaagtc cgaggtcggc gaggttgatg tgctgatcaa  1680
caacgccggt atcacccgcg acgtggtgtt ccgcaagatg acccgcgccg actgggatgc  1740
ggtgatcgac accaacctga cctcgctgtt caacgtcacc aagcaggtga tcgacggcat  1800
ggccgaccgt ggctggggcc gcatcgtcaa catctcgtcg gtgaacgggc agaagggcca  1860
gttcggccag accaactact ccaccgccaa ggccggcctg catggcttca ccatggcact  1920
ggcgcaggaa gtggcgacca agggcgtgac cgtcaacacg gtctctccgg gctatatcgc  1980
caccgacatg gtcaaggcga tccgccagga cgtgctcgac aagatcgtcg cgacgatccc  2040
ggtcaagcgc ctgggcctgc cggaagagat cgcctcgatc tgcgcctggt tgtcgtcgga  2100
ggagtccggt ttctcgaccg gcgccgactt ctcgctcaac ggcggcctgc atatgggctg  2160
aaccggtgca gcccgcctaa tgagcgggct ttttt                              2195

SEQ ID NO: 240          moltype = DNA  length = 3221
FEATURE                 Location/Qualifiers
source                  1..3221
                        mol_type = other DNA
                        organism = synthetic construct
SEQUENCE: 240
tgcctgaacg agaagctatc accgcccagc ctaaacggat atcatcatcg ctcatccgaa  60
aagaatgatg gatcactaga aaattttta aaaaatctct tgacattgga agggagatat  120
gttataataa gaattgcgga attgtgagcg gataacaatt tctagaaata attttgttta  180
actttaagaa ggagatatac atatggcgac cggcaaaggc gcggcagctt ccacgcagga  240
aggcaagtcc caaccattca aggtcacgcc ggggccattc gatccagcca catggctgga  300
atggtcccgc cagtggcagg gcactgaagg caacggccac gcggccgcgt ccggcattcc  360
gggcctggat gcgctggcag gcgtcaagat cgcgccggcg cagctgggtg atatccagca  420
gcgctacatg aaggacttct cagcgctgtg gcaggccatg gccgagggca aggccgaggc  480
caccggtccg ctgcacgacc ggcgcttcgc cggcgacgca tggcgcacca acctcccata  540
```

-continued

```
tcgcttcgct gccgcgttct acctgctcaa tgcgcgcgcc ttgaccgagc tggccgatgc  600
cgtcgaggcc gatgccaaga cccgccagcg catccgcttc gcgatctcgc aatgggtcga  660
tgcgatgtcg cccgccaact tccttgccac caatcccgag gcgcagcgcc tgctgatcga  720
gtcgggcggc gaatcgctgc gtgccggcgt gcgcaacatg atggaagacc tgacacgcgg  780
caagatctcg cagaccgacg agagcgcgtt tgaggtcggc cgcaatgtcg cggtgaccga  840
aggcgccgtg gtcttcgaga acgagtactt ccagctgttg cagtacaagc cgctgaccga  900
caaggtgcac gcgcgcccgc tgctgatggt gccgccgtgc atcaacaagt actacatcct  960
ggacctgcag ccggagagct cgctggtgcg ccatgtggtg gagcagggac atacggtgtt  1020
tctggtgtcg tggcgcaatc cggacgccag catggccggc agcacctggg acgactacat  1080
cgagcacgcg gccatccgcg ccatcgaagt cgcgcgcgac atcagcggcc aggacaagat  1140
caacgtgctc ggcttctgcg tgggcggcac cattgtctcg accgcgctgg cggtgctggc  1200
cgcgcgcggc gagcacccgg ccgccagcgt cacgctgctg accacgctgc tggactttgc  1260
cgacacgggc atcctcgacg tctttgtcga cgagggccat gtgcagttgc gcgaggccac  1320
gctgggcggc ggcgccggcg cgccgtgcgc gctgctgcgc ggccttgagc tggccaatac  1380
cttctcgttc ttgcgcccga acgacctggt gtggaactac gtggtcgaca actacctgaa  1440
gggcaacacg ccggtgccgt tcgacctgct gttctggaac ggcgacgcca ccaacctgcc  1500
ggggccgtgg tactgctggt acctgcgcca cacctacctg cagaacgagc tcaaggtacc  1560
gggcaagctg accgtgtgcg gcgtgccggt ggacctggcc agcatcgacg tgccgaccta  1620
tatctacggc tcgcgcgaag accatatcgt gccgtggacc gcggcctatg cctcgaccgc  1680
gctgctggcg aacaagctgc gcttcgtgct gggtgcgtcg ggccatatcg ccggtgtgat  1740
caacccgccg gccaagaaca agcgcagcca tctggactaac gatgcgctgc cggagtcgcc  1800
gcagcaatgg ctggccggcg ccatcgagca tcacggcagc tggtggccgg actggaccgc  1860
atggctggcc gggcaggccg gcgcgaaacg cgccgcgccc gccaactatg gcaatgcgcg  1920
ctatcgcgca atcgaacccg cgcctgggcg atacgtcaaa gccaaggcat gagctagcat  1980
taactttaaa aaggaggata agataatgac tgacgttgtc atcgtatccg ccgcccgcac  2040
cgcggtcggc aagtttggcg gctcgctggc caagatcccg gcaccggaac tgggtgccgt  2100
ggtcatcaag gccgcgctgg agcgcgccgg cgtcaagccg gagcaggtga gcgaagtcat  2160
catgggccag gtgctgaccg ccggttcggg ccagaacccc gcacgccagg ccgcgatcaa  2220
ggccggcctg ccggcgatgg tgccggccat gaccatcaac aaggtgtgcg gctcgggcct  2280
gaaggccgtg atgctggccg ccaacgcgat catggcgggc gacgccgaga tcgtggtggc  2340
cggcggccag gaaaacatga gcgccgcccc gcacgtgctg ccgggctcgc gcgatggttt  2400
ccgcatgggc gatgccaagc tggtcgacac catgatcgtc gacggcctgt gggacgtgta  2460
caaccagtac cacatgggca tcaccgccga gaacgtggcc aaggaatacg gcatcacacg  2520
cgaggcgcag gatgagttcg ccgtcggctc gcagaacaag gccgaagccg cgcagaaggc  2580
cggcaagttt gacgaagaga tcgtcccggt gctgatcccg cagcgcaagg gcgacccggt  2640
ggccttcaag accgacgagt tcgtgcgcca gggcgccacg ctggacagca tgtccggcct  2700
caagcccgcc ttcgacaagg ccggcacggt gaccgcggcc aacgcctcgg gcctgaacga  2760
cggcgccgcc gcggtggtgg tgatgtcggc ggccaaggcc aaggaactgg gcctgacccc  2820
gctggccacg atcaagagct atgccaacgc cggtgtcgat cccaaggtga tgggcatggg  2880
cccggtgccg gcctccaagc gcgccctgtc gcgcgccgag tggaccccgc aagacctgga  2940
cctgatggag atcaacgagg cctttgccgc gcaggcgctg gcggtgcacc agcagatggg  3000
ctgggacacc tccaaggtca atgtgaacgg cggcgccatc gccatcggcc acccgatcgg  3060
cgcgtcgggc tgccgtatcc tggtgacgct gctgcacgag atgaagcgcc gtgacgcgaa  3120
gaagggcctg gcctcgctgt gcatcggcgg cggcatgggc gtggcgctgg cagtcgagcg  3180
caaataaacc ggtgcagccc gcctaatgag cgggcttttt t                     3221
```

```
SEQ ID NO: 241         moltype = AA  length = 392
FEATURE                Location/Qualifiers
source                 1..392
                       mol_type = protein
                       organism = synthetic construct
SEQUENCE: 241
MTDVVIVSAA RTAVGKFGGS LAKVPAPELG AIVIKAALER AGVKPEQVSE VIMGQVLTAG  60
SGQNPARQAA IKAGLPHMVP AMTINKVCGS GLKAVMLAAN AIASGDAEIV VAGGQENMSA  120
APHVLPGSRD GFRMGDAKLI DTMIVDGLWD VYNQYHMGIT AENVAKEYGI SREAQDEFAV  180
SSQNKAEAAQ KAGRFDEEIV PVMIPQRKGE PVAFATDEFV RHGATLESIA GLKPAFDKAG  240
TVTAANASGI NDGAAAVVVM SAAKARELGL TPLATIRAFA NAGVDPKVMG MGPVPASQRC  300
LSRAGWSVQD LDLMEINEAF AAQALAVHKQ MGWDTDKVNV NGGAIAIGHP IGASGCRILV  360
TLLHEMKRRD AKKGLASLCI GGGMGVALAV ER                                392

SEQ ID NO: 242         moltype = AA  length = 246
FEATURE                Location/Qualifiers
source                 1..246
                       mol_type = protein
                       organism = synthetic construct
SEQUENCE: 242
MTQRIAYVTG GMGGIGTAIC QRLAKDGFRV IAGCGPNSPR RERWLEQQKA LGFDFIASEG  60
NVADWDSTKA AFDKVKAEVG EVDVLINNAG ITRDVVFRKM TRADWDAVID TNLTSLFNVT  120
KQVIDGMADR GWGRIINISS VNGQKGQFGQ TNYSTAKAGL HGFTMALAQE VATKGVTVNT  180
VSPGYIATDM VKAIRQDVLD KIVGTIPVKR LGQPEEIASI CAWLASEESG FATGADFSLN  240
GGLHMG                                                             246

SEQ ID NO: 243         moltype = AA  length = 605
FEATURE                Location/Qualifiers
source                 1..605
                       mol_type = protein
                       organism = synthetic construct
SEQUENCE: 243
MATGKGAAAS GQEEKTTPFS STPGPFDPAT WLEWSRQAQA NGRAAGGMPG ADAFAALGAF  60
```

-continued

```
PGGAFPGAGF PGTAFPGIKI APAQLAEIQQ RFMQGFTDLW RAMAAGDQQQ VQLTDRRFAG  120
DAWRSNAPYR YAAAFYLLTA RAMSEMADAV EADAKTRQRI RFAVTQWVDA MSPANFLATN  180
PEAQRRLIES NGESLRAGLR NMLEDLTRGK ISQTDESAFE VGRNVAVTEG AVVYENEYFQ  240
LLQYKPLTAK VHARPLLMVP PCINKYYILD LQPESSLVRH IVEQGHTVFL VSWRNPDASM  300
AARTWDDYIE HGAIRAIEVA RAISGQPRIN VLGFCVGGTI VSTALAVMAG RGERPAQSLT  360
LLTTLLDFSD TGVLDVFVDE AHVQLREATL GGAAGAPCAL LRGIELANTF SFLRPNDLVW  420
NYVVDNYLKG NTPVPFDLLF WNGDATNLPG PWYCWYLRHT YLQDELKVPG KLTVCGVPVD  480
LGKIDVPTYL YGSREDHIVP WTAAYASTRL LSNDLRFVLG ASGHIAGVIN PPAKNKRSHW  540
LNEDLPDSPN DWLAGATEAP GSWWPDWFAW LGKHAGAKKA APTQYGSRDY PAIEPAPGRY  600
VKAKA                                                              605

SEQ ID NO: 244          moltype = AA  length = 605
FEATURE                 Location/Qualifiers
source                  1..605
                        mol_type = protein
                        organism = synthetic construct
SEQUENCE: 244
MATGKGAAAS GQEEKTTPFS STPGPFDPAT WLEWSRQAQA NGRAAGGMPG ADAFAALGAF  60
PGGAFPGAGF PGTAFPGIKI APAQLAEIQQ RFMQGFTDLW RAMAAGDQQQ VQLTDRRFAG  120
DAWRSNAPYR YAAAFYLLTA RAMSEMADAV EADAKTRQRI RFAVTQWVDA MSPANFLATN  180
PEAQRRLIES NGESLRAGLR NMLEDLTRGK ISQTDESAFE VGRNVAVTEG AVVYENEYFQ  240
LLQYKPLTAK VHARPLLMVP PCINKYYILD LQPESSLVRH IVEQGHTVFL VSWRNPDASM  300
AARTWDDYIE HGAIRAIEVA RAISGQPRIN VLGFCVGGTI VSTALAVMAG RGERPAQSLT  360
LLTTLLDFSD TGVLDVFVDE AHVQLREATL GGAAGAPCAL LRGIELANTF SFLRPNDLVW  420
NYVVDNYLKG NTPVPFDLLF WNGDATNLPG PWYCWYLRHT YLQDELKVPG KLTVCGVPVD  480
LGKIDVPTYL YGSREDHIVP WTAAYASTRL LSNDLRFVLG ASGHIAGVIN PPAKNKRSHW  540
LNEDLPDSPN DWLAGATEAP GSWWPDWFAW LGKHAGAKKA APTQYGSRDY PAIEPAPGRY  600
VKAKA                                                              605

SEQ ID NO: 245          moltype = AA  length = 394
FEATURE                 Location/Qualifiers
source                  1..394
                        mol_type = protein
                        organism = synthetic construct
SEQUENCE: 245
MTREVVVVSG VRTPIGTFGG SLKDLSPTEL GAMVVREALA RASVQGDEVG HVVFGNVIQT  60
EPRDMYLARV AAVEGGVSID APALTVNRLC GSGLQAIVSA AQTVMLGDAD VAIGGGAESM  120
SRAPYLAPVA RWGARMGDAK LLDMMLGALH DPFHSIHMGV TAENVAREYD ISRAQQDEAA  180
LESHRRASAA IREGRFKDQI LPVTLKSRKG DVVFDTDEHV RHDAKAEDMS KLKPVFVKEN  240
GTVTAGNASG LNDGAAAVVL MERGVAERRG LKPLARLVSY GHAGVDPKTM GIGPVPATRK  300
ALERAGLSVA DLDVIEANEA FAAQACAVNK ALGLDPLKVN PNGSGISLGH PIGATGALIT  360
VKALYELQRV QGRYALVTMC IGGGQGIAAI FERI                              394

SEQ ID NO: 246          moltype = AA  length = 524
FEATURE                 Location/Qualifiers
source                  1..524
                        mol_type = protein
                        organism = synthetic construct
SEQUENCE: 246
MRKVPIITAD EAAKLIKDGD TVTTSGFVGN AIPEALDRAV EKRFLETGEP KNITYVYCGS  60
QGNRDGRGAE HFAHEGLLKR YIAGHWATVP ALGKMAMENK MEAYNVSQGA LCHLFRDIAS  120
HKPGVFTKVG IGTFIDPRNG GGKVNDITKE DIVELVEIKG QEYLFYPAFP IHVALIRGTY  180
ADESGNITFE KEVAPLEGTS VCQAVKNSGG IVVVQVERVV KAGTLDPRHV KVPGIYVDYV  240
VVADPEDHQQ SLDCEYDPAL SGEHRRPEVV GEPLPLSAKK VIGRRGAIEL EKDVAVNLGV  300
GAPEYVASVA DEEGIVDFMT LTAESGAIGG VPAGGVRFGA SYNADALIDQ GYQFDYYDGG  360
GLDLCYLGLA ECDEKGNINV SRFGPRIAGC GGFINITQNT PKVFFCGTFT AGGLKVKIED  420
GKVIIVQEGK QKKFLKAVEQ ITFNGDVALA NKQQVTYITE RCVFLLKEDG LHLSEIAPGI  480
DLQTQILDVM DFAPIIDRDA NGQIKLMDAA LFAEGLMGLK EMKS                    524

SEQ ID NO: 247          moltype = AA  length = 548
FEATURE                 Location/Qualifiers
source                  1..548
                        mol_type = protein
                        organism = synthetic construct
SEQUENCE: 247
MMVPTLEHEL APNEANHVPL SPLSFLKRAA QVYPQRDAVI YGARRYSYRQ LHERSRALAS  60
ALERVGVQPG ERVAILAPNI PEMLEAHYGV PGAGAVLVCI NIRLEGRSIA FILRHCAAKV  120
LICDREFGAV ANQALAMLDA PPLLVGIDDD QAERADLAHD LDYEAFLAQG DPARPLSAPQ  180
NEWQSIAINY TSGTTGDPKG VVLHHRGAYL NACAGALIFQ LGPRSVYLWT LPMFHCNGWS  240
HTWAVTLSGG THVCLRKVQP DAINAAIAEH AVTHLSAAPV VMSMLIHAEH ASAPPVPVSV  300
ITGGAAPPSA VIAAMEARGF NITHAYGMTE SYGPSTLCLW QPGVDELPLE ARAQFMSRQG  360
VAHPLLEEAT VLDTDTGRPV PADGLTLGEL VVRGNTVMKG YLHNPEATRA ALANGWLHTG  420
DLAVLHLDGY VEIKDRAKDI IISGGENISS LEIEEVLYQH PEVVEAAVVA RPDSRWGETP  480
HAFVTLRADA LASGDDLVRW CRERLAHFKA PRHVSLVDLP KTATGKIQKF VLREWARQQE  540
AQIADAEH                                                           548

SEQ ID NO: 248          moltype = DNA  length = 1179
FEATURE                 Location/Qualifiers
source                  1..1179
```

```
                        mol_type = other DNA
                        organism = synthetic construct
SEQUENCE: 248
atgaccgatg ttgtgatcgt gtcggcagcc cgtaccgcgg ttggtaaatt cggtgggagt  60
ttagcgaaag ttccggctcc ggaactgggc gcgattgtaa ttaaagcggc gttggagcgc  120
gctggcgtga aaccggagca ggtttccgaa gtaattatgg gccaggtgtt gaccgccggc  180
agtggccaaa atccggcacg ccaggcagcc attaaagccg gactgccgca catggttcct  240
gcgatgacca ttaacaaggt ctgcggctcg ggattgaaag cggtcatgtt agcagccaac  300
gccattgcta gcggtgatgc tgaaatcgtg gtggccggtg gccaggaaaa catgtcagca  360
gctccacatg ttctgccggg ttcacgcgac ggctttcgta tgggcgacgc aaagctgatc  420
gacactatga tcgtggatgg cttatgggat gtgtataacc agtaccacat gggcatcacc  480
gcggaaaacg tcgcgaaaga gtatggcatt tctcgcgaag cgcaagatga attcgcggtc  540
agctcccaga ataaggccga agccgcacag aaagcgggcc gtttcgacga agaaatcgtg  600
cctgtgatga tcccgcagcg caaaggcgaa ccggtagcct ttgcgaccga cgaatttgtc  660
cgccacggcg cgacactgga gtcaattgcg gggctgaaac cggccttcga caaagccggc  720
accgttacag ccgcgaatgc atctggtatc aatgatggag ctgccgccgt ggtggttatg  780
tcggcggcaa aagcccgtga gctgggtctg acgccccttg caactattcg cgcgtttgca  840
aacgctggcg ttgatcccaa agtgatgggc atgggtccgg tcccagcgag ccaacgttgc  900
ttaagccgtg caggctggag cgtacaggat ctggatctga tggaaattaa tgaagcgttt  960
gccgcccaag cactggcggt acataagcag atgggttggg atacggataa ggttaacgta  1020
aatggaggtg cgatcgccat tggccatcct attggggcca gtgggtgtcg cattcttgtg  1080
acgcttctcc atgagatgaa acgccgtgat gcaaagaaag gtctggcgag cctctgtatt  1140
ggaggaggga tgggtgtggc gttagcggtc gaacgttaa                        1179

SEQ ID NO: 249          moltype = DNA  length = 741
FEATURE                 Location/Qualifiers
source                  1..741
                        mol_type = other DNA
                        organism = synthetic construct
SEQUENCE: 249
atgactcagc gcatcgccta tgttacaggc ggcatgggag gtattggcac tgccatctgc  60
cagcgtttgg ccaaagatgg gtttcgcgtt attgcgggtt gcggtccaaa tagtccgcgc  120
cgcgaacgtt ggctggaaca gcagaaggcc ttaggctttg actttattgc gtcggaaggc  180
aatgttgcag actgggattc taccaaagcc gccttcgaca aagtcaaggc agaggttggt  240
gaagtagatg tgctgattaa taatgcaggc atcacccgtg acgtggtttt ccgcaaaatg  300
acccgtgcgg attgggatgc ggtgattgat accaacctta cgagcctgtt caacgtcacc  360
aaacaagtca ttgatggtat ggcagatcgc ggctggggtc gtattattaa catcagcagc  420
gtgaacggac aaaaaggaca atttgggcag acgaattact caactgcgaa agcggggctg  480
cacggcttta ccatggcgtt ggcgcaggaa gtggctacca agggcgtcac ggtgaacaca  540
gtatcgccgg gctatattgc gaccgatatg gtgaaggcga ttcgccagga cgtactggat  600
aaaatcgtgg gcaccatccc ggtaaaacgt ttaggccagc ctgaagagat tgcttccatc  660
tgtgcctggc tggcaagtga ggaatcaggc tttgccacgg gagctgactt cagcctcaac  720
ggtggtcttc atatgggcta a                                           741

SEQ ID NO: 250          moltype = DNA  length = 1818
FEATURE                 Location/Qualifiers
source                  1..1818
                        mol_type = other DNA
                        organism = synthetic construct
SEQUENCE: 250
atggcgactg gcaaaggtgc tgcagcttcc gggcaggaag aaaagaccac accgtttagc  60
tcaacgccag ggccgtttga tccagcgaca tggttggaat ggtcccgtca ggcccaagcc  120
aatggacgtg cagcaggtgg catgccaggt gcagatgcat ttgctgcact tggagcgttt  180
ccaggaggtg catttcctgg agccggattt cccggcacag catttcccgg tatcaaaatt  240
gccccagccc agttggccga aatccagcaa cgcttcatgc aggggtttac cgatttatgg  300
cgtgcaatgg ctgccggcga tcagcaacag gtgcaactga ccgatcgtcg ctttgccgga  360
gatgcctggc gtagcaacgc gccttatcgt tacgccgcgg ccttctatct gttaaccgca  420
cgtgcgatga gcgaaatggc cgatgccgta gaagccgatg cgaaaacacg tcagcgcatt  480
cgctttgcgg tgactcagtg ggttgatgcg atgagtccgg ccaattttct cgcaaccaac  540
cctgaagcac agcgtcgcct tattgaatcg aacggcgaat cgttacgtgc tggtcttcgc  600
aacatgctcg aggacttaac gcgcggtaaa atttcgcaga ccgatgaatc agccttcgaa  660
gttggtcgca atgtcgcggt tactgaaggc gcggtagtct acgagaacga atacttccag  720
ctgctgcagt acaaaccgct taccgccaaa gtgcatgcgc gtccgttatt gatggtgccg  780
ccctgcatca acaagtacta catcctcgac cttcagccgg aaagctcttt ggttcgccac  840
attgtcgagc agggccatac cgtgtttctt gtatcatggc gtaatccgga tgcgagcatg  900
gcggcgcgta cctgggatga ctatatcgag cacggtgcga ttcgtgcgat cgaagtagcg  960
cgcgcgatta gcgggcaacc gcgcattaat gtgctggggt tctgtgtagg cggtactatt  1020
gtgagtaccg cgttagcggt tatggctggc cgcggcgaac gccctgcgca aagccttacg  1080
ctgctgacca cactgctcga tttctctgat accggtgtgt tagatgtgtt cgttgatgaa  1140
gcgcacgtac agttgcgcga agccactctg ggtggcgcgg caggtgcgcc gtgtgcgttg  1200
ctgcgcggca ttgagctggc caatacgttc tcgttcctgc gtccgaacga tctggtctgg  1260
aactacgtgg tcgacaacta tctgaagggc aatacgccgg tgccgtttga cctgctgttc  1320
tggaacggcg atgcgaccaa tctgccaggg ccctggtatt gctggtatct gcgccatacc  1380
tatctgcagg acgagctgaa agttcctggc aaactgaccg tttgcggcgt gccggtcgat  1440
ttaggcaaaa ttgacgtgcc gacctatctg tacggcagtc gcgaggacca tattgtgccg  1500
tggacggctg cctatgcatc aacgcgtctg ttgtccaatg acctgcgctt cgtgctgggc  1560
gcgtctggac atatcgccgg cgttatcaat ccgccggcga aaaacaaacg cagccactgg  1620
ctcaacgaag acctgcccga cagtccgaat gattggctgg ccggtgcgac tgaagcgcct  1680
ggcagctggt ggccggattg gtttgcctgg ttaggcaaac atgccggcgc gaaaaaggcg  1740
```

-continued

```
gcaccgacgc aatatggcag ccgcgactat ccggccattg agccggcacc tggtcgttac  1800
gtcaaggcca aagcttaa                                                1818

SEQ ID NO: 251         moltype = DNA  length = 1185
FEATURE                Location/Qualifiers
source                 1..1185
                       mol_type = other DNA
                       organism = synthetic construct
SEQUENCE: 251
atgacacgtg aggttgtcgt ggtgagcggc gttcgcaccc caattggaac ttttggcggt  60
tctctgaaag acctgagtcc gaccgaactc ggcgcgatgg tagtgcgtga agcgttggcg  120
cgtgcctcgg tacagggcga tgaggtgggc cacgttgttt ttggcaacgt cattcagacc  180
gaaccgcgtg atatgtacct tgcgcgcgtc gcggcagtcg aaggcggtgt ttcaattgac  240
gccccggcgt tgaccgtgaa tcgcttatgc ggtagcggcc ttcaagccat cgtatcggcg  300
gcgcaaaccg ttatgctggg cgatgccgat gtggcgattg gcgggggtgc ggaaagcatg  360
agtcgtgccc cgtatcttgc accggtcgcg cgttggggcg cacgtatggg cgatgccaaa  420
ttattagata tgatgctggg cgctctccat gatccgttcc acagcatcca catgggcgtg  480
actgcagaaa acgttgcgcg cgaatacgac atctctcgcg cgcagcagga tgaagccgcg  540
ctggagagcc atcgccgcgc aagtgcagct atccgcgaag gccgtttcaa agatcagatt  600
ctgccagtca cgctgaaatc ccgcaaaggc gacgtggtgt tcgacacgga cgaacatgtg  660
cgccacgatg cgaaggccga agacatgtcc aaactgaagc ccgtgtttgt gaaagagaac  720
ggtaccgtga cagcggggaa tgcctcagga ctgaatgatg gagctgccgc cgtggttctg  780
atggaacgcg gagtcgcgga acgccgtggt cttaaacctc tcgcgcgctt agtatcgtat  840
ggccatgccg gagtcgatcc gaaaaccatg ggattggtc ctgttcctgc aactcgcaaa  900
gctctggaac gtgctggcct gagcgtggca gatctggacg taattgaggc gaatgaggcg  960
tttgcagccc aggcatgtgc agtgaacaaa gccctgggct tagatccgct gaaggtaaat  1020
cccaacggta gcggtatctc actggggcat ccgatcggcg ctacgggtgc cttgattacg  1080
gttaaggcac tctacgaact gcagcgcgtt caaggtcgtt atgccttggt gaccatgtgc  1140
attggtggtg ggcagggaat cgccgcgatt tttgagcgta tttaa                  1185

SEQ ID NO: 252         moltype = DNA  length = 1575
FEATURE                Location/Qualifiers
source                 1..1575
                       mol_type = other DNA
                       organism = synthetic construct
SEQUENCE: 252
atgagaaagg ttcccattat taccgcagat gaggctgcaa agcttattaa agacggtgat  60
acagttacaa caagtggttt cgttggaaat gcaatccctg aggctcttga tagagctgta  120
gaaaaaagat tcttagaaac aggcgaaccc aaaaacatta catatgttta ttgtggttct  180
caaggtaaca gagacggaag aggtgctgag cactttgctc atgaaggcct tttaaaacgt  240
tacatcgctg gtcactgggc tacagttcct gctttgggta aaatggctat ggaaaataaa  300
atggaagcat ataatgtatc tcagggtgca ttgtgtcatt tgttccgtga tatagcttct  360
cataagccag gcgtatttac aaaggtaggt atcggtactt tcattgaccc cagaaatggc  420
ggcggtaaag taaatgatat taccaaagaa gatattgttg aattggtaga gattaagggt  480
caggaatatt tattctaccc tgcttttcct attcatgtag ctcttattcg tggtacttac  540
gctgatgaaa gcggaaatat cacatttgag aaagaagttg ctcctctgga aggaacttca  600
gtatgccagg ctgttaaaaa cagtggcggt atcgttgtag ttcaggttga aagagtagta  660
aaagctggta ctcttgaccc tcgtcatgta aaagttccag gaatttatgt tgactatgtt  720
gttgttgctg acccagaaga tcatcagcaa tctttagatt gtgaatatga tcctgcatta  780
tcaggcgagc atagaagacc tgaagttgtt ggagaaccac ttcctttgag tgcaaagaaa  840
gttattggtc gtcgtggtgc cattgaatta gaaaaagatg ttgctgtaaa tttaggtgtt  900
ggtgcgcctg aatatgtagc aagtgttgct gatgaagaag gtatcgttga ttttatgact  960
ttaactgctg aaagtggtgc tattggtggt gttcctgctg gtggcgttcg ctttggtgct  1020
tcttataatg cggatgcatt gatcgatcaa ggttatcaat tcgattacta tgatggcggc  1080
ggcttagacc tttgctattt aggcttagct gaatgcgatg aaaaaggcaa tatcaacgtt  1140
tcaagatttg gccctcgtat cgctggttgt ggtggtttca tcaacattac acagaataca  1200
cctaaggtat tcttctgtgg tactttcaca gcaggtggct taaaggttaa aattgaagat  1260
ggcaaggtta ttattgttca agaaggcaag cagaaaaaat tcttgaaagc tgttgagcag  1320
attacattca atggtgacgt tgcacttgct aataagcaac aagtaactta tattacagaa  1380
agatgcgtat tcctttttgaa ggaagatggt ttgcacttat ctgaaattgc acctggtatt  1440
gatttgcaga cacagattct tgacgttatg gattttgcac ctattattga cagagatgca  1500
aacggccaaa tcaaattgat ggacgctgct ttgtttgcag aaggcttaat gggtctgaag  1560
gaaatgaagt cctga                                                   1575

SEQ ID NO: 253         moltype = DNA  length = 1647
FEATURE                Location/Qualifiers
source                 1..1647
                       mol_type = other DNA
                       organism = synthetic construct
SEQUENCE: 253
atgatggttc caaccctcga acacgagctt gctcccaacg aagccaacca tgtcccgctg  60
tcgccgctgt cgttcctcaa gcgtgccgcg caggtgtacc cgcagcgcga tgcggtgatc  120
tatggcgcaa ggcgctacag ctaccgtcag ttgcacgagc gcagccgcgc cctggccagt  180
gccttggagc gggtcggtgt tcagccgggc gagcgggtgg cgatattggc gccgaacatc  240
ccggaaatgc tcgaggccca ctatggcgtg cccggtgccg gggcggtgct ggtgtgcatc  300
aacatccgcc tggaggggcg cagcattgcc ttcatcctgc gtcactgcgc ggccaaggta  360
ttgatctgcg atcgtgagtt cggtgccgtg gccaatcagg cgctggccat gctcgatgcg  420
ccgcccttgc tggtgggcat cgacgatgat caggccgagc gcgccgattt ggcccacgac  480
ctggactacg aagcgttctt ggcccagggc gaccccgcgc ggccgttgag tgcgccacag  540
```

-continued

```
aacgaatggc agtcgatcgc catcaactac acctccggca ccacggggga ccccaagggc  600
gtggtgctgc atcaccgcgg cgcctacctc aacgcctgcg ccggggcgct gatcttccag  660
ttggggccgc gcagcgtcta cttgtggacc ttgccgatgt tccactgcaa cggctggagc  720
catacctggg cggtgacgtt gtccggtggc acccacgtgt gtctgcgcaa ggtccagcct  780
gatgcgatca acgccgccat cgccgagcat gccgtgactc acctgagcgc cgccccagtg  840
gtgatgtcga tgctgatcca cgccgagcat gccagcgccc ctccggtgcc ggtttcggtg  900
atcactggcg gtgccgcccc gcccagtgcg gtcatcgcgg cgatggaggc gcgtggcttc  960
aacatcaccc atgcctatgg catgaccgaa agctacggtc ccagcacatt gtgcctgtgg  1020
cagccgggtg tcgacgagtt gccgctggag gcccgggccc agttcatgag ccgccagggc  1080
gtcgcccacc cgctgctcga ggaggccacg gtgctggata ccgacaccgg ccgcccggtc  1140
ccggccgacg gccttaccct cggcgagctg gtggtgcggg gcaacactgt gatgaaaggc  1200
tacctgcaca acccagaggc tacccgtgcc gcgttggcca acggctggct gcacacgggc  1260
gacctggccg tgctgcacct ggacggctat gtggaaatca aggaccgagc caaggacatc  1320
atcatttctg gcggcgagaa catcagttcg ctggagatag aagaagtgct ctaccagcac  1380
cccgaggtgg tcgaggctgc ggtggtggcg cgtccggatt cgcgctgggg cgagacacct  1440
cacgctttcg tcacgctgcg cgctgatgca ctggccagcg gggacgacct ggtccgctgg  1500
tgccgtgagc gtctggcgca cttcaaggcg ccgcgccatg tgtcgctcgt ggacctgccc  1560
aagaccgcca ctggaaaaat acagaagttc gtcctgcgtg agtgggcccg gcaacaggag  1620
gcgcagatcg ccgacgccga gcattga                                    1647

SEQ ID NO: 254          moltype = DNA  length = 56
FEATURE                 Location/Qualifiers
source                  1..56
                        mol_type = other DNA
                        organism = synthetic construct
SEQUENCE: 254
ttgacaatta atcatccggc tcgtataatg tgtggaattg tgagcggata acaatt      56

SEQ ID NO: 255          moltype = DNA  length = 15
FEATURE                 Location/Qualifiers
source                  1..15
                        mol_type = other DNA
                        organism = synthetic construct
SEQUENCE: 255
taaggaggaa aaaaa                                                   15

SEQ ID NO: 256          moltype = DNA  length = 42
FEATURE                 Location/Qualifiers
source                  1..42
                        mol_type = other DNA
                        organism = synthetic construct
SEQUENCE: 256
tctagaaata attttgttta actttaagaa ggagatatac at                     42

SEQ ID NO: 257          moltype = DNA  length = 5122
FEATURE                 Location/Qualifiers
misc_feature            1..1453
                        note = bcsA 3'
misc_feature            1454..1578
                        note = TR sequence required for integration via
                         CRISPR-Tn6677
misc_feature            1661..1763
                        note = Pgracmax2
misc_feature            1764..1805
                        note = RBS-T7 and spacer
misc_feature            1806..2990
                        note = bktB(QJ1)
misc_feature            2996..3023
                        note = bktB(QJ1)
misc_feature            3024..3764
                        note = phaB(S-6)
misc_feature            3771..3798
                        note = phaB(S-6)
misc_feature            3812..3956
                        note = TL sequence required for integration via
                         CRISPR-Tn6677
misc_feature            3957..5122
                        note = TL sequence required for integration via
                         CRISPR-Tn6677
source                  1..5122
                        mol_type = other DNA
                        organism = synthetic construct
SEQUENCE: 257
tcattgttga gccaaagcct gatccgatgg ttgtgccgtt tcgctccgct ccgggcggcg  60
cggaataaac gatacaaccc aggaaaccag agaagtcagc acacggaata tgcccttcac  120
cgaagaaggc gcaaactccg ccagatggcg gtagccacgg aagccgagct tcagaatatc  180
cagcagactt tccagcggct tatcttccgg gtagctgtcc tgccagagcg cccatgtatc  240
cgcacgggca aacgtacact gcacaaaatc gatatgttgc tgggtggtga gcggcattaa  300
tttcagccca acttcattac ccatcacgcg cgccacctgg gtcgggaaga cgtattcctg  360
```

-continued

```
ctgaccgcgt ttaagcaaca gattcacttt ctgcccttcc agaatctgcg cctgaccgtt  420
gatcttgatc cccaaaccac cgtcggagaa atcctgaacg gtacacgaga agaggtgacc  480
atcttcgcgg gcaattgccg cgggcatcgt catctccacg cggtgcgatc ggcgtacctg  540
tttgctttct accgataccg caactgcgcc gccaagaaca atcaggttgt agaacaccca  600
caccatactg acgaccacgg tgagcatctc ggttggcggg ccatagaagt agcgccagat  660
gcctaccgca acgcccacca ggttgagcag gacaaggaag atgtagggcc gcgagatcac  720
ccagtcgacg tactcttctt ccaccagtcc acctttggcg gtgacgttaa atttgccttt  780
gtgcgggtta atcagcgcca ccagcgtcgg tggtgcgata taccacgcca gcaccgtttc  840
gtagatttca ctccagaaag agtggcgata tttgccctgg atcttggagt tggtcaggct  900
ggcatggatc atatgcggca gcacgaatag ggcgatcatc aacgctggcg catagatgat  960
gtaggcatga agcagcagga acgccagcgg cgcagtcagg aagatcagcc gtggaatgcc  1020
cgacaagaag tggaacatgg cgttgacgta acatagccgc tgagcaaact tcagcccttt  1080
accggtgagc gggttatcga gacggaagat ttgtaccatc ccgcgcgccc agcgaatacg  1140
ctgaccgata tgcgccgaca gactttcggt cgccagcccc gccgcctgcg gaatacgcat  1200
atacgcggag gtatagccac gacggtgcaa ccgcagagaa gtatgcgcat cttcagtcac  1260
ggtttcgaca gcaatgccgc caatttcatc cagcggctta cgacgaatca ccgcacagga  1320
accgcagaag aaagtggcgt cccacatatc gttgccatcc tgcaccagac catagaacag  1380
cgtgccttcg ttcggcgttt tacggaaacg ccccaggttg cgttcaaacg ggtccggtga  1440
gaagaagtgg tgctgttgat acaaccataa aatgataatt acacccataa attgataatt  1500
atcacaccca taaattgata ttgcctcttc atggtctaaa cttcagtaag tttacgacat  1560
tttcctcgag gtcatttccg cagtataagt cgctttccgg cggtgcctga acgagaagct  1620
atcaccgccc agcctaaacg gatatcatca tcgctcatcc gaaaagaatg atggatcact  1680
agaaaatttt ttaaaaaatc tcttgacatt ggaagggaga tatgttataa taagaattgc  1740
ggaattgtga gcggataaca atttctagaa ataattttgt ttaactttaa gaaggagata  1800
tacatatgac acgtgaggtt gtcgtggtga gcggcgttcg caccccaatt ggaacttttg  1860
gcggttctct gaaagacctg agtccgaccg aactcggcgc gatggtagtg cgtgaagcgt  1920
tggcgcgtgc ctcggtacag ggcgatgagg tgggccacgt tgtttttggc aacgtcattc  1980
agaccgaacc gcgtgatatg taccttgcgc gcgtcgcggc agtcgaaggc ggtgtttcaa  2040
ttgacgcccc ggcgttgacc gtgaatcgct tatgcggtag cggccttcaa gccatcgtat  2100
cggcggcgca aaccgttatg ctgggcgatg ccgatgtggc gattggcggg ggtgcggaaa  2160
gcatgagtcg tgcccgtat cttgcaccgg tcgcgcgttg gggcgcacgt atgggcgatg  2220
ccaaattatt agatatgatg ctgggcgctc tccatgatcc gttccacagc atccacatgg  2280
gcgtgactgc agaaaacgtt gcgcgcgaat acgacatctc tcgcgcgcag caggatgaag  2340
ccgcgctgga gagccatcgc cgcgcaagtg cagctatccg cgaaggccgt ttcaaagatc  2400
agattctgcc agtcacgctg aaatcccgca aaggcgacgt ggtgttcgac acggacgaac  2460
atgtgcgcca cgatgcgaag gccgaagaca tgtccaaact gaagcccgtg tttgtgaaag  2520
agaacggtac cgtgacagcg gggaatgcct caggactgaa tgatggagct gccgccgtgg  2580
ttctgatgga acgcggagtc gcggaacgcc gtggtcttaa acctctcgcg cgcttagtat  2640
cgtatggcca tgccggagtc gatccgaaaa ccatggggat tggtcctgtt cctgcaactc  2700
gcaaagctct ggaacgtgct ggcctgagcg tggcagatct ggacgtaatt gaggcgaatg  2760
aggcgtttgc agcccaggca tgtgcagtga acaaagccct gggcttagat ccgctgaagg  2820
taaatcccaa cggtagcggt atctcactgg ggcatccgat cggcgctacg ggtgccttga  2880
ttacggttaa ggcactctac gaactgcagc gcgttcaagg tcgttatgcc ttggtgacca  2940
tgtgcattgg tggtgggcag ggaatcgccg cgatttttga gcgtatttaa accggttaga  3000
ttaactttaa ggaggtcaat aaaatgactc agcgcatcgc ctatgttaca ggcggcatgg  3060
gaggtattgg cactgccatc tgccagcgtt tggccaaaga tgggtttcgc gttattgcgg  3120
gttgcggtcc aaatagtccg cgccgcgaac gttggctgga acagcagaag gccttaggct  3180
ttgactttat tgcgtcggaa ggcaatgttg cagactggga ttctaccaaa gccgccttcg  3240
acaaagtcaa ggcagaggtt ggtgaagtag atgtgctgat taataatgca ggcatcaccc  3300
gtgacgtggt tttccgcaaa atgacccgtg cggattggga tgcggtgatt gataccaacc  3360
ttacgagcct gttcaacgtc accaaacaag tcattgatgg tatggcagat cgcggctggg  3420
gtcgtattat taacatcagc agcgtgaacg gacaaaaagg acaatttggg cagacgaatt  3480
actcaactgc gaaagcgggg ctgcacggct ttaccatggc gttggcgcag gaagtggcta  3540
ccaagggcgt cacggtgaac acagtatcgc cgggctatat tgcgaccgat atggtgaagg  3600
cgattcgcca ggacgtactg gataaaatcg tgggcaccat cccggtaaaa cgtttaggcc  3660
agcctgaaga gattgcttcc atctgtgcct ggctggcaag tgaggaatca ggctttgcca  3720
cgggagctga cttcagcctc aacggtggtc ttcatatggg ctaaactagt gcagcccgcc  3780
taatgagcgg gctttttttgc gatcgcgagt ccttactgca gtagttttgc tgaaatactc  3840
gattcacaaa aatatcaact tatggttgtt ttgtgagata tcaatatatg gttgttttgt  3900
ggttaagttg ctgattataa ataattatta aatatcactt tatggttgca tcaacaggcg  3960
tctgcatcat cgccagctgt tttctttca ggaaccagcc catggtcatt tgcaagaacg  4020
atcgcgttgg tacgtggtcg cagtcgaaaa tcgacacgaa ctcgcctttg gcatatttca  4080
gcgcattgtt gatgttgcct gctttcgcat gttcatgagt ggtgcgggcg atatatttca  4140
cccccacgtt ttgcgcaaac tggcgaaact cttccctgcc gccgtcatca aggatccaga  4200
tattcagctt atctttcggc cagtcgatac ccagcgaggc gtaaatggta tttttcacca  4260
cgttgagatc ttcgttgtaa gtcgggacaa agatatccac cgacggccac agcgacatat  4320
ctttcggcaa tggcaccggc tgacgattca gcggccatac tacctggaag tagccgagca  4380
ccagcacaat ccacgcgtac gtttcagcga agagcagaat aagcccgcac accaggctga  4440
ccggatcgtc ccagttcagc gtagaggtgt aacgccacca gatataacgg caagaaacgg  4500
tcagcgacag cacaatcaac attagcgccg agaagcgccc cggcatccgc cgtacgatca  4560
gcgctacccc ccacagcagc atcaggaaga taaactgcgc cagcgggtta aacggctgag  4620
taacgcagat taacgccaga atcagcgaga aggtgacgat gataccgagg atcaaccgcc  4680
gcgccccggc actcaaatga ccgagctctt ttttctcatc cagatgctgt gttttatggc  4740
taacgcgctc aggcagctcg ttcatccatt gatggtaacg tccacgaata ttttgcagac  4800
ctgaaaatgc ccgcctgcgc ggtttcggcg tttctttgcg cgatgcaccg atcaataacc  4860
agcatgtttg aatgagataa cggaccgggt ccagcggacg cggacgcgag gcgttgatat  4920
gcggatacag gtttttatgt tctgcgcgaa tacgctgcca gcgcgggtgc tccagcggaa  4980
taaaaatcca ggccaggatc atccagaaac agccgagcgt cgcgctgaaa gccgacgcac  5040
cgtgacgacg ataatcgcga taacgcccga taagccgcgc gttgaccggc gggataagca  5100
```

```
accaccgggt caggatactc at                                           5122

SEQ ID NO: 258          moltype = DNA  length = 3211
FEATURE                 Location/Qualifiers
misc_feature            1..584
                        note = endA 3'
misc_feature            585..709
                        note = TR sequence required for integration via
                         CRISPR-Tn6677
misc_feature            792..894
                        note = Pgracmax2
misc_feature            895..936
                        note = RBS-T7 and spacer
misc_feature            937..2121
                        note = bktB(QJ1)
misc_feature            2127..2154
                        note = RBS and spacer
misc_feature            2155..2895
                        note = phaB(S-6)
misc_feature            2902..2929
                        note = trpA terminator
misc_feature            2943..3087
                        note = TL sequence required for integration via
                         CRISPR-Tn6677
misc_feature            3088..3211
                        note = endA 5'
source                  1..3211
                        mol_type = other DNA
                        organism = synthetic construct
SEQUENCE: 258
ttagctcttt cgcgcctggc aagcgcgttg cacatacggg ttatgattgc cctgcacctt  60
cgcgatgcgt tcatcgcgct cgcactccca gtcggtaacc ggatacatct tgttccatgc  120
gttgaacagc tgcgtttgct ggcgagagag tgtcaggttg tattggtcgc gcatatagaa  180
gtaggtgcgc gcaatggcac cgcgtgcacg cgctggtggt tcggcagctt tttctttgaa  240
atcgaccttc atggcgcatt gaccgtactg gccttcaccg ccattccact ggctgtacat  300
aaagttgccg cgatcgccat tcacctcacc gactgacggc tgcaggttat gcatatcgct  360
ttccatcttg cgatagaccg gatctttagc gcagttttta cgtccaccgt cctgccagca  420
ctggcgctgg tgaccgaact gccaggcggg aacgacatgt tcccactcta cgcggctggc  480
gcggttttca tttttgcgca cctgatagcc gcacgattgc agatcaacaa cgcctttttt  540
gccctgccag ttaattttac atccgcaata aaacgtaccg ggcgtgttga tacaaccata  600
aaatgataat tacacccata aattgataat tatcacaccc ataaattgat attgcctctt  660
catggtctaa acttcagtaa gtttacgaca ttttcctcga ggtcatttcc gcagtataag  720
tcgctttccg gcggtgcctg aacgagaagc tatcaccgcc cagcctaaac ggatatcatc  780
atcgctcatc cgaaaagaat gatggatcac tagaaaattt tttaaaaaat ctcttgacat  840
tggaagggag atatgttata ataagaattg cggaattgtg agcggataac aatttctaga  900
aataattttg tttaacttta agaaggagat atacatatga cacgtgaggt tgtcgtggtg  960
agcggcgttc gcaccccaat tggaactttt ggcggttctc tgaaagacct gagtccgacc  1020
gaactcggcg cgatggtagt gcgtgaagcg ttggcgcgtg cctcggtaca gggcgatgag  1080
gtgggccacg ttgtttttgg caacgtcatt cagaccgaac cgcgtgatat gtaccttgcg  1140
cgcgtcgcgg cagtcgaagg cggtgtttca attgacgccc cggcgttgac cgtgaatcgc  1200
ttatgcggta gcggccttca agccatcgta tcggcggcgc aaaccgttat gctgggcgat  1260
gccgatgtgg cgattggcgg gggtgcggaa agcatgagtc gtgccccgta tcttgcaccg  1320
gtcgcgcgtt ggggcgcacg tatgggcgat gccaaattat tagatatgat gctgggcgct  1380
ctccatgatc cgttccacag catccacatg ggcgtgactg cagaaaacgt tgcgcgcgaa  1440
tacgacatct ctcgcgcgca gcaggatgaa gccgcgctgg agagccatcg ccgcgcaagt  1500
gcagctatcc gcgaaggccg tttcaaagat cagattctgc cagtcacgct gaaatcccgc  1560
aaaggcgacg tggtgttcga cacggacgaa catgtgcgcc acgatgcgaa ggccgaagac  1620
atgtccaaac tgaagcccgt gtttgtgaaa gagaacggta ccgtgacagc ggggaatgcc  1680
tcaggactga atgatggagc tgccgccgtg gttctgatgg aacgcggagt cgcggaacgc  1740
cgtggtctta aacctctcgc gcgcttagta tcgtatggcc atgccggagt cgatccgaaa  1800
accatgggga ttggtcctgt tcctgcaact cgcaaagctc tggaacgtgc tggcctgagc  1860
gtggcagatc tggacgtaat tgaggcgaat gaggcgtttg cagcccaggc atgtgcagtg  1920
aacaaagccc tgggcttaga tccgctgaag gtaaatccca acggtagcgg tatctcactg  1980
gggcatccga tcggcgctac gggtgccttg attacggtta aggcactcta cgaactgcag  2040
cgcgttcaag gtcgttatgc cttggtgacc atgtgcattg gtggtgggca gggaatcgcc  2100
gcgatttttg agcgtattta aaccggttag attaacttta aggaggtcaa taaaatgact  2160
cagcgcatcg cctatgttac aggcggcatg ggaggtattg gcactgccat ctgccagcgt  2220
ttggccaaag atgggtttcg cgttattgcg ggttgcggtc caaatagtcc gcgccgcgaa  2280
cgttggctgg aacagcagaa ggccttaggc tttgacttta ttgcgtcgga aggcaatgtt  2340
gcagactggg attctaccaa agccgccttc gacaaagtca aggcagaggt tggtgaagta  2400
gatgtgctga ttaataatgc aggcatcacc cgtgacgtgg ttttccgcaa aatgacccgt  2460
gcggattggg atgcggtgat tgataccaac cttacgagcc tgttcaacgt caccaaacaa  2520
gtcattgatg gtatggcaga tcgcggctgg ggtcgtatta ttaacatcag cagcgtgaac  2580
ggacaaaaag gacaatttgg gcagacgaat tactcaactg cgaaagcggg gctgcacggc  2640
tttaccatgg cgttggcgca ggaagtggct accaagggcg tcacggtgaa cacagtatcg  2700
ccgggctata ttgcgaccga tatggtgaag gcgattcgcc aggacgtact ggataaaatc  2760
gtgggcacca tcccggtaaa acgtttaggc cagcctgaag agattgcttc catctgtgcc  2820
tggctggcaa gtgaggaatc aggctttgcc acgggagctg acttcagcct caacggtggt  2880
cttcatatgg gctaaactag tgcagcccgc ctaatgagcg ggcttttttg cgatcgcgag  2940
```

-continued

```
tccttactgc agtagttttg ctgaaatact cgattcacaa aaatatcaac ttatggttgt  3000
tttgtgagat atcaatatat ggttgttttg tggttaagtt gctgattata aataattatt  3060
aaatatcact ttatggttgc atcaacacgt cagcgtggac ttttaccgcc gcggctttcg  3120
cctgagaaaa actattgata ccttcggcca acgccgggcc ggaaaatgct gcgctcagta  3180
ccaccgcagc aatagacaaa taacggtaca t                                 3211
```